United States Patent
Willms et al.

(10) Patent No.: US 9,776,993 B2
(45) Date of Patent: Oct. 3, 2017

(54) NITROGEN-CONTAINING HETEROCYCLIC COMPOUNDS FOR PLANT DISEASE CONTROL

(71) Applicant: BAYER CROPSCIENCE AG, Monheim (DE)

(72) Inventors: Lothar Willms, Hofheim (DE); Monika H. Schmitt, Frankfurt (DE); Thomas Frenzel, Cologne (DE); Klaus Bernhard Haaf, Kelheim (DE); Isolde Haeuser-Hahn, Leverkusen (DE); Ines Heinemann, Hofheim (DE); Elmar Gatzweiler, Bad Nauheim (DE); Christopher Hugh Rosinger, Hofheim (DE); Heinz Kehne, Hofheim (DE); Jan Dittgen, Frankfurt (DE); Dieter Feucht, Eschborn (DE); Martin Hills, Idstein (DE); Jan Peter Schmidt, Folsom, CA (US); Mazen Es-Sayed, Langenfeld (DE); Philipe Rinolfi, Chatillon d'Azergues (FR); Stephane Brunet, St Andre de Corcy (FR); Marie-Claire Grosjean-Cournoyer, Curis Au Mont d'or (FR); Helene Lachaise, Lyons (FR); Jacky Vidal, Lozanne (FR); Pierre-Yves Coqueron, Lyons (FR); Arounarith Tuch, Lyons (FR)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 15/335,832

(22) Filed: Oct. 27, 2016

(65) Prior Publication Data
US 2017/0057951 A1 Mar. 2, 2017

Related U.S. Application Data

(62) Division of application No. 14/430,919, filed as application No. PCT/EP2013/069893 on Sep. 25, 2013, now Pat. No. 9,510,598.

(30) Foreign Application Priority Data
Sep. 28, 2012 (EP) .................................... 12186485

(51) Int. Cl.
*C07D 413/04* (2006.01)
*A01N 43/80* (2006.01)
*A01N 43/82* (2006.01)
*A01N 43/84* (2006.01)
*A01N 43/90* (2006.01)
*A01N 55/00* (2006.01)
*C07D 413/14* (2006.01)
*C07D 498/04* (2006.01)
*C07F 7/08* (2006.01)

(52) U.S. Cl.
CPC .......... *C07D 413/04* (2013.01); *A01N 43/80* (2013.01); *A01N 43/82* (2013.01); *A01N 43/84* (2013.01); *A01N 43/90* (2013.01); *A01N 55/00* (2013.01); *C07D 413/14* (2013.01); *C07D 498/04* (2013.01); *C07F 7/0812* (2013.01)

(58) Field of Classification Search
CPC ... C07D 413/04; C07D 413/14; C07D 498/04
See application file for complete search history.

(56) References Cited

U.S. PATENT DOCUMENTS 8,044,080 B2 * 10/2011 Shin ...................... C07C 229/22
514/378
2011/0071141 A1 3/2011 Murata et al.

FOREIGN PATENT DOCUMENTS

WO 2006090234 * 8/2006
WO 2006090234 A1 8/2006
WO 2009112275 A1 9/2009

OTHER PUBLICATIONS

International Search Report from corresponding PCT/EP2013/069893, mailed Apr. 4, 2014.
Gucma et al., "Synthesis and biological activity of 3-substituted isoxazolecarboxamides", Monatsh Chem (2010) 141: pp. 461-469.
Gucma e al., "Synthesis and fungicidal activity of substituted isoxazolecarboxamides", Pestycydy/Pesticides, 2010, (1-4), pp. 21-31.

* cited by examiner

*Primary Examiner* — D M Seaman
(74) *Attorney, Agent, or Firm* — McBee Moore Woodward & Vanik IP, LLC; Susan McBee; David Woodward

(57) ABSTRACT

The present invention relates to novel isoxazoline carboxamide derivatives, to processes for preparing these compounds, to compositions comprising these compounds, and to the use thereof as biologically active compounds, especially for control of harmful microorganisms in crop protection and in the protection of materials.

4 Claims, No Drawings

NITROGEN-CONTAINING HETEROCYCLIC COMPOUNDS FOR PLANT DISEASE CONTROL

CROSS REFERENCE TO RELATED APPLICATIONS

This application is a divisional application of Ser. No. 14/430,919 (filed Mar. 25, 2015), which is a §371 National Stage Application of PCT/EP2013/069893 (filed Sep. 25, 2013), which claims priority to EP 12186485.4 (filed Sep. 28, 2012), the contents of each of which are incorporated herein by reference in their entirety.

BACKGROUND

Field of the Invention

The present invention relates to novel isoxazoline carboxamide derivatives, to processes for preparing these compounds, to compositions comprising these compounds, and to the use thereof as biologically active compounds, especially for control of harmful microorganisms in crop protection and in the protection of materials.

Description of Related Art

It is already known that certain phenyl-substituted isoxazolecarboxamides have fungicidal properties (M. Gucma, W. M. Golebiewski, Monatsh. Chemie, 2010, 141, 461-469; M. Gucma, W. M. Golebiewski, A. Michalczyk, Pestycydy, 2011, 1-4, 21).

Since the ecological and economic demands made on modern active ingredients, for example fungicides, are increasing constantly, for example with respect to activity spectrum, toxicity, selectivity, application rate, formation of residues and favourable manufacture, and there can also be problems, for example, with resistances, there is a constant need to develop novel fungicidal compositions which have advantages over the known compositions at least in some areas.

SUMMARY

The present invention now provides novel quinoline-isoxazoline derivatives of formula (I)

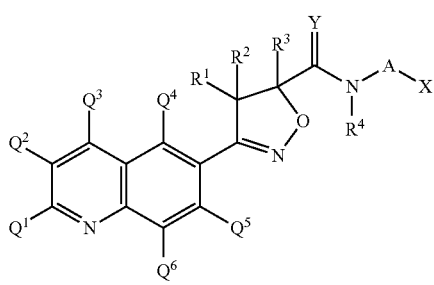

(I)

in which $R^1$ and $R^2$ independently of one another represent hydrogen; substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; cyano; isonitrile; nitro; halogen; substituted or non-substituted $C_1$-$C_8$-alkoxy; $C_1$-$C_8$-haloalkoxy; substituted or non-substituted $C_2$-$C_8$-alkenyloxy; $C_2$-$C_8$-haloalkenyloxy, substituted or non-substituted $C_2$-$C_8$-alkynyloxy; $C_1$-$C_8$-haloalkynyloxy; substituted or non-substituted $C_3$-$C_7$-cycloalkyl; substituted or non-substituted $C_1$-$C_8$-alkylsulfanyl; substituted or non-substituted $C_1$-$C_8$-alkylsulfonyl; substituted or non-substituted $C_1$-$C_8$-alkylsulfinyl; amino; substituted or non-substituted $C_1$-$C_8$-alkylamino; substituted or non-substituted di-$C_1$-$C_8$-alkylamino; substituted or non-substituted $C_1$-$C_8$-alkoxycarbonyl; substituted or non-substituted $C_1$-$C_8$-alkylcarbamoyl; substituted or non-substituted di-$C_1$-$C_8$-alkylcarbamoyl; or substituted or non-substituted N—$C_1$-$C_8$-alkyl-$C_1$-$C_8$-alkoxy-carbamoyl; or $R^1$ and $R^2$ can form together with the carbon atom to which they are attached a substituted or non-substituted $C_3$-$C_7$-cycloalkyl; or $C_3$-$C_7$-halocycloalkyl;

$R^3$ represents hydrogen; substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; cyano; isonitrile; nitro; halogen; substituted or non-substituted $C_1$-$C_8$-alkoxy; $C_1$-$C_8$-haloalkoxy; substituted or non-substituted $C_2$-$C_8$-alkenyloxy; $C_2$-$C_8$-haloalkenyloxy, substituted or non-substituted $C_2$-$C_8$-alkynyloxy; $C_1$-$C_8$-haloalkynyloxy; substituted or non-substituted $C_3$-$C_7$-cycloalkyl; substituted or non-substituted $C_1$-$C_8$-alkylsulfanyl; substituted or non-substituted $C_1$-$C_8$-alkylsulfonyl; substituted or non-substituted $C_1$-$C_8$-alkylsulfinyl; amino; substituted or non-substituted $C_1$-$C_8$-alkylamino; substituted or non-substituted di-$C_1$-$C_8$-alkylamino; substituted or non-substituted tri($C_1$-$C_8$) alkylsilyl-$C_1$-$C_8$-alkyl; substituted or non-substituted tri($C_1$-$C_8$)alkylsilyl-$C_2$-$C_8$-alkenyl; substituted or non-substituted tri($C_1$-$C_8$)alkylsilyl-$C_2$-$C_8$-alkynyl; substituted or non-substituted $C_1$-$C_8$-alkoxycarbonyl; substituted or non-substituted $C_1$-$C_8$-alkylcarbamoyl; substituted or non-substituted di-$C_1$-$C_8$-alkylcarbamoyl; or substituted or non-substituted N—$C_1$-$C_8$-alkyl-$C_1$-$C_8$-alkoxy-carbamoyl; substituted or non-substituted aryl; or substituted or non-substituted 5, 6 or 7 membered heterocycle ring with 1 to 3 heteroatoms; or $R^3$ together with $R^1$ or $R^2$ together with the carbon atoms to which they are attached can form a substituted or non-substituted $C_3$-$C_7$ cycloalkyl; $C_3$-$C_7$-halocycloalkyl; or a substituted or non-substituted saturated 5, 6 or 7 membered heterocycle Y represents an oxygen or sulfur atom, $Q^1$, $Q^2$, $Q^3$, $Q^4$, $Q^5$ and $Q^6$ independently of one another represent hydrogen; halogen; nitro; cyano; isonitrile; hydroxyl; amino; sulfanyl; pentafluoro-$\lambda^6$-sulfanyl; formyl; formyloxy; formylamino; substituted or non-substituted (hydroxyimino)-$C_1$-$C_8$-alkyl; substituted or non-substituted ($C_1$-$C_8$-alkoxyimino)-$C_1$-$C_8$-alkyl; substituted or non-substituted ($C_2$-$C_8$-alkenyloxyimino)-$C_1$-$C_8$-alkyl; substituted or non-substituted ($C_2$-$C_8$-alkynyloxyimino)-$C_1$-$C_8$-alkyl; substituted or non-substituted (benzyloxyimino)-$C_1$-$C_8$-alkyl; carboxy; carbamoyl; N-hydroxycarbamoyl; carbamate; substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; substituted or non-substituted $C_1$-$C_8$-alkoxy; $C_1$-$C_8$-haloalkoxy; substituted or non-substituted $C_1$-$C_8$-alkylsulfanyl; $C_1$-$C_8$-haloalkylsulfanyl; substituted or non-substituted $C_1$-$C_8$-alkylsulfinyl; $C_1$-$C_8$-haloalkylsulfinyl; substituted or non-substituted $C_1$-$C_8$-alkylsulfonyl; $C_1$-$C_8$-haloalkylsulfonyl; substituted or non-substituted $C_1$-$C_8$-alkylamino; substituted or non-substituted di-$C_1$-

$C_8$-alkylamino; substituted or non-substituted $C_2$-$C_8$-alkenyloxy; $C_2$-$C_8$-haloalkenyloxy; substituted or non-substituted $C_3$-$C_8$-alkynyloxy; $C_2$-$C_8$-haloalkynyloxy; substituted or non-substituted $C_3$-$C_7$-cycloalkyl; $C_3$-$C_7$-halocycloalkyl; substituted or non-substituted ($C_3$-$C_7$-cycloalkyl)-$C_1$-$C_8$-alkyl; substituted or non-substituted $C_4$-$C_7$-cycloalkenyl; $C_4$-$C_7$-halocycloalkenyl; substituted or non-substituted ($C_3$-$C_7$-cycloalkyl)-$C_2$-$C_8$-alkenyl; substituted or non-substituted ($C_3$-$C_7$-cycloalkyl)-$C_2$-$C_8$-alkynyl; substituted or non-substituted tri($C_1$-$C_8$)alkylsilyl; substituted or non-substituted tri($C_1$-$C_8$)alkylsilyl-$C_1$-$C_8$-alkyl; substituted or non-substituted tri($C_1$-$C_8$)alkylsilyl-$C_2$-$C_8$-alkenyl; substituted or non-substituted tri($C_1$-$C_8$)alkylsilyl-$C_2$-$C_8$-alkynyl; substituted or non-substituted $C_1$-$C_8$-alkylcarbonyl; $C_1$-$C_8$-haloalkylcarbonyl; substituted or non-substituted $C_1$-$C_8$-alkylcarbonyloxy; $C_1$-$C_8$-haloalkylcarbonyloxy; substituted or non-substituted $C_1$-$C_8$-alkylcarbonylamino; $C_1$-$C_8$-haloalkylcarbonylamino; substituted or non-substituted $C_1$-$C_8$-alkoxycarbonyl; $C_1$-$C_8$-haloalkoxycarbonyl; substituted or non-substituted $C_1$-$C_8$-alkyloxycarbonyloxy; $C_1$-$C_8$-haloalkoxycarbonyloxy; substituted or non-substituted $C_1$-$C_8$-alkylcarbamoyl; substituted or non-substituted di-$C_1$-$C_8$-alkylcarbamoyl; substituted or non-substituted $C_1$-$C_8$-alkylaminocarbonyloxy; substituted or non-substituted di-$C_1$-$C_8$-alkylaminocarbonyloxy; substituted or non-substituted N—($C_1$-$C_8$-alkyl)hydroxy carbamoyl; substituted or non-substituted $C_1$-$C_8$-alkoxycarbamoyl; substituted or non-substituted N—($C_1$-$C_8$-alkyl)-$C_1$-$C_8$-alkoxycarbamoyl; aryl which is optionally substituted by up to 6 identical or different groups $R^a$; $C_1$-$C_8$-arylalkyl which is optionally substituted by up to 6 identical or different groups $R^a$; $C_2$-$C_8$-arylalkenyl which is optionally substituted by up to 6 identical or different groups $R^a$; $C_2$-$C_8$-arylalkynyl which is optionally substituted by up to 6 identical or different groups $R^a$; aryloxy which is optionally substituted by up to 6 identical or different groups $R^a$; arylsulfanyl which is optionally substituted by up to 6 identical or different groups $R^a$; arylamino which is optionally substituted by up to 6 identical or different groups $R^a$; $C_1$-$C_8$-arylalkyloxy which is optionally substituted by up to 6 identical or different groups $R^a$; $C_1$-$C_8$-arylalkylsulfanyl which is optionally substituted by up to 6 identical or different groups $R^a$; $C_1$-$C_8$-arylalkylamino which is optionally substituted by up to 6 identical or different groups $R^a$; 5, 6 or 7 membered heterocycle with 1 to 3 heteroatoms which is optionally substituted by up to 4 identical or different groups $R^a$; wherein $R^a$ independently of one another represent halogen; cyano; nitro; substituted or non-substituted $C_1$-$C_8$-alkyl; $C_1$-$C_8$-haloalkyl; substituted or non-substituted $C_1$-$C_8$-alkoxy; $C_1$-$C_8$-haloalkoxy; substituted or non-substituted $C_1$-$C_8$-alkylsulfanyl; $C_1$-$C_8$-haloalkylsulfanyl; substituted or non-substituted tri($C_1$-$C_8$)alkylsilyl; substituted or non-substituted tri($C_1$-$C_8$)alkylsilyl-$C_1$-$C_8$-alkyl; substituted or non-substituted ($C_1$-$C_8$-alkoxyimino)-$C_1$-$C_8$-alkyl; or substituted or non-substituted (benzyloxyimino)-$C_1$-$C_8$-alkyl;

$R^4$ represents hydrogen, hydroxyl, cyano, substituted or non-substituted $C_1$-$C_8$-alkyl, substituted or non-substituted $C_2$-$C_8$-alkenyl; substituted or non-substituted $C_2$-$C_8$-alkynyl; substituted or non-substituted $C_3$-$C_7$-cycloalkyl, substituted or non-substituted $C_1$-$C_8$-alkoxy; substituted or non-substituted $C_2$-$C_8$-alkenyloxy; substituted or non-substituted $C_3$-$C_8$-alkynyloxy;

A represents a direct bond, O, S, $NR^5$, SO, $SO_2$ or a divalent linking group selected from $A^1$ to $A^6$

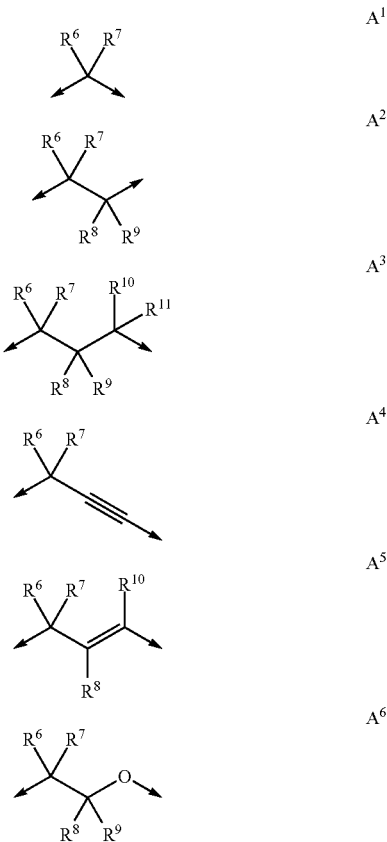

wherein $R^6$, $R^7$, $R^8$, $R^9$, $R^{10}$ or $R^{11}$ independently of one another represent hydrogen; substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; cyano; isonitrile; nitro; halogen; substituted or non-substituted $C_1$-$C_8$-alkoxy; $C_1$-$C_8$-haloalkoxy; substituted or non-substituted $C_2$-$C_8$-alkenyloxy; $C_2$-$C_8$-haloalkenyloxy, substituted or non-substituted $C_2$-$C_8$-alkynyloxy; $C_1$-$C_8$-haloalkynyloxy; substituted or non-substituted $C_3$-$C_7$-cycloalkyl; substituted or non-substituted $C_1$-$C_8$-alkylsulfanyl; substituted or non-substituted $C_1$-$C_8$-alkylsulfonyl; substituted or non-substituted $C_1$-$C_8$-alkylsulfinyl; amino; substituted or non-substituted $C_1$-$C_8$-alkylamino; substituted or non-substituted di-$C_1$-$C_8$-alkylamino; substituted or non-substituted $C_1$-$C_8$-alkoxycarbonyl; substituted or non-substituted $C_1$-$C_8$-alkylcarbamoyl; substituted or non-substituted di-$C_1$-$C_8$-alkylcarbamoyl; or substituted or non-substituted N—$C_1$-$C_8$-alkyl-$C_1$-$C_8$-alkoxy-carbamoyl; or $R^6$ and $R^7$ can form together with the carbon atom to which they are attached a substituted or non-substituted $C_3$-$C_7$-cycloalkyl; or $C_3$-$C_7$-halocycloalkyl; or $R^8$ and $R^9$ can form together with the carbon atom to which they are attached a substituted or non-substituted $C_3$-$C_7$-cycloalkyl; or $C_3$-$C_7$-halocycloalkyl; or $R^{10}$ and $R^{11}$ can form together with the carbon atom to which they are attached a substituted or non-substituted $C_3$-$C_7$-cycloalkyl; or $C_3$-$C_7$-halocycloalkyl; or $R^{13}$ represents hydrogen, substituted or non-substituted $C_1$-$C_8$-alkyl, $C_1$-$C_8$-haloalkyl; substituted or non-substituted $C_2$-$C_8$-alkenyl; substituted or non-substituted $C_2$-$C_8$-alkynyl; substituted or non-substituted $C_3$-$C_7$-cycloalkyl, substituted or non-substituted $C_1$-$C_8$-alkoxy; substituted or non-substituted $C_2$-$C_8$-alkenyloxy; substituted or non-substituted $C_3$-$C_8$-alkynyloxy;

X represents represent hydrogen; halogen; nitro; cyano; isonitrile; hydroxyl; amino; sulfanyl; pentafluoro-$\lambda^6$-sulfanyl; formyl; formyloxy; formylamino; substituted or non-substituted (hydroxyimino)-$C_1$-$C_8$-alkyl; substituted or non-substituted ($C_1$-$C_8$-alkoxyimino)-$C_1$-$C_8$-alkyl; substituted or non-substituted ($C_2$-$C_8$-alkenyloxyimino)-$C_1$-$C_8$-alkyl; substituted or non-substituted ($C_2$-$C_8$-alkynyloxyimino)-$C_1$-$C_8$-alkyl; substituted or non-substituted (benzyloxyimino)-$C_1$-$C_8$-alkyl; carboxy; carbamoyl; N-hydroxycarbamoyl; carbamate; substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; substituted or non-substituted $C_1$-$C_8$-alkoxy; $C_1$-$C_8$-haloalkoxy; substituted or non-substituted $C_1$-$C_8$-alkylsulfanyl; $C_1$-$C_8$-haloalkylsulfanyl; substituted or non-substituted $C_1$-$C_8$-alkylsulfinyl; $C_1$-$C_8$-haloalkylsulfinyl; substituted or non-substituted $C_1$-$C_8$-alkylsulfonyl; $C_1$-$C_8$-haloalkylsulfonyl; substituted or non-substituted $C_1$-$C_8$-alkylamino; substituted or non-substituted di-$C_1$-$C_8$-alkylamino; substituted or non-substituted $C_2$-$C_8$-alkenyloxy; $C_2$-$C_8$-haloalkenyloxy; substituted or non-substituted $C_3$-$C_8$-alkynyloxy; $C_2$-$C_8$-haloalkynyloxy; substituted or non-substituted $C_3$-$C_7$-cycloalkyl; $C_3$-$C_7$-halocycloalkyl; substituted or non-substituted ($C_3$-$C_7$-cycloalkyl)-$C_1$-$C_8$-alkyl; substituted or non-substituted $C_4$-$C_7$-cycloalkenyl; $C_4$-$C_7$-halocycloalkenyl; substituted or non-substituted ($C_3$-$C_7$-cycloalkyl)-$C_2$-$C_8$-alkenyl; substituted or non-substituted ($C_3$-$C_7$-cycloalkyl)-$C_2$-$C_8$-alkynyl; substituted or non-substituted tri($C_1$-$C_8$)alkylsilyl; substituted or non-substituted tri($C_1$-$C_8$)alkylsilyl-$C_1$-$C_8$-alkyl; substituted or non-substituted tri($C_1$-$C_8$)alkylsilyl-$C_2$-$C_8$-alkenyl; substituted or non-substituted tri($C_1$-$C_8$)alkylsilyl-$C_2$-$C_8$-alkynyl; substituted or non-substituted $C_1$-$C_8$-alkylcarbonyl; $C_1$-$C_8$-haloalkylcarbonyl; substituted or non-substituted $C_1$-$C_8$-alkylcarbonyloxy; $C_1$-$C_8$-haloalkylcarbonyloxy; substituted or non-substituted $C_1$-$C_8$-alkylcarbonylamino; $C_1$-$C_8$-haloalkylcarbonylamino; substituted or non-substituted $C_1$-$C_8$-alkoxycarbonyl; $C_1$-$C_8$-haloalkoxycarbonyl; substituted or non-substituted $C_1$-$C_8$-alkylcarbonyloxy; $C_1$-$C_8$-haloalkoxycarbonyloxy; substituted or non-substituted $C_1$-$C_8$-alkylcarbamoyl; substituted or non-substituted di-$C_1$-$C_8$-alkylcarbamoyl; substituted or non-substituted $C_1$-$C_8$-alkylaminocarbonyloxy; substituted or non-substituted di-$C_1$-$C_8$-alkylaminocarbonyloxy; substituted or non-substituted N—($C_1$-$C_8$-alkyl)hydroxy carbamoyl; substituted or non-substituted $C_1$-$C_8$-alkoxycarbamoyl; substituted or non-substituted N—($C_1$-$C_8$-alkyl)-$C_1$-$C_8$-alkoxycarbamoyl; aryl which is optionally substituted by up to 6 identical or different groups $R^b$; $C_1$-$C_8$-arylalkyl which is optionally substituted by up to 6 identical or different groups $R^b$; $C_2$-$C_8$-arylalkenyl which is optionally substituted by up to 6 identical or different groups $R^b$; $C_2$-$C_8$-arylalkynyl which is optionally substituted by up to 6 identical or different groups $R^b$; aryloxy which is optionally substituted by up to 6 identical or different groups $R^b$; arylsulfanyl which is optionally substituted by up to 6 identical or different groups $R^b$; arylamino which is optionally substituted by up to 6 identical or different groups $R^b$; $C_1$-$C_8$-arylalkyloxy which is optionally substituted by up to 6 identical or different groups $R^b$; $C_1$-$C_8$-arylalkylsulfanyl which is optionally substituted by up to 6 identical or different groups $R^b$; $C_1$-$C_8$-arylalkylamino which is optionally substituted by up to 6 identical or different groups $R^b$; 5 or 6 member heterocycle with 1 to 3 heteroatoms which is optionally substituted by up to 4 identical or different groups $R^b$;

wherein $R^b$ independently of one another represent halogen; cyano; nitro; substituted or non-substituted $C_1$-$C_8$-alkyl; $C_1$-$C_8$-haloalkyl; substituted or non-substituted $C_1$-$C_8$-alkoxy; $C_1$-$C_8$-haloalkoxy; substituted or non-substituted $C_1$-$C_8$-alkylsulfanyl; $C_1$-$C_8$-haloalkylsulfanyl; substituted or non-substituted tri($C_1$-$C_8$)alkylsilyl; substituted or non-substituted tri($C_1$-$C_8$)alkylsilyl-$C_1$-$C_8$-alkyl; substituted or non-substituted ($C_1$-$C_8$-alkoxyimino)-$C_1$-$C_8$-alkyl; or substituted or non-substituted (benzyloxyimino)-$C_1$-$C_8$-alkyl; substituted or non-substituted 5, 6 or 7 membered heterocycle with 1 to 3 heteroatoms; or two $R^b$ together can form together with the carbon atoms to which they are attached a substituted or non-substituted 5, 6 or 7 membered heterocycle; or a substituted or non-substituted 5 or 6 membered carbocycle;

or $R^4$ together with A and X can form together with the nitrogen to which A and $R^4$ are attached a substituted or non-substituted 5, 6 or 7 membered heterocycle;

and its salts or N-oxides.

DETAILED DESCRIPTION OF A PREFERRED EMBODIMENT

The salts or N-oxides of the quinoline-isoxazoline derivatives of formula (I) also have fungicidal properties.

The formula (I) provides a general definition of the quinoline-isoxazoline derivatives according to the invention. Preferred radical definitions for the formulae shown above and below are given below. These definitions apply to the end products of the formula (I) and likewise to all intermediates.

$R^1$ and $R^2$ preferably independently of one another represent hydrogen; halogen; substituted or non-substituted $C_1$-$C_8$-alkyl; $C_1$-$C_8$-haloalkyl; substituted or non-substituted $C_1$-$C_8$-alkoxy; or $R^1$ and $R^2$ preferably can form together with the carbon atom to which they are attached a substituted or non-substituted $C_3$-$C_7$-cycloalkyl.

$R^1$ and $R^2$ particularly preferably independently of one another represent hydrogen; bromine; methyl; trifluoromethyl; or methoxy; or $R^1$ and $R^2$ particularly preferably can form together with the carbon atom to which they are attached a substituted or non-substituted cyclopropyl.

$R^1$ and $R^2$ particularly preferably both represent hydrogen or one of $R^1$ and $R^2$ represents hydrogen and the other one of $R^1$ and $R^2$ represents methyl.

$R^3$ preferably represents hydrogen; substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; cyano; halogen; substituted or non-substituted $C_1$-$C_8$-alkoxy; substituted or non-substituted $C_3$-$C_7$-cycloalkyl; substituted or non-substituted $C_1$-$C_8$-alkylsulfanyl; substituted or non-substituted tri($C_1$-$C_8$)alkylsilyl-$C_1$-$C_8$-alkyl; substituted or non-substituted $C_1$-$C_8$-alkoxycarbonyl; substituted or non-substituted aryl; or $R^3$ together with $R^1$ or $R^2$ together with the carbon atoms to which they are attached preferably can form a substituted or non-substituted $C_3$-$C_7$ cycloalkyl; $C_3$-$C_7$-halocycloalkyl; or a substituted or non-substituted saturated 5, 6 or 7 membered heterocycle.

$R^3$ particularly preferably represents hydrogen; halogen; substituted or non-substituted $C_1$-$C_4$-alkyl; $C_1$-$C_4$-haloalkyl; substituted or non-substituted $C_2$-$C_8$-alkenyl; substituted or non-substituted $C_2$-$C_8$-alkynyl; substituted or non-substituted $C_1$-$C_4$-alkoxy; substituted or non-substituted $C_3$-$C_7$-cycloalkyl; substituted or non-substituted aryl; or $R^3$ together with $R^1$ or $R^2$ together with the carbon atoms to which they are attached particularly preferably can form a substituted or non-substituted $C_3$-$C_7$ cycloalkyl; or a substituted or non-substituted saturated 5, 6 or 7 membered heterocycle.

$R^3$ very particularly preferably represents hydrogen; methyl; ethyl; isopropyl; n-butyl; fluoromethyl; chloromethyl; bromomethyl; difluormethyl; trifluoromethyl; chlorodifluoromethyl; 1-hydroxyethyl; benzyl; cyclopropyl; methoxy; vinyl; ethynyl; phenyl; or $R^3$ together with $R^1$ or $R^2$ together with the carbon atoms to which they are attached very particularly preferably can form a substituted or non-substituted 3, 5 or 6 membered carbocyclic ring; a 5 or 6 membered heterocyclic ring having one oxygen atom.

For $R^3$ substituted $C_1$-$C_8$-alkyl or $C_1$-$C_4$-alkyl preferably includes such alkyl substituted by one or more hydroxyl, aryl or cycloalkyl, in particular by hydroxyl, phenyl or cyclopropyl.

Y preferably represents an oxygen atom.

Y also preferably represents a sulfur atom.

$Q^1$, $Q^2$ and $Q^3$ preferably independently of one another represent hydrogen; halogen; cyano; nitro; amino; substituted or non-substituted $C_1$-$C_8$-alkyl; $C_1$-$C_8$-haloalkyl; $C_1$-$C_8$-cyanoalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; substituted or non-substituted $C_3$-$C_7$-cycloalkyl; substituted or non-substituted $C_1$-$C_8$-alkoxy; $C_1$-$C_8$-haloalkoxy; substituted or non-substituted $C_1$-$C_8$-alkylsulfanyl; substituted or non-substituted $C_1$-$C_8$-alkylsulfinyl; substituted or non-substituted $C_1$-$C_8$-alkylsulfonyl; substituted or non-substituted $C_1$-$C_8$-alkylamino; substituted or non-substituted tri($C_1$-$C_8$)alkylsilyl-$C_2$-$C_8$-alkynyl; aryl which is optionally substituted by up to 6 identical or different groups $R^a$; 5, 6 or 7 membered heterocycle with 1 to 3 heteroatoms which is optionally substituted by up to 4 identical or different groups $R^a$;

wherein $R^a$ independently of one another represent halogen; substituted or non-substituted $C_1$-$C_8$-alkyl; $C_1$-$C_8$-haloalkyl; substituted or non-substituted $C_1$-$C_8$-alkoxy; $C_1$-$C_8$-haloalkoxy; substituted or non-substituted tri($C_1$-$C_8$)alkylsilyl; substituted or non-substituted tri($C_1$-$C_8$)alkylsilyl-$C_1$-$C_8$-alkyl;

$Q^1$, $Q^2$ and $Q^3$ particularly preferably independently of one another represent hydrogen; halogen; substituted or non-substituted $C_1$-$C_4$-alkyl; $C_1$-$C_4$-haloalkyl; $C_1$-$C_4$-cyanoalkyl; substituted or non-substituted $C_2$-$C_8$-alkynyl; substituted or non-substituted $C_1$-$C_4$-alkoxy; substituted or non-substituted $C_1$-$C_4$-alkylsulfanyl; substituted or non-substituted $C_1$-$C_4$-alkylsulfinyl; substituted or non-substituted $C_1$-$C_4$-alkylsulfonyl; substituted or non-substituted tri($C_1$-$C_4$)alkylsilyl-$C_2$-$C_4$-alkynyl;

$Q^1$, $Q^2$ and $Q^3$ very particularly preferably independently of one another represent fluorine; chlorine, bromine, iodine; cyano; cyanomethyl; methyl; ethyl; n-, isopropyl; n-, iso-, sec-, tert-butyl; trifluoromethyl; dichlorofluoromethyl; chlorodifluoromethyl; 2,2,2-trifluoroethyl; 2-chloro-2,2-difluoroethyl; 2,2-dichloro-2-fluoroethyl; methoxy; ethoxy; n-, isopropoxy; n-, iso-, sec-, tert-butoxy; methylsulfanyl; ethylsulfanyl; n-propylsulfanyl; methylsulfinyl; ethylsulfinyl; methylsulfonyl; ethylsulfonyl; ethynyl; trimethylsilylethynyl; phenyl; 2-thienyl; 5-pyrimidinyl;

$Q^1$, $Q^2$ and $Q^3$ in particularly preferred embodiments independently of one another represent hydrogen; fluorine; chlorine, bromine, iodine; cyano; cyanomethyl; methyl; ethylmethoxy; ethoxy; methylsulfanyl; propylsulfanyl; methylsulfinyl; methylsulfonyl; ethynyl; trimethylsilylethynyl; phenyl; 2-thienyl; 5-pyrimidinyl;

$Q^1$, $Q^2$ and $Q^3$ in very particularly preferred embodiments independently of one another represent hydrogen; chlorine, bromine, iodine; or ethynyl;

Preferably at least one of $Q^1$, $Q^2$ and $Q^3$ represent hydrogen.

In preferred embodiments of formula (I) $Q^3$ represents hydrogen and at least one of $Q^1$ or $Q^2$ does not represent hydrogen.

In particularly preferred embodiments of formula (I) $Q^3$ represents hydrogen and $Q^2$ does not represent hydrogen.

In very particularly preferred embodiments of formula (I) $Q^3$ and $Q^1$ represents hydrogen and $Q^2$ does not represent hydrogen.

In other very particularly preferred embodiments of formula (I) $Q^3$ represents hydrogen and $Q^2$ and $Q^1$ do not represent hydrogen.

$Q^4$, $Q^5$ and $Q^6$ preferably independently of one another represent hydrogen; halogen; substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; or substituted or non-substituted $C_1$-$C_8$-alkoxy.

$Q^4$, $Q^5$ and $Q^6$ particularly preferably independently of one another represent hydrogen; halogen; substituted or non-substituted $C_1$-$C_8$-alkyl; or substituted or non-substituted $C_1$-$C_8$-alkoxy.

$Q^4$, $Q^5$ and $Q^6$ very particularly preferably independently of one another represent hydrogen; fluorine; methyl; or methoxy.

In preferred embodiments of formula (I) $Q^4$ represents hydrogen and at least one of $Q^5$ or $Q^6$ does not represent hydrogen.

In particularly preferred embodiments of formula (I) $Q^4$ represents hydrogen and $Q^5$ and $Q^6$ do not represent hydrogen.

$R^4$ preferably represents hydrogen, hydroxyl, substituted or non-substituted $C_1$-$C_8$-alkyl; or substituted or non-substituted $C_1$-$C_8$-alkoxy.

$R^4$ particularly preferably represents hydrogen; hydroxyl; or methyl.

$R^4$ very particularly preferably represents hydrogen.

$R^4$ moreover preferably together with A and X can form together with the nitrogen to which A and $R^4$ are attached a 5, 6 or 7 membered heterocycle;

$R^4$ moreover particularly preferably together with A and X can form together with the nitrogen to which A and $R^4$ are attached a 5, 6 or 7 membered saturated heterocycle;

$R^4$ moreover particularly preferably together with A and X can form together with the nitrogen to which A and $R^4$ are attached a 5, 6 or 7 membered saturated heterocycle comprising at least one nitrogen and one oxygen atom;

A preferably represents a direct bond or a divalent linking group selected from $A^1$ to $A^6$; wherein $R^6$, $R^7$, $R^8$, $R^9$, $R^{10}$ or $R^{11}$ independently of one another represent hydrogen; or substituted or non-substituted $C_1$-$C_8$-alkyl.

A particularly preferably represents a direct bond or a divalent linking group selected from $A^1$, $A^2$ $A^3$ or $A^4$; wherein
$R^6$, $R^7$, $R^8$, $R^9$, $R^{10}$ or $R^{11}$ independently of one another represent hydrogen; or substituted or non-substituted $C_1$-$C_8$-alkyl.

A very particularly preferably represents a direct bond or a divalent linking group selected from $A^1$, $A^3$ or $A^4$; wherein
$R^6$ and $R^7$ independently of one another represent hydrogen; or methyl;
$R^8$, $R^9$, $R^{10}$ or R" represent hydrogen.

In particularly preferred embodiments of formula (I) A represents a direct bond.

In other particularly preferred embodiments of formula (I) A represents a methylene group —$CH_2$—(divalent linking group $A^1$ wherein $R^6$ and $R^7$ both represent hydrogen).

In other particularly preferred embodiments of formula (I) A represents a n-propylene group —$(CH_2)_3$— (divalent linking group $A^3$ wherein $R^6$, $R^7$, $R^8$, $R^9$, $R^{10}$, $R^{11}$ all represent hydrogen).

In other particularly preferred embodiments of formula (I) A represents a dimethylmethylene group —$C(CH_3)_2$— (divalent linking group $A^1$ wherein $R^6$ and $R^7$ both represent methyl).

In other particularly preferred embodiments of formula (I) A represents the divalent linking group $A^4$-I or $A^4$-II.

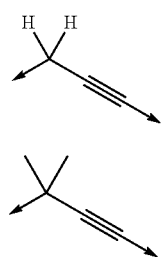

X preferably represents hydrogen; substituted or non-substituted $C_1$-$C_8$-alkyl; substituted or non-substituted $C_2$-$C_8$-alkynyl; substituted or non-substituted $C_1$-$C_8$-alkoxy; substituted or non-substituted $C_3$-$C_7$-cycloalkyl; substituted or non-substituted tri($C_1$-$C_8$)alkylsilyl; substituted or non-substituted tri($C_1$-$C_8$)alkylsilyl-$C_1$-$C_8$-alkyl; aryl which is optionally substituted by up to 6 identical or different groups $R^b$; 5 or 6 member heterocycle with 1 to 3 heteroatoms which is optionally substituted by up to 4 identical or different groups $R^b$;
wherein
$R^b$ independently of one another represent halogen; cyano; nitro; substituted or non-substituted $C_1$-$C_8$-alkyl; $C_1$-$C_8$-haloalkyl; substituted or non-substituted $C_1$-$C_8$-alkoxy; $C_1$-$C_8$-haloalkoxy; substituted or non-substituted $C_1$-$C_8$-alkylsulfanyl; $C_1$-$C_8$-haloalkylsulfanyl; substituted or non-substituted tri($C_1$-$C_8$)alkylsilyl; substituted or non-substituted tri($C_1$-$C_8$)alkylsilyl-$C_1$-$C_8$-alkyl; substituted or non-substituted ($C_1$-$C_8$-alkoxyimino)-$C_1$-$C_8$-alkyl; or substituted or non-substituted (benzyloxyimino)-$C_1$-$C_8$-alkyl; a substituted or non-substituted 5, 6 or 7 membered heterocycle with 1 to 3 heteroatoms; or
two $R^b$ together can form together with the carbon atoms to which they are attached a substituted or non-substituted 5, 6 or 7 membered heterocycle; or a substituted or non-substituted 5 or 6 membered carbocycle.

X particularly preferably represents hydrogen; substituted or non-substituted $C_1$-$C_8$-alkyl; substituted or non-substituted $C_1$-$C_8$-alkoxy; substituted or non-substituted $C_3$-$C_7$-cycloalkyl; phenyl which is optionally substituted by up to 6 identical or different groups $R^b$; a substituted or non-substituted 5 or 6 membered heterocycle with 1 to 3 heteroatoms which is optionally substituted by up to 4 identical or different groups $R^b$;
wherein
$R^b$ independently of one another represent halogen; substituted or non-substituted $C_1$-$C_8$-alkyl; $C_1$-$C_8$-haloalkyl; substituted or non-substituted $C_1$-$C_8$-alkoxy; $C_1$-$C_8$-haloalkoxy; a substituted or non-substituted 5, 6 or 7 membered heterocycle with 1 to 3 heteroatoms; or
two $R^b$ together can form together with the carbon atoms to which they are attached a substituted or non-substituted 5 or 6 membered heterocycle; or a substituted or non-substituted unsaturated 6 membered aromatic carbocycle.

X very particularly preferably represents hydrogen; substituted or non-substituted $C_1$-$C_8$-alkyl; substituted or non-substituted $C_1$-$C_8$-alkoxy; substituted or non-substituted $C_3$-$C_7$-cycloalkyl; phenyl which is optionally substituted by up to 6 identical or different groups $R^b$; pyrazolyl which is optionally substituted by up to 4 identical or different groups $R^b$; pyridinyl which is optionally substituted by up to 4 identical or different groups $R^b$;
wherein
$R^b$ independently of one another represent halogen; substituted or non-substituted $C_1$-$C_8$-alkyl; $C_1$-$C_8$-haloalkyl; substituted or non-substituted $C_1$-$C_8$-alkoxy; $C_1$-$C_8$-haloalkoxy; a substituted or non-substituted 5, 6 or 7 membered heterocycle with 1 to 3 heteroatoms; or
two $R^b$ together can form together with the carbon atoms to which they are attached a substituted or non-substituted 5 or 6 membered heterocycle; or a substituted or non-substituted unsaturated 6 membered aromatic carbocycle.

In particularly preferred embodiments of formula (I) A and X together represent one selected from

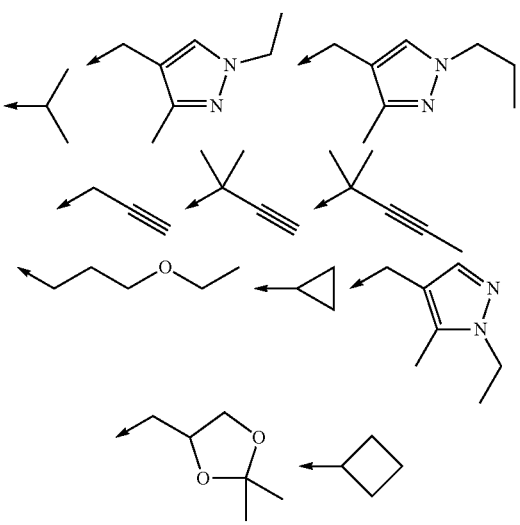

In very particularly preferred embodiments of formula (I) A and X together represent one selected from

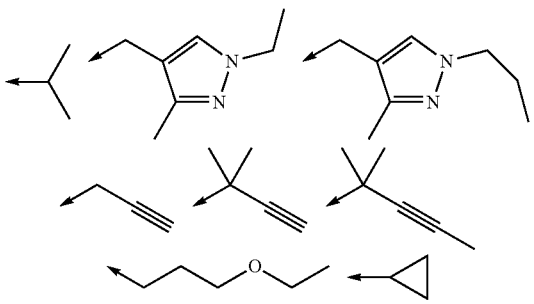

In another very particularly preferred embodiments of formula (I) A and X together represent one selected from

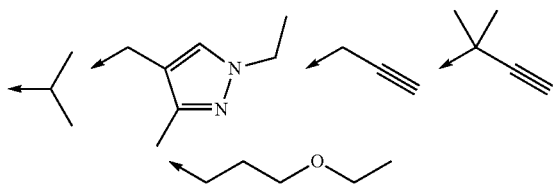

In another very particularly preferred embodiments of formula (I) A and X together represent one selected from

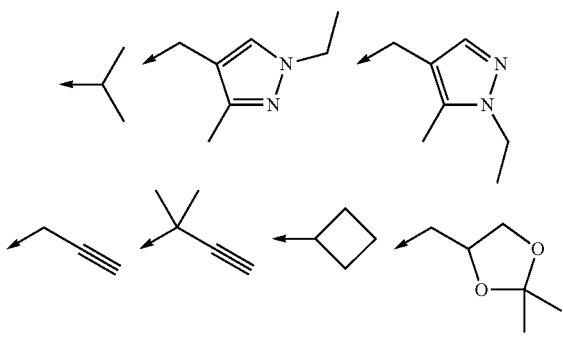

Finally, it has been found that the novel quinoline-isoxazoline derivatives of the formula (I) have very good microbicidal properties and can be used for controlling harmful microorganisms both in crop protection and in the protection of materials.

The radical definitions and explanations given above in general terms or stated within preferred ranges can, however, also be combined with one another as desired, i.e. including between the particular ranges and preferred ranges. They apply both to the end products and correspondingly to precursors and intermediates. In addition, individual definitions may not apply.

Preference is given to those compounds of the formula (I) in which each of the radicals have the abovementioned preferred definitions.

Particular preference is given to those compounds of the formula (I) in which each of the radicals have the abovementioned more preferred definitions.

Very particular preference is given to those compounds of the formula (I) in which each of the radicals have the abovementioned most preferred definitions.

In the definitions of the symbols given in the above formulae, collective terms were used which are generally representative of the following substituents:

The definition $C_1$-$C_8$-alkyl comprises the largest range defined here for an alkyl radical. Specifically, this definition comprises the meanings methyl, ethyl, n-, isopropyl, n-, iso-, sec-, tert-butyl, and also in each case all isomeric pentyls, hexyls, heptyls and octyls, such as methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, n-heptyl, 1-methylhexyl, 1-ethylpentyl, 2-ethylpentyl, 1-propylbutyl, octyl, 1-methylheptyl, 2-methylheptyl, 1-ethylhexyl, 2-ethylhexyl, 1-propylpentyl and 2-propylpentyl, in particular propyl, 1-methylethyl, butyl, 1-methylbutyl, 2-methylbutyl, 3-methylbutyl, 1,1-dimethylethyl, 1,2-dimethylbutyl, 1,3-dimethylbutyl, pentyl, 1-methylbutyl, 1-ethylpropyl, hexyl, 3-methylpentyl, heptyl, 1-methylhexyl, 1-ethyl-3-methylbutyl, 1-methylheptyl, 1,2-dimethylhexyl, 1,3-dimethyloctyl, 4-methyloctyl, 1,2,2,3-tetramethylbutyl, 1,3,3-trimethylbutyl, 1,2,3-trimethylbutyl, 1,3-dimethylpentyl, 1,3-dimethylhexyl, 5-methyl-3-hexyl, 2-methyl-4-heptyl and 1-methyl-2-cyclopropylethyl. A preferred range is $C_1$-$C_4$-alkyl, such as methyl, ethyl, n-, isopropyl, n-, iso-, sec-, tert-butyl.

The definition halogen comprises fluorine, chlorine, bromine and iodine.

Halogen-substituted alkyl-referred to as $C_1$-$C_8$-haloalkyl—represents, for example, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl.

The definition tri($C_1$-$C_8$)alkylsilyl preferably represents the following radicals: $SiMe_3$, $SiMe_2Et$, $SiMe_2CHMe_2$, $SiMe_2CH_2CHMe_2$, $SiMe_2CH_2CMe_3$, $SiMe_2CMe_3$, $SiMe_2CH_2CH_2Me$.

The definition $C_2$-$C_8$-alkenyl comprises the largest range defined here for an alkenyl radical. Specifically, this definition comprises the meanings ethenyl, n-, isopropenyl, n-, iso-, sec-, tert-butenyl, and also in each case all isomeric pentenyls, hexenyls, heptenyls, octenyls, 1-methyl-1-propenyl, 1-ethyl-1-butenyl, 2,4-dimethyl-1-pentenyl, 2,4-dimethyl-2-pentenyl.

The definition $C_2$-$C_8$-alkynyl comprises the largest range defined here for an alkynyl radical. Specifically, this definition comprises the meanings ethynyl, n-, isopropynyl, n-, iso-, sec-, tert-butynyl, and also in each case all isomeric pentynyls, hexynyls, heptynyls, octynyls.

The definition $C_3$-$C_7$-cycloalkyl comprises monocyclic saturated hydrocarbyl groups having 3 to 7 carbon ring members, such as cyclopropyl, cyclobutyl, cyclopentyl, cyclohexyl and cycloheptyl.

The definition aryl comprises unsubstituted or substituted, aromatic, mono-, bi- or tricyclic ring, for example phenyl, naphthyl, anthracenyl (anthryl), phenanthracenyl (phenanthryl).

The definition heterocycle comprises unsubstituted or substituted, unsaturated heterocyclic 5- to 7-membered ring containing up to 4, preferably 1 to 3 heteroatoms selected from N, O and S: for example 2-furyl, 3-furyl, 2-thienyl, 3-thienyl, 2-pyrrolyl, 3-pyrrolyl, 1-pyrrolyl, 3-pyrazolyl, 4-pyrazolyl, 5-pyrazolyl, 1-pyrazolyl, 1H-imidazol-2-yl, 1H-imidazol-4-yl, 1H-imidazol-5-yl, 1H-imidazol-1-yl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 1H-1,2,3-triazol-1- yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-3-yl, 1H-1,2,4-triazol-5-yl, 1H-1,2,4-triazol-1-yl, 4H-1,2,4-triazol-3-yl, 4H-1,2,4-triazol-4-yl, 1H-tetrazol-1-yl, 1H-tetrazol-5-yl, 2H-tetrazol-2-yl, 2H-tetrazol-5-yl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 1,2,3-oxadiazol-4-yl, 1,2,3-oxadiazol-5-yl, 1,2,3-thiadiazol-4-yl, 1,2,3-thiadiazol-5-yl, 1,2,5-oxadiazol-3-yl, 1,2,5-thiadiazol-3-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,4-triazin-6-yl.

The definition heterocycle also comprises unsubstituted or substituted, saturated heterocyclic 5- to 7-membered ring containing up to 4, preferably 1 to 3 heteroatoms selected from N, O and S: for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydroopyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothiopyranyl, 3-hexahydropyridazinyl, 4-hexahy-dropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl.

The definition saturated heterocycle comprises unsubstituted or substituted, heterocyclic 5- to 7-membered ring containing up to 4, preferably 1 to 3 heteroatoms selected from N, O and S: for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2-piperidinyl, 3-piperidinyl, piperidinyl, 4-piperidinyl, 1,3-dioxan-5-yl, 2-tetrahydropyranyl, 4-tetrahydropyranyl, 2-tetrahydrothiopyranyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl, 1,2,4-hexahydrotriazin-3-yl, 2-tetrahydro-1,4-oxazinyl and 3-tetrahydro-1,4-oxazinyl.

Optionally substituted radicals may be mono- or polysubstituted, where in the case of polysubstitution, the substituents may be identical or different. Thus, the definition dialkylamino also embraces an amino group which is substituted asymmetrically by alkyl, such as, for example, methylethylamino.

Halogen-substituted radicals, such as, for example, haloalkyl are mono- or polyhalogenated. In the case of polyhalogenation, the halogen atoms may be identical or different. Preferably such halogen-substituted radicals have 1 to 9 identical or different halogen atoms. Here, halogen represents fluorine, chlorine, bromine and iodine, in particular fluorine, chlorine and bromine.

Unless indicated otherwise, a group or a substituent which is substituted according to the invention preferably can be substituted by one or more group(s) selected from the list consisting of halogen; nitro; hydroxyl; cyano; amino; sulfanyl; pentafluoro-$X^6$-sulfanyl; formyl; formyloxy; formylamino; carbamoyl; N-hydroxycarbamoyl; carbamate; (hydroxyimino)-$C_1$-$C_6$-alkyl; $C_1$-$C_8$-alkyl; tri($C_1$-$C_8$-alkyl)silyl-$C_1$-$C_8$-alkyl; $C_1$-$C_8$-cycloalkyl; tri($C_1$-$C_8$-alkyl)silyl-$C_1$-$C_8$-cyclo alkyl; $C_1$-$C_8$-halogenoalkyl; $C_1$-$C_8$-halogenocycloalkyl; $C_2$-$C_8$-alkenyl; $C_2$-$C_8$-alkynyl; $C_2$-$C_8$-alkenyloxy; $C_2$-$C_8$-alkynyloxy; $C_1$-$C_8$-alkylamino; di-$C_1$-$C_8$-alkylamino; $C_1$-$C_8$-alkoxy; $C_1$-$C_8$-halogenoalkoxy; $C_1$-$C_8$-alkylsulfanyl; $C_1$-$C_8$-halogenoalkylsulfanyl; $C_2$-$C_8$-alkenyloxy; $C_2$-$C_8$-halogenoalkenyloxy; $C_3$-$C_8$-alkynyloxy; $C_3$-$C_8$-halogenoalkynyloxy; $C_1$-$C_8$-alkylcarbonyl; $C_1$-$C_8$-halogenoalkylcarbonyl; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxyarbamoyl; N—$C_1$-$C_8$-alkyl-$C_1$-$C_8$-alkoxycarbamoyl; $C_1$-$C_8$-alkoxycarbonyl; $C_1$-$C_8$-halogenoalkoxycarbonyl; $C_1$-$C_8$-alkylcarbonyloxy; $C_1$-$C_8$-halogenoalkylcarbonyloxy; $C_1$-$C_8$-alkylcarbonylamino; $C_1$-$C_8$-halogenoalkylcarbonylamino; $C_1$-$C_8$-alkylaminocarbonyloxy; di-$C_1$-$C_8$-alkylaminocarbonyloxy; $C_1$-$C_8$-alkyloxycarbonyloxy; $C_1$-$C_8$-alkylsulfinyl; $C_1$-$C_8$-halogenoalkylsulfinyl; $C_1$-$C_8$-alkylsulfonyl; $C_1$-$C_8$-halogenoalkylsulfonyl; $C_1$-$C_8$-alkylaminosulfamoyl; di-$C_1$-$C_8$-alkylaminosulfamoyl; ($C_1$-$C_6$-alkoxyimino)-$C_1$-$C_6$-alkyl; ($C_1$-$C_6$-alkenyloxyimino)-$C_1$-$C_6$-alkyl; ($C_1$-$C_6$-alkynyloxyimino)-$C_1$-$C_6$-alkyl; 2-oxopyrrolidin-1-yl; (benzyloxyimino)-$C_1$-$C_6$-alkyl; $C_1$-$C_8$-alkoxyalkyl; $C_1$-$C_8$-halogenoalkoxyalkyl; benzyloxy; benzylsulfanyl; benzylamino; phenoxy; phenylsulfanyl; or phenylamino.

Unless indicated otherwise, a group or a substituent which is substituted according to the invention preferably can be substituted by one or more group(s) selected from the list consisting of halogen; hydroxyl; nitro, cyano, $C_1$-$C_8$-alkyl; $C_1$-$C_4$-haloalkyl having 1 to 9 identical or different halogen atoms; $C_1$-$C_8$-alkoxy; $C_1$-$C_4$-haloalkoxy having 1 to 9 identical or different halogen atoms; $C_1$-$C_8$-alkylsulfanyl; $C_1$-$C_4$-haloalkylsulfanyl having 1 to 9 identical or different halogen atoms; $C_1$-$C_8$-alkylsulfonyl; $C_1$-$C_4$-haloalkylsulfonyl having 1 to 9 identical or different halogen atoms; $C_2$-$C_8$-alkenyl; $C_2$-$C_8$-alkynyl; $C_3$-$C_7$-cycloalkyl; phenyl; tri($C_1$-$C_8$)alkylsilyl; tri($C_1$-$C_8$)alkylsilyl-$C_1$-$C_8$-alkyl.

The groups defined for X can additionally or alternatively be substituted by one or more group(s) selected from substituted or non-substituted aryl; or substituted or non-substituted 5, 6 or 7 member heterocycle with 1 to 3 heteroatoms:

If appropriate, the compounds according to the invention can be present as mixtures of different possible isomeric forms, in particular of stereoisomers, such as, for example, E and Z, threo and erythro, and also optical isomers, and, if appropriate, also of tautomers. What is claimed are both the E and the Z isomers, and also the threo and erythro, and the optical isomers, any mixtures of these isomers, and the possible tautomeric forms.

If appropriate, the compounds of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions) and to the mixtures of all the possible stereoisomers, in all proportions. The diastereoisomers and/or the optical isomers can be separated according to the methods which are known per se by the man ordinary skilled in the art.

If appropriate, the compounds of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

If appropriate, the compounds of the present invention can also exist in one or more geometric isomer forms depending on the relative position (syn/anti or cis/trans) of the substituents of ring B. The invention thus relates equally to all syn/anti (or cis/trans) isomers and to all possible syn/anti (or cis/trans) mixtures, in all proportions. The syn/anti (or cis/trans) isomers can be separated according to general methods, which are known per se by the man ordinary skilled in the art.

Illustration of the Processes and Intermediates

The compounds of the formula (I) can be prepared in different ways. First of all, the possible processes are shown schematically below. Unless indicated otherwise, the radicals specified are each as defined above. Unless otherwise indicated for all the following schemes, $(Q)_n$ represents the substitutents $Q^1$, $Q^2$, $Q^3$, $Q^4$, $Q^5$ and $Q^6$, for which independent from each other the aforementioned definitions apply. Preferred radical definitions for the formulae and schemes below have already been given above. These definitions apply not only to the end products of the formula (I) but likewise to all intermediates.

Compounds of the formula (I) according to the invention can be synthesised according to Process 1 depicted in Scheme 1. $U^1$ represents a leaving group selected in the list consisting of a halogen atom, a hydroxyl group, —$OR^A$, —$OC(=O)R^A$, $R^A$ being a substituted or non-substituted $C_1$-$C_6$-alkyl, a substituted or non-substituted $C_1$-$C_6$-haloalkyl, a benzyl, 4-methoxybenzyl or a pentafluorophenyl group.

Scheme 1: Process 1

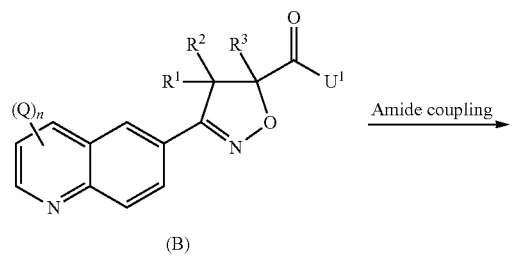

(B)

Amide coupling

-continued

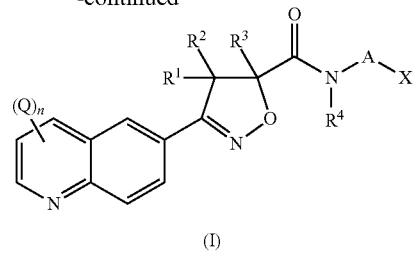

(I)

In case $U^1$ represents a hydroxy group, Process 1 according to the present invention is conducted in the presence of condensing agent. The condensing agent for the amide formation can be for example a carbodiimide like N,N'-diethyl, N,N'-dipropyl, N,N'-diisopropyl, N,N'-dicyclohexylcarbodiimide (DCC), N-[3-(dimethylamino)propyl]-N'-ethylcarbodiimide hydrochloride (EDC), or N,N'-carbonyldiimidazol, or 1,2-oxazolium compounds like 2-ethyl-5-phenyl-1,2-oxazolium-3-sulfate or 2-tert.-butyl-5-methyl-isoxazolium-perchlorate or acylamino compounds like 2-ethoxy-1-ethoxycarbonyl-1,2-dihydrochinolin, or isobutylchloroformiate, 2,4,6-tripropyl-1,3,5,2,4,6-trioxatriphosphinane 2,4,6-trioxide, diethyl phosphorocyanidoate, bis-(2-oxazolidinyl)-phosphoryl chloride, (1H-benzotriazol-1-yloxy)[tris(dimethylamino)]phosphonium hexafluorophosphate, (1H-benzotriazol-1-yloxy)(tripyrrolidin-1-yl)phosphonium hexafluorophosphate (PyBOP), N-[(1H-benzotriazol-1-yloxy)(dimethylamino)methylidene]-N-methylmethanaminium tetrafluoroborate (TBTU), N-[(1H-benzotriazol-1-yloxy)(dimethylamino)methylidene]-N-methylmethanaminium hexafluorophosphate (HBTU), N-{(dimethylamino)[(2-oxopyridin-1(2H)-yl)oxy]methylidene}-N-methylmethanaminium tetrafluoroborate (TPTU), N-[(dimethylamino)(3H-[1,2,3]triazolo[4,5-b]pyridin-3-yloxy)methylidene]-N-methylmethanaminium hexafluorophosphate (HATU) or 1-[bis(dimethylamino)methylidene]-5-chloro-1H-benzotriazol-1-ium 3-oxide tetrafluoroborate (TCTU), if needed in combination with other derivative like 1H-benzotriazol-1-ol (HOBt), propanephosphonic anhydride (T3P) or N-hydroxysuccinimide (HOSu). The condensation can be conducted in the presence of a catalyst. Suitable catalyst may be selected in the list consisting of N,N-dimethylpyridin-4-amine, 1-hydroxy-benzotriazole or N,N-dimethylformamide.

In case $U^1$ represents a halogen atom, Process 1 according to the present invention is conducted in the presence of an acid binder. Suitable acid binders are in each case all inorganic and organic bases that are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as caesium carbonate, sodium carbonate, potassium carbonate, potassium bicarbonate, sodium bicarbonate, alkali metal or alkaline earth metal acetates, such as sodium acetate, potassium acetate, calcium acetate and also tertiary amines, such as trimethylamine, triethylamine, diisopropylethylamine, tributylamine, N,N-dimethylaniline, pyridine, N-methylpiperidine, N,N-dimethylpyridin-4-amine, diazabicyclooctane (DABCO), diazabicyclo-nonene (DBN) or diazabicycloundecene (DBU).

It is also possible to work in the absence of an additional condensing agent or to employ an excess of the amine component, so that it simultaneously acts as acid binder agent.

Suitable solvents for carrying out Process 1 according to the invention can be customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone, or hexamethylphosphoric triamide; alcohols such as methanol, ethanol, propanol, iso-propanol; esters, such as methyl acetate or ethyl acetate, sulfoxides, such as dimethyl sulfoxide, or sulfones, such as sulfolane.

When carrying out Process 1 according to the invention, the amine derivative can be employed as its salt, such as chlorhydrate or any other convenient salt.

When carrying out Process 1 according to the invention, 1 mole or an excess of the amine derivative and from 1 to 3 moles of the acid binder can be employed per mole of the reagent of formula (B).

It is also possible to employ the reaction components in other ratios. Work-up is carried out by known methods.

Process 1 according to the invention is carried out in general in a temperature from −20° C. to +60° C., preferentially 0° C. to +40° C. The reaction can be carried out at normal, high or low pressure (for example from 0.5 to 5 bar). In general the reaction is carried out at normal pressure.

It is also possible to obtain the compounds of formula (I) by direct conversion (Process 2) of ester (II-Me) as shown in Scheme 2.

Scheme 2: Process 2

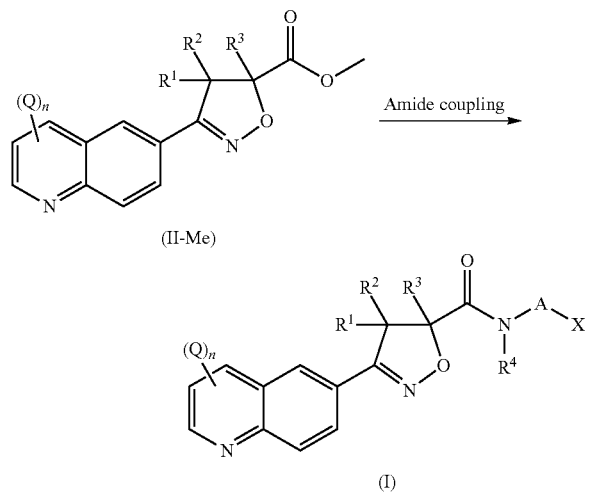

(II-Me)

(I)

Suitable activating reagents for this transformation have been described in the literature (MgBr$_2$, MgCl$_2$Z. Guo et al. Tetrahedron Lett. 2001, 42, 1843; AlMe3, Woodward et al Tetrahedron Lett. 2006, 47, 5767, Tetrahedron Lett. 2008, 49, 5687) under reflux or micro wave irradiation (S. Woodward et al. Tetrahedron Lett. 2008, 49, 5687).

As described, amides are directly prepared by treating esters with amines in presence of trialkylaluminium in an inert solvent. The trialkylaluminium can be for example triethylaluminium, triisobutylaluminium, trimethylaluminium, tripropylaluminium, tri-tert-butylaluminum, tributylaluminum. Trimethylaluminium is preferred.

The organic solvents for direct amidation are ether like diethylether, tetrahydrofurane, dioxane or glycoldimethylether or other solvent like toluene or dichloromethane. Tetrahydrofurane and toluene are preferred solvents.

This step is carried out in general in a temperature range from 0° C. to boiling point, preferentially boiling point. The reaction can be carried out at normal, high or low pressure (for example from 0.5 to 5 bar). In general the reaction is carried out at normal pressure.

The amidation can also be carried out under micro wave irradiation.

Compounds (B), for which $U^1$ represents a hydroxyl group (represented by formula (II-H) in Scheme 2A) can be obtained by saponification of the corresponding ester analogues, e.g. methyl esters according to formula (II-Me) (Scheme 2A). Such saponifications are typically carried out in a suitable solvent in the presence of base or acid as described in R. Larock, C., Comprehensive Organic Transformations: A Guide to Functional Group Preparations, 2nd Ed., Wiley-VCH, New York, 1999. Typical solvents are, for example, methanol, ethanol, tetrahydrofuran, toluene and water, as well as their binary and ternary mixtures. Typical bases are, for example, alkali metal hydroxides such as sodium hydroxide, alkali metal carbonates, such as sodium carbonate or potassium carbonate.

Scheme 2A: Process 2A

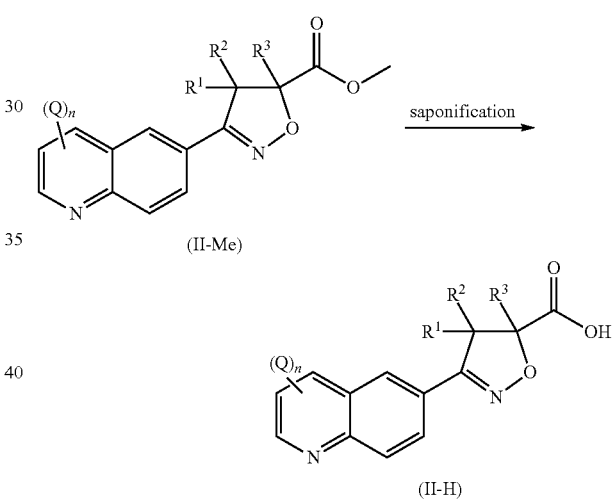

Further modification of compounds of formula (I) can be achieved by transition metal catalysed reactions as depicted in Scheme 3 using for example tributyl(vinyl)tin and a palladium catalyst as described in WO 2011/154240 or via Heck coupling using different olefins and an appropriate palladium catalyst, e.g. Pd(OAc)$_2$ in DMF at elevated temperature see also WO 2011/22216. The olefins obtained are further reacted with differently substituted oxime chloride via [3+2] cycloaddition to the corresponding isoxazolines. For the introduction of carbon bonded substituents in the quinoline ring, such as alkyl, alkenyl, alkynyl, cycloalkyl or aryl substituents (aryl including heteroaryl substituents bonded via carbon to the quinolone ring), a halide, preferably an iodide can be also substituted via a Suzuki coupling using a boronic acid (Tetrahedron, 2011, 67, 4689) or boroxine in DMF and a base as described in WO 2011/154240. The iodide was reacted via Sonogashira coupling with acetylenes, following Tetrahedron Lett., 1999, 40, 4379. These acetylenes are reacted via [3+2] with oxime chlorides as described in US 2007/105904. All reactions are working with the respective halides such as iodide, bromide or chloride in 3-position of the quinoline, but also with the halide in 2-, 4-, 5-, 7- and 8-position of which many are commercially available or described in literature. If not available, the iodide can, amongst other methods known to the man skilled in the art, be made from the corresponding hydroxyl-quinoline via the triflate (Synthesis, 2005, 547), e.g. utilising cobalt catalysis (Synlett, 2006, 881).

Scheme 3: Process 3

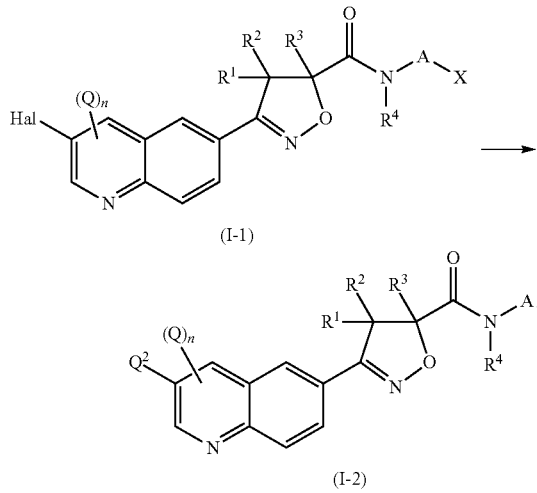

For Scheme 3, $(Q)_n$ represents the substitutents $Q^1$, $Q^3$, $Q^4$, $Q^5$ and $Q^6$, for which independent from each other the aforementioned definitions apply. For Scheme 3, Hal represents Cl, Br or I and $Q^2$ represents carbon bonded substituents in the quinoline ring, such as alkyl, alkenyl, alkynyl, cycloalkyl or aryl substituents (aryl including heteroaryl substituents bonded via carbon to the quinoline ring).

Furthermore, functionalisation at $Q^2$ can also be achieved by introduction of a heteroatom via strong nucleophils, e.g. MeOH or alkyl thiolates, as described for example in WO 2011/144444 (Scheme 4). Iodides (I-1), wherein Hal is represented by Cl, Br or I, can be further reacted under palladium catalysis with heterocycles such as pyrazoles (Angew. Chem. Int. Ed., 2006, 45, 6523; Angew. Chem., 2006, 118, 6673).

Scheme 4: Process 4

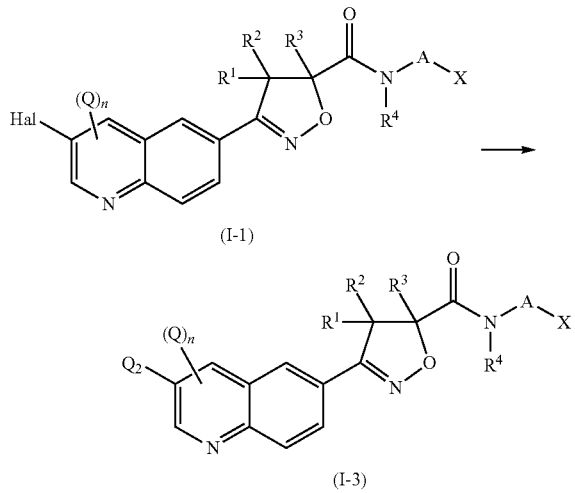

For Scheme 4, $(Q)_n$ represents the substitutents $Q^1$, $Q^3$, $Q^4$, $Q^5$ and $Q^6$, for which independent from each other the aforementioned definitions apply. For Scheme 4, Hal represents Cl, Br or I and $Q^2$ represents hetero atom bonded substituents in the quinoline ring, such as alkoxy, alkylsulfanyl, alkylamino or heterocyclic substituents bonded via hetero atom to the quinoline ring.

The invention further relates to thioamides (I-4) of formula (I), which can be obtained from their amide precursors (I-5) of formula (I) (Scheme 5).

Scheme 5: Process 5

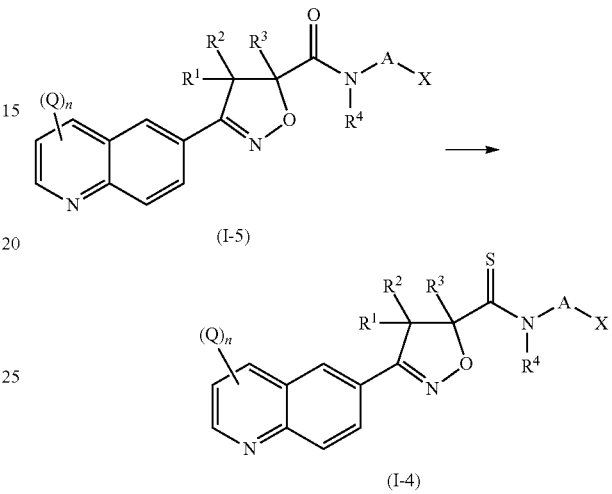

Suitable thionating agents according to Process 5 of the invention can be sulphur (S), sulfhydric acid ($H_2S$), sodium sulfide ($Na_2S$), sodium hydrosulfide (NaHS), boron trisulfide ($B_2S_3$), bis(diethylaluminium) sulfide [$(AlEt_2)_2S$], ammonium sulfide [$(NH_4)_2S$], phosphorous pentasulfide ($P_2S_5$), Lawesson's reagent [2,4-bis(4-methoxyphenyl)-1,2,3,4-dithiadiphosphetane 2,4-disulfide] or a polymer-supported thionating reagent (cf. J. Chem. Soc. Perkin 1, 2001, 358), in the optionally presence of a catalytic or stoichiometric or excess amount, quantity of a base such as an inorganic and organic base. Preference is given to using alkali metal carbonates, such as sodium carbonate, potassium carbonate, potassium bicarbonate, sodium bicarbonate; heterocyclic aromatic bases, such as pyridine, picoline, lutidine, collidine; and also tertiary amines, such as trimethylamine, triethylamine, tributylamine, N,N-dimethylaniline, N,N-dimethylpyridin-4-amine or N-methyl-piperidine. Suitable solvents for carrying out this process according to the invention can be customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin, chlorobenzene, dichlorobenzene, dichloromethane, chloroform, carbon tetrachloride, dichlorethane or trichlorethane, ethers, such as diethyl ether, diisopropyl ether, methyl t-butyl ether, methyl t-amyl ether, dioxane, tetrahydrofuran, 1,2-dimethoxyethane or 1,2-diethoxyethane, nitriles, such as acetonitrile, propionitrile, n- or i-butyronitrile or benzonitrile, sulfurous solvents, such as sulfolane or carbon disulfide.

When carrying out this process according to the invention, 1 mole or an excess of the sulfur equivalent of the thionating agent and from 1 to 3 moles of the base can be employed per mole of the amide reactant (I-4).

It is also possible to employ the reaction components in other ratios. Work-up is carried out by known methods.

Compound (II-Me) according to the invention can be prepared by 1,3-dipolar cycloaddition (Scheme 6).

Scheme 6: Process 6

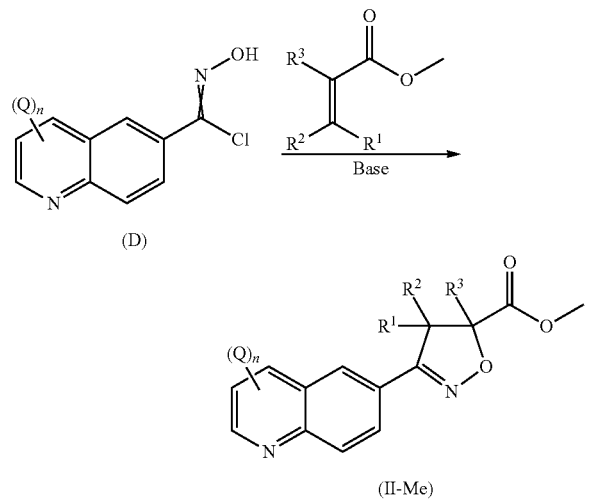

The 1,3-dipolar cycloaddition of oxido azanylidyne acrylate compounds are described in several reviews: 1,3 dipolar Cycloaddition Chemistry, Padwa, ed. Wiley, New-York, 1984; Kanemasa and Tsuge, Heterocycles 1990, 30, 719. The reactions are typically carried out in a solvent in the optional presence of base.

Isoxazoles that are substituted in either $R^1$ or $R^2$ as well as $R^3$ can be obtained by 1,3-dipolar cycloaddtion using a suitably 1,2-disubstituted olefin as dipolarphile. Often, diostereomeric mixtures are obtained from this cycloaddition. The diastereoisomers can be separated using chromatography. Chiral molecules can be obtained from chiral HPLC as well as enantioselective reactions, e.g. enzymatic ester hydrolysis, amide hydrolysis, or chiral cycloaddition as described by Olssen (J. Org. Chem, 1988, 53, 2468.)

As detailed in Scheme 7, commercially available 2-(bromomethyl)acrylic acid methyl ester can be converted to 2-(alkoxymethyl)acrylic acid methyl esters under basic conditions. These 2-(alkoxymethyl)acrylic acid methyl esters will undergo 1,3-dipolar cycloaddition with chloroximes such as (D) (or their respective nitriloxides).

Analogously, thioethers are accessible. These can be further oxidized to give their respective sulfoxides and sulfones.

Diverse 2-alkylacrylic acid methyl esters can be obtained by reacting 2-(bromomethyl)acrylic acid methyl ester with organometallic reagents. Such transformations have been described by Metzger, A.; Piller, F. M.; Knochel, P. Chem. Commun., 2008, 44, 5824) and in WO 2006/33551.

Scheme 7: Process 7

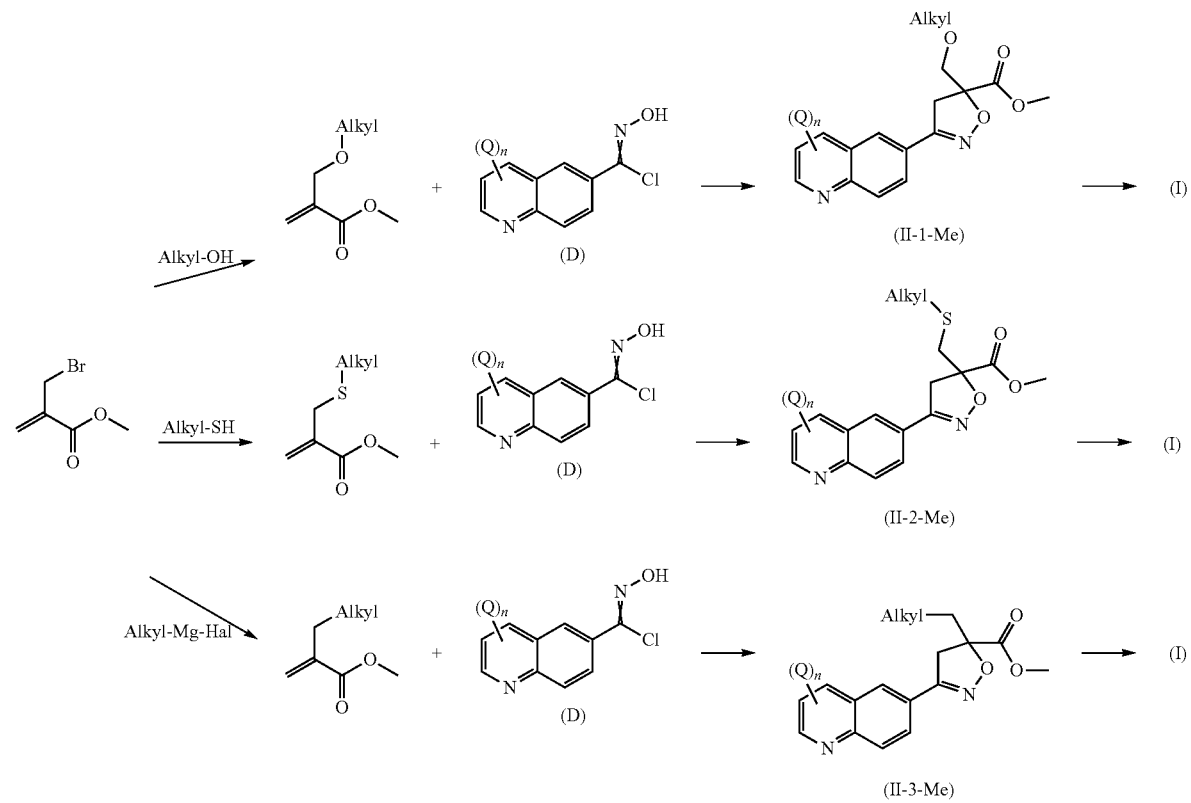

Substances, according to the invention, that bear a cyano group in $R^3$, can be synthesised by using adequate cyanoacrylates, e.g. ethyl-2-cyanoacrylate. For the synthesis of IV or $R^2$ and $R^3$ disubstituted substances according to the invention, adequately substituted crotonic acid esters can be used. These may either be commercially available, or can be synthesised. Such syntheses are described by Birkofer, L.; Hempel, K. Chem. Ber., 1963, 96, 1373; Tanoury, G. J.; Chen, M.; Dong, Y.; Forslund, R. E.; Magdziak, D.; Org. Lett., 2008, 10, 185.

For those substances, that bear a vinyl group or difluoromethyl group in $R^3$, syntheses are described in Scheme 8. As such, commercially available methyl 2-(hydroxymethyl) prop-2-enoate is reacted with chloroximes (D) to provide isoxazoline derivatives (C-4) (J. Med. Chem., 1999, 42, 2760). Upon oxidation and subsequent Wittig reaction, analogues (C-6) can be obtained. Similarly, upon oxidation and subsequent treatment with a fluorinating agent such as diethylaminosulfur trifluoride, the difluoromethyl analogues (C-5) can be obtained (U.S. Pat. No. 4,092,310).

Scheme 8A: Process 8A

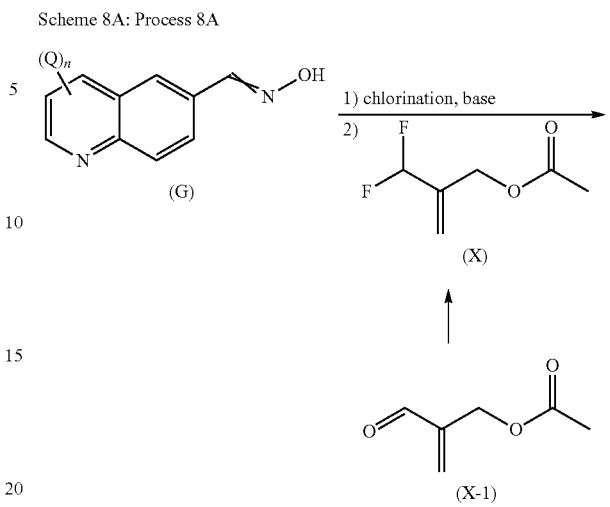

Scheme 8: Process 8

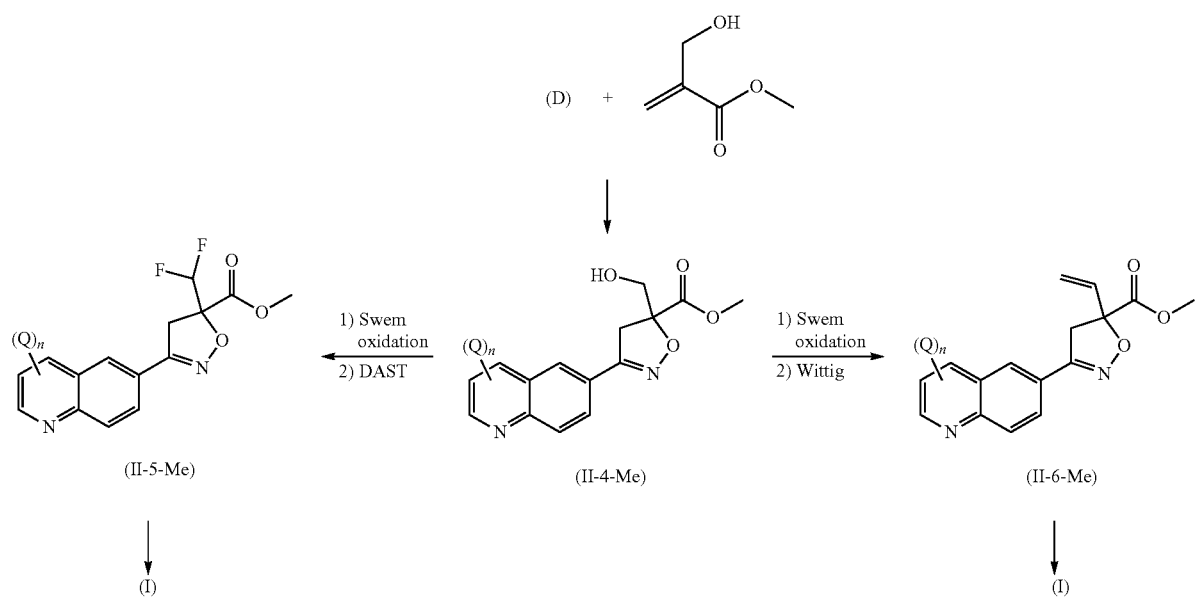

Alternatively to the process shown in Scheme 8, those compounds bearing a difluoromethyl group in $R^3$ can be prepared according to Scheme 8A. Thus, oxime (G) is chlorinated (for example with N-chlorosuccinimide) and reacted with protected difluromethy allylalcohol (X) (prepared from aldehyde (X-1) which is known from Chem. Commun., 2009, 1956) to provide isoxazoline (III-Ac). Upon hydrolytic deprotection to afford alcohol (III-H) and subsequent oxidation, acid derivative (II-H) can be obtained and reacted further to give compounds according to formula (I). It is known to the man skilled in the art that the oxidation of a primary alcohol such as (III-H) to a carboxylic acid (II-H) passes through an aldehyde intermediate (not shown in Scheme 8A).

-continued

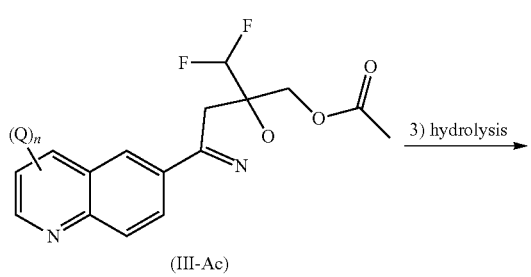

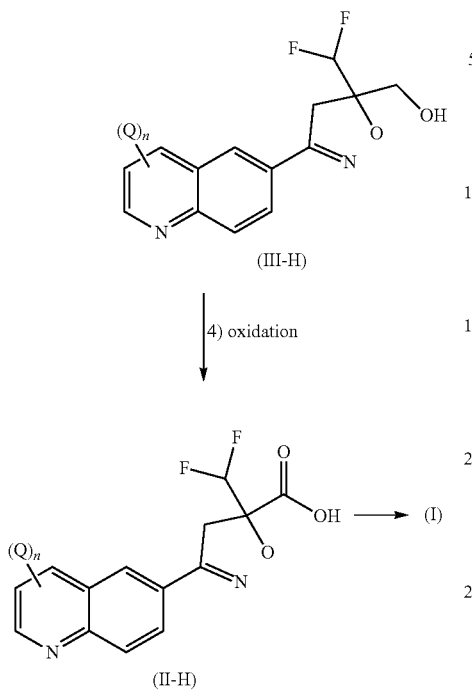

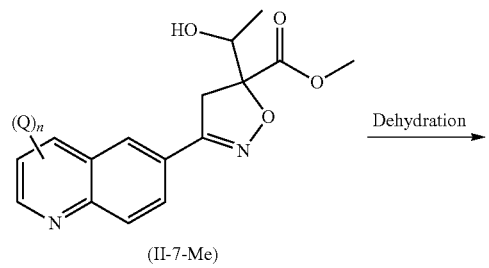

As a further alternative to the process shown in Scheme 8, those compounds bearing a vinyl group in $R^3$ can be prepared according to Scheme 8B. Thus, hydroxyethyl isoxazolines (II-7-Me) can be further treated to obtain vinyl substituted isoxazoline (II-Me) as shown in Scheme 8B. Amongst others, a common strategy for this formal dehydration would be the transformation of the hydroxyl group into a leaving group. Appropriate known leaving groups would encompass for example methanesulfonyloxy (OMs), para-toluenesulfonyloxy (OTs) and trifluoromethanesulfonyloxy (OTf). Likewise, the transformation of the hydroxyl group of (II-7-Me) into a halogen (see for example *Synthesis*, 2011, 342) and subsequent base induced elimination are a further possible option. The respective intermediates from the introduction of the leaving group or halogenation can either be isolated or further reacted without isolation of the intermediates. Suitable bases for inducing the elimination reaction are generically described below. These can be either single bases or combination of two and more bases if required.

Scheme 8B: Process 8B

In order to obtain compounds according to the invention for which $R^3$ comprises an acetylene group, commercially available methyl 3-hydroxy-2-methylidenebutanoate is reacted with chloroximes (D) to provide isoxazoline derivatives (II-7-Me) (Scheme 9). The hydroxyethyl isoxazolines (II-7-Me) can be further treated to furnish the acetylene isoxazolines (II-8-Me) as described by Shi et al. (J. Am. Chem. Soc., 2011, 133, 14944).

Scheme 9: Process 9

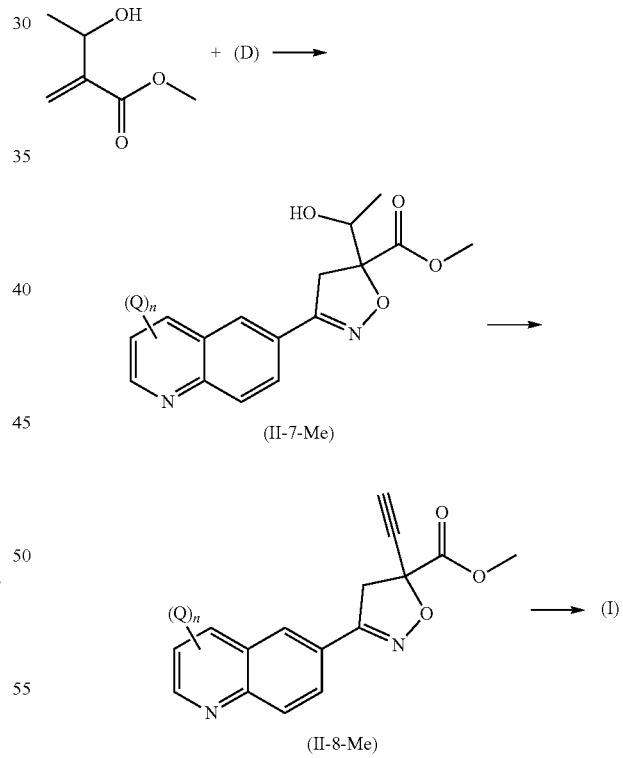

In addition to the transformation described in Scheme 6, 1,3-dipolar cycloaddition between the carboximidoyl chloride (D) and acrylamide derivatives (E) in analogy to what has been previously described in by Toker and co-workers in J. Org. Chem., 2005, 70, 7810 are also a way to furnish the compounds of formula (I) (Scheme 10).

Scheme 10: Process 10

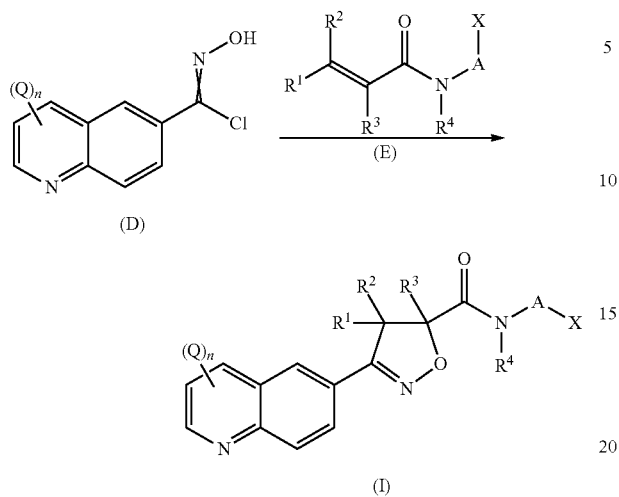

For the activation of acrylic acid derivatives (F), one can employ carbodiimides such as EDCI (Chen, F. M. F.; Benoiton, N. L. Synthesis 1979, 709). For the synthesis of acrylamides (E), see U.S. Pat. No. 2,521,902, JP-A 60112746, Journal of Polymer Science 1979, 17, 1655 (Scheme 11).

Scheme 11: Process 11

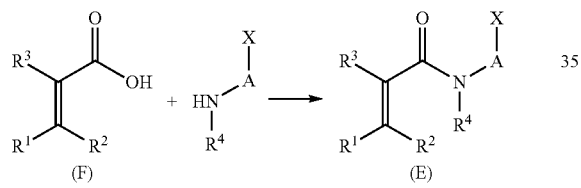

The chloroximes (D) described in Scheme 6 are accessible from their oxime precursors (G) (Scheme 12). Thus, oximes (G) can be treated with chlorination agents such as NCS in a suitable solvent to furnish chloroximes (D).

Scheme 12: Process 12

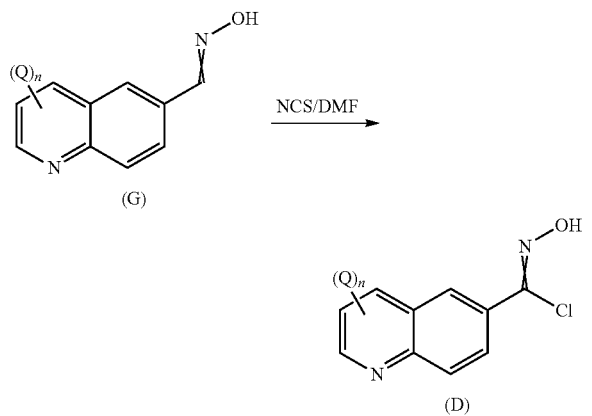

According to the process in Scheme 13 the oximes (G) can be obtained from their carbaldehyde precursors (H) as described in the literature (Scheme 13).

Scheme 13: Process 13

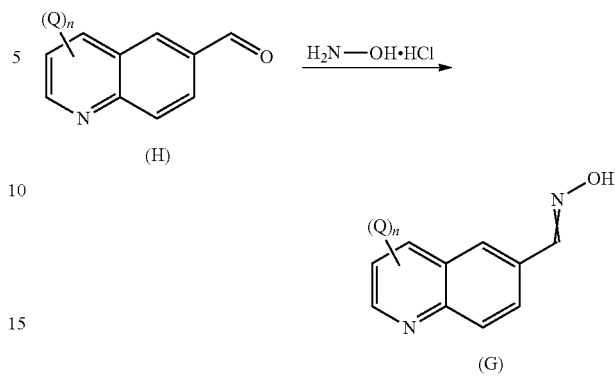

Aldehydes (H) are accessible by a number of routes:
Thus according to Scheme 14, 6-cyanoquinolines (J) can be reduced following the conditions described in Khimiya Geterotsiklicheskikh Soedinenii, 1975, 10, 1364, in close analogy to conditions described in Justus Liebigs Annalen der Chemie, 1966, 699, 98 or by other methods known to the man skilled in the art.

Scheme 14: Process 14

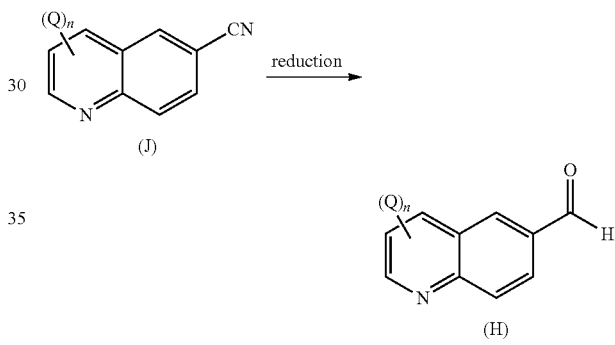

Furthermore, 6-haloquinolines (K), where X denotes a halide atom (Br, I) can be carbonylated to furnish compounds (H) (Scheme 15). The reactions are carried out in a suitable solvent, in the presence of base and a suitable transition metal catalyst, preferably palladium (US-A 2006/4046). Alternatively the 6-hydroxy-quinoline can be reacted to the triflate (Synthesis, 2005, 547), which than is further carbonylated via palladium catalysis (WO 2005/75439, Bioorg. Med. Chem. Lett., 2011, 21, 2264).

Scheme 15: Process 15

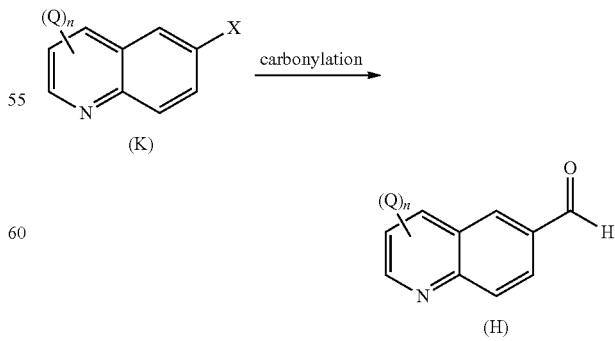

X = Br, I

Similarly, quinoline carbaldehyde derivatives (H) can be accessed by transition metal catalysed carbonylation of the corresponding 6-hydroxyquinolin analogues (L) as depicted in Scheme 16, where OL denotes a leaving group such as trifluoromethylsulfonate (OTf), para-toluenesulfonate (OTs) or methanesulfonate (OMs). The reactions are carried out in a suitable solvent, in the presence of base and a suitable transition metal catalyst, preferably palladium (WO 2005/75439; WO 2012/3145194; Synthesis, 1996, 470).

Scheme 16: Process 16

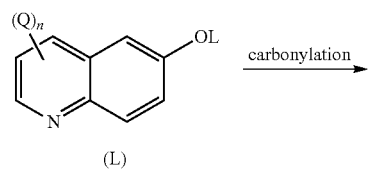

As shown in Scheme 17, the substituted ($Q^1$, $Q^3$, $Q^4$, $Q^5$ and/or $Q^6$) quinoline carbaldehyde derivates (H) are prepared from the respective methyl quinoline derivatives (M) by oxidation with selenium dioxide as described in the literature (Chemistry-A European Journal, 2009, 15, 10144.) and then halogenate in position $Q^2$ with the corresponding halogen or succinimide (e.g. NCS=N-chlorosuccinimide; NIS=N-iodosuccinimide) as describe in literature to give (H-1), (H-2) or (H-3) (WO 2005/040124). These reactions are carried out in a suitable solvent.

For Scheme 17, (Q)$_n$ represents the substitutents $Q^1$, $Q^3$, $Q^4$, $Q^5$ and $Q^6$, for which independent from each other the aforementioned definitions apply and in formulae (M) and (H) $Q^2$ represents H.

$Q^1$, $Q^3$ substituted 6-methylquinolines (M-1) and (M-2) are obtained by oxidation of quinoline derivatives (M) with 3-chloroperoxybenzoic acid, hydrogen peroxide, or trioxirane, in a suitable solvent. Preferred solvents are dichloromethane, chloroform, acetic acid or water. 3-Chloroperoxybenzoic acid is the preferred oxidising agent. Then the reaction of anhydrous quinoline-N-oxide (N) with the adequate reactant (e.g. phosphoryl trichloride) with or without solvent provides a mixture of both isomers (M-1) and (M-2), which can be isolated by chromatography (Tetrahedron, 2005, 61, 9042) (Scheme 18Error! Reference source not found.).

Scheme 18: Process 18

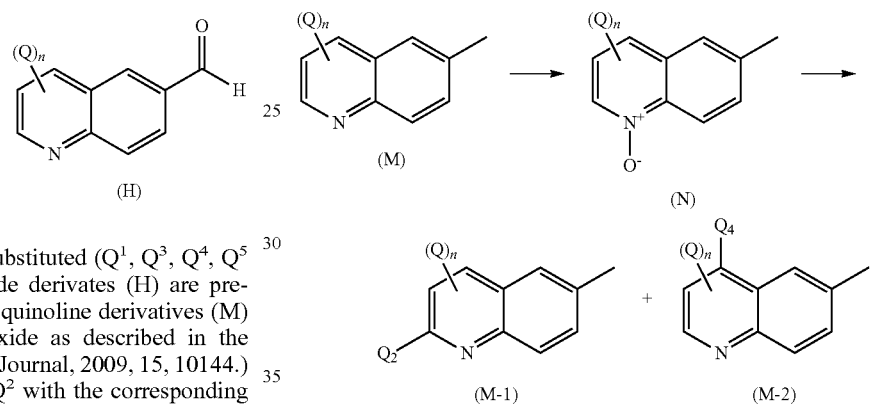

In Scheme 18 (Q)$_n$ represents the substitutents $Q^2$, $Q^4$, $Q^5$ and $Q^6$ and in formulae (M) and (N) $Q^1$ and $Q^3$ represents H.

Scheme 17: Processes 17A and 17B

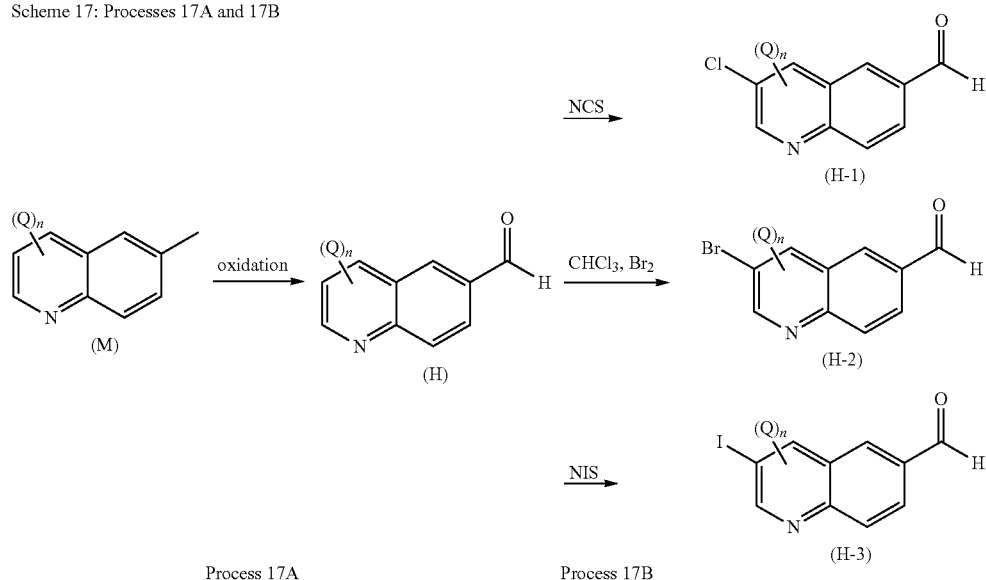

Process 17A  Process 17B

As depicted in Scheme 19, $Q^4$, $Q^5$, $Q^6$ substituted quinolines (M-3) can be synthesised from the respective 4-methyl aniline (O) as described in literature (WO 2010/54006).

Scheme 19: Process 19

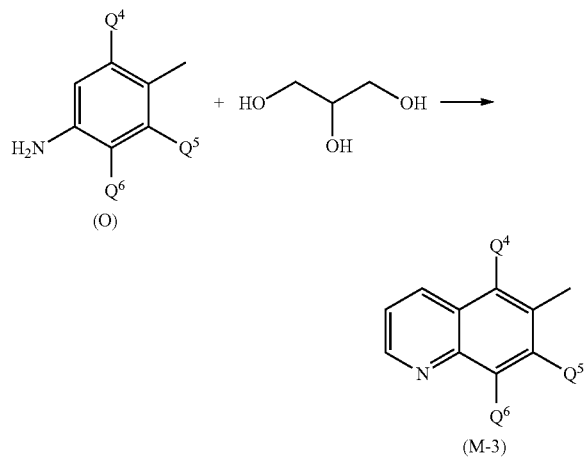

(O)

(M-3)

In Scheme 19 $Q^1$, $Q^2$ and $Q^3$ represent hydrogen.

Alternatively, $Q^4$, $Q^5$, $Q^6$ substituted quinolines (M-4) with bromide in position $Q^2$ are prepared from the corresponding aniline derivatives (O) and tribromopropanal as described in the literature (WO 2008/028624, U.S. Pat. No. 4,489,098) (Scheme 20).

Scheme 20: Process 20

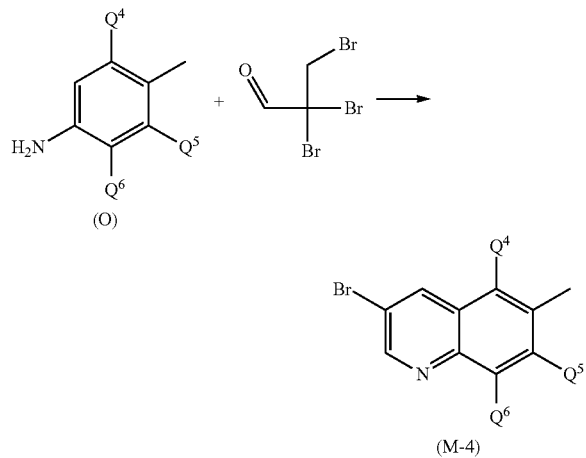

(O)

(M-4)

In Scheme 20 $Q^1$ and $Q^3$ represent hydrogen

If not otherwise denoted, the following definitions are used:

Base

Suitable bases for the processes according to the invention described above are inorganic and organic bases which ar customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as sodium carbonate, potassium carbonate, potassium bicarbonate, sodium bicarbonate, cesium carbonate, alkali metal or alkaline earth metal acetates, such as sodium acetate, potassium acetate, calcium acetate, and also tertiary amines, such as trimethylamine, triethylamine, diisopropylethylamine, tributylamine, N,N-dimethylaniline, pyridine, N-methylpiperidine, N,N-dimethylaminopyridine, 1,4-diazabicyclo [2.2.2]octane (DABCO), 1,5-diazabicyclo[4.3.0]non-5-ene (DBN) or 1,8-diaza-bicyclo[5.4.0]undec-7-ene (DBU).

Solvent

Suitable solvents for carrying out the invention are customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin, chlorobenzene, dichlorobenzene, dichloromethane, chloroform, carbon tetrachloride, dichlorethane or trichlorethane, ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole, nitriles, such as acetonitrile, propionitrile, n- or iso-butyronitrile or benzonitrile, amides, such as N,N-dimethylformamide, N,N-dimethylacetamide, N-methylformanilide, N-methylpyrrolidone or hexamethylphosphoric triamide, esters, such as methyl acetate or ethyl acetate, sulphoxides, such as dimethyl sulphoxide, or sulphones, such as sulpholane.

Transition Metal Catalyst (Pd-Coupling)

Suitable transition metal catalysts for the processes according to the invention described above may be chosen from transition metal salts or complexes. Suitable metal derivatives for this purpose are based on palladium. Suitable metal salts or complexes for this purpose are palladium chloride, palladium acetate, tetrakis(triphenylphosphine) palladium, bis(triphenylphosphine)palladium dichloride or 1,1'-bis(diphenyl-phosphino) ferrocenepalladium(II) chloride.

It is also possible to generate a palladium complex in the reaction mixture by separate addition to the reaction of a palladium salt and a ligand or salt, such as a phosphine, for example triethylphosphine, tri-tert-butylphos-phine, tricyclohexylphosphine, 2-(dicyclohexylphosphine)biphenyl, 2-(di-tert-butylphosphin)biphenyl, 2-(di-cyclohexylphosphine)-2'-(N,N-dimethylamino)-biphenyl, triphenylphosphine, tris-(o-tolyl)phosphine, sodium 3-(diphenylphosphino)benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine)ethane, 1,4-bis-(dicyclohexyl-phosphine)butane, 1,2-bis-(dicyclohexylphosphine)ethane, 2-(dicyclohexylphosphine)-2'-(N,N-dimethyl-amino)-biphenyl, bis(diphenylphosphino) ferrocene, tris-(2,4-tert-butylphenyl)-phosphite, (R)-(−)-1-[(S)-2-(diphenylphosphino)ferrocenyl]-ethyldicytert-butylphosphine, (S)-(+)-1-[(R)-2-(diphenylphosphino) ferrocenyl]-ethyldicyclohexylphosphine, (R)-(−)-1-[(S)-2-(diphenylphosphino)ferrocenyl]-ethyldicyclohexylphosphine, (S)-(+)-1-[(R)-2-(diphenylphosphino)ferrocenyl]-ethyldi-t-butylphosphine or 1,3-bis(2,4,6-trimethylphe-nyl)imidazolium chloride.

It is also advantageous to choose the appropriate catalyst and/or ligand from commercial catalogues such as "Metal Catalysts for Organic Synthesis" by Strem Chemicals or "Phosphorous Ligands and Compounds" by Strem Chemicals.

Acid Activation

Suitable condensing reagents for the processes according to the invention described above may be chosen as being acid halide former, such as phosgene, phosphorous tri-bromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenylphosphine/tetrachloromethane, 4-(4,6-dimethoxy[1.3.5]triazin-2-yl)-4-methylmorpholinium chloride hydrate or bromo-tripyrrolidino-phosphonium-hexafluorophosphate.

Suitable catalysts for carrying out e.g. Process 3 or 4 according to the invention may be chosen as being 4-dimethyl-aminopyridine, 1-hydroxy-benzotriazole or dimethyl-formamide.

Thionation

Suitable thionating agents for the processes according to the invention, e.g. Process 5, described above can be sulphur (S), sulfhydric acid ($H_2S$), sodium sulfide ($Na_2S$), sodium hydrosulfide (NaHS), boron trisulfide ($B_2S_3$), bis(diethyl-aluminium) sulfide [$(AlEt_2)_2S$], ammonium sulfide [$(NH_4)_2S$], phosphorous pentasulfide ($P_2S_5$), Lawesson's reagent [2,4-bis(4-methoxyphenyl)-1,2,3,4-dithiadiphosphetane 2,4-disulfide] or a polymer-supported thionating reagent (cf. J. Chem. Soc. Perkin 1, 2001, 358).

General

It is also possible to employ the reaction components in other ratios. Work-up is carried out by known methods.

In general, the reaction mixture is concentrated under reduced pressure. The residue that remains can be freed by known methods, such as chromatography or recrystallization, from any impurities that can still be present.

When carrying out processes according to the invention, the reaction temperatures can be varied within a relatively wide range. In general, these processes are carried out at temperatures from 0° C. to 160° C., preferably from 10° C. to 120° C. A way to control the temperature for the processes according to the invention is to use micro-wave technology.

Processes according to Schemes 1 to 18 are generally carried out under atmospheric pressure. It is also possible to operate under elevated or reduced pressure.

Compounds according to the invention can be prepared according to the above described processes. It will nevertheless be understood that, on the basis of his general knowledge and of available publications, the skilled worker will be able to adapt these processes according to the specifics of each of the compounds according to the invention that is desired to be synthesized.

The invention further relates to novel acid and ester intermediates of the compound of formula (I) and its salts, which form part of the invention.

Novel quinoline-isoxazoline-5-carboxylic or quinoline-isoxazoline-5-thiocarboxylic acids or acid esters of formula (II) are

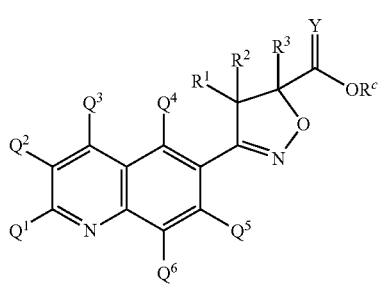

(II)

in which $Q^1$, $Q^2$, $Q^3$, $Q^4$, $Q^5$, $Q^6$, Y, $R^1$, $R^2$ and $R^3$ have the same meaning as defined for formula (I) above and $R^c$ represents hydrogen; substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; substituted or non-substituted aryl; or substituted or non-substituted 5, 6 or 7 membered unsaturated heterocycle ring with 1 to 3 heteroatoms.

$R^c$ preferably represents hydrogen or substituted or non-substituted $C_1$-$C_8$-alkyl.

$R^c$ particularly preferably represents hydrogen or substituted or non-substituted $C_1$-$C_4$-alkyl.

$R^c$ very particularly preferably represents hydrogen, methyl or ethyl.

Preferred radical definitions for $Q^1$, $Q^2$, $Q^3$, $Q^4$, $Q^5$, $Q^6$, Y, $R^1$, $R^2$ and $R^3$ have already been given above for the compounds of fomula (I). Such preferred radical definitions shall also apply for the esters or acids of formula (II).

The invention further relates to novel intermediates according to formula (III) and its salts, which form part of the invention.

Novel compounds of formula (III) are

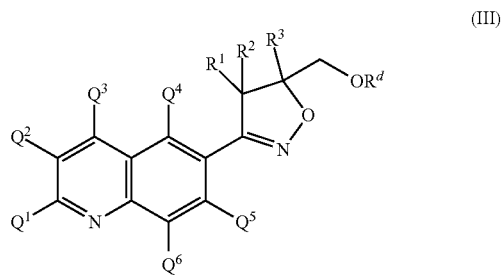

(III)

in which $Q^1$, $Q^2$, $Q^3$, $Q^4$, $Q^5$, $Q^6$, $R^1$, $R^2$ and $R^3$ have the same meaning as defined for formula (I) above and $R^d$ represents hydrogen; substituted or non-substituted $C_1$-$C_8$-alkyl; $C_1$-$C_8$-haloalkyl; substituted or non-substituted $C_3$-$C_7$-cycloalkyl; substituted or non-substituted $C_1$-$C_8$-alkylcarbonyl, substituted or non-substituted $C_1$-$C_8$-alkylaminocarbonyl; substituted or non-substituted aryl; or substituted or non-substituted 5, 6 or 7 membered unsaturated heterocycle ring with 1 to 3 heteroatoms.

$R^d$ preferably represents hydrogen; substituted or non-substituted $C_1$-$C_8$-alkyl; $C_1$-$C_8$-haloalkyl; substituted or non-substituted $C_1$-$C_8$-alkykycarbonyl, substituted or non-substituted $C_1$-$C_8$-alkylaminocarbonyl; or substituted or non-substituted aryl.

$R^d$ particularly preferably represents hydrogen; substituted or non-substituted $C_1$-$C_4$-alkyl; $C_1$-$C_4$-haloalkyl; substituted or non-substituted $C_1$-$C_4$-alkykycarbonyl.

In a preferred embodiment of the present invention compounds of intermediates of formula (III) are represented by the compunds of formula (III-Ac)

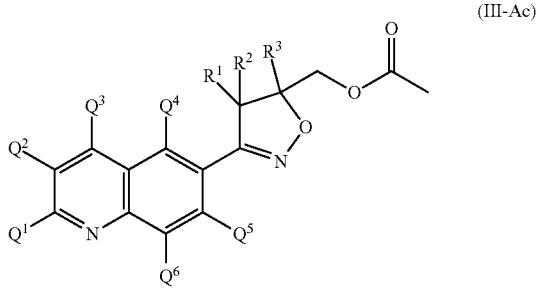

(III-Ac)

in which $Q^1$, $Q^2$, $Q^3$, $Q^4$, $Q^5$, $Q^6$, $R^1$, $R^2$ and $R^3$ have the same meaning as defined for formula (I) above.

In another preferred embodiment of the present invention compounds of intermediates of formula (III) are represented by the compunds of formula (III-H)

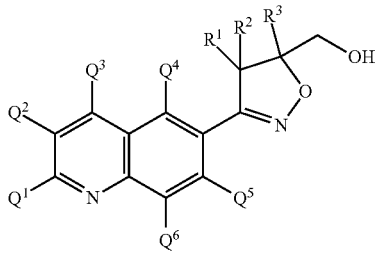

(III-H)

in which $Q^1$, $Q^2$, $Q^3$, $Q^4$, $Q^5$, $Q^6$, $R^1$, $R^2$ and $R^3$ have the same meaning as defined for formula (I) above.

Preferred radical definitions for $Q^1$, $Q^2$, $Q^3$, $Q^4$, $Q^5$, $Q^6$, $R^1$, $R^2$ and $R^3$ have already been given above for the compounds of fomula (I). Such preferred radical definitions shall also apply for the intemediates of formulae (III), (III-Ac) and (III-H).

Although not explicitely shown in Scheme 8A the oxidation of the primary alcohols according to formula (III-H) to the carboxylic acids according to formula (II-H) passes through such aldehyde intermediates according to formula (IV).

Therefore, the invention further relates to novel aldehyde intermediates according to formula (IV) and its salts, which form part of the invention.

Novel compounds of formula (IV) are

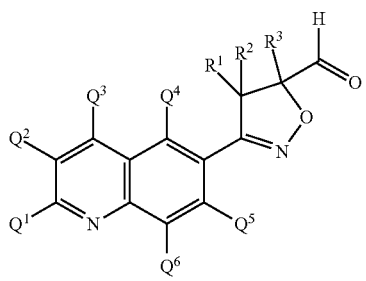

(IV)

in which $Q^1$, $Q^2$, $Q^3$, $Q^4$, $Q^5$, $Q^6$, $R^1$, $R^2$ and $R^3$ have the same meaning as defined for formula (I) above.

Preferred radical definitions for $Q^1$, $Q^2$, $Q^3$, $Q^4$, $Q^5$, $Q^6$, $R^1$, $R^2$ and $R^3$ have already been given above for the compounds of fomula (I). Such preferred radical definitions shall also apply for the aldehyde intermediates of formula (IV).

The invention further relates to novel oxime or chloro oxime intermediates according to formula (V) and its salts, which form part of the invention.

Novel compounds of formula (V) are

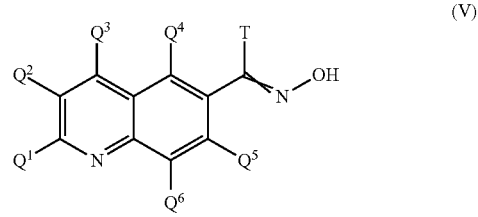

(V)

in which $Q^1$, $Q^2$, $Q^3$, $Q^4$, $Q^5$ and $Q^6$ have the same meaning as defined for formula (I) above and T represents H or Cl, except for the compounds N-hydroxyquinoline-6-carboximidoyl chloride, N-hydroxyquinoline-6-carboximidoyl chloride hydrochloride (1:1), (E)-N-hydroxy-1-(quinolin-6-yl)methanimine, 6-[(E)-(hydroxyimino)methyl]quinolin-5-amine, (E)-N-hydroxy-1-(5-nitroquinolin-6-yl)methanimine, (Z)-N-hydroxy-1-(5-nitroquinolin-6-yl)methanimine, (1R,2R)-6-(dimethylamino)-1-{6-[(E)-(hydroxyimino)methyl]-2-methoxyquinolin-3-yl-}-1,2-diphenylhexan-2-ol, (1R,2S)-4-(dimethylamino)-1-{6-[(E)-(hydroxyimino)methyl]-2-methoxyquinolin-3-yl-}-2-(1-naphthyl)-1-phenylbutan-2-ol, (1R,2R)-4-(dimethylamino)-1-{6-[(E)-(hydroxyimino)methyl]-2-methoxyquinolin-3-yl}-2-(1-naphthyl)-1-phenylbutan-2-ol, (1R,2S)-6-(dimethylamino)-1-{6-[(E)-(hydroxyimino)methyl]-2-methoxyquinolin-3-yl-}-2-(2-naphthyl)-1-phenylhexan-2-ol, (1R,2R)-6-(dimethylamino)-1-{6-[(E)-(hydroxyimino)methyl]-2-methoxyquinolin-3-yl-}-2-(2-naphthyl)-1-phenylhexan-2-ol, (5R,6S)-6-[(1R)-1-hydroxyethyl]-3-{2-[(E)-(hydroxyimino)methyl]phenanthridin-8-yl-}-7-oxo-1-azabicyclo[3.2.0]hept-2-ene-2-carboxylic acid, (5R,6S)-6-[(1R)-1-hydroxyethyl]-3-{2-[(E)-(hydroxyimino)methyl]phenanthridin-8-yl-}-7-oxo-1-azabicyclo[3.2.0]hept-2-ene-2-carboxylic acid-sodium (1:1).

(3aS,4R,9R,10R,11R,13R,15R,15aR)-4-ethyl-7-fluoro-11-{[(2Z)-3-{6-[(E)-(hydroxyimino)methyl]quinolin-3-yl}prop-2-en-1-yl]oxy}-3a,7,9,11,13,15-hexamethyl-2,6,8,14-tetraoxotetradecahydro-2H-oxacyclotetradecino[4,3-d][1,3]oxazol-10-yl-3,4,6-trideoxy-3-(dimethylamino)-beta-D-xylohexopyranoside.

Compounds according to formula (V) are representend in the schemes above as compounds (D) for T represented by Cl or compounds (G) for T represented by H.

Therefore, particularly preferred compounds according to formula (V) are oximes according to formula (G)

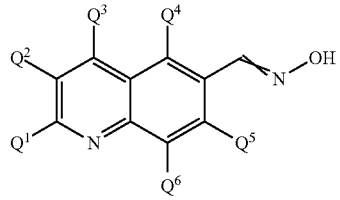

(G)

in which $Q^1$, $Q^2$, $Q^3$, $Q^4$, $Q^5$ and $Q^6$ have the same meaning as defined for formula (I) above, except for the compounds
(E)-N-hydroxy-1-(quinolin-6-yl)methanimine,
6-[(E)-(hydroxyimino)methyl]quinolin-5-amine,
(E)-N-hydroxy-1-(5-nitroquinolin-6-yl)methanimine,
(Z)-N-hydroxy-1-(5-nitroquinolin-6-yl)methanimine,
(1R,2R)-6-(dimethylamino)-1-{6-[(E)-(hydroxyimino) methyl]-2-methoxyquinolin-3-yl -}-1,2-diphenyl-hexan-2-ol,
(1R,2S)-4-(dimethylamino)-1-{6-[(E)-(hydroxyimino) methyl]-2-methoxyquinolin-3-yl -}-2-(1-naphthyl)-1-phenylbutan-2-ol,
(1R,2R)-4-(dimethylamino)-1-{6-[(E)-(hydroxyimino) methyl]-2-methoxyquinolin-3-yl -}-2-(1-naphthyl)-1-phenylbutan-2-ol,
(1R,2S)-6-(dimethylamino)-1-{6-[(E)-(hydroxyimino) methyl]-2-methoxyquinolin-3-yl -}-2-(2-naphthyl)-1-phenylhexan-2-ol,
(1R,2R)-6-(dimethylamino)-1-{6-[(E)-(hydroxyimino) methyl]-2-methoxyquinolin-3-yl -}-2-(2-naphthyl)-1-phenylhexan-2-ol,
(5R,6S)-6-[(1R)-1-hydroxyethyl]-3-{2-(E)-(hydroxyimino)methylthenanthridin-8-yl -}-7-oxo-1-azabicyclo[3.2.0]hept-2-ene-2-carboxylic acid,
(5R,6S)-6-[(1R)-1-hydroxyethyl]-3-{2-[(E)-(hydroxyimino)methyl]phenanthridin-8-yl -}-7-oxo-1-azabicyclo[3.2.0]hept-2-ene-2-carboxylic acid-sodium (1:1),
(3aS,4R,9R,10R,11R,13R,15R,15aR)-4-ethyl-7-fluoro-11-{[(2Z)-3-{6-[(E)-(hydroxyimino)methyl]quinolin-3-yl }prop-2-en-1-yl]oxy}-3a,7,9,11,13,15-hexamethyl-2,6,8,14-tetraoxotetradecahydro-2H-oxacyclotetradecino[4,3-d][1,3]oxazol-10-yl-3,4,6-trideoxy-3-(dimethylamino)-beta-D-xylo-hexopyranoside.

Further particularly preferred compounds according to formula (V) are chloro oximes according to formula (D)

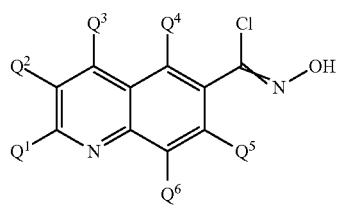

(D)

in which $Q^1$, $Q^2$, $Q^3$, $Q^4$, $Q^5$ and $Q^6$ have the same meaning as defined for formula (I) above, except for the compounds
N-hydroxyquinoline-6-carboximidoyl chloride,
N-hydroxyquinoline-6-carboximidoyl chloride hydrochloride (1:1).

Preferred radical definitions for $Q^1$, $Q^2$, $Q^3$, $Q^4$, $Q^5$ and $Q^6$ have already been given above for the compounds of fomula (I). Such preferred radical definitions shall also apply for the compounds of formula (V).

The compounds of the formula (I) according to the invention can be converted into physiologically acceptable salts, e.g. as acid addition salts or metal salt complexes.

Depending on the nature of the substituents defined above, the compounds of the formula (I) have acidic or basic properties and can form salts, if appropriate also inner salts, or adducts with inorganic or organic acids or with bases or with metal ions. If the compounds of the formula (I) carry amino, alkylamino or other groups which induce basic properties, these compounds can be reacted with acids to give salts, or they are directly obtained as salts in the synthesis. If the compounds of the formula (I) carries hydroxyl, carboxyl or other groups which induce acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, furthermore ammonia, primary, secondary and tertiary amines having $(C_1-C_4)$-alkyl groups, mono-, di- and trialkanolamines of $(C_1-C_4)$-alkanols, choline and also chlorocholine.

The salts obtainable in this manner also have fungicidal properties.

Examples of inorganic acids are hydrohalic acids, such as hydrogen fluoride, hydrogen chloride, hydrogen bromide and hydrogen iodide, sulphuric acid, phosphoric acid and nitric acid, and acidic salts, such as $NaHSO_4$ and $KHSO_4$. Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, maleic acid, fumaric acid, tartaric acid, sorbic acid oxalic acid, alkylsulphonic acids (sulphonic acids having straight-chain or branched alkyl radicals of 1 to 20 carbon atoms), arylsulphonic acids or aryldisulphonic acids (aromatic radicals, such as phenyl and naphthyl, which carry one or two sulphonic acid groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphonic acid radicals), where the alkyl and aryl radicals may carry further substituents, for example p-toluenesulphonic acid, 1,5-naphthalenedisulphonic acid, salicylic acid, p-aminosalicylic acid, 2-phenoxybenzoic acid, 2-acetoxybenzoic acid, etc.

Suitable metal ions are in particular the ions of the elements of the second main group, in particular calcium and magnesium, of the third and fourth main group, in particular aluminium, tin and lead, and also of the first to eighth transition group, in particular chromium, manganese, iron, cobalt, nickel, copper, zinc and others. Particular preference is given to the metal ions of the elements of the fourth period. Here, the metals can be present in various valencies that they can assume.

The acid addition salts of the compounds of the formula (I) can be obtained in a simple manner by customary methods for forming salts, for example by dissolving a compound of the formula (I) in a suitable inert solvent and adding the acid, for example hydrochloric acid, and be isolated in a known manner, for example by filtration, and, if required, be purified by washing with an inert organic solvent.

Suitable anions of the salts are those which are preferably derived from the following acids: hydrohalic acids, such as, for example, hydrochloric acid and hydrobromic acid, furthermore phosphoric acid, nitric acid and sulphuric acid.

The metal salt complexes of compounds of the formula (I) can be obtained in a simple manner by customary processes, for example by dissolving the metal salt in alcohol, for example ethanol, and adding the solution to the compound of the formula (I). Metal salt complexes can be isolated in a known manner, for example by filtration, and, if required, be purified by recrystallization.

N-oxides of compounds of the formula (I) or intermediates thereof can be obtained in a simple manner by customary processes, for example by N-oxidation with hydrogen peroxide ($H_2O_2$), peracids, for example peroxy sulfuric acid or peroxy carboxylic acids, such as meta-chloroperoxybenzoic acid or peroxymonosulfuric acid (Caro's acid).

Composition/Formulation

The present invention further relates to a crop protection composition for controlling harmful microorganisms, especially unwanted fungi and bacteria, comprising an effective and non-phytotoxic amount of the inventive active ingredients. These are preferably fungicidal compositions which comprise agriculturally suitable auxiliaries, solvents, carriers, surfactants or extenders.

In the context of the present invention, "control of harmful microorganisms" means a reduction in infestation by harmful microorganisms, compared with the untreated plant measured as fungicidal efficacy, preferably a reduction by 25-50%, compared with the untreated plant (100%), more preferably a reduction by 40-79%, compared with the untreated plant (100%); even more preferably, the infection by harmful microorganisms is entirely suppressed (by 70-100%). The control may be curative, i.e. for treatment of already infected plants, or protective, for protection of plants which have not yet been infected.

An "effective but non-phytotoxic amount" means an amount of the inventive composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions. Suitable organic solvents include all polar and non-polar organic solvents usually employed for formulation purposes. Preferable the solvents are selected from ketones, e.g. methyl-isobutyl-ketone and cyclohexanone, amides, e.g. dimethyl formamide and alkanecarboxylic acid amides, e.g. N,N-dimethyl decaneamide and N,N-dimethyl octanamide, furthermore cyclic solvents, e.g. N-methyl-pyrrolidone, N-octyl-pyrrolidone, N-dodecyl-pyrrolidone, N-octyl-caprolactame, N-dodecyl-caprolactame and butyrolactone, furthermore strong polar solvents, e.g. dimethylsulfoxide, and aromatic hydrocarbons, e.g. xylol, Solvesso™, mineral oils, e.g. white spirit, petroleum, alkyl benzenes and spindle oil, also esters, e.g. propyleneglycol-monomethylether acetate, adipic acid dibutylester, acetic acid hexylester, acetic acid heptylester, citric acid tri-n-butylester and phthalic acid di-n-butylester, and also alkohols, e.g. benzyl alcohol and 1-methoxy-2-propanol.

According to the invention, a carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture.

Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. Mixtures of such carriers can likewise be used.

Suitable solid filler and carrier include inorganic particles, e.g. carbonates, silikates, sulphates and oxides with an average particle size of between 0.005 and 20 μm, preferably of between 0.02 μm, for example ammonium sulphate, ammonium phosphate, urea, calcium carbonate, calcium sulphate, magnesium sulphate, magnesium oxide, aluminium oxide, silicium dioxide, so-called fine-particle silica, silica gels, natural or synthetic silicates, and alumosilicates and plant products like cereal flour, wood powder/sawdust and cellulose powder.

Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks.

Useful liquefied gaseous extenders or carriers are those liquids which are gaseous at standard temperature and under standard pressure, for example aerosol propellants such as halohydrocarbons, and also butane, propane, nitrogen and carbon dioxide.

In the formulations, it is possible to use tackifiers such as carboxymethylcellulose, and natural and synthetic polymers in the form of powders, granules or latices, such as gum arabic, polyvinyl alcohol and polyvinyl acetate, or else natural phospholipids, such as cephalins and lecithins, and synthetic phospholipids. Further additives may be mineral and vegetable oils.

If the extender used is water, it is also possible to employ, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

Suitable surfactants (adjuvants, emulsifiers, dispersants, protective colloids, wetting agent and adhesive) include all common ionic and non-ionic substances, for example ethoxylated nonylphenols, polyalkylene glycolether of linear or branched alcohols, reaction products of alkyl phenols with ethylene oxide and/or propylene oxide, reaction products of fatty acid amines with ethylene oxide and/or propylene oxide, furthermore fattic acid esters, alkyl sulfonates, alkyl sulphates, alkyl ethersulphates, alkyl etherphosphates, arylsulphate, ethoxylated arylalkylphenols, e.g. tristyrylphenol-ethoxylates, furthermore ethoxylated and propoxylated arylalkylphenols like sulphated or phosphated arylalkylphenol-ethoxylates and -ethoxy-and -propoxylates. Further examples are natural and synthetic, water soluble polymers, e.g. lignosulphonates, gelatine, gum arabic, phospholipides, starch, hydrophobic modified starch and cellulose derivatives, in particular cellulose ester and cellulose ether, further polyvinyl alcohol, polyvinyl acetate, polyvinyl pyrrolidone, polyacrylic acid, polymethacrylic acid and co-polymerisates of (meth)acrylic acid and (meth)acrylic acid esters, and further co-polymerisates of methacrylic acid and methacrylic acid esters which are neutralized with alkali-metal hydroxide and also condensation products of optionally substituted naphthalene sulfonic acid salts with formaldehyde. The presence of a surfactant is necessary if one of the active ingredients and/or one of the inert carriers is insoluble in water and when application is effected in water. The proportion of surfactants is between 5 and 40 percent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Antifoams which may be present in the formulations include e.g. silicone emulsions, longchain alcohols, fattiy acids and their salts as well as fluoroorganic substances and mixtures therof.

Examples of thickeners are polysaccharides, e.g. xanthan gum or veegum, silicates, e.g. attapulgite, bentonite as well as fine-particle silica.

If appropriate, it is also possible for other additional components to be present, for example protective colloids, binders, adhesives, thickeners, thixotropic substances, penetrants, stabilizers, sequestrants, complexing agents. In general, the active ingredients can be combined with any solid or liquid additive commonly used for formulation purposes.

The inventive active ingredients or compositions can be used as such or, depending on their particular physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, gas (under pressure), gas generating product, foams, pastes, pesticide coated seed, suspension concentrates, suspoemulsion concentrates, soluble concentrates, suspensions, wettable powders, soluble powders, dusts and granules, water-soluble and water-dispersible granules or tablets, water-soluble and water-dispersible powders for the treatment of seed, wettable powders, natural products and synthetic substances impregnated with active ingredient, and also microencapsulations in polymeric substances and in coating materials for seed, and also ULV cold-fogging and warm-fogging formulations.

The inventive compositions include not only formulations which are already ready for use and can be applied with a suitable apparatus to the plant or the seed, but also commercial concentrates which have to be diluted with water prior to use. Customary applications are for example dilution in water and subsequent spraying of the resulting spray liquor, application after dilution in oil, direct application without dilution, seed treatment or soil application of granules.

The inventive compositions and formulations generally contain between 0.05 and 99% by weight, 0.01 and 98% by weight, preferably between 0.1 and 95% by weight, more preferably between 0.5 and 90% of active ingredient, most preferably between 10 and 70% by weight. For special applications, e.g. for protection of wood and derived timber products the inventive compositions and formulations generally contain between 0.0001 and 95% by weight, preferably 0.001 to 60% by weight of active ingredient.

The contents of active ingredient in the application forms prepared from the commercial formulations may vary in a broad range. The concentration of the active ingredients in the application forms is generally between 0.000001 to 95% by weight, preferably between 0.0001 and 2% by weight.

The formulations mentioned can be prepared in a manner known per se, for example by mixing the active ingredients with at least one customary extender, solvent or diluent, adjuvant, emulsifier, dispersant, and/or binder or fixative, wetting agent, water repellent, if appropriate desiccants and UV stabilizers and, if appropriate, dyes and pigments, antifoams, preservatives, inorganic and organic thickeners, adhesives, gibberellins and also further processing auxiliaries and also water. Depending on the formulation type to be prepared further processing steps are necessary, e.g. wet grinding, dry grinding and granulation.

The inventive active ingredients may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The inventive treatment of the plants and plant parts with the active ingredients or compositions is effected directly or by action on their surroundings, habitat or storage space by the customary treatment methods, for example by dipping, spraying, atomizing, irrigating, evaporating, dusting, fogging, broadcasting, foaming, painting, spreading-on, watering (drenching), drip irrigating and, in the case of propagation material, especially in the case of seeds, also by dry seed treatment, wet seed treatment, slurry treatment, incrustation, coating with one or more coats, etc. It is also possible to deploy the active ingredients by the ultra-low volume method or to inject the active ingredient preparation or the active ingredient itself into the soil.

Plant/Crop Protection

The inventive active ingredients or compositions have potent microbicidal activity and can be used for control of harmful microorganisms, such as fungi and bacteria, in crop protection and in the protection of materials. The invention also relates to a method for controlling harmful microorganisms, characterized in that the inventive active ingredients are applied to the phytopathogenic fungi, phytopathogenic bacteria and/or their habitat.

Fungicides can be used in crop protection for control of phytopathogenic fungi. They are characterized by an outstanding efficacy against a broad spectrum of phytopathogenic fungi, including soilborne pathogens, which are in particular members of the classes *Plasmodiophoromycetes, Peronosporomycetes* (Syn. *Oomycetes*), *Chytridiomycetes, Zygomycetes, Ascomycetes, Basidiomycetes* and *Deuteromycetes* (Syn. *Fungi imperfecti*). Some fungicides are systemically active and can be used in plant protection as foliar, seed dressing or soil fungicide. Furthermore, they are suitable for controlling fungi, which inter alia infest wood or roots of plant. Bactericides can be used in crop protection for control of *Pseudomonadaceae, Rhizobiaceae, Enterobacteriaceae, Corynebacteriaceae* and *Streptomycetaceae*.

Non-limiting examples of pathogens of fungal diseases which can be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* and *Phakopsora meibomiae*; *Puccinia* species, for example *Puccinia recondite, P. triticina, P. graminis* or *P. striiformis*; *Uromyces* species, for example *Uromyces appendiculatus*;

diseases caused by pathogens from the group of the *Oomycetes*, for example *Albugo* species, for example *Algubo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidia form: Drechslera, Syn: Helminthosporium), *Cochliobolus miyabeanus*; *Colletotrichum* species, for example *Colletotrichum lindemuthanium*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans, Leptosphaeria nodorum*; *Magnaporthe* species, for example *Magnaporthe grisea*; *Microdochium* species, for example *Microdochium nivale*; *Mycosphaerella* species, for example *Mycosphaerella graminicola, M. arachidicola* and *M. fijiensis*; *Phaeosphaeria* species, for example *Phaeosphaeria nodorum*; *Pyrenophora* species, for example *Pyrenophora teres, Pyrenophora tritici repentis*; *Ramularia* species, for example *Ramularia collo-cygni, Ramularia areola*; *Rhynchosporium* species, for example *Rhynchosporium secalis*; *Septoria* species, for example *Septoria apii, Septoria lycopersii*; *Typhula* species, for example *Typhula incarnata*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, such as, for example *Rhizoctonia solani*; *Sarocladium* diseases caused for example by *Sarocladium oryzae*; *Sclerotium* diseases caused for example by *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria spp.*; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Septoria* species, for example *Septoria nodorum*;

diseases caused by smut fungi, for example *Sphacelotheca* species, for example *Sphacelotheca reiliana*; *Tilletia* species, for example *Tilletia caries, T. controversa*; *Urocystis* species, for example *Urocystis occulta*; *Ustilago* species, for example *Ustilago nuda, U. nuda tritici*;

fruit rot caused, for example, by *Aspergillus* species, for example *Aspergillus flavus*; *Botrytis* species, for example *Botrytis cinerea*; *Penicillium* species, for example *Penicillium expansum* and *P. purpurogenum*; *Sclerotinia* species, for example *Sclerotinia sclerotiorum*; *Verticilium* species, for example *Verticilium alboatrum*;

seed and soilborne decay, mould, wilt, rot and damping-off diseases caused, for example, by *Alternaria* species, caused for example by *Alternaria brassicicola*; *Aphanomyces* species, caused for example by *Aphanomyces euteiches*; *Ascochyta* species, caused for example by *Ascochyta lentis*; *Aspergillus* species, caused for example by *Aspergillus flavus*; *Cladosporium* species, caused for example by *Cladosporium herbarum*; *Cochliobolus* species, caused for example by *Cochliobolus sativus*; (Conidiaform: Drechslera, Bipolaris Syn: Helminthosporium); *Colletotrichum* species, caused for example by *Colletotrichum coccodes*; *Fusarium* species, caused for example by *Fusarium culmorum*; *Gibberella* species, caused for example by *Gibberella zeae*; *Macrophomina* species, caused for example by *Macrophomina phaseolina*; *Monographella* species, caused for example by *Monographella nivalis*; *Penicillium* species, caused for example by *Penicillium expansum*; *Phoma* species, caused for example by *Phoma lingam*; *Phomopsis* species, caused for example by *Phomopsis sojae*; *Phytophthora* species, caused for example by *Phytophthora cactorum*; *Pyrenophora* species, caused for example by *Pyrenophora graminea*; *Pyricularia* species, caused for example by *Pyricularia oryzae*; *Pythium* species, caused for example by *Pythium ultimum*; *Rhizoctonia* species, caused for example by *Rhizoctonia solani*; *Rhizopus* species, caused for example by *Rhizopus oryzae*; *Sclerotium* species, caused for example by *Sclerotium rolfsii*; *Septoria* species, caused for example by *Septoria nodorum*; *Typhula* species, caused for example by *Typhula incarnata*; *Verticillium* species, caused for example by *Verticillium dahliae*;

cancers, galls and witches' broom caused, for example, by *Nectria* species, for example *Nectria galligena*; wilt diseases caused, for example, by *Monilinia* species, for example *Monilinia laxa*;

leaf blister or leaf curl diseases caused, for example, by *Exobasidium* species, for example *Exobasidium vexans*; *Taphrina* species, for example *Taphrina deformans*;

decline diseases of wooden plants caused, for example, by Esca disease, caused for example by *Phaemoniella clamydospora, Phaeoacremonium aleophilum* and *Fomitiporia mediterranea*; Eutypa dyeback, caused for example by *Eutypa lata*; Ganoderma diseases caused for example by *Ganoderma boninense*; Rigidoporus diseases caused for example by *Rigidoporus lignosus*;

diseases of flowers and seeds caused, for example, by *Botrytis* species, for example *Botrytis cinerea*; diseases of plant tubers caused, for example, by *Rhizoctonia* species, for example *Rhizoctonia solani*; *Helminthosporium* species, for example *Helminthosporium solani*;

Club root caused, for example, by *Plasmodiophora* species, for example *Plamodiophora brassicae*; diseases caused by bacterial pathogens, for example *Xanthomonas* species, for example *Xanthomonas campestris pv. oryzae*; *Pseudomonas* species, for example *Pseudomonas syringae pv. lachrymans*; *Erwinia* species, for example *Erwinia amylovora*.

The following diseases of soya beans can be controlled with preference:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frog-eye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The inventive fungicidal compositions can be used for curative or protective/preventive control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

The fact that the active ingredients are well tolerated by plants at the concentrations required for controlling plant diseases allows the treatment of above-ground parts of plants, of propagation stock and seeds, and of the soil. According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

The inventive active ingredients, when they are well tolerated by plants, have favourable homeotherm toxicity and are well tolerated by the environment, are suitable for protecting plants and plant organs, for enhancing harvest yields, for improving the quality of the harvested material. They can preferably be used as crop protection compositions. They are active against normally sensitive and resistant species and against all or some stages of development.

Plants which can be treated in accordance with the invention include the following main crop plants: maize, soya bean, alfalfa, cotton, sunflower, Brassica oil seeds such as Brassica napus (e.g. canola, rapeseed), *Brassica rapa, B. juncea* (e.g. (field) mustard) and *Brassica carinata, Arecaceae* sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. *Rosaceae* sp. (e.g. pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae* sp., *Oleaceae* sp. (e.g. olive tree), *Actinidaceae* sp., *Lauraceae* sp. (e.g. avocado, cinnamon, camphor), *Musaceae* sp. (e.g. banana trees and plantations), *Rubiaceae* sp. (e.g. coffee), *Theaceae* sp. (e.g. tea), *Sterculiceae* sp., *Rutaceae* sp. (e.g. lemons, oranges, mandarins and grapefruit); *Solanaceae* sp. (e.g. tomatoes, potatoes, peppers, capsicum, aubergines, tobacco), *Liliaceae* sp., *Compositae* sp. (e.g. lettuce, artichokes and chicory—including root chicory, endive or common chicory), *Umbelliferae* sp. (e.g. carrots, parsley, celery and celeriac), *Cucurbitaceae* sp. (e.g. cucumbers—including gherkins, pumpkins, watermelons, calabashes and melons), *Alliaceae* sp. (e.g. leeks and onions), *Cruciferae* sp. (e.g. white cabbage, red cabbage, broccoli, cauliflower, Brussels sprouts, pak choi, kohlrabi, radishes, horseradish, cress and chinese cabbage), *Leguminosae* sp. (e.g. peanuts, peas, lentils and beans—e.g. common beans and broad beans), *Chenopodiaceae* sp. (e.g. Swiss chard, fodder beet, spinach, beetroot), *Linaceae* sp. (e.g. hemp), *Cannabeacea* sp. (e.g. cannabis), *Malvaceae* sp. (e.g. okra, cocoa), *Papaveraceae* (e.g. poppy), *Asparagaceae* (e.g. asparagus); useful plants and ornamental plants in the garden and woods including turf, lawn, grass and *Stevia rebaudiana*; and in each case genetically modified types of these plants.

Plant Growth Regulation

In some cases, the inventive compounds can, at particular concentrations or application rates, also be used as growth regulators or agents to improve plant properties, or as microbicides, for example as antimycotics, bactericides, viricides (including compositions against viroids) or as compositions against MLO (Mycoplasma-like organisms) and RLO (Rickettsia-like organisms). If appropriate, they can also be used as intermediates or precursors for the synthesis of other active ingredients.

The inventive active ingredients intervene in the metabolism of the plants and can therefore also be used as growth regulators.

Plant growth regulators may exert various effects on plants. The effect of the substances depends essentially on the time of application in relation to the developmental stage of the plant, and also on the amounts of active ingredient applied to the plants or their environment and on the type of application. In each case, growth regulators should have a particular desired effect on the crop plants.

Plant growth-regulating compounds can be used, for example, to inhibit the vegetative growth of the plants. Such inhibition of growth is of economic interest, for example, in the case of grasses, since it is thus possible to reduce the frequency of grass cutting in ornamental gardens, parks and sport facilities, on roadsides, at airports or in fruit crops. Also of significance is the inhibition of the growth of herbaceous and woody plants on roadsides and in the vicinity of pipelines or overhead cables, or quite generally in areas where vigorous plant growth is unwanted.

Also important is the use of growth regulators for inhibition of the longitudinal growth of cereal. This reduces or completely eliminates the risk of lodging of the plants prior to harvest. In addition, growth regulators in the case of cereals can strengthen the culm, which also counteracts lodging. The employment of growth regulators for shortening and strengthening culms allows the deployment of higher fertilizer volumes to increase the yield, without any risk of lodging of the cereal crop.

In many crop plants, inhibition of vegetative growth allows denser planting, and it is thus possible to achieve higher yields based on the soil surface. Another advantage of the smaller plants obtained in this way is that the crop is easier to cultivate and harvest.

Inhibition of the vegetative plant growth may also lead to enhanced yields because the nutrients and assimilates are of more benefit to flower and fruit formation than to the vegetative parts of the plants.

Frequently, growth regulators can also be used to promote vegetative growth. This is of great benefit when harvesting the vegetative plant parts. However, promoting vegetative growth may also promote generative growth in that more assimilates are formed, resulting in more or larger fruits.

In some cases, yield increases may be achieved by manipulating the metabolism of the plant, without any detectable changes in vegetative growth. In addition, growth regulators can be used to alter the composition of the plants, which in turn may result in an improvement in quality of the harvested products. For example, it is possible to increase the sugar content in sugar beet, sugar cane, pineapples and in citrus fruit, or to increase the protein content in soya or cereals. It is also possible, for example, to use growth regulators to inhibit the degradation of desirable ingredients, for example sugar in sugar beet or sugar cane, before or after harvest. It is also possible to positively influence the production or the elimination of secondary plant ingredients. One example is the stimulation of the flow of latex in rubber trees.

Under the influence of growth regulators, parthenocarpic fruits may be formed. In addition, it is possible to influence the sex of the flowers. It is also possible to produce sterile pollen, which is of great importance in the breeding and production of hybrid seed.

Use of growth regulators can control the branching of the plants. On the one hand, by breaking apical dominance, it is possible to promote the development of side shoots, which may be highly desirable particularly in the cultivation of ornamental plants, also in combination with an inhibition of growth. On the other hand, however, it is also possible to inhibit the growth of the side shoots. This effect is of particular interest, for example, in the cultivation of tobacco or in the cultivation of tomatoes.

Under the influence of growth regulators, the amount of leaves on the plants can be controlled such that defoliation of the plants is achieved at a desired time. Such defoliation plays a major role in the mechanical harvesting of cotton, but is also of interest for facilitating harvesting in other crops, for example in viticulture. Defoliation of the plants can also be undertaken to lower the transpiration of the plants before they are transplanted.

Growth regulators can likewise be used to regulate fruit dehiscence. On the one hand, it is possible to prevent premature fruit dehiscence. On the other hand, it is also possible to promote fruit dehiscence or even flower abortion to achieve a desired mass ("thinning"), in order to eliminate alternation. Alternation is understood to mean the characteristic of some fruit species, for endogenous reasons, to deliver very different yields from year to year. Finally, it is possible to use growth regulators at the time of harvest to reduce the forces required to detach the fruits, in order to allow mechanical harvesting or to facilitate manual harvesting.

Growth regulators can also be used to achieve faster or else delayed ripening of the harvested material before or after harvest. This is particularly advantageous as it allows optimal adjustment to the requirements of the market. Moreover, growth regulators in some cases can improve the fruit colour. In addition, growth regulators can also be used to concentrate maturation within a certain period of time. This establishes the prerequisites for complete mechanical or manual harvesting in a single operation, for example in the case of tobacco, tomatoes or coffee. By using growth regulators, it is additionally possible to influence the resting of seed or buds of the plants, such that plants such as pineapple or ornamental plants in nurseries, for example, germinate, sprout or flower at a time when they are normally not inclined to do so. In areas where there is a risk of frost, it may be desirable to delay budding or germination of seeds with the aid of growth regulators, in order to avoid damage resulting from late frosts.

Finally, growth regulators can induce resistance of the plants to frost, drought or high salinity of the soil. This allows the cultivation of plants in regions which are normally unsuitable for this purpose.

Resistance Induction/Plant Health and Other Effects

The active compounds according to the invention also exhibit a potent strengthening effect in plants. Accordingly, they can be used for mobilizing the defences of the plant against attack by undesirable microorganisms.

Plant-strengthening (resistance-inducing) substances are to be understood as meaning, in the present context, those substances which are capable of stimulating the defence system of plants in such a way that the treated plants, when subsequently inoculated with undesirable microorganisms, develop a high degree of resistance to these microorganisms.

The active compounds according to the invention are also suitable for increasing the yield of crops. In addition, they show reduced toxicity and are well tolerated by plants.

Further, in context with the present invention plant physiology effects comprise the following:

Abiotic stress tolerance, comprising temperature tolerance, drought tolerance and recovery after drought stress, water use efficiency (correlating to reduced water consumption), flood tolerance, ozone stress and UV tolerance, tolerance towards chemicals like heavy metals, salts, pesticides (safener) etc.

Biotic stress tolerance, comprising increased fungal resistance and increased resistance against nematodes, viruses and bacteria. In context with the present invention, biotic stress tolerance preferably comprises increased fungal resistance and increased resistance against nematodes Increased plant vigor, comprising plant health/plant quality and seed vigor, reduced stand failure, improved appearance, increased recovery, improved greening effect and improved photosynthetic efficiency.

Effects on plant hormones and/or functional enzymes.

Effects on growth regulators (promoters), comprising earlier germination, better emergence, more developed root system and/or improved root growth, increased ability of tillering, more productive tillers, earlier flowering, increased plant height and/or biomass, shorting of stems, improvements in shoot growth, number of kernels/ear, number of ears/m$^2$, number of stolons and/or number of flowers, enhanced harvest index, bigger leaves, less dead basal leaves, improved phyllotaxy, earlier maturation/earlier fruit finish, homogenous riping, increased duration of grain filling, better fruit finish, bigger fruit/vegetable size, sprouting resistance and reduced lodging.

Increased yield, referring to total biomass per hectare, yield per hectare, kernel/fruit weight, seed size and/or hectolitre weight as well as to increased product quality, comprising:

improved processability relating to size distribution (kernel, fruit, etc.), homogenous riping, grain moisture, better milling, better vinification, better brewing, increased juice yield, harvestability, digestibility, sedimentation value, falling number, pod stability, storage stability, improved fiber length/strength/uniformity, increase of milk and/or meet quality of silage fed animals, adaption to cooking and frying;

further comprising improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.;

further comprising increased desired ingredients such as e.g. protein content, fatty acids, oil content, oil quality, aminoacid composition, sugar content, acid content (pH), sugar/acid ratio (Brix), polyphenols, starch content, nutritional quality, gluten content/index, energy content, taste, etc.;

and further comprising decreased undesired ingredients such as e.g. less mycotoxines, less aflatoxines, geosmin level, phenolic aromas, lacchase, polyphenol oxidases and peroxidases, nitrate content etc. Sustainable agriculture, comprising nutrient use efficiency, especially nitrogen (N)-use efficiency, phosphours (P)-use efficiency, water use efficiency, improved transpiration, respiration and/or $CO_2$ assimilation rate, better nodulation, improved Ca-metabolism etc.

Delayed senescence, comprising improvement of plant physiology which is manifested, for example, in a longer grain filling phase, leading to higher yield, a longer duration of green leaf colouration of the plant and thus comprising colour (greening), water content, dryness etc. Accordingly, in the context of the present invention, it has been found that the specific inventive application of the active compound combination makes it possible to prolong the green leaf area duration, which delays the maturation (senescence) of the plant. The main advantage to the farmer is a longer grain filling phase leading to higher yield. There is also an advantage to the farmer on the basis of greater flexibility in the harvesting time.

Therein "sedimentation value" is a measure for protein quality and describes according to Zeleny (Zeleny value) the degree of sedimentation of flour suspended in a lactic acid solution during a standard time interval. This is taken as a measure of the baking quality. Swelling of the gluten fraction of flour in lactic acid solution affects the rate of sedimentation of a flour suspension. Both a higher gluten content and a better gluten quality give rise to slower sedimentation and higher Zeleny test values. The sedimentation value of flour depends on the wheat protein composition and is mostly correlated to the protein content, the wheat hardness, and the volume of pan and hearth loaves. A stronger correlation between loaf volume and Zeleny sedimentation volume compared to SDS sedimentation volume could be due to the protein content influencing both the volume and Zeleny value (*Czech J. Food Sci. Vol.* 21, *No.* 3: 91-96, 2000).

Further the "falling number" as mentioned herein is a measure for the baking quality of cereals, especially of wheat. The falling number test indicates that sprout damage may have occurred. It means that changes to the physical properties of the starch portion of the wheat kernel has already happened. Therein, the falling number instrument analyzes viscosity by measuring the resistance of a flour and water paste to a falling plunger. The time (in seconds) for this to happen is known as the falling number. The falling number results are recorded as an index of enzyme activity in a wheat or flour sample and results are expressed in time as seconds. A high falling number (for example, above 300 seconds) indicates minimal enzyme activity and sound quality wheat or flour. A low falling number (for example, below 250 seconds) indicates substantial enzyme activity and sprout-damaged wheat or flour.

The term "more developed root system"/"improved root growth" refers to longer root system, deeper root growth, faster root growth, higher root dry/fresh weight, higher root volume, larger root surface area, bigger root diameter, higher root stability, more root branching, higher number of root hairs, and/or more root tips and can be measured by analyzing the root architecture with suitable methodologies and Image analysis programmes (e.g. WinRhizo).

The term "crop water use efficiency" refers technically to the mass of agriculture produce per unit water consumed and economically to the value of product(s) produced per unit water volume consumed and can e.g. be measured in terms of yield per ha, biomass of the plants, thousand-kernel mass, and the number of ears per m2.

The term "nitrogen-use efficiency" refers technically to the mass of agriculture produce per unit nitrogen consumed and economically to the value of product(s) produced per unit nitrogen consumed, reflecting uptake and utilization efficiency.

Improvement in greening/improved colour and improved photosynthetic efficiency as well as the delay of senescence can be measured with well-known techniques such as a HandyPea system (Hansatech). Fv/Fm is a parameter widely used to indicate the maximum quantum efficiency of photosystem II (PSII). This parameter is widely considered to be a selective indication of plant photosynthetic performance with healthy samples typically achieving a maximum Fv/Fm value of approx. 0.85. Values lower than this will be observed if a sample has been exposed to some type of biotic or abiotic stress factor which has reduced the capacity for photochemical quenching of energy within PSII. Fv/Fm is presented as a ratio of variable fluorescence (Fv) over the maximum fluorescence value (Fm). The Performance Index is essentially an indicator of sample vitality. (See e.g. *Advanced Techniques in Soil Microbiology,* 2007, 11, 319-341; *Applied Soil Ecology,* 2000, 15, 169-182.)

The improvement in greening/improved colour and improved photosynthetic efficiency as well as the delay of senescence can also be assessed by measurement of the net photosynthetic rate (Pn), measurement of the chlorophyll content, e.g. by the pigment extraction method of Ziegler and Ehle, measurement of the photochemical efficiency (Fv/Fm ratio), determination of shoot growth and final root and/or canopy biomass, determination of tiller density as well as of root mortality.

Within the context of the present invention preference is given to improving plant physiology effects which are selected from the group comprising: enhanced root growth/more developed root system, improved greening, improved water use efficiency (correlating to reduced water consumption), improved nutrient use efficiency, comprising especially improved nitrogen (N)-use efficiency, delayed senescence and enhanced yield.

Within the enhancement of yield preference is given as to an improvement in the sedimentation value and the falling number as well as to the improvement of the protein and sugar content—especially with plants selected from the group of cereals (preferably wheat).

Preferably the novel use of the fungicidal compositions of the present invention relates to a combined use of a) preventively and/or curatively controlling pathogenic fungi and/or nematodes, with or without resistance management, and b) at least one of enhanced root growth, improved greening, improved water use efficiency, delayed senescence and enhanced yield. From group b) enhancement of root system, water use efficiency and N-use efficiency is particularly preferred.

Seed Treatment

The invention further comprises a method for treating seed.

The invention further relates to seed which has been treated by one of the methods described in the previous paragraph. The inventive seeds are employed in methods for the protection of seed from harmful microorganisms. In these methods, seed treated with at least one inventive active ingredient is used.

The inventive active ingredients or compositions are also suitable for treating seed. A large part of the damage to crop plants caused by harmful organisms is triggered by the infection of the seed during storage or after sowing, and also during and after germination of the plant. This phase is particularly critical since the roots and shoots of the growing plant are particularly sensitive, and even minor damage may result in the death of the plant. There is therefore a great interest in protecting the seed and the germinating plant by using appropriate compositions.

The control of phytopathogenic fungi by treating the seed of plants has been known for a long time and is the subject of constant improvements. However, the treatment of seed entails a series of problems which cannot always be solved in a satisfactory manner For instance, it is desirable to develop methods for protecting the seed and the germinating plant, which dispense with, or at least significantly reduce, the additional deployment of crop protection compositions after planting or after emergence of the plants. It is also desirable to optimize the amount of the active ingredient used so as to provide the best possible protection for the seed and the germinating plant from attack by phytopathogenic fungi, but without damaging the plant itself by the active ingredient employed. In particular, methods for the treatment of seed should also take account of the intrinsic fungicidal properties of transgenic plants in order to achieve optimal protection of the seed and the germinating plant with a minimum expenditure of crop protection compositions.

The present invention therefore also relates to a method for protection of seed and germinating plants from attack by phytopathogenic fungi, by treating the seed with an inventive composition. The invention likewise relates to the use of the inventive compositions for treatment of seed to protect the seed and the germinating plant from phytopathogenic fungi. The invention further relates to seed which has been treated with an inventive composition for protection from phytopathogenic fungi.

The control of phytopathogenic fungi which damage plants post-emergence is effected primarily by treating the soil and the above-ground parts of plants with crop protection compositions. Owing to the concerns regarding a possible influence of the crop protection compositions on the environment and the health of humans and animals, there are efforts to reduce the amount of active ingredients deployed.

One of the advantages of the present invention is that the particular systemic properties of the inventive active ingredients and compositions mean that treatment of the seed with these active ingredients and compositions not only protects the seed itself, but also the resulting plants after emergence, from phytopathogenic fungi. In this way, the immediate treatment of the crop at the time of sowing or shortly thereafter can be dispensed with.

It is likewise considered to be advantageous that the inventive active ingredients or compositions can especially also be used with transgenic seed, in which case the plant growing from this seed is capable of expressing a protein which acts against pests. By virtue of the treatment of such seed with the inventive active ingredients or compositions, merely the expression of the protein, for example an insecticidal protein, can control certain pests. Surprisingly, a further synergistic effect can be observed in this case, which additionally increases the effectiveness for protection against attack by pests.

The inventive compositions are suitable for protecting seed of any plant variety which is used in agriculture, in greenhouses, in forests or in horticulture and viticulture. In particular, this is the seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cocoa, sugar cane, tobacco, vegetables (such as tomato, cucumbers, onions and lettuce), turf and ornamentals (see also below). The treatment of the seed of cereals (such as wheat, barley, rye, triticale and oats), maize and rice is of particular significance.

As also described below, the treatment of transgenic seed with the inventive active ingredients or compositions is of particular significance. This relates to the seed of plants containing at least one heterologous gene. Definition and examples of suitable heterologous genes are given below.

In the context of the present invention, the inventive composition is applied to the seed alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

When treating the seed, care must generally be taken that the amount of the inventive composition applied to the seed and/or the amount of further additives is selected such that the germination of the seed is not impaired, or that the resulting plant is not damaged. This has to be borne in mind in particular in the case of active ingredients which can have phytotoxic effects at certain application rates.

The inventive compositions can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. Nos. 4,272, 417, 4,245,432, 4,808,430, 5,876,739, US 2003/0176428 A1, WO 2002/080675, WO 2002/028186.

The active ingredients usable in accordance with the invention can be converted to the customary seed dressing formulations, such as solutions, emulsions, suspensions, powders, foams, slurries or other coating compositions for seed, and also ULV formulations.

These formulations are prepared in a known manner, by mixing the active ingredients with customary additives, for example customary extenders and also solvents or diluents, dyes, wetting agents, dispersants, emulsifiers, antifoams, preservatives, secondary thickeners, adhesives, gibberellins and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Preference is given to using alkyl naphthalenesulphonates, such as diisopropyl or diisobutyl naphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The gibberellins which may be present in the seed dressing formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz- and Schädlingsbekämpfungsmittel" [Chemistry of the Crop Protection Compositions and Pesticides], vol. 2, Springer Verlag, 1970, p. 401-412).

The seed dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For treatment of seed with the seed dressing formulations usable in accordance with the invention, or the preparations prepared therefrom by adding water, all mixing units usable customarily for the seed dressing are useful. Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying process.

Mycotoxins

In addition, the inventive treatment can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* etc., and also by Aspergillus spec., such as *A. flavus, A. parasiticus, A. nomius, A. ochraceus, A. clavatus, A. terreus, A. versicolor,* Penicillium spec., such as *P. verrucosum, P. viridicatum, P. citrinum, P. expansum, P. claviforme, P. roqueforti,* Claviceps spec., such as *C. purpurea, C. fusiformis, C. paspali, C. africana, Stachybotrys* spec. and others.

Material Protection

The inventive active ingredients or compositions can also be used in the protection of materials, for protection of industrial materials against attack and destruction by harmful microorganisms, for example fungi and insects. In addition, the inventive compounds can be used as antifouling compositions, alone or in combinations with other active ingredients.

Industrial materials in the present context are understood to mean inanimate materials which have been prepared for use in industry. For example, industrial materials which are to be protected by inventive active ingredients from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The inventive active ingredients or compositions may prevent adverse effects, such as rotting, decay, discoloration, decoloration or formation of mould.

In the case of treatment of wood the compounds/compositions according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention or a composition according to the invention; this includes for example direct application, spraying, dipping, injection or any other suitable means.

In addition, the inventive compounds can be used to protect objects which come into contact with saltwater or brackish water, especially hulls, screens, nets, buildings, moorings and signalling systems, from fouling.

The inventive method for controlling unwanted fungi can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive active ingredients may prevent adverse effects, such as rotting, decay, discoloration, decoloration or formation of mould.

Microorganisms capable of degrading or altering the industrial materials include, for example, bacteria, fungi, yeasts, algae and slime organisms. The inventive active ingredients preferably act against fungi, especially moulds, wood-discoloring and wood-destroying fungi (*Ascomycetes, Basidiomycetes, Deuteromycetes* and *Zygomycetes*), and against slime organisms and algae. Examples include microorganisms of the following genera: *Alternaria*, such as *Alternaria tenuis; Aspergillus*, such as *Aspergillus niger; Chaetomium*, such as *Chaetomium globosum; Coniophora*, such as *Coniophora puetana; Lentinus*, such as *Lentinus tigrinus; Penicillium*, such as *Penicillium glaucum; Polyporus*, such as *Polyporus versicolor; Aureobasidium*, such as *Aureobasidium pullulans; Sclerophoma*, such as *Sclerophoma pityophila; Trichoderma*, such as *Trichoderma viride; Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli; Pseudomonas*, such as *Pseudomonas aeruginosa; Staphylococcus*, such as *Staphylococcus aureus, Candida* spp. and *Saccharomyces* spp., such as *Saccharomyces cerevisae*.

Antimycotic Activity

In addition, the inventive active ingredients also have very good antimycotic activity. They have a very broad antimycotic activity spectrum, especially against dermatophytes and yeasts, moulds and diphasic fungi (for example against *Candida* species, such as *C. albicans, C. glabrata*), and *Epidermophyton floccosum, Aspergillus* species, such as *A. niger* and *A. fumigatus, Trichophyton* species, such as *T. mentagrophytes, Microsporon* species such as *M. canis* and *M. audouinii*. The list of these fungi by no means constitutes a restriction of the mycotic spectrum covered, and is merely of illustrative character.

The inventive active ingredients can therefore be used both in medical and in non-medical applications.

GMO

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts" or "parts of plants" or "plant parts" have been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids. Examples of nematode or insect resistant plants are described in e.g. U.S. patent applications Ser. Nos. 11/765,491, 11/765,494, 10/926,819, 10/782,020, 12/032,479, 10/783,417, 10/782,096, 11/657,964, 12/192, 904, 11/396,808, 12/166,253, 12/166,239, 12/166,124, 12/166,209, 11/762,886, 12/364,335, 11/763,947, 12/252, 453, 12/209,354, 12/491,396, 12/497,221, 12/644,632, 12/646,004, 12/701,058, 12/718,059, 12/721,595, 12/638, 591.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069). Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enol-pyruvylshikimate-3-phosphate synthase (EPSPS). Examples of such EPSPS genes are the AroA gene (mutant CT7) of the bacterium *Salmonella typhimurium* (*Science* 1983, 221, 370-371), the CP4 gene of the bacterium *Agrobacterium* sp. (*Curr. Topics Plant Physiol.* 1992, 7, 139-145), the genes encoding a Petunia EPSPS (*Science* 1986, 233, 478-481), a Tomato EPSPS (*J. Biol. Chem.* 1988, 263, 4280-4289), or an Eleusine EPSPS (WO 01/66704). It can also be a mutated EPSPS as described in for example EP 0837944, WO 00/66746, WO 00/66747 or WO 02/26995. Glyphosate-tolerant plants can also be obtained by expressing a gene that encodes a glyphosate oxido-reductase enzyme as described in U.S. Pat. No. 5,776,760 and U.S. Pat. No. 5,463,175. Glyphosate-tolerant plants can also be obtained by expressing a gene that encodes a glyphosate acetyl transferase enzyme as described in for example WO 02/036782, WO 03/092360, WO 2005/012515 and WO 2007/024782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent applications Ser. Nos. 11/517,991, 10/739,610, 12/139,408, 12/352,532, 11/312,866, 11/315,678, 12/421, 292, 11/400,598, 11/651,752, 11/681,285, 11/605,824, 12/468,205, 11/760,570, 11/762,526, 11/769,327, 11/769, 255, 11/943801 or 12/362,774. Plants comprising other genes that confer glyphosate tolerance, such as decarboxylase genes, are described in e.g. U.S. patent applications Ser. Nos. 11/588,811, 11/185,342, 12/364,724, 11/185,560 or 12/423,926.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from Streptomyces species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD). HPPD is an enzyme that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 09/144079, WO 02/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 04/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy-(thio) benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (Weed Science 2002, 50, 700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 2007/024782 and U.S. Patent Application 61/288958.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from Bacillus thuringiensis or an insecticidal portion thereof, such as the insecticidal crystal proteins listed by Crickmore et al. (1998, Microbiology and Molecular Biology Reviews, 62: 807-813), updated by Crickmore et al. (2005) at the Bacillus thuringiensis toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP-A 1 999 141 and WO 2007/107302), or such proteins encoded by synthetic genes as e.g. described in and U.S. patent application Ser. No. 12/249,016 ; or 2) a crystal protein from Bacillus thuringiensis or a portion thereof which is insecticidal in the presence of a second other crystal protein from Bacillus thuringiensis or a portion thereof, such as the binary toxin made up of the Cry34 and Cry35 crystal proteins (Nat. Biotechnol. 2001, 19, 668-72; Applied Environm. Microbiol. 2006, 71, 1765-1774) or the binary toxin made up of the Cry1A or Cry1F proteins and the Cry2Aa or Cry2Ab or Cry2Ae proteins (U.S. patent application Ser. No. 12/214,022 and EP-A 2 300 618); or 3) a hybrid insecticidal protein comprising parts of different insecticidal crystal proteins from Bacillus thuringiensis, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from Bacillus thuringiensis or Bacillus cereus, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from Bacillus thuringiensis or Bacillus cereus which is insecticidal in the presence of a second secreted protein from Bacillus thuringiensis or B. cereus, such as the binary toxin made up of the VIP1A and VIP2A proteins (WO 94/21795); or 7) a hybrid insecticidal protein comprising parts from different secreted proteins from Bacillus thuringiensis or Bacillus cereus, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from Bacillus thuringiensis, such as the binary toxin made up of VIP3 and Cry1A or Cry1F (U.S. Patent Applications 61/126083 and 61/195019), or the binary toxin made up of the VIP3 protein and the Cry2Aa or Cry2Ab or Cry2Ae proteins (U.S. patent application Ser. No. 12/214,022 and EP-A 2 300 618).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO 2006/045633, EP-A 1 807 519, or EP-A 2 018 431.

2) plants which contain a stress tolerance enhancing transgene capable of reducing the expression and/or the activity of the PARG encoding genes of the plants or plants cells, as described e.g. in WO 2004/090140.

3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP-A 1 794 306, WO 2006/133827, WO 2007/107326, EP-A 1 999 263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP-A 0 571 427, WO 95/04826, EP-A 0 719 338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO 99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 04/056999, WO 05/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, WO 2008/017518, WO 2008/080630, WO 2008/080631, WO 2008/090008, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. No. 5,824,790, U.S. Pat. No. 6,013,861, WO 94/04693, WO 94/09144, WO 94/11520, WO 95/35026, WO 97/20936, WO 2010/012796, WO 2010/003701, 2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP-A 0 663 956, WO 96/01904, WO 96/21023, WO 98/39460, and WO 99/24593, plants producing alpha-1,4-glucans as disclosed in WO 95/31553, US 2002031826, U.S. Pat. No. 6,284,479, U.S. Pat. No. 5,712,107, WO 97/47806, WO 97/47807, WO 97/47808 and WO 00/14249, plants producing alpha-1,6 branched alpha-1,4-glucans, as disclosed in WO 00/73422, plants producing alternan, as disclosed in e.g. WO 00/47727, WO 00/73422, U.S. Pat. No. 5,908,975 and EP-A 0 728 213, 3) transgenic plants which produce hyaluronan, as for example disclosed in WO 2006/032538, WO 2007/039314, WO 2007/039315, WO 2007/039316, JP-A 2006-304779, and WO 2005/012529.

4) transgenic plants or hybrid plants, such as onions with characteristics such as 'high soluble solids content', 'low pungency' (LP) and/or 'long storage' (LS), as described in U.S. patent applications Ser. No. 12/020,360.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:
a) Plants, such as cotton plants, containing an altered form of cellulose synthase genes as described in WO 98/00549.
b) Plants, such as cotton plants, containing an altered form of rsw2 or rsw3 homologous nucleic acids as described in WO 2004/053219.
c) Plants, such as cotton plants, with increased expression of sucrose phosphate synthase as described in WO 01/17333.
d) Plants, such as cotton plants, with increased expression of sucrose synthase as described in WO 02/45485.
e) Plants, such as cotton plants, wherein the timing of the plasmodesmatal gating at the basis of the fiber cell is altered, e.g. through downregulation of fiber-selective β-1,3-glucanase as described in WO 2005/017157, or as described in WO 2009/143995.
f) Plants, such as cotton plants, having fibers with altered reactivity, e.g. through the expression of N-acetylglucosaminetransferase gene including nodC and chitin synthase genes as described in WO 2006/136351.

Plants or plant cultivars (that can be obtained by plant biotechnology methods such as genetic engineering) which may also be treated according to the invention are plants, such as oilseed rape or related Brassica plants, with altered oil profile characteristics. Such plants can be obtained by genetic transformation, or by selection of plants contain a mutation imparting such altered oil profile characteristics and include:
a) Plants, such as oilseed rape plants, producing oil having a high oleic acid content as described e.g. in U.S. Pat. No. 5,969,169, U.S. Pat. No. 5,840,946 or U.S. Pat. No. 6,323,392 or U.S. Pat. No. 6,063,947
b) Plants such as oilseed rape plants, producing oil having a low linolenic acid content as described in U.S. Pat. No. 6,270,828, U.S. Pat. No. 6,169,190, or U.S. Pat. No. 5,965,755
c) Plant such as oilseed rape plants, producing oil having a low level of saturated fatty acids as described e.g. in U.S. Pat. No. 5,434,283 or U.S. patent application Ser. No. 12/668303

Plants or plant cultivars (that can be obtained by plant biotechnology methods such as genetic engineering) which may also be treated according to the invention are plants, such as oilseed rape or related Brassica plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Application 61/135,230, WO 2009/068313 and WO 2010/006732.

Plants or plant cultivars (that can be obtained by plant biotechnology methods such as genetic engineering) which may also be treated according to the invention are plants, such as Tobacco plants, with altered post-translational protein modification patterns, for example as described in WO 2010/121818 and WO 2010/145846.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road, Riverdale, Md. 20737, USA), for instance on its interne site (URL http://www.aphis.usda.gov/brs/not_reg.html). On the filing date of this application the petitions for nonregulated status that were pending with APHIS or granted by APHIS were those which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for examplehttp://gmoinfo.jrc.it/gmp_browse.aspx and http://www.agbios.com/dbase.php).

Application Rates and Timing

When using the inventive active ingredients as fungicides, the application rates can be varied within a relatively wide range, depending on the kind of application. The application rate of the inventive active ingredients is in the case of treatment of plant parts, for example leaves: from 0.1 to 10 000 g/ha, preferably from 10 to 1000 g/ha, more preferably from 10 to 800 g/ha, even more preferably from 50 to 300 g/ha (in the case of application by watering or dripping, it is even possible to reduce the application rate, especially when inert substrates such as rockwool or perlite are used);

in the case of seed treatment: from 2 to 200 g per 100 kg of seed, preferably from 3 to 150 g per 100 kg of seed, more preferably from 2.5 to 25 g per 100 kg of seed, even more preferably from 2.5 to 12.5 g per 100 kg of seed;

in the case of soil treatment: from 0.1 to 10 000 g/ha, preferably from 1 to 5000 g/ha.

These application rates are merely by way of example and are not limiting for the purposes of the invention.

The inventive active ingredients or compositions comprising a compound according to formula (I) can thus be used to protect plants from attack by the pathogens mentioned for a certain period of time after treatment. The period for which protection is provided extends generally for 1 to 28 days, preferably for 1 to 14 days, more preferably for 1 to 10 days, most preferably for 1 to 7 days, after the treatment of the plants with the active ingredients, or for up to 200 days after a seed treatment.

The plants listed can particularly advantageously be treated in accordance with the invention with the compounds of the general formula (I) and the inventive compositions. The preferred ranges stated above for the active ingredients or compositions also apply to the treatment of these plants.

Particular emphasis is given to the treatment of plants with the compounds or compositions specifically mentioned in the present text.

The invention is illustrated by the examples below. However, the invention is not limited to the examples.

PREPARATION EXAMPLES

Preparation of 6-quinolinecarbaldehyde (According to Process 17 A)

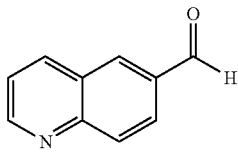 [SMILES: O=Cc1ccc2ncccc2c1]

Into a 50 mL microwave reactor was added selenium(IV) oxide (6.20 g) and 6-methylquinoline (12.0 g). The reaction was then heated for 2 min at 500 W at 150° C., a further 2 min at 300 W and 190° C. and finally 1 h at 190° C. The medium was then poured into dichloromethane (250 mL), filtrated and concentrated under reduced pressure to give a brown oil that was further purified by chromatography on silica gel to furnish the title compound as a yellow powder (12.2 g). Analytical data matched those reported in the literature.

Preparation of 3-iodoquinoline-6-carbaldehyde (According to Process 17 B)

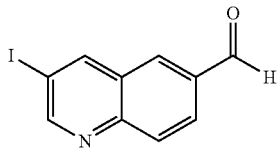 [SMILES: O=Cc1ccc2ncc(I)cc2c1]

3-Iodo-6-methylquinoline (10.0 g) and selenium(IV) oxide (4.95 g) were heated at 160° C. for 8 h. After cooling, the solids were removed by suction filtration and the crude material purified by chromatography on silica gel to furnish the title compound as a brown solid (5.00 g); m.p. 145-149° C.; logP (HCOOH): 2.12.

Preparation of 3-bromoquinoline-6-carbaldehyde (According to Process 17 B)

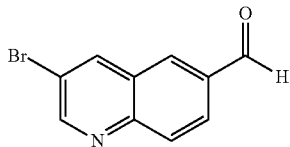 [SMILES: O=Cc1ccc2ncc(Cl)cc2c1]

Bromine (1.10 g) was added dropwise to a stirred solution of 6-quinolinecarbaldehyde (1.00 g) in pyridine (4.90 g) at room temperature. The reaction mixture was warmed to reflux. After 2 h at reflux a further portion of bromine (3.30 g) was added and the mixture kept at reflux for 4 h. The reaction mixture was then cooled to room temperature subsequently poured into ice-water. The organic components were extracted with ethyl acetate, the organic layer washed with aq. NaHSO3 solution (10%) and concentrated. The crude material was purified by chromatography on silica gel to furnish the title compound as a pale yellow solid (1.12 g); m.p. 142-145° C.; logP (HCOOH) 2.08.

Preparation of 3-chloroquinoline-6-carbaldehyde According to Process 17 B

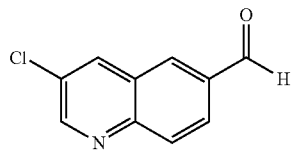

To a stirred solution of quinolin-6-carbaldehyde (2.0 g) in acetic acid (20 mL) at room temperature was added N-chlorosuccinimide (3.4 g). The reaction mixture was then stirred at 80° C. for 16 h. Standard work-up and chromatography on silica gel afforded the title compound as an off-white solid (1.0 g); m.p. 130-132° C.; logP (HCOOH): 1.96.

Preparation of 3-bromo-7,8-difluoroquinoline-6-carbaldehyde (According to Process 14)

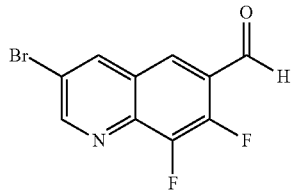 [SMILES: O=Cc1cc2cc(Br)cnc2c(F)c1F]

To a stirred solution of 3-bromo-7,8-difluoroquinoline-6-carbonitrile (4.20 g) in dichloromethane at -5° C. was added di-idobutylaluminium hydride (1M in dichloromethane, 2.66 g). Stirring was continued for 2 h at −5° C. and a further 2 h at room temperature. The reaction mixture was then treated with aq. HCl (1 M, 50 mL) at −5° C. and the organic components extracted with dichloromethane. The organic layer was washed with aq NAHCO3 (10%, 100 mL) and condensed in vacuo. Chromatography on silica gel provided the title compound as a yellow solid (4.10 g); LC-MS: [MH]+ 272 and 274; logP (HCOOH) 2.71

Preparation of 1-(3-chloroquinolin-6-yl)-N-hydroxymethanimine (According to Process 13)

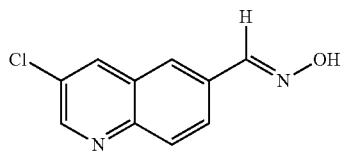 [SMILES: O/N=C/c1ccc2ncc(Cl)cc2c1]

To a stirred solution of 3-chloroquinoline-6-carbaldehyde (7.0 g) in methanol (70 mL) was added at room temperature amberlist (7.0 g) and hydroxylamine hydrochloride (3.0 g). The reaction was stirred for 16 h. Standard work-up furnished the crude material as an off-white solid that could be used without further purification (5.0 g); m.p. 212-214° C.; logP (HCOOH): 1.78.

Preparation of
1-(3-iodoquinolin-6-yl)-N-hydroxymethanimine
(According to Process 13)

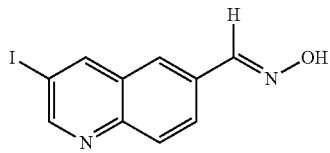 [SMILES: O/N=C/c1ccc2ncc(I)cc2c1]

As above: 3-iodoquinoline-6-carbaldehyde (5.0 g) was converted to the title compound as an off-white solid (4.0 g); m.p. 229-232° C.; logP (HCOOH) 1.98.

Preparation of
3-chloro-N-hydroxyquinoline-6-carboximidoyl
chloride (According to Process 12)

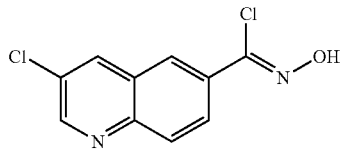 [SMILES: O/N=C(\Cl)c1ccc2ncc(Cl)cc2c1]

To a stirred solution of 1-(3-chloroquinolin-6-yl)-N-hydroxymethanimine (5.0 g) in DMF (25 mL) was added at room temperature N-chlorosuccinimide (2.68 g) and the reaction mixture was stirred at that temperature for 4 h. Standard work-up furnished the crude material that could be used without further purification (3.9 g); logP (HCOOH): 1.96.

Preparation of
3-Iodo-N-hydroxyquinoline-6-carboximidoyl
chloride (According to Process 12)

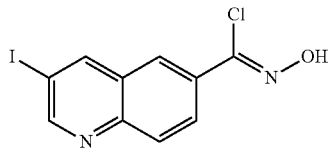 [SMILES: O/N=C(\Cl)c1ccc2ncc(I)cc2c1]

As above: 1-(3-iodoquinolin-6-yl)-N-hydroxymethanimine (4.0 g) was converted into 3-Iodo-N-hydroxyquinoline-6-carboximidoyl chloride as an off-white solid (3.0 g): m.p. 201-205° C.; logP (HCOOH) 2.63.

Preparation of Compound No. 11-23 (According to Process 10)

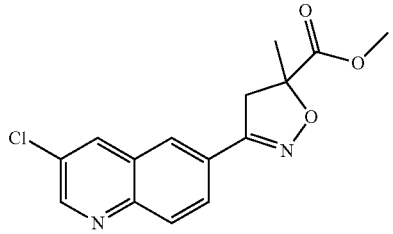 [SMILES: COC(=O)C1(C)CC(c2ccc3ncc(Cl)cc3c2)=NO1]

To a stirred solution of 3-chloro-N-hydroxyquinoline-6-carboximidoyl chloride (3.5 g) and methyl methacrylate (1.45 g) in chloroform (35 mL) at room temperature was added triethylamine (2.93 g) and the resulting mixture was stirred at that temperature for 2 h. Standard work-up and chromatography on silica gel afforded the title compound as an off-white solid (2.0 g); m.p. 113-115° C.; logP (HCOOH) 2.58.

Preparation of Compound No. 11-30 (According to Process 10)

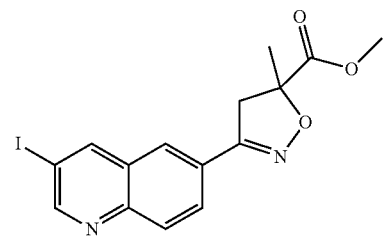 [SMILES: COC(=O)C1(C)CC(c2ccc3ncc(I)cc3c2)=NO1]

As above: 3-iodo-N-hydroxyquinoline-6-carboximidoyl chloride (3.0 g) was converted into the title compound as an off-white solid (2.5 g); m.p. 93-96° C.; logP (HCOOH) 2.71.

Preparation of Compound No. II-01 (According to Process 2A)

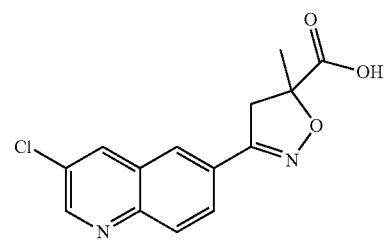 [SMILES: CC1(C(=O)O)CC(c2ccc3ncc(Cl)cc3c2)=NO1]

To a stirred solution of methyl 3-(3-chloroquinolin-6-yl)-5-methyl-4,5-dihydro-1,2-oxazole-5-carboxylate (2.0 g) in methanol (10 mL) at room temperature was added aq. NaOH (2 M, 10 mL). The final mixture was stirred at that temperature for 2 h. Standard acid-base work-up provided the title compound as an off-white solid (1.1 g); m.p. 141-145° C.; logP (HCOOH) 1.87.

Preparation of Compound No. 11-09 (According to Process 2A)

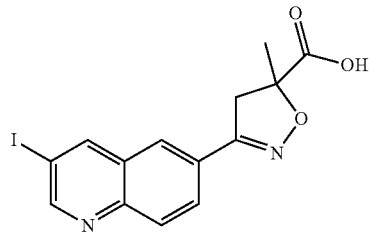 [SMILES: CC1(C(=O)O)CC(c2ccc3ncc(I)cc3c2)=NO1]

As above: methyl 3-(3-chloroquinolin-6-yl)-5-methyl-4,5-dihydro-1,2-oxazole-5-carboxylate (2.5 g) was converted to give the target compound as a yellow solid (1.8 g); m.p. 235-240° C.; logP (HCOOH) 1.93.

Preparation of Compound No. 55 (According to Process 1)

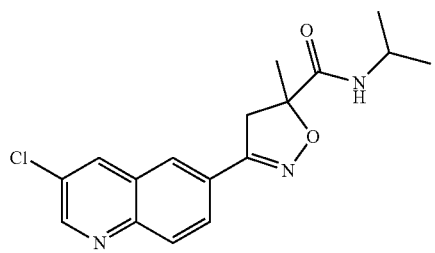 [SMILES: CC(C)NC(=O)C1(C)CC(c2ccc3ncc(Cl)cc3c2)=NO1]

To a stirred solution of 3-(3-chloroquinolin-6-yl)-5-methyl-4,5-dihydro-1,2-oxazole-5-carboxylic acid (500 mg) in DMF (5 mL) were added subsequently at room temperature O-(Benzotriazol-1-yl-N,N,N',N'-tetramethyluronium tetra fluoroborate (664 mg), di-isopropyl ethylamine (667 mg) and isopropylamine (305 mg). The mixture was stirred at that temperature for 1 h. Standard work-up and preparative HPLC provided the target compound as an off-white solid (100 mg); m.p. 167-170° C.; logP (HCOOH) 2.61.

Preparation of Compound No. 38 (According to Process 1)

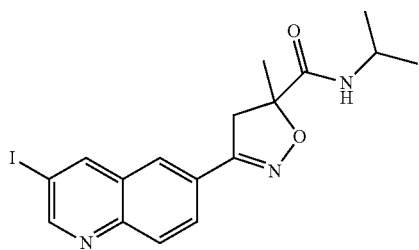 [SMILES: CC(C)NC(=O)C1(C)CC(c2ccc3ncc(I)cc3c2)=NO1]

As above: 3-(3-chloroquinolin-6-yl)-5-methyl-4,5-dihydro-1,2-oxazole-5-carboxylic acid (500 mg) was converted to give the target compound as an off-white solid (390 mg); m.p. 208-210° C.; logP (HCOOH) 2.88.

Preparation of Compound No. 259 (According to Process 3)

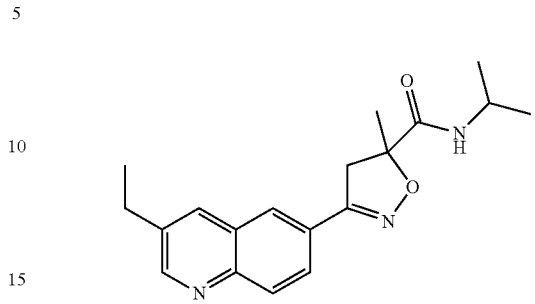

To a stirred solution of 3-(3-iodoquinolin-6-yl-N-isopropyl-5-methyl-4,5-dihydro-1,2-oxazole-5-carboxamide (108 mg) in toluene (2.6 g) and water (200 mg) was added palladium acetate (5.2 mg), tricyclohexylphosphine (12.9 mg) and potassium phosphate (293 mg). The reaction was stirred at 100° C. for 4 h and left to stand for a further 16 h. The reaction mixture was poured into water and extracted three times with ethyl acetate, the organic layers were washed with brine and concentrated in vacuo. The crude product was purified by chromatography on silica gel to afford the target compound as an orange solid (21 mg); logP (HCOOH) 1.94.

Preparation of Compound No. 258 (According to Process 3)

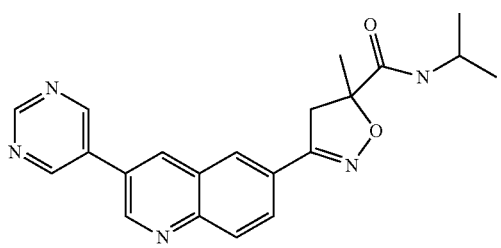 [SMILES: CC(C)NC(=O)C1(C)CC(c2ccc3ncc(-c4cncnc4)cc3c2)=NO1]

To a stirred solution of 3-(3-iodoquinolin-6-yl)-N-Nisopropyl-5-methyl-4,5-dihydro-1,2-oxazole-5-carboxamide (111 mg) in acetonitrile (10 mL) was added pyrimidin-5-boronic acid (35 mg), potassium carbonate (65 mg) and tetrakis(triphenylphosphine)palladium (27 mg). The reaction was stirred at reflux for 4 h and the left to stand for a further 16 h. The reaction mixture was poured into water and extracted three times with ethyl acetate, the organic layers were washed with brine and concentrated in vacuo. The crude product was purified by chromatography on silica gel to afford the target compound as an orange solid (29 mg); logP (HCOOH) 1.79.

Preparation of Compound No. 150 (According to Process 3)

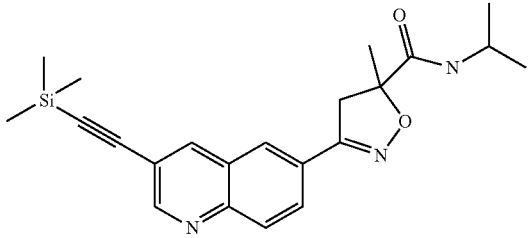 [SMILES: CC(C)NC(=O)C1(C)CC(c2ccc3ncc(C#C[Si](C)(C)C)cc3c2)=NO1]

To a degassed solution of 3-(3-iodoquinolin-6-yl)-N-isopropyl-5-methyl-4,5-dihydro-1,2-oxazole-5-carboxamide (400 mg) in di-isopropyl ethylamine (10 mL) was added copper(I) iodide (4.5 mg), tetrakis(triphenylphosphine)palladium (109 mg) and finally (trimethylsilyl)acetylene (371 mg). The reaction was stirred at 90° C. for 6 h in a sealed tube. After cooling, the reaction mixture was poured into water and extracted three times with ethyl acetate, the organic layers were washed with brine and concentrated in vacuo. The crude product was purified by chromatography on silica gel to afford the target compound (180 mg); logP (HCOOH) 4.41.

Preparation of Compound No. 144 (According to Process 3)

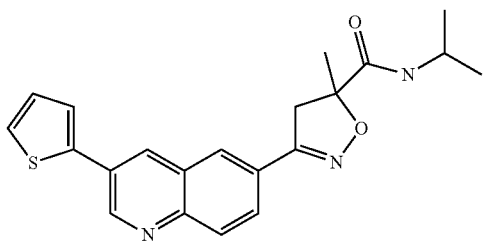 [SMILES: CC(C)NC(=O)C1(C)CC(c2ccc3ncc(-c4cccs4)cc3c2)=NO1]

To a stirred solution of 3-(3-iodoquinolin-6-yl-N-isopropyl-5-methyl-4,5-dihydro-1,2-oxazole-5-carboxamide (60 mg) in DMF (660 mg) was added 2-thiopheneboronic acid (24 mg), palladium acetate (1.6 mg) and potassium carbonate (59 mg). The reaction was then stirred at 100° C. for 2.5 h. The reaction mixture was poured into water and extracted three times with ethyl acetate, the organic layers were washed with brine and concentrated in vacuo. The crude product was purified by chromatography on silica gel to afford the target compound as a brown solid (13 mg); logP (HCOOH) 3.04.

Preparation of Compound No. 141 (According to Process 3)

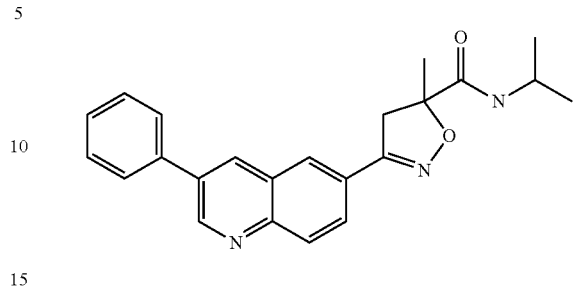

The target compound was prepared in analogous manner as mentioned for Example 19 above to afford the desired compound as an off-white solid (20 mg); logP (HCOOH) 3.02.

Preparation of Compound No. 266 (According to Process 2)

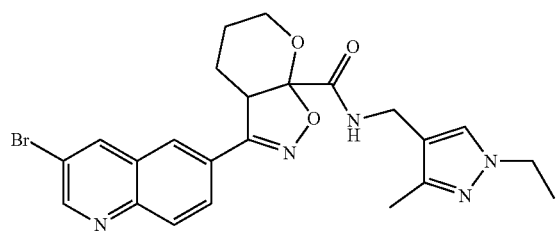 [SMILES: CCn1cc(CNC(=O)C23OCCCC2C(c2ccc4ncc(Br)cc4c2)=NO3)c(C)n1]

To a stirred solution of methyl 3-(3-bromoquinolin-6-yl)-3a,4,5,6-tetrahydro-7aH-pyrano[3,2-d][1,2]oxazole-7a-carboxylate (compound II-32) (120 mg) in toluene (5 mL) was added at room temperature under argon trimethylaluminium (2 M in toluene, 0.5 mL) and 1-(1-ethyl-3-methyl-1H-pyrazol-4-yl)methanamine (51 mg). The final mixture was stirred at room temperatrure for 2 h before it was diluted with ethyl acetate (25 mL) and washed with aq. sat. NaCl (50 mL). After removal of the volatiles in vacuo, the crude material was purified by chromatography on silica gel to afford the target compound (53 mg); logP (HCOOH) 2.59.

Preparation of 2 (difluoromethyl)prop 2 en 1 yl acetate (According to Process in Scheme 8A)

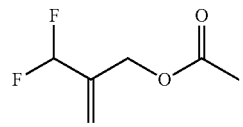

2-(hydroxymethyl)prop-2-en-1-yl acetate (31.5 g) was dissolved in dichloromethane (800 mL) and manganese(IV) dioxide (105 g) was added. The reaction was stirred at room temperature until all starting material had been consumed. The mixture was then filtered and cooled to 0° C. The crude 2-formylprop-2-en-1-yl acetate was treated with diethylaminosulfur trifluoride (78 g) and left to stir at room temperature for 16 h. The mixture was cooled in an ice/salt bath and water (50 mL) and aq. sat. NaHCO₃ (100 mL) were added dropwise. The mixture was washed with aq. sat. NaHCO$_3$, the aqueous layer was extracted with dichloromethane. The combined organic layers were washed with aq. sat. NaCl dried over Na$_2$SO$_4$, filtered and concentrated at 40° C. and 750 mbar to afford the target compound as a light brown liquid (57.5 g, incl. 69% dichloromethane) which was used without further purification.

Preparation of [3-(3-bromoquinolin-6-yl)-5-(difluoromethyl)-4,5-dihydro-1,2-oxazol-5-yl]methyl acetate (According to Process 8A)

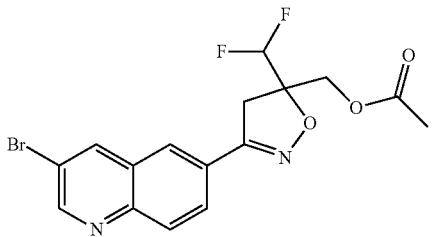 [SMILES: CC(=O)OCC1(C(F)F)CC(c2ccc3ncc(Br)cc3c2)=NO1]

To a suspension of 1-(3-bromoquinolin-6-yl)-N-hydroxymethanimine (12.5 g) in dry N,N-dimethylformamide (250 mL) was added N-chlorosuccinimide (6.65 g). The resulting suspension was stirred at 60° C. for 1 h. The mixture was allowed to cool to room temperature before 2-(difluoromethyl)prop-2-en-1-yl acetate (24.1 g, 31% purity) and NaHCO$_3$ (8.36 g) were added and the mixture was stirred at room temperature for 16 h. The mixture was concentrated, dichloromethane was added and the mixture was filtered. The filtrate was washed with water and aq. sat. NaCl dried over Na$_2$SO$_4$ and concentrated. Chromatography on silica gel provided the target compound as a white solid (7.69 g)

Preparation of [3-(3-bromoquinolin-6-yl)-5-(difluoromethyl)-4,5-dihydro-1,2-oxazol-5-yl]methanol (According to Process 8A)

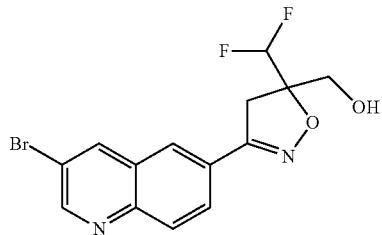 [SMILES: OCC1(C(F)F)CC(c2ccc3ncc(Br)cc3c2)=NO1]

[3-(3-bromoquinolin-6-yl-5-(difluoromethyl)-4,5-dihydro-1,2-oxazol-5-yl]methyl acetate (7.69 g) was dissolved in methanol (150 mL) and aqueous NaOH (1M, 38.5 mL) was added. The mixture was stirred at 50° C. for 90 min, then cooled to room temperature and concentrated. The residue was partitioned between water and dichloromethane. The aqueous layer was extracted using dichloromethane. The combined organic layers were dried over Na$_2$SO$_4$, filtered and concentrated to afford the target compound as an off-white solid (2.65 g). In addition, the aqueous layer was filtered to afford further target compound as an off-white solid (2.97g).

Preparation of 3-(3-bromoquinolin-6-yl)-5-(difluoromethyl)-4,5-dihydro-1,2-oxazole-5-carboxylic acid (According to Process 8A)

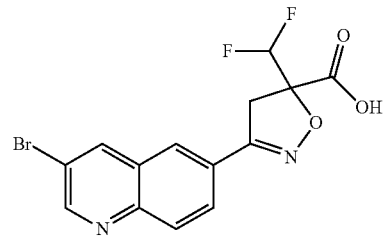 [SMILES: O=C(O)C1(C(F)F)CC(c2ccc3ncc(Br)cc3c2)=NO1]

Sulfuric acid (15.43 g) was added to chromium(VI) oxide (7.87 g) which was diluted with water (100 mL) while cooling in an ice-bath. The obtained mixture was added dropwise to a solution of [3-(3-bromoquinolin-6-yl)-5-(difluoromethy)-4,5-dihydro-1,2-oxazol-5-yl ]methanol (5.62 g) in acetone (100 mL). The yellow mixture was stirred at 50° C. overnight. Propan-2-ol (125 mL) was added after which the green mixture turned blue. Water (750 mL) was added and the mixture was extracted with ethylacetate (EtOAc) (2×500 mL). The combined organic layers were washed with aq. sat. NaCl dried over Na$_2$SO$_4$, filtered and concentrated to afford the title compound as a pale green solid (4.73 g).

Preparation of Compound No. 623 (According to Process 1)

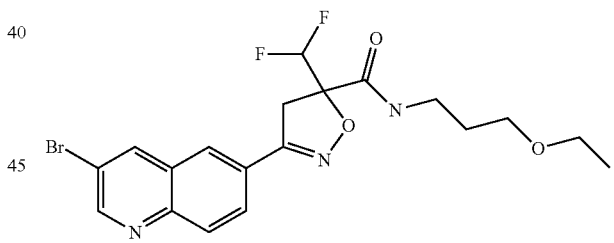

To a solution of 3-(3-bromoquinolin-6-yl)-5-(difluoromethyl)-4,5-dihydro-1,2-oxazole-5-carboxylic acid (300 mg) in dichloromethane was added one drop of N,N-dimethylformamide. Oxalyl chloride (154 mg) was added and the mixture was stirred at room temperature for 30 min before being concentrated and stripped with toluene twice to afford the intermediate 3-(3-bromoquinolin-6-yl)-5-(difluoromethyl-4,5-dihydro-1,2-oxazole-5-carbonyl chloride (315 mg). This acid chloride was dissolved in dichloromethane (10 mL) and dry N,N-dimethylformamide (5 mL). To this was added 3-ethoxypropan-1-amine (92 mg) and N,N-diisopropylethylamine (209 mg). The mixture was stirred at room temperature for 1 h before being concentrated. Chromatography on silica gel provided the target compound as a white solid (227 mg). LC-MS: [MH]$^+$ 456 and 458; logP (HCOOH) 3.06

Preparation of Compound No. 615 (According to Process 3)

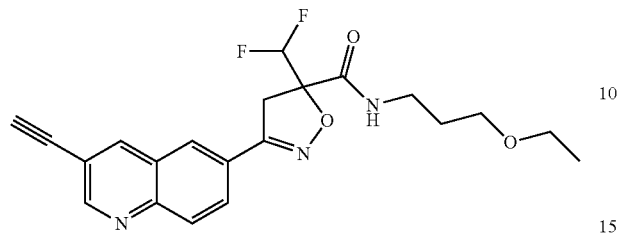

To a solution of 3-(3-bromoquinolin-6-yl-5-(difluoromethyl)-N-(3-ethoxypropy0-4,5-dihydro-1,2-oxazole-5-carboxamide (720 mg) in triethylamine (6 mL) and dry N,N-dimethylformamide (6 mL) was added copper(I) iodide (6 mg) while the mixture was flushed with argon. Trimethylsilylacetylene (465 mg) and tetrakis(triphenylphosphine)palladium(0) (91 mg) were added under argon. The microwave vial as sealed and the mixture was stirred at 100° C. for 30 min while irradiated with microwaves. A solution of tetra-N-butylammonium fluoride in THF (1M, 3.16 mL) was added and the mixture was stirred at room temperature for 1 h. The volatiles were removed and the crude residue purified on silica gel and reversed phase column chromatography to provide the target compound as an off-white solid (329 mg). LC-MS: [MH]$^+$ 402; logP (HCOOH) 2.73

Preparation of methyl 3-(3-bromoquinolin-6-yl)-5-(1-hydroxyethyl)-4,5-dihydro-1,2-oxazole-5-carboxylate (According to Process 9)

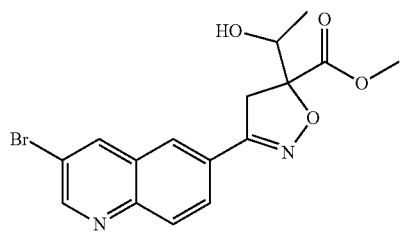 [SMILES: COC(=O)C1(C(C)O)CC(c2ccc3ncc(Br)cc3c2)=NO1]

To a suspension of 3-bomomoquinoline-6-carbaldehyde oxime (11.2 g) in dry N,N-dimethylformamide (250 mL) was added N-chlorosuccinimide (5.96 g). The resulting yellow suspension was stirred at 60° C. for 1 h. The mixture was allowed to cool to room temperature. Methyl 3-hydroxy-2-methylenebutanoate (5.81 g) and sodium hydrogen carbonate (7.49 g) were added and the mixture was stirred at room temperature overnight. The mixture was concentrated, EtOAc was added and the suspension was washed with water and aq. sat. NaCl. The organic layer was dried over Na$_2$SO$_4$, filtered and concentrated. The orange residue was purified on silica to afford the target compound (13.5 g).

Preparation of methyl 3-(3-bromoquinolin-6-yl)-5-(1-{[(trifluoromethyl)sulfonyl]oxy}ethyl)-4,5-dihydro-1,2-oxazole-5-carboxylate (According to Process 8B with Isolation of Intermediate)

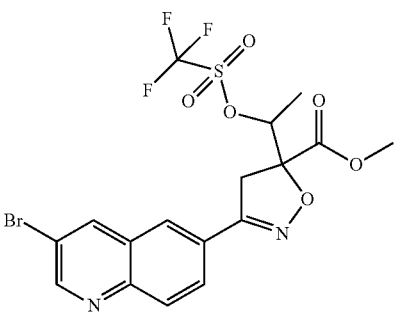 [SMILES: COC(=O)C1(C(C)OS(=O)(=O)C(F)(F)F)CC(c2ccc3ncc(Br)cc3c2)=NO1]

To a solution of methyl 3-(3-bromoquinolin-6-yl)-5-(1-hydroxyethyl)-4,5-dihydro-1,2-oxazole-5-carboxylate (13.5 g) in dichloromethane (500 mL) was added pyridine (5.36 g). The mixture was cooled to 0° C. and trifluoromethanesulfonic anhydride (12.4 g) was added dropwise. The mixture was stirred for 30 min while warming to room temperature. The mixture was then washed with water and aq. sat. NaCl dried over Na$_2$SO$_4$, filtered and concentrated to afford the target compound (18.1 g) that was used in subsequent steps without further purification (ca. 80% purity).

Preparation of methyl 3-(3-bromoquinolin-6-yl)-5-vinyl-4,5-dihydro-1,2-oxazole-5-carboxylate (According to Process 8B)

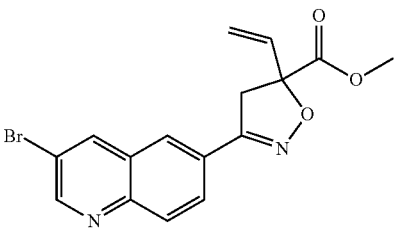 [SMILES: C=CC1(C(=O)OC)CC(c2ccc3ncc(Br)cc3c2)=NO1]

To a solution of methyl 3-(3-bromoquinolin-6-yl)-5-(1-{[(trifluoromethyl)sulfonyl]oxy}ethyl)-4,5-dihydro-1,2-oxazole-5-carboxylate (18.1 g, ca. 80%) in dichloromethane (500 mL) were added caesium carbonate (9.23 g) and 1,8-diazabicyclo[5.4.0]undec-7-ene (DBU, 0.43 g). The mixture was stirred at room temperature overnight. Further DBU (0.65 g) was added and stirring continued for 24 h. A third portion of DBU (0.43 g) was added and stirring continued for 24 h. The mixture was then filtered and concentrated. The residue was purified on silica to afford the target compound as a white solid (9.29 g)

Preparation of 3-(3-bromoquinolin-6-yl)-5-vinyl-4,5-dihydro-1,2-oxazole-5-carboxylic acid (According to Process 2A)

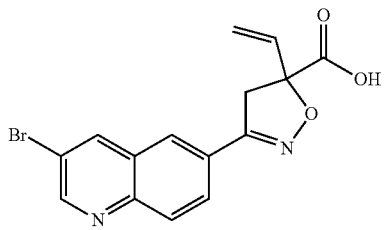 [SMILES: C=CC1(C(=O)O)CC(c2ccc3ncc(Br)cc3c2)=NO1]

A suspension of methyl 3-(3-bromoquinolin-6-yl)-5-vinyl-4,5-dihydro-1,2-oxazole-5-carboxylate (9.29 g) in methanol (500 mL) was gently heated with a heat gun until all solids were dissolved. Lithium hydroxide monohydrate (1.30 g) in wtare (100 mL) was added and the mixture was stirred for 45 min The methanol was evaporated and aq. HCl (1M) was added until pH=1. Then water (500 mL) was added and the product extracted using EtOAc (2×250 mL). The combined organic layers were washed with aq. sat. NaCl dried over $Na_2SO_4$, filtered and concentrated to afford the target compound (8.55 g) as a white foam.

The exemplary compounds according to the invention listed in Table 1, Table 2 and Table 3 have been synthezised analogous to the above mentioned processes.

The following Table 1 illustrates in a non limiting manner examples of compounds according to formula (I).

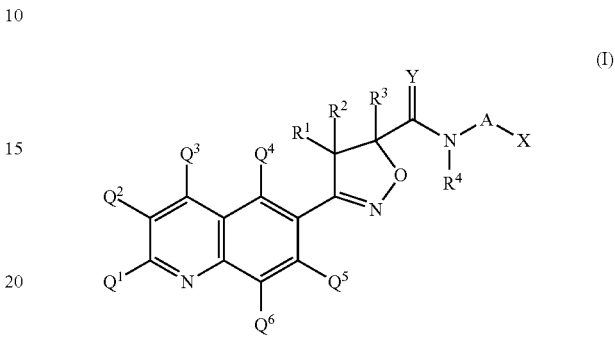

TABLE 1

| Ex-No | $Q^1$ | $Q^2$ | $Q^3$ | $Q^4$ | $Q^5$ | $Q^6$ | $R^1$ | $R^2$ | $R^3$ | Y | $R^4$ |
|---|---|---|---|---|---|---|---|---|---|---|---|
| 1 | H | H | H | H | H | H | H | H | $CH_3$ | O | H |
| 2 | H | H | H | H | H | H | H | H | $CH_3$ | O | H |
| 3 | H | H | H | H | H | H | H | H | $CH_3$ | O | H |
| 4 | H | H | H | H | H | H | H | H | $CH_3$ | O | H |
| 5 | H | bromo | H | H | fluoro | fluoro | H | H | trifluoromethyl | O | H |
| 6 | H | bromo | H | H | fluoro | fluoro | H | H | trifluoromethyl | O | H |
| 7 | H | bromo | H | H | methoxy | fluoro | H | H | $CH_3$ | O | H |
| 8 | H | bromo | H | H | methoxy | methoxy | H | H | $CH_3$ | O | H |
| 9 | H | bromo | H | H | fluoro | fluoro | H | H | $CH_3$ | O | methoxy |
| 10 | H | bromo | H | H | fluoro | fluoro | H | H | $CH_3$ | O | H |
| 11 | H | bromo | H | H | fluoro | fluoro | H | H | $CH_3$ | O | H |
| 12 | H | bromo | H | H | fluoro | fluoro | H | H | $CH_3$ | O | H |
| 13 | H | bromo | H | H | fluoro | fluoro | H | H | $CH_3$ | O | H |
| 14 | H | bromo | H | H | fluoro | fluoro | H | H | $CH_3$ | O | H |
| 15 | H | bromo | H | H | fluoro | fluoro | H | H | trifluoromethyl | O | H |
| 16 | H | bromo | H | H | fluoro | fluoro | H | H | trifluoromethyl | O | H |
| 17 | H | bromo | H | H | fluoro | fluoro | H | H | $CH_3$ | O | H |
| 18 | H | bromo | H | H | fluoro | fluoro | H | H | $CH_3$ | O | H |
| 19 | H | bromo | H | H | fluoro | fluoro | H | H | $CH_3$ | O | H |
| 20 | H | bromo | H | H | fluoro | fluoro | H | H | $CH_3$ | O | H |
| 21 | H | bromo | H | H | fluoro | fluoro | H | H | $CH_3$ | O | H |
| 22 | H | bromo | H | H | fluoro | fluoro | H | H | $CH_3$ | O | H |
| 23 | H | bromo | H | H | methoxy | fluoro | H | H | $CH_3$ | O | H |
| 24 | H | bromo | H | H | methoxy | methoxy | H | H | $CH_3$ | O | H |
| 25 | H | bromo | H | H | methoxy | fluoro | H | H | $CH_3$ | O | H |
| 26 | H | bromo | H | H | methoxy | methoxy | H | H | $CH_3$ | O | H |
| 27 | H | bromo | H | H | methoxy | fluoro | H | H | $CH_3$ | O | H |
| 28 | H | bromo | H | H | methoxy | methoxy | H | H | $CH_3$ | O | H |
| 29 | H | bromo | H | H | methoxy | fluoro | H | H | $CH_3$ | O | H |
| 30 | H | bromo | H | H | methoxy | methoxy | H | H | $CH_3$ | O | H |
| 31 | H | bromo | H | H | H | H | H | H | $CH_3$ | O | H |
| 32 | H | bromo | H | H | H | H | H | H | $CH_3$ | O | H |
| 33 | H | bromo | H | H | H | H | H | H | $CH_3$ | O | H |
| 34 | H | bromo | H | H | H | H | H | H | $CH_3$ | O | H |
| 35 | H | bromo | H | H | H | H | H | H | trifluoromethyl | O | H |
| 36 | H | bromo | H | H | H | H | H | H | trifluoromethyl | O | H |
| 37 | H | bromo | H | H | H | H | H | H | $CH_3$ | O | H |
| 38 | H | iodo | H | H | H | H | H | H | $CH_3$ | O | H |
| 39 | H | iodo | H | H | H | H | H | H | $CH_3$ | O | H |
| 40 | H | ethynyl | H | H | H | H | H | H | $CH_3$ | O | H |
| 41 | H | bromo | H | H | H | H | H | H | trifluoromethyl | O | H |
| 42 | H | iodo | H | H | H | H | H | H | $CH_3$ | O | H |
| 43 | H | ethynyl | H | H | H | H | H | H | $CH_3$ | O | H |
| 44 | H | iodo | H | H | H | H | H | H | $CH_3$ | O | H |
| 45 | H | ethynyl | H | H | H | H | H | H | $CH_3$ | O | H |
| 46 | H | bromo | H | H | H | H | H | H | methoxy | O | H |
| 47 | H | bromo | H | H | H | H | H | H | methoxy | O | H |

TABLE 1-continued

| | | | | | | | | | | | |
|---|---|---|---|---|---|---|---|---|---|---|---|
| 48 | H | bromo | H | H | H | H | H | H | methoxy | O | H |
| 49 | H | bromo | H | H | H | H | H | H | CH$_3$ | O | H |
| 50 | H | bromo | H | H | H | H | H | H | methoxy | O | H |
| 51 | H | bromo | H | H | H | H | H | H | methoxy | O | H |
| 52 | H | bromo | H | H | H | H | H | H | methoxy | O | H |
| 53 | H | methoxy | H | H | H | H | H | H | CH$_3$ | O | H |
| 54 | H | chloro | H | H | H | H | H | H | CH$_3$ | O | H |
| 55 | H | chloro | H | H | H | H | H | H | CH$_3$ | O | H |
| 56 | H | bromo | H | H | H | H | H | H | benzyl | O | H |
| 57 | H | bromo | H | H | H | H | H | H | benzyl | O | H |
| 58 | H | bromo | H | H | H | H | H | H | benzyl | O | H |
| 59 | H | bromo | H | H | H | H | H | H | benzyl | O | H |
| 60 | H | bromo | H | H | H | H | H | H | benzyl | O | H |
| 61 | H | bromo | H | H | H | H | H | H | propan-2-yl | O | H |
| 62 | H | bromo | H | H | H | H | H | H | propan-2-yl | O | H |
| 63 | H | bromo | H | H | H | H | H | H | propan-2-yl | O | H |
| 64 | H | bromo | H | H | H | H | H | H | propan-2-yl | O | H |
| 65 | H | bromo | H | H | H | H | H | H | propan-2-yl | O | H |
| 66 | H | bromo | H | H | H | H | H | H | ethyl | O | H |
| 67 | H | bromo | H | H | H | H | H | H | ethyl | O | H |
| 68 | H | bromo | H | H | H | H | H | H | ethyl | O | H |
| 69 | H | bromo | H | H | H | H | H | H | ethyl | O | H |
| 70 | H | bromo | H | H | H | H | H | H | ethyl | O | H |
| 71 | H | bromo | H | H | H | H | H | H | fluoromethyl | O | H |
| 72 | H | bromo | H | H | H | H | H | H | butyl | O | H |
| 73 | H | bromo | H | H | H | H | H | H | butyl | O | H |
| 74 | H | bromo | H | H | H | H | H | H | butyl | O | H |
| 75 | H | bromo | H | H | H | H | H | H | fluoromethyl | O | H |
| 76 | H | bromo | H | H | H | H | H | H | fluoromethyl | O | H |
| 77 | H | methylsulfinyl | H | H | H | H | H | H | CH$_3$ | O | H |
| 78 | H | ethoxy | H | H | H | H | H | H | CH$_3$ | O | H |
| 79 | H | cyano | H | H | H | H | H | H | CH$_3$ | O | H |
| 80 | H | methylsulfanyl | H | H | H | H | H | H | CH$_3$ | O | H |
| 81 | H | bromo | H | H | H | H | H | H | bromomethyl | O | H |
| 82 | H | ethynyl | H | H | H | H | H | H | CH$_3$ | O | H |
| 83 | H | ethynyl | H | H | H | H | H | H | CH$_3$ | O | H |
| 84 | H | bromo | H | H | H | H | H | H | CH$_3$ | O | H |
| 85 | H | bromo | H | H | H | H | H | H | CH$_3$ | O | H |
| 86 | H | ethynyl | H | H | H | H | H | H | CH$_3$ | O | H |
| 87 | H | ethynyl | H | H | H | H | H | H | CH$_3$ | O | H |
| 88 | H | bromo | H | H | H | H | H | H | CH$_3$ | O | H |
| 89 | H | bromo | H | H | H | H | H | H | CH$_3$ | O | H |
| 90 | H | bromo | H | H | H | H | H | H | CH$_3$ | O | H |
| 91 | H | bromo | H | H | H | H | H | H | CH$_3$ | O | H |
| 92 | H | bromo | H | H | H | H | H | H | CH$_3$ | O | H |
| 93 | H | bromo | H | H | H | H | H | H | CH$_3$ | O | H |
| 94 | H | bromo | H | H | H | H | H | H | CH$_3$ | O | H |
| 95 | H | bromo | H | H | H | H | H | H | CH$_3$ | O | H |
| 96 | H | bromo | H | H | H | H | H | H | CH$_3$ | O | H |
| 97 | H | bromo | H | H | H | H | H | H | CH$_3$ | O | H |
| 98 | H | bromo | H | H | H | H | H | H | CH$_3$ | O | H |
| 99 | H | ethynyl | H | H | H | H | H | H | CH$_3$ | O | H |
| 100 | H | bromo | H | H | H | H | H | H | CH$_3$ | O | H |
| 101 | H | bromo | H | H | H | H | H | H | CH$_3$ | O | H |
| 102 | H | bromo | H | H | H | H | H | H | CH$_3$ | O | H |
| 103 | H | ethynyl | H | H | H | H | H | H | CH$_3$ | O | H |
| 104 | H | bromo | H | H | H | H | H | H | CH$_3$ | O | H |
| 105 | H | bromo | H | H | H | H | H | H | trifluoromethyl | O | H |
| 106 | H | bromo | H | H | H | H | H | H | trifluoromethyl | O | H |
| 107 | H | bromo | H | H | H | H | H | H | trifluoromethyl | O | H |
| 108 | H | bromo | H | H | H | H | H | H | trifluoromethyl | O | H |
| 109 | H | bromo | H | H | H | H | H | H | CH$_3$ | O | H |
| 110 | H | bromo | H | H | H | H | H | H | CH$_3$ | O | H |
| 111 | H | bromo | H | H | H | H | H | H | CH$_3$ | O | H |
| 112 | H | bromo | H | H | H | H | H | H | CH$_3$ | O | H |
| 113 | H | bromo | H | H | H | H | H | H | CH$_3$ | O | H |
| 114 | H | bromo | H | H | H | H | H | H | CH$_3$ | O | H |
| 115 | H | ethynyl | H | H | H | H | H | H | CH$_3$ | O | H |
| 116 | H | bromo | H | H | H | H | H | H | CH$_3$ | O | H |
| 117 | H | bromo | H | H | H | H | H | H | CH$_3$ | O | H |
| 118 | H | bromo | H | H | H | H | H | H | CH$_3$ | O | H |
| 119 | H | bromo | H | H | H | H | H | H | CH$_3$ | O | H |
| 120 | H | ethynyl | H | H | H | H | H | H | CH$_3$ | O | H |
| 121 | H | ethynyl | H | H | H | H | H | H | CH$_3$ | O | H |
| 122 | H | bromo | H | H | H | H | H | H | CH$_3$ | O | H |
| 123 | H | bromo | H | H | H | H | H | H | CH$_3$ | O | H |
| 124 | H | bromo | H | H | H | H | H | H | CH$_3$ | O | H |
| 125 | H | ethynyl | H | H | H | H | H | H | CH$_3$ | O | H |
| 126 | H | bromo | H | H | H | H | H | H | CH$_3$ | O | H |
| 127 | H | bromo | H | H | H | H | H | H | CH$_3$ | O | H |

TABLE 1-continued

| | | | | | | | | | | | |
|---|---|---|---|---|---|---|---|---|---|---|---|
| 128 | H | ethynyl | H | H | H | H | H | H | CH$_3$ | | O | H |
| 129 | H | bromo | H | H | H | H | H | H | CH$_3$ | | O | H |
| 130 | H | bromo | H | H | H | H | H | H | CH$_3$ | | O | H |
| 131 | H | bromo | H | H | H | H | H | H | CH$_3$ | | O | H |
| 132 | H | ethynyl | H | H | H | H | H | H | CH$_3$ | | O | H |
| 133 | methoxy | ethynyl | H | H | H | H | H | H | CH$_3$ | | O | H |
| 134 | chloro | ethynyl | H | H | H | H | H | H | CH$_3$ | | O | H |
| 135 | H | methoxy | H | H | H | H | H | H | CH$_3$ | | O | H |
| 136 | H | bromo | H | H | H | H | H | H | phenyl | | O | H |
| 137 | H | bromo | H | H | H | H | H | H | bromomethyl | | O | H |
| 138 | H | bromo | H | H | H | H | H | H | chloromethyl | | O | H |
| 139 | H | bromo | H | H | H | H | H | H | chloromethyl | | O | H |
| 140 | H | phenyl | H | H | H | H | H | H | CH$_3$ | | O | H |
| 141 | H | phenyl | H | H | H | H | H | H | CH$_3$ | | O | H |
| 142 | H | thiophen-2-yl | H | H | H | H | H | H | CH$_3$ | | O | H |
| 143 | H | H | H | H | H | H | H | H | CH$_3$ | | O | H |
| 144 | H | thiophen-2-yl | H | H | H | H | H | H | CH$_3$ | | O | H |
| 145 | H | methylsulfinyl | H | H | H | H | H | H | CH$_3$ | | O | H |
| 146 | H | methylsulfonyl | H | H | H | H | H | H | CH$_3$ | | O | H |
| 147 | H | methylsulfanyl | H | H | H | H | H | H | CH$_3$ | | O | H |
| 148 | H | (trimethylsilyl)ethynyl | H | H | H | H | H | H | CH$_3$ | | O | H |
| 149 | H | (trimethylsilyl)ethynyl | H | H | H | H | H | H | CH$_3$ | | O | H |
| 150 | H | (trimethylsilyl)ethynyl | H | H | H | H | H | H | CH$_3$ | | O | H |
| 151 | H | methylsulfonyl | H | H | H | H | H | H | CH$_3$ | | O | H |
| 152 | H | bromo | H | H | H | H | H | H | CH$_3$ | | O | H |
| 153 | H | ethynyl | H | H | H | H | H | H | CH$_3$ | | O | H |
| 154 | H | bromo | H | H | H | H | H | H | CH$_3$ | | O | H |
| 155 | H | ethynyl | H | H | H | H | H | H | CH$_3$ | | O | H |
| 156 | H | bromo | H | H | H | H | H | H | CH$_3$ | | O | H |
| 157 | H | ethynyl | H | H | H | H | H | H | CH$_3$ | | O | H |
| 158 | H | bromo | H | H | H | H | H | H | CH$_3$ | | O | H |
| 159 | H | ethynyl | H | H | H | H | H | H | CH$_3$ | | O | H |
| 160 | H | ethynyl | H | H | H | H | H | H | CH$_3$ | | O | H |
| 161 | H | bromo | H | H | H | H | H | H | CH$_3$ | | O | H |
| 162 | H | ethynyl | H | H | H | H | H | H | CH$_3$ | | O | H |
| 163 | H | ethynyl | H | H | H | H | H | H | CH$_3$ | | O | H |
| 164 | H | ethynyl | H | H | H | H | H | H | CH$_3$ | | O | H |
| 165 | H | bromo | H | H | H | H | H | H | CH$_3$ | | O | H |
| 166 | H | ethynyl | H | H | H | H | H | H | CH$_3$ | | O | H |
| 167 | H | ethynyl | H | H | H | H | H | H | CH$_3$ | | O | H |
| 168 | H | ethynyl | H | H | H | H | H | H | CH$_3$ | | O | H |
| 169 | H | ethynyl | H | H | H | H | H | H | CH$_3$ | | O | H |
| 170 | H | ethynyl | H | H | H | H | H | H | CH$_3$ | | O | H |
| 171 | H | bromo | H | H | H | H | H | H | CH$_3$ | | O | H |
| 172 | H | ethynyl | H | H | H | H | H | H | CH$_3$ | | O | H |
| 173 | H | ethynyl | H | H | H | H | H | H | CH$_3$ | | O | H |
| 174 | H | bromo | H | H | H | H | H | H | CH$_3$ | | O | H |
| 175 | H | ethynyl | H | H | H | H | H | H | CH$_3$ | | O | H |
| 176 | H | bromo | H | H | H | H | H | H | CH$_3$ | | O | H |
| 177 | H | bromo | H | H | H | H | H | H | CH$_3$ | | O | H |
| 178 | H | ethynyl | H | H | H | H | H | H | CH$_3$ | | O | H |
| 179 | H | bromo | H | H | H | H | H | H | CH$_3$ | | O | H |
| 180 | H | ethynyl | H | H | H | H | H | H | CH$_3$ | | O | H |
| 181 | H | ethynyl | H | H | H | H | H | H | CH$_3$ | | O | H |
| 182 | H | bromo | H | H | H | H | H | H | CH$_3$ | | O | H |
| 183 | H | ethynyl | H | H | H | H | H | H | CH$_3$ | | O | H |
| 184 | H | bromo | H | H | H | H | H | H | CH$_3$ | | O | H |
| 185 | H | ethynyl | H | H | H | H | H | H | CH$_3$ | | O | H |
| 186 | H | ethynyl | H | H | H | H | H | H | CH$_3$ | | O | H |
| 187 | H | ethynyl | H | H | H | H | H | H | CH$_3$ | | O | H |
| 188 | H | bromo | H | H | H | H | H | H | CH$_3$ | | O | H |
| 189 | H | ethynyl | H | H | H | H | H | H | CH$_3$ | | O | H |
| 190 | H | ethynyl | H | H | H | H | H | H | CH$_3$ | | O | H |
| 191 | H | bromo | H | H | H | H | H | H | CH$_3$ | | O | H |
| 192 | H | ethynyl | H | H | H | H | H | H | CH$_3$ | | O | H |
| 193 | H | ethynyl | H | H | H | H | H | H | CH$_3$ | | O | H |
| 194 | H | ethynyl | H | H | H | H | H | H | CH$_3$ | | O | H |
| 195 | H | ethynyl | H | H | H | H | H | H | CH$_3$ | | O | H |
| 196 | H | ethynyl | H | H | H | H | H | H | CH$_3$ | | O | H |
| 197 | H | ethynyl | H | H | H | H | H | H | CH$_3$ | | O | H |
| 198 | H | ethynyl | H | H | H | H | H | H | CH$_3$ | | O | H |
| 199 | H | bromo | H | H | H | H | H | H | CH$_3$ | | O | H |
| 200 | H | ethynyl | H | H | H | H | H | H | CH$_3$ | | O | H |
| 201 | H | bromo | H | H | H | H | H | H | CH$_3$ | | O | H |
| 202 | H | bromo | H | H | H | H | H | H | CH$_3$ | | O | H |
| 203 | H | bromo | H | H | H | H | H | H | CH$_3$ | | O | H |
| 204 | H | bromo | H | H | H | H | H | H | CH$_3$ | | O | H |
| 205 | H | bromo | H | H | H | H | H | H | CH$_3$ | | O | H |
| 206 | H | ethynyl | H | H | H | H | H | H | CH$_3$ | | O | H |
| 207 | H | bromo | H | H | H | H | H | H | CH$_3$ | | O | H |

TABLE 1-continued

| | | | | | | | | | | | |
|---|---|---|---|---|---|---|---|---|---|---|---|
| 208 | H | ethynyl | H | H | H | H | H | H | CH₃ | O | H |
| 209 | H | ethynyl | H | H | H | H | H | H | CH₃ | O | H |
| 210 | H | ethynyl | H | H | H | H | H | H | CH₃ | O | H |
| 211 | H | bromo | H | H | H | H | H | H | CH₃ | O | H |
| 212 | H | ethynyl | H | H | H | H | H | H | CH₃ | O | H |
| 213 | H | ethynyl | H | H | H | H | H | H | CH₃ | O | H |
| 214 | H | ethynyl | H | H | H | H | H | H | CH₃ | O | H |
| 215 | H | bromo | H | H | H | H | H | H | CH₃ | O | H |
| 216 | H | ethynyl | H | H | H | H | H | H | CH₃ | O | H |
| 217 | H | ethynyl | H | H | H | H | H | H | CH₃ | O | H |
| 218 | H | ethynyl | H | H | H | H | H | H | CH₃ | O | H |
| 219 | H | ethynyl | H | H | H | H | H | H | CH₃ | O | H |
| 220 | H | ethynyl | H | H | H | H | H | H | CH₃ | O | H |
| 221 | H | bromo | H | H | H | H | H | H | CH₃ | O | H |
| 222 | H | ethynyl | H | H | H | H | H | H | CH₃ | O | H |
| 223 | H | ethynyl | H | H | H | H | H | H | CH₃ | O | H |
| 224 | H | bromo | H | H | H | H | H | H | CH₃ | O | H |
| 225 | H | ethynyl | H | H | H | H | H | H | CH₃ | O | H |
| 226 | H | ethynyl | H | H | H | H | H | H | CH₃ | O | H |
| 227 | H | ethynyl | H | H | H | H | H | H | CH₃ | O | H |
| 228 | H | bromo | H | H | H | H | H | H | CH₃ | O | H |
| 229 | H | ethynyl | H | H | H | H | H | H | CH₃ | O | H |
| 230 | H | ethynyl | H | H | H | H | H | H | CH₃ | O | H |
| 231 | H | ethynyl | H | H | H | H | H | H | CH₃ | O | H |
| 232 | H | ethynyl | H | H | H | H | H | H | CH₃ | O | H |
| 233 | H | ethynyl | H | H | H | H | H | H | CH₃ | O | H |
| 234 | H | bromo | H | H | H | H | H | H | CH₃ | O | H |
| 235 | H | bromo | H | H | H | H | H | H | CH₃ | O | H |
| 236 | H | ethynyl | H | H | H | H | H | H | CH₃ | O | H |
| 237 | H | bromo | H | H | H | H | H | H | CH₃ | O | H |
| 238 | H | ethynyl | H | H | H | H | H | H | CH₃ | O | H |
| 239 | H | bromo | H | H | H | H | H | H | CH₃ | O | H |
| 240 | H | bromo | H | H | H | H | H | H | CH₃ | O | H |
| 241 | H | bromo | H | H | H | H | H | H | CH₃ | O | H |
| 242 | H | ethynyl | H | H | H | H | H | H | CH₃ | O | H |
| 243 | H | bromo | H | H | H | H | H | H | CH₃ | O | H |
| 244 | H | ethynyl | H | H | H | H | H | H | CH₃ | O | H |
| 245 | H | ethynyl | H | H | H | H | H | H | CH₃ | O | H |
| 246 | H | ethynyl | H | H | H | H | H | H | CH₃ | O | H |
| 247 | H | ethynyl | H | H | H | H | H | H | CH₃ | O | H |
| 248 | H | bromo | H | H | H | H | H | H | CH₃ | O | H |
| 249 | H | bromo | H | H | H | H | H | H | CH₃ | O | H |
| 250 | H | ethynyl | H | H | H | H | H | H | CH₃ | O | H |
| 251 | H | bromo | H | H | H | H | H | H | CH₃ | O | H |
| 252 | H | bromo | H | H | H | H | H | H | CH₃ | O | H |
| 253 | H | ethynyl | H | H | H | H | H | H | CH₃ | O | H |
| 254 | H | propylsulfanyl | H | H | H | H | H | H | CH₃ | O | H |
| 255 | H | bromo | H | H | H | H | H | CH₂CH₂CH₂ | | O | H |
| 256 | H | ethyl | H | H | H | H | H | H | CH₃ | O | H |
| 257 | H | CH₃ | H | H | H | H | H | H | CH₃ | O | H |
| 258 | H | pyrimidin-5-yl | H | H | H | H | H | H | CH₃ | O | H |
| 259 | H | ethyl | H | H | H | H | H | H | CH₃ | O | H |
| 260 | H | CH₃ | H | H | H | H | H | H | CH₃ | O | H |
| 261 | H | bromo | H | H | H | H | H | CH₂CH₂CH₂ | | O | H |
| 262 | H | ethynyl | H | H | H | H | H | H | CH₃ | O | H |
| 263 | methoxy | bromo | H | H | H | H | H | H | CH₃ | O | H |
| 264 | H | propylsulfanyl | H | H | H | H | H | H | CH₃ | O | H |
| 265 | H | pyrimidin-5-yl | H | H | H | H | H | H | CH₃ | O | H |
| 266 | H | bromo | H | H | H | H | H | CH₂CH₂CH₂O | | O | H |
| 267 | H | Br | H | H | H | H | H | H | Cyclopropyl | O | H |
| 268 | H | Br | H | H | H | H | H | H | Cyclopropyl | O | H |
| 269 | H | Br | H | H | H | H | H | H | Cyclopropyl | O | H |
| 270 | H | Br | H | H | H | H | H | H | Cyclopropyl | O | H |
| 271 | H | Br | H | H | H | H | H | H | Cyclopropyl | O | H |
| 272 | H | Br | H | H | H | H | H | (CH₂)₄ | | O | H |
| 273 | H | Br | H | H | H | H | H | CH₂CH₂CH₂O | | O | H |
| 274 | H | Br | H | H | H | H | Me | H | Me | O | H |
| 275 | OMe | Br | H | H | H | H | H | H | Me | O | H |
| 276 | H | SEt | H | H | H | H | H | H | Me | O | H |
| 277 | H | SEt | H | H | H | H | H | H | Me | O | H |
| 278 | H | Br | H | H | H | H | H | H | Ph | O | H |
| 279 | H | Br | H | H | H | H | H | H | F | O | H |
| 280 | H | Br | H | H | H | H | H | H | F | O | H |
| 281 | H | Br | H | H | H | H | H | H | Ac | O | H |
| 82 | H | Br | H | H | H | H | H | H | Me | O | H |
| 283 | H | Br | H | H | H | H | Et | H | Me | O | H |
| 284 | H | Br | H | H | H | H | H | H | OMe | O | H |
| 285 | H | Br | H | H | H | H | H | H | OMe | O | H |
| 286 | Cl | Br | H | H | H | H | H | H | Me | O | H |
| 287 | Cl | Br | H | H | H | H | H | H | Me | O | H |

TABLE 1-continued

| | | | | | | | | | | | |
|---|---|---|---|---|---|---|---|---|---|---|---|
| 288 | H | CN | H | H | H | H | H | H | Me | O | H |
| 289 | H | H | H | H | H | H | H | H | Me | O | H |
| 290 | H | Br | H | H | H | H | H | H | Me | O | H |
| 291 | H | Br | H | H | H | H | H | H | Me | O | H |
| 292 | H | Br | H | H | H | H | H | H | Me | O | H |
| 293 | H | Br | H | H | H | H | H | H | Me | O | H |
| 294 | H | Br | H | H | H | H | H | H | Me | O | H |
| 295 | H | Br | H | H | H | H | H | H | Me | O | H |
| 296 | H | Br | H | H | H | H | H | H | Me | O | H |
| 297 | H | Br | H | H | H | H | H | H | Me | O | H |
| 298 | H | Br | H | H | H | H | H | H | Me | O | H |
| 299 | H | Br | H | H | H | H | H | H | Me | O | H |
| 300 | H | Br | H | H | H | H | H | H | Me | O | H |
| 301 | H | Br | H | H | H | H | H | H | Me | O | H |
| 302 | CN | Br | H | H | H | H | H | H | Me | O | H |
| 303 | CN | Br | H | H | H | H | H | H | Me | O | H |
| 304 | H | Vinyl | H | H | H | H | H | H | Me | O | H |
| 305 | H | Br | H | H | H | H | H | H | Me | O | H |
| 306 | H | Br | H | H | H | H | H | H | Me | O | H |
| 307 | H | Br | H | H | H | H | H | H | Me | O | H |
| 308 | H | Vinyl | H | H | H | H | H | H | Me | O | H |
| 309 | H | Br | H | H | H | H | H | H | Me | O | H |
| 310 | H | Br | H | H | H | H | H | H | Me | O | H |
| 311 | H | Br | H | H | H | H | H | H | Me | O | H |
| 312 | H | Br | H | H | H | H | H | H | Me | O | H |
| 313 | H | Br | H | H | H | H | H | H | Me | O | H |
| 314 | H | Ethynyl | H | H | H | H | H | H | Me | O | H |
| 315 | H | Br | H | H | H | H | H | H | Me | O | H |
| 316 | H | Ethynyl | H | H | H | H | H | H | Me | O | H |
| 317 | H | Br | H | H | H | H | H | H | Me | O | H |
| 318 | H | Ethynyl | H | H | H | H | H | H | Me | O | H |
| 319 | H | Br | H | H | H | H | H | H | Me | O | H |
| 320 | H | Ethynyl | H | H | H | H | H | H | Me | O | H |
| 321 | H | Br | H | H | H | H | H | H | Me | O | H |
| 322 | H | Ethynyl | H | H | H | H | H | H | Me | O | H |
| 323 | H | Br | H | H | H | H | H | H | Me | O | H |
| 324 | H | Ethynyl | H | H | H | H | H | H | Me | O | H |
| 325 | H | Br | H | H | H | H | H | H | Me | O | H |
| 326 | H | Ethynyl | H | H | H | H | H | H | Me | O | H |
| 327 | H | Br | H | H | H | H | H | H | Me | O | H |
| 328 | H | Br | H | H | H | H | H | H | Me | O | H |
| 329 | H | Ethynyl | H | H | H | H | H | H | Me | O | H |
| 330 | H | Ethynyl | H | H | H | H | H | H | Me | O | H |
| 331 | H | Br | H | H | H | H | H | H | Me | O | H |
| 332 | H | Br | H | H | H | H | H | H | Me | O | H |
| 333 | H | Ethynyl | H | H | H | H | H | H | Me | O | H |
| 334 | H | Ethynyl | H | H | H | H | H | H | Me | O | H |
| 335 | H | Ethynyl | H | H | H | H | H | H | Me | O | H |
| 336 | H | Ethynyl | H | H | H | H | H | H | Me | O | H |
| 337 | H | Br | H | H | H | H | H | H | Me | O | H |
| 338 | H | Ethynyl | H | H | H | H | H | H | Me | O | H |
| 339 | H | Ethynyl | H | H | H | H | H | H | Me | O | H |
| 340 | H | Br | H | H | H | H | H | H | Me | O | H |
| 341 | H | Ethynyl | H | H | H | H | H | H | Me | O | H |
| 342 | H | Ethynyl | H | H | H | H | H | H | Me | O | H |
| 343 | H | Ethynyl | H | H | H | H | H | H | Me | O | H |
| 344 | H | Br | H | H | H | H | H | H | Me | O | H |
| 345 | H | Br | H | H | H | H | H | H | Me | O | H |
| 346 | H | Ethynyl | H | H | H | H | H | H | Me | O | H |
| 347 | H | Ethynyl | H | H | H | H | H | H | Me | O | H |
| 348 | H | Br | H | H | H | H | H | H | Me | O | H |
| 349 | H | Ethynyl | H | H | H | H | H | H | Me | O | H |
| 350 | H | Ethynyl | H | H | H | H | H | H | Me | O | H |
| 351 | H | Ethynyl | H | H | H | H | H | H | Me | O | H |
| 352 | H | Ethynyl | H | H | H | H | H | H | Me | O | H |
| 353 | H | Br | H | H | H | H | H | H | Me | O | H |
| 354 | H | Ethynyl | H | H | H | H | H | H | Me | O | H |
| 355 | H | Ethynyl | H | H | H | H | H | H | Me | O | H |
| 356 | H | Br | H | H | H | H | H | H | Me | O | H |
| 357 | H | Ethynyl | H | H | H | H | H | H | Me | O | H |
| 358 | H | Br | H | H | H | H | H | H | Me | O | H |
| 359 | H | Ethynyl | H | H | H | H | H | H | Me | O | H |
| 360 | H | Br | H | H | H | H | H | H | Me | O | H |
| 361 | H | Ethynyl | H | H | H | H | H | H | Me | O | H |
| 362 | H | Br | H | H | H | H | H | H | Me | O | H |
| 363 | H | Ethynyl | H | H | H | H | H | H | Me | O | H |
| 364 | H | Br | H | H | H | H | H | H | Me | O | H |
| 365 | H | Ethynyl | H | H | H | H | H | H | Me | O | H |
| 366 | H | Ethynyl | H | H | H | H | H | H | Me | O | H |
| 367 | H | Ethynyl | H | H | H | H | H | H | Me | O | H |

TABLE 1-continued

| # | | | | | | | | | | | |
|---|---|---|---|---|---|---|---|---|---|---|---|
| 368 | H | Br | H | H | H | H | H | H | Me | O | H |
| 369 | H | Ethynyl | H | H | H | H | H | H | Me | O | H |
| 370 | H | Br | H | H | H | H | H | H | Me | O | H |
| 371 | H | Br | H | H | H | H | H | H | Me | O | H |
| 372 | H | Br | H | H | H | H | H | H | Me | O | H |
| 373 | H | Br | H | H | H | H | H | H | Me | O | H |
| 374 | H | Br | H | H | H | H | H | H | Me | O | H |
| 375 | H | Br | H | H | H | H | H | H | Me | O | H |
| 376 | H | Br | H | H | H | H | Me | H | H | O | H |
| 377 | H | Br | H | H | H | H | H | H | Me | O | H |
| 378 | H | CCMe | H | H | H | H | H | H | Me | O | H |
| 379 | H | 2-furyl | H | H | H | H | H | H | Me | O | H |
| 380 | H | Br | H | H | H | H | H | H | Me | O | H |
| 381 | H | CCMe | H | H | H | H | H | H | Me | O | H |
| 382 | H | 2-furyl | H | H | H | H | H | H | Me | O | H |
| 383 | H | $CF_3$ | H | H | H | H | H | H | Me | O | H |
| 384 | H | $CF_3$ | H | H | H | H | H | H | Me | O | H |
| 385 | H | Br | H | H | H | H | Me | H | Me | O | H |
| 386 | H | Br | H | H | H | H | H | H | Methoxy-carbonyl-methyl | O | H |
| 387 | H | Br | H | H | H | H | H | H | Methoxy-carbonyl-methyl | O | H |
| 388 | H | Br | H | H | H | H | H | H | Me | O | H |
| 389 | H | Br | H | H | H | H | H | H | Me | O | H |
| 390 | H | Br | H | H | H | H | H | H | Me | O | H |
| 391 | H | Br | H | H | H | H | H | H | Me | O | H |
| 392 | H | Br | H | H | H | H | H | H | Me | O | H |
| 393 | H | Br | H | H | H | H | OEt | H | Me | O | H |
| 394 | H | but-1-yn-1-yl | H | H | H | H | H | H | Me | O | H |
| 395 | H | Br | H | H | H | H | H | H | $CH_2SiMe_3$ | O | H |
| 396 | H | Br | H | H | H | H | H | H | OMe | O | Me |
| 397 | H | Br | H | H | H | H | H | | $CH_2$ | O | H |
| 398 | H | Br | H | H | H | H | H | | $CH_2$ | O | H |
| 399 | H | Br | H | H | H | H | H | | $CH_2$ | O | H |
| 400 | H | Br | H | H | H | H | H | | $CH_2$ | O | H |
| 401 | H | Br | H | H | H | H | H | | $CH_2$ | O | H |
| 402 | H | Br | H | H | H | H | H | H | Ethynyl | O | H |
| 403 | H | Br | H | H | H | H | H | | CH(Me) | O | H |
| 404 | CN | Ethynyl | H | H | H | H | H | H | Me | O | H |
| 405 | H | 1,3,3,3-tetrafluoroprop-1-en-1-yl | H | H | H | H | H | H | Me | O | H |
| 406 | H | Ethynyl | H | H | H | H | H | H | OMe | O | H |
| 407 | H | Ethynyl | H | H | H | H | H | H | OMe | O | H |
| 408 | H | Ethynyl | H | H | H | H | H | H | OMe | O | H |
| 409 | H | Ethynyl | H | H | H | H | H | H | OMe | O | H |
| 410 | H | Br | H | H | H | H | H | H | OMe | S | H |
| 411 | Cl | Ethynyl | H | H | H | H | H | H | Me | O | H |
| 412 | H | O-n-Pr | H | H | H | H | H | H | Me | O | H |
| 413 | H | Br | H | H | H | H | H | H | $CH_2SiMe_3$ | O | H |
| 414 | H | Br | H | H | H | H | H | H | OMe | O | H |
| 415 | H | Br | H | H | H | H | H | H | OEt | O | H |
| 416 | H | Br | H | H | H | H | H | H | OEt | O | H |
| 417 | H | OEt | H | H | H | H | H | H | Me | O | H |
| 418 | H | O-n-Pr | H | H | H | H | H | H | Me | O | H |
| 419 | H | Br | H | H | H | H | OMe | H | Me | O | H |
| 420 | H | Br | H | H | H | H | H | H | (1E)-N-hydroxyethanimidoyl | O | H |
| 421 | H | (tert-butoxycarbonyl)amino | H | H | H | H | H | H | Me | O | H |
| 422 | H | Br | H | H | H | H | H | H | cyclopropylmethyl | O | H |
| 423 | H | Br | H | H | H | H | $CF_3$ | H | Me | O | H |
| 424 | H | Br | H | H | H | H | H | H | cyclopropylmethyl | O | H |
| 425 | H | Br | H | H | H | H | H | H | cyclopropylmethyl | O | H |
| 426 | H | Br | H | H | H | H | H | H | cyclopropylmethyl | O | H |
| 427 | H | Br | H | H | H | H | H | H | cyclopropylmethyl | O | H |
| 428 | H | Ethynyl | H | H | H | H | H | H | Me | O | H |
| 429 | H | Ethynyl | H | H | H | H | H | H | OMe | O | H |
| 430 | H | (tert-butoxycarbonyl)amino | H | H | H | H | H | H | Me | O | H |
| 431 | CN | I | H | H | H | H | H | H | Me | O | H |
| 432 | Cl | I | H | H | H | H | H | H | Me | O | H |
| 433 | H | Br | H | H | H | H | OMe | H | Me | O | H |
| 434 | H | Br | H | H | H | H | H | H | Me | O | H |
| 435 | H | $NH_2$ | H | H | H | H | H | H | Me | O | H |
| 436 | H | I | H | H | H | H | H | H | OMe | O | H |
| 437 | H | I | H | H | H | H | H | H | OMe | O | H |
| 438 | H | Ethynyl | H | H | H | H | H | H | Et | O | H |

TABLE 1-continued

| | | | | | | | | | | | | |
|---|---|---|---|---|---|---|---|---|---|---|---|---|
| 439 | H | Ethynyl | H | H | H | H | H | H | Et | | O | H |
| 440 | H | Ethynyl | H | H | H | H | H | H | Et | | O | H |
| 441 | H | Ethynyl | H | H | H | H | H | H | Et | | O | H |
| 442 | H | Ethynyl | H | H | H | H | H | H | OMe | | O | H |
| 443 | H | Ethynyl | H | H | H | H | H | H | Me | | S | H |
| 444 | H | Ethynyl | H | H | H | H | H | H | Et | | O | H |
| 445 | H | Ethynyl | H | H | H | H | H | H | Et | | O | H |
| 446 | H | Ethynyl | H | H | H | H | H | H | Et | | O | H |
| 447 | H | Ethynyl | H | H | H | H | H | H | Et | | O | H |
| 448 | H | I | H | H | H | H | H | H | OMe | | O | H |
| 449 | H | I | H | H | H | H | H | H | OMe | | O | H |
| 450 | H | I | H | H | H | H | H | H | OMe | | O | H |
| 451 | H | Ethynyl | H | H | H | H | H | H | Me | | S | H |
| 452 | H | $NH_2$ | H | H | H | H | H | H | Me | | O | H |
| 453 | H | Ethynyl | H | H | H | H | H | H | Me | | O | H |
| 454 | H | I | H | H | H | H | H | H | Me | | O | H |
| 455 | H | I | H | H | H | H | H | H | Me | | O | H |
| 456 | H | I | H | H | H | H | H | H | Me | | O | H |
| 457 | H | Ethynyl | H | H | H | H | H | H | OMe | | O | $(CH_2)_4$ |
| 458 | H | Ethynyl | H | H | H | H | H | H | Me | | O | H |
| 459 | H | Ethynyl | H | H | H | H | H | H | Me | | O | H |
| 460 | H | Ethynyl | H | H | H | H | H | H | Me | | O | H |
| 461 | H | Ethynyl | H | H | H | H | H | H | Me | | O | H |
| 462 | H | Ethynyl | H | H | H | H | H | H | Me | | O | H |
| 463 | H | Ethynyl | H | H | H | H | H | H | Me | | O | H |
| 464 | H | Ethynyl | H | H | H | H | H | H | Me | | O | H |
| 465 | H | Ethynyl | H | H | H | H | H | H | Me | | O | H |
| 466 | H | Ethynyl | H | H | H | H | H | H | OMe | | O | s-Bu |
| 467 | H | Ethynyl | H | H | H | H | H | H | OMe | | O | i-Pr |
| 468 | H | Ethynyl | H | H | H | H | H | H | OMe | | O | i-Pr |
| 469 | H | Ethynyl | H | H | H | H | H | H | OMe | | O | i-Pr |
| 470 | H | Ethynyl | H | H | H | H | H | H | Me | | O | H |
| 471 | H | Ethynyl | H | H | H | H | H | H | Me | | O | H |
| 472 | OMe | I | H | H | H | H | H | H | Me | | O | H |
| 473 | H | Ethynyl | H | H | H | H | H | H | OMe | | O | H |
| 474 | H | I | H | H | H | H | H | H | Me | | O | H |
| 475 | H | Ethynyl | H | H | H | H | H | H | OMe | | O | i-Pr |
| 476 | H | Ethynyl | H | H | H | H | H | H | OMe | | O | H |
| 477 | H | Br | H | H | H | H | H | H | OMe | | O | H |
| 478 | H | Br | H | H | H | H | H | H | OMe | | S | H |
| 479 | H | Br | H | H | H | H | H | H | Me | | O | H |
| 480 | H | Br | H | H | H | H | H | H | $CHF_2$ | | O | H |
| 481 | H | Ethynyl | H | H | H | H | H | H | Me | | S | H |
| 482 | H | I | H | H | H | H | H | H | OMe | | O | H |
| 483 | H | I | H | H | H | H | H | H | OMe | | O | H |
| 484 | $CONH2$ | I | H | H | H | H | H | H | Me | | O | H |
| 485 | OMe | I | H | H | H | H | H | H | Me | | O | H |
| 486 | Cl | I | H | H | H | H | H | H | Me | | O | H |
| 487 | H | Br | H | H | H | H | H | H | Me | | O | H |
| 488 | H | Br | H | H | H | H | H | H | Me | | O | H |
| 489 | H | Br | H | H | H | H | H | H | Me | | O | H |
| 490 | OMe | Ethynyl | H | H | H | H | H | H | Me | | O | H |
| 491 | CN | Ethynyl | H | H | H | H | H | H | Me | | O | H |
| 492 | H | Br | H | H | H | H | H | H | Me | | O | H |
| 493 | H | Br | H | H | H | H | H | H | Me | | O | H |
| 494 | H | Br | H | H | H | H | H | H | Me | | O | H |
| 495 | H | Br | H | H | H | H | H | H | Me | | O | H |
| 496 | H | Br | H | H | H | H | H | H | OMe | | O | H |
| 497 | H | I | H | H | H | H | H | H | OMe | | O | H |
| 498 | H | Br | H | H | H | H | H | H | Et | | O | H |
| 499 | H | Br | H | H | H | H | H | H | Et | | O | H |
| 500 | H | Br | H | H | H | H | H | H | Et | | O | H |
| 501 | H | Ethynyl | H | H | H | H | H | H | Me | | O | H |
| 502 | H | Ethynyl | H | H | H | H | H | H | Me | | O | H |
| 503 | H | Ethynyl | H | H | H | H | H | H | Me | | O | H |
| 504 | H | Ethynyl | H | H | H | H | H | H | OMe | | O | H |
| 505 | H | Br | H | H | H | H | H | H | Me | | O | H |
| 506 | H | Ethynyl | H | H | H | H | H | H | Me | | O | H |
| 507 | H | Ethynyl | H | H | H | H | H | H | Et | | S | H |
| 508 | H | Br | H | H | H | H | H | H | OMe | | O | H |
| 509 | H | Ethynyl | H | H | H | H | H | H | OMe | | O | H |
| 510 | CN | I | H | H | H | H | H | H | Me | | O | H |
| 511 | H | Ethynyl | H | H | H | H | H | H | OMe | | O | H |
| 512 | H | Ethynyl | H | H | H | H | H | H | OMe | | O | H |
| 513 | H | Ethynyl | H | H | H | H | H | H | Me | | S | H |
| 514 | H | Ethynyl | H | H | H | H | H | H | OMe | | O | H |
| 515 | H | Ethynyl | H | H | H | H | H | H | Me | | O | H |
| 516 | H | Ethynyl | H | H | H | H | H | H | Me | | O | H |
| 517 | H | Br | H | H | H | H | H | H | prop-1-en-2-yl | | O | H |
| 518 | H | Br | H | H | H | H | H | H | prop-1-en-2-yl | | O | H |

TABLE 1-continued

| | | | | | | | | | | | |
|---|---|---|---|---|---|---|---|---|---|---|---|
| 519 | H | Br | H | H | H | H | H | H | prop-1-en-2-yl | O | H |
| 520 | H | Br | H | H | H | H | H | H | prop-1-en-2-yl | O | H |
| 521 | H | Br | H | H | H | H | H | H | prop-1-en-2-yl | O | H |
| 522 | H | Br | H | H | H | H | H | H | prop-1-en-2-yl | O | H |
| 523 | H | Ethynyl | H | H | H | H | H | H | Me | O | H |
| 524 | H | Ethynyl | H | H | H | H | H | H | Me | O | H |
| 525 | H | Ethynyl | H | H | H | H | H | H | Me | O | H |
| 526 | H | Br | H | H | H | H | H | H | prop-1-en-2-yl | O | H |
| 527 | H | Ethynyl | H | H | H | H | H | H | Me | O | H |
| 528 | H | Br | H | H | H | H | H | H | Me | O | H |
| 529 | H | Ethynyl | H | H | H | H | H | H | Me | O | H |
| 530 | H | Br | H | H | H | H | H | H | SMe | O | H |
| 531 | H | Ethynyl | H | H | H | H | H | H | Me | O | H |
| 532 | H | Br | H | H | H | H | H | H | Me | O | H |
| 533 | H | Ethynyl | H | H | H | Me | H | H | Me | O | H |
| 534 | H | Br | H | H | H | Me | H | H | Me | O | H |
| 535 | H | Ethynyl | H | H | H | Me | H | H | Me | O | H |
| 536 | H | Ethynyl | H | H | H | Me | H | H | Me | O | H |
| 537 | H | Br | H | H | H | Me | H | H | Me | O | H |
| 538 | H | Br | H | H | H | Me | H | H | Me | O | H |
| 539 | H | Br | H | H | H | Cl | H | H | Me | O | H |
| 540 | H | Br | H | H | H | Cl | H | H | Me | O | H |
| 541 | H | Br | H | H | H | Cl | H | H | Me | O | H |
| 542 | H | Br | H | H | H | Cl | H | H | Me | O | H |
| 543 | H | Ethynyl | H | H | H | Cl | H | H | Me | O | H |
| 544 | H | Ethynyl | H | H | H | Cl | H | H | Me | O | H |
| 545 | H | Ethynyl | H | H | H | Cl | H | H | Me | O | H |
| 546 | H | Ethynyl | H | H | H | Me | H | H | Me | O | H |
| 547 | H | Br | H | H | H | Me | H | H | Me | O | H |
| 548 | H | Br | H | H | H | Cl | H | H | Me | O | H |
| 549 | H | Br | H | H | H | Cl | H | H | Me | O | H |
| 550 | H | Ethynyl | H | H | H | Cl | H | H | Me | O | H |
| 551 | H | Ethynyl | H | H | H | Cl | H | H | Me | O | H |
| 552 | H | Br | H | H | H | H | H | H | 1-hydroxyethyl | O | H |
| 553 | H | Br | H | H | H | H | H | H | 1-hydroxyethyl | O | H |
| 554 | H | Br | H | H | H | H | H | H | 1-hydroxyethyl | O | H |
| 555 | H | Br | H | H | H | H | H | H | 1-hydroxyethyl | O | H |
| 556 | H | Br | H | H | H | Cl | H | H | Me | O | H |
| 557 | H | Br | H | H | H | H | H | H | 1-hydroxyethyl | O | H |
| 558 | H | Ethynyl | H | H | H | Cl | H | H | Me | O | H |
| 559 | H | Ethynyl | H | H | H | Cl | H | H | Me | O | H |
| 560 | H | Br | H | H | H | H | H | H | 1-hydroxyethyl | O | H |
| 561 | H | Br | H | H | H | Cl | H | H | Me | O | H |
| 562 | H | Br | H | H | H | H | H | H | 1-hydroxyethyl | O | H |
| 563 | H | Br | H | H | H | H | H | H | 1-hydroxyethyl | O | H |
| 564 | H | Ethynyl | H | H | H | Cl | H | H | Me | O | H |
| 565 | H | Br | H | H | H | H | H | H | SMe | O | H |
| 566 | H | Br | H | H | H | Cl | H | H | OMe | O | H |
| 567 | H | Br | H | H | H | Cl | H | H | OMe | O | H |
| 568 | H | Br | H | H | H | Cl | H | H | OMe | O | H |
| 569 | H | Br | H | H | H | Cl | H | H | OMe | O | H |
| 570 | H | Ethynyl | H | H | H | Me | H | H | Me | O | H |
| 571 | H | Ethynyl | H | H | H | Me | H | H | Me | O | H |
| 572 | H | Br | H | H | H | Me | H | H | Me | O | H |
| 573 | H | Br | H | H | H | Me | H | H | Me | O | H |
| 574 | H | Br | H | H | H | Cl | H | H | OMe | O | H |
| 575 | H | Br | H | H | H | Cl | H | H | OMe | O | H |
| 576 | H | Br | H | H | H | Cl | H | H | OMe | O | H |
| 577 | H | Br | H | H | H | Cl | H | H | OMe | O | H |
| 578 | H | Ethynyl | H | H | H | Me | H | H | Me | O | H |
| 579 | H | Br | H | H | H | Me | H | H | Me | O | H |
| 580 | H | Br | H | H | H | Me | H | H | Me | O | H |
| 581 | H | Ethynyl | H | H | H | Me | H | H | Me | O | H |
| 582 | H | Br | H | H | H | H | H | H | Ac | O | H |
| 583 | H | Br | H | H | H | H | H | H | Ac | O | H |
| 584 | H | Br | H | H | H | H | H | H | Ac | O | H |
| 585 | H | Br | H | H | H | H | H | H | Ac | O | H |
| 586 | H | Br | H | H | H | H | H | H | Ac | O | H |
| 587 | H | Ethynyl | H | H | H | Cl | H | H | OMe | O | H |
| 588 | H | Ethynyl | H | H | H | Cl | H | H | OMe | O | H |
| 589 | H | Ethynyl | H | H | H | Cl | H | H | OMe | O | H |
| 590 | H | Ethynyl | H | H | H | Cl | H | H | OMe | O | H |

TABLE 1-continued

| | | | | | | | | | | | |
|---|---|---|---|---|---|---|---|---|---|---|---|
| 591 | H | Ethynyl | H | H | H | Cl | H | H | OMe | O | H |
| 592 | H | Ethynyl | H | H | H | Cl | H | H | OMe | O | H |
| 593 | H | Ethynyl | H | H | H | Cl | H | H | OMe | O | H |
| 594 | H | Ethynyl | H | H | H | Cl | H | H | OMe | O | H |
| 595 | H | Br | H | H | H | Me | H | H | OMe | O | H |
| 596 | H | Br | H | H | H | Me | H | H | OMe | O | H |
| 597 | H | Br | H | H | H | Me | H | H | OMe | O | H |
| 598 | H | Ethynyl | H | H | H | H | H | H | Me | O | H |
| 599 | H | Br | H | H | H | H | H | H | Vinyl | O | H |
| 600 | H | Br | H | H | H | Me | H | H | OMe | O | H |
| 601 | H | Br | H | H | H | Me | H | H | OMe | O | H |
| 602 | H | Br | H | H | H | Me | H | H | OMe | O | H |
| 603 | H | Br | H | H | H | Me | H | H | OMe | O | H |
| 604 | H | Ethynyl | H | H | H | Me | H | H | OMe | O | H |
| 605 | H | Ethynyl | H | H | H | Me | H | H | OMe | O | H |
| 606 | H | Ethynyl | H | H | H | Me | H | H | OMe | O | H |
| 607 | H | Ethynyl | H | H | H | Me | H | H | OMe | O | H |
| 608 | H | Br | H | H | H | Me | H | H | OMe | O | H |
| 609 | H | Ethynyl | H | H | H | Me | H | H | OMe | O | H |
| 610 | H | Ethynyl | H | H | H | Me | H | H | OMe | O | H |
| 611 | H | Ethynyl | H | H | H | Me | H | H | OMe | O | H |
| 612 | H | Ethynyl | H | H | H | Me | H | H | OMe | O | H |
| 613 | H | Ethynyl | H | H | H | H | H | H | $CHF_2$ | O | H |
| 614 | H | Ethynyl | H | H | H | H | H | H | $CHF_2$ | O | H |
| 615 | H | Ethynyl | H | H | H | H | H | H | $CHF_2$ | O | H |
| 616 | H | Ethynyl | H | H | H | H | H | H | $CHF_2$ | O | H |
| 617 | H | I | H | H | H | H | H | H | $CHF_2$ | O | H |
| 618 | H | I | H | H | H | H | H | H | $CHF_2$ | O | H |
| 619 | H | I | H | H | H | H | H | H | $CHF_2$ | O | H |
| 620 | H | I | H | H | H | H | H | H | $CHF_2$ | O | H |
| 621 | H | Br | H | H | H | H | H | H | $CHF_2$ | O | H |
| 622 | H | Br | H | H | H | H | H | H | $CHF_2$ | O | H |
| 623 | H | Br | H | H | H | H | H | H | $CHF_2$ | O | H |
| 624 | H | Br | H | H | H | H | H | H | Me | O | H |
| 625 | H | Br | H | H | H | H | H | H | Ethynyl | O | H |
| 626 | H | Br | H | H | H | H | H | H | Ethynyl | O | H |
| 627 | H | Br | H | H | H | H | H | H | Ethynyl | O | H |
| 628 | H | Br | H | H | H | H | H | H | Ethynyl | O | H |
| 629 | H | Ethynyl | H | H | H | H | H | H | Me | O | H |
| 630 | H | Br | H | H | H | H | H | H | Me | O | H |
| 631 | H | Ethynyl | H | H | H | H | H | H | Me | O | H |
| 632 | H | Ethynyl | H | H | H | H | H | H | Me | O | H |
| 633 | H | Br | H | H | H | H | H | H | Me | O | H |
| 634 | H | Ethynyl | H | H | H | H | H | H | Me | O | H |
| 635 | H | Ethynyl | H | H | H | H | H | H | Me | O | H |
| 636 | H | Br | H | H | H | H | H | H | Me | O | H |
| 637 | H | Ethynyl | H | H | H | H | H | H | Me | O | H |
| 638 | H | Br | H | H | H | H | H | H | Me | O | H |
| 639 | H | Br | H | H | H | H | H | H | Me | O | H |
| 640 | H | Ethynyl | H | H | H | H | H | H | Me | O | H |
| 641 | H | Br | H | H | H | H | H | H | Me | O | H |
| 642 | H | Br | H | H | H | H | H | H | Me | O | H |
| 643 | H | Ethynyl | H | H | H | H | H | H | Me | O | H |
| 644 | H | Br | H | H | H | H | H | H | Me | O | H |
| 645 | H | Ethynyl | H | H | H | H | H | H | Me | O | H |
| 646 | H | Br | H | H | H | H | H | H | Me | O | H |
| 647 | H | Ethynyl | H | H | H | H | H | H | Me | O | H |
| 648 | H | Ethynyl | H | H | H | H | H | H | Me | O | H |
| 649 | H | Br | H | H | H | H | H | H | Me | O | H |
| 650 | H | Ethynyl | H | H | H | H | H | H | Me | O | i-Pr |
| 651 | H | Br | H | H | H | H | H | H | Me | O | i-Pr |
| 652 | H | Ethynyl | H | H | H | H | H | H | Me | O | H |
| 653 | H | Br | H | H | H | H | H | H | Me | O | H |
| 654 | H | Ethynyl | H | H | H | H | H | H | Me | O | H |
| 655 | H | Br | H | H | H | H | H | H | Me | O | H |
| 656 | H | Ethynyl | H | H | H | H | H | H | Me | O | H |
| 657 | H | Br | H | H | H | H | H | H | Me | O | H |
| 658 | H | Ethynyl | H | H | H | H | H | H | Me | O | s-Bu |
| 659 | H | Br | H | H | H | H | H | H | Me | O | s-Bu |
| 660 | H | Ethynyl | H | H | H | H | H | H | Me | O | H |
| 661 | H | Br | H | H | H | H | H | H | Me | O | H |
| 662 | H | Br | H | H | H | H | H | H | Me | O | H |
| 663 | H | Ethynyl | H | H | H | H | H | H | Me | O | H |
| 664 | H | Br | H | H | H | H | H | H | Me | O | H |
| 665 | H | Ethynyl | H | H | H | H | H | H | Me | O | H |
| 666 | H | Br | H | H | H | H | H | H | Me | O | H |
| 667 | H | Br | H | H | H | H | H | H | Me | O | H |
| 668 | H | Ethynyl | H | H | H | H | H | H | Me | O | H |
| 669 | H | Br | H | H | H | H | H | H | Me | O | H |
| 670 | H | Br | H | H | H | H | H | H | Me | O | H |

TABLE 1-continued

| | | | | | | | | | | | |
|---|---|---|---|---|---|---|---|---|---|---|---|
| 671 | H | Br | H | H | H | H | H | H | Me | O | H |
| 672 | H | Ethynyl | H | H | H | H | H | H | Me | O | H |
| 673 | H | Br | H | H | H | H | H | H | Me | O | H |
| 674 | H | Ethynyl | H | H | H | H | H | H | Me | O | H |
| 675 | H | Br | H | H | H | H | H | H | Me | O | H |
| 676 | H | Ethynyl | H | H | H | H | H | H | Me | O | H |
| 677 | H | Ethynyl | H | H | H | H | H | H | Me | O | H |
| 678 | H | Br | H | H | H | H | H | H | Me | O | H |
| 679 | H | Br | H | H | H | H | H | H | Me | O | H |
| 680 | H | Ethynyl | H | H | H | H | H | H | Me | O | H |
| 681 | H | Ethynyl | H | H | H | H | H | H | Me | O | H |
| 682 | H | Ethynyl | H | H | H | H | H | H | Me | O | H |
| 683 | H | Ethynyl | H | H | H | H | H | H | Me | O | H |
| 684 | H | Br | H | H | H | H | H | H | Me | O | H |
| 685 | H | Ethynyl | H | H | H | H | H | H | Me | O | H |
| 686 | H | Br | H | H | H | H | H | H | Me | O | H |
| 687 | H | Ethynyl | H | H | H | H | H | H | Me | O | H |
| 688 | H | Br | H | H | H | H | H | H | Me | O | H |
| 689 | H | Ethynyl | H | H | H | H | H | H | Me | O | H |
| 690 | H | Br | H | H | H | H | H | H | Me | O | H |
| 691 | H | Ethynyl | H | H | H | H | H | H | Me | O | H |
| 692 | H | Br | H | H | H | H | H | H | Me | O | H |
| 693 | H | Br | H | H | H | H | H | H | Me | O | H |
| 694 | H | Br | H | H | H | H | H | H | Me | O | H |
| 695 | H | Br | H | H | H | H | H | H | Me | O | H |
| 696 | H | Ethynyl | H | H | H | H | H | H | Me | O | H |
| 697 | H | Ethynyl | H | H | H | H | H | H | Me | O | H |
| 698 | H | Br | H | H | H | H | H | H | Me | O | H |
| 699 | H | Ethynyl | H | H | H | H | H | H | Me | O | H |
| 700 | H | Br | H | H | H | H | H | H | Ethynyl | O | H |
| 701 | H | Ethynyl | H | H | H | H | H | H | Me | O | H |
| 702 | H | I | H | H | H | H | H | H | OMe | O | H |
| 703 | H | Br | H | H | H | H | H | H | Me | O | H |
| 704 | H | Br | H | H | H | H | H | H | Me | O | H |
| 705 | H | Ethynyl | H | H | H | H | H | H | OMe | O | H |
| 706 | H | Br | H | H | H | H | H | H | Me | O | H |
| 707 | H | Br | H | H | H | H | H | H | Me | O | H |
| 708 | H | Ethynyl | H | H | H | H | H | H | OMe | O | H |
| 709 | H | Br | H | H | H | H | H | H | CN | O | H |
| 710 | H | Br | H | H | H | H | H | H | Me | O | H |
| 711 | H | Br | H | H | H | H | H | H | OMe | O | H |
| 712 | H | Br | H | H | H | H | H | H | OMe | O | H |
| 713 | H | Br | H | H | H | H | H | H | Me | O | H |
| 714 | H | Br | H | H | H | H | H | H | Me | O | H |
| 715 | H | Br | H | H | H | H | H | H | Me | O | H |
| 716 | H | Br | H | H | H | H | H | H | Me | O | H |
| 717 | H | Br | H | H | H | H | H | H | Me | O | H |
| 718 | H | Br | H | H | H | H | H | H | Me | O | H |
| 719 | H | Ethynyl | H | H | H | H | H | H | OMe | O | H |
| 720 | H | Br | H | H | H | H | H | H | Me | O | H |
| 721 | H | Br | H | H | H | H | H | H | Me | O | H |
| 722 | H | Br | H | H | H | H | H | H | Me | O | H |
| 723 | H | Br | H | H | H | H | H | H | Me | O | H |
| 724 | H | Ethynyl | H | H | H | H | H | H | Vinyl | O | H |
| 725 | H | Ethynyl | H | H | H | H | H | H | Vinyl | O | H |
| 726 | H | Ethynyl | H | H | H | H | H | H | Vinyl | O | H |
| 727 | H | Ethynyl | H | H | H | H | H | H | Vinyl | O | H |
| 728 | H | I | H | H | H | H | H | H | Vinyl | O | H |
| 729 | H | I | H | H | H | H | H | H | Vinyl | O | H |
| 730 | H | I | H | H | H | H | H | H | Vinyl | O | H |
| 731 | H | I | H | H | H | H | H | H | Vinyl | O | H |
| 732 | H | Br | H | H | H | H | H | H | Vinyl | O | H |
| 733 | H | Br | H | H | H | H | H | H | Vinyl | O | H |
| 734 | H | Br | H | H | H | H | H | H | Vinyl | O | H |
| 735 | H | Br | Cl | H | H | H | H | H | Me | O | H |
| 736 | H | Br | Cl | H | H | H | H | H | Me | O | H |
| 737 | H | Br | H | H | H | H | H | H | CN | O | H |
| 738 | H | Br | H | H | H | H | H | H | Me | O | H |
| 739 | H | Br | H | H | H | H | H | H | Me | O | H |
| 740 | H | Br | H | H | H | H | H | H | Me | O | H |
| 741 | H | Br | H | H | H | H | H | H | Me | O | H |
| 742 | H | Br | H | H | H | H | H | H | Me | O | H |
| 743 | H | Br | H | H | H | H | H | H | Me | O | H |
| 744 | H | Br | H | H | H | H | H | H | Me | O | H |
| 745 | H | Ethynyl | H | H | H | H | H | H | Me | O | H |
| 746 | H | Br | H | H | H | H | H | H | Me | O | H |
| 747 | H | Ethynyl | H | H | H | H | H | H | Me | O | H |
| 748 | H | Br | H | H | H | H | H | H | Me | O | H |
| 749 | H | Ethynyl | H | H | H | H | H | H | Me | O | H |
| 750 | H | Br | H | H | H | H | H | H | Me | O | H |

TABLE 1-continued

| | | | | | | | | | | | |
|---|---|---|---|---|---|---|---|---|---|---|---|
| 751 | H | Ethynyl | H | H | H | H | H | H | Me | O | H |
| 752 | H | Br | H | H | H | H | H | H | Me | O | H |
| 753 | H | Ethynyl | H | H | H | H | H | H | Me | O | H |
| 754 | H | Br | H | H | H | H | H | H | Me | O | H |
| 755 | H | Br | H | H | H | H | H | H | Me | O | H |
| 756 | H | Ethynyl | H | H | H | H | H | H | Me | O | H |
| 757 | H | Br | H | H | H | H | H | H | Me | O | H |
| 758 | H | Ethynyl | H | H | H | H | H | H | Me | O | H |
| 759 | H | Br | H | H | H | H | H | H | Me | O | H |
| 760 | H | Ethynyl | H | H | H | H | H | H | Me | O | H |
| 761 | H | Br | H | H | H | H | H | H | Me | O | H |
| 762 | H | Ethynyl | H | H | H | H | H | H | Me | O | H |
| 763 | H | Br | H | H | H | H | H | H | Me | O | H |
| 764 | H | Ethynyl | H | H | H | H | H | H | Me | O | H |
| 765 | H | Br | H | H | H | H | H | H | Me | O | H |
| 766 | H | Ethynyl | H | H | H | H | H | H | Me | O | H |
| 767 | H | Br | H | H | H | H | H | H | Me | O | H |
| 768 | H | Ethynyl | H | H | H | H | H | H | Me | O | H |
| 769 | H | Br | H | H | H | H | H | H | Me | O | H |
| 770 | H | Ethynyl | H | H | H | H | H | H | Me | O | H |
| 771 | H | Br | H | H | H | H | H | H | Me | O | Oxydiethan-2,1-diyl |
| 772 | H | Ethynyl | H | H | H | H | H | H | Me | O | H |
| 773 | H | Br | H | H | H | H | H | H | Me | O | H |
| 774 | H | Ethynyl | H | H | H | H | H | H | Me | O | Oxydiethan-2,1-diyl |
| 775 | H | Br | H | H | H | H | H | H | Me | O | H |
| 776 | H | Ethynyl | H | H | H | H | H | H | Me | O | H |
| 777 | H | Br | H | H | H | H | H | H | Me | O | H |
| 778 | H | Ethynyl | H | H | H | H | H | H | Me | O | H |
| 779 | H | Ethynyl | H | H | H | H | H | H | Me | O | H |
| 780 | H | Br | H | H | H | H | H | H | Me | O | H |
| 781 | H | Ethynyl | H | H | H | H | H | H | Me | O | H |
| 782 | H | Br | H | H | H | H | H | H | Me | O | H |
| 783 | H | Ethynyl | H | H | H | H | H | H | Me | O | H |
| 784 | H | Br | H | H | H | H | H | H | Me | O | H |
| 785 | H | Ethynyl | H | H | H | H | H | H | Me | O | H |
| 786 | H | Br | H | H | H | H | H | H | Me | O | H |
| 787 | H | Ethynyl | H | H | H | H | H | H | Me | O | H |
| 788 | H | Br | H | H | H | H | H | H | Me | O | H |
| 789 | H | Ethynyl | H | H | H | H | H | H | Me | O | H |
| 790 | H | Br | H | H | H | H | H | H | Me | O | H |
| 791 | H | Ethynyl | H | H | H | H | H | H | Me | O | H |
| 792 | H | Br | H | H | H | H | H | H | Me | O | H |
| 793 | H | Ethynyl | H | H | H | H | H | H | Me | O | H |
| 794 | H | Br | H | H | H | H | H | H | Me | O | H |
| 795 | H | Br | H | H | H | H | H | H | Me | O | H |
| 796 | H | Ethynyl | H | H | H | H | H | H | Me | O | H |
| 797 | H | Br | H | H | H | H | H | H | Me | O | H |
| 798 | H | Ethynyl | H | H | H | H | H | H | Me | O | H |
| 799 | H | Br | H | H | H | H | H | H | Me | O | H |
| 800 | H | Ethynyl | H | H | H | H | H | H | Me | O | H |
| 801 | H | Br | H | H | H | H | H | H | Me | O | H |
| 802 | H | Ethynyl | H | H | H | H | H | H | Me | O | H |
| 803 | H | Br | H | H | H | H | H | H | Me | O | H |
| 804 | H | Ethynyl | H | H | H | H | H | H | Me | O | H |
| 805 | H | Ethynyl | H | H | H | H | H | H | Me | O | H |
| 806 | H | Ethynyl | H | H | H | H | H | H | Me | O | H |
| 807 | H | Br | H | H | H | H | H | H | Me | O | H |
| 808 | H | Ethynyl | H | H | H | H | H | H | Me | O | H |
| 809 | H | Ethynyl | H | H | H | H | H | H | Me | O | H |
| 810 | H | Br | H | H | H | H | H | H | Me | O | H |
| 811 | H | Br | H | H | H | H | H | H | Me | O | H |
| 812 | H | Ethynyl | H | H | H | H | H | H | Me | O | H |
| 813 | H | Ethynyl | H | H | H | H | H | H | Me | O | H |
| 814 | H | Br | H | H | H | H | H | H | Me | O | H |
| 815 | H | Br | H | H | H | H | H | H | Me | O | Cyclopropyl |
| 816 | H | Ethynyl | H | H | H | H | H | H | Me | O | Cyclopropyl |
| 817 | H | Br | H | H | H | H | H | H | Me | O | H |
| 818 | H | Ethynyl | H | H | H | H | H | H | OMe | O | H |
| 819 | H | Br | H | H | H | H | H | H | Me | O | H |
| 820 | H | Ethynyl | H | H | H | H | H | H | OMe | O | H |
| 821 | H | Br | H | H | H | H | H | H | Me | O | H |
| 822 | H | Br | H | H | H | H | H | H | OMe | O | H |
| 823 | H | Br | H | H | H | H | H | H | OMe | O | H |

TABLE 1-continued

| Ex-No | A | R⁶ | R⁷ | R⁸ | R⁹ | R¹⁰ | R¹¹ | X | Log P |
|---|---|---|---|---|---|---|---|---|---|
| 1 | A⁴ | CH₃ | CH₃ | | | | | CH₃ | 1.8[a] |
| 2 | Direct bond | | | | | | | CH₃ | 1.3[a] |
| 3 | Direct bond | | | | | | | cyclopropyl | 1.04[a] |
| 4 | A¹ | H | H | | | | | 1-ethyl-3-methyl-1H-pyrazol-4-yl | |
| 5 | A⁴ | CH₃ | CH₃ | | | | | H | 3.99[a] |
| 6 | A¹ | H | H | | | | | 1-ethyl-3-methyl-1H-pyrazol-4-yl | 3.23[a] |
| 7 | A⁴ | CH₃ | CH₃ | | | | | H | 3.25[a] |
| 8 | A⁴ | CH₃ | CH₃ | | | | | H | 3.23[a] |
| 9 | O | | | | | | | CH₃ | 2.92[a] |
| 10 | A⁴ | H | H | | | | | H | 2.69[a] |
| 11 | A⁴ | CH₃ | CH₃ | | | | | H | 3.29[a] |
| 12 | A⁴ | CH₃ | CH₃ | | | | | CH₃ | 3.67[a] |
| 13 | A¹ | H | H | | | | | 1-ethyl-1H-pyrazol-4-yl | 2.5[a] |
| 14 | A³ | H | H | H | H | H | H | ethoxy | 2.98[a] |
| 15 | A² | CH₃ | H | H | H | | | CH₃ | 4.04[a] |
| 16 | A³ | H | H | H | H | H | H | ethoxy | 3.71[a] |
| 17 | A¹ | H | H | | | | | 1-ethyl-3-methyl-1H-pyrazol-4-yl | 2.69[a] |
| 18 | Direct bond | | | | | | | 1,3-dimethyl-1H-pyrazol-5-yl | 2.6[a] |
| 19 | A¹ | H | H | | | | | 3,4-dimethoxyphenyl | 3.02[a] |
| 20 | A⁴ | CH₃ | CH₃ | | | | | methoxymethyl | 3.37[a] |
| 21 | A⁴ | CH₃ | CH₃ | | | | | ethyl | 4.13[a] |
| 22 | A² | CH₃ | H | H | H | | | CH₃ | 3.31[a] |
| 23 | A⁴ | CH₃ | CH₃ | | | | | CH₃ | 3.64[a] |
| 24 | A⁴ | CH₃ | CH₃ | | | | | CH₃ | 3.62[a] |
| 25 | A⁴ | CH₃ | CH₃ | | | | | methoxymethyl | 3.42[a] |
| 26 | A⁴ | CH₃ | CH₃ | | | | | methoxymethyl | 3.29[a] |
| 27 | A² | CH₃ | H | H | H | | | CH₃ | 3.29[a] |
| 28 | A² | CH₃ | H | H | H | | | CH₃ | 3.21[a] |
| 29 | A¹ | H | H | | | | | 1-ethyl-3-methyl-1H-pyrazol-4-yl | 2.47[a] |
| 30 | A¹ | H | H | | | | | 1-ethyl-3-methyl-1H-pyrazol-4-yl | 2.42[a] |
| 31 | A¹ | CH₃ | H | | | | | CH₃ | 2.75[a] |
| 32 | A³ | H | H | H | H | H | H | ethoxy | 2.69[a] |
| 33 | A⁴ | H | H | | | | | H | 2.31[a] |
| 34 | A¹ | H | H | | | | | 1-ethyl-3-methyl-1H-pyrazol-4-yl | 2.39[a] |
| 35 | A¹ | H | H | | | | | 1-ethyl-3-methyl-1H-pyrazol-4-yl | 3.02[a] |
| 36 | A¹ | CH₃ | H | | | | | CH₃ | 3.52[a] |
| 37 | A⁴ | CH₃ | CH₃ | | | | | CH₃ | 3.32[a] |
| 38 | A¹ | CH₃ | H | | | | | CH₃ | 2.88[a] |
| 39 | A¹ | H | H | | | | | 1-ethyl-3-methyl-1H-pyrazol-4-yl | 2.49[a] |
| 40 | A¹ | CH₃ | H | | | | | CH₃ | 2.28[a] |
| 41 | A⁴ | CH₃ | CH₃ | | | | | CH₃ | 4.04[a] |
| 42 | A⁴ | CH₃ | CH₃ | | | | | CH₃ | 3.45[a] |
| 43 | A¹ | H | H | | | | | 1-ethyl-3-methyl-1H-pyrazol-4-yl | 2.14[a] |
| 44 | A⁴ | H | H | | | | | H | 2.52[a] |
| 45 | A⁴ | H | H | | | | | H | 2.14[a] |
| 46 | A⁴ | CH₃ | CH₃ | | | | | CH₃ | 3.27[a] |
| 47 | A¹ | H | H | | | | | 1-ethyl-3-methyl-1H-pyrazol-4-yl | 2.31[a] |
| 48 | A¹ | CH₃ | H | | | | | CH₃ | 2.64[a] |
| 49 | A¹ | H | H | | | | | 3-methyl-1-propyl-1H-pyrazol-4-yl | 2.64[a] |
| 50 | A¹ | H | H | | | | | 3-methyl-1-propyl-1H-pyrazol-4-yl | |
| 51 | A⁴ | H | H | | | | | H | 2.37[a] |
| 52 | A³ | H | H | H | H | H | H | ethoxy | 2.68[a] |
| 53 | A¹ | CH₃ | H | | | | | CH₃ | 2.08[a] |
| 54 | A¹ | H | H | | | | | 1-ethyl-3-methyl-1H-pyrazol-4-yl | 2.28[a] |
| 55 | A¹ | CH₃ | H | | | | | CH₃ | 2.61[a] |
| 56 | A¹ | H | H | | | | | 1-ethyl-3-methyl-1H-pyrazol-4-yl | 3.23[a] |
| 57 | A¹ | CH₃ | H | | | | | CH₃ | 3.87[a] |
| 58 | A⁴ | H | H | | | | | H | 3.37[a] |
| 59 | A³ | H | H | H | H | H | H | ethoxy | 3.8[a] |
| 60 | Direct bond | | | | | | | cyclopropyl | 3.46[a] |
| 61 | A¹ | H | H | | | | | 1-ethyl-3-methyl-1H-pyrazol-4-yl | 2.94[a] |
| 62 | A¹ | CH₃ | H | | | | | CH₃ | 3.51[a] |
| 63 | A⁴ | H | H | | | | | H | 3.04[a] |
| 64 | A³ | H | H | H | H | H | H | ethoxy | 3.46[a] |
| 65 | Direct bond | | | | | | | cyclopropyl | 3.11[a] |
| 66 | A¹ | CH₃ | H | | | | | CH₃ | 3.13[a] |
| 67 | A⁴ | H | H | | | | | H | 2.71[a] |
| 68 | A³ | H | H | H | H | H | H | ethoxy | 3.11[a] |
| 69 | Direct bond | | | | | | | cyclopropyl | 2.75[a] |
| 70 | A¹ | H | H | | | | | 1-ethyl-3-methyl-1H-pyrazol-4-yl | 2.66[a] |
| 71 | A⁴ | H | H | | | | | H | 2.43[a] |

TABLE 1-continued

| # | | | | | | | | | |
|---|---|---|---|---|---|---|---|---|---|
| 72 | A¹ | H | H | | | | | 1-ethyl-3-methyl-1H-pyrazol-4-yl | 3.37[a] |
| 73 | A¹ | CH₃ | H | | | | | CH₃ | 4.01[a] |
| 74 | A⁴ | H | H | | | | | H | 3.51[a] |
| 75 | A¹ | H | H | | | | | 1-ethyl-3-methyl-1H-pyrazol-4-yl | 2.31[a] |
| 76 | A¹ | CH₃ | H | | | | | CH₃ | 2.46[a] |
| 77 | A¹ | CH₃ | H | | | | | CH₃ | 1.49[a] |
| 78 | A¹ | CH₃ | H | | | | | CH₃ | 2.43[a] |
| 79 | A¹ | CH₃ | H | | | | | CH₃ | 2.12[a] |
| 80 | A¹ | CH₃ | H | | | | | CH₃ | 2.44[a] |
| 81 | A¹ | CH₃ | H | | | | | CH₃ | 3.04[a] |
| 82 | A³ | H | H | H | H | H | H | ethoxy | 2.45[a] |
| 83 | A¹ | H | H | | | | | 3-methyl-1-propyl-1H-pyrazol-4-yl | 2.39[a] |
| 84 | A¹ | H | H | | | | | 4-phenoxyphenyl | 4.24[a] |
| 85 | A¹ | H | H | | | | | 5-methylpyrazin-2-yl | 2.2[a] |
| 86 | A¹ | H | H | | | | | 4-(1,2,3-thiadiazol-4-yl)phenyl | 2.82[a] |
| 87 | A¹ | H | H | | | | | 1-ethyl-3,5-dimethyl-1H-pyrazol-4-yl | 2.08[a] |
| 88 | A¹ | H | H | | | | | 1-ethyl-3,5-dimethyl-1H-pyrazol-4-yl | 2.32[a] |
| 89 | A¹ | H | H | | | | | thiophen-2-yl | 3.06[a] |
| 90 | A¹ | H | H | | | | | 5-methyl-2-furyl | 3.15[a] |
| 91 | A¹ | H | H | | | | | phenyl | 3.21[a] |
| 92 | A¹ | H | H | | | | | pyridin-3-yl | 1.41[a] |
| 93 | A¹ | H | H | | | | | 2-chlorophenyl | 3.61[a] |
| 94 | A¹ | H | H | | | | | 4-chlorophenyl | 3.61[a] |
| 95 | A¹ | H | H | | | | | 2,4-dichlorophenyl | 4.16[a] |
| 96 | A¹ | H | H | | | | | 2-phenyl-2H-1,2,3-triazol-4-yl | 3.5[a] |
| 97 | A¹ | H | H | | | | | 3,5-dichlorophenyl | 4.16[a] |
| 98 | A¹ | H | H | | | | | 2-(morpholin-4-yl)pyridin-4-yl | 1.51[a] |
| 99 | A¹ | H | H | | | | | pyridin-4-yl | 1.2[a] |
| 100 | A¹ | H | H | | | | | 1-ethyl-5-methyl-1H-pyrazol-4-yl | 2.37[a] |
| 101 | A¹ | H | H | | | | | 4-(trifluoromethoxy)phenyl | 3.92[a] |
| 102 | A¹ | H | H | | | | | pyridin-4-yl | 1.34[a] |
| 103 | A¹ | H | H | | | | | pyridin-3-yl | 1.26[a] |
| 104 | A¹ | H | H | | | | | 6-chloropyridin-3-yl | 2.73[a] |
| 105 | A³ | H | H | H | H | H | H | ethoxy | 3.57[a] |
| 106 | A⁴ | H | H | | | | | H | 3.08[a] |
| 107 | A¹ | H | H | | | | | 3-methyl-1-propyl-1H-pyrazol-4-yl | 3.33[a] |
| 108 | Direct bond | | | | | | | 1-methyl-1H-pyrrol-3-yl | 3.5[a] |
| 109 | A¹ | H | H | | | | | 1-4-[(1R,4S)-7-oxabicyclo[2.2.1]hept-2-yl] | 2.56[a] |
| 110 | A² | H | H | H | H | | | 2,4-dichlorophenyl | 4.16[a] |
| 111 | A² | H | H | H | H | | | 4-chlorophenyl | 3.68[a] |
| 112 | A¹ | H | H | | | | | 3,4-dihydro-2H-chromen-4-yl | 3.48[a] |
| 113 | A¹ | H | H | | | | | 2-phenyltetrahydro-2H-pyran-3-yl | 3.5[a] |
| 114 | A¹ | H | H | | | | | 2-methyl-1H-indol-5-yl | 3.17[a] |
| 115 | A¹ | H | H | | | | | 1H-indol-5-yl | 2.63[a] |
| 116 | A¹ | H | H | | | | | 1H-indol-5-yl | 2.92[a] |
| 117 | A¹ | H | H | | | | | 3,4-dihydro-1H-isochromen-1-yl | 3.33[a] |
| 118 | A¹ | H | H | | | | | 2,3-dihydro-1,4-benzodioxin-6-yl | 3.04[a] |
| 119 | A¹ | H | H | | | | | 4-(trifluoromethyl)cyclohexyl | 4.01[a] |
| 120 | Direct bond | | | | | | | cyclobutyl | 2.58[a] |
| 121 | A¹ | H | H | | | | | 4-(trifluoromethyl)cyclohexyl | 3.61[a] |
| 122 | A¹ | H | H | | | | | 2,3-dihydro-1-benzofuran-5-yl | 3.13[a] |
| 123 | A¹ | H | H | | | | | 2,3-dihydro-1-benzofuran-6-yl | 3.17[a] |
| 124 | A¹ | H | H | | | | | 1-methyl-5-oxopyrrolidin-2-yl | 1.85[a] |
| 125 | A¹ | H | H | | | | | 2,2-dimethyl-1,3-dioxolan-4-yl | 2.35[a] |
| 126 | A¹ | H | H | | | | | 1-ethylpyrrolidin-2-yl | 1.37[a] |
| 127 | A¹ | H | H | | | | | tetrahydrofuran-3-yl | 2.2[a] |
| 128 | A¹ | H | H | | | | | 2-methyltetrahydrofuran-2-yl | 2.42[a] |
| 129 | A¹ | H | H | | | | | 2,2-dimethyl-1,3-dioxolan-4-yl | 2.64[a] |
| 130 | A¹ | H | H | | | | | tetrahydrofuran-2-yl | 2.45[a] |
| 131 | A¹ | H | H | | | | | 2-methyltetrahydrofuran-2-yl | 2.73[a] |
| 132 | A¹ | H | H | | | | | tetrahydrofuran-2-yl | 2.17[a] |
| 133 | A¹ | CH₃ | H | | | | | CH₃ | 3.09[a] |
| 134 | A¹ | CH₃ | H | | | | | CH₃ | 3.08[a] |
| 135 | A¹ | H | H | | | | | 1-ethyl-3-methyl-1H-pyrazol-4-yl | 1.83[a] |
| 136 | A¹ | CH₃ | H | | | | | CH₃ | 3.78[a] |
| 137 | A¹ | H | H | | | | | 1-ethyl-3-methyl-1H-pyrazol-4-yl | 2.62[a] |
| 138 | A¹ | H | H | | | | | 1-ethyl-3-methyl-1H-pyrazol-4-yl | 2.56[a] |
| 139 | A¹ | CH₃ | H | | | | | CH₃ | 3.01[a] |
| 140 | A¹ | H | H | | | | | 1-ethyl-3-methyl-1H-pyrazol-4-yl | 2.63[a] |
| 141 | A¹ | CH₃ | H | | | | | CH₃ | 3.02[a] |
| 142 | A¹ | H | H | | | | | 1-ethyl-3-methyl-1H-pyrazol-4-yl | 2.63[a] |
| 143 | A¹ | CH₃ | H | | | | | CH₃ | 1.44[a] |
| 144 | A¹ | CH₃ | H | | | | | CH₃ | 3.04[a] |
| 145 | A¹ | H | H | | | | | 1-ethyl-3-methyl-1H-pyrazol-4-yl | 1.34[a] |
| 146 | A¹ | CH₃ | H | | | | | CH₃ | 1.81[a] |

TABLE 1-continued

| # | | | | | | | |
|---|---|---|---|---|---|---|---|
| 147 | A[1] | H | H | | | 1-ethyl-3-methyl-1H-pyrazol-4-yl | 2.09[a] |
| 148 | A[4] | H | H | | | H | 3.9[a] |
| 149 | A[1] | H | H | | | 1-ethyl-3-methyl-1H-pyrazol-4-yl | 3.79[a] |
| 150 | A[1] | CH[3] | H | | | CH[3] | 4.41[a] |
| 151 | A[1] | H | H | | | 1-ethyl-3-methyl-1H-pyrazol-4-yl | 1.6[a] |
| 152 | A[1] | H | H | | | 1,5-dimethyl-1H-pyrrol-2-yl | 3.21[a] |
| 153 | A[1] | H | H | | | 1,5-dimethyl-1H-pyrrol-2-yl | 2.88[a] |
| 154 | A[1] | H | H | | | 4-ethyl-4H-1,2,4-triazol-3-yl | 1.72[a] |
| 155 | A[1] | H | H | | | 1-methyl-1H-imidazol-5-yl | 1.91[a] |
| 156 | A[1] | H | H | | | 3-chloro-5-(trifluoromethyl)pyridin-2-yl | 3.89[a] |
| 157 | A[1] | H | H | | | 3-chloro-5-(trifluoromethyl)pyridin-2-yl | 3.48[a] |
| 158 | A[1] | H | H | | | 2-(pyrrolidin-1-yl)pyridin-4-yl | 1.53[a] |
| 159 | A[1] | H | H | | | 4-ethyl-4H-1,2,4-triazol-3-yl | 1.54[a] |
| 160 | A[1] | H | H | | | 6-chloropyridin-3-yl | 2.44[a] |
| 161 | A[1] | H | H | | | furan-2-yl | 2.82[a] |
| 162 | A[1] | H | H | | | thiophen-2-yl | 2.73[a] |
| 163 | A[1] | H | H | | | 5-methyl-2-furyl | 2.8[a] |
| 164 | A[1] | H | H | | | furan-2-yl | 2.51[a] |
| 165 | A[1] | H | H | | | quinolin-2-yl | 2.75[a] |
| 166 | A[1] | H | H | | | 2-(pyrrolidin-1-yl)pyridin-4-yl | 1.42[a] |
| 167 | A[1] | H | H | | | 5-methylpyrazin-2-yl | 1.98[a] |
| 168 | A[1] | H | H | | | 2-chlorophenyl | 3.23[a] |
| 169 | A[1] | H | H | | | phenyl | 2.86[a] |
| 170 | A[1] | H | H | | | 5-methyl-1,2,4-oxadiazol-3-yl | 1.99[a] |
| 171 | A[1] | H | H | | | 5-methyl-1,2,4-oxadiazol-3-yl | 2.23[a] |
| 172 | A[1] | H | H | | | 2,3-dichlorophenyl | 3.58[a] |
| 173 | A[1] | H | H | | | 4-(trifluoromethoxy)phenyl | 3.53[a] |
| 174 | A[1] | H | H | | | 2,3-dichlorophenyl | 4.01[a] |
| 175 | A[1] | H | H | | | 4-phenoxyphenyl | 3.8[a] |
| 176 | A[1] | H | H | | | 1-methyl-1H-pyrazol-4-yl | 2.07[a] |
| 177 | A[1] | H | H | | | 1,3,5-trimethyl-1H-pyrazol-4-yl | 2.13[a] |
| 178 | A[1] | H | H | | | 1,5-dimethyl-1H-pyrazol-4-yl | 1.93[a] |
| 179 | A[1] | H | H | | | 1,5-dimethyl-1H-pyrazol-4-yl | 2.15[a] |
| 180 | A[1] | H | H | | | 1-methyl-1H-pyrazol-4-yl | 1.86[a] |
| 181 | A[1] | H | H | | | 1-ethyl-1H-pyrazol-4-yl | 2.04[a] |
| 182 | A[1] | H | H | | | 1-ethyl-1H-pyrazol-4-yl | 2.27[a] |
| 183 | A[1] | H | H | | | 1,3,5-trimethyl-1H-pyrazol-4-yl | 1.91[a] |
| 184 | A[1] | H | H | | | 1-isopropyl-3,5-dimethyl-1H-pyrazol-4-yl | 2.6[a] |
| 185 | A[1] | H | H | | | 1-benzyl-1H-pyrazol-4-yl | 2.64[a] |
| 186 | A[1] | H | H | | | 1-phenyl-1H-pyrazol-4-yl | 2.78[a] |
| 187 | A[1] | H | H | | | 2-phenoxyphenyl | 3.89[a] |
| 188 | A[1] | H | H | | | 3-(trifluoromethoxy)phenyl | 3.89[a] |
| 189 | A[1] | H | H | | | 2-phenyl-2H-1,2,3-triazol-4-yl | 3.11[a] |
| 190 | A[1] | H | H | | | 3-(trifluoromethoxy)phenyl | 3.48[a] |
| 191 | A[1] | H | H | | | 5-(2-thienyl)-1H-pyrazol-4-yl | 2.51[a] |
| 192 | A[1] | H | H | | | 5-(2-thienyl)-1H-pyrazol-4-yl | 2.25[a] |
| 193 | A[1] | H | H | | | 3,5-dichlorophenyl | 3.71[a] |
| 194 | A[1] | H | H | | | 2-(morpholin-4-yl)pyridin-4-yl | 1.36[a] |
| 195 | A[1] | H | H | | | 1-ethyl-5-methyl-1H-pyrazol-4-yl | 2.11[a] |
| 196 | A[1] | H | H | | | 1-isopropyl-3,5-dimethyl-1H-pyrazol-4-yl | 2.32[a] |
| 197 | A[1] | H | H | | | 1-isopropyl-1H-pyrazol-4-yl | 2.23[a] |
| 198 | A[1] | H | H | | | 2,4-dichlorophenyl | 3.73[a] |
| 199 | A[1] | H | H | | | 1-isopropyl-1H-pyrazol-4-yl | 2.5[a] |
| 200 | A[1] | H | H | | | 4-chlorophenyl | 3.23[a] |
| 201 | A[1] | H | H | | | 1-benzyl-1H-pyrazol-4-yl | 2.94[a] |
| 202 | A[1] | H | H | | | 1-phenyl-1H-pyrazol-4-yl | 3.11[a] |
| 203 | A[1] | H | H | | | 1-methyl-1H-imidazol-5-yl | 2.14[a] |
| 204 | A[1] | H | H | | | 1,3,4-oxadiazol-2-yl | 2.17[a] |
| 205 | A[1] | CH[3] | H | | | pyridin-2-yl | 2.14[a] |
| 206 | A[1] | CH[3] | H | | | pyridin-2-yl | 1.9[a] |
| 207 | A[1] | H | H | | | 2-phenoxyphenyl | 4.32[a] |
| 208 | A[1] | H | H | | | 2,3-dihydro-1,4-benzodioxin-6-yl | 2.71[a] |
| 209 | A[2] | H | H | H | H | 4-(trifluoromethoxy)phenyl | 3.55[a] |
| 210 | A[2] | H | H | H | H | 4-chlorophenyl | 3.25[a] |
| 211 | A[2] | H | H | H | H | 4-(trifluoromethoxy)phenyl | 3.96[a] |
| 212 | A[2] | H | H | H | H | 2,4-dichlorophenyl | 3.7[a] |
| 213 | A[1] | H | H | | | 1-methyl-5-oxopyrrolidin-2-yl | 1.65[a] |
| 214 | A[1] | H | H | | | tetrahydrofuran-3-yl | 1.98[a] |
| 215 | Direct bond | | | | | 1,1'-bi(cyclopropyl)-2-yl | 3.29[a] |
| 216 | Direct bond | | | | | 1,1'-bi(cyclopropyl)-2-yl | 2.92[a] |
| 217 | Direct bond | | | | | 1,2,2,6,6-pentamethylpiperidin-4-yl | 1.34[a] |
| 218 | Direct bond | | | | | 1-ethynylcyclohexyl | 3.48[a] |

TABLE 1-continued

| | | | | | | | | | |
|---|---|---|---|---|---|---|---|---|---|
| 219 | A¹ | H | H | | | | | 2,3-dihydro-1-benzofuran-5-yl | 2.78[a] |
| 220 | A¹ | H | H | | | | | 2,3-dihydro-1-benzofuran-6-yl | 2.82[a] |
| 221 | A¹ | H | H | | | | | 1-(4-fluorophenyl)cyclopropyl | 3.81[a] |
| 222 | A¹ | H | H | | | | | 2-phenyltetrahydro-2H-pyran-3-yl | 3.11[a] |
| 223 | A¹ | H | H | | | | | 3,4-dihydro-2H-chromen-4-yl | 3.11[a] |
| 224 | A¹ | H | H | | | | | 1-naphthyl | 3.85[a] |
| 225 | A¹ | H | H | | | | | 1-naphthyl | 3.46[a] |
| 226 | A¹ | H | H | | | | | 2-methyl-1H-indol-5-yl | 2.84[a] |
| 227 | A¹ | H | H | | | | | quinolin-6-yl | 1.59[a] |
| 228 | A² | H | H | H | H | | | trimethylsilyl | 4.14[a] |
| 229 | A¹ | H | H | | | | | (4-chlorophenyl)ethynyl | 3.65[a] |
| 230 | Direct bond | | | | | | | 2-oxoazepan-3-yl | 1.98[a] |
| 231 | A² | H | H | H | H | | | trimethylsilyl | 3.7[a] |
| 232 | A¹ | H | H | | | | | 1-ethylpyrrolidin-2-yl | 1.22[a] |
| 233 | A¹ | H | H | | | | | 4-oxo-5-(prop-2-yn-1-yloxy)-4H-pyran-2-yl | 1.98[a] |
| 234 | Direct bond | | | | | | | cyclobutyl | 2.9[a] |
| 235 | Direct bond | | | | | | | oxetan-3-yl | 1.99[a] |
| 236 | Direct bond | | | | | | | cyclohexyl | 3.25[a] |
| 237 | Direct bond | | | | | | | 1-ethynylcyclohexyl | 3.9[a] |
| 238 | Direct bond | | | | | | | oxetan-3-yl | 1.75[a] |
| 239 | Direct bond | | | | | | | cyclohexyl | 3.63[a] |
| 240 | Direct bond | | | | | | | 1,2,2,6,6-pentamethylpiperidin-4-yl | 1.47[a] |
| 241 | A¹ | H | H | | | | | 5-chloro-1-benzothiophen-3-yl | 4.21[a] |
| 242 | A¹ | H | H | | | | | 1-benzofuran-6-yl | 3[a] |
| 243 | A¹ | H | H | | | | | 1,3-benzothiazol-6-yl | 2.7[a] |
| 244 | A¹ | H | H | | | | | 5-chloro-1-benzothiophen-3-yl | 3.74[a] |
| 245 | A¹ | H | H | | | | | 3,4-dihydro-1H-isochromen-1-yl | 2.92[a] |
| 246 | A¹ | H | H | | | | | cyclohexyl | 3.55[a] |
| 247 | A¹ | H | H | | | | | 1-4-[(1R,4S)-7-oxabicyclo[2.2.1]hept-2-yl] | 2.15[a] |
| 248 | A¹ | H | H | | | | | (4-chlorophenyl)ethynyl | 4.06[a] |
| 249 | A¹ | H | H | | | | | cyclohexyl | 3.96[a] |
| 250 | A¹ | H | H | | | | | adamantan-2-yl | 4.46[a] |
| 251 | A¹ | H | H | | | | | 4-oxo-5-(prop-2-yn-1-yloxy)-4H-pyran-2-yl | 2.2[a] |
| 252 | Direct bond | | | | | | | 2-oxoazepan-3-yl | 2.23[a] |
| 253 | A¹ | H | H | | | | | quinolin-2-yl | 2.45[a] |
| 254 | A¹ | CH₃ | H | | | | | CH₃ | 3.26[a] |
| 255 | A¹ | CH₃ | H | | | | | CH₃ | 3.19[a] |
| 256 | A¹ | H | H | | | | | 1-ethyl-3-methyl-1H-pyrazol-4-yl | 1.72[a] |
| 257 | A¹ | H | H | | | | | 1-ethyl-3-methyl-1H-pyrazol-4-yl | 1.46[a] |
| 258 | A¹ | CH₃ | H | | | | | CH₃ | 1.79[a] |
| 259 | A¹ | CH₃ | H | | | | | CH₃ | 1.94[a] |
| 260 | A¹ | CH₃ | H | | | | | CH₃ | 1.63[a] |
| 261 | A¹ | H | H | | | | | 1-ethyl-3-methyl-1H-pyrazol-4-yl | 2.75[a] |
| 262 | A¹ | H | H | | | | | 3,4-dihydro-1H-isochromen-1-yl | 3.13[a] |
| 263 | A¹ | H | H | | | | | 1-ethyl-3-methyl-1H-pyrazol-4-yl | 2.96[a] |
| 264 | A¹ | H | H | | | | | 1-ethyl-3-methyl-1H-pyrazol-4-yl | 2.76[a] |
| 265 | A¹ | H | H | | | | | 1-ethyl-3-methyl-1H-pyrazol-4-yl | 1.62[a] |
| 266 | A¹ | H | H | | | | | 1-ethyl-3-methyl-1H-pyrazol-4-yl | 2.59[a] |
| 267 | Direct bond | | | | | | | i-Pr | 3.25[a] |
| 268 | A1 | H | H | | | | | 1-ethyl-3-methyl-1H-pyrazol-4-yl | 2.73[a] |
| 269 | Direct bond | | | | | | | Cyclopropyl | 2.88[a] |
| 270 | A3 | H | H | H | H | H | H | OEt | 3.21[a] |
| 271 | A4 | H | H | | | | | H | 2.84[a] |
| 272 | Direct bond | | | | | | | i-Pr | 3.55[a] |
| 273 | Direct bond | | | | | | | i-Pr | 2.90[a] |
| 274 | Direct bond | | | | | | | i-Pr | 3.04[a] |
| 275 | Direct bond | | | | | | | i-Pr | 3.54[a] |
| 276 | A1 | H | H | | | | | 1-ethyl-3-methyl-1H-pyrazol-4-yl | 2.39[a] |
| 277 | Direct bond | | | | | | | i-Pr | 2.81[a] |
| 278 | A1 | H | H | | | | | 1-ethyl-3-methyl-1H-pyrazol-4-yl | 3.18[a] |
| 279 | A1 | H | H | | | | | 1-ethyl-3-methyl-1H-pyrazol-4-yl | 2.38[a] |

TABLE 1-continued

| | | | | | | | | | |
|---|---|---|---|---|---|---|---|---|---|
| 280 | Direct bond | | | | | | | i-Pr | 2.69[a] |
| 281 | Direct bond | | | | | | | i-Pr | 2.88[a] |
| 82 | Direct bond | | | | | | | 2,3,5,6-tetrafluoropyridin-4-yl | 3.63[a] |
| 283 | Direct bond | | | | | | | i-Pr | 3.76[a] |
| 284 | Direct bond | | | | | | | i-Pr | 2.58[a] |
| 285 | Direct bond | | | | | | | i-Pr | 2.57[a] |
| 286 | A1 | H | H | | | | | 1-ethyl-3-methyl-1H-pyrazol-4-yl | 3.12[a] |
| 287 | Direct bond | | | | | | | i-Pr | 3.46[a] |
| 288 | A1 | H | H | | | | | 1-ethyl-3-methyl-1H-pyrazol-4-yl | 1.80[a] |
| 289 | Direct bond | | | | | | | 1-carboxy-2-{4-[(2,6-dichlorobenzoyl)amino]phenyl}ethyl | 2.17 + 1.98[a] |
| 290 | A1 | H | H | | | | | dimethoxymethyl | 2.39[a] |
| 291 | Direct bond | | | | | | | 1-(tetrahydrofuran-3-yl)ethyl | 2.46[a] |
| 292 | Direct bond | | | | | | | 1-phenylethyl | 3.46[a] |
| 293 | Direct bond | | | | | | | 1-(4,5-dihydro-1,2-oxazol-3-yl)ethyl | 2.34[a] |
| 294 | Direct bond | | | | | | | 1-(2-chlorophenyl)ethyl | 3.85[a] |
| 295 | Direct bond | | | | | | | 1-(3-thienyl)ethyl | 3.35[a] |
| 296 | Direct bond | | | | | | | 1-(2,4-dimethyl-1,3-thiazol-5-yl)ethyl | 2.46[a] |
| 297 | A3 | H | H | H | H | H | H | NMe$_2$ | 1.23[a] |
| 298 | Direct bond | | | | | | | (1E)-1-(methoxyimino)-2-methylpropan-2-yl | 3.29[a] |
| 299 | Direct bond | | | | | | | 5-methoxy-2-methylpent-3-yn-2-yl | 3.19[a] |
| 300 | A4 | H | H | | | | | CH$_2$OMe | 2.50[a] |
| 301 | Direct bond | | | | | | | 1-cyano-1-cyclopropylethyl | 3.11 + 3.13[a] |
| 302 | A1 | H | H | | | | | 1-ethyl-3-methyl-1H-pyrazol-4-yl | 2.57[a] |
| 303 | Direct bond | | | | | | | i-Pr | 3.00[a] |
| 304 | Direct bond | | | | | | | i-Pr | 2.20[a] |
| 305 | Direct bond | | | | | | | 1,3-dimethoxypropan-2-yl | 2.56[a] |
| 306 | O | | | | | | | prop-2-yn-1-yl | 2.22[a] |
| 307 | Direct bond | | | | | | | tetrahydro-2H-pyran-4-yl | 2.27[a] |
| 308 | A1 | H | H | | | | | 1-ethyl-3-methyl-1H-pyrazol-4-yl | 1.95[a] |
| 309 | Direct bond | | | | | | | 3-methyltetrahydro-2H-pyran-4-yl | 2.49 + 2.54 + 2.59 + 2.46[a] |
| 310 | Direct bond | | | | | | | 1-(1,3-thiazol-2-yl)ethyl | 2.56[a] |
| 311 | Direct bond | | | | | | | 1-(1-ethyl-3-methyl-1H-pyrazol-4-yl)propyl | 2.77[a] |
| 312 | Direct bond | | | | | | | 1-(1-ethyl-3-methyl-1H-pyrazol-4-yl)ethyl | 2.52[a] |
| 313 | Direct bond | | | | | | | 1-cyano-2-methylcyclopentyl | 3.27[a] |
| 314 | Direct bond | | | | | | | Cyclopropyl | 2.13[a] |
| 315 | Direct bond | | | | | | | 1-cyclopropyl-2-(4-fluorophenoxy)ethyl | 3.99[a] |
| 316 | Direct bond | | | | | | | 4-methylpentan-2-yl | 3.37[a] |
| 317 | Direct bond | | | | | | | Cyclopropyl | 2.40[a] |
| 318 | Direct bond | | | | | | | 1-cyclopropyl-2-(4-fluorophenoxy)ethyl | 3.58[a] |
| 319 | Direct bond | | | | | | | t-Bu | 3.39[a] |
| 320 | Direct bond | | | | | | | 2,3-dimethylbutan-2-yl | 3.71[a] |
| 321 | Direct bond | | | | | | | 4-methylpentan-2-yl | 3.80[a] |
| 322 | Direct bond | | | | | | | t-Bu | 3.00[a] |
| 323 | A3 | H | H | H | H | H | H | 2,2,2-trifluoroethoxy | 3.11[a] |

TABLE 1-continued

| No. | Col1 | | | | | | | Substituent | Value |
|---|---|---|---|---|---|---|---|---|---|
| 324 | Direct bond | | | | | | | cyano(phenyl)methyl | 2.88[a] |
| 325 | Direct bond | | | | | | | 2,3-dimethylbutan-2-yl | 4.19[a] |
| 326 | A3 | H | H | H | H | H | H | 2,2,2-trifluoroethoxy | 2.77[a] |
| 327 | Direct bond | | | | | | | 1-(1,4-dimethyl-5-oxo-4,5-dihydro-1H-1,2,4-triazol-3-yl)ethyl | 1.99[a] |
| 328 | Direct bond | | | | | | | 5-methylhexan-2-yl | 4.21[a] |
| 329 | Direct bond | | | | | | | 1-(3-isopropyl-1,2,4-oxadiazol-5-yl)ethyl | 2.94[a] |
| 330 | Direct bond | | | | | | | 1-cyclopropylethyl | 2.78[a] |
| 331 | Direct bond | | | | | | | 1-(3-isopropyl-1,2,4-oxadiazol-5-yl)ethyl | 3.23[a] |
| 332 | Direct bond | | | | | | | 1-cyclopropylethyl | 3.17[a] |
| 333 | Direct bond | | | | | | | 1-(2,4-dimethyl-1,3-thiazol-5-yl)ethyl | 2.20[a] |
| 334 | Direct bond | | | | | | | 1-(1,3-thiazol-2-yl)ethyl | 2.28[a] |
| 335 | Direct bond | | | | | | | 1-(pyridin-4-yl)ethyl | 1.28[a] |
| 336 | Direct bond | | | | | | | 1-(3-thienyl)ethyl | 2.96[a] |
| 337 | Direct bond | | | | | | | 1-(pyridin-4-yl)ethyl | 1.44[a] |
| 338 | Direct bond | | | | | | | 1-(4,5-dihydro-1,2-oxazol-3-yl)ethyl | 2.08[a] |
| 339 | Direct bond | | | | | | | 1-(1-naphthyl)ethyl | 3.85[a] |
| 340 | Direct bond | | | | | | | 1-(1-naphthyl)ethyl | 4.09[a] |
| 341 | Direct bond | | | | | | | 1-(tetrahydrofuran-3-yl)ethyl | 2.18[a] |
| 342 | Direct bond | | | | | | | 1-[4-(trifluoromethoxy)phenyl]ethyl | 3.71[a] |
| 343 | Direct bond | | | | | | | 1,1,1-trifluoropropan-2-yl | 2.77[a] |
| 344 | Direct bond | | | | | | | 1-[4-(trifluoromethoxy)phenyl]ethyl | 4.16[a] |
| 345 | Direct bond | | | | | | | 1,1,1-trifluoropropan-2-yl | 3.13[a] |
| 346 | Direct bond | | | | | | | 1-(4-chlorophenyl)ethyl | 3.44[a] |
| 347 | Direct bond | | | | | | | 1-(1-ethyl-3-methyl-1H-pyrazol-4-yl)propyl | 2.52[a] |
| 348 | Direct bond | | | | | | | 1-(4-chlorophenyl)ethyl | 3.87[a] |
| 349 | Direct bond | | | | | | | 1-(2-chlorophenyl)ethyl | 3.42[a] |
| 350 | Direct bond | | | | | | | 1-phenylethyl | 3.06[a] |
| 351 | Direct bond | | | | | | | 1-(1-ethyl-3-methyl-1H-pyrazol-4-yl)ethyl | 2.28[a] |
| 352 | Direct bond | | | | | | | 1-(1,4-dimethyl-5-oxo-4,5-dihydro-1H-1,2,4-triazol-3-yl)ethyl | 1.76[a] |
| 353 | A2 | H | H | H | H | | | Ethynyl | 2.52[a] |
| 354 | Direct bond | | | | | | | 2,2,2-trifluoro-1-(3-methylphenyl)ethyl | 3.92[a] |
| 355 | A2 | H | H | H | H | | | Ethynyl | 2.25[a] |
| 356 | Direct bond | | | | | | | cyano(phenyl)methyl | 3.25[a] |
| 357 | Direct bond | | | | | | | 1-(3-chlorophenyl)-2,2,2-trifluoroethyl | 3.94[a] |
| 358 | Direct bond | | | | | | | 2,2,2-trifluoro-1-(3-methylphenyl)ethyl | 4.36[a] |
| 359 | Direct bond | | | | | | | 1-cyclopropyl-2-[methyl(phenyl)amino]ethyl | 3.69[a] |
| 360 | Direct bond | | | | | | | 1-(3-chlorophenyl)-2,2,2-trifluoroethyl | 4.39[a] |
| 361 | Direct bond | | | | | | | 1-cyclopropyl-2-(pyrrolidin-1-yl)ethyl | 1.37[a] |
| 362 | Direct bond | | | | | | | 1-cyclopropyl-2-[methyl(phenyl)amino]ethyl | 4.19[a] |
| 363 | A3 | H | H | H | H | H | H | NMe$_2$ | 1.11[a] |
| 364 | Direct bond | | | | | | | 1-cyclopropyl-2-(pyrrolidin-1-yl)ethyl | 1.53[a] |
| 365 | Direct bond | | | | | | | 1-methoxypropan-2-yl | 2.26[a] |

TABLE 1-continued

| | | | | | | | | | |
|---|---|---|---|---|---|---|---|---|---|
| 366 | A1 | H | H | | | | | dimethoxymethyl | 2.13[a] |
| 367 | Direct bond | | | | | | | octan-2-yl | 4.19[a] |
| 368 | Direct bond | | | | | | | 1-methoxypropan-2-yl | 2.54[a] |
| 369 | Direct bond | | | | | | | 5-methylhexan-2-yl | 3.73[a] |
| 370 | Direct bond | | | | | | | octan-2-yl | 4.73[a] |
| 371 | A6 | H | H | H | H | | | Et | 2.52[a] |
| 372 | Direct bond | | | | | | | 2,6-dimethylcyclohexyl | 4.29[a] |
| 373 | O | | | | | | | t-Bu | 2.66[a] |
| 374 | Direct bond | | | | | | | 1-ethoxypropan-2-yl | 2.94 + 2.86[a] |
| 375 | O | | | | | | | 1-cyclopropylethyl | 2.73[a] |
| 376 | Direct bond | | | | | | | i-Pr | 2.64[a] |
| 377 | Direct bond | | | | | | | 1-methoxybutan-2-yl | 2.88[a] |
| 378 | A1 | H | H | | | | | 1-ethyl-3-methyl-1H-pyrazol-4-yl | 2.35[a] |
| 379 | A1 | H | H | | | | | 1-ethyl-3-methyl-1H-pyrazol-4-yl | 2.37[a] |
| 380 | Direct bond | | | | | | | H | 1.82[a] |
| 381 | Direct bond | | | | | | | i-Pr | 2.73[a] |
| 382 | Direct bond | | | | | | | i-Pr | 2.77[a] |
| 383 | A1 | H | H | | | | | 1-ethyl-3-methyl-1H-pyrazol-4-yl | 2.45[a] |
| 384 | Direct bond | | | | | | | i-Pr | 2.90[a] |
| 385 | A1 | H | H | | | | | 1-ethyl-3-methyl-1H-pyrazol-4-yl | 2.55[a] |
| 386 | A1 | H | H | | | | | 1-ethyl-3-methyl-1H-pyrazol-4-yl | 2.31[a] |
| 387 | Direct bond | | | | | | | i-Pr | 2.66[a] |
| 388 | O | | | | | | | i-Pr | 2.44[a] |
| 389 | O | | | | | | | Et | 2.17[a] |
| 390 | Direct bond | | | | | | | Cyclopentyl | 3.29[a] |
| 391 | A6 | H | H | H | H | | | i-Pr | 2.86[a] |
| 392 | A6 | H | H | H | H | | | Me | 2.26[a] |
| 393 | Direct bond | | | | | | | i-Pr | 3.35[a] |
| 394 | A1 | H | H | | | | | 1-ethyl-3-methyl-1H-pyrazol-4-yl | 2.75[a] |
| 395 | Direct bond | | | | | | | i-Pr | 4.66[a] |
| 396 | A1 | H | H | | | | | H | 2.51[a] |
| 397 | Direct bond | | | | | | | i-Pr | 2.82[a] |
| 398 | Direct bond | | | | | | | Cyclopropyl | 2.50[a] |
| 399 | A1 | H | H | | | | | 1-ethyl-3-methyl-1H-pyrazol-4-yl | 2.44[a] |
| 400 | A1 | H | H | | | | | 2,2-dimethyl-1,3-dioxolan-4-yl | 2.75[a] |
| 401 | A3 | H | H | H | H | H | H | OEt | 2.84[a] |
| 402 | Direct bond | | | | | | | i-Pr | 2.92[a] |
| 403 | Direct bond | | | | | | | i-Pr | 3.11[a] |
| 404 | Direct bond | | | | | | | i-Pr | 2.77[a] |
| 405 | A1 | H | H | | | | | 1-ethyl-3-methyl-1H-pyrazol-4-yl | 2.84[a] |
| 406 | Direct bond | | | | | | | i-Pr | 2.35[a] |
| 407 | A4 | H | H | | | | | H | 2.10[a] |
| 408 | A3 | H | H | H | H | H | H | OEt | 2.39[a] |
| 409 | A1 | H | H | | | | | 4-methyl-1-propyl-1H-pyrazol-5-yl | 2.33[a] |
| 410 | Direct bond | | | | | | | i-Pr | 3.69[a] |
| 411 | A1 | H | H | | | | | 1-ethyl-3-methyl-1H-pyrazol-4-yl | 2.59[a] |
| 412 | Direct bond | | | | | | | i-Pr | 2.16[a] |
| 413 | A1 | H | H | | | | | 1-ethyl-3-methyl-1H-pyrazol-4-yl | 2.83[a] |
| 414 | Direct bond | | | | | | | Cyclobutyl | 2.84[a] |
| 415 | Direct bond | | | | | | | i-Pr | 2.98[a] |
| 416 | A1 | H | H | | | | | 1-ethyl-3-methyl-1H-pyrazol-4-yl | 1.95[a] |
| 417 | A1 | H | H | | | | | 1-ethyl-3-methyl-1H-pyrazol-4-yl | 2.09[a] |
| 418 | A1 | H | H | | | | | 1-ethyl-3-methyl-1H-pyrazol-4-yl | 2.46[a] |

TABLE 1-continued

| No. | Col2 | Col3 | Col4 | Col5 | Col6 | Col7 | Col8 | Substituent | Value |
|---|---|---|---|---|---|---|---|---|---|
| 419 | Direct bond | | | | | | | i-Pr | 2.91[a] |
| 420 | Direct bond | | | | | | | i-Pr | 2.58[a] |
| 421 | A1 | H | H | | | | | 1-ethyl-3-methyl-1H-pyrazol-4-yl | 2.44[a] |
| 422 | Direct bond | | | | | | | i-Pr | 3.60[a] |
| 423 | Direct bond | | | | | | | i-Pr | 3.71[a] |
| 424 | A1 | H | H | | | | | 3-methyl-1-propyl-1H-pyrazol-4-yl | 3.33[a] |
| 425 | A1 | H | H | | | | | 1-ethyl-3-methyl-1H-pyrazol-4-yl | 3.01[a] |
| 426 | A3 | H | H | H | H | H | H | OEt | 3.55[a] |
| 427 | Direct bond | | | | | | | Cyclopropyl | 3.20[a] |
| 428 | A6 | H | H | H | H | | | Me | 2.02[a] |
| 429 | Direct bond | | | | | | | Cyclobutyl | 2.54[a] |
| 430 | Direct bond | | | | | | | i-Pr | 2.77[a] |
| 431 | A1 | H | H | | | | | 1-ethyl-3-methyl-1H-pyrazol-4-yl | 2.57[a] |
| 432 | A1 | H | H | | | | | 1-ethyl-3-methyl-1H-pyrazol-4-yl | 2.94[a] |
| 433 | A1 | H | H | | | | | 1-ethyl-3-methyl-1H-pyrazol-4-yl | 2.44[a] |
| 434 | Direct bond | | | | | | | 1-methyl-1H-pyrazol-4-yl | 2.17[a] |
| 435 | Direct bond | | | | | | | i-Pr | 1.19[a] |
| 436 | Direct bond | | | | | | | i-Pr | 2.75[a] |
| 437 | A1 | H | H | | | | | 1-ethyl-3-methyl-1H-pyrazol-4-yl | 2.44[a] |
| 438 | A1 | H | H | | | | | 1-ethyl-3-methyl-1H-pyrazol-4-yl | 2.37[a] |
| 439 | Direct bond | | | | | | | Cyclopropyl | 2.44[a] |
| 440 | A3 | H | H | H | H | H | H | OEt | 2.73[a] |
| 441 | A1 | H | H | | | | | 2,2-dimethyl-1,3-dioxolan-4-yl | 2.66[a] |
| 442 | A1 | H | H | | | | | 1-ethyl-3-methyl-1H-pyrazol-4-yl | 2.14[a] |
| 443 | A1 | H | H | | | | | 1,5-dimethyl-1H-pyrazol-4-yl | 2.76[a] |
| 444 | A4 | H | H | | | | | H | 2.41[a] |
| 445 | A1 | H | H | | | | | 3-methyl-1-propyl-1H-pyrazol-4-yl | 2.64[a] |
| 446 | Direct bond | | | | | | | i-Pr | 2.76[a] |
| 447 | Direct bond | | | | | | | Cyclobutyl | 2.94[a] |
| 448 | A3 | H | H | H | H | H | H | OEt | 2.80[a] |
| 449 | A1 | H | H | | | | | 3-methyl-1-propyl-1H-pyrazol-4-yl | 2.73[a] |
| 450 | Direct bond | | | | | | | Cyclopropyl | 2.48[a] |
| 451 | A1 | H | H | | | | | 1-methyl-1H-pyrazol-4-yl | 2.62[a] |
| 452 | A1 | H | H | | | | | 1-ethyl-3-methyl-1H-pyrazol-4-yl | 1.12[a] |
| 453 | Direct bond | | | | | | | 4-ethoxy-4-oxobutan-2-yl | 2.57[a] |
| 454 | Direct bond | | | | | | | Cyclobutyl | 3.06[a] |
| 455 | A1 | H | H | | | | | 3-methyl-1-propyl-1H-pyrazol-4-yl | 2.75[a] |
| 456 | A3 | H | H | H | H | H | H | OEt | 2.86[a] |
| 457 | O | | | | | | | (CH$_2$)$_4$ | 2.41[a] |
| 458 | A6 | H | H | H | H | | | Et | 2.25[a] |
| 459 | Direct bond | | | | | | | 1,3-dimethoxypropan-2-yl | 2.30[a] |
| 460 | Direct bond | | | | | | | 4,5-dihydro-1,3-oxazol-2-yl | 1.52[a] |
| 461 | A1 | H | H | | | | | 1-isopropyl-3-methyl-1H-pyrazol-4-yl | 2.34[a] |
| 462 | Direct bond | | | | | | | 1-methyl-1H-pyrazol-4-yl | 1.98[a] |
| 463 | Direct bond | | | | | | | (1E)-1-(methoxyimino)-2-methylpropan-2-yl | 2.92[a] |
| 464 | A1 | H | H | | | | | 1,5-diethyl-1H-pyrazol-4-yl | 2.37[a] |
| 465 | Direct bond | | | | | | | 5-methoxy-2-methylpent-3-yn-2-yl | 2.82[a] |
| 466 | O | | | | | | | Me | 3.31[a] |
| 467 | Direct bond | | | | | | | Cyclopropyl | 3.35[a] |
| 468 | O | | | | | | | Me | 2.96[a] |
| 469 | A1 | H | H | | | | | CHF$_2$ | 3.60[a] |
| 470 | Direct bond | | | | | | | 3-methyltetrahydro-2H-pyran-4-yl | 2.21[a] |
| 471 | O | | | | | | | 1-cyclopropylethyl | 2.43[a] |
| 472 | A1 | H | H | | | | | 1-ethyl-3-methyl-1H-pyrazol-4-yl | 3.11[a] |
| 473 | A1 | H | H | | | | | 1,2-dihydroxyethyl | 1.44[a] |
| 474 | A1 | H | H | | | | | 2,2-dimethyl-1,3-dioxolan-4-yl | 2.78[a] |

TABLE 1-continued

| No. | Col2 | | | | | | | Substituent | Value |
|---|---|---|---|---|---|---|---|---|---|
| 475 | O | | | | | | | H | 2.08[a] |
| 476 | A1 | H | H | | | | | 2,2-dimethyl-1,3-dioxolan-4-yl | 2.35[a] |
| 477 | A1 | H | H | | | | | 1,2-dihydroxyethyl | 1.59[a] |
| 478 | A1 | H | H | | | | | 1-ethyl-3-methyl-1H-pyrazol-4-yl | 3.15[a] |
| 479 | A1 | H | H | | | | | 3-thienyl | 3.07[a] |
| 480 | Direct bond | | | | | | | i-Pr | |
| 481 | A1 | H | H | | | | | 5-methylpyrazin-2-yl | 2.84[a] |
| 482 | Direct bond | | | | | | | Cyclobutyl | 2.95[a] |
| 483 | A1 | H | H | | | | | 2,2-dimethyl-1,3-dioxolan-4-yl | 2.73[a] |
| 484 | A1 | H | H | | | | | 1-ethyl-3-methyl-1H-pyrazol-4-yl | 1.60[a] |
| 485 | Direct bond | | | | | | | i-Pr | 3.72[a] |
| 486 | Direct bond | | | | | | | i-Pr | 3.50[a] |
| 487 | A1 | H | H | | | | | 4-methyl-1,3-thiazol-5-yl | 2.28[a] |
| 488 | A1 | H | H | | | | | 1,3-thiazol-2-yl | 2.32[a] |
| 489 | Direct bond | | | | | | | 1-ethyl-3-methyl-1H-pyrazol-4-yl | 2.50[a] |
| 490 | A1 | H | H | | | | | 1-ethyl-3-methyl-1H-pyrazol-4-yl | 2.55[a] |
| 491 | A1 | H | H | | | | | 1-ethyl-3-methyl-1H-pyrazol-4-yl | 2.39[a] |
| 492 | Direct bond | | | | | | | 1-ethyl-3,5-dimethyl-1H-pyrazol-4-yl | 2.41[a] |
| 493 | A1 | H | H | | | | | $CF_3$ | 2.84[a] |
| 494 | Direct bond | | | | | | | 2-(1,2-oxazol-3-yl)propan-2-yl | 2.86[a] |
| 495 | Direct bond | | | | | | | 4,5-dihydro-1,3-oxazol-2-yl | 1.71[a] |
| 496 | A1 | H | H | | | | | 2,2-dimethyl-1,3-dioxolan-4-yl | 2.62[a] |
| 497 | A4 | H | H | | | | | H | 2.48[a] |
| 498 | Direct bond | | | | | | | Cyclobutyl | 3.31[a] |
| 499 | A1 | H | H | | | | | 2,2-dimethyl-1,3-dioxolan-4-yl | 2.99[a] |
| 500 | A1 | H | H | | | | | 3-methyl-1-propyl-1H-pyrazol-4-yl | 2.91[a] |
| 501 | A4 | H | H | | | | | $CH_2OMe$ | 2.21[a] |
| 502 | Direct bond | | | | | | | tetrahydro-2H-pyran-4-yl | 2.01[a] |
| 503 | O | | | | | | | prop-2-yn-1-yl | 1.95[a] |
| 504 | Direct bond | | | | | | | Cyclopropyl | 2.08[a] |
| 505 | Direct bond | | | | | | | 4-ethoxy-4-oxobutan-2-yl | 2.84 + 2.95[a] |
| 506 | Direct bond | | | | | | | 1-ethoxypropan-2-yl | 2.55[a] |
| 507 | A1 | H | H | | | | | 1-ethyl-3-methyl-1H-pyrazol-4-yl | 3.31[a] |
| 508 | Direct bond | | | | | | | Cyclopropyl | 2.35[a] |
| 509 | Direct bond | | | | | | | 2-(1,2-oxazol-3-yl)propan-2-yl | 2.52[a] |
| 510 | Direct bond | | | | | | | i-Pr | 3.04[a] |
| 511 | Direct bond | | | | | | | 2-(4-methylpyridin-2-yl)propan-2-yl | 1.95[a] |
| 512 | Direct bond | | | | | | | 4-methoxy-4-oxobutan-2-yl | 2.28[a] |
| 513 | A1 | H | H | | | | | 2,2-dimethyl-1,3-dioxolan-4-yl | 3.44[a] |
| 514 | Direct bond | | | | | | | 2-(4-methyl-1,3-thiazol-2-yl)propan-2-yl | 2.90[a] |
| 515 | A1 | H | H | | | | | 3-thienyl | 2.71[a] |
| 516 | Direct bond | | | | | | | 2-(4-methyl-1,3-thiazol-2-yl)propan-2-yl | 2.92[a] |
| 517 | Direct bond | | | | | | | i-Pr | 3.41[a] |
| 518 | A3 | H | H | H | H | H | H | OEt | 3.37[a] |
| 519 | A1 | H | H | | | | | 3-methyl-1-propyl-1H-pyrazol-4-yl | 3.17[a] |
| 520 | A1 | H | H | | | | | 2,2-dimethyl-1,3-dioxolan-4-yl | 3.29[a] |
| 521 | Direct bond | | | | | | | Cyclobutyl | 3.61[a] |
| 522 | A4 | H | H | | | | | H | 2.98[a] |
| 523 | Direct bond | | | | | | | 1-cyano-1-cyclopropylethyl | 2.75[a] |
| 524 | Direct bond | | | | | | | 1-methoxybutan-2-yl | 2.58[a] |
| 525 | Direct bond | | | | | | | 1-(6-chloropyridin-3-yl)ethyl | 2.68[a] |
| 526 | A1 | H | H | | | | | 1-ethyl-3-methyl-1H-pyrazol-4-yl | 2.91[a] |
| 527 | A2 | H | H | H | H | | | H | 2.12[a] |
| 528 | A2 | H | H | H | H | | | H | 2.39[a] |

TABLE 1-continued

| No. | Group | | | | | | | Substituent | Value |
|---|---|---|---|---|---|---|---|---|---|
| 529 | Direct bond | | | | | | | 1-ethyl-3-methyl-1H-pyrazol-4-yl | 2.26[a] |
| 530 | Direct bond | | | | | | | i-Pr | 2.88[a] |
| 531 | A1 | H | H | | | | | H | 1.84[a] |
| 532 | A1 | H | H | | | | | H | 2.07[a] |
| 533 | A1 | H | H | | | | | 3-methyl-1-propyl-1H-pyrazol-4-yl | 2.90[a] |
| 534 | A1 | H | H | | | | | 3-methyl-1-propyl-1H-pyrazol-4-yl | 3.29[a] |
| 535 | A1 | H | H | | | | | 5-methylpyrazin-2-yl | 2.50[a] |
| 536 | A1 | H | H | | | | | 2,2-dimethyl-1,3-dioxolan-4-yl | 2.98[a] |
| 537 | A1 | H | H | | | | | 5-methylpyrazin-2-yl | 2.84[a] |
| 538 | A1 | H | H | | | | | 2,2-dimethyl-1,3-dioxolan-4-yl | 3.39[a] |
| 539 | Direct bond | | | | | | | Cyclobutyl | 3.48[a] |
| 540 | A1 | H | H | | | | | 2,2-dimethyl-1,3-dioxolan-4-yl | 3.17[a] |
| 541 | Direct bond | | | | | | | i-Pr | 3.29[a] |
| 542 | A3 | H | H | H | H | H | H | OEt | 3.25[a] |
| 543 | Direct bond | | | | | | | i-Pr | 2.96[a] |
| 544 | Direct bond | | | | | | | Cyclobutyl | 3.15[a] |
| 545 | A3 | H | H | H | H | H | H | OEt | 2.94[a] |
| 546 | A3 | H | H | H | H | H | H | OEt | 3.04[a] |
| 547 | A3 | H | H | H | H | H | H | OEt | 3.48[a] |
| 548 | A1 | H | H | | | | | 1-ethyl-3-methyl-1H-pyrazol-4-yl | 2.77[a] |
| 549 | A1 | H | H | | | | | 3-methyl-1-propyl-1H-pyrazol-4-yl | 3.06[a] |
| 550 | A1 | H | H | | | | | 1-ethyl-3-methyl-1H-pyrazol-4-yl | 2.53[a] |
| 551 | A1 | H | H | | | | | 3-methyl-1-propyl-1H-pyrazol-4-yl | 2.78[a] |
| 552 | Direct bond | | | | | | | i-Pr | 2.23[a] |
| 553 | A4 | H | H | | | | | H | 1.99 + 1.95[a] |
| 554 | A1 | H | H | | | | | 3-methyl-1-propyl-1H-pyrazol-4-yl | 2.20 + 2.25[a] |
| 555 | A1 | H | H | | | | | 2,2-dimethyl-1,3-dioxolan-4-yl | 2.21 + 2.18[a] |
| 556 | A1 | H | H | | | | | 5-methylpyrazin-2-yl | 2.64[a] |
| 557 | A1 | H | H | | | | | 1-ethyl-3-methyl-1H-pyrazol-4-yl | 1.99 + 2.04[a] |
| 558 | A1 | H | H | | | | | 5-methylpyrazin-2-yl | 2.39[a] |
| 559 | A1 | H | H | | | | | 2,2-dimethyl-1,3-dioxolan-4-yl | 2.84[a] |
| 560 | A3 | H | H | H | H | H | H | OEt | 2.27[a] |
| 561 | A4 | H | H | | | | | H | 2.84[a] |
| 562 | A1 | H | H | | | | | 5-methylpyrazin-2-yl | 1.91 + 1.87[a] |
| 563 | Direct bond | | | | | | | Cyclobutyl | 2.41[a] |
| 564 | A4 | H | H | | | | | H | 2.57[a] |
| 565 | A1 | H | H | | | | | 1-ethyl-3-methyl-1H-pyrazol-4-yl | 2.51[a] |
| 566 | A1 | H | H | | | | | 1-ethyl-3-methyl-1H-pyrazol-4-yl | 2.78[a] |
| 567 | A1 | H | H | | | | | 3-methyl-1-propyl-1H-pyrazol-4-yl | 3.08[a] |
| 568 | A1 | H | H | | | | | 2,2-dimethyl-1,3-dioxolan-4-yl | 3.11[a] |
| 569 | Direct bond | | | | | | | i-Pr | 3.15[a] |
| 570 | A4 | H | H | | | | | H | 2.68[a] |
| 571 | Direct bond | | | | | | | i-Pr | 3.06[a] |
| 572 | A4 | H | H | | | | | H | 3.06[a] |
| 573 | Direct bond | | | | | | | i-Pr | 3.51[a] |
| 574 | A4 | H | H | | | | | H | 2.82[a] |
| 575 | A1 | H | H | | | | | 5-methylpyrazin-2-yl | 2.62[a] |
| 576 | Direct bond | | | | | | | Cyclobutyl | 3.33[a] |
| 577 | A3 | H | H | H | H | H | H | OEt | 3.19[a] |
| 578 | Direct bond | | | | | | | Cyclobutyl | 3.25[a] |
| 579 | Direct bond | | | | | | | Cyclobutyl | 3.71[a] |
| 580 | A1 | H | H | | | | | 1-ethyl-3-methyl-1H-pyrazol-4-yl | 2.96[a] |
| 581 | A1 | H | H | | | | | 1-ethyl-3-methyl-1H-pyrazol-4-yl | 2.62[a] |
| 582 | A3 | H | H | H | H | H | H | OEt | 2.90[a] |
| 583 | Direct bond | | | | | | | Cyclobutyl | 3.06[a] |
| 584 | A1 | H | H | | | | | 5-methylpyrazin-2-yl | 2.37[a] |
| 585 | A1 | H | H | | | | | 1-ethyl-3-methyl-1H-pyrazol-4-yl | 2.53[a] |
| 586 | A1 | H | H | | | | | 3-methyl-1-propyl-1H-pyrazol-4-yl | 2.80[a] |
| 587 | A1 | H | H | | | | | 1-ethyl-3-methyl-1H-pyrazol-4-yl | 2.53[a] |
| 588 | A1 | H | H | | | | | 3-methyl-1-propyl-1H-pyrazol-4-yl | 2.80[a] |
| 589 | A1 | H | H | | | | | 2,2-dimethyl-1,3-dioxolan-4-yl | 2.82[a] |
| 590 | Direct bond | | | | | | | i-Pr | 2.84[a] |

TABLE 1-continued

| | | | | | | | | | |
|---|---|---|---|---|---|---|---|---|---|
| 591 | A1 | H | H | | | | | 5-methylpyrazin-2-yl | 2.37[a] |
| 592 | Direct bond | | | | | | | Cyclobutyl | 3.02[a] |
| 593 | A4 | H | H | | | | | H | 2.55[a] |
| 594 | A3 | H | H | H | H | H | H | OEt | 2.88[a] |
| 595 | A1 | H | H | | | | | 3-methyl-1-propyl-1H-pyrazol-4-yl | 3.27[a] |
| 596 | A1 | H | H | | | | | 5-methylpyrazin-2-yl | 2.78[a] |
| 597 | A3 | H | H | H | H | H | H | OEt | 3.39[a] |
| 598 | Direct bond | | | | | | | 1-methylpiperidin-4-yl | 1.17[a] |
| 599 | A1 | H | H | | | | | 1-ethyl-3-methyl-1H-pyrazol-4-yl | 2.61[a] |
| 600 | A1 | H | H | | | | | 1-ethyl-3-methyl-1H-pyrazol-4-yl | 2.96[a] |
| 601 | A1 | H | H | | | | | 2,2-dimethyl-1,3-dioxolan-4-yl | 3.33[a] |
| 602 | A4 | H | H | | | | | H | 3.02[a] |
| 603 | Direct bond | | | | | | | Cyclobutyl | 3.58[a] |
| 604 | Direct bond | | | | | | | i-Pr | 2.94[a] |
| 605 | A1 | H | H | | | | | 2,2-dimethyl-1,3-dioxolan-4-yl | 2.92[a] |
| 606 | A4 | H | H | | | | | H | 2.66[a] |
| 607 | A3 | H | H | H | H | H | H | OEt | 3.00[a] |
| 608 | Direct bond | | | | | | | i-Pr | 3.37[a] |
| 609 | A1 | H | H | | | | | 1-ethyl-3-methyl-1H-pyrazol-4-yl | 2.62[a] |
| 610 | A1 | H | H | | | | | 3-methyl-1-propyl-1H-pyrazol-4-yl | 2.90[a] |
| 611 | A1 | H | H | | | | | 5-methylpyrazin-2-yl | 2.46[a] |
| 612 | Direct bond | | | | | | | Cyclobutyl | 3.15[a] |
| 613 | A1 | H | H | | | | | 1-ethyl-3-methyl-1H-pyrazol-4-yl | 2.39[a] |
| 614 | A1 | H | H | | | | | 2,2-dimethyl-1,3-dioxolan-4-yl | 2.64[a] |
| 615 | A3 | H | H | H | H | H | H | OEt | 2.73[a] |
| 616 | Direct bond | | | | | | | i-Pr | 2.73[a] |
| 617 | A1 | H | H | | | | | 1-ethyl-3-methyl-1H-pyrazol-4-yl | 2.73[a] |
| 618 | A1 | H | H | | | | | 2,2-dimethyl-1,3-dioxolan-4-yl | 3.06[a] |
| 619 | A3 | H | H | H | H | H | H | OEt | 3.19[a] |
| 620 | Direct bond | | | | | | | i-Pr | 3.17[a] |
| 621 | A1 | H | H | | | | | 1-ethyl-3-methyl-1H-pyrazol-4-yl | 2.64[a] |
| 622 | A1 | H | H | | | | | 2,2-dimethyl-1,3-dioxolan-4-yl | 2.96[a] |
| 623 | A3 | H | H | H | H | H | H | OEt | 3.06[a] |
| 624 | Direct bond | | | | | | | 2-methylbut-3-yn-2-yl | 3.08[a] |
| 625 | Direct bond | | | | | | | Cyclobutyl | 3.11[a] |
| 626 | A1 | H | H | | | | | 1-ethyl-3-methyl-1H-pyrazol-4-yl | 2.57[a] |
| 627 | A3 | H | H | H | H | H | H | OEt | 2.94[a] |
| 628 | A1 | H | H | | | | | 5-methylpyrazin-2-yl | 2.41[a] |
| 629 | A1 | H | H | | | | | 1-cyclopentyl-3-methyl-1H-pyrazol-4-yl | 2.71[a] |
| 630 | A1 | H | H | | | | | 1-cyclopentyl-3-methyl-1H-pyrazol-4-yl | 3.04[a] |
| 631 | A1 | H | H | | | | | 5-methoxypyridin-2-yl | 1.96[a] |
| 632 | A1 | H | H | | | | | 1-cyclobutyl-3-methyl-1H-pyrazol-4-yl | 2.63[a] |
| 633 | A1 | H | H | | | | | 1-cyclobutyl-3-methyl-1H-pyrazol-4-yl | 2.92[a] |
| 634 | A1 | H | H | | | | | 3-bromo-1-ethyl-1H-pyrazol-4-yl | 2.56[a] |
| 635 | A1 | H | H | | | | | 1-ethyl-3-(methylsulfanyl)-1H-pyrazol-4-yl | 2.51[a] |
| 636 | A1 | H | H | | | | | 3-bromo-1-ethyl-1H-pyrazol-4-yl | 2.86[a] |
| 637 | A1 | H | H | | | | | 1-ethyl-3-methoxy-1H-pyrazol-4-yl | 2.35[a] |
| 638 | A1 | H | H | | | | | 1-ethyl-3-(methylsulfanyl)-1H-pyrazol-4-yl | 2.78[a] |
| 639 | A1 | H | H | | | | | 1-ethyl-3-methoxy-1H-pyrazol-4-yl | 2.63[a] |
| 640 | A2 | H | H | H | H | | | F | 2.05[a] |
| 641 | A2 | H | H | H | H | | | F | 2.30[a] |
| 642 | A1 | H | H | | | | | pyrimidin-4-yl | 2.01[a] |
| 643 | A1 | H | H | | | | | 4,6-dimethylpyrimidin-2-yl | 2.23[a] |
| 644 | A1 | H | H | | | | | 3-methoxypyridin-2-yl | 2.26[a] |
| 645 | A1 | H | H | | | | | 3-methoxypyridin-2-yl | 2.01[a] |
| 646 | A1 | H | H | | | | | 1-(2,2-difluoroethyl)-1H-pyrazol-4-yl | 2.42[a] |
| 647 | A1 | H | H | | | | | 1-(2,2-difluoroethyl)-1H-pyrazol-4-yl | 2.17[a] |
| 648 | A1 | H | H | | | | | 4-methyl-1,3-thiazol-2-yl | 2.26[a] |
| 649 | A1 | H | H | | | | | 4-methyl-1,3-thiazol-2-yl | 2.56[a] |
| 650 | O | | | | | | | Me | 3.15[a] |

TABLE 1-continued

| | | | | | | | | |
|---|---|---|---|---|---|---|---|---|
| 651 | O | | | | | | Me | 3.59[a] |
| 652 | A1 | H | H | | | | CHF$_2$ | 2.26[a] |
| 653 | A1 | H | H | | | | CHF$_2$ | 2.56[a] |
| 654 | A1 | H | H | | | | 3-methyl-1-pentyl-1H-pyrazol-4-yl | 2.96[a] |
| 655 | A1 | H | H | | | | 3-methyl-1-pentyl-1H-pyrazol-4-yl | 3.31[a] |
| 656 | A1 | H | H | | | | 1-butyl-3-methyl-1H-pyrazol-4-yl | 2.64[a] |
| 657 | A1 | H | H | | | | 1-butyl-3-methyl-1H-pyrazol-4-yl | 2.96[a] |
| 658 | O | | | | | | Me | 3.50[a] |
| 659 | O | | | | | | Me | 3.96[a] |
| 660 | A1 | H | H | | | | 6-isopropylpyridin-2-yl | 2.07[a] |
| 661 | A1 | H | H | | | | pyrimidin-2-yl | 2.13[a] |
| 662 | A1 | H | H | | | | 4,6-dimethylpyrimidin-2-yl | 2.51[a] |
| 663 | A1 | H | H | | | | pyrimidin-4-yl | 1.78[a] |
| 664 | A1 | H | H | | | | 4-methoxypyridin-2-yl | 1.49[a] |
| 665 | A1 | H | H | | | | 6-methoxypyridin-2-yl | 2.77[a] |
| 666 | A1 | H | H | | | | 5-methoxypyridin-2-yl | 2.20[a] |
| 667 | A1 | H | H | | | | 6-methoxypyridin-2-yl | 3.11[a] |
| 668 | A1 | H | H | | | | 1-cyclopropyl-3-methyl-1H-pyrazol-4-yl | 2.26[a] |
| 669 | A1 | H | H | | | | 1-cyclopropyl-3-methyl-1H-pyrazol-4-yl | 2.52[a] |
| 670 | A1 | H | H | | | | 4-methoxypyridin-3-yl | 1.40[a] |
| 671 | A1 | H | H | | | | 2-methoxypyridin-4-yl | 2.54[a] |
| 672 | A1 | H | H | | | | 4-methoxypyridin-3-yl | 1.27[a] |
| 673 | A1 | H | H | | | | 3-methoxypyridin-4-yl | 1.56[a] |
| 674 | A1 | H | H | | | | 2-methoxypyridin-4-yl | 2.26[a] |
| 675 | A1 | H | H | | | | 6-methoxypyridazin-3-yl | 2.28[a] |
| 676 | A1 | H | H | | | | 3-methoxypyridin-4-yl | 1.40[a] |
| 677 | A1 | H | H | | | | 4-methoxypyridin-2-yl | 1.34[a] |
| 678 | A1 | H | H | | | | 2-methoxypyridin-3-yl | 2.82[a] |
| 679 | A1 | H | H | | | | 6-methoxypyridin-3-yl | 2.66[a] |
| 680 | A1 | H | H | | | | 2-methoxypyridin-3-yl | 2.52[a] |
| 681 | A1 | H | H | | | | 6-methoxypyridin-3-yl | 2.37[a] |
| 682 | A1 | H | H | | | | 4-methylpyridin-3-yl | 1.29[a] |
| 683 | A1 | H | H | | | | 3-methylpyridin-4-yl | 1.29[a] |
| 684 | A1 | H | H | | | | 2-methylpyridin-4-yl | 1.40[a] |
| 685 | A1 | H | H | | | | 2-methylpyridin-4-yl | 1.27[a] |
| 686 | A1 | H | H | | | | 6-isopropylpyridin-2-yl | 2.33[a] |
| 687 | A1 | H | H | | | | 6-methoxypyridazin-3-yl | 2.05[a] |
| 688 | A1 | H | H | | | | 2-methoxypyrimidin-5-yl | 2.25[a] |
| 689 | A1 | H | H | | | | 2-methoxypyrimidin-5-yl | 2.01[a] |
| 690 | A1 | H | H | | | | 6-methylpyridin-2-yl | 1.60[a] |
| 691 | A1 | H | H | | | | 6-methylpyridin-2-yl | 1.43[a] |
| 692 | A1 | H | H | | | | pyrimidin-5-yl | 1.95[a] |
| 693 | A1 | H | H | | | | 4-methylpyridin-3-yl | 1.43[a] |
| 694 | Direct bond | | | | | | 1-ethyl-1H-pyrazol-4-yl | 2.45[a] |
| 695 | A1 | H | H | | | | 3-methylpyridin-4-yl | 1.46[a] |
| 696 | A1 | H | H | | | | 5-methoxypyridin-3-yl | 1.59[a] |
| 697 | A1 | H | H | | | | pyrimidin-5-yl | 1.74[a] |
| 698 | A1 | H | H | | | | 5-methoxypyridin-3-yl | 1.78[a] |
| 699 | Direct bond | | | | | | 1-ethyl-1H-pyrazol-4-yl | 2.17[a] |
| 700 | A1 | H | H | | | | 3-methyl-1-propyl-1H-pyrazol-4-yl | 2.78[a] |
| 701 | Direct bond | | | | | | 1-(dimethylamino)propan-2-yl | 1.42[a] |
| 702 | Direct bond | | | | | | 1-methylpiperidin-4-yl | 1.67[a] |
| 703 | A3 | H | H | H | H | H | Me | 3.17[a] |
| 704 | A1 | H | H | | | | 3-chloro-1-ethyl-1H-pyrazol-4-yl | 2.84[a] |
| 705 | A1 | H | H | | | | 3-chloro-1-ethyl-1H-pyrazol-4-yl | 2.51[a] |
| 706 | A1 | H | H | | | | pyrazin-2-yl | 2.10[a] |
| 707 | Direct bond | | | | | | 6-[({[(Z)-(4-methyl-5-oxo-4,5-dihydro-1,2,4-oxadiazol-3-yl)(phenyl)methylene]amino}oxy)methyl]pyridin-2-yl | 4.49[a] |
| 708 | A1 | H | H | | | | pyrazin-2-yl | 1.85[a] |
| 709 | A1 | H | H | | | | 1-ethyl-3-methyl-1H-pyrazol-4-yl | 2.51[a] |
| 710 | A2 | H | H | H | H | | Cyclopropyl | 3.17[a] |
| 711 | Direct bond | | | | | | 6-[({[(Z)-(4-methyl-5-oxo-4,5-dihydro-1,2,4-oxadiazol-3-yl)(phenyl)methylene]amino}oxy)methyl]pyridin-2-yl | 4.39[a] |
| 712 | A2 | H | H | H | H | | 3,4-dimethoxyphenyl | 2.94[a] |
| 713 | A2 | H | H | H | H | | tetrahydrofuran-2-yl | 2.39[a] |
| 714 | A3 | H | H | H | H | H | H | 2.75[a] |
| 715 | A1 | H | H | | | | prop-1-en-2-yl | 2.90[a] |
| 716 | Direct bond | | | | | | 2-cyanopropan-2-yl | 2.68[a] |

TABLE 1-continued

| # | | | | | | | | | |
|---|---|---|---|---|---|---|---|---|---|
| 717 | Direct bond | | | | | | | 3-ethylpent-1-yn-3-yl | 3.96[a] |
| 718 | Direct bond | | | | | | | 1-ethynylcyclopropyl | 2.64[a] |
| 719 | A2 | H | H | H | H | | | Cyclopropyl | 2.78[a] |
| 720 | A2 | H | H | H | H | | | CN | 2.15[a] |
| 721 | Direct bond | | | | | | | 1-cyanopropyl | 2.75[a] |
| 722 | Direct bond | | | | | | | 3-ethynyloxetan-3-yl | 2.37[a] |
| 723 | Direct bond | | | | | | | (1E)—N-hydroxyethanimidoyl | 2.04[a] |
| 724 | A1 | H | H | | | | | 1-ethyl-3-methyl-1H-pyrazol-4-yl | 2.37[a] |
| 725 | A1 | H | H | | | | | 2,2-dimethyl-1,3-dioxolan-4-yl | 2.66[a] |
| 726 | A3 | H | H | H | H | H | H | OEt | 2.73[a] |
| 727 | Direct bond | | | | | | | i-Pr | 2.73[a] |
| 728 | A1 | H | H | | | | | 1-ethyl-3-methyl-1H-pyrazol-4-yl | 2.75[a] |
| 729 | A1 | H | H | | | | | 2,2-dimethyl-1,3-dioxolan-4-yl | 3.11[a] |
| 730 | A3 | H | H | H | H | H | H | OEt | 3.19[a] |
| 731 | Direct bond | | | | | | | i-Pr | 3.21[a] |
| 732 | A1 | H | H | | | | | 2,2-dimethyl-1,3-dioxolan-4-yl | 2.98[a] |
| 733 | A3 | H | H | H | H | H | H | OEt | 3.06[a] |
| 734 | Direct bond | | | | | | | i-Pr | 3.08[a] |
| 735 | A1 | H | H | | | | | 1-ethyl-3-methyl-1H-pyrazol-4-yl | 2.69[a] |
| 736 | Direct bond | | | | | | | i-Pr | 2.39[a] |
| 737 | Direct bond | | | | | | | i-Pr | 2.86[a] |
| 738 | Direct bond | | | | | | | (1E)—N-hydroxy-2-methylpropanimidoyl | 2.50[a] |
| 739 | Direct bond | | | | | | | (1E)—N-hydroxy-2,2-dimethylpropanimidoyl | 2.88[a] |
| 740 | Direct bond | | | | | | | (E)-cyclopropyl(hydroxyimino)methyl | 2.35[a] |
| 741 | Direct bond | | | | | | | (E)-(hydroxyimino)(pyridin-3-yl)methyl | 2.10[a] |
| 742 | Direct bond | | | | | | | s-Bu | 3.37[a] |
| 743 | A1 | H | H | | | | | i-Pr | 3.15[a] |
| 744 | A1 | H | H | | | | | 5-ethylpyridin-2-yl | 2.05[a] |
| 745 | A1 | H | H | | | | | 4-ethylpyridin-2-yl | 1.64[a] |
| 746 | A1 | H | H | | | | | 6-ethylpyridin-2-yl | 1.88[a] |
| 747 | A1 | H | H | | | | | 5-ethylpyridin-2-yl | 1.82[a] |
| 748 | A1 | H | H | | | | | 4-cyanopyridin-2-yl | 2.48[a] |
| 749 | A1 | H | H | | | | | 6-ethylpyridin-2-yl | 1.67[a] |
| 750 | A1 | H | H | | | | | 4-isopropylpyridin-2-yl | 2.05[a] |
| 751 | A1 | H | H | | | | | 4-cyanopyridin-2-yl | 2.20[a] |
| 752 | A1 | H | H | | | | | 4-ethylpyridin-2-yl | 1.82[a] |
| 753 | A1 | H | H | | | | | 1-methylcyclobutyl | 3.27[a] |
| 754 | A1 | H | H | | | | | 3,3-difluorocyclobutyl | 2.98[a] |
| 755 | Direct bond | | | | | | | 3,3-difluorocyclobutyl | 2.86[a] |
| 756 | A1 | H | H | | | | | 4,4-dioxido-1,4-oxathian-2-yl | 1.93[a] |
| 757 | A1 | H | H | | | | | 1-methylcyclobutyl | 3.65[a] |
| 758 | A1 | H | H | | | | | 2-hydroxypyridin-4-yl | 1.54[a] |
| 759 | A1 | H | H | | | | | 2-sec-butoxypyridin-4-yl | 3.48[a] |
| 760 | A1 | H | H | | | | | 2-sec-butoxypyridin-4-yl | 3.06[a] |
| 761 | A1 | H | H | | | | | 2-(cyclopropylamino)pyridin-4-yl | 1.58[a] |
| 762 | A1 | H | H | | | | | 2-(trifluoromethyl)pyridin-4-yl | 2.64[a] |
| 763 | A1 | H | H | | | | | 2-isopropoxypyridin-4-yl | 3.09[a] |
| 764 | A1 | H | H | | | | | 2-isopropoxypyridin-4-yl | 2.71[a] |
| 765 | A1 | H | H | | | | | 2-hydroxypyridin-4-yl | 1.72[a] |
| 766 | A2 | H | H | H | H | | | 2-chloro-4-(trifluoromethyl)phenyl | 3.76[a] |
| 767 | Direct bond | | | | | | | (1-cyclopropylethyl)amino | 2.51[a] |
| 768 | Direct bond | | | | | | | dicyclopropylmethyl | 3.21[a] |
| 769 | A2 | H | H | H | H | | | 2-chloro-4-(trifluoromethyl)phenyl | 4.21[a] |
| 770 | Direct bond | | | | | | | (1-cyclopropylethyl)amino | 2.21[a] |
| 771 | Direct bond | | | | | | | Oxydiethan-2,1-diyl | 2.48[a] |
| 772 | A1 | H | H | | | | | 1-(2,2,2-trifluoroethyl)-1H-pyrazol-4-yl | 2.34[a] |
| 773 | Direct bond | | | | | | | dicyclopropylmethyl | 3.57[a] |

TABLE 1-continued

| | | | | | | | |
|---|---|---|---|---|---|---|---|
| 774 | Direct bond | | | | | Oxydiethan-2,1-diyl | 2.18[a] |
| 775 | A1 | H | H | | | Cyclobutyl | 3.25[a] |
| 776 | Direct bond | | | | | 3,3-difluorocyclobutyl | 2.57[a] |
| 777 | A1 | H | H | | | 1-(2,2,2-trifluoroethyl)-1H-pyrazol-4-yl | 2.60[a] |
| 778 | A1 | H | H | | | Cyclobutyl | 2.88[a] |
| 779 | A1 | H | H | | | 5-cyanopyridin-3-yl | 2.10[a] |
| 780 | A1 | H | H | | | 2-(dimethylamino)pyridin-3-yl | 1.60[a] |
| 781 | A1 | H | H | | | 5-fluoropyridin-3-yl | 2.13[a] |
| 782 | A1 | H | H | | | 5-cyanopyridin-3-yl | 2.35[a] |
| 783 | A1 | H | H | | | 2-fluoropyridin-3-yl | 2.23[a] |
| 784 | A1 | H | H | | | 5-fluoropyridin-3-yl | 2.37[a] |
| 785 | A1 | H | H | | | 2-ethoxypyridin-3-yl | 2.84[a] |
| 786 | A1 | H | H | | | 2-fluoropyridin-3-yl | 2.51[a] |
| 787 | A1 | H | H | | | 5-chloropyrazin-2-yl | 2.43[a] |
| 788 | A1 | H | H | | | 2-ethoxypyridin-3-yl | 3.21[a] |
| 789 | A1 | H | H | | | 6-chloropyrazin-2-yl | 2.41[a] |
| 790 | A1 | H | H | | | 5-chloropyrazin-2-yl | 2.73[a] |
| 791 | A1 | H | H | | | 6-methoxypyrazin-2-yl | 2.25[a] |
| 792 | A1 | H | H | | | 6-chloropyrazin-2-yl | 2.71[a] |
| 793 | A1 | H | H | | | 4-isopropylpyridin-2-yl | 1.84[a] |
| 794 | A1 | H | H | | | 6-methoxypyrazin-2-yl | 2.53[a] |
| 795 | A1 | H | H | | | 2-(trifluoromethyl)pyridin-4-yl | 2.96[a] |
| 796 | A1 | H | H | | | 2-(tert-butylsulfanyl)pyridin-4-yl | 3.02[a] |
| 797 | A1 | H | H | | | 2-(tert-butylsulfanyl)pyridin-4-yl | 3.44[a] |
| 798 | A1 | H | H | | | 2-(methylsulfanyl)pyridin-4-yl | 2.32[a] |
| 799 | A1 | H | H | | | 2-(methylsulfanyl)pyridin-4-yl | 2.62[a] |
| 800 | A1 | H | H | | | 2-(dimethylamino)pyridin-4-yl | 1.36[a] |
| 801 | A1 | H | H | | | 2-(dimethylamino)pyridin-4-yl | 1.49[a] |
| 802 | A1 | H | H | | | 2-fluoropyridin-4-yl | 2.23[a] |
| 803 | A1 | H | H | | | 2-fluoropyridin-4-yl | 2.51[a] |
| 804 | A1 | H | H | | | 3-fluoropyridin-4-yl | 2.02[a] |
| 805 | A1 | H | H | | | 2-hydroxypyridin-3-yl | 1.64[a] |
| 806 | A1 | H | H | | | 6-hydroxypyridin-3-yl | 1.54[a] |
| 807 | A1 | H | H | | | 6-hydroxypyridin-3-yl | 1.72[a] |
| 808 | A1 | H | H | | | 2-(dimethylamino)pyridin-3-yl | 1.43[a] |
| 809 | A1 | H | H | | | 2-(cyclopropylamino)pyridin-4-yl | 1.45[a] |
| 810 | A1 | H | H | | | 4,4-dioxido-1,4-oxathian-2-yl | 2.15[a] |
| 811 | A1 | H | H | | | 3-fluoropyridin-4-yl | 2.27[a] |
| 812 | A1 | H | H | | | 2-cyanopyridin-3-yl | 1.70[a] |
| 813 | A1 | H | H | | | 3,3-difluorocyclobutyl | 2.71[a] |
| 814 | A1 | H | H | | | 2-cyanopyridin-3-yl | 1.91[a] |
| 815 | A1 | H | H | | | 3-fluoro-8,8-dimethyl-5,6,7,8-tetrahydronaphthalen-1-yl | 6.11[a] |
| 816 | A1 | H | H | | | 3-fluoro-8,8-dimethyl-5,6,7,8-tetrahydronaphthalen-1-yl | 5.54[a] |
| 817 | A1 | H | H | | | 2-hydroxypyridin-3-yl | 1.88[a] |
| 818 | A2 | H | H | H | H | tetrahydrofuran-2-yl | 2.11[a] |
| 819 | A1 | H | H | | | 2-tert-butoxypyridin-3-yl | 4.46[a] |
| 820 | A1 | H | H | | | 1-ethyl-3-(trifluoromethyl)-1H-pyrazol-4-yl | 2.80[a] |
| 821 | A1 | H | H | | | 1-ethyl-3-(trifluoromethyl)-1H-pyrazol-4-yl | 3.13[a] |
| 822 | A2 | H | H | H | H | Cyclopropyl | 3.03[a] |
| 823 | A2 | H | H | H | H | tetrahydrofuran-3-yl | 2.27[a] |

Measurement of logP values was performed according EEC directive 79/831 Annex V.A8 by HPLC (High Performance Liquid Chromatography) on reversed phase columns with the following methods:
[a]Measurement of LC-MS was done at pH 2.7 with 0.1% formic acid in water and with acetonitrile (contains 0.1% formic acid) as eluent with a linear gradient from 10% acetonitrile to 95% acetonitrile. Calibration was done with not branched alkan2-ones (with 3 to 16 carbon atoms) with known logP-values (measurement of logP values using retention times with linear interpolation between successive alkanones). lambda-maX-values were determined using UV-spectra from 200 nm to 400 nm and the peak values of the chromatographic signals.

NMR Peak lists

1H-NMR data of selected examples are written in form of 1H-NMR-peak lists. To each signal peak are listed the δ-value in ppm and the signal intensity in round brackets.

Between the δ-value - signal intensity pairs are semicolon deliminators.

The peak list of an example has therefore the form:

$\delta_1$ (intensity$_1$); $\delta_2$ (intensity$_2$); ... ; $\delta_i$ (intensity$_i$); ... ; $\delta_n$ (intensity$_n$)

NMR Peak Lists Table 1

Example 1: $^1$H-NMR(400.0 MHz, DMSO):
8.960(1.5); 8.956(1.6); 8.950(1.6); 8.946(1.5); 8.444(1.2); 8.425(1.3); 8.257(2.3); 8.252(2.4); 8.158(1.2); 8.153(1.0); 8.136(1.8); 8.131(1.7); 8.063(2.5); 8.040(1.6); 7.623(1.4); 7.613(1.4); 7.603(1.4); 7.592(1.4); 7.532(2.3); 3.925(2.0); 3.903(7.0); 3.882(2.4); 3.491(2.3); 3.447(1.9); 3.331(108.7); 3.174(0.7); 3.165(0.7); 2.672(0.4); 2.525(1.2); 2.512(26.7); 2.507(53.0); 2.503(68.9); 2.498(49.5); 2.494(24.1); 2.330(0.4); 1.726(16.0); 1.597(11.9); 1.515(14.4); 0.000(2.9)

NMR Peak Lists Table 1

Example 2: ¹H-NMR(400.0 MHz, DMSO):
8.962(1.4); 8.958(1.5); 8.952(1.5); 8.948(1.4); 8.443(1.2); 8.425(1.3); 8.222(2.3); 8.217(2.5); 8.142(1.1); 8.137(1.0); 8.119(1.9); 8.115(1.7); 8.064(2.6); 8.042(1.4); 7.624(1.4); 7.614(1.4); 7.604(1.4); 7.593(1.3); 4.014(2.1); 3.971(2.6); 3.903(4.8); 3.737(16.0); 3.606(2.5); 3.563(2.1); 3.332(85.0); 3.311(0.5); 2.672(0.4); 2.511(23.8); 2.507(46.2); 2.503(60.0); 2.498(43.7); 2.329(0.4); 1.654(13.0); 1.235(0.4); 0.000(2.1)

Example 3: ¹H-NMR(400.0 MHz, DMSO):
8.956(2.1); 8.952(2.0); 8.945(2.2); 8.941(1.9); 8.440(1.8); 8.420(1.9); 8.312(0.6); 8.228(3.3); 8.225(3.2); 8.163(1.5); 8.152(1.5); 8.141(1.8); 8.137(1.4); 8.119(2.5); 8.114(2.3); 8.056(3.4); 8.034(2.0); 7.618(1.7); 7.607(1.7); 7.597(1.7); 7.587(1.6); 3.935(2.7); 3.901(7.1); 3.891(3.3); 3.477(3.0); 3.434(2.6); 3.331(103.6); 3.171(0.6); 2.725(0.6); 2.718(0.7); 2.707(1.3); 2.697(1.1); 2.686(0.6); 2.679(0.9); 2.673(0.6); 2.668(0.6); 2.508(68.7); 2.504(84.8); 2.499(61.2); 2.331(0.5); 1.585(16.0); 0.624(0.4); 0.612(0.8); 0.601(1.3); 0.593(2.3); 0.584(1.7); 0.576(2.1); 0.570(1.8); 0.562(2.1); 0.550(3.9); 0.544(2.9); 0.536(1.0); 0.000(3.2)

Example 4, Solvent: CDCl3, Spectrometer: 300,16 MHz
8.9749 (1.13); 8.9703 (1.22); 8.9611 (1.24); 8.9568 (1.15); 8.1949 (1.31); 8.1899 (1.32); 8.1661 (1.61); 8.1620 (1.59); 8.1346 (3.18); 8.1288 (4.81); 8.0961 (0.42); 7.8906 (2.67); 7.4872(1.44); 7.4730 (1.43); 7.4596 (1.37); 7.4453 (1.33); 7.2714 (5.04); 7.2499 (3.86); 6.9623 (0.53); 6.9459 (0.91); 6.9298 (0.55); 4.3652(0.74); 4.3463 (0.75); 4.3157 (1.57); 4.2967 (1.56); 4.2309 (1.58); 4.2140 (1.61); 4.1815 (0.79); 4.1645 (0.78); 4.0762 (1.25); 4.0518 (3.82); 4.0274(4.00); 4.0164 (2.70); 4.0031 (1.44); 3.9592 (2.92); 3.3938 (2.76); 3.3366 (2.36); 2.1899 (16.00); 2.0463 (0.72); 1.8242 (1.32); 1.7806 (14.37); 1.4436 (4.62); 1.4192 (9.47); 1.3948 (4.52); 1.2594 (0.56); −0.0002 (2.49)

Example 5, Solvent: CDCl3, Spectrometer: 250,13 MHz
8.9514 (1.67); 8.9430 (1.73); 8.8853 (1.60); 8.8767 (1.66); 8.3095 (1.17); 8.3030 (1.57); 8.2966 (1.18); 8.2350 (0.99); 8.2281 (1.45); 8.2212 (1.02); 7.9453 (0.92); 7.9364 (0.97); 7.9191 (0.90); 7.9103 (0.91); 7.8533 (1.71); 7.8459 (1.75); 7.1975 (2.73); 6.8450(0.94); 6.8135 (1.06); 4.1462 (5.98); 4.1316 (5.68); 4.1013 (0.75); 4.0862 (0.92); 4.0799 (0.91); 4.0261 (1.39); 3.9063 (1.25); 3.8942 (2.47); 3.8316 (0.73); 3.8235 (0.84); 3.8189 (1.25); 2.3177 (6.90); 1.6366 (13.48); 1.6210 (16.00); 1.1777 (0.94); −0.0006 (6.91); −0.0771 (1.45)

Example 6, Solvent: CDCl3, Spectrometer: 250,13 MHz
8.9613 (2.29); 8.9533 (2.05); 8.8964 (2.50); 8.8881 (2.16); 8.3011 (2.31); 8.2263 (2.34); 7.9331 (1.39); 7.9244 (1.34); 7.9069 (1.46); 7.8982(1.44); 7.8358 (2.34); 7.8287 (1.92); 7.2399(6.42); 7.1927 (12.57); 6.8488 (1.40); 4.3984 (1.16); 4.3738 (1.22); 4.3383 (2.32); 4.3149 (2.18); 4.2496 (2.21); 4.2395 (2.27); 4.2296 (2.26); 4.2199 (2.06); 4.1896 (2.68); 4.1805 (2.58); 4.1476 (8.05); 4.1329 (8.28); 4.1202(2.49); 4.1083 (2.15); 4.0930 (2.29); 4.0672 (2.94); 4.0374 (6.89); 4.0086 (5.46); 3.9792 (2.18); 3.9262 (4.04); 3.8514 (2.06); 3.7552 (0.35); 3.0047 (0.33); 2.8978 (0.86); 2.8223 (0.73); 2.2803 (0.52); 2.1581 (16.00); 1.9751 (0.44); 1.6393 (0.42); 1.6098 (0.49); 1.4138 (6.73); 1.3846 (12.06); 1.3553 (6.18); 1.2642 (1.17); 1.2200 (2.32); 1.1821 (5.27); 1.1374 (0.80); 1.1013 (0.61); 1.0825 (0.49); 0.9503 (0.39); 0.8821 (0.51); 0.8444 (0.57); 0.8065 (0.91); 0.7837 (0.85); 0.7572(0.47); 0.0875 (1.12); −0.0006 (35.25); −0.0729 (7.26)

Example 7: ¹H-NMR(499.9 MHz, CDCl3):
8.940(3.0); 8.936(2.9); 8.291(2.0); 8.289(2.5); 7.859(3.0); 7.856(2.9); 7.269(0.8); 6.925(1.7); 4.175(9.3); 4.168(9.0); 3.979(2.9); 3.943(3.2); 3.377(3.0); 3.342(2.7); 2.341(6.9); 1.757(0.5); 1.752(0.9); 1.736(16.0); 1.672(15.7); 1.665(15.9); 1.263(0.8); 1.254(0.9); 0.895(0.4); 0.881(1.0); 0.867(0.5)

Example 8, Solvent: CDCl3, Spectrometer: 250,13 MHz
8.9665 (2.61); 8.9576 (2.39); 8.3183 (2.53); 8.3096 (2.29); 7.8381 (4.29); 7.3177 (0.36); 7.0024 (1.48); 4.1758 (15.57); 4.0942 (16.00); 4.0629(2.01); 3.9916 (2.43); 3.4460(2.32); 3.3748 (1.88); 2.3821 (5.02); 1.7833 (11.89); 1.7157 (14.12); 1.7101 (12.41); 1.2992(0.76)

Example 9: ¹H-NMR(400.1 MHz, CDCl3):
8.992(2.5); 8.987(2.6); 8.342(2.4); 8.339(1.8); 7.976(1.2); 7.971(1.3); 7.960(1.2); 7.955(1.3); 7.262(2.3); 4.305(0.8); 4.260(0.8); 3.820(16.0); 3.297(2.0); 3.291(2.8); 3.283(4.5); 3.253(1.4); 3.248(1.3); 1.755(15.6); 1.559(6.7); 1.262(1.0); 0.898(0.4); 0.882(1.1); 0.864(0.5); 0.008(1.2); 0.000(26.8); −0.008(1.1)

Example 10: ¹H-NMR(400.1 MHz, CDCl3):
9.004(2.6); 8.999(2.6); 8.352(1.7); 8.348(2.2); 8.344(1.7); 7.946(1.3); 7.940(1.4); 7.929(1.3); 7.924(1.3); 7.262(2.6); 7.008(0.8); 4.158(0.5); 4.151(0.5); 4.144(0.5); 4.138(0.5); 4.114(1.3); 4.107(1.3); 4.100(1.3); 4.094(1.2); 4.064(1.3); 4.058(1.3); 4.052(1.3); 4.045(1.3); 4.020(0.6); 4.013(1.5); 4.007(1.8); 4.001(0.6); 3.968(1.6); 3.963(1.6); 3.446(1.5); 3.441(1.5); 3.402(1.3); 3.397(1.3); 2.268(1.8); 2.262(3.5); 2.255(1.7); 1.783(16.0); 1.563(6.4); 1.254(0.5); 0.008(1.2); 0.000(30.1); −0.009(1.0)

Example 11: ¹H-NMR(400.1 MHz, CDCl3):
9.003(2.5); 8.999(2.0); 8.354(2.3); 8.353(2.3); 7.936(1.3); 7.932(1.2); 7.920(1.3); 7.916(1.0); 7.264(0.8); 6.878(1.6); 4.025(1.2); 4.022(1.0); 3.981(1.5); 3.977(1.2); 3.405(1.4); 3.401(1.2); 3.360(1.2); 3.356(1.0); 2.343(4.3); 1.757(11.2); 1.665(16.0); 1.586(1.9); 1.260(0.5); 0.000(10.2)

Example 12: Solvent: CDCl3, Spectrometer: 250,13 MHz
8.9974 (3.05); 8.9895 (2.65); 8.3588 (2.52); 8.3532 (2.89); 7.9445 (1.50); 7.9359 (1.54); 7.9182 (1.54); 7.9097 (1.44); 7.2763 (2.14); 6.8946 (1.82); 4.0291 (1.41); 4.0213 (1.29); 3.9578 (1.80); 3.9499 (1.59); 3.4078 (1.64); 3.4001 (1.53); 3.3365 (1.36); 3.3287 (1.22); 1.8081 (16.00); 1.7870 (0.45); 1.7470 (13.97); 1.7200 (2.56); 1.7024 (0.81); 1.6924 (0.96); 1.6715 (1.01); 1.6359 (13.19); 1.6223 (12.15); 1.4912 (0.35); 1.4425 (2.51); 1.4040 (0.85); −0.0006 (1.54)

Example 13: ¹H-NMR(400.1 MHz, CDCl3):
9.002(2.8); 8.996(2.8); 8.347(2.0); 8.343(2.5); 7.916(1.4); 7.911(1.4); 7.900(1.4); 7.894(1.3); 7.425(4.1); 7.360(4.2); 7.263(2.1); 6.986(0.6); 6.973(0.9); 6.960(0.5); 4.402(0.8); 4.388(0.8); 4.365(1.7); 4.350(1.6); 4.293(1.7); 4.280(1.7); 4.256(0.9); 4.243(0.8); 4.160(1.6); 4.142(4.8); 4.123(4.9); 4.105(1.6); 4.020(1.4); 4.015(1.3); 3.976(1.6); 3.970(1.5); 3.435(1.5); 3.431(1.5); 3.391(1.4); 3.386(1.3); 1.773(16.0); 1.598(5.3); 1.484(5.4); 1.466(10.8); 1.448(5.2); 1.255(0.6); 0.008(1.2); 0.000(24.6); −0.009(0.8)

Example 14: ¹H-NMR(400.1 MHz, CDCl3):
8.996(3.1); 8.992(3.1); 8.344(3.2); 7.935(1.6); 7.931(1.7); 7.919(1.6); 7.915(1.6); 7.427(1.2); 7.264(1.4); 4.002(1.5); 3.999(1.5); 3.958(1.8); 3.954(1.7); 3.557(0.6); 3.547(1.4); 3.536(2.5); 3.534(2.5); 3.521(4.0); 3.504(5.0); 3.486(5.4); 3.469(2.5); 3.452(1.4); 3.437(1.3); 3.421(0.5); 3.406(1.8); 3.403(1.8); 3.389(0.5); 3.374(1.2); 3.359(2.7); 3.342(0.9); 3.325(0.7); 1.834(0.6); 1.820(1.7); 1.805(2.4); 1.791(1.7); 1.761(16.0); 1.601(4.3); 1.282(4.8); 1.264(9.5); 1.247(4.7); 0.000(15.2)

Example 15: Solvent: CDCl3, Spectrometer: 250,13 MHz
9.1194 (0.34); 9.0325 (8.61); 9.0241 (9.35); 8.9454(0.44); 8.3848 (6.52); 8.3784 (8.35); 8.3719 (6.01); 8.2896 (0.35); 8.1254 (0.43); 8.1163 (0.44); 8.0991 (0.54); 8.0901 (0.50); 8.0110 (3.63); 8.0042 (3.13); 7.9853 (3.57); 7.9781 (2.93); 7.3526 (1.02); 7.2646 (34.54); 7.1765 (0.88); 6.6220 (1.32); 6.5917 (1.89); 6.5636 (1.22); 4.3939 (0.56); 4.2344 (2.68);

NMR Peak Lists Table 1

4.1593 (4.67); 4.0661 (0.50); 4.0405 (0.64); 4.0128 (1.18); 4.0048 (1.91); 3.9836 (7.23); 3.9767 (7.95); 3.9619 (8.19); 3.9526 (2.82); 3.9251 (1.64); 3.9184 (1.88); 3.9093 (3.62); 3.9017 (3.79); 3.8660 (0.32); 3.1576 (0.68); 3.1448 (0.65); 1.6748 (0.52); 1.6401 (0.54); 1.6273 (0.98); 1.5893 (11.11); 1.5664 (2.98); 1.5557 (4.69); 1.5420 (2.34); 1.5263 (6.16); 1.4982 (4.70); 1.4695 (1.73); 1.4403 (0.55); 1.4239 (0.56); 1.3817 (0.40); 1.3195 (0.82); 1.3083 (0.78); 1.2934 (0.93); 1.2814 (1.05); 1.2533 (3.46); 1.2315 (15.99); 1.2052 (16.00); 1.1910 (14.70); 1.1644 (14.23); 1.1436 (0.93); 1.1174 (0.73); 1.1032 (0.65); 1.0761 (0.55); 1.0636 (0.40); 1.0327 (0.56); 1.0060 (0.63); 0.9744 (6.83); 0.9448 (13.64); 0.9170 (10.41); 0.8885 (15.34); 0.8585 (6.87); 0.8287 (0.92); 0.8006 (0.77); 0.7698 (0.37); 0.0873 (0.69); 0.0124 (0.68); −0.0006 (29.32); −0.0136 (1.06); −0.0886 (0.76)

Example 16, Solvent: CDCl3, Spectrometer: 250,13 MHz
9.0509 (3.77); 9.0424 (3.79); 8.4030 (2.61); 8.3964 (3.45); 8.3898 (2.58); 8.0483 (2.11); 8.0393 (2.16); 8.0221 (2.03); 8.0132 (2.07); 7.8003 (1.10); 7.2880 (3.37); 4.2496 (1.12); 4.2428(1.10); 4.1756 (1.84); 4.1679 (1.84); 3.9931 (2.66); 3.9855 (2.89); 3.9188 (1.61); 3.9110 (1.61); 3.6256 (3.81); 3.6034 (6.15); 3.5816 (6.83); 3.5539 (7.90); 3.5316 (2.23); 3.5257 (7.48); 3.5161 (1.41); 3.5103 (1.17); 3.4973 (3.15); 3.4683 (1.65); 3.4464(0.91); 3.4385 (0.85); 3.4143 (0.62); 3.3919 (0.33); 1.9123 (0.75); 1.8883 (2.26); 1.8660 (2.79); 1.8442(2.06); 1.8185 (0.67); 1.6483 (4.32); 1.3991 (0.51); 1.3710 (0.35); 1.3415 (7.92); 1.3136 (16.00); 1.2855 (8.24); 1.2774 (3.04); 1.2555 (0.80); 1.2273 (0.76); 1.1993 (0.43); 0.9434 (0.42); 0.9144 (0.36); 0.9028 (0.43); 0.8764 (0.38)

Example 17, Solvent: CDCl3, Spectrometer: 250,13 MHz
8.7616 (1.54); 8.7531 (1.58); 8.1188 (1.04); 8.1122(1.41); 8.1055 (1.03); 7.7802 (1.83); 7.6816 (0.83); 7.6728 (0.86); 7.6551 (0.80); 7.6464 (0.82); 7.0549 (2.54); 7.0456 (0.60); 6.6679 (0.55); 4.1380 (0.38); 4.1154 (0.37); 4.0787 (1.06); 4.0562 (1.03); 4.0196 (1.07); 3.9988 (1.07); 3.9604(0.40); 3.9392(0.43); 3.8781 (0.83); 3.8489 (2.51); 3.8196 (2.60); 3.8045 (0.79); 3.7959 (0.88); 3.7907 (1.01); 3.7333 (0.99); 3.7252(0.94); 3.2164 (0.85); 3.2085 (0.91); 3.1452 (0.71); 3.1373 (0.72); 2.8136 (0.49); 2.7255 (16.00); 2.6480 (13.25); 2.5675 (1.95); 2.5607 (0.51); 2.0599 (0.37); 1.9718 (10.69); 1.8839 (0.36); 1.5389 (8.64); 1.2380 (3.01); 1.2088 (6.27); 1.1795 (2.91); 1.0159 (0.42)

Example 18, Solvent: CDCl3, Spectrometer: 250,13 MHz
9.2507 (1.67); 9.2424 (1.43); 8.7944 (1.29); 8.6110(1.47); 8.6056 (1.57); 8.2558 (2.05); 8.1994 (1.05); 8.1907 (1.04); 8.1731 (0.99); 8.1647 (0.87); 7.5123 (0.50); 6.3975 (2.36); 4.3660(0.80); 4.3580 (0.68); 4.2944 (1.05); 4.2865 (0.85); 3.9440 (9.33); 3.8574 (0.33); 3.7843 (1.00); 3.7769 (0.85); 3.7128 (0.80); 3.7053 (0.67); 3.2948 (0.42); 3.2899 (0.46); 3.2112 (3.49); 3.1989 (13.51); 3.1312 (3.69); 3.1216 (12.20); 3.0530 (3.48); 3.0406 (16.00); 2.9548 (0.53); 2.9497 (0.45); 2.5582 (0.35); 2.4673 (8.27); 2.3805 (1.09); 2.3211 (0.38); 2.2127 (0.34); 2.1218 (7.59); 1.4906 (0.74)

Example 19, Solvent: CDCl3, Spectrometer: 250,13 MHz
9.1892(2.00); 9.1807 (2.09); 8.5307 (1.35); 8.5240 (1.85); 8.5175 (1.39); 8.0924 (1.06); 8.0836 (1.11); 8.0659 (1.05); 8.0572 (1.08); 7.4549 (0.80); 7.3297 (0.41); 7.3069 (0.72); 7.2834(0.42); 6.9968 (6.88); 6.9722 (2.60); 4.7064 (0.64); 4.6818 (0.61); 4.6482 (1.27); 4.6236 (1.26); 4.5486 (1.29); 4.5264 (1.30); 4.4905 (0.63); 4.4682 (0.62); 4.2524 (0.95); 4.2441 (0.99); 4.1814 (1.22); 4.1730 (1.21); 4.1378 (0.42); 4.1100 (0.41); 4.0495 (16.00); 4.0219 (15.49); 3.9610 (0.42); 3.9333 (0.39); 3.6532 (1.13); 3.6453 (1.19); 3.5821 (0.94); 3.5742(0.94); 3.0028 (0.37); 1.9886 (11.49); 1.9000 (0.36); 1.8534 (1.05); 1.4410 (0.37)

Example 20, Solvent: CDCl3, Spectrometer: 250,13 MHz
8.9693 (1.37); 8.9608 (1.42); 8.3296 (0.97); 8.3229 (1.29); 8.3162 (0.98); 7.9174 (0.78); 7.9085 (0.81); 7.8910 (0.76); 7.8822 (0.78); 7.2327 (0.76); 6.8572 (0.97); 4.0629 (7.90); 3.9885 (0.71); 3.9800 (0.83); 3.9170 (0.91); 3.9088 (0.90); 3.4041 (0.37); 3.3805 (0.84); 3.3725 (0.89); 3.3180(14.16); 3.3010 (0.82); 3.2320 (0.37); 1.7124 (8.85); 1.6913 (0.34); 1.6284 (16.00); 1.5425 (0.56); 1.2180 (0.89)

Example 21, Solvent: CDCl3, Spectrometer: 250,13 MHz
8.9302 (2.67); 8.9217 (2.76); 8.2875 (1.82); 8.2807 (2.45); 8.2741 (1.84); 7.8745 (1.43); 7.8656 (1.49); 7.8481 (1.41); 7.8393 (1.45); 7.1966 (1.08); 6.8236 (1.71); 3.9558 (1.30); 3.9478 (1.35); 3.8845 (1.69); 3.8765 (1.65); 3.3318 (1.54); 3.3238 (1.58); 3.2605 (1.29); 3.2524 (1.27); 2.1531 (1.43); 2.1231 (4.66); 2.0931 (4.85); 2.0633 (1.74); 1.7610 (0.50); 1.6729 (16.00); 1.6404(0.84); 1.5711 (13.65); 1.5519 (13.62); 1.4833 (0.54); 1.4641 (0.50); 1.1820 (2.52); 1.1539 (0.48); 1.1241 (0.48); 1.0658 (5.45); 1.0360 (10.89); 1.0059 (4.92); 0.9481 (0.35); 0.8331 (0.35); 0.8079 (1.01); 0.7798 (0.48)

Example 22: $^1$H-NMR(499.9 MHz, CDCl3):
9.001(2.9); 8.997(2.8); 8.349(2.5); 7.923(0.7); 7.919(0.8); 7.909(1.4); 7.900(0.8); 7.896(0.8); 7.263(2.7); 6.611(0.5); 6.596(0.8); 6.581(0.5); 4.013(0.7); 4.009(0.7); 4.001(0.8); 3.998(0.8); 3.977(0.8); 3.973(0.8); 3.966(0.9); 3.962(0.9); 3.907(0.5); 3.893(0.8); 3.877(0.7); 3.864(0.5); 3.415(0.9); 3.411(1.0); 3.408(1.0); 3.404(0.9); 3.379(0.8); 3.375(0.9); 3.373(0.9); 3.369(0.8); 1.769(16.0); 1.753(0.5); 1.749(0.5); 1.578(18.3); 1.554(0.3); 1.539(0.7); 1.533(0.7); 1.525(0.8); 1.518(1.0); 1.511(0.8); 1.504(0.8); 1.495(0.8); 1.480(0.7); 1.471(0.7); 1.467(0.6); 1.456(0.9); 1.442(0.7); 1.428(0.4); 1.254(0.8); 1.184(4.8); 1.170(4.8); 1.128(4.4); 1.115(4.4); 0.951(2.2); 0.936(4.5); 0.921(2.1); 0.852(2.4); 0.837(4.8); 0.822(2.2); 0.006(0.4); 0.000(9.1); −0.007(0.5)

Example 23, Solvent: CDCl3, Spectrometer: 250,13 MHz
8.8969 (2.46); 8.8879 (2.47); 8.2543 (2.22); 8.2453 (2.16); 7.7680 (4.11); 7.2377 (0.46); 6.9348 (1.22); 4.0969 (16.00); 4.0145 (15.87); 3.9724 (1.88); 3.9013 (2.28); 3.3487 (2.11); 3.2775 (1.74); 1.7674(14.20); 1.6922 (10.84); 1.5997 (9.68); 1.5895 (9.77); 1.2165 (0.43)

Example 24, Solvent: CDCl3, Spectrometer: 250,13 MHz
8.9057 (2.22); 8.8970 (2.27); 8.2648 (1.35); 8.2577 (1.93); 8.2507 (1.34); 7.8298 (2.36); 7.8224 (2.38); 7.2384 (0.45); 6.9044(1.29); 4.1412 (8.33); 4.1281 (8.69); 3.9498 (2.13); 3.8783 (2.60); 3.3427 (2.50); 3.2713 (2.02); 1.9320 (0.67); 1.8582 (0.43); 1.7703 (16.00); 1.6884(12.42); 1.6004 (10.91); 1.5891 (10.81); 1.5122 (0.36); 1.5015 (0.34); 1.2167 (0.68)

Example 25, Solvent: CDCl3, Spectrometer: 250,13 MHz
8.8975 (1.73); 8.8888 (1.77); 8.2549 (1.07); 8.2478 (1.49); 8.2407 (1.03); 7.8215 (1.84); 7.8141 (1.83); 7.2184(1.41); 6.8906 (1.07); 4.1294 (6.71); 4.1163 (6.52); 4.0503 (8.31); 3.9327 (1.66); 3.8613 (2.07); 3.3415 (1.95); 3.3071 (14.71); 3.2700 (1.59); 3.2172 (0.33); 1.7098 (0.41); 1.6787 (9.36); 1.6203 (16.00); 1.5844(4.11); 1.5306 (0.52); 1.2054 (0.43)

Example 26, Solvent: CDCl3, Spectrometer: 250,13 MHz
8.8882 (2.19); 8.8793 (2.23); 8.2440 (1.90); 8.2350 (1.84); 7.7641 (3.49); 7.2343 (0.59); 6.9341 (1.09); 4.1843 (0.35); 4.0942 (13.79); 4.0603 (8.10); 4.0128 (13.43); 3.9657 (1.59); 3.9228 (0.34); 3.8945 (1.91); 3.4071 (0.34); 3.3603 (1.80); 3.3170 (13.85); 3.2890(1.50); 1.7214 (0.70); 1.6935 (9.26); 1.6317 (16.00); 1.6039 (0.46); 1.5420(0.49); 1.2167 (0.53)

Example 27, Solvent: CDCl3, Spectrometer: 250,13 MHz
9.1593 (2.76); 9.1507 (2.84); 8.5128 (1.18); 8.5063 (2.22); 8.4992(2.02); 8.0720 (1.91); 8.0646 (1.98); 8.0567 (1.31); 8.0493 (1.30); 7.4915 (0.72); 6.8789 (0.60); 6.8458 (0.59); 4.3988 (7.94); 4.3858 (7.81); 4.3619 (0.50); 4.2890 (0.48); 4.1960 (1.91); 4.1920 (1.40); 4.1713 (0.35); 4.1449(0.74); 4.1368 (0.52); 4.1245 (2.56); 4.1204 (2.28); 4.1105 (0.86);

| NMR Peak Lists Table 1 |
|---|
| 4.0832 (0.69); 4.0564 (0.35); 3.6380 (2.45); 3.5666 (1.91); 2.0863 (0.71); 2.0599 (0.68); 1.9694 (16.00); 1.8798 (0.46); 1.7980 (0.32); 1.7694 (1.08); 1.7405 (1.92); 1.7120 (1.90); 1.6833 (1.31); 1.6542 (0.65); 1.4727 (1.57); 1.4526 (0.43); 1.4259 (0.38); 1.4107 (3.42); 1.3843 (3.42); 1.3619 (5.63); 1.3355 (5.51); 1.1862 (2.62); 1.1568 (5.26); 1.1399 (0.45); 1.1268 (2.23); 1.1037 (1.76); 1.0742 (3.42); 1.0443 (1.42) |
| Example 28, Solvent: CDCl3, Spectrometer: 250,13 MHz |
| 8.8397 (2.73); 8.8307 (2.75); 8.1900 (1.03); 8.1828 (2.38); 8.1744(1.84); 7.7037 (1.67); 7.6929 (3.42); 7.1858 (1.08); 6.6133 (0.49); 6.5786 (0.52); 4.1324 (0.42); 4.0933 (0.38); 4.0800 (0.38); 4.0575 (0.60); 4.0417 (15.00); 3.9672 (16.00); 3.9524 (0.59); 3.9104 (0.82); 3.9004 (1.65); 3.8768 (0.48); 3.8394(1.42); 3.8295 (2.20); 3.8169 (0.60); 3.8116 (0.60); 3.7810 (0.45); 3.3529 (1.85); 3.3441(0.94); 3.2819 (1.48); 3.2730(0.76); 1.7600 (0.33); 1.6694 (12.60); 1.6204 (1.38); 1.5793 (0.49); 1.4650 (0.55); 1.4370 (0.98); 1.4127 (1.08); 1.4083 (1.21); 1.3842 (1.16); 1.3555 (0.79); 1.3288 (0.33); 1.1710(1.40); 1.1083 (5.19); 1.0819 (5.13); 1.0583 (2.47); 1.0318(2.40); 0.8846 (1.08); 0.8551 (2.20); 0.8252 (0.98); 0.8043 (2.49); 0.7748 (5.01); 0.7450 (2.05) |
| Example 29, Solvent: CDCl3, Spectrometer: 250,13 MHz |
| 8.8010(2.42); 8.1399 (3.74); 7.8012 (0.36); 7.6917 (3.49); 7.1604 (1.73); 7.1367 (1.39); 6.7969 (1.69); 5.1645 (0.44); 4.2283 (0.71); 4.1691 (2.73); 4.1464 (3.43); 4.1223 (2.16); 4.0320 (12.70); 4.0191 (9.92); 3.9562 (3.57); 3.9281 (3.05); 3.8999 (1.20); 3.8457 (2.46); 3.7742 (2.87); 3.3049 (2.26); 3.2336 (1.77); 2.3329 (0.69); 2.0810 (10.60); 2.0092 (0.45); 1.6608 (2.51); 1.6164 (16.00); 1.5486 (0.42); 1.3373 (4.49); 1.3093 (6.99); 1.2816 (2.76); 1.1149 (0.89) |
| Example 30, Solvent: CDCl3, Spectrometer: 250,13 MHz |
| 8.9745 (3.24); 8.3149 (3.73); 7.9937 (0.47); 7.8193 (3.20); 7.3401 (3.16); 7.0186 (2.11); 4.4141 (0.88); 4.3525 (3.35); 4.3311 (4.08); 4.3071 (2.31); 4.2463 (1.78); 4.2271 (2.11); 4.2143 (2.38); 4.1705 (14.04); 4.1350 (5.52); 4.1066 (12.17); 4.0899 (16.00); 4.0474(2.87); 3.9941 (2.07); 3.9761 (2.69); 3.5047 (2.38); 3.4335 (1.85); 2.9423 (0.72); 2.3494 (0.86); 2.2671 (13.62); 2.1758 (0.77); 1.8899 (1.06); 1.8524 (2.55); 1.8239 (8.11); 1.8078 (14.83); 1.7169 (0.91); 1.5722 (0.57); 1.5139 (5.11); 1.5073 (5.10); 1.4899 (8.17); 1.4617 (3.51); 1.4276 (0.37); 1.3982 (0.53); 1.3701 (0.37); 1.3040 (1.30) |
| Example 31, Solvent: CDCl3, Spectrometer: 300,16 MHz |
| 9.0630(4.62); 8.5322 (4.89); 8.1668 (1.78); 8.1368 (3.69); 8.0783 (3.47); 8.0488 (1.77); 7.7605 (5.00); 7.2665 (5.49); 7.0848 (2.29); 4.1616 (0.85); 4.1534 (0.85); 4.1026 (2.43); 4.0946(2.44); 4.0418 (2.58); 4.0345 (2.59); 3.9710 (3.20); 3.9130(2.94); 3.3712 (2.90); 3.3140 (2.42); 2.2505 (4.29); 1.7838 (16.00); 1.6456(2.49); 1.2531 (0.44); −0.0002 (3.69) |
| Example 32: $^1$H-NMR(400.0 MHz, DMSO): |
| 8.998(1.9); 8.993(2.7); 8.989(2.0); 8.760(1.7); 8.755(2.5); 8.308(0.6); 8.304(0.6); 8.300(0.4); 8.210(3.0); 8.173(1.6); 8.169(1.4); 8.151(3.1); 8.147(3.1); 8.075(2.4); 8.053(1.5); 3.874(2.8); 3.831(3.3); 3.476(1.9); 3.433(1.7); 3.430(1.5); 3.370(2.7); 3.352(9.9); 3.341(161.3); 3.338(192.4); 3.333(215.3); 3.316(5.6); 3.206(0.4); 3.191(0.8); 3.173(1.8); 3.156(2.3); 3.140(1.9); 3.123(0.8); 3.107(0.3); 2.895(1.4); 2.736(1.2); 2.679(0.5); 2.674(0.7); 2.670(0.5); 2.527(2.2); 2.514(42.4); 2.510(85.0); 2.505(111.7); 2.501(79.9); 2.496(37.9); 2.336(0.5); 2.332(0.7); 2.327(0.5); 1.687(0.7); 1.670(2.4); 1.654(3.6); 1.638(2.3); 1.621(1.0); 1.609(16.0); 1.330(0.4); 1.235(0.3); 1.082(4.8); 1.065(9.7); 1.047(4.6); 0.060(0.4); 0.000(3.3); −0.058(0.9) |
| Example 33: $^1$H-NMR(400.0 MHz, DMSO): 9.001(2.0); 8.995(3.1); 8.990(1.7); 8.985(1.0); 8.759(1.6); 8.753(2.4); 8.747(1.6); 8.636(1.2); 8.308(0.7); 8.302(0.4); 8.296(0.5); 8.219(3.1); 8.177(1.7); 8.172(1.3); 8.155(2.5); 8.150(2.1); 8.079(2.1); 8.057(1.4); 7.953(0.5); 3.887(2.6); 3.869(3.6); 3.863(3.9); 3.854(3.9); 3.848(4.2); 3.844(3.9); 3.511(1.8); 3.506(1.3); 3.468(1.5); 3.463(1.1); 3.345(166.8); 3.342(152.6); 3.333(186.0); 3.027(1.2); 3.025(1.3); 3.018(1.0); 3.013(0.7); 3.007(0.7); 3.002(0.7); 2.996(0.5); 2.896(4.1); 2.737(3.2); 2.680(0.6); 2.675(0.8); 2.670(0.5); 2.528(2.3); 2.515(46.2); 2.510(92.7); 2.506(121.0); 2.501(86.3); 2.497(40.8); 2.337(0.5); 2.333(0.7); 2.328(0.5); 1.615(16.0); 1.494(0.5); 1.237(0.3); 0.000(3.8) |
| Example 34, Solvent: CDCl3, Spectrometer: 499,93 MHz |
| 8.9391 (2.83); 8.9346 (2.96); 8.3164 (2.57); 8.3124 (2.61); 8.1455 (1.08); 8.1420 (1.13); 8.1277 (2.09); 8.1242 (2.25); 8.0923 (2.99); 8.0745 (1.48); 7.8059 (2.80); 7.8031 (2.89); 7.2667 (5.15); 7.2486 (4.31); 6.9179 (0.60); 6.9080 (1.03); 6.8982 (0.62); 5.2974 (0.78); 4.3483 (0.96); 4.3369 (0.96); 4.3185 (1.50); 4.3071 (1.48); 4.2197 (1.49); 4.2096 (1.51); 4.1899 (0.96); 4.1798 (0.95); 4.0628 (1.32); 4.0481 (3.96); 4.0335 (3.99); 4.0188 (1.33); 3.9781 (2.49); 3.9439 (2.77); 3.3527 (2.69); 3.3186 (2.45); 2.1999 (0.34); 2.1870 (16.00); 1.7756 (14.63); 1.7109 (1.80); 1.4375 (4.37); 1.4229 (8.84); 1.4083 (4.31); −0.0002 (3.57) |
| Example 35, Solvent: CDCl3, Spectrometer: 300,16 MHz |
| 8.9640 (3.12); 8.9564 (3.22); 8.3329 (2.68); 8.3254 (2.66); 8.1180(5.20); 8.1140 (6.64); 7.8573 (2.97); 7.2938 (3.91); 7.2778 (2.84); 7.0254 (0.49); 7.0084 (0.86); 6.9911 (0.54); 5.3024 (0.98); 4.4679 (0.79); 4.4484 (0.80); 4.4183 (1.38); 4.3988 (1.36); 4.2903 (1.42); 4.2740 (1.46); 4.2407 (0.86); 4.2244 (0.85); 4.1867 (1.24); 4.1269 (2.01); 4.1025 (1.28); 4.0781 (3.88); 4.0537 (3.98); 4.0294 (1.35); 3.9508 (3.01); 3.8910(1.94); 2.2089 (16.00); 2.0473 (0.40); 1.9158 (2.19); 1.4683 (4.77); 1.4440 (9.98); 1.4196 (4.71); 1.2602 (0.58); 0.8800 (0.39); −0.0002 (1.73) |
| Example 36, Solvent: CDCl3, Spectrometer: 300,16 MHz |
| 8.9742 (5.94); 8.9666 (6.14); 8.3461 (4.82); 8.3385 (4.78); 8.1760(0.92); 8.1703 (0.80); 8.1462 (5.93); 8.1406 (7.04); 8.1343 (7.47); 8.1048 (1.04); 7.8682 (4.77); 7.2649 (18.06); 6.7204 (1.13); 6.6944 (1.18); 5.3026 (3.40); 4.1702 (2.59); 4.1553 (1.23); 4.1334 (1.70); 4.1286 (1.38); 4.1107 (5.25); 4.0847 (1.25); 4.0629 (0.50); 3.9193 (6.69); 3.8595 (4.35); 1.6168 (12.43); 1.2552(16.00); 1.2335 (15.36); 1.2129 (15.62); 1.1909 (15.36); 0.0713 (1.61); 0.0106 (0.36); −0.0002 (11.54); −0.0111 (0.50) |
| Example 37: $^1$H-NMR(400.0 MHz, DMSO): |
| 9.005(2.0); 8.999(2.2); 8.766(1.7); 8.761(1.8); 8.311(0.4); 8.238(1.9); 8.233(2.2); 8.186(1.3); 8.181(1.0); 8.164(1.9); 8.159(1.7); 8.081(2.1); 8.059(1.4); 7.952(0.5); 7.544(1.6); 3.903(1.8); 3.860(2.2); 3.466(1.9); 3.423(1.7); 3.337(166.0); 2.893(4.3); 2.733(3.5); 2.678(0.3); 2.673(0.5); 2.668(0.3); 2.526(1.7); 2.522(2.6); 2.513(28.0); 2.509(56.4); 2.504(74.0); 2.499(52.6); 2.495(24.7); 2.331(0.5); 2.326(0.3); 1.727(16.0); 1.600(10.7); 1.515(11.9); 1.511(11.8); 0.000(2.6) |
| Example 38, Solvent: CDCl3, Spectrometer: 300,16 MHz |
| 9.0455 (4.63); 8.5170 (4.98); 8.1688 (2.04); 8.1393 (3.55); 8.0654 (3.50); 8.0371 (1.97); 7.7565 (5.10); 7.2898 (0.98); 7.2856 (0.96); 6.7242 (2.18); 6.7039 (2.20); 5.3067 (1.91); 5.3025 (1.87); 4.0473 (1.71); 4.0419 (1.69); 4.0352 (1.63); 3.9697 (2.56); 3.9121 (2.97); 3.3451 (2.96); 3.2876 (2.47); 2.0461 (0.89); 1.7587 (16.00); 1.2054(10.40); 1.1977 (8.98); 1.1442 (10.44); 1.1364(9.02); −0.0002 (0.54) |
| Example 39, Solvent: CDCl3, Spectrometer: 300,16 MHz |
| 9.0606 (4.58); 8.5339 (4.88); 8.1521 (1.80); 8.1232 (3.62); 8.0713 (3.56); 8.0426 (1.75); 7.7619 (4.95); 7.2631 (5.75); 7.2558 (5.30); 6.9265 (2.47); 4.3585 (1.18); 4.3093 (2.43); 4.2201 (2.72); 4.1700 (1.36); 4.0564 (4.21); 4.0326 (4.28); 3.9870 (2.49); 3.9294 (2.89); 3.3644 (2.83); 3.3076 (2.37); 2.1882(16.00); 2.0476 (0.67); 1.8406 (2.77); 1.7776 (15.73); 1.4489 (4.30); 1.4253 (8.32); 1.4012 (4.31); 1.2581 (0.74); −0.0002(2.04) |

| NMR Peak Lists Table 1 |
|---|

Example 40: ¹H-NMR(300.2 MHz, CDCl3):
8.968(2.7); 8.962(2.7); 8.280(2.3); 8.273(2.2); 8.187(1.1); 8.180(1.0); 8.157(2.4); 8.151(2.5); 8.113(3.0); 8.083(1.3); 7.847(2.6); 7.841(2.5); 7.268(7.1); 6.711(0.7); 6.685(0.7); 4.077(0.6); 4.055(0.9); 4.050(0.7); 4.033(0.8); 4.028(0.9); 4.011(0.4); 4.007(0.6); 3.981(2.8); 3.923(3.3); 3.356(3.1); 3.329(6.0); 3.298(2.7); 1.757(16.0); 1.685(7.2); 1.215(8.2); 1.193(8.1); 1.153(8.2); 1.131(8.2); 0.000(5.0)
Example 41: ¹H-NMR(400.0 MHz, DMSO):
9.044(2.2); 9.039(2.3); 8.737(1.9); 8.732(1.8); 8.380(2.1); 8.375(2.1); 8.201(1.1); 8.196(1.0); 8.178(1.9); 8.174(1.9); 8.117(3.5); 8.095(1.4); 4.250(0.7); 4.203(2.1); 4.168(2.0); 4.122(0.7); 3.386(0.5); 3.337(253.2); 2.892(2.2); 2.732(1.8); 2.677(0.4); 2.673(0.5); 2.668(0.4); 2.526(1.9); 2.521(2.9); 2.513(31.9); 2.508(63.7); 2.504(83.0); 2.499(58.6); 2.494(27.1); 2.335(0.4); 2.330(0.5); 2.326(0.4); 1.741(15.8); 1.538(16.0); 0.000(2.7)
Example 42: ¹H-NMR(400.0 MHz, DMSO):
9.163(0.6); 9.089(2.9); 9.084(3.1); 8.918(2.1); 8.913(2.0); 8.188(1.8); 8.184(2.4); 8.169(1.5); 8.164(1.0); 8.147(1.9); 8.142(1.6); 8.041(2.2); 8.019(1.6); 7.952(0.4); 7.543(2.5); 3.894(1.8); 3.850(2.2); 3.840(1.4); 3.456(2.1); 3.413(1.8); 3.330(226.6); 2.891(2.8); 2.732(2.3); 2.676(0.4); 2.672(0.6); 2.667(0.4); 2.525(1.9); 2.512(34.4); 2.507(69.4); 2.503(91.3); 2.498(65.1); 2.494(30.8); 2.334(0.4); 2.329(0.6); 2.325(0.4); 1.725(16.0); 1.596(10.7); 1.512(11.9); 1.509(11.9); 0.000(3.0)
Example 43, Solvent: CDCl3, Spectrometer: 499,93 MHz
8.9630 (2.83); 8.9590 (2.84); 8.2694 (2.36); 8.2657 (2.33); 8.1490(1.01); 8.1453 (1.01); 8.1313 (2.18); 8.1276 (2.26); 8.1011 (2.91); 8.0834 (1.36); 7.8381 (2.59); 7.8347 (2.57); 7.2732 (3.45); 7.2491 (3.99); 6.9376 (0.53); 6.9275 (0.94); 6.9173 (0.58); 4.3490 (0.91); 4.3375 (0.92); 4.3192(1.44); 4.3078 (1.43); 4.2208 (1.43); 4.2106 (1.47); 4.1910 (0.95); 4.1808 (0.95); 4.0606 (1.29); 4.0460 (3.95); 4.0313 (4.03); 4.0167 (1.40); 3.9868 (2.53); 3.9527 (2.79); 3.3640 (2.64); 3.3309 (7.10); 2.1993 (0.38); 2.1887 (16.00); 1.8394 (1.77); 1.7766 (14.14); 1.4348 (4.55); 1.4202 (9.35); 1.4055 (4.61); −0.0002 (2.43)
Example 44, Solvent: CDCl3, Spectrometer: 300,16 MHz
8.9031 (4.82); 8.2772 (5.26); 8.1628 (1.93); 8.1337 (3.62); 8.0755 (3.73); 8.0464 (2.03); 7.7819 (5.33); 7.3209 (0.46); 6.7596 (2.13); 6.7371 (2.20); 4.0674 (1.59); 4.0474(1.64); 3.9835 (2.65); 3.9260 (3.06); 3.3579 (3.02); 3.3006 (2.54); 2.3918 (0.66); 1.7675 (16.00); 1.2260 (8.83); 1.2198 (8.61); 1.2139 (8.70); 1.2056 (9.10); 1.1651 (8.99); 1.1593 (8.75); 1.1530 (8.76); 1.1446 (9.18)
Example 45, Solvent: CDCl3, Spectrometer: 300,16 MHz
8.9637 (4.69); 8.2667 (5.03); 8.1715 (1.48); 8.1421 (3.85); 8.1090(4.01); 8.0800 (1.55); 7.8312 (5.19); 7.2710 (2.89); 7.1103 (2.39); 4.1648 (0.93); 4.1570 (0.94); 4.1069 (2.62); 4.0989 (2.59); 4.0442 (2.65); 4.0379 (2.64); 3.9874 (3.41); 3.9303 (3.01); 3.3881 (2.98); 3.3327 (7.42); 2.2531 (4.34); 2.0480(0.54); 1.7867 (16.00); 1.7391 (2.89); 1.2604 (1.48); 0.8810 (0.58); −0.0002 (1.87)
Example 46: ¹H-NMR(400.0 MHz, DMSO):
9.019(1.2); 9.014(1.5); 8.749(1.3); 8.308(0.4); 8.297(1.8); 8.200(0.9); 8.195(0.9); 8.177(1.4); 8.173(1.4); 8.105(1.5); 8.083(0.9); 7.785(0.9); 3.949(1.3); 3.903(1.8); 3.719(1.4); 3.673(1.0); 3.339(88.0); 3.336(127.9); 3.334(127.1); 3.287(12.5); 2.894(2.2); 2.735(1.8); 2.674(0.4); 2.527(1.4); 2.513(24.6); 2.509(49.7); 2.504(65.3); 2.500(46.7); 2.495(22.0); 2.331(0.4); 1.763(14.4); 1.552(16.0); 0.000(2.1)
Example 47: ¹H-NMR(300.2 MHz, CDCl3):
8.948(2.6); 8.940(2.7); 8.341(2.0); 8.334(1.9); 8.183(1.1); 8.177(0.9); 8.153(2.0); 8.147(2.1); 8.114(2.6); 8.085(1.0); 7.862(2.1); 7.857(2.1); 7.334(3.5); 7.272(3.2); 6.897(0.4); 6.881(0.7); 6.864(0.4); 4.367(1.9); 4.360(2.1); 4.349(2.0); 4.342(2.0); 4.116(1.1); 4.110(0.5); 4.092(3.4); 4.067(3.5); 4.043(1.2); 4.027(2.0); 3.967(2.5); 3.557(2.5); 3.497(2.0); 3.387(16.0); 2.804(0.6); 2.294(0.5); 2.257(14.2); 2.046(0.9); 1.780(1.4); 1.484(4.1); 1.473(0.5); 1.460(8.6); 1.435(4.1); 1.260(0.5); 0.000(2.7)
Example 48, Solvent: CDCl3, Spectrometer: 499,93 MHz
8.9439 (2.29); 8.9396 (2.42); 8.3364 (2.34); 8.3323 (2.43); 8.1810(1.09); 8.1774 (1.16); 8.1632 (1.83); 8.1597 (1.95); 8.1119 (2.46); 8.0942 (1.47); 7.8627 (2.56); 7.8596 (2.66); 7.2672 (3.25); 6.6600 (0.65); 6.6449 (0.66); 4.1687 (0.57); 4.1555 (0.84); 4.1533 (0.75); 4.1398 (0.87); 4.1265 (0.60); 3.9737 (2.31); 3.9377 (2.70); 3.5389 (2.72); 3.5029 (2.33); 3.4032 (16.00); 1.6864 (1.36); 1.3013 (0.40); 1.2879 (0.53); 1.2574 (8.14); 1.2442 (7.63); 1.2335 (7.59); 1.2203 (7.31); 0.8947 (0.91); 0.8812 (2.18); 0.8670 (1.06); −0.0002 (2.28)
Example 49, Solvent: CDCl3, Spectrometer: 300,16 MHz
8.9374 (3.74); 8.3175 (3.97); 8.1558 (1.15); 8.1255 (3.05); 8.0966 (3.17); 8.0676 (1.17); 7.8023 (4.06); 7.2719 (2.97); 7.2345 (4.12); 6.9272 (2.00); 5.3030 (4.82); 4.3575 (0.97); 4.3084 (1.97); 4.2176 (2.18); 4.1690(1.11); 3.9943 (1.95); 3.9365 (6.62); 3.3700 (2.25); 3.3129 (1.89); 2.1864 (12.66); 1.8264 (2.81); 1.7792 (16.00); 1.2573 (0.92); 0.9034 (3.63); 0.8804 (6.83); 0.8565 (3.44); −0.0002(2.10)
Example 50: ¹H-NMR(499.9 MHz, CDCl3):
8.950(2.6); 8.946(2.7); 8.349(2.1); 8.345(2.1); 8.187(0.4); 8.181(1.2); 8.177(1.2); 8.163(2.0); 8.160(2.0); 8.114(2.3); 8.096(1.4); 8.021(1.0); 7.866(2.3); 7.862(2.3); 7.325(3.4); 7.279(3.7); 6.918(0.5); 6.908(0.9); 6.897(0.5); 4.400(0.4); 4.389(0.4); 4.371(1.6); 4.360(1.7); 4.353(1.7); 4.342(1.6); 4.323(0.5); 4.312(0.5); 4.013(2.1); 3.993(1.9); 3.977(4.8); 3.964(2.1); 3.556(2.4); 3.520(2.2); 3.388(16.0); 3.124(0.5); 3.109(0.5); 2.965(7.4); 2.889(6.2); 2.807(0.7); 2.298(0.5); 2.257(12.7); 1.892(0.4); 1.877(1.3); 1.863(2.2); 1.848(2.3); 1.834(1.4); 1.819(0.4); 1.476(0.4); 1.475(0.4); 1.462(0.6); 1.432(0.9); 1.417(1.7); 1.402(0.9); 0.933(3.7); 0.918(7.5); 0.903(3.6); 0.074(2.5); 0.000(3.2)
Example 51: ¹H-NMR(400.0 MHz, DMSO):
9.596(0.5); 9.048(1.2); 9.043(1.3); 9.024(12.8); 9.018(12.8); 8.856(3.1); 8.842(6.1); 8.827(3.7); 8.758(10.9); 8.753 (11.1); 8.610(1.0); 8.606(1.0); 8.334(0.6); 8.330(0.6); 8.317(0.9); 8.303(11.2); 8.299(11.6); 8.197(6.3); 8.192(5.1); 8.174(9.2); 8.170(8.2); 8.160(1.2); 8.106(12.5); 8.084(7.7); 7.954(1.0); 7.817(2.0); 4.310(0.5); 4.292(1.4); 4.275(1.4); 4.257(0.5); 4.104(1.0); 4.099(1.6); 4.090(1.0); 4.084(1.0); 4.073(0.8); 4.027(1.0); 3.980(0.8); 3.973(0.9); 3.965(1.0); 3.958(1.4); 3.951(7.9); 3.937(5.4); 3.931(6.0); 3.923(9.0); 3.917(9.3); 3.904(16.0); 3.881(1.0); 3.874(1.0); 3.866(0.9); 3.860(0.8); 3.820(0.5); 3.806(1.0); 3.763(11.5); 3.717(7.4); 3.465(0.4); 3.344(9.5); 3.331(167.4); 3.288(67.3); 3.223 (0.6); 3.216(1.1); 3.210(0.6); 3.123(5.7); 3.117(11.6); 3.111(5.6); 2.892(6.4); 2.733(5.6); 2.673(1.1); 2.669(0.9); 2.508(148.3); 2.504(187.1); 2.500(136.3); 2.447(0.6); 2.427(0.5); 2.335(1.0); 2.331(1.3); 2.326(1.0); 1.301(1.6); 1.283(3.1); 1.265(1.5); 0.008(1.8); 0.000(43.4); −0.008(2.2)
Example 53: ¹H-NMR(400.0 MHz, DMSO):
8.305(5.1); 7.951(2.4); 3.942(3.8); 3.503(1.5); 3.406(3.0); 3.338(2938.7); 3.252(3.3); 2.894(16.0); 2.735(13.7); 2.678(7.1); 2.673(9.3); 2.669(6.8); 2.526(30.3); 2.513(504.7); 2.509(1001.6); 2.504(1305.7); 2.500(930.5); 2.495(439.6); 2.336(5.5); 2.331(7.7); 2.327(5.5); 2.126(1.2); 1.591(3.0); 1.329(3.8); 1.299(1.5); 1.261(1.8); 1.236 (2.6); 1.111(2.0); 1.094(2.1); 1.066(2.1); 1.050(2.0); 0.057(2.3); 0.000(35.4)

-continued

NMR Peak Lists Table 1

Example 54, Solvent: CDCl3, Spectrometer: 400,13 MHz
8.8668 (2.41); 8.8609 (2.35); 8.1528 (2.89); 8.1466 (3.08); 8.1240 (3.13); 8.1198 (3.41); 8.1131 (3.51); 8.0908 (0.64); 7.8223 (2.73); 7.3144 (0.76); 7.2639 (44.70); 6.9295 (0.59); 6.9158 (0.93); 6.9043 (0.55); 5.6784 (0.35); 5.3290 (0.36); 5.3030 (0.40); 4.3573 (0.94); 4.3430 (0.93); 4.3203 (1.61); 4.3119 (0.83); 4.3060 (1.61); 4.2992 (0.70); 4.2194 (1.66); 4.2068 (1.65); 4.1822 (0.98); 4.1697 (0.96); 4.0799 (0.81); 4.0623 (1.96); 4.0440(1.94); 4.0257 (0.73); 3.9907 (2.75); 3.9479 (3.08); 3.3686 (2.95); 3.3258 (2.62); 2.2424 (1.70); 2.2269 (0.56); 2.2080(0.47); 2.1892 (15.49); 1.9615 (1.12); 1.7800 (16.00); 1.6235 (3.50); 1.4926 (0.34); 1.4732 (0.90); 1.4548 (1.48); 1.4458 (5.19); 1.4364 (1.15); 1.4276 (10.42); 1.4093 (5.05); 1.3766 (0.35); 1.3327 (0.77); 1.3013 (1.09); 1.2844 (1.30); 1.2529 (5.70); 0.8960 (0.55); 0.8801 (1.17); 0.8580 (1.03); 0.8421 (1.25); 0.8350 (1.01); 0.0699 (1.00); 0.0079 (0.97); −0.0002 (24.76); −0.0084 (1.05)
Example 55: $^1$H-NMR(300.2 MHz, CDCl3):
8.861(2.8); 8.853(2.9); 8.168(0.8); 8.162(0.8); 8.148(2.5); 8.139(4.6); 8.133(3.1); 8.116(3.2); 8.086(0.9); 7.827(2.4); 7.822(2.4); 7.264(13.7); 6.700(0.6); 6.675(0.6); 4.076(0.6); 4.054(0.9); 4.049(0.7); 4.032(0.7); 4.027(0.9); 4.006(0.7); 3.976(2.7); 3.919(3.2); 3.348(3.0); 3.291(2.5); 1.756(16.0); 1.606(7.8); 1.256(0.5); 1.214(8.1); 1.193(8.0); 1.153(8.0); 1.131(7.9); 0.882(0.4); 0.000(9.7); −0.011(0.4)
Example 56, Solvent: CDCl3, Spectrometer: 499,93 MHz
8.9384 (3.02); 8.9339 (3.07); 8.3181 (2.27); 8.3138 (2.26); 8.1230(1.01); 8.1193 (1.00); 8.1052 (2.24); 8.1015 (2.31); 8.0771 (2.87); 8.0593 (1.28); 7.7753 (2.47); 7.7719 (2.43); 7.3315 (1.13); 7.3280 (1.54); 7.3239 (0.73); 7.3148 (3.19); 7.3123 (3.10); 7.3031 (1.41); 7.2999 (1.68); 7.2956 (1.09); 7.2867 (3.35); 7.2833 (1.47); 7.2714 (2.14); 7.2663 (20.63); 7.2607 (1.37); 7.2565 (0.86); 7.2503 (1.50); 7.2430 (0.50); 7.2392(0.46); 7.2365 (0.46); 7.2091 (0.35); 7.2064 (0.38); 7.0436 (0.45); 6.9348 (3.98); 6.7035 (0.57); 6.6991 (0.98); 6.6826 (0.62); 5.7335 (0.44); 4.2339 (0.71); 4.2314(1.00); 4.2240 (0.66); 4.2193 (0.96); 4.2015 (1.26); 4.1895 (1.25); 4.0514 (1.29); 4.0419 (1.39); 4.0283 (1.36); 4.0257 (0.85); 4.0217 (1.19); 4.0136 (4.39); 3.9991 (3.89); 3.9845 (1.32); 3.9525 (2.23); 3.9182 (2.51); 3.6681 (0.64); 3.5210(1.74); 3.4929 (2.10); 3.4387 (2.26); 3.4043 (2.02); 3.2541 (2.08); 3.2260 (1.73); 2.0982 (1.90); 2.0419 (16.00); 1.6506 (11.95); 1.4329 (0.66); 1.4245 (4.65); 1.4181 (1.50); 1.4099 (9.80); 1.4037 (1.03); 1.3953 (4.68); −0.0002 (7.86); −0.0068 (0.37)
Example 57, Solvent: CDCl3, Spectrometer: 499,93 MHz
8.9353 (3.06); 8.9308 (3.16); 8.3168 (2.48); 8.3125 (2.50); 8.1414 (1.19); 8.1377 (1.22); 8.1236 (2.13); 8.1199 (2.24); 8.0798 (2.88); 8.0620 (1.61); 7.7807 (2.72); 7.7773 (2.74); 7.3479 (1.33); 7.3449 (1.93); 7.3310 (3.88); 7.3124(2.11); 7.3087 (0.75); 7.2983 (3.71); 7.2832 (1.90); 7.2656 (19.00); 7.2522 (0.88); 7.2471 (1.72); 7.2418 (0.46); 7.2355 (0.37); 7.2329 (0.51); 6.4406 (0.99); 6.4243 (1.04); 3.9516 (2.68); 3.9385 (0.65); 3.9252 (0.91); 3.9221 (0.90); 3.9172 (2.98); 3.9123 (0.98); 3.9091 (1.00); 3.8959 (0.63); 3.4866 (1.95); 3.4586 (2.38); 3.4106 (2.55); 3.3762 (2.27); 3.2382 (2.37); 3.2102 (1.92); 1.6162 (16.00); 1.0484 (7.63); 1.0352 (7.75); 0.8850 (7.53); 0.8719 (7.63); −0.0002 (7.83); −0.0067 (0.46)
Example 58, Solvent: CDCl3, Spectrometer: 499,93 MHz
8.9272 (9.26); 8.9227 (9.65); 8.2965 (7.27); 8.2921 (7.44); 8.1075 (3.01); 8.1038 (3.08); 8.0897 (7.04); 8.0860 (7.54); 8.0772 (0.59); 8.0727 (0.52); 8.0634 (9.33); 8.0456 (4.08); 7.7482 (7.82); 7.7448 (7.99); 7.3329 (1.23); 7.3284 (2.51); 7.3159 (24.24); 7.3123 (13.57); 7.3024(12.44); 7.2985 (3.88); 7.2905 (2.64); 7.2866 (3.68); 7.2758 (0.80); 7.2663 (24.68); 7.2574 (2.98); 7.2506 (3.73); 7.2441 (1.54); 7.2425 (1.43); 7.2380 (1.54); 7.2336 (0.92); 6.9163 (1.85); 6.9056 (3.57); 6.8949 (2.11); 3.9701 (4.95); 3.9653 (6.85); 3.9615 (6.26); 3.9593 (6.36); 3.9557 (6.96); 3.9544 (6.83); 3.9509 (5.83); 3.9316 (0.44); 3.9264 (0.36); 3.9207 (0.32); 3.9154 (0.37); 3.9062 (7.36); 3.8718 (8.35); 3.5071 (6.03); 3.4788 (7.39); 3.4197 (7.71); 3.3852 (6.77); 3.2521 (7.50); 3.2238 (6.18); 2.1873 (4.80); 2.1822 (10.06); 2.1771 (5.17); 1.6612 (16.00); −0.0002(9.02); −0.0068 (0.53)
Example 59, Solvent: CDCl3, Spectrometer: 499,93 MHz
8.9286 (2.60); 8.9241 (2.68); 8.3066 (2.06); 8.3023 (2.09); 8.1311 (1.04); 8.1274 (1.05); 8.1133 (1.79); 8.1097 (1.85); 8.0652 (2.35); 8.0475 (1.39); 7.7596 (2.29); 7.7561 (2.29); 7.3473 (1.18); 7.3443 (1.68); 7.3304 (3.28); 7.3094 (1.75); 7.3057 (0.64); 7.2952 (3.10); 7.2801 (1.65); 7.2653 (23.68); 7.2592(1.41); 7.2562 (1.66); 7.2466 (0.84); 7.2419 (1.96); 7.2367 (0.88); 7.2280 (1.26); 7.2188 (0.62); 3.9173 (2.04); 3.8831 (2.31); 3.4975 (1.64); 3.4694 (1.99); 3.4080 (0.58); 3.4037 (0.60); 3.3970 (2.25); 3.3897 (1.67); 3.3840 (0.66); 3.3756 (1.70); 3.3699 (1.75); 3.3626 (2.62); 3.3559 (2.06); 3.3515 (1.59); 3.3446 (0.92); 3.3388 (1.91); 3.3302(1.02); 3.3257 (1.62); 3.3165 (0.83); 3.2629 (0.63); 3.2538 (0.82); 3.2446 (2.48); 3.2398 (1.06); 3.2348 (0.74); 3.2297 (0.63); 3.2167(1.74); 3.2104(0.49); 3.1996 (0.64); 3.1952(0.46); 3.1891 (0.45); 3.1844 (0.76); 3.1732 (0.65); 3.1680 (0.37); 3.1619 (0.32); 3.1575 (0.48); 1.6367 (0.47); 1.6331 (0.47); 1.6228 (0.64); 1.6085 (16.00); 1.5846 (0.47); 1.5816 (0.49); 1.5712 (0.61); 1.5674 (0.46); 1.5606 (0.45); 1.5576 (0.48); 1.5465 (0.36); 1.5427 (0.33); 1.2272 (4.04); 1.2132 (8.27); 1.1992(4.09); 0.0063 (0.40); −0.0002 (12.50); −0.0068 (0.66)
Example 60, Solvent: CDCl3, Spectrometer: 499,93 MHz
8.9319 (15.96); 8.9274(16.00); 8.3085 (13.99); 8.3042 (13.65); 8.1246 (6.12); 8.1210 (6.06); 8.1068 (11.95); 8.1032 (12.17); 8.0723 (15.84); 8.0545 (7.78); 7.7693 (15.28); 7.7661 (14.89); 7.3325 (4.27); 7.3286 (6.81); 7.3129 (36.05); 7.2997 (21.66); 7.2845 (8.85); 7.2733 (6.26); 7.2686 (35.60); 7.2566 (6.76); 7.2500 (2.06); 7.2470 (1.92); 7.2435 (2.44); 7.2400 (1.69); 7.2263 (0.75); 7.2214 (0.47); 7.2028 (1.18); 7.1882 (0.81); 6.6603 (7.19); 6.6543 (7.20); 5.6764 (1.07); 5.3048 (1.64); 5.2130 (0.85); 3.9651 (13.03); 3.9307 (14.60); 3.6401 (1.83); 3.6213 (0.40); 3.4849 (10.98); 3.4569 (13.40); 3.4116 (13.57); 3.3772 (12.09); 3.2334 (13.33); 3.2053 (10.86); 2.9158 (0.45); 2.7841 (0.45); 2.5985 (1.05); 2.5910 (2.85); 2.5838 (4.66); 2.5766 (6.52); 2.5693 (6.57); 2.5621 (4.78); 2.5550 (2.95); 2.5475 (1.10); 1.7224 (3.99); 1.2613 (0.34); 1.2511 (0.42); 0.8808 (0.47); 0.7579 (0.80); 0.7467 (0.82); 0.7440 (0.69); 0.7318 (0.50); 0.7172 (0.58); 0.7089 (1.50); 0.7064 (1.29); 0.6949 (4.60); 0.6893 (7.09); 0.6757 (12.17); 0.6620 (7.59); 0.6557 (4.46); 0.6422 (1.62); 0.6334 (0.73); 0.6191 (0.49); 0.4127 (0.70); 0.4098 (0.74); 0.4051 (0.71); 0.4024 (0.69); 0.3108 (0.43); 0.3031 (0.51); 0.2954 (1.23); 0.2828 (5.47); 0.2749 (14.33); 0.2669 (14.03); 0.2610 (5.06); 0.2588 (5.08); 0.2459 (1.06); 0.2383 (0.47); 0.2304 (0.39); 0.0062 (0.67); −0.0002 (14.69); −0.0066 (0.81)
Example 61, Solvent: CDCl3, Spectrometer: 300,16 MHz
8.9348 (4.57); 8.3168 (4.84); 8.1625 (1.51); 8.1334 (3.65); 8.0945 (3.84); 8.0653 (1.61); 7.8171 (5.00); 7.2643 (8.04); 6.9216 (2.27); 4.3802 (0.98); 4.3635 (0.99); 4.3318 (1.83); 4.3142 (1.83); 4.2096 (2.11); 4.1604 (1.22); 4.0813 (1.46); 4.0571 (4.11); 4.0333 (4.20); 4.0093 (1.50); 3.8606 (2.21); 3.8023 (2.99); 3.4819 (2.92); 3.4238 (2.18); 2.3957 (1.24); 2.3734 (1.66); 2.3508 (1.30); 2.3299 (0.57); 2.1955 (16.00); 2.0473 (0.55); 1.7711 (4.07); 1.4463 (4.19); 1.4222 (8.22); 1.3982(4.22); 1.2582 (0.93); 1.0678 (8.10); 1.0451 (15.46); 1.0228 (8.28); −0.0002 (2.62)
Example 62, Solvent: CDCl3, Spectrometer: 300,16 MHz
8.9296 (5.61); 8.3134 (5.96); 8.1819 (2.09); 8.1525 (4.17); 8.0965 (4.28); 8.0672 (2.18); 7.8203 (6.11); 7.2732 (2.67); 6.7177 (2.23); 6.6933 (2.29); 4.1076 (1.03); 4.0870 (1.71); 4.0658 (1.76); 4.0441 (1.12); 3.8457 (2.68); 3.7877 (3.60); 3.4622 (3.55); 3.4035 (2.64); 2.3846 (1.45); 2.3625 (2.02); 2.3417 (1.61); 2.3209 (0.72); 1.7824 (1.28); 1.2542 (0.62);

| NMR Peak Lists Table 1 |
|---|

1.2178 (9.85); 1.1976 (10.05); 1.1590 (9.95); 1.1385 (10.07); 1.0770 (9.71); 1.0469 (16.00); 1.0216 (9.98); −0.0002 (1.82)
Example 63, Solvent: CDCl3, Spectrometer: 300,16 MHz
8.9275 (5.48); 8.2997 (5.78); 8.1681 (1.99); 8.1385 (4.20); 8.0899 (4.35); 8.0607 (2.07); 7.8092 (5.96); 7.2780 (1.70); 7.1449 (2.69); 4.2119 (1.16); 4.2030 (1.18); 4.1536 (2.16); 4.1444(2.19); 4.0205 (2.48); 4.0131 (2.50); 3.9623 (1.35); 3.9549 (1.34); 3.8526 (2.65); 3.7945 (3.61); 3.4876 (3.55); 3.4293 (2.60); 2.4043 (1.44); 2.3821 (2.00); 2.3603 (1.59); 2.3382 (0.76); 2.2467 (4.85); 1.8544 (0.78); 1.2597 (3.58); 1.0987 (9.53); 1.0706 (16.00); 1.0443 (9.87); 0.8807 (1.96); 0.8595 (1.08); −0.0002 (1.14)
Example 64, Solvent: CDCl3, Spectrometer: 300,16 MHz
8.9317 (5.19); 8.3147 (5.53); 8.1847 (2.08); 8.1554 (3.80); 8.0908 (3.96); 8.0622(2.12); 7.8131 (5.72); 7.4200 (2.58); 7.2659 (7.34); 3.8404 (2.54); 3.7824 (3.41); 3.4911 (9.85); 3.4629 (8.96); 3.3975 (2.59); 3.3193 (1.83); 3.2960 (1.45); 2.3881 (1.44); 2.3658 (1.94); 2.3438 (1.52); 1.7979 (4.74); 1.6543 (5.24); 1.2536 (11.07); 1.2305 (5.03); 1.0797 (9.45); 1.0533 (16.00); 1.0275 (9.32); 0.8811 (0.90); −0.0002 (5.13)
Example 65, Solvent: CDCl3, Spectrometer: 300,16 MHz
8.9329 (5.12); 8.3145 (5.37); 8.1685 (1.77); 8.1388 (3.93); 8.0946 (4.05); 8.0655 (1.84); 7.8149 (5.52); 7.2691 (4.10); 6.9122 (3.28); 3.8577 (2.47); 3.7995 (3.30); 3.4630 (3.24); 3.4045 (2.43); 2.7576 (1.96); 2.7460 (2.20); 2.7366 (1.92); 2.3795 (1.33); 2.3575 (1.85); 2.3350 (1.47); 1.6990(2.41); 1.2584(1.50); 1.0641 (8.86); 1.0359 (16.00); 1.0123 (9.15); 0.8726 (0.80); 0.7974 (4.23); 0.5348 (6.85); −0.0002 (2.76)
Example 66, Solvent: CDCl3, Spectrometer: 300,16 MHz
8.9288 (8.26); 8.3104 (8.75); 8.1800 (3.21); 8.1504 (6.43); 8.0957 (6.90); 8.0661 (3.45); 7.8078 (9.29); 7.2786 (3.12); 6.7372 (3.04); 6.7117 (3.11); 4.1318 (0.54); 4.1102 (1.57); 4.0873 (2.59); 4.0648 (2.66); 4.0427 (1.65); 4.0208 (0.61); 3.8940 (4.55); 3.8361 (5.67); 3.3715 (5.53); 3.3138 (4.49); 2.2676(0.47); 2.2437 (1.52); 2.2196 (2.30); 2.1964 (2.81); 2.1721 (2.38); 2.1475 (0.83); 2.0329 (0.71); 2.0092(2.24); 1.9851 (2.84); 1.9617 (2.36); 1.9380 (1.64); 1.9147 (0.60); 1.8738 (1.76); 1.3378 (0.39); 1.3158 (0.44); 1.2556 (1.30); 1.2213 (15.85); 1.1999 (15.85); 1.1624 (16.00); 1.1407 (15.91); 1.0591 (7.99); 1.0349 (15.43); 1.0107 (7.59); 0.8964 (0.34); 0.8791 (0.56); 0.8560 (0.40); −0.0002 (2.01)
Example 67, Solvent: CDCl3, Spectrometer: 300,16 MHz
8.9386 (8.77); 8.3159 (9.25); 8.1730 (3.09); 8.1436 (7.03); 8.1018 (7.39); 8.0727 (3.31); 7.8071 (9.71); 7.2650(14.20); 7.0980 (3.88); 5.3028 (2.19); 4.1938 (1.57); 4.1765 (1.55); 4.1358 (3.53); 4.1183 (3.43); 4.0324 (3.73); 4.0246 (3.79); 3.9746 (1.78); 3.9664 (1.79); 3.8911 (4.70); 3.8332 (5.92); 3.4038 (5.80); 3.3455 (4.61); 2.2805 (0.52); 2.2442(8.15); 2.2086 (3.09); 2.1844 (2.54); 2.1603 (0.99); 2.0667 (0.79); 2.0435 (3.04); 2.0192 (3.02); 1.9960 (2.44); 1.9715 (1.66); 1.9483 (0.62); 1.6192 (7.72); 1.2589 (2.08); 1.0774 (8.20); 1.0531 (16.00); 1.0288 (7.76); 0.8791 (0.67); 0.8617 (0.45); −0.0002 (8.67)
Example 68, Solvent: CDCl3, Spectrometer: 300,16 MHz
8.9307 (7.29); 8.3135 (7.64); 8.1828 (2.84); 8.1535 (5.43); 8.0923 (5.72); 8.0625 (3.09); 7.8002 (8.02); 7.4476 (3.08); 7.2672 (8.85); 3.8819 (3.84); 3.8240 (4.78); 3.5088 (9.98); 3.4912(11.77); 3.4673 (8.71); 3.4442(3.28); 3.3694 (5.45); 3.3513 (2.37); 3.3289 (2.61); 3.3100 (5.46); 3.2866 (1.41); 2.2663 (0.39); 2.2412 (1.28); 2.2175 (1.92); 2.1946 (2.37); 2.1706 (2.04); 2.1453 (0.73); 2.0424 (0.75); 2.0192 (1.93); 1.9945 (2.43); 1.9716 (2.01); 1.9471 (1.43); 1.9226 (0.54); 1.8189 (4.43); 1.7991 (6.37); 1.7796 (4.36); 1.6797 (5.76); 1.2778 (7.76); 1.2552 (16.00); 1.2321 (7.23); 1.0610 (6.68); 1.0369 (13.06); 1.0126 (6.30); 0.8816 (0.96); 0.8586 (0.56); −0.0002 (6.24)
Example 69, Solvent: CDCl3, Spectrometer: 300,16 MHz
8.9327 (9.00); 8.3115 (9.58); 8.1656 (3.10); 8.1365 (7.11); 8.0938 (7.46); 8.0645 (3.30); 7.8025 (9.97); 7.2744(4.45); 6.9306 (5.38); 3.9040(4.70); 3.8461 (5.85); 3.3793 (5.74); 3.3214(4.65); 2.7696 (3.16); 2.7591 (3.65); 2.7480 (3.26); 2.7370 (2.27); 2.2575 (0.49); 2.2334 (1.57); 2.2087 (2.40); 2.1856 (2.97); 2.1615 (2.52); 2.1373 (0.91); 2.0371 (0.79); 2.0124 (2.35); 1.9882 (3.00); 1.9650 (2.47); 1.9410 (1.70); 1.9190 (0.62); 1.7967 (2.16); 1.2572 (3.08); 1.0446 (8.24); 1.0205 (16.00); 0.9963 (7.81); 0.8758 (1.50); 0.8039 (7.22); 0.7465 (1.01); 0.5790 (1.41); 0.5427 (11.51); −0.0002 (2.91)
Example 70, Solvent: CDCl3, Spectrometer: 300,16 MHz
8.9206 (4.42); 8.2974(4.61); 8.1512 (1.48); 8.1217 (3.47); 8.0815 (3.54); 8.0531 (1.56); 7.7936 (4.71); 7.2971 (0.99); 7.2929 (0.99); 7.2674(4.71); 6.9763 (2.17); 5.3030 (0.61); 4.3937 (0.92); 4.3794 (0.96); 4.3449 (1.68); 4.3302 (1.73); 4.2199 (2.05); 4.1705 (1.15); 4.0768 (1.38); 4.0548 (3.79); 4.0321 (3.90); 4.0088 (1.46); 3.9056 (2.12); 3.8480 (2.66); 3.4017 (2.59); 3.3445 (2.09); 2.2518 (0.84); 2.1981 (16.00); 2.0373 (1.16); 2.0133 (1.42); 1.9892 (1.23); 1.9676 (0.83); 1.9450 (0.32); 1.4434 (3.89); 1.4226 (7.52); 1.3990 (4.00); 1.2553 (0.38); 1.0506 (3.84); 1.0282 (7.34); 1.0056 (3.73); −0.0002 (0.49)
Example 71, Solvent: DMSO, Spectrometer: 499,93 MHz
9.2105 (0.48); 9.0370 (1.08); 9.0324 (1.17); 9.0261 (0.52); 9.0211 (0.62); 9.0076 (15.35); 9.0030 (16.00); 8.9087 (0.39); 8.8380(4.27); 8.8264 (9.17); 8.8150 (4.58); 8.7463 (14.15); 8.7420(14.04); 8.5028 (1.00); 8.4994 (1.03); 8.4497 (0.33); 8.3086 (0.77); 8.2478 (14.58); 8.2446 (15.74); 8.2183 (0.70); 8.2145 (0.66); 8.2004 (0.89); 8.1968 (0.94); 8.1813 (7.70); 8.1776 (7.01); 8.1636 (10.86); 8.1599 (10.38); 8.1161 (1.09); 8.0982 (1.58); 8.0905 (14.77); 8.0728 (10.25); 6.0301 (0.42); 5.7647 (0.35); 5.0734 (0.72); 4.9213 (4.76); 4.9009 (6.77); 4.8283 (5.18); 4.8081 (6.53); 4.7773 (5.99); 4.7570 (5.16); 4.6825 (6.36); 4.6623 (5.07); 4.1466 (1.01); 4.1417 (1.09); 4.1356 (1.10); 4.1307 (1.04); 3.9734 (0.36); 3.9686 (0.42); 3.9624(0.44); 3.9574 (0.45); 3.9131 (14.11); 3.9082 (15.50); 3.9015 (15.73); 3.8966 (14.77); 3.8358 (0.41); 3.8140 (5.51); 3.8120 (5.42); 3.7784 (10.23); 3.7511 (0.45); 3.7287 (0.45); 3.7013 (14.73); 3.6660 (8.29); 3.3185 (88.33); 3.2961 (2.16); 3.1528 (0.48); 3.1479 (0.94); 3.1431 (0.48); 3.0839 (0.38); 3.0442 (7.31); 3.0393 (14.48); 3.0346 (7.29); 3.0129 (0.33); 2.5171 (9.48); 2.5137 (12.65); 2.5103 (9.60); 1.2375 (1.81); 1.1193 (0.42); 1.1054 (0.70); 1.0913 (0.39)
Example 72, Solvent: CDCl3, Spectrometer: 300,16 MHz
8.9273 (4.55); 8.3070(4.74); 8.1540 (1.48); 8.1245 (3.66); 8.0884 (3.77); 8.0591 (1.52); 7.7964 (4.88); 7.2844 (1.71); 7.2634 (5.07); 6.9556 (2.21); 4.3851 (0.95); 4.3675 (0.97); 4.3360 (1.76); 4.3181 (1.76); 4.2225 (1.76); 4.2084 (1.84); 4.1736 (0.99); 4.1587 (1.03); 4.0803 (1.41); 4.0565 (4.02); 4.0323 (4.10); 4.0083 (1.45); 3.9141 (2.24); 3.8565 (2.79); 3.4035 (2.71); 3.3460(2.20); 2.1950 (16.00); 2.1345 (1.18); 2.0234 (3.18); 1.9851 (0.84); 1.9550(1.40); 1.9153 (0.84); 1.5069 (0.84); 1.4829 (1.01); 1.4477 (4.94); 1.4234 (8.90); 1.3989 (5.82); 1.3703 (3.49); 1.3548 (4.08); 1.2584(1.11); 0.9287 (3.95); 0.9106 (7.24); 0.8890 (3.81); 0.8589 (0.43); −0.0002 (0.88)
Example 73, Solvent: CDCl3, Spectrometer: 300,16 MHz
8.9297 (8.57); 8.3118 (9.03); 8.1795 (3.22); 8.1499 (6.53); 8.0957 (6.93); 8.0662(3.44); 7.8063 (9.40); 7.2786 (3.15); 6.7338 (3.47); 6.7078 (3.56); 4.1253 (0.58); 4.1038 (1.60); 4.0816(2.64); 4.0595 (2.68); 4.0373 (1.67); 4.0155 (0.61); 3.8996 (4.49); 3.8418 (5.58); 3.3773 (5.44); 3.3196 (4.41); 2.2035 (1.27); 2.1606 (2.99); 2.1218 (2.07); 1.9687 (1.41); 1.9593 (1.41); 1.9361 (2.66); 1.8767 (2.89); 1.5010 (1.77); 1.4796(1.94); 1.4622 (1.71); 1.4290 (1.94); 1.4049 (3.94);

-continued

NMR Peak Lists Table 1

1.3813 (7.06); 1.3616 (7.91); 1.2597 (1.27); 1.2216 (15.86); 1.2003 (15.82); 1.1583 (16.00); 1.1368 (15.87); 0.9418 (7.80); 0.9213 (14.17); 0.9009 (7.21); 0.8633 (0.58); 0.0767 (0.34); −0.0002 (1.63)

Example 74, Solvent: CDCl3, Spectrometer: 300,16 MHz
8.9255 (10.02); 8.2948 (10.50); 8.1626 (3.49); 8.1331 (7.75); 8.0885 (8.09); 8.0589 (3.69); 7.7897 (10.85); 7.2784 (3.12); 7.1503 (4.88); 4.1894 (1.73); 4.1802 (1.72); 4.1307 (4.06); 4.1211 (4.02); 4.0409 (4.42); 4.0334 (4.39); 3.9826 (1.93); 3.9762 (1.89); 3.9031 (5.01); 3.8453 (6.29); 3.4085 (6.15); 3.3508(4.94); 2.2504 (8.32); 2.2151 (1.68); 2.1722 (3.76); 2.1318 (2.56); 1.9965 (1.82); 1.9636 (3.04); 1.9242 (1.65); 1.8612(3.46); 1.5174(2.20); 1.4932 (2.41); 1.3671 (9.91); 1.3088 (1.86); 1.2577 (6.18); 0.9386 (9.11); 0.9223 (16.00); 0.9005 (9.86); 0.8572 (1.97); −0.0002 (1.70)

Example 75, Solvent: CDCl3, Spectrometer: 499,93 MHz
8.9497 (2.90); 8.9453 (2.97); 8.3222 (2.56); 8.3179 (2.56); 8.1425 (0.98); 8.1389 (1.02); 8.1329 (0.37); 8.1247 (2.40); 8.1212 (2.61); 8.1042 (3.23); 8.0936 (0.34); 8.0865 (1.18); 7.8262(2.68); 7.8232 (2.73); 7.2654 (7.17); 7.2593 (4.38); 7.2505 (0.44); 7.0193 (0.64); 7.0093 (0.99); 6.9993 (0.61); 4.9167 (1.02); 4.8967 (1.42); 4.8229 (1.07); 4.8028 (1.62); 4.7985 (1.52); 4.7782 (1.05); 4.7045 (1.36); 4.6844(1.01); 4.3892 (1.03); 4.3776 (1.06); 4.3593 (1.48); 4.3478 (1.48); 4.2393 (1.51); 4.2292 (1.56); 4.2094 (1.05); 4.1993 (1.03); 4.0683 (1.46); 4.0536 (3.98); 4.0390 (3.96); 4.0243 (1.37); 4.0188 (0.39); 3.8668 (1.28); 3.8638 (1.31); 3.8322 (1.59); 3.8293 (1.66); 3.6037 (2.70); 3.5692 (2.10); 2.2983 (0.50); 2.2059 (0.48); 2.1859 (16.00); 2.0418 (0.63); 1.6876 (3.48); 1.4688 (0.43); 1.4541 (0.41); 1.4433 (4.62); 1.4287 (9.12); 1.4141 (4.50); 1.4036 (0.75); 1.3889 (0.45); 1.2718 (0.39); 1.2642(0.46); 1.2575 (0.84); 0.8814 (0.50); −0.0002 (4.55)

Example 76, Solvent: DMSO, Spectrometer: 499,93 MHz
8.9938 (6.05); 8.9891 (6.29); 8.7337 (5.46); 8.7292 (5.30); 8.2329 (5.47); 8.2295 (6.09); 8.1771 (2.98); 8.1734 (2.68); 8.1594(4.12); 8.1557 (3.92); 8.0793 (6.14); 8.0715 (2.92); 8.0615 (4.77); 8.0552 (2.81); 7.7102 (0.33); 7.6754 (0.34); 4.9003 (1.93); 4.8801 (2.66); 4.8071 (2.07); 4.7870 (2.60); 4.7502 (2.38); 4.7300 (2.06); 4.6553 (2.55); 4.6352 (2.03); 4.2160 (0.34); 4.2128 (0.33); 4.2034 (0.32); 4.0052(0.47); 3.9919 (1.25); 3.9786 (1.81); 3.9763 (1.57); 3.9626 (1.85); 3.9493 (1.28); 3.9360 (0.48); 3.8235 (2.27); 3.8208 (2.31); 3.7880(3.42); 3.7856 (3.52); 3.6599 (5.52); 3.6247 (3.75); 3.3192 (19.99); 3.2952(0.64); 2.5173 (1.95); 2.5138 (2.69); 2.5103 (2.01); 1.2903 (0.45); 1.2811 (0.48); 1.2652 (0.60); 1.2523 (0.74); 1.2393 (0.92); 1.2304 (1.79); 1.2173 (0.95); 1.1287 (15.46); 1.1155 (15.46); 1.0972 (16.00); 1.0840 (15.68); 0.8658 (0.48); 0.8564 (0.95); 0.8533 (0.94); 0.8437 (0.84); 0.8371 (0.95); 0.8236 (1.15); 0.8125 (0.58); 0.7396 (0.37)

Example 77: $^1$H-NMR(400.0 MHz, DMSO):
9.171(3.1); 9.166(3.1); 8.767(2.3); 8.762(2.2); 8.402(2.4); 8.397(2.4); 8.262(1.2); 8.258(1.1); 8.240(1.9); 8.235(1.8); 8.163(2.6); 8.141(1.7); 7.891(1.1); 7.871(1.1); 3.934(0.6); 3.919(2.0); 3.898(0.8); 3.878(1.9); 3.481(1.7); 3.438(1.5); 3.334(205.3); 2.958(16.0); 2.892(2.3); 2.732(1.9); 2.677(0.4); 2.672(0.5); 2.668(0.3); 2.525(1.4); 2.512(29.2); 2.508(58.0); 2.503(75.3); 2.499(53.7); 2.494(25.4); 2.334(0.4); 2.330(0.5); 2.325(0.3); 1.600(11.9); 1.111(6.9); 1.095(6.8); 1.066(7.1); 1.050(7.0); 0.000(2.1)

Example 78: $^1$H-NMR(400.0 MHz, DMSO):
8.668(3.9); 8.661(3.9); 8.121(3.0); 8.116(3.0); 7.982(1.4); 7.960(4.3); 7.943(3.3); 7.938(3.0); 7.921(1.1); 7.916(1.1); 7.871(1.3); 7.851(1.3); 7.807(2.7); 7.800(2.6); 4.236(1.3); 4.219(4.4); 4.202(4.4); 4.184(1.3); 3.928(0.7); 3.912(1.0); 3.908(0.8); 3.895(0.9); 3.891(1.1); 3.879(3.0); 3.836(3.2); 3.455(3.2); 3.412(2.7); 3.379(0.3); 3.334(245.6); 2.891(1.4); 2.732(1.2); 2.677(0.4); 2.672(0.6); 2.668(0.5); 2.525(1.9); 2.512(34.2); 2.508(68.6); 2.503(89.9); 2.498(64.4); 2.494(30.6); 2.334(0.4); 2.330(0.6); 2.325(0.4); 1.586(16.0); 1.449(4.6); 1.432(9.9); 1.415(4.4); 1.108(9.0); 1.091(8.9); 1.063(9.3); 1.046(9.1); 0.000(3.3)

Example 79: $^1$H-NMR(400.0 MHz, DMSO):
9.224(4.1); 9.219(4.3); 9.093(2.9); 9.089(2.6); 8.336(2.4); 8.332(3.6); 8.327(2.9); 8.322(1.1); 8.315(0.4); 8.305(2.7); 8.300(2.1); 8.174(2.9); 8.152(2.2); 7.953(0.4); 7.899(1.2); 7.878(1.2); 3.931(0.7); 3.915(3.6); 3.898(0.9); 3.894(1.0); 3.877(1.0); 3.872(3.3); 3.861(0.3); 3.491(3.1); 3.448(2.7); 3.332(239.4); 2.892(3.3); 2.733(2.7); 2.732(2.6); 2.677(0.4); 2.672(0.6); 2.668(0.4); 2.525(2.2); 2.512(35.6); 2.508(70.5); 2.503(91.6); 2.498(64.9); 2.494(30.4); 2.334(0.4); 2.330(0.6); 2.325(0.4); 1.599(16.0); 1.109(9.0); 1.093(8.8); 1.064(9.2); 1.048(9.1); 0.000(3.2)

Example 80: $^1$H-NMR(400.0 MHz, DMSO):
8.817(1.7); 8.815(1.3); 8.812(2.3); 8.807(0.8); 8.308(0.4); 8.214(1.4); 8.209(1.9); 8.144(2.2); 8.044(0.7); 8.039(0.6); 8.022(2.1); 8.017(2.1); 8.001(2.5); 7.979(0.7); 7.868(0.6); 7.848(0.6); 3.931(0.5); 3.915(0.8); 3.911(0.6); 3.898(0.7); 3.894(0.9); 3.887(2.2); 3.878(0.6); 3.844(2.5); 3.452(1.6); 3.409(1.4); 3.345(68.9); 3.338(84.2); 3.333(97.2); 2.894(1.8); 2.736(1.5); 2.678(0.3); 2.674(0.5); 2.669(0.3); 2.637(16.0); 2.527(1.4); 2.514(25.4); 2.509(50.8); 2.505(66.3); 2.500(47.0); 2.496(21.9); 2.332(0.4); 1.592(11.6); 1.111(6.5); 1.094(6.5); 1.066(6.7); 1.050(6.6); 0.000(2.3)

Example 81: $^1$H-NMR(400.0 MHz, DMSO):
9.009(2.9); 9.004(4.4); 9.001(3.5); 8.999(3.5); 8.759(4.0); 8.308(1.1); 8.305(0.9); 8.303(1.2); 8.298(0.8); 8.295(0.7); 8.248(5.3); 8.179(2.6); 8.174(2.3); 8.157(4.1); 8.152(3.9); 8.087(5.8); 8.065(4.2); 7.952(0.7); 4.040(2.8); 4.012(5.2); 3.998(0.6); 3.981(1.4); 3.964(6.8); 3.948(1.8); 3.945(2.1); 3.933(3.1); 3.929(2.6); 3.922(5.3); 3.798(0.4); 3.688(5.3); 3.644(4.1); 3.344(277.1); 3.339(289.7); 3.332(365.1); 2.895(4.9); 2.737(4.0); 2.679(1.1); 2.674(1.5); 2.670(1.1); 2.527(5.0); 2.514(87.1); 2.510(173.4); 2.505(228.1); 2.501(165.3); 2.496(80.0); 2.341(0.4); 2.337(1.0); 2.332(1.4); 2.328(1.0); 2.323(0.5); 1.235(0.6); 1.133(15.6); 1.117(15.4); 1.094(16.0); 1.077(15.7); 0.057(0.4); 0.000(7.4)

Example 82, Solvent: CDCl3, Spectrometer: 300,16 MHz
8.9397 (4.39); 8.2413 (4.67); 8.1787 (1.74); 8.1733 (1.77); 8.1496 (3.26); 8.0874 (3.28); 8.0613 (1.77); 7.8118 (4.71); 7.5096 (2.55); 7.3269 (0.44); 3.9808 (2.20); 3.9238 (2.64); 3.4991 (8.21); 3.4828 (7.37); 3.4684 (6.15); 3.3679 (8.47); 3.3053 (2.93); 2.4937 (0.82); 1.8145 (4.65); 1.7770 (16.00); 1.2599 (8.23); 1.2543 (8.30); 1.2470 (8.02)

Example 83, Solvent: CDCl3, Spectrometer: 300,16 MHz
8.9647 (4.29); 8.2729 (4.55); 8.1612 (1.25); 8.1319 (3.86); 8.1114(4.39); 7.8373 (4.65); 7.2874 (1.77); 7.2814 (1.83); 7.2364 (4.57); 6.9553 (2.52); 4.3642 (1.08); 4.3567 (1.08); 4.3148 (2.30); 4.3087 (2.27); 4.2263 (2.45); 4.1776 (1.29); 4.0024(2.21); 3.9421 (7.32); 3.3811 (2.57); 3.3401 (5.47); 2.1932 (13.65); 2.1883 (14.09); 1.9896 (4.83); 1.7807 (16.00); 1.2596 (0.44); 0.8823 (7.93); 0.8762 (7.95); −0.0002 (1.08)

Example 84: $^1$H-NMR(400.0 MHz, DMSO):
9.001(3.3); 8.995(3.3); 8.803(0.9); 8.787(1.9); 8.771(0.9); 8.752(2.8); 8.747(2.8); 8.215(3.3); 8.177(1.7); 8.173(1.4); 8.155(2.5); 8.151(2.2); 8.074(4.3); 8.052(2.2); 7.957(0.7); 7.372(0.4); 7.366(2.5); 7.361(1.0); 7.348(4.0); 7.345(3.9); 7.331(1.2); 7.326(3.2); 7.320(0.4); 7.253(4.7); 7.232(5.3); 7.225(0.7); 7.124(1.6); 7.105(2.6); 7.087(1.1); 6.957(3.7); 6.954(4.5); 6.935(4.0); 6.923(6.1); 6.919(2.0); 6.907(1.8); 6.902(5.3); 6.895(0.6); 4.295(3.8); 4.279(3.7); 3.914(2.8); 3.871(3.3); 3.523(3.0); 3.479(2.5); 3.341(10.4); 2.893(5.1); 2.757(0.4); 2.753(0.5); 2.735(4.3); 2.530(0.3); 2.525(0.6); 2.516(7.9); 2.512(15.8); 2.507(20.8); 2.503(15.1); 2.498(7.3); 1.870(0.3); 1.650(16.0); 1.269(0.5); 1.228(0.6); 0.000(5.7)

NMR Peak Lists Table 1

Example 85: ¹H-NMR(400.0 MHz, DMSO):
9.007(3.7); 9.002(3.8); 8.864(0.9); 8.849(1.8); 8.834(0.9); 8.764(3.0); 8.758(2.9); 8.425(3.6); 8.358(3.7); 8.355(3.4); 8.230(2.9); 8.226(3.3); 8.190(1.9); 8.185(1.5); 8.168(2.7); 8.163(2.8); 8.087(3.8); 8.065(2.2); 4.424(4.0); 4.409(4.0); 4.273(0.4); 4.255(1.2); 4.237(1.3); 4.219(0.5); 3.927(2.8); 3.884(3.3); 3.538(3.2); 3.495(2.7); 3.345(2.3); 2.894(1.5); 2.756(0.4); 2.752(0.3); 2.734(1.1); 2.556(0.8); 2.529(0.4); 2.516(9.3); 2.511(18.9); 2.507(24.9); 2.502(18.1); 2.498 (8.8); 2.476(0.7); 2.469(0.6); 2.436(15.0); 1.883(0.3); 1.662(16.0); 1.280(1.4); 1.262(2.9); 1.244(1.6); 1.230(0.6); 0.000(4.6)
Example 86: ¹H-NMR(400.0 MHz, DMSO):
9.551(10.1); 8.959(2.8); 8.955(2.8); 8.904(0.9); 8.889(2.0); 8.873(0.9); 8.608(3.3); 8.603(3.1); 8.260(3.3); 8.256(3.6); 8.197(1.9); 8.192(1.6); 8.175(2.8); 8.170(2.6); 8.104(0.4); 8.089(3.3); 8.067(2.5); 8.058(5.7); 8.041(2.2); 8.037(6.1); 7.409(5.0); 7.388(4.7); 4.595(7.9); 4.384(3.3); 4.368(3.2); 4.293(0.9); 4.275(0.9); 3.947(2.7); 3.904(3.2); 3.550(3.1); 3.507(2.7); 3.334(13.8); 2.892(1.4); 2.754(0.3); 2.750(1.1); 2.733(0.4); 2.527(0.9); 2.523(1.4); 2.514(18.5); 2.510 (37.4); 2.505(49.1); 2.500(35.3); 2.496(16.9); 2.332(0.3); 1.905(0.7); 1.671(16.0); 1.291(1.1); 1.274(2.3); 1.260(0.3); 1.256(1.1); 1.231(0.8); 0.008(0.5); 0.000(16.6); −0.009(0.5)
Example 87: ¹H-NMR(400.0 MHz, DMSO):
8.954(2.8); 8.949(2.8); 8.603(2.2); 8.598(2.1); 8.280(0.6); 8.266(1.3); 8.252(0.6); 8.229(2.2); 8.224(2.4); 8.154(1.2); 8.149(1.1); 8.131(2.0); 8.127(1.9); 8.070(2.5); 8.048(1.5); 4.594(5.2); 4.311(0.5); 4.293(1.4); 4.275(1.4); 4.257(0.5); 4.103(0.4); 4.088(0.5); 4.066(1.6); 4.051(1.7); 4.045(1.7); 4.031(1.7); 4.008(0.5); 3.994(0.4); 3.911(1.1); 3.893(3.6); 3.885(2.2); 3.875(3.6); 3.857(1.2); 3.842(2.3); 3.484(2.2); 3.441(1.9); 3.335(5.8); 2.892(1.1); 2.753(1.2); 2.749(1.0); 2.732(0.5); 2.526(0.5); 2.513(12.0); 2.509(24.2); 2.504(31.8); 2.499(22.9); 2.495(11.0); 2.479(0.3); 2.167(0.4); 2.157(0.5); 2.143(1.4); 2.136(15.8); 2.068(0.4); 2.059(0.5); 2.024(16.0); 1.769(0.4); 1.597(11.1); 1.290(1.6); 1.273 (3.3); 1.260(0.5); 1.255(1.7); 1.247(0.4); 1.242(0.4); 1.230(0.8); 1.204(4.1); 1.186(8.8); 1.168(3.9); 0.000(2.7)
Example 88: ¹H-NMR(400.0 MHz, DMSO):
9.001(3.2); 8.995(3.3); 8.759(2.2); 8.753(2.1); 8.284(0.6); 8.270(1.2); 8.256(0.6); 8.206(2.2); 8.201(2.5); 8.155(1.4); 8.150(1.1); 8.132(2.1); 8.128(2.0); 8.070(2.6); 8.048(1.5); 4.307(0.3); 4.289(1.0); 4.271(1.1); 4.254(0.4); 4.104(0.4); 4.089(0.5); 4.067(1.6); 4.052(1.7); 4.047(1.7); 4.032(1.7); 4.010(0.5); 3.996(0.4); 3.911(1.1); 3.893(3.5); 3.876(4.1); 3.857(1.1); 3.835(2.3); 3.477(2.3); 3.433(2.0); 3.339(3.8); 2.893(0.8); 2.754(0.7); 2.733(0.5); 2.528(0.5); 2.514(8.0); 2.510(16.1); 2.505(21.2); 2.501(15.2); 2.496(7.2); 2.230(0.5); 2.167(0.5); 2.158(0.4); 2.150(0.7); 2.137(15.8); 2.069(0.5); 2.025(16.0); 1.599(11.3); 1.290(1.2); 1.277(0.4); 1.272(2.5); 1.259(0.7); 1.254(1.3); 1.245(0.5); 1.242 (0.5); 1.230(0.9); 1.205(4.1); 1.187(8.9); 1.169(3.9); 0.000(3.3)
Example 89: ¹H-NMR(400.0 MHz, DMSO):
9.004(3.6); 8.998(3.7); 8.896(0.8); 8.881(1.7); 8.865(0.9); 8.763(3.0); 8.757(2.9); 8.221(3.1); 8.218(3.3); 8.174(1.7); 8.169(1.4); 8.152(2.6); 8.147(2.3); 8.078(3.4); 8.056(2.2); 7.331(2.2); 7.326(1.7); 7.321(1.9); 7.315(2.3); 6.918(8.4); 6.913(2.9); 6.908(3.9); 6.899(1.0); 4.458(4.8); 4.443(4.7); 3.890(2.7); 3.847(3.3); 3.529(3.1); 3.485(2.5); 3.340(19.3); 2.893(2.2); 2.755(0.4); 2.734(1.7); 2.528(0.4); 2.515(9.6); 2.510(18.9); 2.506(24.5); 2.501(17.8); 2.497(8.7); 1.630 (16.0); 1.271(0.4); 1.253(0.8); 1.235(0.6); 1.230(0.6); 1.059(0.3); 0.000(4.5)
Example 90: ¹H-NMR(400.0 MHz, DMSO):
9.003(3.8); 8.997(3.9); 8.760(3.1); 8.754(3.0); 8.600(0.9); 8.586(1.7); 8.571(0.9); 8.221(3.1); 8.217(3.4); 8.174(1.8); 8.170(1.5); 8.152(2.7); 8.147(2.4); 8.077(3.5); 8.055(2.2); 6.005(2.4); 5.997(2.9); 5.937(2.3); 5.935(2.4); 5.930(2.0); 5.928(1.8); 4.282(1.0); 4.264(1.0); 4.246(0.5); 4.233(4.0); 4.219(4.0); 3.900(2.7); 3.856(3.3); 3.508(3.1); 3.465(2.6); 3.337(1.9); 2.893(0.4); 2.528(0.4); 2.514(9.8); 2.510(19.6); 2.505(25.6); 2.501(18.8); 2.497(9.3); 2.168(14.3); 1.627(16.0); 1.288(1.1); 1.270(2.2); 1.252(1.1); 1.230(0.6); 0.000(5.3)
Example 91: ¹H-NMR(400.0 MHz, DMSO):
• = 9.006(4.3); 9.000(4.5); 8.805(0.8); 8.790(1.6); 8.773(0.9); 8.764(3.3); 8.758(3.0); 8.229(3.1); 8.224(3.5); 8.186 (2.0); 8.181(1.5); 8.164(2.9); 8.159(2.6); 8.085(3.5); 8.063(2.3); 7.955(0.5); 7.289(1.9); 7.284(1.3); 7.281(0.6); 7.266(3.5); 7.264(2.7); 7.254(1.3); 7.249(4.3); 7.223(5.4); 7.206(3.2); 7.195(0.9); 7.189(2.0); 7.183(0.5); 7.176(0.4); 7.172(0.6); 4.310(4.1); 4.295(4.0); 4.276(0.4); 4.258(0.9); 4.240(0.9); 4.223(0.3); 3.917(2.8); 3.873(3.3); 3.740(0.4); 3.523(3.2); 3.480(2.7); 3.338(2.1); 2.947(0.4); 2.892(4.9); 2.755(1.6); 2.751(0.6); 2.733(3.3); 2.554(0.4); 2.528(0.5); 2.514(10.3); 2.510(20.7); 2.505(27.2); 2.501(19.8); 2.496(9.6); 1.673(0.8); 1.651(16.0); 1.280(1.2); 1.262(2.4); 1.245(1.3); 1.230(0.8); 1.076(1.2); 1.059(0.8); 1.041(0.4); 0.000(6.9)
Example 92: ¹H-NMR(400.0 MHz, DMSO):
9.006(4.3); 9.000(4.5); 8.912(0.8); 8.897(1.7); 8.881(0.8); 8.760(3.1); 8.754(3.0); 8.451(2.3); 8.447(2.3); 8.422(1.6); 8.418(1.6); 8.410(1.6); 8.407(1.6); 8.224(3.1); 8.219(3.5); 8.181(2.0); 8.176(1.6); 8.159(2.9); 8.154(2.6); 8.082(3.5); 8.060(2.3); 7.638(1.0); 7.633(1.5); 7.628(1.0); 7.618(1.2); 7.613(1.7); 7.609(1.1); 7.320(1.5); 7.308(1.5); 7.300(1.4); 7.290(1.3); 7.288(1.3); 4.332(2.5); 4.329(2.5); 4.317(2.4); 4.313(2.5); 4.280(0.4); 4.262(1.3); 4.245(1.2); 4.227(0.4); 3.911(2.8); 3.867(3.4); 3.526(3.2); 3.483(2.7); 3.342(1.4); 2.893(1.0); 2.807(0.4); 2.755(1.9); 2.751(0.5); 2.733(0.4); 2.528(0.4); 2.524(0.6); 2.515(9.2); 2.511(19.0); 2.506(25.4); 2.501(18.5); 2.497(9.0); 1.873(0.3); 1.639(16.0); 1.282 (1.4); 1.264(2.9); 1.246(1.5); 1.231(0.9); 1.059(0.3); 0.000(6.1)
Example 93: ¹H-NMR(400.0 MHz, DMSO):
9.011(4.1); 9.005(4.3); 8.829(0.9); 8.814(1.8); 8.799(0.9); 8.772(3.2); 8.766(3.1); 8.244(3.1); 8.239(3.6); 8.203(2.0); 8.198(1.6); 8.181(2.9); 8.176(2.6); 8.097(3.5); 8.075(2.4); 7.630(1.0); 7.601(0.4); 7.422(1.8); 7.415(1.3); 7.411(1.7); 7.406(1.1); 7.400(2.3); 7.392(0.4); 7.269(0.5); 7.258(3.2); 7.251(2.3); 7.247(2.5); 7.241(2.8); 7.234(4.7); 7.228(5.7); 7.222(1.1); 7.213(2.5); 7.207(1.1); 7.200(1.3); 7.189(0.8); 4.375(4.4); 4.360(4.4); 4.308(0.7); 4.290(1.9); 4.272(2.0); 4.255(0.7); 4.251(0.4); 3.941(2.8); 3.897(3.3); 3.550(3.2); 3.506(2.8); 3.341(1.6); 2.893(1.7); 2.755(0.8); 2.751(0.8); 2.733(0.8); 2.528(0.5); 2.515(10.9); 2.510(21.6); 2.506(28.2); 2.501(20.3); 2.497(9.7); 1.907(0.3); 1.691(16.0); 1.657(0.4); 1.290(2.1); 1.277(0.6); 1.273(4.3); 1.260(0.9); 1.255(2.1); 1.242(0.5); 1.230(0.8); 0.000(7.0)
Example 94: ¹H-NMR(400.0 MHz, DMSO):
9.006(3.9); 9.001(4.0); 8.860(0.8); 8.844(1.7); 8.829(0.9); 8.762(3.1); 8.756(2.9); 8.222(3.0); 8.218(3.4); 8.182(1.9); 8.177(1.5); 8.160(2.8); 8.155(2.5); 8.085(3.5); 8.062(2.3); 7.919(0.4); 7.898(0.5); 7.568(0.5); 7.547(0.4); 7.401(0.3); 7.380(0.6); 7.344(4.5); 7.339(1.6); 7.327(2.2); 7.322(7.2); 7.317(1.0); 7.256(6.1); 7.235(3.8); 4.313(0.4); 4.290(2.1); 4.279(3.7); 4.261(2.4); 4.243(0.7); 4.225(0.4); 3.902(2.8); 3.858(3.3); 3.522(3.1); 3.478(2.7); 3.345(2.6); 2.893(2.0); 2.756(0.7); 2.752(0.5); 2.734(1.4); 2.554(0.4); 2.529(0.5); 2.515(10.2); 2.511(20.4); 2.506(26.7); 2.502(19.3); 2.497 (9.2); 1.639(16.0); 1.287(1.3); 1.269(2.7); 1.256(0.7); 1.252(1.4); 1.238(0.5); 1.230(0.7); 0.000(6.6)
Example 95: ¹H-NMR(400.0 MHz, DMSO):
9.013(4.2); 9.007(4.4); 8.862(0.9); 8.847(1.8); 8.832(0.8); 8.775(3.2); 8.769(3.1); 8.239(3.1); 8.234(3.6); 8.196(2.0); 8.191(1.6); 8.174(2.9); 8.169(2.6); 8.096(3.5); 8.073(2.3); 7.954(0.4); 7.628(0.3); 7.623(0.4); 7.617(0.4); 7.598(0.4); 7.584(3.9); 7.578(4.1); 7.374(2.0); 7.369(1.8); 7.353(2.5); 7.348(2.5); 7.239(3.4); 7.218(2.6); 4.387(0.4); 4.372(0.4);

NMR Peak Lists Table 1

4.347(2.4); 4.333(3.0); 4.321(2.1); 4.296(0.4); 4.282(0.8); 4.264(1.3); 4.247(1.3); 4.229(0.5); 3.923(2.7); 3.879(3.2); 3.543(3.1); 3.500(2.7); 3.329(10.5); 2.891(3.4); 2.837(0.6); 2.752(0.7); 2.748(0.7); 2.732(2.5); 2.677(0.4); 2.672(0.5); 2.668(0.4); 2.551(0.5); 2.525(1.5); 2.512(30.6); 2.508(61.6); 2.503(80.9); 2.498(58.3); 2.494(27.9); 2.334(0.4); 2.330(0.5); 2.325(0.4); 1.899(0.5); 1.671(16.0); 1.281(1.9); 1.263(3.5); 1.245(1.9); 1.233(1.3); 1.056(0.4); 0.008(0.8); 0.000(25.0); −0.009(0.8)

Example 96: $^1$H-NMR(400.0 MHz, DMSO):
9.011(4.2); 9.005(4.4); 8.902(0.9); 8.887(1.9); 8.872(0.9); 8.758(3.1); 8.753(3.0); 8.427(0.3); 8.234(3.1); 8.229(3.5); 8.195(2.0); 8.190(1.6); 8.173(2.9); 8.168(2.6); 8.147(0.4); 8.089(3.6); 8.067(2.5); 7.995(0.6); 7.992(0.8); 7.987(0.6); 7.973(0.7); 7.971(0.7); 7.966(0.5); 7.956(1.0); 7.907(3.1); 7.904(4.4); 7.899(1.2); 7.885(4.3); 7.883(4.1); 7.877(0.7); 7.864(7.7); 7.619(0.4); 7.601(0.3); 7.585(0.5); 7.580(0.4); 7.563(0.8); 7.545(0.6); 7.481(2.4); 7.477(1.1); 7.463(4.4); 7.446(1.4); 7.442(3.3); 7.437(0.8); 7.417(0.5); 7.374(1.1); 7.372(1.9); 7.369(1.2); 7.357(0.9); 7.353(2.6); 7.349(0.8); 7.337(0.6); 7.335(1.0); 7.332(0.6); 4.479(4.7); 4.464(4.6); 4.286(0.4); 4.268(0.5); 4.250(1.0); 4.232(0.4); 3.943(2.7); 3.900(3.3); 3.544(3.1); 3.501(2.7); 3.340(9.8); 2.893(1.0); 2.816(0.4); 2.751(0.5); 2.733(0.7); 2.528(0.7); 2.523(1.2); 2.515(16.1); 2.510(32.4); 2.506(42.8); 2.501(31.0); 2.497(15.0); 1.880(0.6); 1.670(16.0); 1.283(1.3); 1.265(2.6); 1.248(1.4); 1.231(1.0); 0.000(5.7)

Example 97: $^1$H-NMR(400.0 MHz, DMSO):
9.006(3.9); 9.000(4.1); 8.952(0.8); 8.936(1.8); 8.920(0.8); 8.760(3.1); 8.754(3.0); 8.234(3.0); 8.230(3.5); 8.195(1.9); 8.190(1.5); 8.173(2.7); 8.168(2.4); 8.086(3.4); 8.064(2.3); 7.956(1.0); 7.425(1.8); 7.420(3.3); 7.416(1.9); 7.233(7.3); 7.228(7.0); 4.347(0.4); 4.331(0.4); 4.308(2.1); 4.293(3.3); 4.278(3.1); 4.260(1.4); 4.243(0.7); 3.906(2.7); 3.862(3.3); 3.537(3.1); 3.494(2.6); 3.340(3.0); 2.893(8.2); 2.816(0.4); 2.751(0.4); 2.734(6.6); 2.555(0.6); 2.529(0.5); 2.515(11.1); 2.511(22.7); 2.506(30.1); 2.502(21.9); 2.497(10.7); 1.891(0.4); 1.657(16.0); 1.287(1.4); 1.269(2.9); 1.256(0.5); 1.251(1.5); 1.238(0.4); 1.230(0.8); 0.000(5.0)

Example 98: $^1$H-NMR(400.0 MHz, DMSO):
9.015(4.0); 9.010(4.2); 8.876(0.9); 8.860(1.8); 8.845(0.9); 8.768(3.2); 8.762(3.0); 8.243(3.1); 8.239(3.6); 8.197(2.0); 8.192(1.6); 8.175(2.9); 8.170(2.6); 8.101(3.6); 8.079(2.3); 7.993(3.3); 7.980(3.4); 6.541(2.4); 6.528(2.7); 6.519(3.9); 4.325(0.8); 4.309(0.8); 4.285(1.5); 4.283(1.5); 4.269(1.5); 4.264(2.4); 4.247(2.1); 4.229(0.7); 4.205(1.4); 4.190(1.6); 4.165(0.8); 4.150(0.8); 3.952(2.8); 3.909(3.3); 3.701(0.9); 3.689(1.1); 3.677(0.9); 3.532(3.7); 3.523(4.3); 3.511(6.4); 3.510(6.4); 3.498(5.5); 3.489(3.4); 3.470(0.5); 3.448(0.5); 3.421(1.1); 3.409(1.4); 3.402(1.2); 3.397(1.3); 3.353(1.3); 3.303(0.9); 3.291(0.8); 3.269(4.8); 3.260(5.6); 3.254(5.7); 3.246(3.4); 3.223(0.5); 3.211(0.9); 2.893(1.1); 2.819(0.7); 2.755(1.2); 2.751(0.7); 2.733(0.5); 2.554(0.6); 2.528(0.4); 2.523(0.7); 2.515(9.6); 2.510(19.5); 2.506(25.8); 2.501 (18.6); 2.497(8.9); 1.891(0.6); 1.682(16.0); 1.661(0.4); 1.282(2.3); 1.264(4.7); 1.247(2.3); 1.231(0.9); 0.000(5.2)

Example 99: $^1$H-NMR(400.0 MHz, DMSO):
9.107(0.3); 8.963(3.7); 8.958(4.0); 8.938(1.1); 8.922(2.0); 8.907(1.0); 8.802(0.4); 8.613(3.6); 8.609(3.7); 8.466(0.7); 8.444(0.6); 8.292(0.5); 8.261(3.5); 8.257(3.9); 8.237(0.5); 8.232(0.5); 8.222(0.4); 8.196(1.9); 8.192(1.7); 8.174(2.8); 8.169(2.6); 8.154(0.4); 8.149(0.4); 8.134(0.5); 8.112(0.4); 8.093(3.7); 8.071(2.5); 8.056(0.4); 7.955(0.4); 7.629(0.4); 7.600(0.4); 7.211(2.9); 4.598(6.8); 4.350(0.4); 4.326(2.5); 4.316(2.9); 4.312(2.8); 4.302(2.3); 4.293(0.9); 4.275(1.8); 4.257(1.6); 4.239(0.5); 3.937(2.6); 3.914(0.4); 3.893(3.2); 3.572(0.4); 3.551(3.2); 3.529(0.4); 3.508(3.7); 3.451(0.5); 3.434(0.4); 3.407(0.7); 3.338(3.9); 2.995(0.5); 2.892(3.1); 2.863(0.5); 2.754(2.7); 2.750(1.7); 2.733(2.0); 2.674(0.3); 2.553(0.4); 2.509(38.5); 2.505(49.3); 2.500(36.5); 1.670(16.0); 1.625(0.3); 1.607(1.2); 1.285(1.6); 1.267(3.1); 1.249 (1.6); 1.232(1.0); 1.058(0.4); 0.000(7.5)

Example 100: $^1$H-NMR(400.0 MHz, DMSO):
9.000(2.6); 8.995(3.1); 8.755(2.6); 8.750(2.9); 8.435(0.8); 8.420(1.6); 8.406(0.9); 8.204(3.3); 8.160(1.3); 8.156(1.3); 8.138(1.9); 8.134(2.1); 8.069(2.9); 8.047(1.8); 7.199(4.9); 4.296(0.9); 4.278(0.9); 4.260(0.4); 4.077(4.0); 4.062(4.2); 3.989(1.4); 3.971(4.0); 3.953(4.0); 3.935(1.4); 3.874(2.1); 3.831(2.6); 3.486(2.5); 3.443(2.1); 3.332(3.1); 2.892(0.4); 2.753(0.5); 2.732(0.3); 2.684(0.4); 2.527(0.8); 2.508(19.3); 2.504(26.7); 2.500(22.7); 2.255(0.3); 2.195(0.7); 2.186 (0.6); 2.171(16.0); 2.136(0.4); 1.598(13.1); 1.291(1.3); 1.274(2.5); 1.256(1.7); 1.232(4.8); 1.214(8.5); 1.206(1.7); 1.196(4.2); 0.000(4.5); −0.009(0.8)

Example 101: $^1$H-NMR(400.0 MHz, DMSO):
9.008(3.9); 9.002(4.1); 8.889(0.9); 8.873(1.8); 8.858(0.9); 8.765(3.2); 8.759(3.1); 8.227(3.1); 8.223(3.6); 8.184(1.9); 8.180(1.5); 8.162(2.7); 8.158(2.5); 8.086(3.5); 8.063(2.3); 7.354(3.4); 7.333(6.2); 7.280(4.3); 7.259(2.5); 4.371(0.4); 4.355(0.4); 4.333(2.0); 4.318(3.6); 4.303(2.0); 4.280(0.4); 4.275(0.6); 4.265(0.4); 4.257(1.5); 4.240(1.5); 4.222(0.5); 3.911(2.7); 3.868(3.3); 3.528(3.1); 3.485(2.6); 3.336(3.7); 2.893(1.7); 2.751(0.3); 2.734(0.7); 2.554(1.8); 2.527(0.7); 2.514(13.6); 2.510(27.2); 2.505(35.8); 2.501(26.2); 2.496(12.9); 1.647(16.0); 1.280(1.7); 1.262(3.4); 1.244(1.8); 1.232(0.8); 0.008(0.3); 0.000(9.6); −0.009(0.3)

Example 102: $^1$H-NMR(400.0 MHz, DMSO):
9.013(4.2); 9.007(4.4); 8.937(0.8); 8.922(1.7); 8.907(0.8); 8.773(3.1); 8.768(3.0); 8.453(4.2); 8.449(2.9); 8.441(2.9); 8.438(4.2); 8.241(3.1); 8.237(3.5); 8.197(2.0); 8.193(1.6); 8.175(2.8); 8.170(2.5); 8.095(3.4); 8.073(2.3); 7.204(4.3); 7.189(4.1); 4.326(2.2); 4.317(2.3); 4.311(2.3); 4.302(2.1); 4.276(0.4); 4.261(0.4); 4.251(0.5); 4.233(1.4); 4.215(1.3); 4.197(0.5); 3.926(2.7); 3.882(3.3); 3.542(3.1); 3.499(2.7); 3.332(8.0); 2.944(0.4); 2.891(1.5); 2.828(0.7); 2.752(2.0); 2.748(0.7); 2.732(0.7); 2.677(0.4); 2.672(0.5); 2.667(0.4); 2.551(0.8); 2.525(1.6); 2.512(28.4); 2.508(56.5); 2.503 (73.9); 2.498(53.2); 2.494(25.4); 2.334(0.4); 2.330(0.5); 2.325(0.4); 1.906(0.6); 1.669(16.0); 1.271(1.7); 1.253(3.4); 1.235(2.5); 0.008(0.6); 0.000(17.4); −0.009(0.6)

Example 103: $^1$H-NMR(400.0 MHz, DMSO):
8.960(4.2); 8.954(4.4); 8.909(0.9); 8.894(1.8); 8.878(0.9); 8.606(3.2); 8.601(3.1); 8.497(0.6); 8.468(0.8); 8.450(2.7); 8.446(2.6); 8.420(1.7); 8.417(1.8); 8.409(1.7); 8.405(1.7); 8.248(3.3); 8.243(3.5); 8.181(1.9); 8.176(1.7); 8.158(2.9); 8.154(2.7); 8.146(0.8); 8.083(3.6); 8.061(2.3); 7.678(0.4); 7.658(0.5); 7.653(0.5); 7.631(0.8); 7.627(1.5); 7.617(1.6); 7.612(1.9); 7.607(1.2); 7.600(0.5); 7.568(0.3); 7.375(0.4); 7.363(0.5); 7.355(0.5); 7.343(0.5); 7.319(1.7); 7.307(1.7); 7.299(1.5); 7.287(1.4); 4.596(7.0); 4.354(0.3); 4.329(3.1); 4.315(2.8); 4.273(0.4); 4.224(0.4); 4.201(0.4); 4.190(0.4); 4.172(0.4); 3.918(2.7); 3.874(3.2); 3.534(3.2); 3.491(2.7); 3.340(24.2); 2.892(0.4); 2.806(0.6); 2.754(0.6); 2.750(0.6); 2.527(0.9); 2.514(17.2); 2.509(34.6); 2.505(45.5); 2.500(32.9); 2.496(15.9); 1.871(0.8); 1.636(16.0); 1.258(0.5); 1.240(1.1); 1.232(1.0); 1.222(0.5); 0.000(6.4)

Example 104: $^1$H-NMR(400.0 MHz, DMSO):
9.006(3.5); 9.000(3.5); 8.936(0.9); 8.920(1.8); 8.905(0.9); 8.759(3.0); 8.754(2.9); 8.282(2.9); 8.276(2.8); 8.218(3.1); 8.214(3.4); 8.177(1.8); 8.173(1.4); 8.155(2.6); 8.151(2.3); 8.082(3.4); 8.060(2.1); 7.724(1.7); 7.718(1.7); 7.703(2.0); 7.697(1.9); 7.456(3.4); 7.436(2.9); 4.364(0.5); 4.349(0.5); 4.326(2.3); 4.311(4.7); 4.296(2.2); 4.293(2.0); 4.274(0.8); 4.258(0.4); 3.899(2.7); 3.856(3.3); 3.524(3.1); 3.481(2.6); 3.345(9.5); 3.148(0.4); 3.081(0.4); 2.894(0.8); 2.752(0.3);

NMR Peak Lists Table 1

2.735(0.5); 2.547(0.4); 2.530(0.6); 2.516(10.2); 2.512(20.3); 2.508(26.6); 2.503(19.4); 2.499(9.5); 1.629(16.0); 1.605(0.5); 1.297(1.3); 1.279(2.6); 1.266(0.3); 1.262(1.3); 1.230(0.6); 0.000(2.3)
Example 105, Solvent: CDCl3, Spectrometer: 300,16 MHz
8.9688 (4.85); 8.9612 (5.01); 8.3436 (3.54); 8.3361 (3.53); 8.1770(1.11); 8.1711 (1.08); 8.1474 (4.25); 8.1414 (4.69); 8.1266 (5.28); 8.0969 (1.29); 7.8603 (3.62); 7.8551 (3.63); 7.7889(1.11); 7.2653 (15.50); 5.3025 (0.40); 4.1636 (1.91); 4.1039 (3.02); 3.9094 (5.08); 3.8498 (3.36); 3.5945 (0.49); 3.5837 (2.72); 3.5658 (5.46); 3.5480 (3.83); 3.5307 (1.76); 3.5267 (1.67); 3.5198 (6.89); 3.5125 (1.50); 3.5083 (1.87); 3.4964 (7.23); 3.4731 (2.53); 3.4674 (0.96); 3.4490 (1.38); 3.4315 (1.12); 3.4273 (1.31); 3.4093 (0.81); 3.4027 (0.76); 3.3828 (0.62); 3.3639 (0.35); 1.8758 (0.57); 1.8725 (0.59); 1.8582 (1.55); 1.8536 (1.95); 1.8345 (2.44); 1.8177 (1.88); 1.8127 (1.52); 1.7990 (0.60); 1.7947 (0.57); 1.6327 (16.00); 1.3109 (7.72); 1.2876 (15.92); 1.2642 (7.57); 0.0107 (0.33); −0.0002 (10.12); −0.0111 (0.40)
Example 106, Solvent: CDCl3, Spectrometer: 300,16 MHz
8.9779 (7.38); 8.9703 (7.57); 8.3450 (6.30); 8.3375 (6.21); 8.1698(0.49); 8.1647 (0.35); 8.1399 (9.50); 8.1350 (16.00); 8.1060 (0.61); 7.8643 (6.78); 7.2649 (21.13); 7.1285 (1.76); 7.1137(1.11); 5.3027 (2.22); 4.1673 (3.38); 4.1609 (6.66); 4.1523 (6.63); 4.1429 (6.81); 4.1343 (6.64); 4.1083 (5.18); 3.9569(8.44); 3.8970 (5.06); 2.3078 (3.97); 2.2993 (8.33); 2.2907 (4.04); 1.6189 (15.27); 1.2606 (0.38); 1.2535 (0.48); 0.0107 (0.38); −0.0002 (12.48); −0.0111 (0.54)
Example 107, Solvent: CDCl3, Spectrometer: 300,16 MHz
8.9697 (2.94); 8.9622 (3.01); 8.3387 (2.74); 8.3313 (2.69); 8.1221 (5.84); 8.1190 (6.70); 7.8595 (3.09); 7.2727 (7.59); 7.0012 (0.53); 6.9843 (0.91); 6.9672 (0.57); 5.3023 (1.34); 4.4718 (0.84); 4.4521 (0.85); 4.4221 (1.40); 4.4024 (1.38); 4.2801 (1.44); 4.2638 (1.47); 4.2304 (0.91); 4.2141 (0.91); 4.1852(1.34); 4.1254 (2.13); 3.9849 (2.32); 3.9612 (3.94); 3.9480 (3.30); 3.9374 (2.68); 3.8882 (1.94); 2.2070 (16.00); 1.8736 (1.34); 1.8493 (2.55); 1.8254 (2.64); 1.8012 (4.25); 1.7769 (0.47); 0.9221 (4.22); 0.8976 (8.51); 0.8728 (3.92); −0.0002 (2.34)
Example 108, Solvent: CDCl3, Spectrometer: 300,16 MHz
8.9552 (3.01); 8.9476 (3.09); 8.5889 (1.50); 8.3128 (2.44); 8.3053 (2.42); 8.1519 (0.41); 8.1464 (0.36); 8.1222 (3.03); 8.1164 (3.99); 8.1120 (3.87); 8.0824 (0.47); 7.8546 (2.44); 7.2673 (2.03); 7.1920 (1.38); 7.1851 (2.20); 7.1782 (1.45); 6.4760 (1.37); 6.4672 (2.45); 6.4585 (1.47); 6.0755 (1.81); 6.0696 (2.04); 6.0661 (1.99); 6.0601 (1.75); 5.2979 (1.83); 4.2468 (1.19); 4.1869 (1.90); 3.9987 (2.87); 3.9389 (1.93); 3.6076 (16.00); 1.8104(1.25); −0.0002 (1.21)
Example 109: $^1$H-NMR(400.0 MHz, DMSO):
9.003(7.2); 8.997(7.6); 8.765(4.9); 8.759(4.8); 8.300(0.4); 8.285(1.3); 8.271(1.3); 8.258(1.0); 8.244(1.1); 8.229(0.7); 8.220(4.2); 8.216(6.0); 8.175(2.7); 8.170(2.0); 8.153(4.1); 8.148(3.4); 8.079(5.9); 8.056(3.8); 7.629(0.5); 7.625(0.4); 7.616(0.4); 7.599(0.5); 7.576(0.3); 7.568(0.4); 7.550(0.3); 4.428(1.7); 4.416(1.0); 4.398(0.5); 4.391(0.6); 4.384(1.0); 4.378(1.1); 4.371(0.6); 4.365(0.6); 4.287(0.4); 4.275(0.9); 4.263(0.6); 4.255(0.5); 4.242(1.3); 4.231(0.6); 4.217(1.8); 4.208(1.9); 3.895(2.3); 3.878(1.6); 3.864(1.1); 3.851(2.8); 3.835(1.9); 3.483(1.0); 3.476(3.3); 3.440(1.4); 3.433(2.8); 3.331(32.1); 3.197(0.5); 3.183(0.4); 3.175(0.7); 3.166(0.7); 3.159(0.7); 3.154(1.0); 3.142(0.6); 3.136(0.8); 3.126(0.5); 3.120(0.5); 3.104(0.4); 3.068(0.4); 3.052(0.4); 3.047(0.4); 3.035(0.5); 3.032(0.5); 3.020(0.5); 3.014(0.5); 2.999(0.6); 2.986(0.4); 2.980(0.3); 2.968(0.6); 2.953(0.5); 2.947(0.6); 2.933(0.5); 2.892(2.5); 2.872(0.8); 2.856(0.7); 2.839(0.5); 2.825(0.7); 2.810(0.7); 2.794(0.6); 2.777(0.6); 2.762(0.4); 2.753(1.0); 2.750(1.6); 2.733(1.6); 2.678(0.3); 2.673(0.5); 2.669(0.3); 2.527(1.1); 2.522(1.8); 2.514(27.1); 2.509(55.8); 2.504(74.1); 2.500(53.6); 2.495(25.8); 2.336(0.4); 2.331(0.5); 2.327(0.4); 2.266(0.4); 2.253(0.5); 2.238(0.4); 1.951(0.6); 1.946(0.7); 1.941(0.8); 1.936(0.9); 1.930(0.7); 1.925(0.7); 1.920(0.7); 1.840(0.4); 1.831(0.5); 1.823(0.5); 1.810(0.5); 1.804(0.5); 1.795(0.5); 1.788(0.6); 1.774(0.3); 1.741(0.4); 1.735(0.5); 1.728(0.4); 1.720(0.5); 1.712(0.7); 1.706(0.7); 1.699(0.7); 1.692(0.5); 1.683(0.4); 1.677(0.4); 1.670(0.3); 1.656(0.3); 1.613(13.7); 1.605(16.0); 1.558(0.3); 1.538(0.6); 1.530(0.7); 1.510(1.6); 1.499(2.3); 1.489(2.4); 1.479(2.8); 1.469(2.4); 1.459(1.5); 1.448(1.1); 1.436(0.4); 1.422(0.4); 1.407(0.4); 1.393(0.7); 1.382(0.6); 1.371(0.9); 1.364(0.9); 1.347(2.1); 1.342(2.0); 1.328(2.2); 1.313(1.8); 1.306(1.2); 1.300(1.1); 1.291(0.6); 1.281(0.5); 1.275(1.1); 1.257(2.0); 1.239(1.3); 1.237(1.1); 1.232(1.2); 1.218(0.5); 1.200(0.6); 1.197(0.3); 1.183(0.3); 1.161(0.8); 1.147(0.9); 1.137(0.7); 1.130(0.8); 1.122(0.7); 1.057(0.5); 0.968(0.6); 0.956(0.8); 0.944(0.6); 0.938(0.6); 0.927(0.7); 0.914(0.5); 0.008(0.5); 0.000(16.6); −0.009(0.5)
Example 110: $^1$H-NMR(400.0 MHz, DMSO):
9.011(4.4); 9.005(4.7); 8.772(3.2); 8.767(3.2); 8.285(0.9); 8.270(1.7); 8.255(1.0); 8.176(4.0); 8.171(2.8); 8.166(1.2); 8.149(3.5); 8.144(2.8); 8.099(3.7); 8.077(2.2); 7.955(0.6); 7.430(4.1); 7.424(4.3); 7.207(3.2); 7.186(4.1); 7.021(2.4); 7.016(2.4); 7.001(2.1); 6.995(2.2); 4.285(0.7); 4.267(0.8); 4.249(0.3); 3.718(2.6); 3.675(3.3); 3.452(0.7); 3.435(4.1); 3.419(1.6); 3.403(1.4); 3.392(2.9); 3.364(0.8); 3.348(2.2); 3.331(19.5); 3.302(1.9); 3.285(0.7); 2.893(5.2); 2.878(1.4); 2.870(1.5); 2.863(2.4); 2.854(2.4); 2.847(1.5); 2.836(1.5); 2.820(0.6); 2.754(0.7); 2.750(0.9); 2.734(3.8); 2.527(0.8); 2.522(1.2); 2.514(16.6); 2.509(34.0); 2.505(45.5); 2.500(33.6); 2.496(17.5); 2.486(4.2); 1.557(16.0); 1.538(1.1); 1.288(0.9); 1.276(0.4); 1.271(1.8); 1.258(0.8); 1.253(1.0); 1.240(0.5); 1.232(0.8); 0.000(9.4); −0.009(0.4); −0.020(0.3)
Example 111: $^1$H-NMR(400.0 MHz, DMSO):
9.011(4.4); 9.005(4.6); 8.772(3.2); 8.766(3.1); 8.220(0.8); 8.205(1.6); 8.190(1.0); 8.182(2.9); 8.178(3.9); 8.169(2.2); 8.165(1.1); 8.147(3.2); 8.143(2.6); 8.097(3.7); 8.075(2.0); 7.153(1.4); 7.147(0.8); 7.138(1.4); 7.131(10.2); 7.123(11.1); 7.117(1.3); 7.108(0.8); 7.101(1.5); 4.249(0.5); 4.231(0.5); 3.724(2.6); 3.680(3.3); 3.441(3.3); 3.398(2.7); 3.377(1.1); 3.360(1.6); 3.330(12.4); 3.298(1.5); 3.281(1.0); 3.266(0.6); 2.892(1.3); 2.752(2.8); 2.734(4.4); 2.717(1.7); 2.673(0.4); 2.527(0.9); 2.522(1.4); 2.513(16.9); 2.509(33.8); 2.504(44.1); 2.500(31.5); 2.495(14.9); 1.557(16.0); 1.277(0.7); 1.259(1.5); 1.241(1.1); 1.232(0.7); 0.008(0.4); 0.000(10.3)
Example 112: $^1$H-NMR(400.0 MHz, DMSO):
9.009(8.4); 9.003(8.8); 8.775(6.3); 8.770(6.0); 8.482(1.5); 8.467(2.8); 8.453(1.5); 8.234(3.2); 8.230(3.8); 8.224(3.3); 8.219(3.8); 8.198(2.2); 8.193(1.9); 8.190(2.3); 8.186(1.7); 8.176(3.0); 8.171(3.1); 8.168(3.3); 8.163(2.7); 8.096(3.8); 8.091(4.3); 8.074(2.5); 8.069(2.5); 7.954(1.1); 7.628(0.4); 7.599(0.3); 7.189(0.2); 7.169(0.5); 7.118(1.9); 7.104(2.8); 7.087(2.2); 7.071(1.3); 7.067(1.1); 7.049(1.9); 7.040(1.0); 7.032(1.4); 7.025(2.0); 7.005(1.2); 7.001(1.1); 6.865(0.4); 6.846(0.6); 6.802(1.3); 6.799(1.4); 6.783(2.2); 6.780(2.3); 6.765(1.2); 6.762(1.2); 6.748(0.4); 6.738(0.5); 6.721(7.7); 6.701(7.7); 6.684(1.3); 6.681(1.0); 4.285(0.6); 4.267(2.0); 4.249(2.1); 4.241(0.7); 4.231(0.8); 4.158(0.6); 4.148(1.0); 4.131(2.1); 4.120(2.7); 4.112(1.8); 4.103(2.8); 4.094(2.8); 4.068(2.1); 4.042(0.8); 3.910(2.6); 3.867(3.2); 3.856(2.6); 3.813(3.1); 3.522(3.1); 3.512(3.2); 3.479(2.7); 3.469(2.7); 3.447(0.4); 3.422(0.9); 3.408(1.5); 3.389(1.8); 3.371(2.5); 3.330(34.5); 3.291(2.1); 3.272(1.8); 3.258(1.3); 3.250(1.3); 3.238(1.0); 3.233(1.0); 3.217(0.7); 2.974(1.6); 2.962(1.5); 2.892(9.2); 2.804(1.7); 2.753(1.6); 2.749(2.0); 2.733(7.1); 2.677(0.5); 2.673(0.7); 2.668(0.5); 2.552(0.7); 2.526(1.6); 2.513(38.4); 2.508(76.8); 2.504(100.4); 2.499(72.3); 2.495(34.7); 2.335(0.5); 2.331(0.7); 2.326(0.5); 1.874(0.6); 1.861(0.8); 1.851(1.1); 1.845(1.3); 1.840(1.4); 1.826(1.6); 1.815(1.5); 1.803(1.2); 1.792(0.7); 1.776(1.3); 1.767(1.7); 1.758(1.6); 1.749(1.4); 1.740(1.2); 1.731(0.9); 1.722(0.9); 1.714(0.7); 1.647(16.0); 1.635(16.0); 1.282(2.5); 1.265 (5.1); 1.251(2.0); 1.247(2.7); 1.233(2.2); 1.075(0.5); 1.057(0.9); 1.040(0.5); 0.008(0.5); 0.000(15.4); −0.009(0.5)

-continued

NMR Peak Lists Table 1

Example 113: ¹H-NMR(400.0 MHz, DMSO):
8.997(5.3); 8.994(5.1); 8.991(4.9); 8.756(5.7); 8.187(3.5); 8.180(3.5); 8.176(3.7); 8.157(1.4); 8.137(3.0); 8.118(2.2); 8.115(2.1); 8.074(3.1); 8.064(3.5); 8.052(1.9); 8.042(1.9); 7.954(3.5); 7.939(1.0); 7.875(0.5); 7.848(0.8); 7.822(0.5); 7.628(0.4); 7.599(0.4); 7.549(0.3); 7.386(0.6); 7.371(0.6); 7.352(0.6); 7.312(11.1); 7.301(12.4); 7.280(5.6); 7.274(5.1); 7.262(2.0); 7.253(2.4); 7.241(1.7); 7.229(1.3); 7.218(1.0); 7.195(1.2); 7.175(1.1); 7.158(0.4); 4.598(2.2); 4.593(2.3); 4.278(0.5); 4.260(1.7); 4.242(1.7); 4.224(0.7); 4.072(0.8); 4.054(0.7); 3.955(1.5); 3.945(1.6); 3.931(1.6); 3.920(2.0); 3.882(1.0); 3.795(1.2); 3.787(1.5); 3.780(1.3); 3.758(1.6); 3.752(1.6); 3.744(1.9); 3.737(1.6); 3.715(1.7); 3.557(0.5); 3.530(0.7); 3.512(0.7); 3.485(0.5); 3.419(3.1); 3.412(2.5); 3.402(1.4); 3.376(3.3); 3.369(3.2); 3.331(49.6); 2.921(0.4); 2.892(16.0); 2.865(0.8); 2.849(0.6); 2.826(0.5); 2.808(0.4); 2.749(2.0); 2.732(12.8); 2.672(1.0); 2.649(0.8); 2.638(0.7); 2.609(0.9); 2.577(0.7); 2.558(1.0); 2.547(1.1); 2.508(80.4); 2.504(104.7); 2.499(76.5); 2.495(37.6); 2.330(0.7); 2.183(0.7); 1.901(1.0); 1.869(1.6); 1.846(1.7); 1.730(0.9); 1.707(1.2); 1.648(1.0); 1.609(0.7); 1.549(7.9); 1.536(10.0); 1.530(8.5); 1.519(8.9); 1.302(0.6); 1.280(2.6); 1.262(4.9); 1.245(3.4); 1.232(2.4); 1.211(1.1); 1.075(0.5); 1.057(0.9); 1.040(0.4); 0.008(0.5); 0.000(16.0); −0.009(0.5)

Example 114: ¹H-NMR(400.0 MHz, DMSO):
10.778(1.0); 9.007(2.4); 9.001(2.7); 8.760(2.0); 8.754(2.0); 8.613(0.6); 8.598(1.1); 8.582(0.6); 8.224(1.8); 8.219(2.2); 8.179(1.2); 8.175(1.1); 8.157(1.7); 8.153(1.7); 8.117(0.4); 8.081(2.3); 8.059(1.6); 7.953(2.1); 7.207(2.0); 7.136(1.5); 7.115(1.8); 6.889(1.2); 6.885(1.3); 6.868(1.1); 6.864(1.2); 5.926(1.7); 4.339(1.1); 4.325(1.8); 4.311(1.3); 4.290(0.4); 4.275(0.4); 4.269(0.6); 4.262(0.4); 4.252(1.1); 4.234(1.1); 4.216(0.5); 3.903(1.6); 3.860(1.9); 3.511(1.8); 3.468(1.6); 3.330(8.7); 2.890(16.0); 2.753(1.3); 2.749(1.0); 2.731(13.1); 2.672(0.3); 2.525(0.7); 2.512(17.7); 2.507(36.2); 2.503(48.3); 2.498(35.6); 2.494(17.8); 2.359(0.4); 2.334(0.5); 2.330(0.5); 2.325(0.4); 2.309(8.0); 2.200(0.4); 2.086 (0.4); 1.639(9.5); 1.618(0.8); 1.607(0.6); 1.520(0.7); 1.277(1.3); 1.259(2.6); 1.242(1.5); 1.232(0.9); 0.008(0.4); 0.000(12.0); −0.009(0.5)

Example 115: ¹H-NMR(400.0 MHz, DMSO):
10.976(1.6); 8.957(3.8); 8.952(3.9); 8.656(1.0); 8.641(1.9); 8.625(1.0); 8.603(3.4); 8.598(3.3); 8.249(3.3); 8.245(3.6); 8.183(1.9); 8.179(1.6); 8.161(2.7); 8.156(2.6); 8.081(3.6); 8.058(2.4); 7.953(1.3); 7.628(0.3); 7.361(3.7); 7.278(2.8); 7.267(2.6); 7.260(4.9); 6.995(2.3); 6.991(2.2); 6.974(2.0); 6.970(1.9); 6.270(2.0); 6.265(2.8); 6.260(1.8); 4.592(7.8); 4.366(2.8); 4.363(2.8); 4.351(2.9); 4.348(2.9); 4.282(0.6); 4.264(1.7); 4.246(1.7); 4.228(0.6); 3.921(2.6); 3.878(3.2); 3.523(3.1); 3.480(2.6); 3.330(13.4); 2.890(10.1); 2.752(2.4); 2.749(1.7); 2.732(8.0); 2.676(0.3); 2.672(0.4); 2.525(1.2); 2.512(27.2); 2.507(53.8); 2.503(70.1); 2.498(50.9); 2.494(25.1); 2.334(0.4); 2.329(0.5); 2.325(0.4); 1.854(0.6); 1.642(16.0); 1.281(2.1); 1.263(4.2); 1.245(2.2); 1.233(1.2); 1.210(0.8); 1.194(0.8); 0.008(0.5); 0.000(15.8); −0.008(0.6)

Example 116: ¹H-NMR(400.0 MHz, DMSO):
10.977(1.5); 9.005(4.2); 9.000(4.4); 8.759(3.3); 8.753(3.2); 8.660(0.9); 8.644(1.8); 8.629(0.9); 8.226(3.2); 8.222(3.7); 8.185(2.0); 8.180(1.6); 8.163(2.8); 8.158(2.6); 8.082(3.6); 8.060(2.4); 7.953(0.6); 7.361(3.6); 7.278(2.7); 7.269(2.3); 7.262(3.9); 7.256(4.4); 6.995(2.1); 6.991(2.1); 6.974(1.9); 6.971(1.9); 6.272(1.8); 6.267(2.7); 6.262(1.8); 4.365(3.0); 4.349(3.1); 4.259(0.8); 4.241(0.8); 4.224(0.3); 3.912(2.7); 3.869(3.2); 3.515(3.1); 3.471(2.6); 3.332(24.2); 2.890(5.5); 2.753(1.1); 2.749(0.9); 2.731(3.9); 2.672(0.3); 2.525(1.0); 2.512(19.8); 2.507(39.4); 2.503(51.8); 2.498(38.3); 2.494(19.2); 2.330(0.3); 1.643(16.0); 1.280(1.1); 1.262(2.2); 1.244(1.2); 1.232(0.8); 0.008(0.4); 0.000(11.9); −0.008(0.5)

Example 117: ¹H-NMR(400.0 MHz, DMSO):
9.016(4.4); 9.010(5.4); 9.008(5.8); 9.002(5.4); 8.785(3.3); 8.779(3.3); 8.769(3.6); 8.763(3.2); 8.226(3.0); 8.221(3.5); 8.210(0.6); 8.205(0.6); 8.185(1.9); 8.180(1.6); 8.163(3.1); 8.158(2.7); 8.146(3.6); 8.139(1.7); 8.134(1.7); 8.123(2.8); 8.118(5.6); 8.115(5.9); 8.111(1.8); 8.090(6.2); 8.067(3.6); 7.954(1.2); 7.940(0.9); 7.926(1.7); 7.912(0.9); 7.780(0.8); 7.768(1.2); 7.751(0.9); 7.628(0.4); 7.228(0.4); 7.210(0.4); 7.193(0.3); 7.186(0.5); 7.173(0.8); 7.153(1.3); 7.148(1.2); 7.134(4.3); 7.127(4.3); 7.123(4.9); 7.118(5.4); 7.098(4.5); 7.081(2.1); 7.059(0.7); 6.956(0.9); 6.952(0.8); 6.937(1.4); 6.921(0.9); 6.916(0.9); 6.798(2.1); 6.779(1.6); 4.834(2.0); 4.820(2.7); 4.806(1.0); 4.304(0.9); 4.286(2.7); 4.268(2.9); 4.250(1.0); 4.051(0.7); 4.039(1.7); 4.028(1.7); 4.010(1.9); 4.000(1.9); 3.988(1.0); 3.945(0.5); 3.866(2.6); 3.822(3.2); 3.738(3.2); 3.707(0.8); 3.696(1.1); 3.688(1.0); 3.677(1.6); 3.667(1.3); 3.659(1.8); 3.648(1.6); 3.639(2.3); 3.630(1.1); 3.621(1.9); 3.604(1.9); 3.586(1.1); 3.538(2.7); 3.524(5.2); 3.509(2.7); 3.504(3.9); 3.489(1.5); 3.478(4.7); 3.467(1.1); 3.460(3.3); 3.451(4.6); 3.407(1.5); 3.329(23.5); 3.205(0.3); 2.892(11.3); 2.871(0.4); 2.830(0.4); 2.818(0.5); 2.799 (0.6); 2.788(1.2); 2.775(1.3); 2.753(3.1); 2.749(2.6); 2.732(8.0); 2.716(1.9); 2.703(0.8); 2.686(0.5); 2.673(1.3); 2.663(0.6); 2.620(0.7); 2.610(1.2); 2.599(0.7); 2.579(0.5); 2.568(0.9); 2.556(1.0); 2.526(2.1); 2.513(39.4); 2.508 (79.1); 2.504(103.7); 2.499(74.5); 2.495(35.3); 2.335(0.5); 2.330(0.7); 2.326(0.5); 1.658(2.5); 1.625(0.8); 1.602 (15.9); 1.539(16.0); 1.288(3.3); 1.276(1.1); 1.271(6.7); 1.258(1.9); 1.253(3.4); 1.240(1.2); 1.232(1.6); 1.075(0.4); 1.057(0.8); 1.040(0.4); 0.008(0.9); 0.000(24.4); −0.009(0.7)

Example 118: ¹H-NMR(400.0 MHz, DMSO):
9.003(2.8); 8.997(2.9); 8.758(2.4); 8.753(2.3); 8.702(0.6); 8.687(1.3); 8.671(0.6); 8.219(2.3); 8.215(2.6); 8.176(1.3); 8.172(1.1); 8.154(1.9); 8.150(1.8); 8.079(2.6); 8.057(1.7); 6.740(1.4); 6.719(3.8); 6.705(2.2); 6.701(3.0); 6.688(2.2); 6.683(1.5); 6.667(1.0); 6.662(0.8); 4.284(0.4); 4.267(0.5); 4.208(0.4); 4.173(3.6); 4.157(16.0); 4.147(1.1); 3.892 (1.9); 3.848(2.3); 3.508(2.2); 3.464(1.9); 3.333(4.0); 2.892(0.7); 2.750(0.4); 2.527(0.4); 2.509(16.6); 2.505(21.7); 2.500(16.1); 1.628(11.3); 1.288(0.5); 1.271(1.0); 1.253(0.5); 1.231(0.4); 0.000(4.5)

Example 119: ¹H-NMR(400.0 MHz, DMSO):
9.004(4.2); 8.998(4.5); 8.765(3.2); 8.762(3.4); 8.274(0.6); 8.259(1.2); 8.244(0.7); 8.215(4.1); 8.199(0.5); 8.183(0.9); 8.174(2.2); 8.170(2.1); 8.152(2.9); 8.147(2.9); 8.079(3.9); 8.056(2.5); 4.285(0.6); 4.267(1.7); 4.249(1.8); 4.231(0.7); 3.882(1.2); 3.875(1.8); 3.839(1.5); 3.832(2.2); 3.488(2.3); 3.483(1.7); 3.445(2.0); 3.440(1.5); 3.332(4.5); 3.160(0.3); 3.142(0.8); 3.123(1.5); 3.106(1.4); 3.087(0.9); 3.071(0.4); 2.993(0.6); 2.976(0.8); 2.955(0.9); 2.938(0.6); 2.893(1.2); 2.750(0.6); 2.552(1.7); 2.509(38.9); 2.504(51.5); 2.500(40.1); 2.331(0.4); 2.225(0.4); 2.213(0.5); 2.201(0.5); 2.191 (0.4); 2.179(0.3); 1.825(1.3); 1.794(0.9); 1.717(0.7); 1.685(0.7); 1.616(16.0); 1.588(0.5); 1.543(1.5); 1.532(1.4); 1.516(1.7); 1.499(1.7); 1.490(1.6); 1.475(2.1); 1.463(2.5); 1.453(2.5); 1.426(1.1); 1.393(0.4); 1.283(2.1); 1.265(4.2); 1.247(2.3); 1.232(1.2); 1.197(0.4); 1.166(0.8); 1.159(0.8); 1.134(0.8); 1.127(0.8); 1.103(0.3); 0.962(0.4); 0.936(0.7); 0.931(0.7); 0.905(0.6); 0.899(0.6); 0.008(0.3); 0.000(8.6); −0.008(0.5)

Example 120: ¹H-NMR(400.0 MHz, DMSO):
8.954(3.3); 8.949(3.4); 8.603(3.1); 8.598(3.0); 8.361(1.5); 8.341(1.5); 8.234(3.1); 8.230(3.4); 8.173(1.7); 8.168(1.4); 8.151(2.5); 8.146(2.3); 8.075(3.3); 8.053(2.2); 4.591(6.3); 4.297(0.3); 4.279(1.2); 4.261(1.6); 4.238(1.4); 4.217(1.3); 4.196(0.7); 3.901(2.5); 3.858(3.0); 3.460(2.9); 3.416(2.6); 3.332(22.3); 2.892(1.0); 2.749(1.3); 2.733(0.6); 2.673(0.3); 2.508(40.8); 2.504(52.3); 2.500(39.0); 2.331(0.4); 2.133(0.7); 2.120(1.2); 2.115(1.2); 2.106(1.4); 2.097(2.4); 2.075 (2.4); 2.057(2.6); 2.036(2.1); 2.012(0.9); 1.653(0.4); 1.649(0.3); 1.626(1.0); 1.589(16.0); 1.562(1.1); 1.558(1.1); 1.537(0.5); 1.286(1.3); 1.268(2.6); 1.251(1.4); 1.232(0.9); 0.000(5.9)

NMR Peak Lists Table 1

Example 121: ¹H-NMR(400.0 MHz, DMSO):
8.955(3.9); 8.950(4.1); 8.604(3.3); 8.272(0.8); 8.256(1.2); 8.240(4.0); 8.236(4.1); 8.195(0.6); 8.181(0.9); 8.173(2.2); 8.168(2.0); 8.151(3.0); 8.146(2.9); 8.077(3.9); 8.055(2.5); 7.955(0.4); 7.629(0.3); 4.592(8.3); 4.262(0.7); 4.244(0.7); 3.891(1.3); 3.884(1.9); 3.848(1.5); 3.840(2.2); 3.497(2.3); 3.491(1.6); 3.453(1.9); 3.448(1.4); 3.331(18.1); 3.142(0.8); 3.123(1.7); 3.107(1.5); 3.089(0.8); 2.994(0.6); 2.977(0.8); 2.972(0.7); 2.956(0.8); 2.939(0.6); 2.893(3.5); 2.754(1.0); 2.750(1.9); 2.733(2.5); 2.674(0.3); 2.527(0.9); 2.513(20.8); 2.509(41.8); 2.505(54.9); 2.500(40.3); 2.496(19.9); 2.331(0.4); 2.225(0.4); 2.214(0.5); 2.201(0.5); 2.191(0.4); 2.178(0.3); 1.855(0.5); 1.845(0.7); 1.834(1.1); 1.825(1.2); 1.801(1.1); 1.795(1.1); 1.719(0.7); 1.687(0.8); 1.654(0.4); 1.615(16.0); 1.589(0.6); 1.576(0.6); 1.544(1.5); 1.533(1.5); 1.517(1.7); 1.500(1.7); 1.491(1.7); 1.476(2.1); 1.464(2.5); 1.454(2.4); 1.426(1.0); 1.281(1.1); 1.264(2.0); 1.246(1.2); 1.232(1.0); 1.212(1.2); 1.196(1.3); 1.168(0.8); 1.159(0.8); 1.135(0.8); 1.127(0.7); 1.103(0.4); 0.963(0.4); 0.938(0.7); 0.932(0.7); 0.907(0.6); 0.900(0.6); 0.000(8.4)
Example 122: ¹H-NMR(400.0 MHz, DMSO):
9.004(4.1); 8.998(4.3); 8.761(3.3); 8.755(3.1); 8.666(0.8); 8.651(1.7); 8.636(0.8); 8.221(3.1); 8.216(3.6); 8.176(1.8); 8.171(1.5); 8.154(2.8); 8.149(2.5); 8.080(3.6); 8.058(2.3); 7.071(3.1); 6.957(1.5); 6.936(1.7); 6.640(3.5); 6.620(3.1); 4.465(3.5); 4.443(7.2); 4.421(3.6); 4.272(0.7); 4.254(0.8); 4.237(0.4); 4.204(4.3); 4.189(4.3); 3.892(2.7); 3.849(3.2); 3.505(3.1); 3.462(2.6); 3.330(8.1); 3.076(2.1); 3.054(3.9); 3.033(1.9); 2.891(1.1); 2.753(0.3); 2.749(0.6); 2.732(0.5); 2.526(0.8); 2.512(17.1); 2.508(34.4); 2.503(45.4); 2.499(33.1); 2.494(16.2); 1.659(0.6); 1.626(16.0); 1.284(0.9); 1.266(1.8); 1.253(0.4); 1.248(0.9); 1.232(0.7); 0.000(10.5); −0.009(0.4)
Example 123: ¹H-NMR(400.0 MHz, DMSO):
9.006(4.0); 9.000(4.2); 8.761(3.4); 8.756(3.2); 8.732(0.9); 8.717(1.7); 8.701(0.9); 8.224(3.3); 8.219(3.7); 8.179(1.9); 8.174(1.5); 8.156(2.8); 8.152(2.5); 8.081(3.6); 8.059(2.3); 7.096(2.3); 7.077(2.5); 6.685(2.1); 6.666(2.0); 6.610(3.9); 4.472(3.2); 4.451(7.0); 4.429(3.6); 4.293(1.0); 4.275(3.2); 4.257(3.3); 4.239(1.2); 4.219(3.9); 4.204(3.9); 3.895(2.6); 3.852(3.2); 3.509(3.2); 3.466(2.7); 3.333(2.8); 3.106(2.3); 3.084(4.3); 3.062(2.1); 2.892(1.3); 2.753(0.5); 2.749(0.7); 2.546(4.5); 2.526(1.0); 2.512(20.2); 2.508(39.7); 2.504(51.7); 2.499(37.8); 2.495(18.7); 2.330(0.3); 1.655(0.4); 1.631(16.0); 1.285(3.5); 1.267(7.3); 1.249(3.9); 1.233(1.0); 0.008(0.4); 0.000(11.1); −0.008(0.4)
Example 124: ¹H-NMR(400.0 MHz, DMSO):
9.006(7.1); 9.000(7.7); 8.775(3.0); 8.769(5.6); 8.763(3.1); 8.384(0.7); 8.367(1.8); 8.351(2.0); 8.334(0.8); 8.219(2.8); 8.214(3.3); 8.195(2.9); 8.190(3.2); 8.168(1.7); 8.162(2.6); 8.157(1.7); 8.140(4.4); 8.135(2.6); 8.080(5.1); 8.058(3.2); 4.307(0.6); 4.290(1.9); 4.272(2.0); 4.254(0.7); 4.251(0.6); 3.902(2.4); 3.859(3.0); 3.814(0.4); 3.803(2.3); 3.759(3.0); 3.621(0.3); 3.610(0.8); 3.600(1.3); 3.590(1.7); 3.581(1.6); 3.571(1.4); 3.562(0.9); 3.516(3.0); 3.496(2.8); 3.473(2.4); 3.453(2.4); 3.424(0.4); 3.398(0.8); 3.381(1.1); 3.364(2.1); 3.331(73.2); 3.296(2.2); 3.285(1.8); 3.270(1.3); 3.262(0.8); 3.247(1.4); 3.236(1.4); 3.222(1.1); 3.213(1.0); 3.203(0.9); 3.188(0.7); 3.149(0.9); 3.118(0.8); 2.892(2.0); 2.775(0.5); 2.753(1.0); 2.749(1.2); 2.732(0.5); 2.697(16.0); 2.677(15.5); 2.547(1.3); 2.536(1.2); 2.526(2.0); 2.513(39.4); 2.508(79.2); 2.504(104.1); 2.499(75.3); 2.495(36.3); 2.335(0.6); 2.330(0.7); 2.326(0.6); 2.300(0.4); 2.279(0.4); 2.205(0.5); 2.181(0.7); 2.160(1.0); 2.140(1.4); 2.118(1.5); 2.095(1.0); 2.085(0.9); 2.074(1.0); 2.060(1.1); 2.049(1.1); 2.033(0.8); 2.020(1.0); 2.008(1.4); 1.997(1.2); 1.969(1.7); 1.961(1.6); 1.952(1.2); 1.941(1.3); 1.932(1.2); 1.916(0.9); 1.911(0.7); 1.895(0.4); 1.887(0.3); 1.850(0.9); 1.842(0.6); 1.835(0.5); 1.828(1.0); 1.819(1.0); 1.806(1.1); 1.796(0.9); 1.784(1.0); 1.774(0.9); 1.766(0.5); 1.760(0.4); 1.750(0.5); 1.739(0.4); 1.615(14.7); 1.601(14.8); 1.587(1.8); 1.289(2.3); 1.277(0.8); 1.272(4.7); 1.259(1.4); 1.254(2.4); 1.241(0.9); 1.233(1.4); 0.008(0.4); 0.000(12.5); −0.009(0.4)
Example 125: ¹H-NMR(300.2 MHz, CDCl3):
8.965(3.1); 8.959(3.1); 8.271(2.6); 8.265(2.6); 8.179(0.6); 8.173(1.1); 8.167(0.7); 8.150(1.5); 8.144(2.8); 8.138(1.6); 8.108(2.7); 8.106(2.7); 8.078(1.1); 7.834(2.9); 7.274(3.3); 7.259(0.3); 7.239(0.6); 7.212(0.6); 7.191(0.3); 4.264(0.4); 4.260(0.5); 4.244(0.9); 4.231(0.9); 4.224(0.9); 4.211(0.7); 4.134(0.4); 4.110(0.4); 4.063(0.9); 4.041(0.9); 4.034(1.1); 4.014(1.3); 3.993(1.0); 3.984(1.9); 3.963(1.9); 3.927(1.7); 3.905(1.8); 3.683(1.0); 3.663(0.9); 3.655(0.9); 3.635(0.8); 3.593(1.0); 3.578(0.4); 3.572(1.1); 3.565(1.4); 3.558(0.5); 3.544(1.1); 3.531(0.6); 3.526(0.5); 3.518(1.0); 3.512(0.7); 3.500(0.9); 3.495(0.7); 3.479(0.6); 3.447(0.6); 3.435(0.7); 3.430(0.7); 3.418(1.0); 3.400(1.1); 3.390(1.9); 3.377(2.0); 3.353(0.5); 3.335(7.6); 3.319(1.6); 2.046(1.9); 1.805(2.7); 1.789(16.0); 1.482(6.6); 1.398(6.6); 1.339(6.6); 1.320(6.7); 1.283(0.7); 1.259(1.2); 1.236(0.6); 0.000(2.6)
Example 126: ¹H-NMR(400.0 MHz, DMSO):
19.278(0.4); 9.007(5.5); 9.001(5.7); 8.766(4.5); 8.761(4.3); 8.217(4.6); 8.171(2.5); 8.166(2.0); 8.149(3.8); 8.144(3.4); 8.081(4.9); 8.059(3.1); 7.990(0.7); 4.202(0.4); 4.184(1.3); 4.167(1.3); 4.149(0.4); 3.871(3.4); 3.828(4.1); 3.516(3.9); 3.472(3.3); 3.333(12.3); 3.070(1.9); 2.892(1.2); 2.835(0.7); 2.802(0.7); 2.749(0.9); 2.732(0.6); 2.673(1.0); 2.512(34.6); 2.508(66.4); 2.504(84.9); 2.499(62.3); 2.495(31.1); 2.331(1.2); 1.815(0.9); 1.769(0.6); 1.748(0.8); 1.728(0.7); 1.701(0.7); 1.628(16.0); 1.625(15.6); 1.585(1.2); 1.545(0.8); 1.530(0.8); 1.516(0.8); 1.422(0.5); 1.256(1.5); 1.238(3.3); 1.220(1.5); 1.164(0.4); 1.146(0.8); 1.128(0.4); 1.074(0.4); 1.057(0.8); 1.044(3.0); 1.026(5.3); 1.019(3.2); 1.008(3.2); 1.001(4.7); 0.983(2.2); 0.000(9.6)
Example 127: ¹H-NMR(400.0 MHz, DMSO):
9.004(4.1); 8.998(4.2); 8.765(3.3); 8.759(3.1); 8.352(0.8); 8.337(1.6); 8.322(0.8); 8.217(3.4); 8.176(1.8); 8.171(1.5); 8.154(2.7); 8.149(2.6); 8.079(3.6); 8.057(2.3); 7.628(0.4); 7.616(0.3); 7.598(0.4); 4.223(0.4); 3.886(2.1); 3.843(2.6); 3.720(0.4); 3.714(0.3); 3.697(0.8); 3.676(1.4); 3.660(1.6); 3.642(1.2); 3.625(0.6); 3.607(1.4); 3.589(2.5); 3.567(1.9); 3.564(2.0); 3.544(1.6); 3.525(0.6); 3.488(3.1); 3.445(2.6); 3.386(1.8); 3.372(2.0); 3.365(2.0); 3.351(2.5); 3.331(68.0); 3.155(0.4); 3.145(0.5); 3.129(0.8); 3.122(0.9); 3.112(1.0); 3.104(1.0); 3.097(1.1); 3.084(1.2); 3.076(1.0); 3.067(1.1); 3.058(0.8); 3.040(0.4); 2.974(0.3); 2.892(0.5); 2.763(0.4); 2.749(0.4); 2.732(0.4); 2.673(0.3); 2.526(1.0); 2.513(20.4); 2.508(40.8); 2.504(53.9); 2.499(40.5); 2.495(20.7); 2.439(0.5); 2.424(0.8); 2.406(1.0); 2.388(0.8); 2.373(0.4); 2.331 (0.4); 1.881(0.4); 1.874(0.4); 1.860(0.7); 1.847(0.7); 1.841(0.8); 1.829(0.8); 1.823(0.7); 1.817(0.6); 1.809(0.7); 1.803(0.4); 1.797(0.7); 1.789(0.3); 1.614(16.0); 1.556(0.4); 1.548(0.4); 1.517(1.0); 1.512(0.9); 1.506(0.9); 1.497(0.9); 1.475(0.4); 1.466(0.4); 1.256(0.5); 1.238(1.0); 1.232(0.9); 1.221(0.4); 0.000(5.5)
Example 128: ¹H-NMR(400.0 MHz, DMSO):
9.106(0.4); 9.101(0.4); 8.957(5.8); 8.952(5.9); 8.608(4.8); 8.603(4.6); 8.282(0.3); 8.251(4.9); 8.246(5.3); 8.173(1.6); 8.169(2.6); 8.164(1.4); 8.151(2.5); 8.147(4.2); 8.142(2.4); 8.120(0.4); 8.078(5.4); 8.055(3.5); 7.767(0.7); 7.752(1.4); 7.735(1.3); 7.719(1.3); 7.703(0.7); 7.628(0.4); 7.625(0.4); 7.599(0.4); 4.593(11.7); 4.280(0.4); 4.263(1.2); 4.245(1.2); 4.227(0.4); 3.897(2.6); 3.894(2.6); 3.854(3.2); 3.851(3.2); 3.724(0.8); 3.718(0.6); 3.702(3.5); 3.685(6.3); 3.678(1.8); 3.669(3.8); 3.531(2.8); 3.525(2.8); 3.487(2.4); 3.481(2.3); 3.328(37.0); 3.222(0.8); 3.210(0.8); 3.206(0.9); 3.193(1.1); 3.189(1.9); 3.177(2.4); 3.173(2.1); 3.160(2.0); 3.150(3.2); 3.135(3.4); 3.117(1.3); 3.102(1.2); 2.892(0.5); 2.783(0.3); 2.752(0.6); 2.749(1.2); 2.677(0.5); 2.673(0.7); 2.668(0.5); 2.526(1.7); 2.521(2.7); 2.513(37.6); 2.508(76.1); 2.504 (100.3); 2.499(71.7); 2.494(33.9); 2.335(0.5); 2.330(0.7); 2.326(0.5); 1.863(0.5); 1.858(0.5); 1.846(0.9); 1.842(1.4); 1.826(3.8); 1.815(4.5); 1.802(1.7); 1.798(1.8); 1.792(1.0); 1.783(1.2); 1.779(1.2); 1.771(0.8); 1.762(0.8); 1.752(1.0);

-continued

NMR Peak Lists Table 1

1.738(1.4); 1.731(1.1); 1.721(1.7); 1.715(1.6); 1.703(1.7); 1.695(1.7); 1.689(1.2); 1.668(0.7); 1.643(14.9); 1.634(14.1); 1.540(0.4); 1.521(0.5); 1.509(1.1); 1.502(0.9); 1.496(1.1); 1.489(1.3); 1.480(1.3); 1.465(1.3); 1.459(1.0); 1.454(0.7); 1.447(0.5); 1.281(1.8); 1.263(3.6); 1.245(1.9); 1.232(1.4); 1.211(0.8); 1.195(0.8); 1.122(0.4); 1.092(0.7); 1.087(0.8); 1.061(16.0); 1.025(15.2); 0.008(0.8); 0.000(24.4); −0.009(0.7)

Example 129: $^1$H-NMR(400.0 MHz, DMSO):
9.004(4.9); 8.998(5.0); 8.763(3.5); 8.758(3.3); 8.214(3.7); 8.172(1.7); 8.169(2.0); 8.150(2.9); 8.147(3.0); 8.145(2.9); 8.142(2.2); 8.133(1.1); 8.117(0.5); 8.078(4.0); 8.056(2.5); 4.224(0.3); 4.131(0.8); 4.124(0.8); 4.116(1.1); 4.109(1.1); 4.103(0.9); 4.096(0.9); 4.082(0.3); 3.922(1.3); 3.907(1.2); 3.901(1.7); 3.898(1.2); 3.883(2.8); 3.877(1.4); 3.865(1.6); 3.862(1.2); 3.840(2.1); 3.822(1.8); 3.667(1.4); 3.653(1.3); 3.646(1.2); 3.632(1.1); 3.610(1.1); 3.595(1.1); 3.589(1.0); 3.574(1.0); 3.516(1.8); 3.505(2.0); 3.473(1.5); 3.462(1.7); 3.329(53.1); 3.304(0.5); 3.292(0.5); 3.289(0.5); 3.276(0.5); 3.270(0.8); 3.259(1.4); 3.252(1.1); 3.244(1.5); 3.236(1.5); 3.222(1.0); 3.208(1.2); 3.193(0.8); 3.175(0.6); 3.159(0.4); 2.892(0.9); 2.767(0.4); 2.750(0.5); 2.733(0.7); 2.527(0.9); 2.522(1.4); 2.513(18.5); 2.509(37.5); 2.504(49.3); 2.500(35.5); 2.495(16.9); 1.615(16.0); 1.334(0.8); 1.328(1.2); 1.291(9.8); 1.279(8.6); 1.265(0.5); 1.250(1.5); 1.232 (1.0); 1.218(10.0); 1.211(8.6); 0.000(6.0)

Example 130: $^1$H-NMR(400.0 MHz, DMSO):
9.005(5.7); 8.999(5.9); 8.764(4.4); 8.758(4.1); 8.222(4.3); 8.217(4.8); 8.175(2.1); 8.170(1.8); 8.153(3.1); 8.148(2.9); 8.079(4.9); 8.057(3.5); 8.038(1.4); 8.023(1.1); 8.009(0.8); 7.994(0.4); 7.954(0.4); 4.283(0.4); 4.265(1.1); 4.247(1.1); 4.229(0.4); 3.911(0.9); 3.896(2.0); 3.879(2.7); 3.876(3.4); 3.864(1.4); 3.848(0.4); 3.832(3.5); 3.738(1.1); 3.722(1.8); 3.718(1.7); 3.702(2.2); 3.685(1.1); 3.603(1.3); 3.585(2.4); 3.568(1.7); 3.549(0.8); 3.504(2.1); 3.499(3.2); 3.460(1.7); 3.456(2.6); 3.332(45.7); 3.188(0.4); 3.173(2.0); 3.170(2.1); 3.164(1.8); 3.158(3.5); 3.155(3.6); 3.149(3.0); 3.143(2.0); 3.140(1.9); 3.134(1.5); 3.116(0.3); 2.892(3.1); 2.764(0.5); 2.749(0.8); 2.732(2.3); 2.673(0.5); 2.668(0.3); 2.526(1.3); 2.513(27.3); 2.508(54.9); 2.504(72.4); 2.499(52.7); 2.495(25.6); 2.335(0.4); 2.331(0.5); 2.326(0.4); 1.840(0.5); 1.833(0.6); 1.824(0.9); 1.819(1.0); 1.816(0.9); 1.801(1.8); 1.789(2.0); 1.773(2.5); 1.761(1.4); 1.757(1.7); 1.754(1.6); 1.746(1.8); 1.739(1.2); 1.729(1.8); 1.718(0.7); 1.712(1.0); 1.695(0.3); 1.617(10.3); 1.612(16.0); 1.557(0.4); 1.544(0.5); 1.537(0.6); 1.529(0.8); 1.521(0.6); 1.512(1.2); 1.505(0.6); 1.496(1.0); 1.479(0.8); 1.474(0.5); 1.464(0.6); 1.458(0.3); 1.448(0.5); 1.282(1.5); 1.264(3.0); 1.249(0.9); 1.246(1.6); 1.232(1.3); 0.008(0.4); 0.000(13.1); −0.009(0.4)

Example 131: $^1$H-NMR(400.0 MHz, DMSO):
9.006(6.3); 9.000(6.8); 8.766(5.9); 8.761(5.9); 8.229(6.0); 8.226(6.7); 8.171(2.8); 8.149(4.5); 8.080(6.6); 8.057(4.2); 7.772(0.8); 7.756(1.6); 7.740(1.5); 7.723(1.6); 7.708(0.8); 7.629(0.3); 4.592(0.5); 4.292(0.4); 4.274(1.2); 4.256(1.2); 4.238(0.5); 3.888(3.2); 3.844(4.0); 3.701(3.7); 3.685(7.6); 3.669(4.3); 3.524(3.3); 3.518(3.3); 3.480(2.7); 3.474(2.7); 3.329(41.9); 3.223(0.9); 3.206(1.1); 3.189(2.1); 3.176(2.8); 3.160(2.3); 3.150(3.7); 3.135(3.8); 3.117(1.4); 3.102(1.3); 2.892(1.6); 2.749(0.7); 2.733(0.7); 2.699(0.7); 2.678(1.0); 2.508(73.7); 2.504(92.7); 2.500(69.3); 2.331(0.6); 1.859(0.4); 1.842(1.5); 1.826(3.5); 1.815(4.8); 1.799(2.1); 1.779(1.4); 1.762(3.0); 1.752(1.1); 1.738(1.4); 1.730(1.1); 1.720(1.6); 1.713(1.8); 1.703(1.8); 1.695(1.8); 1.689(1.4); 1.668(0.8); 1.644(15.6); 1.636(15.8); 1.615(0.9); 1.601(0.7); 1.539(0.3); 1.519(0.4); 1.509(1.1); 1.502(0.9); 1.495(1.2); 1.489(1.5); 1.480(1.5); 1.464(1.4); 1.453(0.8); 1.285(1.5); 1.267(2.9); 1.249(1.6); 1.233(1.2); 1.186(0.3); 1.061(15.9); 1.025(16.0); 0.008(0.6); 0.000(12.0)

Example 132: $^1$H-NMR(400.0 MHz, DMSO):
8.956(5.2); 8.951(5.7); 8.605(5.1); 8.601(5.4); 8.275(0.3); 8.239(5.8); 8.172(2.3); 8.169(2.3); 8.149(3.6); 8.147(3.7); 8.119(0.4); 8.096(0.3); 8.077(5.4); 8.055(3.8); 8.034(1.6); 8.019(1.6); 8.005(1.6); 7.990(0.8); 7.628(0.5); 7.616(0.4); 7.598(0.4); 7.568(0.4); 7.550(0.4); 4.592(9.4); 4.301(0.5); 4.284(1.4); 4.266(1.5); 4.248(0.6); 4.221(0.3); 3.927(0.5); 3.911(1.4); 3.896(2.7); 3.882(5.0); 3.864(1.6); 3.839(3.9); 3.739(1.3); 3.722(2.4); 3.703(2.8); 3.686(1.4); 3.603(1.7); 3.586(3.2); 3.568(2.5); 3.549(1.0); 3.508(3.3); 3.464(2.7); 3.330(47.6); 3.203(0.4); 3.188(0.6); 3.173(3.1); 3.158(5.5); 3.143(3.3); 3.117(0.5); 2.892(0.9); 2.764(0.7); 2.749(2.1); 2.732(0.5); 2.673(0.6); 2.508(70.8); 2.504(92.7); 2.500(74.3); 2.330(0.6); 1.840(0.9); 1.824(1.6); 1.801(3.0); 1.790(3.0); 1.773(3.1); 1.761(2.3); 1.746(2.9); 1.729(3.0); 1.712(1.9); 1.696(0.7); 1.648(0.6); 1.616(15.2); 1.612(16.0); 1.557(0.6); 1.530(1.0); 1.512(1.5); 1.496(1.4); 1.480(1.0); 1.465(1.0); 1.448(0.9); 1.288(1.8); 1.270(3.6); 1.252(2.0); 1.233(1.6); 1.212(0.5); 1.196(0.5); 1.057(0.4); 0.000(9.8)

Example 133: $^1$H-NMR(400.0 MHz, DMSO):
8.772(0.5); 8.514(4.2); 8.141(2.3); 8.136(2.5); 8.067(1.5); 8.062(1.3); 8.045(1.7); 8.040(1.6); 7.860(1.1); 7.839(1.1); 7.821(2.4); 7.799(2.0); 4.865(0.7); 4.560(5.6); 4.055(16.0); 3.924(0.6); 3.907(0.8); 3.904(0.7); 3.891(1.0); 3.887(0.9); 3.870(0.7); 3.859(2.0); 3.848(0.3); 3.816(2.3); 3.431(2.3); 3.388(2.0); 3.328(131.7); 2.892(1.4); 2.732(1.2); 2.677(0.4); 2.672(0.5); 2.667(0.4); 2.525(1.7); 2.512(32.3); 2.507(64.6); 2.503(84.4); 2.498(60.2); 2.494(28.6); 2.334(0.4); 2.330(0.5); 2.325(0.4); 1.590(1.7); 1.576(11.8); 1.104(7.2); 1.088(7.1); 1.061(7.7); 1.044(7.6); 0.000(2.8)

Example 134: $^1$H-NMR(400.0 MHz, DMSO):
8.771(5.5); 8.282(3.0); 8.277(3.3); 8.210(2.0); 8.205(1.7); 8.188(2.4); 8.183(2.2); 8.017(3.2); 7.995(2.6); 7.887(1.4); 7.866(1.4); 4.864(7.8); 3.927(0.7); 3.911(1.1); 3.907(0.9); 3.890(3.7); 3.874(0.8); 3.857(0.4); 3.847(3.2); 3.460(3.1); 3.417(2.7); 3.332(209.8); 2.892(2.3); 2.732(1.9); 2.677(0.4); 2.672(0.6); 2.668(0.4); 2.526(1.8); 2.512(33.2); 2.508(66.4); 2.503(86.9); 2.499(62.1); 2.494(29.5); 2.335(0.4); 2.330(0.6); 2.325(0.4); 1.591(16.0); 1.106(9.1); 1.090(9.0); 1.062(9.4); 1.045(9.3); 0.000(2.4)

Example 135: $^1$H-NMR(400.0 MHz, DMSO):
8.689(2.9); 8.681(2.9); 8.367(0.6); 8.353(1.1); 8.338(0.6); 8.136(2.2); 8.132(2.3); 7.991(1.2); 7.969(2.8); 7.953(0.7); 7.940(2.1); 7.935(2.1); 7.918(0.9); 7.913(1.0); 7.825(2.0); 7.817(2.0); 7.398(1.8); 4.086(1.6); 4.071(1.8); 4.063(1.7); 3.954(1.4); 3.940(16.0); 3.937(5.0); 3.918(3.7); 3.900(4.9); 3.876(1.8); 3.833(2.2); 3.485(2.2); 3.442(1.8); 3.379(0.4); 3.373(0.4); 3.333(238.0); 3.308(0.4); 2.891(5.2); 2.731(4.2); 2.676(0.5); 2.672(0.6); 2.667(0.4); 2.538(0.3); 2.525(1.9); 2.520(2.9); 2.512(34.1); 2.507(68.3); 2.503(89.2); 2.498(63.0); 2.493(29.3); 2.334(0.4); 2.329(0.5); 2.325(0.4); 2.168(0.9); 2.047(15.1); 1.603(10.9); 1.591(1.0); 1.255(4.4); 1.237(9.7); 1.219(4.3); 1.214(0.8); 0.000(3.0)

Example 136: $^1$H-NMR(400.0 MHz, DMSO):
9.012(7.5); 9.006(7.7); 8.755(5.5); 8.749(5.2); 8.310(5.6); 8.305(5.9); 8.217(6.1); 8.212(4.1); 8.195(7.0); 8.190(5.0); 8.093(5.9); 8.071(4.1); 7.953(0.6); 7.575(4.6); 7.571(6.8); 7.566(2.0); 7.553(7.9); 7.454(2.4); 7.451(3.9); 7.447(1.5); 7.433(8.3); 7.430(3.8); 7.414(5.1); 7.389(2.0); 7.386(3.6); 7.383(2.1); 7.374(1.3); 7.368(4.3); 7.361(0.9); 7.353(0.8); 7.350(1.2); 4.402(4.8); 4.359(5.5); 3.949(0.5); 3.932(1.3); 3.916(1.8); 3.912(1.5); 3.899(1.5); 3.895(1.9); 3.879(1.3); 3.862(0.6); 3.850(5.4); 3.806(4.8); 3.730(0.4); 3.431(0.3); 3.417(0.4); 3.334(588.8); 3.018(0.3); 2.892(4.8); 2.732(3.9); 2.681(0.5); 2.677(1.1); 2.672(1.5); 2.668(1.5); 2.663(0.5); 2.525(5.0); 2.520(7.8); 2.512(85.8); 2.508(172.0); 2.503(226.0); 2.499(163.3); 2.494(79.0); 2.339(0.5); 2.334(1.0); 2.330(1.4); 2.325(1.0); 2.321(0.5); 1.234(0.6); 1.081(16.0); 1.065(15.8); 1.025(15.6); 1.008(15.4); 0.061(0.4); 0.000(7.8)

Example 137: $^1$H-NMR(400.0 MHz, DMSO):
9.005(1.2); 8.999(1.9); 8.993(1.4); 8.988(0.7); 8.749(1.5); 8.743(1.1); 8.553(0.8); 8.302(0.7); 8.295(0.7); 8.291(0.4); 8.288(0.7); 8.286(0.6); 8.244(2.1); 8.169(1.0); 8.165(1.0); 8.146(1.6); 8.142(1.7); 8.082(1.6); 8.060(1.0); 7.952(1.6);

-continued

NMR Peak Lists Table 1

7.433(2.5); 4.148(0.3); 4.126(1.7); 4.113(2.8); 4.099(1.7); 4.076(0.4); 4.063(1.3); 4.035(1.8); 3.978(1.8); 3.974(2.4); 3.965(0.6); 3.956(4.6); 3.949(2.7); 3.938(4.4); 3.919(1.4); 3.904(2.4); 3.721(2.1); 3.677(1.5); 3.400(0.4); 3.342(149.9); 3.338(171.3); 3.333(184.2); 3.298(0.6); 2.898(12.8); 2.739(10.2); 2.680(0.6); 2.676(0.8); 2.671(0.6); 2.529(2.6); 2.524(4.0); 2.516(48.4); 2.511(97.8); 2.506(128.4); 2.502(91.0); 2.497(42.3); 2.338(0.6); 2.333(0.8); 2.329(0.6); 2.192(1.0); 2.081(16.0); 1.465(2.1); 1.338(0.6); 1.331(0.4); 1.283(2.2); 1.280(3.0); 1.265(4.5); 1.262(6.3); 1.247(2.5); 1.244(3.1); 1.228(1.2); 0.000(3.9)
Example 138: $^1$H-NMR(400.0 MHz, DMSO):
9.015(3.4); 9.009(3.5); 8.763(2.3); 8.758(2.2); 8.585(0.6); 8.570(1.2); 8.556(0.6); 8.314(0.4); 8.252(2.3); 8.248(2.6); 8.170(1.3); 8.165(1.2); 8.148(2.1); 8.143(2.1); 8.088(2.6); 8.066(1.6); 7.952(2.0); 7.426(4.1); 4.181(1.7); 4.152(2.8); 4.142(0.4); 4.121(1.7); 4.111(1.9); 4.106(2.0); 4.097(1.7); 4.086(2.7); 4.075(0.5); 4.057(1.7); 3.968(1.2); 3.961(0.4); 3.950(3.8); 3.932(3.9); 3.914(1.3); 3.897(1.6); 3.852(2.4); 3.727(2.3); 3.683(1.5); 3.372(0.5); 3.332(308.9); 3.299(0.4); 2.891(15.9); 2.732(12.3); 2.731(12.9); 2.676(0.6); 2.672(0.8); 2.667(0.6); 2.525(2.5); 2.520(3.9); 2.512(45.3); 2.507(90.9); 2.503(119.4); 2.498(85.9); 2.493(40.9); 2.334(0.5); 2.329(0.7); 2.325(0.5); 2.184(1.0); 2.070(16.0); 1.270(4.8); 1.259(0.8); 1.252(10.5); 1.233(5.1); 1.220(0.7); 0.000(4.2)
Example 139: $^1$H-NMR(400.0 MHz, DMSO):
9.015(7.5); 9.009(7.6); 8.768(5.6); 8.762(5.3); 8.315(0.5); 8.255(5.5); 8.250(6.0); 8.180(3.0); 8.176(2.6); 8.158(4.8); 8.154(4.5); 8.100(3.0); 8.091(6.8); 8.080(2.9); 8.069(4.1); 7.953(0.6); 4.154(4.1); 4.125(7.0); 4.066(6.8); 4.037(4.0); 3.998(0.5); 3.982(1.2); 3.965(1.8); 3.961(1.5); 3.948(1.5); 3.945(1.8); 3.928(1.4); 3.915(4.4); 3.870(5.9); 3.794(0.5); 3.695(5.7); 3.650(4.0); 3.330(407.8); 2.891(4.5); 2.732(3.9); 2.676(0.8); 2.672(1.2); 2.667(0.9); 2.663(0.4); 2.525(4.2); 2.512(71.2); 2.507(141.0); 2.503(184.6); 2.498(133.6); 2.494(64.7); 2.339(0.4); 2.334(0.8); 2.330(1.2); 2.325(0.8); 2.321(0.4); 1.234(0.4); 1.124(15.7); 1.108(15.6); 1.089(16.0); 1.073(15.7); 0.000(5.8); −0.063(0.6)
Example 140, Solvent: CDCl3, Spectrometer: 300,16 MHz
9.2128 (2.92); 9.2052(2.94); 8.2957 (2.71); 8.2883 (2.66); 8.1346 (6.74); 8.1006 (0.33); 7.9430 (3.07); 7.7288 (2.05); 7.7240 (2.82); 7.7175 (1.00); 7.7006 (3.50); 7.5751 (1.05); 7.5711 (1.56); 7.5651 (0.70); 7.5476 (3.47); 7.5424 (1.80); 7.5223 (2.21); 7.4918 (0.97); 7.4875 (1.57); 7.4832 (0.97); 7.4711 (0.63); 7.4634 (1.71); 7.4547 (0.44); 7.4430 (0.38); 7.4390 (0.52); 7.2753 (2.83); 7.2576 (4.12); 6.9934 (0.60); 6.9760 (1.12); 6.9586 (0.67); 5.2954 (0.64); 4.3744 (0.72); 4.3555 (0.73); 4.3249 (1.53); 4.3060 (1.52); 4.2410 (1.52); 4.2241 (1.56); 4.1915 (0.77); 4.1746 (0.75); 4.0771 (1.39); 4.0527 (4.08); 4.0285 (4.84); 4.0040 (1.47); 3.9748 (2.66); 3.4079 (2.50); 3.3507 (2.15); 2.1968 (16.00); 2.0436 (0.55); 2.0274 (1.16); 1.7886 (13.08); 1.4454(4.85); 1.4210 (9.96); 1.3966 (4.73); 1.2571 (0.42); −0.0002 (1.30)
Example 141, Solvent: CDCl3, Spectrometer: 300,16 MHz
9.2107 (2.94); 9.2032 (2.99); 8.2974 (2.97); 8.2899 (2.96); 8.1467 (7.61); 7.9474 (3.28); 7.7290 (2.22); 7.7240 (3.18); 7.7175 (1.01); 7.7007 (3.83); 7.6974 (3.30); 7.6900(0.64); 7.5746(1.17); 7.5705 (1.08); 7.5645 (0.71); 7.5470 (3.89); 7.5418 (1.93); 7.5260 (1.28); 7.5217 (2.44); 7.4908 (1.02); 7.4865 (1.75); 7.4821 (1.05); 7.4701 (0.66); 7.4623 (1.94); 7.4536 (0.47); 7.4421(0.41); 7.4380 (0.59); 7.4339 (0.34); 7.2713 (3.00); 6.7510 (0.90); 6.7243 (0.94); 4.0859 (0.65); 4.0640 (0.95); 4.0592 (0.76); 4.0420 (0.81); 4.0372 (0.95); 4.0096 (2.92); 3.9935 (0.34); 3.9523 (3.28); 3.3858 (3.11); 3.3285 (2.66); 1.9349 (2.63); 1.7661 (16.00); 1.7401 (0.37); 1.2557 (0.50); 1.2193 (8.59); 1.1975 (8.54); 1.1603 (8.71); 1.1384 (8.64); 0.8800 (0.40); −0.0002 (1.52)
Example 142, Solvent: CDCl3, Spectrometer: 300,16 MHz
9.2271 (2.33); 9.2197 (2.40); 8.2629 (2.66); 8.2554 (2.65); 8.0931 (6.50); 8.0903 (6.82); 7.8940 (3.12); 7.5294 (1.80); 7.5262 (1.99); 7.5174 (2.09); 7.5143 (2.10); 7.4436 (1.75); 7.4406 (1.75); 7.4267 (2.08); 7.4236 (1.91); 7.2732 (3.78); 7.2566 (4.28); 7.2000 (1.78); 7.1878 (1.85); 7.1832 (1.78); 7.1710(1.52); 6.9753 (0.61); 6.9579 (1.14); 6.9405 (0.70); 4.3725 (0.76); 4.3535 (0.77); 4.3230 (1.59); 4.3040 (1.58); 4.2374 (1.58); 4.2205 (1.62); 4.1879 (0.81); 4.1710 (0.79); 4.1567 (0.33); 4.1328 (0.85); 4.1090 (0.89); 4.0785 (1.41); 4.0541 (4.13); 4.0297 (4.25); 4.0160 (2.46); 4.0054 (1.62); 3.9589 (2.65); 3.3932 (2.52); 3.3360 (2.16); 2.1957 (16.00); 2.0455 (3.59); 1.9046 (2.76); 1.7849 (13.33); 1.4463 (4.72); 1.4220 (9.49); 1.3976 (4.59); 1.2825 (0.99); 1.2587 (2.04); 1.2349 (0.98); −0.0002 (1.86)
Example 143, Solvent: CDCl3, Spectrometer: 300,16 MHz
8.9687 (1.26); 8.9637 (1.36); 8.9548 (1.41); 8.9498 (1.31); 8.1912(1.41); 8.1849 (1.59); 8.1774 (0.92); 8.1635 (1.69); 8.1537 (2.94); 8.1477 (2.87); 8.1287 (3.51); 8.0990 (1.03); 7.8935 (2.73); 7.8886 (2.66); 7.4811 (1.57); 7.4669 (1.58); 7.4534 (1.52); 7.4392 (1.47); 7.2802 (2.23); 6.7403 (0.72); 6.7145 (0.75); 4.0790 (0.63); 4.0570 (0.92); 4.0523 (0.74); 4.0350 (0.80); 4.0302 (0.92); 4.0082 (0.71); 3.9950 (2.82); 3.9377 (3.25); 3.3722 (3.10); 3.3148 (2.63); 2.0237 (0.45); 1.7587 (16.00); 1.2545 (0.33); 1.2149 (8.27); 1.1931 (8.26); 1.1528 (8.31); 1.1309 (8.27); −0.0002(1.44)
Example 144, Solvent: CDCl3, Spectrometer: 300,16 MHz
9.2257 (3.45); 9.2181 (3.54); 8.2668 (2.68); 8.2592 (2.68); 8.1429 (0.45); 8.1375 (0.39); 8.1133 (3.45); 8.1076 (4.67); 8.1035 (4.45); 8.0741 (0.51); 7.8993 (2.75); 7.5297 (2.05); 7.5260 (2.32); 7.5176 (2.32); 7.5139 (2.42); 7.4434(2.01); 7.4399 (2.00); 7.4265 (2.39); 7.4229 (2.22); 7.2697 (4.93); 7.2002 (2.30); 7.1881 (2.25); 7.1833 (2.15); 7.1711 (1.94); 6.7378 (0.80); 6.7111 (0.84); 4.0828 (0.63); 4.0609 (0.91); 4.0560 (0.73); 4.0389 (0.76); 4.0340 (0.92); 4.0168 (0.39); 4.0121 (0.68); 3.9939 (2.91); 3.9366 (3.30); 3.3715 (3.10); 3.3142(2.66); 2.0471 (0.45); 1.8184 (5.42); 1.7625 (16.00); 1.2597 (0.36); 1.2178 (8.46); 1.1960 (8.43); 1.1587 (8.57); 1.1368 (8.52); −0.0002 (2.80)
Example 145: $^1$H-NMR(400.0 MHz, DMSO):
9.171(3.3); 9.166(3.3); 8.765(2.2); 8.760(2.1); 8.400(2.3); 8.396(2.4); 8.384(0.6); 8.369(1.2); 8.355(0.6); 8.315(0.4); 8.249(1.2); 8.244(1.1); 8.227(1.9); 8.222(1.8); 8.160(2.5); 8.138(1.5); 7.953(0.7); 7.406(3.6); 4.083(2.0); 4.069(2.0); 3.958(1.1); 3.940(3.2); 3.922(3.4); 3.916(1.5); 3.914(1.3); 3.904(1.2); 3.873(1.5); 3.871(1.5); 3.509(1.5); 3.507(1.5); 3.465(1.2); 3.463(1.2); 3.329(191.8); 2.957(16.0); 2.891(5.5); 2.732(4.3); 2.731(4.5); 2.676(0.5); 2.672(0.7); 2.667 (0.5); 2.525(2.2); 2.512(40.3); 2.507(79.7); 2.503(102.9); 2.498(72.6); 2.493(33.8); 2.334(0.5); 2.329(0.6); 2.325 (0.4); 2.172(0.8); 2.050(15.4); 1.614(10.4); 1.602(0.9); 1.336(0.4); 1.258(3.3); 1.242(6.3); 1.240(6.6); 1.224(3.1); 1.222(3.0); 1.215(0.6); 0.000(3.6)
Example 146: $^1$H-NMR(400.0 MHz, DMSO):
9.356(4.3); 9.350(4.4); 9.071(3.0); 9.066(2.8); 8.511(3.1); 8.506(3.2); 8.360(1.9); 8.355(1.7); 8.337(2.5); 8.332(2.4); 8.216(3.2); 8.194(2.4); 7.953(0.3); 7.904(1.4); 7.883(1.4); 3.934(0.9); 3.926(2.8); 3.918(1.2); 3.914(0.9); 3.901(0.9); 3.898(1.1); 3.883(3.9); 3.479(3.1); 3.436(3.3); 3.426(20.9); 3.364(0.6); 3.331(225.2); 2.892(2.6); 2.732(2.1); 2.677 (0.5); 2.672(0.7); 2.667(0.5); 2.525(2.0); 2.520(3.1); 2.512(38.7); 2.507(77.4); 2.503(100.8); 2.498(71.4); 2.494(33.5); 2.334(0.4); 2.330(0.6); 2.325(0.4); 1.607(16.0); 1.112(9.2); 1.095(9.1); 1.067(9.5); 1.050(9.4); 0.861(0.6); 0.829(0.7); 0.000(3.3)
Example 147: $^1$H-NMR(400.0 MHz, DMSO):
8.823(2.7); 8.817(2.8); 8.370(0.5); 8.355(1.0); 8.341(0.5); 8.215(2.0); 8.210(2.0); 8.148(1.8); 8.145(2.0); 8.033(0.5); 8.029(0.4); 8.011(2.4); 8.007(2.6); 8.000(3.0); 7.978(0.5); 7.952(0.7); 7.399(3.5); 4.084(1.5); 4.077(1.6); 4.069(1.6); 4.063(1.6); 3.955(1.1); 3.937(3.2); 3.919(3.3); 3.901(1.1); 3.879(1.6); 3.836(1.9); 3.483(1.9); 3.440(1.7); 3.331(182.8);

NMR Peak Lists Table 1

2.891(5.2); 2.731(4.4); 2.676(0.4); 2.671(0.5); 2.667(0.4); 2.637(16.0); 2.525(1.5); 2.512(27.8); 2.507(55.6); 2.502(72.8); 2.498(51.6); 2.493(24.1); 2.334(0.3); 2.329(0.5); 2.325(0.3); 2.168(0.8); 2.047(13.4); 1.604(9.7); 1.592(0.8); 1.256(3.9); 1.238(8.5); 1.219(3.8); 1.214(0.6); 0.000(2.5)
Example 148, Solvent: CDCl3, Spectrometer: 400,13 MHz
8.9404 (0.76); 8.9353 (0.76); 8.2354 (0.55); 8.2306 (0.54); 8.1281 (0.58); 8.1234 (0.60); 8.0941 (0.71); 7.8161 (0.61); 7.8117 (0.58); 7.2633 (6.03); 3.9686 (0.63); 3.9257 (0.72); 3.3755 (0.67); 3.3326 (0.60); 2.2547 (0.42); 2.2483 (0.86); 2.2419 (0.41); 1.7832 (3.55); 1.5897 (5.38); 0.3165 (0.60); 0.3078 (16.00); 0.2989 (0.54); 0.1817 (0.35); −0.0002(4.02)
Example 149, Solvent: CDCl3, Spectrometer: 300,16 MHz
8.9412 (0.77); 8.9345 (0.77); 8.2373 (0.68); 8.2310 (0.65); 8.1139 (0.67); 8.1081 (0.71); 8.0905 (0.88); 7.8169 (0.69); 7.8122 (0.67); 7.2654 (3.75); 7.2509 (1.13); 4.3184(0.41); 4.2994 (0.41); 4.2243 (0.42); 4.2076 (0.42); 4.0800 (0.35); 4.0556 (1.07); 4.0312(1.10); 4.0069 (0.38); 3.9935 (0.62); 3.9364 (0.72); 3.3745 (0.69); 3.3173 (0.59); 2.1907 (4.42); 1.7777 (3.62); 1.6549 (4.47); 1.4479 (1.26); 1.4236 (2.59); 1.3992 (1.23); 0.3207 (0.60); 0.3094 (16.00); 0.2976 (0.74); −0.0002 (2.44)
Example 150, Solvent: CDCl3, Spectrometer: 300,16 MHz
8.9383 (0.74); 8.9315 (0.72); 8.2370 (0.59); 8.2308 (0.56); 8.1340(0.61); 8.1278 (0.62); 8.0945 (0.75); 7.8204(0.64); 7.8147 (0.60); 7.2649 (3.24); 3.9707 (0.62); 3.9134 (0.73); 3.3508 (0.70); 3.2934 (0.59); 1.7543 (3.62); 1.6269 (3.38); 1.2135 (1.95); 1.1916 (1.93); 1.1525 (1.97); 1.1306 (1.96); 0.3199 (0.58); 0.3083 (16.00); 0.2966 (0.67); −0.0002 (2.15)
Example 151: $^1$H-NMR(400.0 MHz, DMSO):
9.356(3.1); 9.350(3.1); 9.068(2.3); 9.063(2.1); 8.507(2.2); 8.502(2.3); 8.394(0.6); 8.380(1.2); 8.365(0.6); 8.347(1.4); 8.342(1.3); 8.325(1.9); 8.320(1.8); 8.312(0.4); 8.213(2.3); 8.191(1.7); 7.952(1.1); 7.408(4.0); 4.087(2.4); 4.072(2.4); 3.961(1.2); 3.953(0.3); 3.943(3.9); 3.924(4.2); 3.920(2.3); 3.906(1.3); 3.877(2.2); 3.505(2.1); 3.461(1.9); 3.425(14.0); 3.394(0.4); 3.388(0.5); 3.338(341.8); 2.892(9.3); 2.732(7.5); 2.677(0.4); 2.672(0.6); 2.668(0.4); 2.526(2.2); 2.521(3.3); 2.512(36.2); 2.508(72.7); 2.503(95.2); 2.499(67.5); 2.494(31.5); 2.335(0.4); 2.330(0.6); 2.325(0.4); 2.172(0.7); 2.050(16.0); 1.621(11.1); 1.610(0.8); 1.262(4.5); 1.244(9.6); 1.234(0.7); 1.226(4.4); 1.216(0.5); 0.000(3.5)
Example 152: $^1$H-NMR(400.0 MHz, DMSO):
9.011(0.6); 9.004(4.5); 8.999(4.4); 8.991(0.4); 8.985(0.4); 8.765(3.9); 8.760(3.4); 8.304(0.8); 8.290(1.6); 8.276(0.8); 8.220(3.4); 8.216(4.2); 8.177(0.7); 8.168(2.1); 8.163(1.7); 8.155(0.9); 8.150(1.1); 8.146(2.9); 8.141(2.6); 8.088(0.5); 8.076(3.9); 8.054(2.6); 7.953(2.0); 7.755(2.9); 5.746(3.2); 5.625(2.3); 5.618(2.2); 4.295(0.3); 4.280(0.4); 4.257(2.1); 4.243(3.6); 4.230(2.1); 4.206(0.5); 4.192(0.4); 3.905(2.6); 3.890(0.6); 3.862(3.2); 3.847(0.8); 3.830(0.5); 3.800(1.4); 3.734(0.8); 3.497(3.0); 3.454(2.8); 3.440(0.8); 3.397(0.6); 3.334(26.8); 3.326(98.8); 3.294(0.6); 3.286(0.8); 3.274(0.5); 3.269(0.5); 2.891(16.0); 2.751(0.4); 2.732(12.8); 2.676(0.5); 2.672(0.7); 2.667(0.5); 2.609(0.6); 2.597(0.3); 2.525(1.6); 2.512(39.9); 2.507(80.3); 2.503(107.1); 2.498(79.1); 2.494(38.6); 2.338(0.4); 2.334(0.6); 2.329(0.8); 2.325(0.6); 2.247(1.1); 2.236(0.6); 2.095(14.5); 2.012(0.3); 1.983(0.4); 1.734(0.6); 1.694(0.8); 1.649(0.3); 1.641(0.5); 1.620(15.6); 1.605(4.0); 1.564(0.4); 1.338(0.7); 1.280(0.3); 1.275(0.4); 1.234(0.7); 0.008(0.5); 0.000(15.8); −0.009(0.6)
Example 153: $^1$H-NMR(400.0 MHz, DMSO):
8.955(4.6); 8.949(4.7); 8.940(0.3); 8.606(3.6); 8.601(3.4); 8.299(0.8); 8.285(1.7); 8.270(0.9); 8.241(3.4); 8.236(4.0); 8.175(0.5); 8.170(0.6); 8.166(2.1); 8.161(1.7); 8.153(0.7); 8.148(0.9); 8.144(3.1); 8.139(2.9); 8.087(0.4); 8.074(3.8); 8.052(2.6); 7.953(1.0); 5.755(3.0); 5.747(3.4); 5.627(2.4); 5.624(2.4); 5.618(2.2); 5.616(2.2); 4.591(8.2); 4.296(0.4); 4.281(0.4); 4.258(2.1); 4.243(3.8); 4.230(2.1); 4.206(0.5); 4.192(0.4); 3.914(2.7); 3.899(0.5); 3.870(3.3); 3.856(0.6); 3.831(0.4); 3.800(0.9); 3.506(3.2); 3.462(2.7); 3.456(0.6); 3.449(0.7); 3.405(0.4); 3.335(31.0); 3.327(105.5); 3.296(0.6); 3.290(0.6); 3.285(0.7); 3.277(0.5); 3.274(0.5); 2.891(8.6); 2.751(0.4); 2.733(6.7); 2.731(6.7); 2.676(0.5); 2.672(0.6); 2.667(0.5); 2.525(1.1); 2.521(2.1); 2.512(35.6); 2.507(73.2); 2.503(98.6); 2.498(72.3); 2.494(34.6); 2.339(0.4); 2.334(0.6); 2.329(0.8); 2.325(0.6); 2.247(0.6); 2.094(14.6); 1.693(0.5); 1.665(0.3); 1.648(0.4); 1.640(0.4); 1.619(16.0); 1.605(3.1); 1.567(0.3); 1.337(0.3); 1.234(0.8); 0.008(0.5); 0.000(17.8); −0.009(0.5)
Example 154: $^1$H-NMR(400.0 MHz, DMSO):
9.006(4.2); 9.000(4.3); 8.788(0.9); 8.774(2.1); 8.767(3.7); 8.761(3.8); 8.450(7.5); 8.222(3.3); 8.218(3.5); 8.169(1.9); 8.164(1.6); 8.147(3.0); 8.142(2.6); 8.078(3.6); 8.056(2.2); 4.529(0.7); 4.514(0.7); 4.490(2.4); 4.475(2.3); 4.462(2.2); 4.448(2.4); 4.423(0.8); 4.409(0.7); 4.325(1.1); 4.307(3.4); 4.289(3.4); 4.281(0.4); 4.272(1.1); 4.017(0.4); 3.999(1.5); 3.995(1.5); 3.981(2.0); 3.977(4.6); 3.958(4.7); 3.940(1.5); 3.904(2.7); 3.830(1.0); 3.530(3.1); 3.486(2.6); 3.326(52.5); 2.891(1.2); 2.751(0.4); 2.748(0.6); 2.732(1.0); 2.676(0.8); 2.671(1.0); 2.667(0.7); 2.663(0.4); 2.551(2.0); 2.539(1.2); 2.525(2.8); 2.520(4.5); 2.511(58.6); 2.507(115.6); 2.502(151.2); 2.498(110.3); 2.493(52.6); 2.334(0.7); 2.329(1.0); 2.324(0.7); 1.631(16.0); 1.294(3.7); 1.277(7.7); 1.263(1.0); 1.259(3.7); 1.245(5.8); 1.235(1.4); 1.227(12.2); 1.209(5.4); 1.159(1.3); 1.142(2.6); 1.124(1.0); 0.008(0.8); 0.000(26.5); −0.008(0.8)
Example 155: $^1$H-NMR(300.2 MHz, CDCl3):
8.974(2.9); 8.968(2.8); 8.282(2.7); 8.276(2.6); 8.160(0.7); 8.155(0.7); 8.130(2.9); 8.125(3.2); 8.114(3.8); 8.085(0.8); 7.846(2.9); 7.412(3.0); 7.269(5.3); 7.091(0.7); 7.073(1.2); 7.055(0.7); 6.977(2.9); 4.586(0.8); 4.566(0.8); 4.534(1.5); 4.514(1.4); 4.429(1.5); 4.412(1.5); 4.377(0.8); 4.360(0.8); 3.995(2.2); 3.938(2.6); 3.551(15.2); 3.398(2.6); 3.337(5.8); 1.849(0.4); 1.796(16.0); 1.785(14.8); 0.000(4.2)
Example 156: $^1$H-NMR(400.0 MHz, DMSO):
• = 9.012(4.2); 9.006(4.5); 8.814(2.7); 8.811(2.6); 8.776(3.1); 8.770(3.0); 8.616(0.9); 8.602(1.9); 8.588(0.9); 8.442 (2.8); 8.438(2.7); 8.248(3.0); 8.244(3.5); 8.197(2.0); 8.192(1.6); 8.175(2.8); 8.170(2.6); 8.091(3.4); 8.069(2.3); 4.596 (1.6); 4.582(3.0); 4.567(1.6); 3.916(2.6); 3.872(3.2); 3.563(3.1); 3.520(3.0); 3.324(105.3); 2.892(1.2); 2.732(0.9); 2.676(0.5); 2.672(0.7); 2.667(0.5); 2.525(1.7); 2.520(2.7); 2.512(38.2); 2.507(77.6); 2.503(103.9); 2.498(75.7); 2.494(35.9); 2.334(0.5); 2.329(0.7); 2.325(0.5); 1.673(16.0); 1.234(0.6); 0.008(0.6); 0.000(19.8); −0.009(0.5)
Example 157: $^1$H-NMR(400.0 MHz, DMSO):
8.962(4.0); 8.957(3.9); 8.814(3.0); 8.616(3.9); 8.612(4.2); 8.599(2.2); 8.585(1.0); 8.442(3.1); 8.438(3.0); 8.316(0.4); 8.269(3.4); 8.264(3.6); 8.195(1.8); 8.190(1.6); 8.173(2.7); 8.168(2.5); 8.089(3.6); 8.066(2.4); 7.953(0.5); 4.625(0.3); 4.594(8.9); 4.581(3.3); 4.567(1.8); 3.924(2.6); 3.881(3.2); 3.570(3.1); 3.527(2.5); 3.324(276.5); 2.891(3.7); 2.750(0.4); 2.731(3.1); 2.675(1.1); 2.671(1.6); 2.667(1.2); 2.524(4.0); 2.510(93.3); 2.506(182.7); 2.502(241.3); 2.497(179.5); 2.493(89.4); 2.333(1.2); 2.329(1.6); 2.324(1.2); 1.672(16.0); 1.281(0.3); 1.235(1.7); 0.008(1.1); 0.000(35.7); −0.008(1.4)
Example 158: $^1$H-NMR(400.0 MHz, DMSO):
9.021(4.6); 9.015(4.8); 8.859(0.8); 8.844(1.6); 8.828(0.8); 8.772(3.2); 8.767(3.0); 8.256(3.1); 8.251(3.5); 8.206(2.0); 8.201(1.6); 8.184(3.0); 8.179(2.7); 8.101(3.5); 8.079(2.3); 7.953(1.4); 7.890(3.1); 7.877(3.1); 6.385(1.8); 6.371(1.7); 6.074(2.7); 4.321(0.8); 4.304(0.8); 4.281(1.2); 4.264(1.2); 4.145(1.1); 4.131(1.2); 4.105(0.8); 4.090(0.8); 3.949(2.6); 3.905(3.1); 3.542(3.0); 3.498(2.6); 3.325(74.0); 3.110(3.5); 3.104(3.4); 2.891(11.4); 2.751(0.4); 2.732(8.9); 2.731(9.1); 2.676(0.4); 2.671(0.6); 2.667(0.4); 2.534(0.4); 2.525(1.7); 2.520(2.9); 2.512(34.4); 2.507(68.7); 2.502(91.3);

| NMR Peak Lists Table 1 |
| --- |
| 2.498(66.4); 2.493(31.4); 2.334(0.4); 2.329(0.6); 2.325(0.4); 1.689(16.0); 1.672(0.8); 1.652(2.1); 1.642(3.7); 1.635(3.6); 1.606(0.5); 1.234(0.8); 0.008(0.7); 0.000(22.9); −0.009(0.7)<br>Example 159: $^1$H-NMR(400.0 MHz, DMSO):<br>8.955(3.8); 8.950(3.9); 8.785(1.0); 8.771(2.0); 8.756(1.0); 8.606(3.3); 8.601(3.2); 8.448(7.2); 8.241(3.4); 8.237(3.6); 8.166(1.7); 8.161(1.5); 8.144(2.7); 8.139(2.5); 8.075(3.7); 8.053(2.3); 7.952(0.8); 4.592(6.4); 4.528(0.7); 4.513(0.7); 4.489(2.4); 4.474(2.3); 4.461(2.3); 4.447(2.5); 4.423(0.8); 4.408(0.7); 3.994(1.5); 3.976(4.6); 3.958(4.7); 3.940(1.6); 3.913(2.6); 3.869(3.2); 3.537(3.1); 3.494(2.6); 3.323(123.6); 2.891(6.1); 2.731(5.2); 2.675(0.7); 2.671(1.0); 2.666(0.8); 2.506(114.1); 2.502(150.2); 2.497(112.9); 2.333(0.7); 2.328(1.0); 2.324(0.7); 1.630(16.0); 1.245(5.6); 1.227(11.9); 1.208(5.4); 0.008(0.9); 0.000(24.4); −0.009(1.0)<br>Example 160: $^1$H-NMR(400.0 MHz, DMSO):<br>8.958(4.2); 8.953(4.3); 8.925(0.9); 8.910(1.9); 8.894(0.9); 8.604(3.1); 8.599(3.0); 8.316(0.4); 8.277(2.7); 8.272(2.7); 8.242(3.2); 8.237(3.5); 8.176(1.9); 8.171(1.6); 8.154(2.8); 8.149(2.7); 8.082(3.6); 8.059(2.3); 7.953(0.9); 7.719(1.7); 7.713(1.7); 7.698(2.0); 7.692(1.9); 7.627(0.4); 7.623(0.4); 7.597(0.4); 7.453(3.5); 7.433(2.9); 4.592(7.5); 4.358(0.4); 4.342(0.4); 4.319(2.0); 4.305(3.5); 4.290(2.0); 4.267(0.4); 4.252(0.4); 3.903(2.7); 3.860(3.3); 3.529(3.1); 3.486(2.6); 3.324(253.7); 2.891(8.0); 2.732(6.2); 2.680(0.5); 2.676(1.0); 2.671(1.3); 2.667(1.0); 2.662(0.5); 2.525(3.6); 2.520(5.6); 2.511(74.0); 2.507(149.2); 2.502(199.1); 2.497(145.8); 2.493(69.7); 2.338(0.5); 2.333(1.0); 2.329(1.3); 2.324(1.0); 2.320(0.5); 1.622(16.0); 1.235(1.1); 0.008(0.8); 0.000(25.5); −0.009(0.8)<br>Example 161: $^1$H-NMR(400.0 MHz, DMSO):<br>9.006(4.1); 9.000(4.2); 8.766(3.1); 8.760(2.9); 8.674(0.8); 8.659(1.6); 8.644(0.8); 8.227(3.0); 8.222(3.4); 8.176(1.9); 8.172(1.5); 8.154(2.9); 8.149(2.6); 8.080(3.4); 8.058(2.2); 7.953(0.5); 7.523(2.4); 7.519(2.7); 7.517(2.5); 6.352(2.1); 6.348(2.3); 6.344(2.4); 6.340(2.2); 6.146(2.2); 6.144(2.3); 6.138(2.1); 6.136(2.1); 4.291(4.1); 4.276(4.1); 3.901(2.7); 3.857(3.3); 3.513(3.1); 3.469(2.6); 3.324(100.6); 2.891(4.6); 2.732(3.5); 2.731(3.5); 2.676(0.5); 2.671(0.7); 2.667(0.5); 2.525(1.8); 2.520(2.9); 2.511(40.3); 2.507(81.2); 2.502(108.3); 2.498(79.4); 2.493(38.1); 2.334(0.5); 2.329(0.7); 2.324(0.5); 1.625(16.0); 1.235(0.7); 0.008(0.7); 0.000(21.1); −0.009(0.7)<br>Example 162: $^1$H-NMR(400.0 MHz, DMSO):<br>8.955(3.4); 8.951(3.9); 8.941(0.8); 8.887(1.2); 8.872(2.3); 8.857(1.2); 8.602(4.0); 8.241(4.3); 8.168(1.8); 8.146(2.8); 8.076(3.8); 8.054(2.4); 7.328(1.9); 7.318(2.3); 7.313(2.4); 7.303(0.5); 6.915(7.6); 6.905(5.4); 6.897(1.5); 4.591(6.1); 4.582(1.4); 4.454(5.3); 4.439(5.4); 3.895(2.5); 3.852(3.2); 3.534(3.1); 3.491(2.5); 3.326(50.5); 3.317(11.9); 2.891(1.0); 2.731(0.9); 2.672(0.4); 2.503(64.4); 2.330(0.4); 1.626(16.0); 1.232(0.5); 0.000(6.6); −0.010(1.6)<br>Example 163: $^1$H-NMR(400.0 MHz, DMSO):<br>8.955(4.2); 8.950(4.1); 8.605(3.4); 8.600(3.2); 8.592(1.0); 8.577(1.7); 8.562(0.8); 8.245(3.3); 8.241(3.5); 8.173(1.9); 8.168(1.6); 8.151(2.9); 8.146(2.7); 8.077(3.6); 8.055(2.3); 6.002(2.3); 5.994(2.8); 5.935(2.3); 5.933(2.3); 5.928(1.9); 5.925(1.8); 4.591(7.0); 4.230(3.8); 4.215(3.8); 3.906(2.7); 3.863(3.3); 3.515(3.1); 3.471(2.7); 3.325(34.1); 2.891(1.8); 2.733(1.4); 2.732(1.4); 2.672(0.4); 2.525(1.2); 2.512(22.6); 2.507(44.8); 2.503(59.0); 2.498(42.6); 2.494(20.0); 2.335(0.5); 2.330(0.4); 2.325(0.4); 2.180(0.5); 2.166(14.0); 1.648(0.3); 1.623(16.0); 1.233(0.5); 0.008(0.4); 0.000(11.9); −0.009(0.4)<br>Example 164: $^1$H-NMR(400.0 MHz, DMSO):<br>8.956(4.3); 8.951(4.3); 8.672(0.9); 8.657(1.8); 8.642(0.9); 8.605(3.2); 8.600(3.0); 8.246(3.3); 8.242(3.4); 8.174(1.9); 8.170(1.6); 8.152(2.9); 8.147(2.7); 8.078(3.5); 8.056(2.3); 7.954(0.3); 7.524(2.7); 7.522(3.0); 7.519(2.9); 7.517(2.6); 6.352(2.4); 6.348(2.5); 6.344(2.6); 6.340(2.4); 6.147(2.5); 6.145(2.5); 6.139(2.3); 6.137(2.2); 4.592(7.3); 4.293(4.3); 4.278(4.3); 3.910(2.7); 3.867(3.3); 3.521(3.1); 3.477(2.6); 3.326(39.5); 2.892(2.7); 2.733(2.1); 2.732(2.1); 2.672(0.4); 2.525(1.2); 2.512(23.1); 2.508(44.2); 2.503(57.1); 2.498(41.5); 2.494(19.8); 2.330(0.4); 1.625(16.0); 1.234(0.4); 0.008(0.6); 0.000(13.0); −0.009(0.4)<br>Example 165: $^1$H-NMR(400.0 MHz, DMSO):<br>9.017(4.3); 9.011(4.5); 9.005(0.6); 8.999(0.5); 8.925(0.9); 8.910(1.9); 8.896(0.9); 8.781(3.4); 8.775(3.2); 8.356(0.4); 8.335(0.5); 8.318(0.6); 8.292(3.0); 8.271(3.3); 8.263(3.6); 8.259(3.8); 8.241(0.4); 8.237(0.4); 8.221(2.4); 8.216(1.9); 8.199(3.1); 8.194(2.7); 8.177(0.3); 8.154(0.4); 8.102(3.5); 8.080(2.8); 8.057(0.4); 7.953(0.4); 7.929(1.9); 7.908(2.2); 7.864(2.1); 7.843(2.5); 7.686(1.3); 7.683(1.2); 7.669(1.8); 7.665(2.3); 7.662(1.2); 7.648(1.4); 7.644(1.3); 7.563(1.6); 7.561(1.6); 7.543(2.4); 7.541(1.6); 7.526(1.1); 7.523(1.0); 7.410(3.7); 7.388(3.7); 4.600(4.6); 4.585(4.6); 3.974(2.7); 3.931(3.2); 3.574(3.1); 3.530(2.6); 3.406(0.3); 3.330(282.5); 3.205(0.5); 2.891(2.9); 2.751(0.6); 2.749(0.4); 2.732(2.0); 2.677(0.9); 2.672(1.2); 2.667(0.9); 2.663(0.4); 2.552(3.1); 2.540(6.7); 2.526(6.0); 2.520(6.5); 2.512(70.8); 2.507(137.1); 2.503(177.9); 2.498(130.7); 2.494(63.9); 2.378(0.7); 2.362(0.7); 2.334(0.9); 2.330(1.2); 2.325(0.8); 1.800(0.4); 1.792(0.4); 1.717(16.0); 1.654(1.4); 1.593(0.4); 1.234(1.4); 0.008(0.6); 0.000(15.2); −0.009(0.6)<br>Example 166: $^1$H-NMR(400.0 MHz, DMSO):<br>8.970(4.1); 8.964(4.2); 8.852(0.9); 8.837(1.8); 8.821(1.0); 8.612(3.3); 8.607(3.3); 8.276(3.3); 8.272(3.5); 8.204(1.9); 8.200(1.6); 8.182(2.8); 8.178(2.6); 8.099(3.6); 8.077(2.4); 7.953(1.7); 7.890(3.3); 7.877(3.4); 6.374(2.2); 6.361(2.1); 6.056(3.7); 4.596(7.4); 4.322(0.9); 4.305(0.9); 4.281(1.3); 4.265(1.3); 4.138(1.3); 4.124(1.4); 4.098(0.9); 4.084(0.9); 3.960(2.6); 3.916(3.2); 3.548(3.0); 3.505(2.6); 3.325(75.5); 3.097(4.0); 2.891(12.8); 2.732(10.6); 2.676(0.4); 2.672(0.6); 2.667(0.4); 2.525(1.4); 2.511(34.2); 2.507(68.4); 2.502(90.7); 2.498(66.5); 2.494(32.2); 2.334(0.5); 2.329(0.6); 2.325(0.5); 1.689(16.0); 1.655(0.8); 1.635(2.4); 1.625(4.1); 1.618(4.0); 1.588(0.7); 1.234(0.8); 0.008(0.5); 0.000(16.9); −0.009(0.6)<br>Example 167: $^1$H-NMR(300.2 MHz, DMSO):<br>8.961(4.6); 8.845(2.9); 8.607(5.0); 8.502(0.3); 8.426(5.2); 8.358(5.3); 8.252(5.1); 8.192(2.5); 8.163(3.7); 8.090(4.2); 8.060(2.7); 4.659(0.3); 4.597(6.0); 4.426(6.1); 4.408(5.8); 3.944(2.5); 3.887(3.2); 3.553(3.2); 3.495(2.5); 3.332(10.1); 2.649(0.3); 2.506(7.2); 2.436(16.8); 1.661(16.0); 0.000(0.8)<br>Example 168: $^1$H-NMR(400.0 MHz, DMSO):<br>8.963(4.5); 8.958(4.6); 8.822(0.8); 8.807(1.8); 8.792(0.8); 8.616(3.1); 8.611(3.0); 8.267(3.1); 8.262(3.5); 8.202(2.0); 8.197(1.7); 8.179(2.9); 8.175(2.7); 8.096(3.5); 8.074(2.3); 7.954(1.1); 7.421(1.7); 7.414(1.3); 7.411(1.7); 7.405(1.0); 7.399(2.3); 7.391(0.3); 7.267(0.5); 7.256(3.0); 7.249(2.1); 7.245(2.5); 7.238(2.9); 7.232(4.5); 7.226(0.5); 7.220(1.0); 7.217(0.6); 7.210(2.3); 7.204(1.0); 7.197(1.3); 7.194(0.8); 7.186(0.8); 4.594(7.8); 4.372(4.2); 4.357(4.3); 3.946(2.8); 3.903(3.3); 3.556(3.2); 3.512(2.7); 3.326(67.1); 2.891(9.9); 2.733(7.5); 2.732(7.6); 2.672(0.4); 2.525(1.2); 2.521(1.7); 2.512(22.8); 2.508(46.5); 2.503(62.3); 2.498(45.2); 2.494(21.3); 2.330(0.4); 1.686(16.0); 1.233(0.5); 0.008(0.4); 0.000(11.9); −0.009(0.3)<br>Example 169: $^1$H-NMR(300.2 MHz, CDCl3):<br>8.963(2.7); 8.957(2.7); 8.262(2.8); 8.256(2.7); 8.162(0.9); 8.156(0.9); 8.133(2.6); 8.127(2.7); 8.100(3.6); 8.070(1.3); 7.835(3.0); 7.830(2.9); 7.341(0.4); 7.333(0.7); 7.310(1.7); 7.303(1.6); 7.288(4.3); 7.275(2.3); 7.266(3.0); 7.260(5.7); |

NMR Peak Lists Table 1

7.234(2.8); 4.587(0.9); 4.566(0.9); 4.538(1.6); 4.517(1.5); 4.404(1.6); 4.386(1.6); 4.355(1.0); 4.337(0.9); 4.027(2.7); 3.970(3.2); 3.392(3.1); 3.333(7.4); 1.843(0.4); 1.807(16.0); 1.257(0.6); 0.880(0.4); 0.000(1.6)
Example 170: $^1$H-NMR(400.0 MHz, DMSO):
8.959(4.0); 8.953(4.1); 8.785(0.9); 8.770(1.9); 8.755(0.9); 8.610(3.1); 8.605(3.0); 8.249(3.1); 8.244(3.4); 8.182(1.8); 8.178(1.6); 8.160(2.7); 8.155(2.6); 8.084(3.5); 8.062(2.2); 4.592(7.2); 4.373(3.0); 4.367(2.9); 4.358(2.9); 4.352(3.0); 3.884(2.6); 3.840(3.3); 3.546(3.1); 3.503(2.6); 3.326(58.2); 2.892(0.7); 2.732(0.5); 2.676(0.4); 2.672(0.4); 2.525(1.3); 2.513(40.3); 2.508(40.5); 2.503(53.6); 2.498(39.3); 2.494(18.9); 2.330(0.4); 1.631(16.0); 1.234(0.4); 0.008(0.4); 0.000(10.1)
Example 171: $^1$H-NMR(400.0 MHz, DMSO):
9.008(4.0); 9.003(3.8); 8.788(1.1); 8.771(5.0); 8.765(3.9); 8.228(3.6); 8.224(3.7); 8.184(1.9); 8.180(1.5); 8.162(2.9); 8.158(2.4); 8.087(3.5); 8.065(2.3); 7.627(0.4); 4.372(3.3); 4.366(3.2); 4.358(3.2); 4.351(3.0); 3.875(2.6); 3.831(3.2); 3.538(3.1); 3.495(2.5); 3.326(82.6); 3.302(0.3); 2.892(1.4); 2.732(1.2); 2.676(0.5); 2.672(0.5); 2.667(0.3); 2.513(45.1); 2.507(58.0); 2.503(70.0); 2.499(51.3); 2.334(0.4); 2.330(0.5); 2.325(0.3); 1.631(16.0); 1.234(0.5); 0.000(9.5); −0.008(0.5)
Example 172: $^1$H-NMR(400.0 MHz, DMSO):
8.963(4.2); 8.958(4.3); 8.902(0.9); 8.887(1.9); 8.872(0.9); 8.615(3.2); 8.610(3.2); 8.265(3.3); 8.261(3.6); 8.200(1.9); 8.195(1.6); 8.177(2.8); 8.173(2.6); 8.095(3.6); 8.073(2.4); 7.953(0.5); 7.528(1.8); 7.524(1.9); 7.508(2.2); 7.504(2.2); 7.298(1.9); 7.278(4.0); 7.259(2.4); 7.185(2.2); 7.182(2.3); 7.166(1.6); 7.163(1.5); 4.594(7.2); 4.395(3.1); 4.380(2.9); 3.943(2.7); 3.900(3.3); 3.558(3.1); 3.515(2.6); 3.326(88.2); 3.309(0.4); 2.892(3.9); 2.733(3.2); 2.732(3.1); 2.677(0.3); 2.672(0.5); 2.668(0.4); 2.525(1.3); 2.521(2.1); 2.512(27.2); 2.508(54.7); 2.503(72.9); 2.498(53.6); 2.494(25.8); 2.334(0.4); 2.330(0.5); 2.325(0.4); 1.684(16.0); 1.234(0.6); 0.008(0.4); 0.000(13.7); −0.009(0.4)
Example 173: $^1$H-NMR(400.0 MHz, DMSO):
8.959(4.4); 8.954(4.4); 8.882(0.9); 8.866(1.9); 8.851(0.9); 8.607(3.2); 8.602(3.0); 8.249(3.3); 8.245(3.5); 8.183(2.0); 8.178(1.6); 8.161(2.9); 8.156(2.7); 8.084(3.6); 8.062(2.3); 7.352(3.5); 7.331(6.2); 7.324(0.9); 7.278(4.3); 7.258(2.5); 4.592(7.8); 4.368(0.4); 4.352(0.4); 4.330(1.9); 4.315(3.3); 4.301(1.9); 4.278(0.4); 4.263(0.5); 3.918(2.7); 3.874(3.3); 3.534(3.2); 3.491(2.7); 3.326(78.4); 2.677(0.4); 2.672(0.5); 2.668(0.4); 2.525(1.5); 2.521(2.4); 2.512(27.7); 2.508 (55.0); 2.503(72.4); 2.498(52.2); 2.494(24.4); 2.334(0.4); 2.330(0.5); 2.325(0.3); 1.643(16.0); 1.234(0.5); 0.008(0.5); 0.000(14.8); −0.009(0.4)
Example 174: $^1$H-NMR(400.0 MHz, DMSO):
9.013(4.1); 9.007(4.2); 8.903(1.0); 8.888(1.9); 8.873(0.9); 8.775(3.4); 8.770(3.2); 8.245(3.4); 8.241(3.7); 8.201(2.0); 8.196(1.6); 8.179(2.8); 8.174(2.5); 8.097(3.6); 8.075(2.4); 7.953(0.6); 7.528(1.8); 7.525(1.9); 7.508(2.2); 7.505(2.2); 7.298(1.8); 7.279(3.8); 7.259(2.2); 7.184(2.3); 7.181(2.3); 7.165(1.6); 4.394(3.1); 4.382(2.9); 3.933(2.7); 3.890(3.2); 3.550(3.1); 3.507(2.6); 3.324(87.7); 2.891(4.2); 2.732(3.4); 2.676(0.5); 2.672(0.7); 2.667(0.5); 2.511(43.0); 2.507 (79.6); 2.502(101.7); 2.498(74.9); 2.494(36.6); 2.334(0.5); 2.329(0.7); 2.325(0.5); 1.684(16.0); 1.234(0.7); 0.008(0.9); 0.000(17.8); −0.009(0.6)
Example 175: $^1$H-NMR(400.0 MHz, DMSO):
8.955(4.5); 8.950(4.6); 8.790(0.9); 8.775(2.0); 8.759(0.9); 8.601(3.3); 8.596(3.1); 8.245(3.3); 8.240(3.6); 8.176(2.0); 8.172(1.7); 8.154(2.9); 8.149(2.7); 8.075(3.6); 8.053(2.4); 7.953(0.4); 7.372(0.5); 7.366(2.9); 7.361(1.1); 7.353(0.6); 7.347(4.4); 7.345(4.1); 7.339(0.6); 7.331(1.4); 7.326(3.9); 7.320(0.5); 7.248(4.7); 7.226(5.3); 7.219(0.6); 7.125(1.0); 7.122(1.8); 7.119(1.1); 7.104(2.9); 7.088(0.8); 7.085(1.3); 7.082(0.7); 6.957(4.1); 6.954(5.0); 6.949(1.3); 6.940(1.5); 6.938(2.4); 6.935(4.3); 6.933(3.8); 6.921(6.6); 6.916(2.0); 6.905(1.9); 6.900(5.8); 6.893(0.6); 4.592(8.5); 4.287(3.6); 4.272(3.6); 3.917(2.7); 3.873(3.3); 3.528(3.2); 3.485(2.7); 3.325(118.2); 2.891(3.6); 2.731(2.8); 2.676(0.5); 2.672(0.6); 2.667(0.4); 2.525(1.9); 2.520(3.1); 2.512(36.7); 2.507(72.8); 2.503(96.0); 2.498(69.6); 2.493(32.8); 2.334(0.5); 2.329(0.6); 2.325(0.5); 1.642(16.0); 1.234(0.7); 0.008(0.6); 0.000(15.0); −0.009(0.5)
Example 176: $^1$H-NMR(400.0 MHz, DMSO):
9.004(2.8); 8.998(2.8); 8.762(2.2); 8.756(2.0); 8.526(0.6); 8.511(1.1); 8.496(0.6); 8.217(2.2); 8.212(2.4); 8.169(1.3); 8.165(1.0); 8.147(1.9); 8.142(1.8); 8.076(2.4); 8.054(1.5); 7.491(3.4); 7.253(3.3); 4.119(1.7); 4.112(1.8); 4.105(1.7); 4.097(1.7); 3.881(1.8); 3.838(2.2); 3.736(16.0); 3.491(2.1); 3.448(1.8); 3.327(142.7); 2.891(1.5); 2.732(1.2); 2.676 (0.4); 2.671(0.6); 2.667(0.4); 2.525(1.7); 2.511(32.5); 2.507(63.2); 2.502(82.8); 2.498(61.3); 2.493(30.0); 2.334(0.4); 2.329(0.5); 2.325(0.4); 1.602(10.9); 1.234(0.5); 0.008(0.3); 0.000(7.6)
Example 177: $^1$H-NMR(400.0 MHz, DMSO):
9.004(3.2); 8.998(3.3); 8.763(2.2); 8.757(2.0); 8.292(0.6); 8.278(1.2); 8.263(0.6); 8.209(2.2); 8.204(2.4); 8.156(1.3); 8.151(1.1); 8.134(2.1); 8.129(2.0); 8.073(2.5); 8.051(1.5); 4.050(1.7); 4.036(2.3); 4.023(1.7); 4.001(0.3); 3.870(1.9); 3.827(2.3); 3.555(15.0); 3.472(2.2); 3.429(1.9); 3.323(125.9); 2.891(1.5); 2.731(1.2); 2.675(0.6); 2.671(0.8); 2.666 (0.6); 2.524(2.5); 2.519(3.9); 2.511(46.8); 2.506(93.7); 2.502(124.6); 2.497(90.2); 2.493(42.4); 2.333(0.6); 2.329(0.8); 2.324(0.6); 2.129(16.0); 2.012(15.3); 1.589(11.3); 1.235(0.5); 0.008(1.0); 0.000(29.2); −0.009(0.9)
Example 178: $^1$H-NMR(300.2 MHz, CDCl3):
8.971(2.6); 8.964(2.6); 8.280(2.2); 8.274(2.2); 8.163(0.7); 8.157(0.7); 8.133(2.3); 8.128(2.4); 8.108(3.0); 8.078(0.9); 7.839(2.4); 7.834(2.3); 7.339(3.6); 7.265(9.2); 6.913(0.9); 6.896(0.6); 4.358(0.7); 4.339(0.7); 4.309(1.5); 4.290(1.4); 4.216(1.5); 4.200(1.5); 4.167(0.8); 4.150(0.7); 3.994(2.1); 3.936(2.5); 3.753(16.0); 3.373(2.4); 3.329(4.9); 3.315(2.2); 2.195(13.8); 1.769(12.4); 1.645(7.0); 0.000(8.2); −0.011(0.5)
Example 179: $^1$H-NMR(400.0 MHz, DMSO):
9.003(2.8); 8.998(2.9); 8.761(2.1); 8.755(2.0); 8.434(0.5); 8.419(1.1); 8.404(0.5); 8.212(2.1); 8.207(2.3); 8.162(1.2); 8.157(1.0); 8.140(1.9); 8.135(1.7); 8.073(2.4); 8.051(1.5); 7.172(4.0); 4.064(3.2); 4.050(3.2); 3.865(1.8); 3.822(2.2); 3.635(16.0); 3.482(2.1); 3.439(1.8); 3.351(0.5); 3.326(171.0); 2.891(1.7); 2.732(1.4); 2.676(0.5); 2.671(0.7); 2.667(0.5); 2.525(1.9); 2.520(2.9); 2.511(38.5); 2.507(78.0); 2.502(104.2); 2.498(75.8); 2.493(36.0); 2.333(0.5); 2.329(0.7); 2.324(0.5); 2.162(14.5); 1.588(10.8); 1.235(0.5); 0.000(10.0)
Example 180: $^1$H-NMR(300.2 MHz, CDCl3):
9.061(2.5); 9.054(2.6); 8.546(1.9); 8.540(1.8); 8.187(1.0); 8.181(1.0); 8.158(1.8); 8.151(1.8); 8.082(2.2); 8.052(1.2); 7.816(2.1); 7.810(2.0); 7.284(1.1); 6.703(0.5); 6.677(0.6); 4.188(0.5); 4.166(0.7); 4.162(0.6); 4.144(0.6); 4.140(0.7); 4.118(0.5); 3.987(2.0); 3.927(2.5); 3.494(2.0); 3.404(16.0); 1.930(0.5); 1.303(0.3); 1.283(0.6); 1.265(8.1); 1.242(10.4); 1.219(6.5); 0.901(0.7); 0.879(2.2); 0.856(0.8); 0.000(0.9)
Example 181: $^1$H-NMR(300.2 MHz, CDCl3):
8.968(3.1); 8.961(3.1); 8.274(2.6); 8.267(2.5); 8.166(0.9); 8.160(0.9); 8.136(2.6); 8.130(2.8); 8.105(3.5); 8.075(1.2); 7.838(2.8); 7.832(2.7); 7.420(3.9); 7.339(4.0); 7.271(3.9); 7.066(0.6); 7.049(1.0); 7.031(0.6); 4.418(0.8); 4.399(0.8); 4.369(1.7); 4.349(1.6); 4.279(1.7); 4.262(1.7); 4.230(0.9); 4.212(0.8); 4.152(1.5); 4.127(4.8); 4.103(4.9); 4.078(1.7);

| NMR Peak Lists Table 1 |
|---|
| 3.997(2.6); 3.940(3.1); 3.379(3.0); 3.333(6.3); 3.322(2.7); 2.046(1.6); 1.776(16.0); 1.471(5.2); 1.447(10.4); 1.422(5.1); 1.283(0.4); 1.259(0.9); 1.236(0.4); 0.000(3.5) |
| Example 182: $^1$H-NMR(400.0 MHz, DMSO): |
| 9.003(4.4); 8.998(4.5); 8.760(3.2); 8.755(2.9); 8.523(0.8); 8.508(1.7); 8.493(0.8); 8.219(3.1); 8.215(3.4); 8.170(2.0); 8.165(1.5); 8.148(3.0); 8.143(2.6); 8.075(3.5); 8.053(2.2); 7.523(5.0); 7.265(4.9); 4.128(4.2); 4.113(4.1); 4.046(1.9); 4.028(6.1); 4.010(6.1); 3.992(2.0); 3.890(2.7); 3.847(3.3); 3.494(3.2); 3.450(2.7); 3.324(56.5); 2.891(0.4); 2.732(0.3); 2.672(0.4); 2.525(1.3); 2.512(24.4); 2.507(47.9); 2.503(62.9); 2.498(45.5); 2.494(21.3); 2.329(0.4); 1.610(16.0); 1.288(6.6); 1.270(14.0); 1.252(6.5); 1.234(0.4); 0.008(0.6); 0.000(15.7); −0.009(0.5) |
| Example 183: $^1$H-NMR(400.0 MHz, DMSO): |
| 8.953(3.1); 8.948(3.1); 8.602(2.2); 8.597(2.1); 8.289(0.6); 8.274(1.3); 8.260(0.6); 8.228(2.3); 8.223(2.4); 8.154(1.3); 8.149(1.1); 8.132(2.1); 8.127(2.0); 8.070(2.6); 8.048(1.5); 7.591(1.6); 4.591(5.6); 4.051(1.8); 4.038(2.4); 4.025(1.8); 4.003(0.3); 3.880(1.9); 3.837(2.3); 3.556(15.1); 3.480(2.2); 3.437(1.9); 3.326(25.4); 2.891(1.8); 2.732(1.4); 2.525(1.0); 2.520(1.6); 2.512(17.7); 2.507(35.0); 2.503(46.3); 2.498(33.6); 2.494(15.8); 2.130(16.0); 2.014(15.4); 1.590(11.2); 1.294(0.4); 1.277(0.8); 1.259(0.4); 0.008(0.4); 0.000(11.3); −0.009(0.3) |
| Example 184: $^1$H-NMR(400.0 MHz, DMSO): |
| 9.004(3.0); 8.998(3.1); 8.765(2.5); 8.759(2.3); 8.316(0.6); 8.247(0.7); 8.233(1.4); 8.211(2.5); 8.207(2.7); 8.155(1.3); 8.151(1.1); 8.133(2.1); 8.128(1.9); 8.072(2.7); 8.050(1.6); 7.953(0.7); 4.360(0.4); 4.343(1.0); 4.327(1.4); 4.311(1.0); 4.294(0.4); 4.113(0.5); 4.098(0.5); 4.076(1.5); 4.061(1.5); 4.049(1.5); 4.035(1.6); 4.013(0.5); 3.999(0.5); 3.879(1.9); 3.836(2.3); 3.478(2.3); 3.434(1.9); 3.321(199.7); 2.890(5.4); 2.731(4.5); 2.675(1.5); 2.670(2.0); 2.666(1.5); 2.661(0.7); 2.510(124.9); 2.506(232.8); 2.501(302.3); 2.497(224.8); 2.493(112.3); 2.333(1.5); 2.328(2.0); 2.324(1.5); 2.133(15.3); 2.032(16.0); 1.598(11.9); 1.388(0.3); 1.280(0.8); 1.267(14.1); 1.250(14.0); 1.235(1.7); 0.008(3.5); 0.000(63.0); −0.008(2.6) |
| Example 185: $^1$H-NMR(400.0 MHz, DMSO): |
| 8.957(4.1); 8.951(4.2); 8.599(3.3); 8.595(3.3); 8.562(0.9); 8.547(1.9); 8.532(1.0); 8.233(3.4); 8.229(3.7); 8.162(1.8); 8.158(1.5); 8.140(2.8); 8.136(2.7); 8.074(3.8); 8.052(2.3); 7.954(0.8); 7.608(5.7); 7.309(5.8); 7.276(0.8); 7.272(1.2); 7.267(0.6); 7.255(3.9); 7.251(2.2); 7.237(4.5); 7.230(1.5); 7.225(2.4); 7.221(1.6); 7.215(0.6); 7.208(2.0); 7.199(0.3); 7.193(0.4); 7.190(0.5); 7.154(3.6); 7.150(4.1); 7.133(3.1); 5.221(10.9); 4.593(7.4); 4.133(4.5); 4.118(4.4); 3.886(2.7); 3.842(3.2); 3.498(3.1); 3.455(2.6); 3.326(74.4); 2.891(5.9); 2.732(4.9); 2.676(0.4); 2.672(0.5); 2.667(0.4); 2.546(0.4); 2.525(1.4); 2.511(28.9); 2.507(56.6); 2.503(74.1); 2.498(54.7); 2.494(26.8); 2.334(0.4); 2.329(0.5); 2.325(0.4); 1.601(16.0); 1.234(0.6); 0.008(0.5); 0.000(13.6); −0.008(0.5) |
| Example 186: $^1$H-NMR(400.0 MHz, DMSO): |
| 8.956(4.1); 8.951(4.2); 8.679(1.0); 8.664(2.0); 8.595(3.3); 8.590(3.2); 8.255(6.0); 8.248(3.6); 8.243(3.8); 8.179(1.9); 8.174(1.7); 8.157(2.8); 8.152(2.7); 8.074(3.6); 8.052(2.4); 7.953(0.4); 7.722(3.2); 7.720(4.3); 7.701(4.6); 7.699(4.4); 7.607(6.1); 7.437(2.8); 7.432(1.1); 7.419(4.4); 7.397(3.2); 7.271(1.7); 7.252(2.6); 7.234(1.1); 4.591(7.7); 4.243(4.4); 4.228(4.4); 3.937(2.7); 3.894(3.3); 3.520(3.1); 3.477(2.7); 3.326(82.6); 2.891(3.5); 2.732(2.8); 2.677(0.4); 2.672(0.5); 2.667(0.4); 2.525(1.6); 2.512(28.3); 2.508(55.9); 2.503(74.3); 2.498(54.6); 2.494(26.5); 2.334(0.4); 2.330(0.5); 2.325(0.3); 1.638(16.0); 1.233(0.7); 0.008(0.5); 0.000(11.3); −0.009(0.4) |
| Example 187: $^1$H-NMR(400.0 MHz, DMSO): |
| 8.961(4.4); 8.955(4.5); 8.649(0.9); 8.634(2.0); 8.619(1.1); 8.611(3.4); 8.606(3.2); 8.239(3.3); 8.235(3.6); 8.186(2.0); 8.181(1.6); 8.164(3.0); 8.159(2.7); 8.091(3.7); 8.069(2.3); 7.953(0.5); 7.352(0.4); 7.346(2.9); 7.341(1.1); 7.333(0.6); 7.327(4.3); 7.324(4.2); 7.319(0.6); 7.311(1.3); 7.306(3.7); 7.300(0.5); 7.247(3.8); 7.228(5.1); 7.210(1.5); 7.206(0.9); 7.088(1.5); 7.085(1.6); 7.081(1.1); 7.078(1.8); 7.076(1.2); 7.067(2.7); 7.060(3.0); 7.050(1.1); 7.048(1.1); 7.044(0.9); 7.041(1.3); 7.039(0.8); 6.940(3.9); 6.937(4.8); 6.932(1.3); 6.921(2.3); 6.918(4.3); 6.916(3.6); 6.909(0.4); 6.850(2.3); 6.848(2.4); 6.843(0.8); 6.829(2.3); 6.826(1.6); 4.592(7.9); 4.330(2.6); 4.313(2.6); 3.878(2.7); 3.835(3.3); 3.513(3.1); 3.470(2.7); 3.354(0.4); 3.327(218.2); 3.304(0.5); 2.891(4.3); 2.732(3.3); 2.676(0.6); 2.672(0.8); 2.667(0.6); 2.525(2.2); 2.520(3.5); 2.512(44.6); 2.507(89.4); 2.502(119.2); 2.498(86.9); 2.493(41.3); 2.334(0.6); 2.329(0.8); 2.325(0.6); 1.636(16.0); 1.234(0.9); 0.008(0.5); 0.000(13.8); −0.009(0.4) |
| Example 188: $^1$H-NMR(400.0 MHz, DMSO): |
| 9.009(4.3); 9.003(4.5); 8.948(0.8); 8.932(1.7); 8.916(0.8); 8.766(3.2); 8.760(2.9); 8.317(0.9); 8.231(3.1); 8.226(3.5); 8.187(2.0); 8.182(1.5); 8.164(2.9); 8.160(2.6); 8.084(3.5); 8.062(2.3); 7.954(1.3); 7.425(1.6); 7.406(3.5); 7.386(2.4); 7.259(2.0); 7.239(1.6); 7.184(1.3); 7.163(1.1); 7.140(2.3); 4.345(3.6); 4.330(3.6); 3.905(2.7); 3.862(3.3); 3.535(3.1); 3.492(2.6); 3.326(79.7); 3.303(0.5); 2.891(10.6); 2.733(8.3); 2.732(8.3); 2.677(0.3); 2.672(0.5); 2.667(0.3); 2.525(1.2); 2.512(26.4); 2.508(52.3); 2.503(68.6); 2.498(49.6); 2.494(23.4); 2.334(0.3); 2.330(0.4); 1.653(16.0); 1.233(0.4); 0.008(0.4); 0.000(12.0); −0.009(0.3) |
| Example 189: $^1$H-NMR(400.0 MHz, DMSO): |
| 8.962(4.0); 8.957(4.1); 8.894(1.0); 8.879(2.1); 8.864(1.0); 8.602(3.3); 8.597(3.3); 8.257(3.3); 8.253(3.7); 8.193(1.9); 8.188(1.6); 8.171(2.7); 8.166(2.6); 8.087(3.6); 8.065(2.4); 7.906(3.1); 7.882(4.5); 7.860(7.3); 7.477(2.3); 7.473(1.0); 7.458(4.5); 7.438(3.3); 7.369(1.8); 7.350(2.6); 7.332(0.9); 4.593(7.1); 4.475(4.7); 4.460(4.7); 3.950(2.7); 3.907(3.2); 3.550(3.1); 3.506(2.6); 3.326(100.6); 2.891(2.3); 2.732(1.9); 2.677(0.4); 2.672(0.6); 2.668(0.4); 2.525(1.5); 2.512(31.6); 2.507(62.6); 2.503(83.1); 2.498(62.4); 2.494(31.0); 2.334(0.4); 2.330(0.5); 2.325(0.4); 1.666(16.0); 1.234(0.7); 0.008(0.5); 0.000(12.8); −0.009(0.4) |
| Example 190: $^1$H-NMR(400.0 MHz, DMSO): |
| 8.959(2.4); 8.953(2.5); 8.946(0.6); 8.929(1.2); 8.914(0.6); 8.606(2.0); 8.601(1.9); 8.251(2.0); 8.246(2.2); 8.184(1.1); 8.180(0.9); 8.162(1.6); 8.157(1.5); 8.082(2.2); 8.060(1.4); 7.953(2.2); 7.425(0.9); 7.405(2.1); 7.385(1.4); 7.258(1.3); 7.239(1.0); 7.184(0.9); 7.163(0.8); 7.141(1.5); 4.591(4.3); 4.345(2.3); 4.329(2.3); 3.914(1.6); 3.871(1.9); 3.543(1.9); 3.499(1.5); 3.326(56.2); 2.891(16.0); 2.732(13.4); 2.672(0.3); 2.525(1.0); 2.511(20.0); 2.507(39.0); 2.503(51.1); 2.498(37.7); 2.494(18.5); 2.329(0.3); 1.652(9.5); 0.000(7.3) |
| Example 191: $^1$H-NMR(400.0 MHz, DMSO): |
| 12.746(1.1); 9.007(4.0); 9.002(4.1); 8.770(3.0); 8.764(2.9); 8.518(0.6); 8.504(1.0); 8.490(0.5); 8.214(2.7); 8.210(2.8); 8.156(1.1); 8.152(0.9); 8.134(1.9); 8.129(1.6); 8.075(3.3); 8.053(2.0); 7.953(2.0); 7.565(2.1); 7.382(1.4); 7.369(1.3); 7.273(1.3); 7.265(1.3); 7.028(0.9); 7.018(1.1); 7.006(0.8); 4.364(2.0); 4.350(2.1); 3.912(2.3); 3.869(2.8); 3.502(2.7); 3.459(2.4); 3.326(101.3); 2.891(16.0); 2.751(0.4); 2.731(12.9); 2.676(0.4); 2.671(0.6); 2.667(0.4); 2.547(1.2); 2.534(0.5); 2.525(1.7); 2.511(32.6); 2.507(65.0); 2.502(86.2); 2.498(63.1); 2.493(30.3); 2.334(0.4); 2.329(0.6); 2.325(0.4); 1.630(14.1); 1.234(0.6); 0.008(0.6); 0.000(18.1); −0.009(0.6) |
| Example 192: $^1$H-NMR(400.0 MHz, DMSO): |
| 12.745(0.6); 8.958(3.6); 8.953(3.6); 8.611(2.7); 8.606(2.6); 8.507(0.9); 8.235(2.7); 8.231(2.9); 8.155(1.4); 8.150(1.2); 8.133(2.2); 8.128(2.0); 8.073(3.1); 8.050(1.9); 7.953(1.9); 7.563(0.9); 7.379(0.7); 7.275(0.8); 7.022(0.7); 4.593(6.4); |

| NMR Peak Lists Table 1 |
| --- |

4.359(1.7); 4.347(1.8); 4.316(0.7); 4.298(0.6); 3.922(2.2); 3.878(2.6); 3.510(2.5); 3.467(2.2); 3.327(66.8); 2.891(16.0); 2.751(0.5); 2.748(0.8); 2.731(12.8); 2.676(0.5); 2.672(0.6); 2.667(0.5); 2.559(1.1); 2.546(2.3); 2.532(1.4); 2.525(1.9); 2.511(35.3); 2.507(69.6); 2.502(91.9); 2.498(67.0); 2.493(32.1); 2.334(0.4); 2.329(0.6); 2.325(0.4); 1.652(0.6); 1.630(12.9); 1.297(0.5); 1.280(1.2); 1.262(0.5); 1.234(0.7); 0.008(0.7); 0.000(18.5); −0.009(0.5)

Example 193: $^1$H-NMR(400.0 MHz, DMSO):
8.958(4.4); 8.953(4.7); 8.945(1.3); 8.929(2.0); 8.914(1.0); 8.604(3.4); 8.599(3.3); 8.257(3.5); 8.253(3.7); 8.193(2.0); 8.188(1.8); 8.171(2.9); 8.166(2.7); 8.085(3.6); 8.063(2.4); 7.954(1.3); 7.425(2.0); 7.420(3.6); 7.415(2.2); 7.232(7.9); 7.227(7.5); 4.591(7.4); 4.344(0.4); 4.328(0.4); 4.305(2.1); 4.290(3.5); 4.276(2.1); 4.252(0.4); 4.236(0.3); 3.911(2.7); 3.868(3.2); 3.542(3.1); 3.499(2.6); 3.327(103.8); 2.892(9.7); 2.733(7.7); 2.732(7.7); 2.677(0.4); 2.672(0.5); 2.668(0.4); 2.512(31.9); 2.508(59.1); 2.503(76.8); 2.499(58.3); 2.494(30.9); 2.335(0.4); 2.330(0.5); 2.325(0.4); 1.653(16.0); 1.233(0.5); 0.008(0.4); 0.000(8.4); −0.008(0.6)

Example 194: $^1$H-NMR(400.0 MHz, DMSO):
8.967(4.3); 8.962(4.4); 8.869(1.0); 8.853(1.9); 8.838(0.9); 8.613(3.4); 8.608(3.3); 8.268(3.4); 8.264(3.7); 8.195(1.9); 8.191(1.6); 8.173(2.9); 8.168(2.7); 8.100(3.8); 8.078(2.4); 7.990(3.3); 7.977(3.4); 7.953(1.4); 6.538(2.5); 6.525(2.6); 6.512(4.0); 4.598(7.6); 4.323(0.8); 4.307(0.8); 4.283(1.5); 4.267(1.4); 4.198(1.4); 4.183(1.5); 4.158(0.9); 4.143(0.8); 3.958(2.7); 3.915(3.2); 3.538(3.2); 3.513(4.3); 3.501(7.0); 3.495(5.5); 3.489(5.6); 3.325(77.0); 3.263(4.7); 3.254(5.5); 3.248(5.7); 3.239(3.3); 2.891(11.2); 2.751(0.3); 2.732(9.0); 2.676(0.6); 2.672(0.6); 2.667(0.4); 2.534(0.3); 2.525(1.6); 2.511(33.1); 2.507(65.9); 2.502(87.2); 2.498(63.9); 2.493(30.7); 2.334(0.4); 2.329(0.6); 2.325(0.4); 1.677(16.0); 1.234(0.7); 0.008(0.7); 0.000(19.2); −0.009(0.5)

Example 195: $^1$H-NMR(300.2 MHz, CDCl3):
8.969(2.7); 8.962(2.8); 8.276(2.3); 8.270(2.3); 8.161(0.8); 8.155(0.8); 8.132(2.4); 8.126(2.5); 8.104(3.2); 8.074(1.0); 7.837(2.5); 7.832(2.5); 7.363(4.0); 7.270(3.8); 6.931(0.5); 6.915(0.9); 6.898(0.6); 4.366(0.8); 4.347(0.8); 4.317(1.6); 4.298(1.6); 4.222(1.6); 4.205(1.6); 4.173(0.9); 4.156(0.9); 4.095(1.3); 4.071(4.1); 4.046(4.2); 4.022(1.4); 3.999(2.4); 3.942(2.8); 3.375(2.7); 3.333(5.7); 3.318(2.3); 2.201(16.0); 2.175(0.4); 2.046(1.0); 1.774(14.3); 1.412(4.3); 1.388(9.0); 1.364(4.3); 1.260(0.6); 0.000(3.4)

Example 196: $^1$H-NMR(400.0 MHz, DMSO):
8.953(2.9); 8.948(3.0); 8.604(2.3); 8.599(2.2); 8.245(0.7); 8.230(3.5); 8.225(2.9); 8.217(0.7); 8.153(1.2); 8.148(1.1); 8.131(2.0); 8.126(1.9); 8.069(2.6); 8.047(1.6); 7.953(0.5); 4.590(5.4); 4.360(0.4); 4.343(1.0); 4.327(1.3); 4.310(1.0); 4.294(0.4); 4.115(0.5); 4.100(0.5); 4.078(1.5); 4.063(1.4); 4.051(1.4); 4.037(1.5); 4.014(0.5); 4.001(0.5); 3.888(1.9); 3.845(2.3); 3.486(2.2); 3.442(1.8); 3.325(50.7); 2.891(3.8); 2.732(3.2); 2.672(0.3); 2.525(0.9); 2.512(18.8); 2.507(37.5); 2.503(50.0); 2.498(36.6); 2.494(17.5); 2.329(0.3); 2.134(15.1); 2.034(16.0); 1.599(11.1); 1.267(13.3); 1.250(13.2); 1.234(0.4); 0.008(0.3); 0.000(10.4)

Example 197: $^1$H-NMR(400.0 MHz, DMSO):
8.954(3.2); 8.949(3.4); 8.602(2.4); 8.597(2.4); 8.510(0.7); 8.495(1.4); 8.480(0.7); 8.244(2.5); 8.239(2.7); 8.170(1.4); 8.165(1.3); 8.147(2.2); 8.143(2.1); 8.074(2.8); 8.051(1.8); 7.526(4.2); 7.265(4.0); 4.591(6.0); 4.406(0.5); 4.389(1.3); 4.372(1.7); 4.356(1.3); 4.339(0.5); 4.136(3.4); 4.121(3.3); 3.906(2.1); 3.863(2.5); 3.503(2.4); 3.460(2.0); 3.325(46.3); 2.891(1.2); 2.732(0.9); 2.672(0.4); 2.525(1.0); 2.512(20.0); 2.507(40.3); 2.503(53.9); 2.498(40.0); 2.494(19.7); 2.329(0.4); 1.615(12.3); 1.313(16.0); 1.296(15.9); 1.234(0.4); 0.008(0.4); 0.000(12.1); −0.009(0.4)

Example 198: $^1$H-NMR(400.0 MHz, DMSO):
9.009(0.6); 9.003(0.7); 8.962(4.2); 8.957(4.3); 8.857(1.0); 8.842(2.0); 8.827(1.0); 8.766(0.5); 8.761(0.5); 8.615(3.4); 8.610(3.3); 8.258(3.4); 8.254(3.7); 8.231(0.5); 8.226(0.6); 8.194(1.9); 8.189(1.7); 8.182(0.4); 8.172(2.8); 8.167(2.7); 8.160(0.5); 8.093(3.7); 8.084(0.7); 8.071(2.4); 8.062(0.4); 7.953(0.7); 7.582(3.9); 7.577(4.1); 7.405(0.5); 7.385(0.4); 7.372(1.9); 7.367(1.8); 7.352(2.5); 7.346(2.5); 7.257(0.4); 7.238(3.8); 7.217(2.6); 7.140(0.4); 4.594(7.7); 4.346(2.6); 4.332(3.1); 4.321(2.2); 4.296(0.3); 3.931(2.7); 3.904(0.5); 3.888(3.3); 3.861(0.5); 3.550(3.1); 3.535(0.5); 3.507(2.7); 3.492(0.4); 3.327(206.6); 3.293(0.3); 2.891(5.3); 2.731(4.4); 2.676(0.6); 2.672(0.9); 2.667(0.6); 2.525(2.6); 2.511(49.3); 2.507(96.8); 2.502(128.1); 2.498(95.6); 2.494(47.5); 2.334(0.6); 2.329(0.9); 2.325(0.6); 1.669(16.0); 1.653(2.8); 1.234(0.9); 0.008(0.4); 0.000(10.1); −0.008(0.4)

Example 199: $^1$H-NMR(400.0 MHz, DMSO):
9.004(3.5); 8.998(3.6); 8.762(2.6); 8.756(2.5); 8.513(0.7); 8.498(1.4); 8.483(0.7); 8.223(2.6); 8.219(2.9); 8.172(1.6); 8.167(1.3); 8.149(2.4); 8.145(2.1); 8.076(2.9); 8.054(1.9); 7.528(4.4); 7.265(4.3); 4.407(0.5); 4.391(1.3); 4.374(1.8); 4.357(1.3); 4.341(0.5); 4.136(3.7); 4.121(3.7); 3.898(2.2); 3.854(2.7); 3.496(2.6); 3.452(2.2); 3.325(51.8); 2.892(2.1); 2.732(1.8); 2.672(0.4); 2.525(1.0); 2.520(1.6); 2.512(22.7); 2.507(45.4); 2.503(60.2); 2.498(44.2); 2.494(21.4); 2.329(0.4); 1.616(13.3); 1.315(16.0); 1.298(15.9); 1.234(0.5); 0.008(0.4); 0.000(12.8); −0.009(0.4)

Example 200: $^1$H-NMR(400.0 MHz, DMSO):
8.958(4.1); 8.953(4.1); 8.851(0.9); 8.836(1.9); 8.821(0.9); 8.607(3.4); 8.602(3.2); 8.246(3.3); 8.241(3.6); 8.180(1.9); 8.175(1.6); 8.158(2.8); 8.153(2.5); 8.084(3.7); 8.062(2.3); 7.916(1.1); 7.911(0.4); 7.899(0.4); 7.894(1.2); 7.566(1.2); 7.562(0.4); 7.550(0.4); 7.545(1.0); 7.400(0.7); 7.383(0.4); 7.378(1.5); 7.342(4.8); 7.337(1.7); 7.325(2.7); 7.320(7.4); 7.315(1.1); 7.254(6.2); 7.233(3.9); 4.592(6.9); 4.463(0.9); 4.448(0.9); 4.309(0.4); 4.286(2.2); 4.274(2.7); 4.260(2.1); 4.237(0.3); 3.907(2.7); 3.864(3.3); 3.527(3.1); 3.484(2.6); 3.325(43.2); 2.892(0.4); 2.733(0.4); 2.677(0.3); 2.672(0.5); 2.668(0.3); 2.525(1.8); 2.512(27.6); 2.508(52.6); 2.503(68.3); 2.498(49.8); 2.494(24.2); 2.334(0.3); 2.330(0.5); 1.634(16.0); 1.234(0.5); 0.008(0.5); 0.000(12.1); −0.009(0.4)

Example 201: $^1$H-NMR(400.0 MHz, DMSO):
9.006(3.8); 9.000(4.0); 8.757(3.3); 8.751(3.2); 8.564(0.9); 8.549(1.8); 8.534(0.9); 8.212(3.2); 8.208(3.7); 8.164(1.7); 8.159(1.5); 8.142(2.7); 8.137(2.6); 8.076(3.7); 8.054(2.2); 7.953(0.6); 7.607(5.1); 7.308(5.7); 7.278(0.7); 7.273(1.1); 7.256(3.9); 7.238(4.2); 7.232(1.5); 7.227(2.3); 7.223(1.6); 7.217(0.6); 7.210(1.9); 7.191(0.4); 7.153(3.4); 7.149(4.1); 7.132(3.0); 5.220(10.6); 4.132(4.4); 4.117(4.4); 3.876(2.6); 3.833(3.2); 3.490(3.0); 3.447(2.6); 3.325(80.7); 2.891(5.7); 2.731(4.8); 2.676(0.4); 2.671(0.6); 2.667(0.4); 2.524(1.6); 2.507(64.8); 2.502(86.9); 2.498(66.0); 2.333(0.4); 2.329 (0.6); 2.325(0.4); 1.601(16.0); 1.234(0.7); 0.008(0.4); 0.000(13.2); −0.008(0.5)

Example 202: $^1$H-NMR(400.0 MHz, DMSO):
9.005(4.2); 8.999(4.3); 8.752(3.3); 8.747(3.1); 8.681(0.9); 8.666(1.9); 8.651(0.9); 8.255(5.5); 8.226(3.2); 8.222(3.6); 8.180(2.0); 8.176(1.6); 8.158(2.9); 8.153(2.6); 8.076(3.5); 8.054(2.3); 7.723(3.1); 7.720(4.0); 7.701(4.4); 7.699(4.1); 7.606(5.9); 7.439(2.7); 7.434(1.0); 7.420(4.2); 7.399(3.0); 7.394(0.4); 7.272(1.6); 7.253(2.5); 7.235(1.1); 4.242(4.3); 4.227(4.3); 3.927(2.7); 3.884(3.2); 3.512(3.1); 3.469(2.6); 3.327(122.2); 2.891(2.5); 2.731(2.0); 2.676(0.4); 2.672(0.6); 2.667(0.4); 2.525(1.9); 2.512(35.0); 2.507(68.0); 2.503(89.0); 2.498(65.0); 2.494(31.1); 2.334(0.4); 2.330(0.6); 2.325(0.4); 1.639(16.0); 1.234(0.5); 0.008(0.3); 0.000(8.8)

-continued

NMR Peak Lists Table 1

Example 203: ¹H-NMR(400.0 MHz, DMSO):
9.008(2.5); 9.003(2.5); 8.786(0.6); 8.768(2.6); 8.762(2.1); 8.317(0.4); 8.227(2.0); 8.222(2.1); 8.176(1.1); 8.171(0.9); 8.154(1.7); 8.149(1.5); 8.082(2.1); 8.060(1.3); 7.953(0.3); 7.244(3.5); 7.240(4.2); 6.032(2.4); 6.027(2.3); 4.338(2.8); 4.323(2.9); 3.899(1.6); 3.856(2.0); 3.745(16.0); 3.518(1.9); 3.474(1.6); 3.328(222.5); 2.891(2.4); 2.731(2.0); 2.675 (0.9); 2.671(1.2); 2.667(0.9); 2.510(76.0); 2.506(143.5); 2.502(180.5); 2.497(129.8); 2.493(63.4); 2.333(0.8); 2.329 (1.1); 2.324(0.8); 1.626(9.7); 0.008(1.4); 0.000(36.8); −0.009(1.7)

Example 204: ¹H-NMR(400.0 MHz, DMSO):
11.015(3.1); 9.020(3.5); 9.015(3.6); 8.994(1.0); 8.989(0.9); 8.803(3.1); 8.797(2.9); 8.770(0.9); 8.764(0.9); 8.316(0.5); 8.274(3.2); 8.270(3.3); 8.182(2.2); 8.177(1.6); 8.160(2.7); 8.155(2.5); 8.097(3.4); 8.074(2.5); 8.049(0.6); 7.952(0.7); 7.871(4.3); 4.303(2.6); 4.259(2.9); 4.150(3.0); 3.929(0.5); 3.886(0.5); 3.675(2.7); 3.631(2.5); 3.430(0.5); 3.402(0.4); 3.330(369.9); 2.891(4.6); 2.748(0.5); 2.732(4.0); 2.676(1.5); 2.672(2.1); 2.667(1.5); 2.507(268.0); 2.502(339.0); 2.498(240.6); 2.440(0.4); 2.334(1.6); 2.329(2.1); 2.325(1.5); 1.772(16.0); 1.615(0.6); 1.575(1.3); 1.235(0.5); 1.068 (0.5); 0.146(0.5); 0.008(3.5); 0.000(89.1); −0.008(3.2); −0.149(0.4)

Example 205: ¹H-NMR(400.0 MHz, DMSO):
9.011(4.1); 9.006(4.3); 8.998(4.2); 8.992(4.4); 8.774(3.0); 8.769(2.8); 8.751(3.1); 8.745(2.9); 8.552(1.4); 8.549(1.6); 8.547(1.7); 8.545(1.5); 8.540(1.6); 8.537(1.9); 8.535(2.0); 8.533(2.1); 8.528(2.3); 8.524(2.2); 8.508(2.3); 8.504(2.2); 8.493(1.5); 8.491(1.7); 8.489(1.8); 8.486(1.5); 8.481(1.5); 8.479(1.7); 8.476(1.7); 8.474(1.4); 8.253(2.9); 8.248(3.3); 8.214(3.1); 8.209(4.9); 8.204(1.8); 8.186(2.7); 8.181(2.5); 8.172(2.0); 8.167(1.6); 8.150(2.9); 8.145(2.6); 8.093(3.2); 8.070(5.6); 8.048(2.3); 7.812(1.1); 7.808(1.1); 7.793(2.0); 7.789(2.0); 7.774(1.3); 7.770(1.3); 7.705(1.1); 7.701(1.1); 7.686(2.1); 7.681(2.1); 7.667(1.4); 7.662(1.3); 7.628(0.4); 7.422(2.4); 7.402(2.1); 7.329(2.5); 7.309(2.3); 7.303(1.4); 7.301(1.3); 7.291(1.2); 7.288(1.3); 7.284(1.3); 7.282(1.2); 7.272(1.2); 7.270(1.1); 7.237(1.3); 7.234(1.3); 7.225(1.3); 7.222(1.4); 7.218(1.4); 7.216(1.2); 7.206(1.2); 7.203(1.1); 5.016(1.3); 4.998(2.1); 4.982(2.1); 4.965(1.3); 3.948(2.6); 3.905(3.1); 3.885(2.7); 3.842(3.3); 3.530(3.0); 3.514(3.2); 3.486(2.6); 3.471(2.7); 3.326(130.9); 2.892(1.4); 2.752(0.4); 2.733(1.1); 2.732(1.1); 2.677(0.6); 2.672(0.9); 2.668(0.6); 2.546(0.3); 2.526(2.4); 2.521(3.9); 2.512(48.7); 2.508(97.2); 2.503(128.7); 2.499(94.0); 2.494(44.7); 2.334(0.6); 2.330(0.9); 2.325(0.6); 1.677(16.0); 1.627(15.3); 1.441(8.3); 1.424(8.2); 1.388(8.2); 1.371(8.0); 1.234(1.0); 0.008(0.9); 0.000(27.3); −0.009(0.8)

Example 206: ¹H-NMR(300.2 MHz, CDCl3):
8.970(2.6); 8.963(2.6); 8.947(3.3); 8.940(3.3); 8.607(1.0); 8.593(1.1); 8.538(1.3); 8.535(1.2); 8.524(1.4); 8.288(1.9); 8.282(1.9); 8.248(2.5); 8.242(2.5); 8.229(1.2); 8.222(1.1); 8.199(1.8); 8.193(1.9); 8.163(1.3); 8.156(1.3); 8.133(2.7); 8.126(4.4); 8.094(2.3); 8.076(3.4); 8.062(1.0); 8.046(1.9); 8.037(0.9); 7.876(2.2); 7.871(2.2); 7.813(2.8); 7.807(2.8); 7.698(0.7); 7.692(0.7); 7.672(1.4); 7.666(1.4); 7.647(0.9); 7.641(0.9); 7.605(0.9); 7.599(0.9); 7.580(1.8); 7.574(1.8); 7.554(1.2); 7.548(1.1); 7.268(8.1); 7.252(1.7); 7.230(1.7); 7.226(2.1); 7.214(0.7); 7.211(0.9); 7.206(1.0); 7.202(0.8); 7.189(0.9); 7.186(0.9); 7.177(2.2); 7.159(1.5); 7.155(1.9); 7.151(2.1); 7.143(1.4); 7.139(1.7); 7.134(1.3); 7.131(1.0); 7.118(1.1); 7.114(0.9); 5.130(1.1); 5.107(2.2); 5.083(2.3); 5.060(1.3); 4.028(2.1); 3.971(2.8); 3.965(3.1); 3.908(3.3); 3.387(2.4); 3.351(3.2); 3.331(6.7); 3.317(6.5); 3.294(2.7); 2.046(0.6); 1.821(16.0); 1.770(3.0); 1.742(12.5); 1.535(8.4); 1.512(8.4); 1.468(6.6); 1.445(6.6); 1.283(0.3); 1.259(1.0); 0.881(0.7); 0.000(7.1)

Example 207: ¹H-NMR(400.0 MHz, DMSO):
10.036(0.5); 9.045(0.4); 9.009(1.7); 9.003(1.6); 8.962(0.5); 8.957(0.6); 8.783(0.6); 8.770(1.3); 8.765(1.1); 8.315(3.1); 8.255(0.5); 8.233(1.1); 8.229(1.2); 8.218(0.6); 8.187(0.8); 8.182(0.6); 8.172(0.6); 8.165(1.1); 8.160(1.0); 8.119(0.9); 8.093(0.7); 8.087(1.2); 8.065(0.9); 7.952(0.8); 7.882(0.4); 7.865(0.4); 7.705(0.4); 7.695(0.5); 7.686(0.4); 7.672(0.4); 7.646(1.4); 7.643(1.5); 7.631(1.5); 7.627(2.6); 7.623(2.4); 7.614(2.1); 7.597(2.9); 7.593(1.5); 7.583(0.7); 7.574(1.9); 7.566(2.1); 7.556(1.6); 7.551(1.8); 7.548(1.8); 7.537(1.0); 7.530(0.9); 7.484(0.6); 7.464(0.8); 7.443(0.7); 7.440(0.7); 7.420(0.9); 7.402(2.8); 7.395(3.5); 7.390(2.8); 7.376(6.2); 7.373(6.5); 7.362(4.8); 7.355(5.7); 7.346(3.5); 7.338(2.7); 7.323(2.2); 7.307(1.6); 7.302(1.6); 7.282(2.4); 7.264(3.0); 7.251(2.5); 7.246(3.2); 7.237(1.7); 7.232(1.9); 7.226(2.0); 7.218(2.6); 7.207(1.5); 7.201(1.7); 7.187(1.5); 7.173(2.3); 7.168(2.4); 7.157(0.7); 7.150(2.8); 7.146(2.4); 7.139(2.7); 7.131(3.3); 7.123(2.5); 7.112(3.7); 7.093(2.1); 7.060(0.9); 7.038(0.9); 7.016(0.9); 7.004(0.7); 6.993(0.8); 6.976(2.6); 6.973(3.0); 6.968(1.7); 6.959(3.8); 6.955(6.0); 6.952(5.6); 6.938(3.4); 6.933(4.2); 6.906(1.1); 6.886(1.6); 6.868(2.8); 6.859(2.1); 6.850(2.4); 6.840(1.8); 6.095(0.6); 5.896(0.6); 5.876(0.6); 4.999(0.5); 4.825(0.3); 4.623(0.5); 4.604(0.4); 4.593(0.9); 4.497(0.4); 4.483(0.4); 4.438(0.5); 4.415(1.7); 4.399(1.7); 4.376(0.9); 4.362(0.9); 4.331(0.8); 4.310(2.1); 4.295(1.9); 4.290(1.4); 4.251(0.9); 4.236(1.1); 4.223(1.1); 4.204(8.4); 4.194(1.9); 4.179(1.8); 4.165(0.3); 4.147(0.4); 4.139(0.4); 4.130(0.5); 4.112(1.0); 4.094(1.2); 3.927(0.4); 3.913(1.0); 3.886(0.5); 3.869(1.2); 3.787(1.2); 3.736(1.1); 3.550(0.4); 3.521(1.0); 3.506(0.8); 3.478(0.8); 3.324(1867.3); 3.267(0.9); 3.253(0.5); 2.891(6.7); 2.799(5.0); 2.758 (0.8); 2.732(5.1); 2.680(2.9); 2.675(6.0); 2.671(8.2); 2.666(5.8); 2.524(7.1); 2.524(27.1); 2.511(486.5); 2.506(942.8); 2.502(1229.4); 2.497(889.7); 2.493(422.2); 2.338(3.1); 2.333(6.2); 2.328(8.3); 2.324(6.0); 2.320(2.8); 2.299(0.6); 2.281(0.8); 2.262(0.5); 2.239(0.3); 2.216(0.3); 2.198(0.3); 2.178(0.6); 2.160(0.4); 2.124(0.7); 1.841(3.1); 1.744(0.8); 1.715(0.8); 1.668(1.9); 1.646(5.7); 1.636(1.7); 1.619(0.9); 1.609(0.9); 1.528(0.6); 1.494(0.7); 1.388(2.4); 1.352(0.5); 1.336(0.6); 1.298(1.2); 1.281(4.1); 1.259(2.5); 1.235(16.0); 1.217(2.1); 1.199(2.9); 1.193(1.3); 1.181(1.6); 1.174(2.0); 1.148(2.0); 1.110(0.8); 1.086(0.9); 1.056(0.8); 1.025(0.4); 0.894(0.7); 0.876(1.5); 0.870(1.0); 0.863(1.3); 0.854(2.3); 0.837(0.9); 0.146(0.6); 0.061(1.9); 0.051(1.1); 0.008(6.8); 0.000(160.1); −0.009(5.0); −0.149(0.6)

Example 208: ¹H-NMR(400.0 MHz, DMSO):
8.957(3.0); 8.952(3.1); 8.698(0.6); 8.682(1.3); 8.667(0.6); 8.606(2.3); 8.601(2.2); 8.244(2.3); 8.239(2.5); 8.177(1.3); 8.172(1.1); 8.154(2.0); 8.150(1.9); 8.081(2.6); 8.058(1.7); 6.739(1.9); 6.719(4.0); 6.703(2.1); 6.699(3.0); 6.686(2.3); 6.681(1.4); 6.666(1.0); 6.661(0.8); 4.590(5.3); 4.170(3.4); 4.155(16.0); 4.144(1.0); 3.897(1.9); 3.853(2.3); 3.516(2.2); 3.473(1.9); 3.341(237.2); 2.891(1.1); 2.732(0.9); 2.672(0.4); 2.526(1.1); 2.521(1.7); 2.512(23.1); 2.508(46.7); 2.503(62.6); 2.499(46.0); 2.494(22.2); 2.330(0.4); 1.624(11.3); 0.000(0.3)

Example 209: ¹H-NMR(400.0 MHz, DMSO):
8.962(4.3); 8.957(4.4); 8.607(3.2); 8.601(3.0); 8.241(0.9); 8.227(1.7); 8.212(0.9); 8.197(3.1); 8.192(3.6); 8.167(1.9); 8.162(1.3); 8.145(3.1); 8.140(2.7); 8.089(3.7); 8.067(2.2); 7.255(0.5); 7.248(4.7); 7.243(1.6); 7.231(1.8); 7.226(5.8); 7.219(0.6); 7.053(3.7); 7.034(3.1); 4.589(7.0); 3.731(2.6); 3.688(3.4); 3.451(3.2); 3.407(2.9); 3.389(1.0); 3.372(1.5); 3.356(1.8); 3.329(175.5); 3.306(1.5); 3.290(0.5); 2.891(0.5); 2.794(1.7); 2.777(2.9); 2.759(1.3); 2.732(0.4); 2.676 (0.5); 2.672(0.7); 2.667(0.5); 2.525(1.7); 2.520(2.7); 2.512(37.2); 2.507(75.5); 2.503(100.9); 2.498(73.6); 2.494(35.0); 2.334(0.5); 2.329(0.6); 2.325(0.5); 1.542(16.0); 1.234(0.6); 0.000(5.7)

Example 210: ¹H-NMR(400.0 MHz, DMSO):
8.962(4.2); 8.957(4.2); 8.615(3.4); 8.610(3.2); 8.215(1.1); 8.203(4.8); 8.199(5.2); 8.187(1.0); 8.169(1.9); 8.164(1.4); 8.147(3.1); 8.142(2.7); 8.096(3.8); 8.074(2.1); 7.954(0.7); 7.154(1.5); 7.147(0.9); 7.132(10.7); 7.124(11.3); 7.118(1.4); 7.109(0.8); 7.102(1.5); 4.593(7.5); 3.729(2.5); 3.686(3.3); 3.449(3.3); 3.405(2.7); 3.392(0.7); 3.376(1.2); 3.358(2.0);

-continued

NMR Peak Lists Table 1

3.330(194.2); 3.296(1.6); 3.279(1.0); 3.264(0.5); 2.891(5.4); 2.751(2.4); 2.732(7.9); 2.716(1.6); 2.677(0.5); 2.672(0.6);
2.668(0.5); 2.525(2.7); 2.512(38.5); 2.507(71.7); 2.503(92.1); 2.498(67.4); 2.494(32.6); 2.334(0.5); 2.330(0.6);
2.325(0.4); 1.554(16.0); 1.234(0.5); 0.000(5.0)
Example 211: $^1$H-NMR(400.0 MHz, DMSO):
9.013(4.4); 9.007(4.6); 8.766(3.2); 8.761(3.1); 8.244(0.8); 8.229(1.7); 8.215(0.9); 8.169(5.8); 8.147(3.4); 8.142(2.5);
8.092(3.4); 8.070(2.0); 7.254(0.5); 7.247(4.6); 7.242(1.6); 7.230(1.8); 7.225(5.7); 7.218(0.6); 7.048(3.6); 7.028(3.0);
3.719(2.6); 3.676(3.4); 3.443(3.3); 3.427(0.3); 3.409(0.8); 3.400(2.8); 3.394(1.2); 3.376(1.9); 3.343(185.7); 3.324(2.6);
3.306(1.2); 3.291(0.7); 2.893(0.9); 2.795(1.7); 2.777(2.8); 2.760(1.2); 2.734(0.8); 2.674(0.3); 2.527(1.1); 2.522(1.8);
2.514(19.8); 2.509(38.8); 2.505(50.8); 2.500(36.5); 2.496(17.1); 2.332(0.3); 1.545(16.0); 1.233(0.4); 0.000(1.0)
Example 212: $^1$H-NMR(400.0 MHz, DMSO):
8.963(4.4); 8.957(4.6); 8.616(3.2); 8.611(3.2); 8.281(0.9); 8.267(1.7); 8.252(0.9); 8.201(3.1); 8.196(3.8); 8.170(1.9);
8.166(1.4); 8.148(3.2); 8.144(2.8); 8.098(3.9); 8.076(2.1); 7.953(1.0); 7.432(4.2); 7.426(4.3); 7.208(3.3); 7.187(4.1);
7.021(2.5); 7.016(2.4); 7.001(2.0); 6.995(2.0); 4.592(7.9); 3.723(2.6); 3.680(3.3); 3.452(0.8); 3.443(3.4); 3.436(1.4);
3.420(1.4); 3.399(3.2); 3.387(0.7); 3.376(0.6); 3.336(326.0); 3.315(2.2); 3.299(1.0); 3.283(0.5); 2.892(8.0); 2.878(1.2);
2.870(1.3); 2.862(2.2); 2.853(2.2); 2.836(1.1); 2.751(0.4); 2.7324(6.3); 2.7315(6.1); 2.677(0.5); 2.672(0.7); 2.668(0.5);
2.526(1.9); 2.521(2.8); 2.512(38.4); 2.508(78.2); 2.503(104.6); 2.499(76.6); 2.494(36.6); 2.335(0.5); 2.330(0.7);
2.326(0.5); 1.554(16.0); 1.234(0.6); 0.000(1.4)
Example 213: $^1$H-NMR(400.0 MHz, DMSO):
8.957(7.5); 8.952(7.8); 8.615(3.3); 8.611(5.8); 8.381(0.8); 8.364(1.9); 8.347(2.0); 8.331(0.8); 8.240(2.9); 8.235(3.2);
8.216(3.1); 8.212(3.1); 8.166(1.7); 8.160(2.4); 8.155(1.5); 8.144(2.8); 8.138(4.1); 8.133(2.5); 8.078(5.0); 8.056(2.9);
7.953(0.4); 4.593(10.7); 4.325(0.9); 4.307(2.9); 4.290(3.0); 4.281(0.7); 4.272(1.0); 4.263(0.7); 3.910(2.4); 3.867(3.0);
3.822(0.4); 3.811(2.3); 3.767(2.9); 3.610(0.8); 3.600(1.2); 3.589(1.6); 3.580(1.6); 3.571(1.3); 3.560(0.8); 3.550(0.3);
3.524(2.9); 3.504(2.8); 3.481(2.4); 3.475(0.6); 3.461(2.4); 3.431(0.4); 3.405(0.3); 3.394(0.8); 3.381(0.9); 3.377(1.0);
3.365(1.5); 3.359(1.9); 3.328(191.4); 3.296(1.6); 3.285(1.4); 3.280(1.4); 3.270(1.1); 3.261(0.6); 3.249(1.1); 3.235(1.3);
3.224(1.0); 3.215(0.8); 3.205(0.8); 3.200(0.6); 3.190(0.6); 2.891(3.1); 2.751(0.6); 2.748(0.6); 2.732(2.5); 2.731(2.4);
2.697(15.2); 2.677(16.0); 2.667(1.2); 2.662(0.6); 2.564(0.4); 2.550(0.7); 2.545(0.5); 2.542(0.6); 2.534(0.9); 2.525(3.5);
2.520(5.2); 2.512(66.6); 2.507(134.3); 2.502(178.9); 2.498(130.1); 2.493(61.8); 2.338(0.4); 2.334(0.8); 2.329(1.2);
2.325(0.8); 2.320(0.4); 2.180(0.5); 2.161(0.9); 2.140(1.3); 2.118(1.3); 2.097(0.8); 2.084(0.7); 2.073(0.8); 2.059(1.0);
2.047(1.0); 2.034(0.7); 2.023(0.8); 2.018(0.7); 2.009(1.2); 2.000(1.0); 1.992(0.6); 1.971(1.7); 1.961(1.5); 1.951(1.0);
1.947(0.7); 1.940(1.1); 1.936(0.8); 1.932(1.1); 1.927(0.6); 1.915(0.8); 1.911(0.7); 1.907(0.7); 1.848(0.9); 1.840(0.5);
1.834(0.5); 1.826(1.0); 1.815(0.9); 1.806(1.0); 1.791(0.9); 1.783(1.0); 1.773(0.9); 1.765(0.4); 1.759(0.4); 1.750(0.4);
1.612(14.4); 1.599(14.5); 1.585(2.0); 1.294(3.3); 1.281(1.3); 1.276(7.0); 1.263(1.7); 1.259(3.3); 1.245(0.8); 1.234(1.1);
0.008(0.5); 0.000(16.2); −0.009(0.5)
Example 214: $^1$H-NMR(400.0 MHz, DMSO):
8.955(4.0); 8.950(4.1); 8.607(3.2); 8.602(3.1); 8.350(0.8); 8.334(1.7); 8.319(0.8); 8.241(3.0); 8.238(3.3); 8.174(1.8);
8.169(1.6); 8.152(2.8); 8.147(2.6); 8.078(3.6); 8.056(2.3); 4.593(7.0); 3.895(2.1); 3.852(2.6); 3.694(0.5); 3.675(1.2);
3.659(1.2); 3.641(0.7); 3.610(1.0); 3.607(1.0); 3.589(2.2); 3.586(1.5); 3.571(1.3); 3.563(1.9); 3.544(1.6); 3.524(0.6);
3.496(3.1); 3.453(2.7); 3.385(1.8); 3.372(1.8); 3.364(1.6); 3.350(1.7); 3.327(86.5); 3.144(0.4); 3.128(0.8); 3.121(0.8);
3.111(0.9); 3.103(1.0); 3.098(0.9); 3.087(1.0); 3.083(1.0); 3.076(0.8); 3.073(0.8); 3.066(0.9); 3.057(0.8); 2.891(1.6);
2.732(1.3); 2.672(0.4); 2.525(1.3); 2.512(24.8); 2.507(49.1); 2.503(64.8); 2.498(47.7); 2.494(23.1); 2.440(0.4);
2.424(0.8); 2.406(1.0); 2.388(0.7); 2.373(0.3); 2.330(0.4); 1.860(0.5); 1.853(0.5); 1.846(0.5); 1.840(0.6);
1.829(0.7); 1.823(0.6); 1.816(0.5); 1.809(0.6); 1.612(16.0); 1.539(0.5); 1.537(0.5); 1.531(0.5); 1.525(0.6); 1.517(0.7);
1.511(0.7); 1.505(0.6); 1.497(0.6); 1.491(0.4); 1.486(0.4); 1.234(0.4); 0.000(5.0)
Example 215: $^1$H-NMR(400.0 MHz, DMSO):
9.005(5.4); 9.000(6.9); 8.995(2.6); 8.777(1.7); 8.768(5.8); 8.762(5.3); 8.229(1.6); 8.224(1.9); 8.215(2.9); 8.210(3.9);
8.203(3.7); 8.177(1.1); 8.172(1.0); 8.168(1.9); 8.163(2.8); 8.158(1.6); 8.155(2.2); 8.149(3.5); 8.146(4.3); 8.141(6.2);
8.136(4.0); 8.127(2.7); 8.122(1.7); 8.077(4.4); 8.067(1.9); 8.055(2.7); 8.045(1.1); 7.954(1.6); 7.945(0.9); 7.924(0.8);
7.913(0.8); 3.961(1.4); 3.918(1.7); 3.908(2.5); 3.893(1.9); 3.865(3.6); 3.850(2.2); 3.824(1.6); 3.494(1.7); 3.471(1.7);
3.451(4.4); 3.428(1.7); 3.405(3.4); 3.335(720.6); 3.303(1.1); 3.287(0.5); 2.891(7.6); 2.751(0.7); 2.732(5.7); 2.731(6.1);
2.681(0.7); 2.677(1.1); 2.672(1.5); 2.668(1.3); 2.663(0.8); 2.650(0.7); 2.637(0.6); 2.632(0.6); 2.628(0.5); 2.619(0.5);
2.609(0.5); 2.600(0.5); 2.589(0.3); 2.542(0.7); 2.526(4.6); 2.521(7.3); 2.512(79.4); 2.508(157.8); 2.503(209.1);
2.499(152.5); 2.494(72.7); 2.434(0.4); 2.424(1.1); 2.414(1.8); 2.404(2.1); 2.394(1.7); 2.384(1.0); 2.339(0.5); 2.335(1.0);
2.330(1.4); 2.325(1.0); 2.321(0.4); 1.641(7.9); 1.615(7.9); 1.576(13.4); 1.572(16.0); 1.234(1.3); 1.050(0.5); 1.040(0.8);
1.035(0.8); 1.026(1.4); 1.016(1.5); 1.006(0.9); 1.002(1.0); 0.992(0.6); 0.875(0.5); 0.866(0.4); 0.863(0.5); 0.854(1.1);
0.843(1.3); 0.834(1.0); 0.823(1.7); 0.811(1.3); 0.802(1.1); 0.799(1.0); 0.790(0.8); 0.782(0.7); 0.774(0.3); 0.766(0.5);
0.758(0.5); 0.743(0.5); 0.693(0.5); 0.680(0.8); 0.671(1.2); 0.667(0.8); 0.658(2.3); 0.647(2.6); 0.637(1.6); 0.634(2.5);
0.624(1.8); 0.621(1.7); 0.610(1.0); 0.600(0.4); 0.594(0.7); 0.579(0.7); 0.567(0.6); 0.556(0.5); 0.553(0.4); 0.542(0.7);
0.530(0.6); 0.450(0.5); 0.441(1.0); 0.426(1.5); 0.422(1.2); 0.417(1.3); 0.413(1.2); 0.405(1.8); 0.398(1.0); 0.393(1.2);
0.389(1.1); 0.383(1.4); 0.369(0.8); 0.361(0.5); 0.357(0.5); 0.347(0.5); 0.341(0.9); 0.333(1.5); 0.327(2.2); 0.322(2.0);
0.320(2.0); 0.312(2.3); 0.310(2.1); 0.307(2.9); 0.306(2.9); 0.301(2.4); 0.290(2.3); 0.285(1.3); 0.282(1.1); 0.278(1.2);
0.270(1.2); 0.187(0.4); 0.176(0.6); 0.164(0.7); 0.153(0.5); 0.127(0.6); 0.121(0.6); 0.114(1.2); 0.108(1.5); 0.102(1.6);
0.097(1.3); 0.089(2.1); 0.081(1.8); 0.077(1.8); 0.072(1.5); 0.067(2.4); 0.059(2.2); 0.053(1.5); 0.046(2.4); 0.041(2.0);
0.036(1.5); 0.032(1.4); 0.025(0.8); 0.018(0.6); 0.013(0.4); 0.008(0.5); 0.000(5.2); −0.082(0.3); −0.090(0.6);
−0.100(0.4); −0.103(0.5)
Example 216: $^1$H-NMR(400.0 MHz, DMSO):
8.955(5.6); 8.954(5.7); 8.950(7.6); 8.945(2.4); 8.618(1.7); 8.609(6.3); 8.604(5.9); 8.249(1.6); 8.244(1.8); 8.235(3.0);
8.229(4.2); 8.223(4.1); 8.175(1.0); 8.171(1.0); 8.166(1.9); 8.161(3.0); 8.156(1.9); 8.153(2.1); 8.147(3.4); 8.144(4.2);
8.139(6.4); 8.134(5.1); 8.124(3.0); 8.120(1.8); 8.074(4.8); 8.065(1.9); 8.052(2.9); 8.043(1.1); 7.953(1.9); 7.941(0.9);
7.919(0.8); 7.908(0.8); 4.591(14.6); 3.970(1.3); 3.927(1.6); 3.916(2.5); 3.901(2.4); 3.873(3.1); 3.858(2.8); 3.833(1.6);
3.501(1.6); 3.479(1.7); 3.458(5.0); 3.436(1.6); 3.428(0.5); 3.415(3.4); 3.413(3.5); 3.340(828.2); 3.285(0.7); 3.265(0.3);
3.258(0.4); 2.892(9.9); 2.751(0.7); 2.733(7.6); 2.732(7.5); 2.682(0.6); 2.677(1.0); 2.673(1.6); 2.668(1.2); 2.664(0.8);
2.653(0.6); 2.638(0.6); 2.634(0.6); 2.620(0.7); 2.609(0.5); 2.601(0.4); 2.546(0.5); 2.543(0.5); 2.535(0.8); 2.526(3.6);
2.521(5.5); 2.513(75.8); 2.508(155.0); 2.504(207.8); 2.499(151.6); 2.494(72.3); 2.434(0.5); 2.424(1.3); 2.414(2.0);
2.404(2.3); 2.394(2.0); 2.384(1.2); 2.374(0.4); 2.340(0.5); 2.335(1.0); 2.330(1.4); 2.326(1.0); 2.321(0.5); 1.640(7.7);
1.615(7.7); 1.575(15.9); 1.572(16.0); 1.281(0.4); 1.234(1.2); 1.051(0.5); 1.041(0.9); 1.038(0.9); 1.026(1.4); 1.017(1.5);
1.006(1.0); 1.003(1.1); 0.994(0.6); 0.875(0.5); 0.867(0.5); 0.863(0.6); 0.855(1.3); 0.843(1.5); 0.834(1.1); 0.831(1.1);
0.823(1.9); 0.811(1.4); 0.802(1.0); 0.799(1.0); 0.790(0.9); 0.782(0.7); 0.767(0.5); 0.760(0.5); 0.744(0.5); 0.694(0.4);

| NMR Peak Lists Table 1 |
|---|
| 0.680(0.8); 0.671(1.3); 0.668(0.8); 0.658(2.6); 0.648(3.2); 0.635(2.8); 0.624(2.1); 0.611(1.0); 0.601(0.4); 0.594(0.6); 0.588(0.4); 0.578(0.7); 0.567(0.6); 0.556(0.5); 0.542(0.7); 0.530(0.6); 0.453(0.5); 0.441(1.3); 0.434(0.4); 0.427(1.5); 0.422(1.4); 0.418(1.3); 0.413(1.1); 0.405(2.0); 0.398(1.3); 0.394(1.8); 0.390(1.2); 0.383(1.7); 0.375(0.4); 0.370(1.0); 0.362(0.5); 0.358(0.5); 0.348(0.5); 0.341(1.0); 0.334(1.6); 0.327(2.6); 0.324(2.0); 0.321(2.2); 0.313(2.5); 0.307(3.3); 0.306(3.2); 0.301(2.6); 0.290(2.3); 0.285(1.3); 0.282(1.1); 0.278(1.2); 0.270(1.3); 0.249(0.3); 0.187(0.4); 0.177(0.6); 0.164(0.7); 0.153(0.6); 0.140(0.4); 0.131(0.7); 0.126(0.7); 0.117(1.0); 0.112(1.5); 0.103(1.9); 0.096(1.6); 0.091(2.4); 0.082(1.7); 0.078(1.6); 0.068(2.2); 0.059(2.2); 0.055(2.0); 0.049(2.1); 0.046(2.2); 0.041(2.0); 0.036(1.5); 0.032(1.4); 0.025(1.0); 0.013(0.4); 0.008(0.4); 0.000(1.3); −0.081(0.4); −0.089(0.5); −0.098(0.4); −0.102(0.5) |
| Example 217: $^1$H-NMR(400.0 MHz, DMSO): |
| 8.961(0.5); 8.956(5.0); 8.951(4.8); 8.613(3.2); 8.608(3.0); 8.239(3.3); 8.234(3.7); 8.204(5.5); 8.176(2.1); 8.171(1.7); 8.154(3.1); 8.149(2.9); 8.079(3.6); 8.057(2.3); 7.953(0.3); 7.923(1.5); 7.903(1.5); 4.600(0.8); 4.594(8.1); 4.026(0.3); 4.015(0.6); 4.006(0.7); 3.995(0.6); 3.985(0.8); 3.975(0.6); 3.964(0.4); 3.955(0.8); 3.922(2.8); 3.879(3.3); 3.632(0.4); 3.605(0.5); 3.500(1.2); 3.471(4.2); 3.457(1.6); 3.428(4.2); 3.400(1.7); 3.397(1.7); 3.392(1.8); 2.891(2.8); 2.733(2.2); 2.731(2.2); 2.677(0.5); 2.672(0.6); 2.667(0.4); 2.525(1.5); 2.521(2.3); 2.512(33.5); 2.508(68.5); 2.503(92.1); 2.498 (67.0); 2.494(31.6); 2.334(0.5); 2.330(0.6); 2.325(0.5); 2.175(14.3); 1.612(1.5); 1.599(16.0); 1.576(0.9); 1.570(1.2); 1.561(0.8); 1.526(0.4); 1.516(0.5); 1.510(0.5); 1.491(2.0); 1.479(1.0); 1.463(2.3); 1.434(1.9); 1.404(0.6); 1.319(0.8); 1.284(0.9); 1.262(0.7); 1.233(0.7); 1.224(0.8); 1.081(12.0); 1.043(12.1); 1.011(13.1); 0.975(13.1); 0.000(8.2) |
| Example 218: $^1$H-NMR(300.2 MHz, CDCl3): |
| 8.973(3.1); 8.966(3.2); 8.284(2.7); 8.278(2.7); 8.192(1.1); 8.186(1.1); 8.162(2.4); 8.156(2.5); 8.116(3.4); 8.086(1.5); 7.854(3.0); 7.849(2.9); 7.261(29.5); 6.861(2.0); 4.010(2.6); 3.953(3.1); 3.347(3.0); 3.325(6.0); 3.289(2.6); 2.381(6.4); 2.106(1.2); 2.089(1.2); 2.066(0.6); 1.864(0.5); 1.835(1.2); 1.804(1.4); 1.766(16.0); 1.701(0.7); 1.692(0.8); 1.660(1.3); 1.564(3.4); 1.322(0.4); 1.289(0.6); 1.263(0.6); 0.000(27.7) |
| Example 219: $^1$H-NMR(400.0 MHz, DMSO): |
| 8.956(4.4); 8.951(4.5); 8.663(0.8); 8.648(1.7); 8.632(0.8); 8.606(3.1); 8.601(3.0); 8.243(3.1); 8.238(3.4); 8.176(1.9); 8.171(1.6); 8.153(2.9); 8.149(2.7); 8.081(3.6); 8.059(2.3); 7.070(2.8); 6.957(1.4); 6.953(1.3); 6.936(1.6); 6.932(1.5); 6.640(3.6); 6.620(3.2); 4.590(7.8); 4.463(3.6); 4.442(7.8); 4.420(3.9); 4.204(4.0); 4.188(4.0); 3.898(2.7); 3.855(3.3); 3.515(3.2); 3.471(2.8); 3.347(337.6); 3.074(2.0); 3.052(3.7); 3.030(1.8); 2.891(1.5); 2.732(1.2); 2.678(0.4); 2.673(0.5); 2.668(0.4); 2.526(1.3); 2.522(2.0); 2.513(27.1); 2.508(55.1); 2.504(74.0); 2.499(53.9); 2.495(25.5); 2.335(0.3); 2.331(0.5); 2.326(0.3); 1.657(0.4); 1.625(16.0); 1.233(0.4); 0.000(7.4) |
| Example 220: $^1$H-NMR(400.0 MHz, DMSO): |
| 8.957(4.5); 8.952(4.6); 8.729(0.8); 8.713(1.7); 8.698(0.8); 8.605(3.1); 8.600(3.0); 8.244(3.2); 8.240(3.5); 8.178(2.0); 8.173(1.6); 8.156(2.9); 8.151(2.7); 8.080(3.6); 8.058(2.3); 7.953(0.6); 7.096(2.2); 7.077(2.4); 6.687(1.9); 6.684(2.0); 6.669(1.7); 6.665(1.9); 6.610(3.5); 4.589(8.0); 4.472(3.2); 4.450(7.8); 4.428(4.0); 4.219(3.5); 4.203(3.5); 3.902(2.7); 3.858(3.3); 3.737(0.4); 3.518(3.2); 3.474(2.7); 3.341(315.2); 3.312(1.0); 3.303(0.7); 3.277(0.4); 3.105(2.1); 3.083(3.9); 3.062(2.0); 2.891(5.7); 2.733(4.4); 2.731(4.4); 2.677(0.4); 2.673(0.6); 2.668(0.4); 2.526(1.4); 2.521(2.2); 2.513(31.3); 2.508(63.4); 2.503(84.9); 2.499(61.7); 2.494(29.2); 2.335(0.4); 2.330(0.6); 2.326(0.4); 1.656(0.4); 1.647(0.4); 1.629(16.0); 1.233(0.5); 0.000(0.6) |
| Example 221: $^1$H-NMR(400.0 MHz, DMSO): |
| 9.014(4.2); 9.009(4.4); 8.780(3.2); 8.775(3.1); 8.181(2.8); 8.177(3.9); 8.169(2.3); 8.164(1.1); 8.147(3.3); 8.142(2.6); 8.098(3.8); 8.076(2.0); 8.036(0.8); 8.021(1.6); 8.005(0.8); 7.231(2.8); 7.225(1.2); 7.217(3.2); 7.209(3.4); 7.200(1.3); 7.195(0.5); 7.187(0.3); 6.865(0.3); 6.857(3.2); 6.852(1.0); 6.840(1.0); 6.835(5.7); 6.829(1.2); 6.818(1.0); 6.813(2.8); 3.678(2.5); 3.635(3.4); 3.449(1.1); 3.431(1.5); 3.426(3.4); 3.415(1.5); 3.398(1.4); 3.382(2.5); 3.327(100.3); 3.201(1.3); 3.187(1.4); 3.167(1.1); 3.153(1.0); 2.892(0.3); 2.677(0.4); 2.672(0.5); 2.667(0.4); 2.525(1.5); 2.512(28.2); 2.508(55.4); 2.503(72.3); 2.498(53.0); 2.494(25.5); 2.334(0.3); 2.330(0.5); 2.325(0.3); 1.536(16.0); 1.233(0.5); 0.882(0.9); 0.866 (4.6); 0.853(1.0); 0.669(1.0); 0.656(4.4); 0.640(0.8); 0.000(6.3) |
| Example 222: $^1$H-NMR(400.0 MHz, DMSO): |
| 8.951(3.1); 8.949(3.9); 8.946(3.5); 8.944(3.5); 8.599(4.0); 8.594(3.0); 8.209(2.3); 8.202(2.5); 8.197(2.4); 8.157(0.9); 8.155(0.9); 8.153(0.9); 8.135(2.2); 8.131(1.6); 8.118(1.6); 8.113(1.5); 8.073(2.1); 8.063(2.5); 8.051(1.3); 8.041(1.4); 7.953(2.3); 7.937(0.6); 7.872(0.4); 7.854(0.5); 7.844(0.5); 7.836(0.4); 7.818(0.3); 7.312(7.1); 7.301(8.8); 7.281(3.4); 7.274(3.2); 7.269(2.2); 7.262(1.2); 7.252(1.6); 7.247(0.8); 7.241(1.2); 7.230(0.9); 7.219(0.6); 7.212(0.5); 7.208(0.4); 7.195(0.8); 7.189(0.4); 7.176(0.7); 4.599(1.6); 4.588(10.5); 4.071(0.5); 3.955(1.0); 3.945(1.1); 3.931(1.1); 3.920(1.3); 3.907(0.6); 3.881(0.7); 3.802(0.9); 3.794(1.1); 3.787(0.9); 3.766(1.1); 3.759(1.1); 3.751(1.4); 3.744(1.1); 3.723(1.3); 3.533(0.4); 3.510(0.4); 3.428(2.0); 3.421(1.8); 3.400(0.9); 3.390(2.0); 3.386(2.1); 3.377(2.2); 3.336(416.1); 3.289(0.7); 3.269(0.4); 2.891(16.0); 2.877(0.4); 2.864(0.5); 2.850(0.4); 2.844(0.3); 2.751(0.7); 2.732(12.4); 2.731(12.1); 2.681(0.4); 2.677(0.7); 2.672(1.0); 2.668(0.7); 2.663(0.4); 2.635(0.5); 2.622(0.4); 2.609(0.6); 2.602(0.6); 2.590(0.4); 2.576(0.5); 2.566(0.4); 2.557(0.7); 2.545(0.8); 2.534(1.0); 2.525(3.4); 2.521(5.3); 2.512(57.5); 2.508(114.3); 2.503(152.0); 2.498(110.9); 2.494(52.6); 2.339(0.4); 2.334(0.8); 2.330(1.0); 2.325(0.7); 2.321(0.4); 2.200(0.4); 2.180(0.4); 1.910(0.4); 1.899(0.6); 1.888(0.7); 1.876(1.0); 1.867(1.0); 1.855(0.9); 1.844(1.0); 1.822(0.4); 1.729(0.4); 1.702(0.6); 1.682(0.4); 1.668(0.4); 1.658(0.3); 1.647(0.4); 1.607(0.4); 1.547(5.5); 1.534(7.1); 1.527(5.9); 1.517(6.3); 1.280(0.5); 1.269(0.4); 1.234(1.5); 1.213(0.6); 1.208(0.6); 0.000(3.4) |
| Example 223: $^1$H-NMR(400.0 MHz, DMSO): |
| 8.961(7.7); 8.956(7.8); 8.618(6.7); 8.613(6.5); 8.478(1.7); 8.463(3.2); 8.448(1.7); 8.256(3.5); 8.251(4.0); 8.245(3.6); 8.241(3.8); 8.196(1.9); 8.189(2.2); 8.184(1.7); 8.174(2.9); 8.169(3.3); 8.167(3.2); 8.162(2.6); 8.094(4.0); 8.089(4.0); 8.072(2.6); 8.067(2.6); 7.953(1.9); 7.118(2.0); 7.104(3.0); 7.087(2.0); 7.070(1.0); 7.066(0.9); 7.050(2.0); 7.039(1.1); 7.031(1.4); 7.024(2.2); 7.004(1.3); 7.001(1.1); 6.801(1.4); 6.799(1.4); 6.783(2.4); 6.781(2.3); 6.764(1.1); 6.762(1.1); 6.720(8.0); 6.701(7.4); 6.684(1.3); 4.595(11.8); 4.158(0.4); 4.148(0.8); 4.130(1.6); 4.120(2.3); 4.112(1.7); 4.102(2.6); 4.093(2.8); 4.067(2.2); 4.041(0.8); 3.917(2.6); 3.874(3.2); 3.864(2.7); 3.821(3.1); 3.530(3.2); 3.520(3.2); 3.487(2.7); 3.477(2.7); 3.419(0.8); 3.405(1.6); 3.387(1.7); 3.372(2.7); 3.357(1.9); 3.328(332.7); 3.292(1.8); 3.273(1.4); 3.268(1.7); 3.259(1.0); 3.249(1.2); 3.235(1.0); 3.216(0.6); 2.984(1.3); 2.973(1.8); 2.961(1.7); 2.950(1.2); 2.891(13.9); 2.751(0.7); 2.732(11.8); 2.676(1.0); 2.672(1.4); 2.667(1.0); 2.541(0.6); 2.525(4.0); 2.507(153.7); 2.502(201.0); 2.498(148.4); 2.334(1.0); 2.329(1.3); 2.325(1.0); 1.874(0.5); 1.860(0.7); 1.850(1.0); 1.839(1.3); 1.825(1.4); 1.815(1.3); 1.803(1.1); 1.792(0.6); 1.782(0.6); 1.774(1.2); 1.765(1.7); 1.756(1.6); 1.748(1.5); 1.739(1.1); 1.730(0.8); 1.721(0.8); 1.713(0.7); 1.644(16.0); 1.632(16.0); 1.610(0.4); 1.234(1.3); 0.008(0.4); 0.000(11.9); −0.008(0.4) |
| Example 224: $^1$H-NMR(400.0 MHz, DMSO): |
| 9.013(4.1); 9.007(4.2); 8.828(0.9); 8.813(1.8); 8.798(0.9); 8.773(3.3); 8.768(3.1); 8.317(0.5); 8.234(3.3); 8.230(3.5); 8.173(1.8); 8.168(1.5); 8.151(2.8); 8.146(2.5); 8.108(1.5); 8.102(1.4); 8.085(5.2); 8.063(2.2); 7.953(1.5); 7.925(1.6); 7.916(0.9); 7.908(1.6); 7.901(1.7); 7.812(1.9); 7.792(2.1); 7.530(0.5); 7.526(0.7); 7.513(1.9); 7.505(2.4); 7.497(3.9); |

NMR Peak Lists Table 1

7.488(2.4); 7.482(1.7); 7.469(0.6); 7.465(0.4); 7.420(1.4); 7.402(2.8); 7.382(2.5); 7.357(2.6); 7.341(1.3); 4.781(3.8); 4.766(3.8); 3.947(2.6); 3.904(3.2); 3.545(3.1); 3.501(2.6); 3.329(170.3); 2.891(10.9); 2.751(0.6); 2.732(9.2); 2.676 (0.7); 2.672(1.0); 2.667(0.7); 2.542(0.6); 2.525(3.4); 2.511(62.1); 2.507(121.7); 2.503(156.9); 2.498(111.4); 2.494 (52.9); 2.334(0.7); 2.329(1.0); 2.325(0.7); 1.677(16.0); 1.235(0.4); 0.008(1.5); 0.000(37.5); −0.008(1.3)
Example 225: $^1$H-NMR(400.0 MHz, DMSO):
8.963(4.1); 8.958(4.0); 8.821(1.1); 8.806(2.1); 8.791(1.0); 8.614(3.7); 8.609(3.4); 8.253(3.8); 8.249(3.8); 8.170(1.9); 8.166(1.6); 8.148(3.0); 8.144(2.7); 8.108(1.7); 8.103(1.6); 8.083(5.2); 8.061(2.4); 7.925(1.8); 7.916(1.0); 7.907(1.9); 7.901(1.9); 7.812(2.1); 7.792(2.4); 7.530(0.5); 7.526(0.7); 7.513(2.1); 7.509(2.1); 7.505(2.4); 7.497(4.0); 7.489(2.5); 7.486(2.1); 7.481(1.9); 7.468(0.7); 7.420(1.4); 7.402(3.0); 7.382(2.5); 7.360(2.9); 7.343(1.5); 4.782(4.3); 4.767(4.2); 4.597(7.7); 3.956(2.6); 3.912(3.2); 3.553(3.1); 3.510(2.7); 3.384(0.4); 3.333(280.0); 2.890(0.8); 2.731(0.7); 2.676 (0.5); 2.672(0.7); 2.667(0.5); 2.507(81.0); 2.502(99.6); 2.498(73.6); 2.334(0.5); 2.329(0.6); 2.325(0.5); 1.677(16.0); 1.234(0.5); 0.000(2.4)
Example 226: $^1$H-NMR(400.0 MHz, DMSO):
10.776(1.9); 8.959(4.2); 8.954(4.4); 8.604(3.9); 8.599(3.9); 8.578(1.0); 8.246(3.4); 8.241(3.8); 8.230(0.4); 8.178(1.9); 8.173(1.7); 8.156(2.9); 8.151(2.8); 8.081(3.9); 8.058(2.5); 7.952(1.0); 7.207(3.6); 7.134(2.6); 7.113(3.1); 6.887(2.2); 6.883(2.1); 6.866(1.9); 6.863(1.9); 5.925(3.0); 4.591(7.6); 4.375(0.4); 4.359(0.5); 4.338(2.0); 4.323(3.5); 4.309(2.0); 4.287(0.5); 4.272(0.5); 3.910(2.7); 3.867(3.2); 3.736(1.1); 3.519(3.1); 3.476(2.7); 3.335(318.7); 3.300(0.6); 3.288(0.4); 2.890(8.0); 2.751(0.4); 2.731(6.7); 2.676(0.5); 2.672(0.7); 2.667(0.5); 2.525(1.7); 2.511(38.2); 2.507(77.8); 2.502 (104.7); 2.498(78.0); 2.494(38.4); 2.465(0.4); 2.333(0.8); 2.329(0.9); 2.324(0.7); 2.306(14.5); 2.197(0.3); 1.655(1.2); 1.637(16.0); 1.614(0.7); 1.231(0.9); 0.000(1.3)
Example 227: $^1$H-NMR(499.9 MHz, CDCl3):
8.972(3.1); 8.968(3.2); 8.884(1.4); 8.880(1.6); 8.875(1.5); 8.872(1.4); 8.262(2.5); 8.258(2.5); 8.163(1.3); 8.160(1.5); 8.146(2.4); 8.142(2.7); 8.132(0.4); 8.128(0.3); 8.111(3.1); 8.093(1.5); 8.058(2.0); 8.041(2.2); 8.013(1.4); 7.998(1.4); 7.996(1.4); 7.848(2.7); 7.844(2.6); 7.646(2.4); 7.608(1.7); 7.604(1.5); 7.591(1.4); 7.587(1.4); 7.380(0.6); 7.367(1.0); 7.356(2.2); 7.347(1.9); 7.339(1.7); 7.331(1.6); 7.263(5.9); 5.084(0.5); 4.734(0.8); 4.721(0.8); 4.704(1.2); 4.691(1.2); 4.606(1.3); 4.594(1.3); 4.576(0.8); 4.564(0.8); 4.127(0.7); 4.113(0.7); 4.029(2.8); 3.995(3.1); 3.400(3.0); 3.365(2.7); 3.325(6.1); 2.038(3.1); 1.832(16.0); 1.707(1.3); 1.270(0.8); 1.255(1.7); 1.241(0.8); 0.000(5.3); −0.007(0.3)
Example 228: $^1$H-NMR(400.0 MHz, DMSO):
9.032(4.3); 9.026(4.4); 8.794(3.0); 8.789(2.8); 8.238(3.0); 8.233(3.4); 8.197(2.0); 8.192(1.5); 8.175(3.1); 8.170(2.9); 8.164(0.9); 8.150(1.6); 8.136(0.8); 8.105(3.4); 8.083(2.1); 3.891(2.7); 3.848(3.3); 3.503(3.1); 3.460(2.7); 3.362(204.5); 3.340(0.6); 3.215(1.2); 3.200(1.6); 3.195(1.6); 3.191(1.1); 3.187(1.1); 3.180(1.5); 3.175(1.7); 3.160(1.3); 2.920(1.3); 2.761(1.0); 2.760(1.0); 2.706(0.3); 2.701(0.5); 2.696(0.3); 2.554(1.3); 2.541(26.1); 2.536(52.0); 2.532(68.6); 2.527(49.7); 2.523(23.4); 2.359(0.4); 1.625(16.0); 1.261(0.4); 0.824(2.6); 0.809(1.8); 0.804(2.5); 0.799(1.9); 0.784(2.4); 0.138(0.4); 0.028(2.5); 0.000(3.5); −0.008(80.0); −0.017(2.9); −0.158(0.4)
Example 229: $^1$H-NMR(400.0 MHz, DMSO):
8.958(2.1); 8.953(2.1); 8.749(0.5); 8.735(1.0); 8.721(0.5); 8.602(1.8); 8.597(1.6); 8.317(0.3); 8.251(1.7); 8.247(1.8); 8.180(1.0); 8.175(0.9); 8.158(1.4); 8.153(1.3); 8.079(1.9); 8.057(1.2); 7.953(1.4); 7.917(0.5); 7.895(0.5); 7.574(0.6); 7.553(0.5); 7.445(2.0); 7.437(0.5); 7.431(0.5); 7.418(0.7); 7.399(0.5); 7.378(16.0); 7.355(0.3); 4.595(4.0); 4.335(0.4); 4.322(0.4); 4.135(2.6); 4.121(2.6); 3.919(1.3); 3.876(1.6); 3.539(1.6); 3.495(1.3); 3.328(147.3); 2.891(10.1); 2.748(0.3); 2.732(8.6); 2.676(0.7); 2.671(1.0); 2.667(0.7); 2.541(0.6); 2.524(3.1); 2.507(122.1); 2.502(158.1); 2.498(114.1); 2.333(0.7); 2.329(1.0); 2.325(0.7); 1.662(0.3); 1.656(0.3); 1.634(8.2); 1.235(0.6); 0.008(1.1); 0.000(32.1); −0.008(1.4)
Example 230: $^1$H-NMR(400.0 MHz, DMSO):
8.959(4.2); 8.954(5.8); 8.950(3.2); 8.601(4.8); 8.255(3.2); 8.250(4.8); 8.244(2.6); 8.181(1.8); 8.176(1.6); 8.170(1.4); 8.165(1.2); 8.159(2.7); 8.154(2.6); 8.147(2.0); 8.143(1.8); 8.079(3.6); 8.072(2.6); 8.057(2.5); 8.049(2.4); 8.036(1.1); 8.032(1.1); 8.010(2.0); 7.995(2.4); 7.988(2.6); 7.973(2.2); 7.954(0.5); 4.595(9.4); 4.388(0.8); 4.372(0.9); 4.361(1.4); 4.345(1.4); 4.334(0.7); 4.319(0.6); 3.864(4.1); 3.820(5.2); 3.576(3.0); 3.551(2.1); 3.532(2.4); 3.507(1.7); 3.330(158.9); 3.246(0.4); 3.233(0.4); 3.207(1.0); 3.196(0.8); 3.180(0.8); 3.168(1.1); 3.157(0.5); 3.141(0.4); 3.129(0.4); 3.081(0.5); 3.066(0.8); 3.049(1.0); 3.030(0.8); 3.016(0.5); 2.892(3.1); 2.732(2.5); 2.677(0.5); 2.672(0.6); 2.668(0.5); 2.547(0.6); 2.534(0.5); 2.526(1.6); 2.521(2.4); 2.512(36.0); 2.508(73.2); 2.503(98.0); 2.499(72.4); 2.494(35.2); 2.335(0.5); 2.330(0.6); 2.325(0.5); 1.923(0.8); 1.897(1.0); 1.839(1.5); 1.812(1.6); 1.750(0.9); 1.739(0.8); 1.725(0.8); 1.714(1.0); 1.668(0.6); 1.635(11.6); 1.620(16.0); 1.394(0.6); 1.363(0.6); 1.338(0.5); 1.311(0.9); 1.280(0.8); 1.252(0.5); 1.247(0.5); 1.233(0.7); 1.217(0.7); 1.185(1.0); 1.155(0.8); 0.000(6.9)
Example 231: $^1$H-NMR(400.0 MHz, DMSO):
8.982(4.1); 8.976(4.2); 8.635(3.2); 8.630(3.1); 8.257(3.2); 8.253(3.5); 8.195(1.8); 8.190(1.5); 8.173(2.9); 8.168(2.8); 8.160(0.9); 8.146(1.7); 8.132(0.9); 8.103(3.6); 8.081(2.3); 4.618(7.5); 3.899(2.7); 3.856(3.2); 3.510(3.1); 3.467(2.7); 3.364(246.0); 3.330(0.3); 3.214(1.3); 3.200(1.8); 3.195(1.7); 3.187(1.2); 3.180(1.7); 3.174(1.8); 3.160(1.4); 2.705(0.4); 2.701(0.5); 2.696(0.4); 2.554(1.5); 2.540(29.0); 2.536(57.3); 2.531(75.8); 2.527(55.9); 2.522(27.2); 2.363(0.4); 2.358(0.5); 2.354(0.4); 1.624(16.0); 1.261(0.5); 0.824(2.7); 0.808(1.9); 0.803(2.7); 0.799(2.0); 0.783(2.5); 0.139(0.4); 0.028(2.7); 0.000(3.3); −0.008(76.9); −0.016(3.2); −0.158(0.4)
Example 232: $^1$H-NMR(400.0 MHz, DMSO):
8.956(6.1); 8.951(6.2); 8.607(4.8); 8.603(4.7); 8.243(2.9); 8.238(5.1); 8.233(3.2); 8.181(4.3); 8.168(2.6); 8.164(2.2); 8.146(4.0); 8.142(3.7); 8.078(5.4); 8.055(3.3); 7.918(0.7); 7.903(1.5); 7.885(1.3); 7.869(0.7); 4.593(11.0); 3.875(3.1); 3.832(3.9); 3.658(0.4); 3.514(5.3); 3.471(5.4); 3.359(12.7); 3.277(3.7); 3.267(3.3); 3.260(3.0); 3.250(3.1); 3.242(2.9); 3.234(2.8); 3.226(2.6); 3.217(2.6); 3.208(2.0); 3.202(1.8); 3.192(1.7); 3.121(0.5); 3.028(1.9); 3.014(2.6); 3.005(2.7); 2.998(2.9); 2.982(2.3); 2.968(0.9); 2.794(0.9); 2.784(0.6); 2.776(1.0); 2.766(1.4); 2.757(0.7); 2.748(1.4); 2.738(1.1); 2.731(0.6); 2.719(1.0); 2.701(0.3); 2.677(0.7); 2.672(1.0); 2.667(0.7); 2.576(0.4); 2.561(1.1); 2.552(1.3); 2.546(1.4); 2.540(1.4); 2.525(3.3); 2.512(58.3); 2.507(113.6); 2.503(149.3); 2.498(110.5); 2.494(54.2); 2.334(0.8); 2.330(1.1); 2.325(0.8); 2.266(0.4); 2.249(0.9); 2.237(0.7); 2.231(1.1); 2.220(1.6); 2.202(1.6); 2.190(1.0); 2.185(0.7); 2.173(0.9); 2.155(0.3); 2.134(0.5); 2.112(1.2); 2.098(1.3); 2.093(1.4); 2.080(1.2); 2.071(0.7); 2.057(0.6); 1.751(0.7); 1.742(0.3); 1.731(0.8); 1.722(0.9); 1.710(0.5); 1.701(1.4); 1.692(0.4); 1.680(1.2); 1.671(0.7); 1.659(0.5); 1.650(1.0); 1.622(15.6); 1.618(16.0); 1.594(1.4); 1.568(1.2); 1.549(1.4); 1.530(1.3); 1.510(0.9); 1.500(0.9); 1.485(0.9); 1.473(0.6); 1.458(0.5); 1.451(0.4); 1.413(0.4); 1.399(0.6); 1.382(0.7); 1.369(0.6); 1.358(0.4); 1.350(0.4); 1.234(1.1); 1.019(3.6); 1.001(7.4); 0.991(4.3); 0.983(3.9); 0.973(7.9); 0.955(3.7); 0.000(7.8)
Example 233: $^1$H-NMR(400.0 MHz, DMSO):
8.961(4.4); 8.956(4.6); 8.922(0.3); 8.902(1.1); 8.888(2.2); 8.872(1.1); 8.610(4.4); 8.606(4.1); 8.317(0.7); 8.260(4.1); 8.256(4.1); 8.227(0.5); 8.187(2.0); 8.183(1.8); 8.165(3.1); 8.160(3.0); 8.149(8.8); 8.088(4.1); 8.066(2.7); 7.953(1.6); 6.650(0.6); 6.118(6.4); 6.105(0.8); 4.690(8.1); 4.684(8.1); 4.647(0.3); 4.596(7.7); 4.281(0.6); 4.265(0.6); 4.194(3.0);

NMR Peak Lists Table 1

4.180(3.0); 4.017(0.3); 3.999(0.9); 3.981(0.9); 3.964(0.4); 3.947(0.4); 3.926(2.7); 3.904(0.5); 3.882(3.3); 3.637(2.1); 3.632(3.9); 3.626(2.0); 3.561(3.3); 3.518(2.8); 3.481(0.5); 3.446(0.8); 3.330(361.0); 2.891(10.5); 2.747(1.1); 2.731 (9.1); 2.676(1.7); 2.672(2.2); 2.667(1.6); 2.507(280.6); 2.502(350.9); 2.498(254.5); 2.389(1.8); 2.333(1.7); 2.329(2.1); 2.325(1.6); 1.655(16.0); 1.622(2.1); 1.267(0.5); 1.249(0.4); 1.235(0.9); 1.159(0.9); 1.141(1.7); 1.124(0.9); 0.000(57.3); −0.008(2.7)

Example 234: $^1$H-NMR(400.0 MHz, DMSO):
9.003(4.2); 8.997(4.4); 8.762(2.9); 8.756(2.7); 8.364(1.3); 8.344(1.3); 8.214(2.8); 8.209(3.2); 8.174(1.9); 8.170(1.5); 8.152(2.9); 8.147(2.5); 8.077(3.3); 8.055(2.1); 4.257(0.6); 4.237(1.1); 4.215(1.1); 4.195(0.6); 3.892(2.7); 3.849(3.2); 3.452(3.1); 3.408(2.7); 3.327(88.9); 2.891(1.8); 2.732(1.3); 2.731(1.4); 2.672(0.4); 2.525(1.2); 2.521(1.9); 2.512(22.1); 2.508(43.9); 2.503(58.1); 2.498(42.1); 2.494(19.9); 2.330(0.4); 2.132(0.5); 2.119(0.9); 2.114(0.9); 2.105(0.9); 2.096 (1.9); 2.072(1.8); 2.055(2.0); 2.047(1.2); 2.035(1.7); 2.025(0.5); 2.012(0.7); 1.626(0.8); 1.617(0.6); 1.607(1.3); 1.602(1.5); 1.589(16.0); 1.562(0.7); 1.557(0.8); 1.233(0.4); 0.000(6.2)

Example 235: $^1$H-NMR(400.0 MHz, DMSO):
9.006(4.2); 9.000(4.3); 8.932(1.4); 8.916(1.4); 8.768(3.0); 8.762(2.8); 8.217(2.9); 8.212(3.4); 8.180(2.0); 8.175(1.5); 8.158(2.9); 8.153(2.5); 8.083(3.4); 8.060(2.2); 7.953(0.4); 4.839(0.6); 4.821(1.4); 4.804(1.6); 4.785(0.9); 4.673(1.4); 4.658(2.2); 4.638(2.4); 4.622(2.2); 4.603(1.7); 4.591(2.1); 4.575(2.8); 4.557(2.4); 4.540(2.8); 4.524(1.3); 3.904(2.7); 3.861(3.3); 3.736(0.4); 3.491(3.2); 3.448(2.7); 3.326(202.6); 2.891(3.1); 2.732(2.4); 2.731(2.4); 2.676(0.6); 2.671(0.9); 2.667(0.6); 2.541(0.4); 2.524(2.6); 2.520(4.2); 2.511(49.4); 2.507(98.1); 2.502(129.5); 2.497(94.0); 2.493(44.3); 2.333(0.6); 2.329(0.9); 2.324(0.6); 1.614(16.0); 1.234(0.6); 0.008(0.4); 0.000(11.7); −0.009(0.3)

Example 236: $^1$H-NMR(400.0 MHz, DMSO):
8.954(3.9); 8.949(3.9); 8.607(3.1); 8.602(3.0); 8.317(0.4); 8.240(3.1); 8.236(3.4); 8.173(1.7); 8.169(1.5); 8.151(2.6); 8.146(2.4); 8.074(3.4); 8.052(2.2); 7.845(1.5); 7.825(1.5); 4.593(7.1); 3.897(2.6); 3.854(3.1); 3.558(0.7); 3.548(0.6); 3.537(0.7); 3.530(0.6); 3.510(0.3); 3.472(3.0); 3.429(2.6); 3.329(193.9); 2.891(1.4); 2.732(1.2); 2.676(0.7); 2.672(1.0); 2.667(0.7); 2.525(3.2); 2.511(60.3); 2.507(118.9); 2.503(153.9); 2.498(110.7); 2.494(53.6); 2.334(0.7); 2.329(0.9); 2.325(0.7); 1.691(1.5); 1.662(1.4); 1.631(1.5); 1.593(16.0); 1.568(0.9); 1.536(0.9); 1.335(0.8); 1.325(0.8); 1.295(1.4); 1.286(1.1); 1.276(1.1); 1.261(1.7); 1.232(1.5); 1.224(1.5); 1.195(0.9); 1.110(0.4); 1.080(0.7); 1.050(0.6); 0.008(1.3); 0.000(34.4); −0.009(1.3)

Example 237: $^1$H-NMR(300.2 MHz, CDCl3):
8.941(3.1); 8.933(3.2); 8.323(2.5); 8.316(2.5); 8.185(1.1); 8.179(1.2); 8.155(2.4); 8.149(2.5); 8.103(3.0); 8.073(1.4); 7.818(2.8); 7.812(2.7); 7.269(4.9); 6.860(1.8); 5.302(2.6); 4.002(2.7); 3.944(3.1); 3.338(3.0); 3.281(2.6); 2.386(7.1); 2.125(0.9); 2.107(1.1); 2.092(1.0); 2.046(0.4); 1.877(0.4); 1.865(0.5); 1.845(0.8); 1.834(1.1); 1.803(1.2); 1.792(0.9); 1.766(16.0); 1.736(0.5); 1.725(0.4); 1.691(1.4); 1.670(1.0); 1.661(1.1); 1.640(1.2); 1.628(1.3); 1.617(1.3); 1.609(1.4); 1.578(1.6); 1.548(1.2); 1.535(1.0); 1.321(0.4); 1.300(0.5); 1.287(0.7); 1.260(0.9); 1.236(0.3); 0.000(3.3)

Example 238: $^1$H-NMR(400.0 MHz, DMSO):
8.956(4.2); 8.951(4.2); 8.931(1.6); 8.915(1.6); 8.607(3.0); 8.602(2.9); 8.236(3.0); 8.232(3.3); 8.178(1.9); 8.173(1.5); 8.156(2.8); 8.151(2.6); 8.080(3.4); 8.058(2.2); 4.840(0.6); 4.822(1.4); 4.805(1.6); 4.787(1.0); 4.674(1.5); 4.659(2.3); 4.639(2.6); 4.622(2.3); 4.604(1.8); 4.593(9.5); 4.577(3.0); 4.558(2.4); 4.542(3.0); 4.526(1.3); 3.914(2.8); 3.870(3.3); 3.499(3.2); 3.456(2.7); 3.327(80.0); 2.891(0.8); 2.731(0.6); 2.672(0.4); 2.525(1.2); 2.520(2.0); 2.512(23.8); 2.507 (47.3); 2.503(62.7); 2.498(45.5); 2.494(21.5); 2.330(0.4); 1.614(16.0); 1.233(0.4); 0.000(6.5)

Example 239: $^1$H-NMR(400.0 MHz, DMSO):
9.005(3.9); 8.999(4.1); 8.767(3.0); 8.762(2.8); 8.220(2.9); 8.216(3.3); 8.175(1.8); 8.170(1.4); 8.153(2.7); 8.148(2.4); 8.077(3.3); 8.055(2.1); 7.845(1.3); 7.824(1.3); 3.888(2.6); 3.845(3.1); 3.557(0.6); 3.548(0.5); 3.536(0.6); 3.529(0.5); 3.464(3.0); 3.421(2.6); 3.327(187.2); 2.891(1.3); 2.731(1.0); 2.676(0.7); 2.671(0.9); 2.667(0.7); 2.662(0.3); 2.525(2.5); 2.520(3.8); 2.511(49.6); 2.507(99.9); 2.502(133.4); 2.498(97.5); 2.493(46.7); 2.334(0.6); 2.329(0.9); 2.324(0.6); 1.691(1.3); 1.662(1.2); 1.631(1.3); 1.594(16.0); 1.568(0.7); 1.537(0.7); 1.334(0.7); 1.324(0.7); 1.295(1.3); 1.286(0.9); 1.275(1.0); 1.261(1.5); 1.234(1.8); 1.225(1.3); 1.195(0.8); 1.111(0.3); 1.080(0.6); 1.057(0.4); 1.050(0.5); 0.008(0.4); 0.000(12.6); −0.009(0.4)

Example 240: $^1$H-NMR(400.0 MHz, DMSO):
9.013(0.7); 9.007(5.4); 9.001(5.0); 8.774(3.5); 8.768(3.0); 8.219(3.4); 8.214(3.9); 8.177(2.2); 8.173(1.7); 8.158(5.7); 8.155(3.5); 8.151(3.0); 8.082(3.6); 8.060(2.3); 7.985(0.8); 7.967(0.8); 4.034(0.5); 4.024(0.6); 4.014(0.5); 4.003(0.6); 3.994(0.5); 3.915(2.7); 3.872(3.2); 3.500(0.7); 3.468(3.5); 3.457(1.0); 3.425(3.7); 3.335(7.4); 3.159(0.3); 2.891(0.7); 2.732(0.5); 2.676(0.6); 2.672(0.8); 2.667(0.6); 2.525(2.0); 2.520(3.1); 2.512(43.8); 2.507(89.3); 2.503(119.6); 2.498(87.2); 2.493(41.4); 2.334(0.6); 2.329(0.8); 2.325(0.6); 2.239(4.9); 1.644(0.6); 1.616(2.8); 1.602(16.0); 1.562 (0.7); 1.542(1.5); 1.513(1.7); 1.485(1.2); 1.454(0.4); 1.373(1.3); 1.338(1.6); 1.296(1.0); 1.234(1.0); 1.123(7.3); 1.086(7.5); 1.055(7.6); 1.020(7.6); 0.000(10.0)

Example 241: $^1$H-NMR(400.0 MHz, DMSO):
9.005(4.5); 8.999(4.7); 8.882(0.9); 8.867(1.9); 8.852(0.9); 8.760(3.3); 8.754(3.1); 8.205(3.3); 8.200(3.6); 8.148(1.9); 8.143(1.6); 8.126(3.1); 8.121(2.8); 8.066(3.8); 8.044(2.3); 8.003(4.2); 7.998(4.2); 7.991(4.2); 7.970(4.3); 7.573(5.1); 7.359(2.3); 7.354(2.2); 7.338(2.1); 7.333(2.0); 4.518(2.1); 4.510(2.2); 4.504(2.2); 4.496(2.0); 3.910(2.7); 3.867(3.3); 3.531(3.2); 3.487(2.7); 3.356(0.6); 3.331(191.2); 3.310(0.6); 2.891(1.5); 2.731(1.2); 2.677(0.4); 2.672(0.5); 2.668(0.4); 2.525(1.5); 2.512(30.1); 2.508(60.0); 2.503(79.7); 2.498(58.3); 2.494(27.9); 2.334(0.4); 2.330(0.5); 2.325(0.4); 1.633(16.0); 1.233(0.8); 0.000(4.9)

Example 242: $^1$H-NMR(400.0 MHz, DMSO):
8.959(4.4); 8.953(4.5); 8.861(0.8); 8.845(1.8); 8.829(0.9); 8.605(3.1); 8.600(3.0); 8.251(3.1); 8.246(3.5); 8.186(1.9); 8.181(1.6); 8.164(2.8); 8.159(2.6); 8.083(3.6); 8.061(2.4); 7.908(4.4); 7.903(4.7); 7.552(3.2); 7.532(3.5); 7.413(3.6); 7.159(2.2); 7.156(2.2); 7.139(2.0); 7.136(2.0); 6.891(3.1); 6.889(3.2); 6.886(3.2); 6.883(3.0); 4.593(7.8); 4.412(3.9); 4.397(3.9); 3.927(2.7); 3.884(3.2); 3.533(3.1); 3.490(2.6); 3.330(151.6); 2.891(1.2); 2.731(1.0); 2.677(0.4); 2.672(0.5); 2.668(0.4); 2.525(1.4); 2.521(2.0); 2.512(27.5); 2.508(56.0); 2.503(75.1); 2.498(54.9); 2.494(26.3); 2.334(0.3); 2.330(0.5); 2.325(0.4); 1.648(16.0); 1.232(0.6); 0.000(4.2)

Example 243: $^1$H-NMR(400.0 MHz, DMSO):
9.308(8.4); 9.012(4.4); 9.006(4.6); 8.927(0.8); 8.911(1.8); 8.896(0.8); 8.765(3.2); 8.759(3.1); 8.235(3.1); 8.230(3.6); 8.194(2.0); 8.189(1.6); 8.172(2.9); 8.167(2.6); 8.093(3.5); 8.071(2.3); 7.995(3.4); 7.974(3.7); 7.938(3.2); 7.936(3.2); 7.438(2.1); 7.433(2.0); 7.416(1.9); 7.412(1.9); 4.457(3.8); 4.442(3.8); 3.925(2.7); 3.882(3.3); 3.532(3.1); 3.489(2.7); 3.372(0.3); 3.355(0.9); 3.333(208.3); 2.891(2.0); 2.751(0.3); 2.731(1.6); 2.677(0.4); 2.672(0.6); 2.667(0.4); 2.525(1.6); 2.521(2.3); 2.512(31.9); 2.508(64.6); 2.503(86.5); 2.498(63.2); 2.494(30.2); 2.334(0.4); 2.330(0.6); 2.325(0.4); 1.660(16.0); 1.233(0.6); 0.000(4.9)

| NMR Peak Lists Table 1 |
|---|

Example 244: ¹H-NMR(400.0 MHz, DMSO):
8.956(4.3); 8.951(4.4); 8.879(1.0); 8.864(2.0); 8.849(1.0); 8.602(3.3); 8.597(3.3); 8.226(3.4); 8.221(3.7); 8.146(1.8); 8.142(1.6); 8.124(3.0); 8.120(2.9); 8.064(3.8); 8.042(2.3); 8.004(4.1); 7.999(4.2); 7.991(4.1); 7.969(4.3); 7.953(1.6); 7.573(5.3); 7.359(2.2); 7.354(2.2); 7.337(2.1); 7.332(2.0); 4.594(7.5); 4.517(2.3); 4.511(2.3); 4.503(2.3); 4.496(2.2); 3.918(2.7); 3.875(3.3); 3.539(3.1); 3.495(2.7); 3.375(0.3); 3.332(256.7); 3.301(0.4); 2.891(12.4); 2.732(9.8); 2.731 (10.0); 2.677(0.5); 2.672(0.7); 2.667(0.5); 2.525(1.8); 2.521(2.7); 2.512(37.1); 2.507(75.0); 2.503(100.0); 2.498(74.5); 2.494(36.6); 2.334(0.4); 2.330(0.6); 2.325(0.5); 1.632(16.0); 1.234(0.6); 0.000(4.7)

Example 245: ¹H-NMR(400.0 MHz, DMSO):
8.968(4.5); 8.963(4.6); 8.628(3.3); 8.623(3.1); 8.137(4.5); 8.115(3.8); 8.110(3.0); 8.089(4.0); 8.068(1.5); 7.776(0.9); 7.764(1.2); 7.760(1.2); 7.747(0.9); 7.117(0.7); 7.102(2.9); 7.097(4.1); 7.081(1.8); 7.078(1.8); 7.061(0.6); 7.059(0.6); 6.954(0.9); 6.950(0.7); 6.934(1.5); 6.932(1.4); 6.918(1.0); 6.914(0.9); 6.796(2.2); 6.778(1.7); 4.841(0.9); 4.833(1.1); 4.823(1.1); 4.816(1.0); 4.601(8.5); 4.050(0.6); 4.038(1.4); 4.025(0.8); 4.022(0.9); 4.009(1.6); 3.997(0.7); 3.668(0.7); 3.658(1.1); 3.648(0.9); 3.637(2.2); 3.630(0.9); 3.620(2.0); 3.609(0.9); 3.603(1.7); 3.586(0.8); 3.529(1.4); 3.500(1.0); 3.486(4.8); 3.480(1.4); 3.466(1.0); 3.459(4.6); 3.446(0.7); 3.415(1.3); 3.327(124.6); 2.891(1.6); 2.787(0.4); 2.774(0.4); 2.766(0.4); 2.751(0.7); 2.747(0.7); 2.732(1.8); 2.726(0.7); 2.713(0.5); 2.676(0.4); 2.672(0.6); 2.667(0.4); 2.619(0.6); 2.608(1.2); 2.597(0.7); 2.578(0.5); 2.567(0.8); 2.556(0.5); 2.525(1.1); 2.520(2.3); 2.512(30.7); 2.507(62.1); 2.502(82.9); 2.498(60.5); 2.493(28.8); 2.334(0.4); 2.329(0.5); 2.325(0.4); 1.600(16.0); 1.234(0.6); 0.000(7.3)

Example 246: ¹H-NMR(400.0 MHz, DMSO):
8.954(3.5); 8.949(3.5); 8.607(2.9); 8.602(2.8); 8.240(3.0); 8.236(3.2); 8.171(1.6); 8.167(1.4); 8.149(2.4); 8.144(2.2); 8.120(0.8); 8.105(1.5); 8.090(0.8); 8.076(3.3); 8.054(2.0); 4.592(6.3); 3.885(2.4); 3.842(2.9); 3.484(2.8); 3.440(2.4); 3.329(120.4); 2.978(0.3); 2.962(1.2); 2.947(2.0); 2.933(2.2); 2.917(1.2); 2.901(0.4); 2.892(0.4); 2.672(0.4); 2.512(25.8); 2.508(48.7); 2.503(63.2); 2.499(46.7); 2.494(23.2); 2.330(0.4); 1.610(16.0); 1.571(2.1); 1.489(0.4); 1.480(0.5); 1.471(0.5); 1.462(0.7); 1.453(0.6); 1.445(0.5); 1.436(0.4); 1.234(0.4); 1.133(0.8); 1.102(2.0); 1.078(1.4); 1.048(0.3); 0.860(0.5); 0.836(1.1); 0.807(1.0); 0.777(0.3); 0.000(5.5)

Example 247: ¹H-NMR(400.0 MHz, DMSO):
8.955(6.9); 8.950(7.0); 8.610(5.7); 8.606(5.6); 8.281(0.7); 8.266(0.8); 8.254(1.5); 8.241(7.6); 8.237(8.0); 8.174(2.7); 8.152(4.2); 8.079(6.0); 8.057(3.9); 7.953(0.4); 7.648(0.4); 7.644(0.5); 7.627(0.7); 7.625(0.7); 7.615(0.6); 7.598(0.8); 7.576(0.5); 7.568(0.5); 7.559(0.5); 7.550(0.5); 4.590(12.0); 4.428(0.9); 4.416(0.5); 4.397(1.0); 4.391(1.2); 4.384(2.0); 4.378(2.0); 4.371(1.2); 4.365(1.0); 4.286(0.8); 4.274(1.7); 4.262(1.0); 4.255(0.9); 4.243(1.7); 4.232(0.9); 4.216(1.0); 4.207(1.0); 3.901(2.3); 3.883(0.8); 3.870(1.9); 3.858(2.8); 3.840(0.9); 3.827(2.2); 3.491(2.7); 3.485(3.3); 3.448(2.3); 3.442(2.8); 3.344(663.1); 3.229(0.6); 3.215(0.6); 3.211(0.6); 3.196(1.1); 3.174(1.3); 3.166(1.4); 3.153(2.0); 3.141(1.2); 3.136(1.7); 3.126(1.0); 3.120(0.9); 3.104(0.8); 3.092(0.4); 3.086(0.5); 3.070(0.5); 3.033(0.3); 2.968(0.4); 2.948(0.4); 2.892(3.2); 2.870(0.5); 2.854(0.4); 2.824(0.3); 2.809(0.4); 2.793(0.3); 2.751(0.6); 2.732(2.6); 2.677(0.9); 2.673(1.1); 2.668(0.8); 2.549(0.5); 2.546(0.5); 2.543(0.5); 2.526(3.3); 2.512(67.7); 2.508(129.7); 2.504(167.7); 2.499(122.9); 2.495(59.8); 2.335(0.9); 2.330(1.2); 2.326(0.8); 2.282(0.5); 2.264(0.8); 2.252(0.9); 2.235(0.9); 1.950(0.4); 1.940(0.4); 1.934(0.5); 1.925(0.4); 1.919(0.4); 1.861(0.5); 1.838(0.7); 1.830(1.0); 1.822(0.9); 1.809(0.9); 1.803(1.0); 1.794(0.9); 1.777(0.5); 1.748(0.3); 1.741(0.6); 1.734(0.6); 1.727(0.6); 1.719(0.8); 1.712(1.1); 1.705(1.1); 1.698(1.1); 1.691(0.8); 1.683(0.6); 1.676(0.6); 1.669(0.6); 1.662(0.4); 1.609(15.0); 1.603(16.0); 1.499(1.7); 1.490(1.8); 1.480(1.8); 1.470(1.5); 1.459(0.9); 1.448(0.6); 1.436(0.4); 1.422(0.5); 1.406(0.4); 1.391(0.8); 1.382(0.7); 1.371(1.3); 1.353(2.2); 1.343(1.7); 1.328(2.5); 1.316(1.4); 1.312(1.4); 1.300(0.9); 1.291(0.5); 1.281(0.5); 1.234(1.1); 1.151(0.4); 1.127(0.4); 0.967(1.0); 0.956(1.5); 0.944(1.1); 0.938(1.0); 0.927(1.4); 0.915(0.9); 0.000(0.5)

Example 248: ¹H-NMR(400.0 MHz, DMSO):
9.008(2.3); 9.002(2.4); 8.761(1.7); 8.755(1.7); 8.748(0.6); 8.733(1.1); 8.719(0.5); 8.229(1.6); 8.225(1.8); 8.181(1.1); 8.177(0.9); 8.159(1.5); 8.154(1.4); 8.081(1.8); 8.059(1.2); 7.953(0.7); 7.435(0.4); 7.377(16.0); 4.136(2.5); 4.122(2.5); 3.910(1.4); 3.867(1.7); 3.531(1.6); 3.488(1.4); 3.360(0.4); 3.329(166.0); 3.308(0.5); 2.891(6.0); 2.751(0.6); 2.731(4.8); 2.676(0.3); 2.672(0.5); 2.667(0.3); 2.534(0.4); 2.525(1.4); 2.520(2.2); 2.512(26.3); 2.507(52.4); 2.503(69.8); 2.498 (51.0); 2.493(24.4); 2.334(0.3); 2.329(0.5); 2.325(0.3); 1.635(8.3); 1.234(0.5); 0.000(4.4)

Example 249: ¹H-NMR(400.0 MHz, DMSO):
9.004(3.8); 8.998(4.0); 8.765(2.8); 8.760(2.7); 8.218(2.8); 8.214(3.2); 8.174(1.8); 8.169(1.4); 8.152(2.7); 8.147(2.4); 8.124(0.7); 8.109(1.4); 8.094(0.7); 8.078(3.2); 8.056(2.1); 3.877(2.4); 3.834(2.9); 3.476(2.9); 3.433(2.5); 3.341(200.9); 2.963(1.2); 2.948(1.9); 2.933(2.0); 2.917(1.2); 2.901(0.3); 2.892(0.7); 2.733(0.6); 2.732(0.6); 2.673(0.4); 2.527(1.0); 2.522(1.6); 2.513(20.8); 2.509(41.5); 2.504(54.7); 2.500(39.8); 2.495(18.9); 2.331(0.4); 1.611(16.0); 1.571(1.9); 1.489(0.4); 1.480(0.4); 1.470(0.5); 1.462(0.6); 1.453(0.5); 1.444(0.4); 1.435(0.4); 1.233(0.4); 1.133(0.8); 1.102(1.8); 1.078(1.3); 0.860(0.5); 0.835(1.0); 0.807(0.9); 0.000(2.6)

Example 250: ¹H-NMR(400.0 MHz, DMSO):
8.955(3.8); 8.950(3.9); 8.608(3.0); 8.603(2.9); 8.236(3.0); 8.232(3.3); 8.167(1.7); 8.162(1.5); 8.145(3.0); 8.140(3.2); 8.126(1.7); 8.111(0.8); 8.076(3.5); 8.054(2.2); 4.593(7.4); 3.868(2.5); 3.825(3.0); 3.482(2.9); 3.439(2.5); 3.326(125.4); 3.271(0.3); 3.267(0.3); 3.253(1.1); 3.234(2.0); 3.219(2.1); 3.200(1.1); 3.183(0.9); 2.891(2.0); 2.751(0.5); 2.731(1.6); 2.676(0.4); 2.671(0.6); 2.667(0.4); 2.525(1.5); 2.511(33.5); 2.507(66.7); 2.502(88.5); 2.498(64.8); 2.493(31.2); 2.334(0.4); 2.329(0.6); 2.325(0.4); 1.900(0.8); 1.871(1.7); 1.849(2.0); 1.825(1.3); 1.818(1.3); 1.778(0.9); 1.772(1.1); 1.748(2.7); 1.722(1.1); 1.716(1.0); 1.650(4.9); 1.627(3.5); 1.598(16.0); 1.453(0.9); 1.421(1.8); 1.388(1.0); 1.234(0.9); 0.000(8.8)

Example 251: ¹H-NMR(400.0 MHz, DMSO):
9.012(4.4); 9.006(4.6); 8.901(1.0); 8.886(2.2); 8.870(1.0); 8.770(3.9); 8.764(3.8); 8.239(3.6); 8.235(4.1); 8.189(2.0); 8.184(1.7); 8.167(3.0); 8.162(2.9); 8.149(9.5); 8.090(4.1); 8.068(2.6); 7.953(0.5); 6.649(0.5); 6.118(6.2); 6.105(0.7); 4.691(8.1); 4.685(8.2); 4.281(0.6); 4.266(0.5); 4.196(2.6); 4.192(2.6); 4.177(2.6); 3.917(2.7); 3.874(3.3); 3.638(1.9); 3.632(4.0); 3.626(1.9); 3.553(3.3); 3.510(2.7); 3.327(113.8); 2.891(3.9); 2.751(0.4); 2.731(3.2); 2.676(0.5); 2.672(0.7); 2.667(0.5); 2.525(2.0); 2.511(38.4); 2.507(76.1); 2.502(101.0); 2.498(74.8); 2.494(36.7); 2.390(1.6); 2.334(0.5); 2.329(0.7); 2.325(0.5); 2.047(0.4); 1.665(2.7); 1.656(16.0); 1.643(0.8); 1.605(0.7); 1.268(0.5); 1.234(0.6); 0.000(8.9)

Example 252: ¹H-NMR(400.0 MHz, DMSO):
9.009(4.5); 9.003(5.2); 8.999(3.0); 8.762(4.4); 8.757(4.2); 8.235(3.1); 8.229(4.0); 8.222(2.3); 8.182(2.0); 8.177(1.6); 8.172(1.3); 8.167(1.1); 8.160(2.9); 8.155(2.7); 8.150(1.9); 8.145(1.7); 8.082(3.4); 8.074(2.3); 8.060(2.3); 8.052(1.8); 8.035(1.0); 8.030(1.0); 8.009(1.7); 7.994(2.0); 7.986(2.4); 7.971(2.0); 7.954(0.8); 4.386(0.7); 4.372(0.8); 4.360(1.2); 4.346(1.2); 4.334(0.6); 4.319(0.5); 3.854(3.9); 3.810(5.0); 3.568(3.0); 3.543(1.9); 3.524(2.4); 3.500(1.6); 3.328(219.3); 3.303(0.5); 3.246(0.4); 3.233(0.4); 3.216(0.4); 3.207(0.9); 3.196(0.7); 3.179(0.7); 3.167(0.9); 3.158(0.4); 3.140(0.4); 3.128(0.3); 3.080(0.4); 3.066(0.8); 3.048(0.9); 3.030(0.7); 3.017(0.4); 2.891(6.0); 2.732(4.6); 2.677(0.6); 2.672(0.8);

NMR Peak Lists Table 1

2.667(0.6); 2.525(2.0); 2.521(3.2); 2.512(44.7); 2.507(90.6); 2.503(120.6); 2.498(87.6); 2.494(41.4); 2.334(0.6); 2.330(0.8); 2.325(0.6); 1.923(0.7); 1.896(0.9); 1.838(1.3); 1.810(1.4); 1.750(0.8); 1.739(0.7); 1.726(0.7); 1.715(0.9); 1.666(0.5); 1.636(10.7); 1.620(16.0); 1.394(0.5); 1.389(0.7); 1.362(0.5); 1.337(0.5); 1.311(0.8); 1.281(0.8); 1.252(0.4); 1.246(0.4); 1.234(1.0); 1.217(0.6); 1.186(0.9); 1.153(0.7); 0.008(0.4); 0.000(13.3); −0.009(0.4)

Example 253: $^1$H-NMR(400.0 MHz, DMSO):
8.968(4.2); 8.963(4.3); 8.956(0.5); 8.951(0.4); 8.927(1.0); 8.912(2.0); 8.897(0.9); 8.621(3.4); 8.616(3.2); 8.317(0.5); 8.291(3.2); 8.284(3.5); 8.280(3.7); 8.270(3.1); 8.219(2.0); 8.215(1.7); 8.197(2.7); 8.193(2.4); 8.100(3.5); 8.078(2.7); 7.953(1.5); 7.926(1.9); 7.908(2.2); 7.862(2.1); 7.841(2.5); 7.683(1.2); 7.679(1.2); 7.665(1.7); 7.662(2.2); 7.658(1.2); 7.644(2.0); 7.641(1.6); 7.627(1.3); 7.624(1.2); 7.615(1.1); 7.598(1.3); 7.575(0.9); 7.567(1.1); 7.562(2.0); 7.559(2.1); 7.549(1.1); 7.542(2.5); 7.539(1.8); 7.531(0.5); 7.525(1.1); 7.522(1.0); 7.409(3.7); 7.388(3.7); 4.598(12.1); 4.584(4.7); 3.984(2.6); 3.940(3.2); 3.736(0.7); 3.582(3.1); 3.538(2.6); 3.330(259.7); 3.204(0.5); 2.891(11.0); 2.748(0.4); 2.732 (8.9); 2.676(0.9); 2.672(1.2); 2.667(0.9); 2.663(0.5); 2.542(0.9); 2.525(4.2); 2.512(74.6); 2.507(147.8); 2.503(192.2); 2.498(137.2); 2.494(65.3); 2.334(0.9); 2.329(1.2); 2.325(0.9); 1.716(16.0); 1.652(1.2); 1.604(0.4); 1.235(0.5); 0.008 (1.9); 0.000(44.8); −0.008(1.6)

Example 254: $^1$H-NMR(400.0 MHz, DMSO):
8.839(3.9); 8.833(3.9); 8.330(3.0); 8.324(2.9); 8.179(3.0); 8.174(3.2); 8.068(1.3); 8.063(1.1); 8.046(2.7); 8.041(2.6); 8.011(3.7); 7.989(1.7); 7.882(1.4); 7.862(1.3); 3.934(0.7); 3.917(1.3); 3.908(15.2); 3.897(3.6); 3.881(0.8); 3.864(0.4); 3.853(3.1); 3.461(3.0); 3.418(2.6); 3.340(61.8); 3.142(3.2); 3.124(5.0); 3.106(3.3); 2.682(0.4); 2.677(0.6); 2.673(0.4); 2.530(2.2); 2.517(39.4); 2.513(75.6); 2.508(96.8); 2.504(70.2); 2.500(34.7); 2.339(0.4); 2.335(0.6); 2.330(0.4); 1.722(0.4); 1.703(1.8); 1.685(3.3); 1.667(3.4); 1.649(1.9); 1.631(0.5); 1.594(16.0); 1.113(9.1); 1.096(9.0); 1.068(9.2); 1.051(9.5); 1.045(6.4); 1.027(11.5); 1.009(5.1)

Example 255, Solvent: DMSO, Spectrometer: 300,16 MHz
9.0039 (7.30); 8.9961 (7.89); 8.7759 (5.47); 8.7684 (5.24); 8.3033 (5.38); 8.2974 (5.88); 8.1926 (3.00); 8.1863 (2.61); 8.1630 (4.80); 8.1566 (4.64); 8.0788 (6.23); 8.0492 (3.75); 7.9335 (2.74); 7.9059 (2.86); 4.3860 (2.56); 4.3606 (2.55); 4.3548 (2.32); 3.9990 (0.41); 3.9775 (1.20); 3.9552 (1.78); 3.9502(1.46); 3.9284 (1.76); 3.9062 (1.24); 3.8837 (0.46); 3.3312 (85.45); 2.5152(10.51); 2.5093 (23.42); 2.5032 (32.91); 2.4972 (24.52); 2.4912 (12.08); 2.2235 (0.37); 2.2037 (0.41); 2.1779 (1.53); 2.1582 (2.32); 2.1404 (3.98); 2.1220 (4.24); 2.1052 (1.63); 2.0949 (1.47); 2.0828 (1.14); 2.0520 (0.71); 1.9902 (0.38); 1.9471 (1.20); 1.9280(1.47); 1.9045 (1.05); 1.8840 (1.58); 1.8470(1.24); 1.8249 (1.26); 1.5609 (0.51); 1.5415 (0.78); 1.5212 (1.15); 1.5006 (0.99); 1.4825 (0.98); 1.4595 (0.69); 1.4423 (0.36); 1.2448 (0.60); 1.1189 (15.29); 1.0970 (15.37); 1.0697 (16.00); 1.0477 (15.89); 0.8577 (0.63); 0.8350 (0.35); 0.0109 (0.82); −0.0002 (29.65); −0.0111 (1.41)

Example 256, Solvent: CDCl3, Spectrometer: 300,16 MHz
8.8267 (2.35); 8.8195 (2.27); 8.0659 (6.35); 8.0609 (3.68); 7.9268 (2.00); 7.9209 (1.87); 7.8397 (2.72); 7.2885 (2.28); 7.2514 (3.75); 7.0062 (0.51); 6.9891 (0.92); 6.9719 (0.53); 4.3631 (0.67); 4.3442 (0.67); 4.3136 (1.47); 4.2947 (1.45); 4.2360 (1.48); 4.2190 (1.50); 4.1866 (0.70); 4.1695 (0.68); 4.0716 (1.25); 4.0473 (3.87); 4.0229 (3.96); 4.0056 (2.58); 3.9987 (1.53); 3.9485 (2.77); 3.3893 (2.61); 3.3321 (2.23); 2.8986 (0.81); 2.8734 (2.50); 2.8482 (2.60); 2.8230 (0.91); 2.2164(1.47); 2.1890 (16.00); 1.7775 (13.46); 1.4395 (4.80); 1.4151 (10.07); 1.3909 (8.75); 1.3660 (9.47); 1.3407 (4.19); 0.0797 (9.55); 0.0674 (0.41); −0.0002 (0.94)

Example 257, Solvent: CDCl3, Spectrometer: 300,16 MHz
8.7926 (2.24); 8.7857 (2.17); 8.0507 (6.38); 8.0461 (3.76); 7.9057 (1.93); 7.8006 (2.76); 7.3050 (1.43); 7.2547 (3.88); 7.0371 (0.53); 7.0198 (0.97); 7.0025 (0.56); 4.3651 (0.69); 4.3461 (0.69); 4.3155 (1.50); 4.2966 (1.48); 4.2370 (1.51); 4.2200 (1.54); 4.1876 (0.73); 4.1705 (0.71); 4.0680 (1.28); 4.0436 (3.92); 4.0193 (4.03); 4.0001 (2.63); 3.9952 (1.70); 3.9430 (2.72); 3.3856 (2.58); 3.3284 (2.20); 2.5294 (9.83); 2.4655 (1.17); 2.1892 (16.00); 1.7761 (13.32); 1.4351 (4.83); 1.4243 (0.32); 1.4108 (10.11); 1.3986 (0.36); 1.3864(4.72); −0.0002 (0.56)

Example 258, Solvent: CDCl3, Spectrometer: 300,16 MHz
9.3505 (0.48); 9.3348 (5.38); 9.3176 (0.72); 9.3103 (0.62); 9.1877 (3.42); 9.1806 (3.22); 9.1171 (11.88); 9.0142 (0.70); 8.4775 (0.53); 8.4705 (0.49); 8.3812 (3.24); 8.3739 (2.98); 8.2596 (0.89); 8.2549 (0.87); 8.2299 (2.91); 8.2251 (3.00); 8.2039 (4.28); 8.1742 (1.27); 8.0308 (0.67); 8.0102 (3.44); 7.2904 (2.53); 7.2890 (2.55); 6.7503 (1.27); 6.7238 (1.27); 4.1112(0.41); 4.0888 (0.80); 4.0668 (1.17); 4.0407 (1.53); 4.0254 (3.08); 3.9966 (0.38); 3.9827 (0.65); 3.9684 (3.06); 3.4098 (0.51); 3.3919 (2.96); 3.3526 (0.47); 3.3346 (2.52); 2.9655 (1.46); 2.8881 (1.38); 2.0487 (1.28); 2.0350(1.64); 1.7760 (16.00); 1.3571 (0.64); 1.3355 (0.61); 1.2614 (0.53); 1.2275 (9.10); 1.2057 (9.04); 1.1661 (8.93); 1.1442 (8.79); 0.0014 (1.22); −0.0002 (1.24)

Example 259: $^1$H-NMR(499.9 MHz, CDCl3):
8.825(2.4); 8.821(2.3); 8.096(0.3); 8.092(0.4); 8.086(0.5); 8.075(6.7); 8.073(6.4); 7.919(2.1); 7.916(2.0); 7.843(3.1); 7.261(10.2); 6.706(0.7); 6.691(0.7); 4.059(0.7); 4.046(1.0); 4.043(0.7); 4.033(0.8); 4.030(0.9); 4.017(0.6); 3.963(2.8); 3.929(3.1); 3.342(3.2); 3.307(2.9); 2.951(0.3); 2.882(1.1); 2.867(2.9); 2.852(2.9); 2.837(1.0); 1.761(0.4); 1.747(16.0); 1.628(1.8); 1.381(4.6); 1.366(9.4); 1.351(4.5); 1.324(0.5); 1.311(0.5); 1.256(0.4); 1.206(8.3); 1.193(8.2); 1.144(8.2); 1.131(8.1); 0.000(5.3)

Example 260, Solvent: CDCl3, Spectrometer: 300,16 MHz
8.8032 (1.96); 8.7964(2.00); 8.0731 (5.57); 8.0691 (6.87); 7.9165 (1.90); 7.9139 (1.93); 7.8115 (3.02); 7.2765 (3.05); 6.7424 (0.64); 6.7160 (0.67); 4.0771 (0.60); 4.0552 (0.88); 4.0502(0.69); 4.0332 (0.72); 4.0283 (0.87); 4.0111(0.35); 4.0063 (0.64); 3.9793 (2.87); 3.9220 (3.34); 3.3611 (3.14); 3.3038 (2.67); 2.5369 (10.50); 1.7528 (16.00); 1.2131 (8.18); 1.1912 (8.12); 1.1517 (8.21); 1.1298 (8.14); 0.0757 (6.00); −0.0002(1.49)

Example 261, Solvent: CDCl3, Spectrometer: 300,16 MHz
8.9301 (3.07); 8.9225 (3.14); 8.3355 (2.21); 8.3283 (2.16); 8.1583 (0.91); 8.1521 (0.90); 8.1286 (2.40); 8.1224 (2.53); 8.0935 (2.96); 8.0638 (1.10); 7.8666 (2.40); 7.8609 (2.32); 7.2866 (2.36); 7.2746 (3.86); 7.0253 (0.50); 7.0079 (0.93); 6.9905 (0.55); 4.3993 (0.72); 4.3803 (0.74); 4.3495 (2.41); 4.3306 (1.58); 4.3230(1.24); 4.3170 (1.09); 4.2526 (1.44); 4.2358 (1.48); 4.2032 (0.77); 4.1864 (0.75); 4.1339 (0.36); 4.1102(0.37); 4.0844 (1.27); 4.0599 (3.85); 4.0355 (3.93); 4.0112 (1.33); 2.4187 (0.35); 2.3956 (0.66); 2.3740 (0.74); 2.3524 (1.32); 2.3318 (0.80); 2.2783 (0.90); 2.2649 (1.03); 2.2588 (1.14); 2.2464 (0.55); 2.2351 (0.91); 2.2249 (0.57); 2.2143 (0.82); 2.1983 (16.00); 2.0850 (3.74); 2.0568 (0.73); 2.0473 (2.00); 2.0367 (0.48); 2.0321 (0.46); 2.0120 (0.79); 1.9915 (0.52); 1.9855 (0.43); 1.9706 (0.60); 1.9494 (0.64); 1.7525 (0.47); 1.7315 (0.62); 1.7106 (0.59); 1.6898 (0.50); 1.6686 (0.33); 1.4537 (4.83); 1.4293 (10.14); 1.4050 (4.74); 1.2839 (0.43); 1.2601 (0.87); 1.2363 (0.43); −0.0002 (0.99)

Example 262: $^1$H-NMR(400.0 MHz, DMSO):
8.985(0.7); 8.979(0.7); 8.968(1.3); 8.960(4.1); 8.954(4.1); 8.655(0.6); 8.628(0.9); 8.623(1.1); 8.613(3.4); 8.608(3.1); 8.316(1.3); 8.249(3.1); 8.245(3.3); 8.222(0.6); 8.184(1.7); 8.180(1.5); 8.162(2.6); 8.157(2.4); 8.149(0.9); 8.138(1.2); 8.127(0.5); 8.115(1.1); 8.088(4.1); 8.080(1.1); 8.066(2.5); 8.057(0.7); 8.046(0.4); 7.973(0.7); 7.953(2.5); 7.938(1.5);

| NMR Peak Lists Table 1 |
| --- |
| 7.926(1.8); 7.914(1.4); 7.762(0.4); 7.647(0.4); 7.643(0.4); 7.628(0.8); 7.624(0.7); 7.606(0.5); 7.458(0.5); 7.439(0.8); 7.420(1.1); 7.401(0.7); 7.306(0.3); 7.283(0.3); 7.236(0.4); 7.217(0.5); 7.181(0.5); 7.171(0.6); 7.165(0.8); 7.153(1.3); 7.148(1.4); 7.134(4.8); 7.127(4.7); 7.123(5.0); 7.118(5.2); 7.099(2.1); 7.058(0.4); 7.035(0.5); 7.016(0.4); 6.933(0.4); 6.795(0.5); 6.776(0.3); 6.724(0.6); 6.681(1.2); 6.663(0.3); 6.201(0.3); 4.833(1.3); 4.818(2.0); 4.804(1.0); 4.610(1.3); 4.595(7.4); 4.525(0.4); 4.516(1.5); 4.501(2.2); 4.486(1.4); 4.041(0.8); 4.028(1.4); 4.013(1.3); 3.999(1.6); 3.987(0.8); 3.956(0.4); 3.946(0.4); 3.932(0.4); 3.922(0.5); 3.899(0.7); 3.873(2.5); 3.860(0.8); 3.853(0.8); 3.830(3.0); 3.765(0.4); 3.734(0.4); 3.720(0.6); 3.706(0.9); 3.695(1.2); 3.688(1.1); 3.677(1.6); 3.667(1.1); 3.659(1.2); 3.648(1.0); 3.637(0.8); 3.629(0.5); 3.620(0.7); 3.604(0.6); 3.587(0.5); 3.568(0.5); 3.536(2.8); 3.522(4.9); 3.511(4.2); 3.485(1.6); 3.468(2.9); 3.459(1.5); 3.444(1.0); 3.414(1.0); 3.398(1.2); 3.330(898.1); 3.268(0.5); 3.076(1.0); 3.061(1.6); 3.047(0.9); 2.891(16.0); 2.856(0.5); 2.830(0.5); 2.813(0.8); 2.798(0.6); 2.788(1.0); 2.771(1.2); 2.759(0.9); 2.747(1.3); 2.731(14.4); 2.715(1.7); 2.703(1.1); 2.676(3.5); 2.672(4.1); 2.667(2.8); 2.610(0.8); 2.507(440.9); 2.502(540.9); 2.498(377.1); 2.333(2.6); 2.329(3.3); 2.325(2.3); 1.691(0.4); 1.614(2.0); 1.600(3.3); 1.537(13.5); 1.518(1.0); 1.509(2.4); 1.261(1.4); 1.237(0.5); 0.146(0.5); 0.008(7.8); 0.000(102.2); −0.008(3.6); −0.150(0.5) |
| Example 263: $^1$H-NMR(400.0 MHz, DMSO): |
| 8.718(4.0); 8.360(0.6); 8.346(1.2); 8.331(0.6); 8.139(2.2); 8.135(2.4); 8.069(1.3); 8.064(1.1); 8.047(1.5); 8.042(1.4); 7.847(2.2); 7.825(1.8); 7.404(3.8); 4.082(16.0); 4.068(2.3); 3.964(1.1); 3.945(3.3); 3.927(3.3); 3.908(14.7); 3.854(1.6); 3.811(1.9); 3.461(2.0); 3.417(1.7); 3.337(38.2); 3.174(0.4); 2.681(0.4); 2.677(0.5); 2.513(66.9); 2.508(84.4); 2.504(61.5); 2.339(0.4); 2.335(0.5); 2.330(0.4); 2.173(0.6); 2.052(13.6); 1.599(10.1); 1.265(3.8); 1.247(7.8); 1.229(3.6); 1.222(0.6) |
| Example 264: $^1$H-NMR(400.0 MHz, DMSO): |
| 8.835(2.5); 8.829(2.5); 8.371(0.5); 8.356(0.9); 8.342(0.4); 8.321(1.7); 8.316(1.8); 8.170(1.7); 8.165(1.8); 8.051(0.7); 8.047(0.6); 8.029(1.8); 8.024(1.8); 8.003(2.2); 7.981(0.8); 7.397(3.0); 4.084(1.3); 4.076(1.4); 4.070(1.4); 4.062(1.3); 3.953(0.9); 3.935(2.8); 3.917(2.9); 3.903(16.0); 3.884(1.4); 3.840(1.7); 3.484(1.6); 3.441(1.5); 3.354(0.8); 3.335(80.1); 3.319(1.5); 3.303(0.3); 3.169(0.5); 3.136(2.0); 3.119(2.9); 3.100(2.1); 2.677(0.3); 2.672(0.4); 2.525(1.3); 2.521(2.4); 2.512(28.6); 2.507(55.9); 2.503(71.7); 2.498(50.5); 2.494(23.5); 2.482(0.8); 2.477(0.5); 2.330(0.4); 2.168(0.7); 2.048(12.0); 1.698(1.0); 1.680(1.9); 1.662(2.0); 1.643(1.1); 1.625(0.9); 1.604(8.5); 1.592(0.6); 1.253(3.5); 1.234(7.7); 1.216(3.4); 1.040(3.7); 1.022(7.7); 1.003(3.3 |
| Example 265, Solvent: CDCl3, Spectrometer: 499,93 MHz |
| 9.3266 (4.33); 9.1834 (2.72); 9.1789 (2.81); 9.1091 (8.25); 8.3688 (2.54); 8.3643 (2.59); 8.2217 (0.57); 8.2184 (0.55); 8.2039 (2.58); 8.2006 (2.83); 8.1935 (3.71); 8.1758 (0.81); 8.0015 (2.66); 7.9996 (2.71); 7.2792 (3.12); 7.2619 (4.14); 6.9683 (0.62); 6.9578 (1.14); 6.9473 (0.68); 4.3558 (0.91); 4.3443 (0.94); 4.3260 (1.49); 4.3145 (1.49); 4.2348 (1.48); 4.2245 (1.54); 4.2050 (0.97); 4.1947 (0.95); 4.1278 (0.37); 4.1135 (0.38); 4.0673 (1.28); 4.0527 (3.93); 4.0381 (4.04); 4.0263 (2.78); 3.9923 (2.65); 3.3947 (2.55); 3.3606 (2.33); 2.1904 (16.00); 2.0408 (1.59); 1.9197 (0.94); 1.7914 (13.76); 1.7733 (0.40); 1.4403 (4.39); 1.4321 (0.56); 1.4256 (8.92); 1.4110 (4.48); 1.2716 (0.71); 1.2575 (2.31); 1.2431 (0.68); 0.8798 (0.42); 0.8655 (0.41); 0.8601 (0.33); 0.8516 (0.38); 0.8455 (0.34); 0.0769 (0.54); −0.0002 (1.67) |
| Example 266: $^1$H-NMR(300.2 MHz, CDCl3): |
| 8.943(3.0); 8.936(3.1); 8.356(2.5); 8.348(2.5); 8.112(6.0); 8.107(3.5); 8.077(0.3); 7.941(2.7); 7.319(3.9); 7.310(0.8); 7.293(1.9); 6.897(0.5); 6.880(0.8); 6.863(0.5); 4.343(1.0); 4.334(3.2); 4.316(4.1); 4.291(0.7); 4.101(1.3); 4.076(3.9); 4.052(4.1); 4.047(1.3); 4.028(1.7); 4.011(0.4); 3.940(1.8); 3.918(3.0); 3.894(2.0); 2.240(16.0); 2.197(0.2); 2.183(0.4); 2.176(0.5); 2.162(0.4); 2.085(0.4); 2.075(0.4); 2.067(0.4); 2.057(0.6); 2.047(1.3); 2.039(0.7); 2.021(0.7); 2.001(0.6); 1.983(0.9); 1.966(1.0); 1.950(0.5); 1.936(0.4); 1.920(0.4); 1.773(0.5); 1.751(0.5); 1.748(0.5); 1.730(0.6); 1.529(0.4); 1.510(0.5); 1.491(0.5); 1.483(0.5); 1.470(5.3); 1.446(10.8); 1.421(5.0); 1.295(0.4); 1.260(0.6); 0.000(0.6) |
| Example 267: $^1$H-NMR(300.2 MHz, CDCl3): |
| 8.939(5.5); 8.931(5.6); 8.322(4.7); 8.315(4.5); 8.165(2.0); 8.159(2.0); 8.135(5.1); 8.129(5.3); 8.097(6.1); 8.067(2.4); 7.820(5.1); 7.814(4.9); 7.271(9.1); 6.605(1.5); 6.578(1.5); 5.303(0.4); 4.129(0.4); 4.107(1.2); 4.085(1.7); 4.080(1.4); 4.063(1.5); 4.058(1.7); 4.041(0.7); 4.036(1.2); 4.014(0.5); 3.995(5.1); 3.938(6.3); 3.695(0.3); 3.509(5.7); 3.451(4.6); 1.754(2.3); 1.643(0.6); 1.625(1.3); 1.615(1.4); 1.606(0.9); 1.596(2.3); 1.579(1.5); 1.569(1.5); 1.551(0.8); 1.256(2.6); 1.222(16.0); 1.200(15.8); 1.162(16.0); 1.140(15.9); 1.116(0.5); 1.107(0.5); 0.903(0.7); 0.881(2.1); 0.858(1.0); 0.718 (1.0); 0.709(1.0); 0.699(1.1); 0.696(1.1); 0.686(1.2); 0.679(1.7); 0.673(1.3); 0.667(1.1); 0.662(1.3); 0.658(1.2); 0.637(0.5); 0.631(0.7); 0.625(0.6); 0.607(1.4); 0.600(1.7); 0.591(2.7); 0.584(2.8); 0.578(3.0); 0.567(1.9); 0.563(2.8); 0.557(3.2); 0.551(2.3); 0.543(1.7); 0.539(1.9); 0.536(1.9); 0.530(1.6); 0.519(2.1); 0.514(2.7); 0.498(1.5); 0.492(1.3); 0.480(1.2); 0.473(1.0); 0.073(0.6); 0.000(4.2) |
| Example 268: $^1$H-NMR(300.2 MHz, CDCl3): |
| 8.943(3.1); 8.935(3.2); 8.325(2.3); 8.318(2.2); 8.145(0.8); 8.139(0.7); 8.115(2.7); 8.109(2.9); 8.092(3.3); 8.063(0.9); 7.816(2.3); 7.810(2.3); 7.269(8.2); 7.259(3.9); 6.827(0.5); 6.810(0.9); 6.793(0.5); 5.302(0.4); 4.401(0.8); 4.382(0.8); 4.352(1.4); 4.332(1.3); 4.230(1.4); 4.214(1.4); 4.181(0.8); 4.164(0.8); 4.089(1.2); 4.064(3.8); 4.040(3.9); 4.015(1.8); 4.012(2.6); 3.954(2.9); 3.531(2.6); 3.473(2.1); 2.200(16.0); 2.047(0.6); 1.736(5.0); 1.658(0.6); 1.648(0.6); 1.639(0.4); 1.630(1.1); 1.612(0.7); 1.603(0.7); 1.585(0.4); 1.456(5.0); 1.432(10.5); 1.407(4.9); 1.260(0.5); 1.255(0.4); 0.708(0.5); 0.701(0.4); 0.694(0.5); 0.688(0.6); 0.677(0.8); 0.669(0.7); 0.666(0.5); 0.660(0.5); 0.653(0.5); 0.643(0.4); 0.635(0.4); 0.618(0.6); 0.608(0.8); 0.598(1.0); 0.590(1.2); 0.583(1.0); 0.572(1.3); 0.565(1.0); 0.555(0.9); 0.547(0.7); 0.544(0.8); 0.537(0.7); 0.529(0.8); 0.521(0.9); 0.516(0.9); 0.512(0.8); 0.499(0.6); 0.494(0.5); 0.491(0.5); 0.480(0.5); 0.473(0.3); 0.000(5.4) |
| Example 269: $^1$H-NMR(300.2 MHz, CDCl3): |
| 8.942(14.3); 8.935(14.7); 8.323(11.7); 8.316(11.6); 8.151(4.3); 8.145(4.2); 8.121(13.1); 8.115(13.9); 8.093(16.0); 8.064(5.0); 7.813(12.4); 7.807(12.2); 7.267(38.3); 7.253(0.6); 7.252(0.5); 7.249(0.4); 7.246(0.4); 6.798(4.5); 6.789(4.7); 5.302(0.8); 4.006(12.7); 3.949(15.7); 3.510(14.3); 3.453(11.6); 2.808(0.9); 2.795(2.6); 2.783(3.9); 2.771(6.0); 2.759(6.1); 2.747(4.3); 2.735(3.0); 2.722(1.1); 2.047(0.4); 1.660(15.1); 1.646(2.0); 1.628(3.2); 1.618(3.4); 1.609(2.1); 1.600(6.5); 1.592(2.3); 1.582(3.7); 1.572(3.7); 1.554(1.9); 1.305(0.5); 1.260(2.9); 0.903(0.9); 0.881(3.1); 0.871(1.4); 0.859(1.7); 0.847(2.8); 0.836(1.3); 0.828(4.5); 0.822(10.0); 0.814(9.4); 0.804(4.7); 0.798(9.3); 0.790(10.4); 0.778(1.7); 0.767(3.8); 0.757(1.1); 0.754(1.1); 0.743(1.7); 0.725(1.0); 0.708(2.5); 0.702(2.9); 0.690(2.7); 0.686(3.0); 0.683(3.2); 0.676(2.2); 0.669(4.2); 0.661(3.5); 0.652(3.0); 0.643(2.7); 0.632(2.0); 0.623(1.5); 0.605(4.8); 0.595(5.1); 0.589(8.3); 0.583(7.7); 0.576(7.3); 0.566(5.9); 0.561(9.9); 0.555(13.8); 0.546(14.3); 0.541(14.3); 0.533(10.1); 0.527(5.5); 0.523(4.4); 0.518(4.9); 0.511(6.4); 0.499(4.8); 0.492(5.3); 0.482(2.9); 0.477(3.8); 0.471(3.4); 0.459(3.2); 0.452(2.7); 0.437(0.5); 0.419(0.4); 0.011(0.9); 0.000(28.0); −0.011(1.3) |

NMR Peak Lists Table 1

Example 270: ¹H-NMR(300.2 MHz, CDCl3):
8.934(4.8); 8.927(3.9); 8.321(4.6); 8.315(3.7); 8.165(2.3); 8.159(2.1); 8.135(4.5); 8.129(3.8); 8.089(4.6); 8.060(2.0); 7.812(5.1); 7.807(4.0); 7.355(6.3); 7.273(2.0); 3.993(3.6); 3.936(4.4); 3.574(1.2); 3.554(2.5); 3.542(4.6); 3.532(5.5); 3.521(8.1); 3.519(7.9); 3.515(7.3); 3.512(7.2); 3.505(10.2); 3.495(10.9); 3.472(8.8); 3.454(4.2); 3.448(6.0); 3.435(1.1); 3.387(1.1); 3.366(1.9); 3.348(1.9); 3.326(1.4); 3.320(1.1); 3.303(1.0); 3.281(0.4); 1.846(2.5); 1.825(5.3); 1.804(9.9); 1.766(1.2); 1.656(0.9); 1.638(1.6); 1.629(1.6); 1.620(1.4); 1.611(2.3); 1.593(1.5); 1.584(1.3); 1.565(0.8); 1.554(0.4); 1.275(9.2); 1.251(16.0); 1.228(7.0); 0.881(0.4); 0.857(0.3); 0.734(1.3); 0.727(1.2); 0.716(1.6); 0.696(2.1); 0.683(1.3); 0.657(0.6); 0.642(0.6); 0.621(1.3); 0.602(2.3); 0.586(3.8); 0.580(4.1); 0.575(3.2); 0.559(3.8); 0.553(3.6); 0.546(3.5); 0.539(3.3); 0.522(2.8); 0.506(1.4); 0.488(1.0); 0.482(0.7); 0.000(4.6)

Example 271: ¹H-NMR(499.9 MHz, CDCl3):
8.939(13.6); 8.935(15.3); 8.318(13.3); 8.313(14.7); 8.141(5.0); 8.137(5.6); 8.123(10.8); 8.119(12.5); 8.094(16.0); 8.076(7.1); 7.815(14.6); 7.813(16.0); 7.261(47.7); 6.954(5.5); 5.296(0.4); 4.150(2.4); 4.145(2.7); 4.139(2.7); 4.134(2.7); 4.115(5.5); 4.110(6.3); 4.104(6.2); 4.099(6.1); 4.062(5.4); 4.057(6.3); 4.052(6.4); 4.047(6.2); 4.027(2.4); 4.022(2.8); 4.017(2.8); 4.012(2.7); 3.975(12.9); 3.941(14.9); 3.514(14.4); 3.479(12.6); 2.248(7.2); 2.243(14.9); 2.238(8.8); 2.041(0.5); 2.031(0.4); 1.628(1.8); 1.618(3.9); 1.612(4.7); 1.607(4.3); 1.600(11.7); 1.593(81.3); 1.574(2.9); 1.316(0.5); 1.303(0.9); 1.288(1.2); 1.265(3.6); 1.255(5.4); 0.895(1.9); 0.882(4.4); 0.868(2.2); 0.744(1.5); 0.738(2.7); 0.734(3.6); 0.729(4.2); 0.719(5.1); 0.711(4.7); 0.701(2.6); 0.635(1.2); 0.628(1.3); 0.618(3.8); 0.610(4.7); 0.607(4.8); 0.602(8.4); 0.595(7.6); 0.586(8.6); 0.578(6.1); 0.570(5.0); 0.560(1.7); 0.550(3.2); 0.539(4.8); 0.532(4.4); 0.527(3.6); 0.521(4.1); 0.516(3.7); 0.513(2.9); 0.506(1.9); 0.000(31.5)

Example 272: ¹H-NMR(300.2 MHz, CDCl3):
8.934(5.8); 8.926(6.0); 8.328(4.5); 8.321(4.4); 8.179(2.3); 8.173(2.3); 8.149(4.8); 8.143(5.1); 8.098(5.8); 8.068(2.7); 7.915(5.1); 7.909(5.0); 7.269(12.7); 6.754(1.5); 6.727(1.6); 4.061(1.9); 4.036(2.2); 4.027(2.6); 4.003(2.6); 3.985(1.8); 3.980(1.4); 3.963(1.4); 3.958(1.7); 3.941(0.7); 3.936(1.2); 3.914(0.5); 2.198(1.7); 2.187(1.4); 2.174(1.0); 2.147(2.1); 2.136(1.3); 2.104(1.0); 2.087(1.5); 2.064(1.2); 2.046(1.6); 2.037(0.8); 2.014(0.7); 1.996(0.8); 1.786(0.7); 1.769(0.8); 1.732(1.7); 1.703(3.7); 1.666(1.1); 1.590(0.4); 1.574(0.4); 1.547(0.7); 1.538(0.8); 1.527(0.7); 1.511(0.8); 1.502(0.9); 1.495(0.9); 1.488(0.8); 1.471(1.1); 1.463(1.0); 1.435(1.4); 1.425(0.8); 1.406(0.7); 1.396(1.0); 1.369(0.4); 1.358(0.5); 1.313(0.7); 1.301(0.7); 1.279(1.0); 1.268(1.4); 1.255(1.9); 1.235(1.1); 1.230(1.1); 1.223(0.9); 1.196(0.6); 1.183(0.5); 1.167(15.9); 1.145(15.8); 1.070(16.0); 1.048(15.9); 0.000(6.0)

Example 273: ¹H-NMR(300.2 MHz, CDCl3):
8.947(2.8); 8.939(2.9); 8.350(2.7); 8.343(2.7); 8.113(6.5); 8.108(3.8); 8.078(0.3); 7.935(2.8); 7.272(4.0); 6.622(0.5); 6.597(0.5); 4.326(0.8); 4.310(1.5); 4.293(0.9); 4.159(0.3); 4.135(1.0); 4.130(0.7); 4.111(1.2); 4.108(1.1); 4.103(0.8); 4.086(1.0); 4.081(0.9); 4.064(0.4); 4.059(0.7); 3.957(2.3); 3.936(3.5); 3.933(3.2); 3.912(2.5); 3.806(0.8); 2.082(0.4); 2.073(0.4); 2.063(0.4); 2.048(4.2); 2.036(0.9); 2.017(0.7); 1.998(0.5); 1.994(0.5); 1.977(1.0); 1.961(1.1); 1.944(0.6); 1.930(0.5); 1.914(0.5); 1.776(0.5); 1.754(3.5); 1.733(0.7); 1.713(0.3); 1.709(0.3); 1.526(0.4); 1.508(0.6); 1.489(0.6); 1.481(0.4); 1.471(0.5); 1.463(0.5); 1.444(0.4); 1.404(0.3); 1.284(1.1); 1.260(2.5); 1.246(8.4); 1.237(1.9); 1.224(16.0); 1.202(8.3); 0.000(2.0)

Example 274: ¹H-NMR(300.2 MHz, CDCl3):
8.943(1.4); 8.364(2.4); 8.356(2.4); 8.333(1.7); 8.187(0.8); 8.181(0.8); 8.157(2.8); 8.152(2.6); 8.132(3.7); 8.129(3.8); 8.109(2.2); 8.100(1.1); 8.080(0.6); 7.931(1.7); 7.926(1.7); 7.914(2.5); 7.909(2.3); 7.276(5.3); 6.745(0.5); 6.719(0.6); 6.655(0.7); 6.629(0.7); 4.205(0.4); 4.188(0.7); 4.180(1.4); 4.166(1.0); 4.161(1.0); 4.155(1.5); 4.145(0.8); 4.139(1.0); 4.135(0.8); 4.131(0.6); 4.122(0.4); 4.118(0.7); 4.112(0.6); 4.033(0.4); 4.011(0.6); 4.006(0.5); 3.989(0.5); 3.984(0.6); 3.962(0.5); 3.669(0.6); 3.645(2.0); 3.620(2.0); 3.596(0.6); 2.048(2.1); 1.850(0.5); 1.839(0.5); 1.625(16.0); 1.619(12.6); 1.290(8.3); 1.283(6.2); 1.266(8.6); 1.258(6.9); 1.247(8.7); 1.237(1.5); 1.225(8.3); 1.213(8.3); 1.190(11.1); 1.167(6.0); 1.087(5.8); 1.065(5.8); 0.000(2.6)

Example 275: ¹H-NMR(400.0 MHz, DMSO):
8.713(4.2); 8.137(2.2); 8.132(2.5); 8.076(1.5); 8.071(1.2); 8.054(1.7); 8.049(1.5); 7.954(0.3); 7.864(1.1); 7.844(3.3); 7.822(1.9); 4.078(16.0); 3.924(0.5); 3.908(0.8); 3.904(0.6); 3.891(0.7); 3.888(0.8); 3.871(0.6); 3.855(2.1); 3.812(2.3); 3.427(2.2); 3.384(2.0); 3.331(128.2); 2.892(2.6); 2.733(2.1); 2.672(0.4); 2.526(1.7); 2.512(25.8); 2.508(50.3); 2.503(65.2); 2.499(46.7); 2.494(22.2); 2.330(0.4); 1.579(11.7); 1.104(6.7); 1.088(6.6); 1.061(6.9); 1.045(6.7); 0.000(2.1); −0.062(0.6)

Example 276: ¹H-NMR(400.0 MHz, DMSO):
8.832(3.1); 8.826(3.1); 8.371(0.6); 8.356(1.3); 8.341(0.7); 8.323(2.5); 8.317(2.4); 8.166(2.4); 8.162(2.6); 8.054(0.9); 8.050(0.8); 8.032(2.3); 8.028(2.4); 8.007(3.2); 7.985(1.1); 7.953(0.4); 7.397(4.3); 4.084(1.9); 4.077(2.1); 4.070(2.0); 4.062(2.0); 3.954(1.3); 3.936(3.9); 3.918(3.9); 3.899(1.3); 3.883(1.9); 3.839(2.3); 3.441(1.9); 3.363(0.3); 3.328(132.0); 3.184(1.4); 3.166(4.4); 3.148(4.5); 3.130(1.4); 2.892(3.1); 2.732(2.6); 2.676(0.4); 2.672(0.6); 2.667(0.4); 2.525(1.9); 2.512(33.2); 2.507(64.9); 2.503(84.0); 2.498(60.4); 2.494(29.1); 2.334(0.4); 2.330(0.5); 2.325(0.4); 2.168(0.9); 2.049(16.0); 1.605(11.8); 1.593(1.0); 1.332(4.9); 1.313(10.0); 1.295(4.7); 1.254(4.5); 1.235(9.8); 1.217(4.4); 0.000(2.6)

Example 277: ¹H-NMR(400.0 MHz, DMSO):
8.831(3.9); 8.826(3.9); 8.326(2.9); 8.320(2.7); 8.169(2.9); 8.165(3.0); 8.066(1.3); 8.061(1.1); 8.044(2.8); 8.039(2.8); 8.010(3.7); 7.988(1.6); 7.878(1.3); 7.857(1.3); 3.929(0.7); 3.912(1.0); 3.908(0.8); 3.890(3.2); 3.875(0.8); 3.858(0.3); 3.847(3.1); 3.457(3.0); 3.414(2.6); 3.328(147.1); 3.185(1.7); 3.166(5.5); 3.148(5.6); 3.130(1.8); 2.891(2.0); 2.732(1.6); 2.676(0.4); 2.672(0.6); 2.667(0.4); 2.525(1.6); 2.512(32.2); 2.507(64.8); 2.503(85.2); 2.498(60.9); 2.494(28.9); 2.334(0.4); 2.330(0.5); 2.325(0.4); 1.589(16.0); 1.332(6.0); 1.313(12.4); 1.295(5.7); 1.108(9.0); 1.091(8.9); 1.063(9.0); 1.046(8.9); 0.000(2.8)

Example 278: ¹H-NMR(400.0 MHz, DMSO):
9.011(2.5); 9.005(2.6); 8.755(2.1); 8.750(2.2); 8.693(0.6); 8.679(1.1); 8.665(0.6); 8.308(2.3); 8.303(2.5); 8.205(1.3); 8.200(1.3); 8.183(1.9); 8.178(2.0); 8.092(2.4); 8.070(1.7); 7.953(1.4); 7.563(1.9); 7.559(2.7); 7.554(0.9); 7.546(1.9); 7.542(3.4); 7.539(2.8); 7.533(0.5); 7.529(0.5); 7.444(0.9); 7.441(1.3); 7.436(0.7); 7.424(3.2); 7.404(2.2); 7.386(1.5); 7.375(0.5); 7.368(1.5); 7.350(0.4); 7.263(3.9); 7.097(0.5); 4.424(1.9); 4.416(0.4); 4.381(2.2); 4.373(0.4); 4.117(0.3); 4.101(0.4); 4.080(1.5); 4.064(2.4); 4.048(1.6); 4.026(0.4); 4.011(0.3); 3.942(0.5); 3.924(0.6); 3.915(1.3); 3.896(3.8); 3.878(3.9); 3.860(2.8); 3.816(1.6); 3.335(192.6); 3.333(192.5); 2.892(10.8); 2.734(8.7); 2.733(8.6); 2.677(0.5); 2.672(0.7); 2.668(0.5); 2.526(2.6); 2.512(43.8); 2.508(86.0); 2.503(111.7); 2.499(79.4); 2.494(37.5); 2.335(0.5); 2.330(0.7); 2.325(0.5); 2.124(0.6); 2.093(1.9); 1.967(16.0); 1.356(0.9); 1.235(0.4); 1.220(4.6); 1.202(10.2); 1.187(1.7); 1.184(4.6); 1.170(0.6); 0.000(3.6)

NMR Peak Lists Table 1

Example 279: ¹H-NMR(400.0 MHz, DMSO):
9.366(0.7); 9.352(1.3); 9.338(0.6); 9.043(3.3); 9.037(3.4); 8.825(2.3); 8.820(2.2); 8.585(2.5); 8.580(2.5); 8.316(1.5); 8.312(1.3); 8.294(1.9); 8.289(1.9); 8.188(2.4); 8.166(1.8); 7.756(0.8); 7.748(0.5); 7.739(4.2); 4.280(3.3); 4.266(3.2); 4.036(0.4); 4.031(1.3); 4.013(3.9); 4.003(0.4); 3.995(3.9); 3.985(0.4); 3.977(0.5); 3.333(219.7); 2.892(1.7); 2.732(1.4); 2.677(0.5); 2.672(0.7); 2.668(0.5); 2.565(0.5); 2.551(0.9); 2.537(1.0); 2.525(2.9); 2.512(43.4); 2.508(85.2); 2.503 (110.3); 2.498(78.2); 2.494(36.6); 2.334(0.5); 2.330(0.7); 2.325(0.5); 2.274(1.0); 2.160(16.0); 2.129(0.8); 1.335(4.8); 1.316(10.1); 1.298(4.7); 1.275(0.6); 1.257(0.4); 1.234(0.8); 0.000(3.5)

Example 280: ¹H-NMR(400.0 MHz, DMSO):
9.051(6.9); 9.045(8.2); 9.039(1.4); 8.932(0.4); 8.912(0.4); 8.824(0.8); 8.819(0.8); 8.779(4.9); 8.773(4.6); 8.687(1.7); 8.667(1.6); 8.602(0.9); 8.598(0.9); 8.368(4.9); 8.363(5.1); 8.330(0.5); 8.325(0.5); 8.314(0.6); 8.308(0.7); 8.303(0.7); 8.204(2.5); 8.199(2.2); 8.192(1.0); 8.182(4.7); 8.177(4.7); 8.170(0.4); 8.165(0.4); 8.136(5.8); 8.114(3.0); 7.739(2.5); 4.377(1.4); 4.330(2.0); 4.275(1.4); 4.228(2.1); 4.131(2.2); 4.110(4.7); 4.092(0.4); 4.083(1.6); 4.071(2.7); 4.039(0.4); 4.023(2.3); 4.006(1.6); 3.987(1.5); 3.970(1.0); 3.954(0.4); 3.909(0.5); 3.379(0.5); 3.332(434.5); 3.289(0.3); 3.176(0.7); 3.163(0.7); 2.892(2.5); 2.732(2.0); 2.681(0.4); 2.677(0.8); 2.672(1.1); 2.668(0.8); 2.525(3.6); 2.512(64.8); 2.508(129.5); 2.503(169.7); 2.499(121.4); 2.494(57.6); 2.334(0.8); 2.330(1.0); 2.325(0.8); 1.212(5.3); 1.195(5.3); 1.163(15.7); 1.156(16.0); 1.147(15.9); 1.140(15.4); 0.000(3.5)

Example 281: ¹H-NMR(300.2 MHz, CDCl3):
8.955(2.3); 8.948(2.4); 8.340(1.8); 8.332(1.8); 8.167(0.6); 8.161(0.6); 8.137(2.0); 8.131(2.1); 8.121(0.4); 8.110(2.4); 8.080(0.7); 7.872(1.9); 7.867(1.8); 7.270(2.7); 6.850(0.6); 6.824(0.6); 4.360(2.0); 4.301(2.4); 4.172(0.5); 4.150(0.7); 4.145(0.5); 4.128(0.6); 4.123(0.7); 4.101(0.5); 3.694(2.4); 3.635(2.0); 2.371(16.0); 1.707(0.6); 1.337(0.4); 1.315(0.4); 1.276(6.1); 1.254(6.3); 1.218(6.1); 1.196(6.1); 0.000(2.1)

Example 282: ¹H-NMR(300.2 MHz, DMSO):
8.991(4.5); 8.983(4.9); 8.776(3.4); 8.769(3.3); 8.214(8.9); 8.187(3.4); 8.181(2.5); 8.077(2.8); 8.046(2.0); 4.113(2.8); 4.065(0.7); 4.056(3.3); 4.042(1.5); 4.018(1.5); 3.994(0.5); 3.419(2.2); 3.362(3.1); 3.331(13.8); 2.516(3.7); 2.510(8.1); 2.504(11.3); 2.498(8.4); 2.492(4.1); 1.991(6.2); 1.756(6.3); 1.644(16.0); 1.199(1.7); 1.176(3.4); 1.152(1.7); 0.011(0.4); 0.000(12.0); −0.011(0.6); −0.059(1.0)

Example 284: ¹H-NMR(499.9 MHz, DMSO):
9.016(3.3); 9.011(3.5); 8.753(2.6); 8.749(2.6); 8.289(2.7); 8.285(3.0); 8.189(1.5); 8.185(1.5); 8.171(2.3); 8.168(2.3); 8.100(2.8); 8.082(2.1); 8.069(1.2); 8.053(1.2); 3.994(0.6); 3.981(0.9); 3.978(0.8); 3.967(0.8); 3.964(1.0); 3.951(0.7); 3.938(0.3); 3.930(2.4); 3.893(3.1); 3.698(3.1); 3.662(2.4); 3.286(19.6); 3.280(21.1); 2.507(5.0); 2.503(10.4); 2.499 (14.6); 2.496(11.1); 2.492(6.0); 1.144(8.2); 1.131(16.0); 1.118(8.6); 0.006(0.4); 0.000(11.2); −0.007(0.7)

Example 285: ¹H-NMR(499.9 MHz, DMSO):
9.015(3.3); 9.010(3.5); 8.752(2.6); 8.748(2.6); 8.289(2.8); 8.285(3.0); 8.189(1.6); 8.185(1.5); 8.172(2.3); 8.168(2.2); 8.100(2.8); 8.082(2.1); 8.072(1.2); 8.055(1.2); 3.995(0.7); 3.982(1.0); 3.979(0.8); 3.969(0.8); 3.966(1.0); 3.952(0.7); 3.939(0.4); 3.931(2.4); 3.894(3.1); 3.700(3.1); 3.663(2.4); 3.288(8.8); 3.281(20.4); 2.508(2.6); 2.504(5.3); 2.500(7.3); 2.497(5.5); 2.493(2.8); 1.153(0.6); 1.144(8.2); 1.131(16.0); 1.118(8.6); 0.000(6.6); −0.007(0.4)

Example 286: ¹H-NMR(400.0 MHz, DMSO):
8.960(2.5); 8.383(0.4); 8.368(0.7); 8.354(0.4); 8.259(1.3); 8.254(1.5); 8.199(0.8); 8.195(0.7); 8.177(1.0); 8.172(1.0); 8.020(1.4); 7.998(1.1); 7.404(2.4); 4.079(1.9); 4.064(1.8); 3.961(0.7); 3.943(2.2); 3.925(2.2); 3.903(16.0); 3.876(1.1); 3.833(1.3); 3.481(1.3); 3.438(1.1); 3.337(38.4); 3.169(0.3); 2.672(0.4); 2.525(1.1); 2.512(23.5); 2.507(46.4); 2.503 (60.2); 2.498(43.6); 2.494(21.3); 2.330(0.4); 2.170(0.6); 2.049(9.0); 1.605(6.7); 1.594(0.6); 1.263(2.5); 1.245(5.5); 1.235(0.5); 1.227(2.5); 1.217(0.4)

Example 287: ¹H-NMR(400.0 MHz, DMSO):
8.962(3.3); 8.262(1.8); 8.258(2.0); 8.211(1.1); 8.206(0.9); 8.189(1.3); 8.184(1.1); 8.021(1.8); 7.999(1.4); 7.891(0.8); 7.870(0.8); 3.927(0.5); 3.903(16.0); 3.891(0.9); 3.884(1.7); 3.874(0.5); 3.841(1.8); 3.454(1.7); 3.411(1.5); 3.328(58.7); 2.672(0.4); 2.508(50.9); 2.503(64.2); 2.499(47.0); 2.330(0.4); 1.592(9.4); 1.106(5.2); 1.090(5.2); 1.062(5.3); 1.046(5.3)

Example 288: ¹H-NMR(400.0 MHz, DMSO):
9.224(3.0); 9.219(3.3); 9.091(2.5); 9.086(2.4); 8.391(0.6); 8.376(1.3); 8.362(0.6); 8.333(2.1); 8.329(2.9); 8.314(1.7); 8.309(1.1); 8.292(1.9); 8.287(1.7); 8.172(2.4); 8.150(1.8); 7.953(0.5); 7.406(1.9); 4.083(3.2); 4.068(3.1); 3.960(1.3); 3.954(0.4); 3.942(3.9); 3.924(3.9); 3.908(2.4); 3.865(2.3); 3.518(2.3); 3.475(1.9); 3.330(155.3); 2.891(3.4); 2.731(2.9); 2.676(0.4); 2.672(0.5); 2.667(0.4); 2.525(2.0); 2.511(30.9); 2.507(60.9); 2.503(79.4); 2.498(57.3); 2.494(27.7); 2.334(0.4); 2.329(0.5); 2.325(0.3); 2.171(0.9); 2.050(16.0); 1.613(11.7); 1.601(1.0); 1.260(4.5); 1.242(9.4); 1.234(0.7); 1.224(4.3); 1.215(0.6); 0.000(2.4)

Example 289: ¹H-NMR(400.1 MHz, DMSO):
10.699(5.1); 10.549(2.4); 8.949(4.2); 8.941(4.1); 8.457(1.3); 8.438(3.6); 8.419(2.6); 8.232(6.1); 8.204(0.5); 8.174(0.4); 8.156(1.2); 8.153(1.2); 8.135(3.5); 8.131(3.3); 8.113(3.1); 8.109(3.0); 8.080(2.3); 8.051(4.4); 8.029(2.7); 7.983(1.9); 7.964(2.1); 7.936(1.2); 7.917(1.2); 7.613(2.8); 7.602(4.6); 7.589(10.9); 7.585(9.9); 7.567(16.0); 7.542(5.9); 7.518(4.0); 7.502(3.6); 7.496(2.9); 7.488(2.0); 7.479(2.1); 7.465(0.9); 7.437(0.5); 7.414(0.4); 7.404(0.7); 7.363(2.5); 7.342(2.9); 7.284(0.4); 7.265(0.4); 7.222(0.6); 7.183(5.1); 7.162(4.8); 7.027(2.5); 7.007(2.4); 6.563(0.9); 4.342(2.0); 4.329(2.1); 3.868(2.5); 3.824(3.0); 3.744(1.2); 3.701(1.7); 3.597(0.4); 3.540(2.1); 3.500(4.1); 3.457(3.6); 3.373(3.0); 3.358(3.0); 3.167(4.2); 3.156(1.4); 3.144(1.3); 3.122(2.2); 3.110(2.1); 3.086(2.0); 3.067(2.2); 3.054(1.5); 3.033(2.1); 3.020(2.0); 3.000(1.4); 2.965(0.7); 2.891(0.4); 2.869(0.4); 2.851(0.4); 2.825(0.3); 2.783(0.4); 2.690(0.2); 2.547(0.3); 2.506(19.6); 1.991(0.8); 1.913(1.3); 1.800(1.3); 1.600(8.2); 1.582(1.3); 1.558(1.1); 1.515(14.8); 1.477(1.0); 1.440(0.3); 1.233(1.1); 1.193(0.4); 1.185(0.4); 1.175(0.5); 0.000(4.5)

Example 290: ¹H-NMR(601.6 MHz, DMSO):
9.004(2.3); 9.000(2.3); 8.766(1.7); 8.762(1.6); 8.220(1.8); 8.217(1.9); 8.168(1.1); 8.165(1.0); 8.153(1.5); 8.150(1.4); 8.103(0.5); 8.093(0.9); 8.083(0.5); 8.077(1.8); 8.062(1.3); 4.451(1.0); 4.442(2.1); 4.433(1.0); 3.856(1.7); 3.828(1.9); 3.504(1.8); 3.475(1.6); 3.318(10.3); 3.259(2.3); 3.222(16.0); 3.219(16.0); 3.206(2.1); 3.196(2.0); 3.186(0.8); 2.891 (0.5); 2.732(0.4); 2.523(0.4); 2.520(0.5); 2.517(0.6); 2.508(12.6); 2.505(27.2); 2.502(37.3); 2.499(26.4); 2.496(12.1); 1.612(9.5); 1.273(0.4); 1.261(0.9); 1.250(0.4); 0.000(1.2)

Example 291: ¹H-NMR(601.6 MHz, DMSO):
19.276(0.7); 9.003(8.2); 9.000(8.1); 8.768(6.7); 8.764(6.5); 8.224(5.7); 8.174(3.0); 8.172(3.7); 8.160(3.9); 8.157(5.1); 8.098(0.8); 8.081(3.6); 8.077(5.1); 8.062(4.9); 8.048(1.2); 7.953(1.5); 7.623(0.4); 7.616(0.4); 7.605(0.4); 7.552(0.4); 4.263(1.8); 4.252(5.4); 4.240(5.7); 4.228(2.5); 4.216(0.8); 3.913(1.6); 3.904(1.9); 3.884(1.8); 3.876(2.2); 3.870(2.0); 3.863(2.2); 3.842(2.1); 3.834(2.5); 3.773(1.2); 3.768(0.9); 3.761(3.8); 3.751(1.6); 3.746(2.2); 3.737(2.2); 3.731(2.3); 3.724(1.5); 3.718(1.5); 3.710(0.8); 3.703(1.6); 3.697(1.1); 3.690(1.4); 3.679(1.6); 3.671(1.0); 3.666(1.1); 3.657(1.5); 3.644(1.2); 3.640(1.3); 3.633(1.2); 3.627(0.8); 3.620(1.1); 3.613(0.7); 3.607(1.4); 3.600(1.3); 3.595(1.5); 3.587(1.1);

-continued

NMR Peak Lists Table 1

3.581(0.7); 3.575(0.6); 3.568(0.5); 3.563(1.1); 3.555(1.1); 3.549(0.7); 3.546(0.8); 3.541(0.7); 3.533(1.5); 3.520(1.5); 3.508(2.1); 3.502(0.8); 3.496(1.6); 3.490(1.6); 3.484(2.2); 3.474(2.6); 3.463(2.1); 3.455(2.8); 3.445(2.3); 3.435(1.7); 3.425(2.0); 3.413(0.4); 3.400(0.4); 3.378(1.3); 3.366(1.6); 3.352(1.8); 3.319(14.7); 3.288(1.8); 3.276(1.6); 3.262(1.2); 3.242(1.3); 3.230(1.5); 3.216(1.2); 2.891(11.5); 2.752(0.4); 2.748(0.3); 2.732(9.2); 2.731(9.2); 2.617(1.0); 2.614(1.4); 2.611(0.9); 2.523(2.4); 2.520(3.1); 2.517(3.4); 2.508(73.0); 2.505(156.2); 2.502(214.6); 2.499(157.3); 2.496(72.7); 2.407(0.4); 2.389(1.3); 2.386(1.6); 2.383(1.3); 2.361(0.6); 2.344(0.5); 2.328(0.8); 2.315(1.2); 2.302(1.0); 2.289(0.5); 1.909(0.9); 1.900(0.7); 1.887(0.8); 1.880(1.0); 1.875(0.6); 1.867(1.1); 1.860(0.8); 1.854(0.9); 1.846(0.6); 1.725(0.4); 1.718(0.7); 1.704(0.6); 1.697(0.4); 1.617(9.2); 1.613(11.1); 1.605(14.0); 1.602(12.2); 1.586(0.7); 1.573(0.7); 1.566(0.6); 1.553(0.5); 1.521(0.7); 1.508(0.8); 1.501(0.7); 1.487(0.7); 1.474(0.5); 1.466(0.7); 1.461(0.9); 1.453(0.9); 1.448(0.9); 1.441(1.0); 1.433(0.6); 1.428(0.7); 1.272(7.5); 1.260(16.0); 1.256(2.1); 1.248(7.8); 1.244(3.5); 1.232(2.6); 1.208(1.1); 1.197(1.1); 1.189(1.7); 1.178(1.7); 1.140(1.3); 1.129(1.3); 1.117(6.3); 1.106(6.3); 1.070(5.7); 1.066(6.0); 1.059(5.8); 1.055(6.0); 1.045(0.6); 1.016(4.6); 1.005(4.5); 0.000(6.8)
Example 292: $^1$H-NMR(601.6 MHz, DMSO):
19.277(0.5); 9.008(3.7); 9.004(3.9); 8.998(4.4); 8.994(4.4); 8.777(2.4); 8.773(2.3); 8.750(2.8); 8.746(2.7); 8.556(1.4); 8.542(1.4); 8.524(1.6); 8.510(1.6); 8.236(2.5); 8.233(2.8); 8.199(2.9); 8.196(3.5); 8.193(2.2); 8.190(1.6); 8.179(2.3); 8.175(2.1); 8.168(2.1); 8.165(1.7); 8.153(3.1); 8.150(2.5); 8.086(2.6); 8.073(3.8); 8.059(2.4); 7.953(1.7); 7.627(0.4); 7.622(0.5); 7.616(0.5); 7.605(0.5); 7.568(0.4); 7.563(0.3); 7.556(0.4); 7.551(0.4); 7.474(1.0); 7.471(1.4); 7.460(3.2); 7.458(2.8); 7.449(2.3); 7.445(0.6); 7.437(2.9); 7.434(1.1); 7.424(1.3); 7.391(0.6); 7.388(1.1); 7.386(0.6); 7.380(0.5); 7.377(1.3); 7.373(0.5); 7.364(2.2); 7.352(3.7); 7.333(3.1); 7.329(1.0); 7.321(3.9); 7.313(1.1); 7.307(2.0); 7.300(0.6); 7.282(2.9); 7.270(4.4); 7.258(0.8); 7.234(1.4); 7.232(0.9); 7.227(2.9); 7.225(4.7); 7.222(2.5); 7.150(1.5); 7.148(0.9); 7.138(2.1); 7.126(0.8); 4.987(0.9); 4.975(1.2); 4.962(0.9); 4.944(0.8); 4.932(1.1); 4.919(0.8); 4.409(1.3); 4.398(1.1); 4.386(1.1); 4.375(0.4); 4.191(1.0); 4.179(3.0); 4.167(3.1); 4.155(1.0); 3.949(0.3); 3.939(2.5); 3.910(2.8); 3.836(2.9); 3.808(3.4); 3.688(6.3); 3.466(6.2); 3.437(5.1); 3.319(45.7); 2.891(13.3); 2.732(10.6); 2.731(10.0); 2.617 (0.8); 2.614(1.1); 2.611(0.7); 2.523(2.0); 2.520(2.6); 2.517(3.0); 2.508(57.7); 2.505(122.2); 2.502(167.6); 2.499(122.0); 2.496(56.2); 2.389(0.7); 2.386(1.0); 2.383(0.7); 1.909(0.6); 1.831(0.4); 1.654(16.0); 1.576(13.5); 1.481(5.8); 1.469(5.8); 1.432(7.9); 1.420(7.9); 1.396(6.7); 1.385(6.7); 1.357(0.8); 1.345(0.8); 1.314(0.9); 1.303(1.0); 1.297(0.4); 1.292(1.0); 1.286(0.4); 1.281(0.9); 1.248(3.4); 1.237(7.3); 1.225(3.4); 1.151(0.7); 1.139(1.3); 1.127(0.7); 0.000(5.4)
Example 293: $^1$H-NMR(601.6 MHz, DMSO):
9.006(2.3); 9.004(2.4); 9.002(2.4); 9.000(2.3); 8.772(1.5); 8.768(2.7); 8.764(1.4); 8.475(0.9); 8.469(0.9); 8.462(1.0); 8.456(0.9); 8.231(1.6); 8.227(1.7); 8.224(1.6); 8.220(1.7); 8.177(1.0); 8.174(1.0); 8.172(1.1); 8.169(0.9); 8.163(1.4); 8.159(1.4); 8.157(1.5); 8.154(1.2); 8.079(2.4); 8.064(1.8); 7.953(0.5); 4.751(0.5); 4.745(0.5); 4.737(0.7); 4.733(0.7); 4.726(0.5); 4.720(0.5); 4.295(1.0); 4.283(3.1); 4.271(3.2); 4.262(0.9); 4.259(1.1); 4.250(0.8); 4.210(0.9); 4.203(0.8); 4.195(0.9); 4.192(1.1); 4.188(1.1); 4.185(0.9); 4.177(0.8); 4.170(0.9); 4.127(1.3); 4.110(2.5); 4.093(1.4); 3.929(1.5); 3.900(1.7); 3.889(1.5); 3.861(1.7); 3.502(1.6); 3.491(1.6); 3.474(1.5); 3.462(1.4); 3.319(6.5); 2.958(0.5); 2.942(0.6); 2.926(0.8); 2.909(0.6); 2.891(4.5); 2.864(0.6); 2.847(0.9); 2.842(0.5); 2.830(0.5); 2.824(0.9); 2.808(0.4); 2.731(3.2); 2.617(0.4); 2.614(0.6); 2.611(0.4); 2.523(1.3); 2.520(1.7); 2.517(1.8); 2.517(2.0); 2.508(31.5); 2.505(66.2); 2.502(89.9); 2.499 (62.9); 2.496(28.6); 2.389(0.4); 2.386(0.6); 2.383(0.4); 1.622(16.0); 1.356(4.5); 1.344(4.5); 1.319(4.5); 1.308(4.5); 1.282(4.1); 1.270(9.4); 1.258(6.3); 1.245(2.1); 1.232(0.8); 1.209(0.7); 1.206(0.3); 1.198(0.7); 0.000(2.8)
Example 294: $^1$H-NMR(601.6 MHz, DMSO):
19.277(0.6); 9.009(2.7); 9.005(2.9); 9.000(3.1); 8.996(3.1); 8.781(3.1); 8.777(2.2); 8.768(1.3); 8.750(2.3); 8.746(2.5); 8.730(1.3); 8.235(2.1); 8.232(2.3); 8.195(1.5); 8.191(2.5); 8.187(2.8); 8.180(2.1); 8.177(3.2); 8.174(1.2); 8.163(2.1); 8.160(1.7); 8.088(2.1); 8.081(2.4); 8.073(1.7); 8.066(1.8); 7.953(1.9); 7.639(0.6); 7.629(0.7); 7.563(1.3); 7.560(1.3); 7.550(2.1); 7.547(1.5); 7.539(0.9); 7.537(0.9); 7.488(0.6); 7.475(0.4); 7.435(0.5); 7.432(0.6); 7.416(1.3); 7.409(2.5); 7.406(2.2); 7.401(1.5); 7.395(1.8); 7.393(1.8); 7.373(0.3); 7.365(0.8); 7.354(1.6); 7.342(1.8); 7.339(1.6); 7.335(1.3); 7.332(1.0); 7.327(1.7); 7.276(1.7); 7.248(1.0); 7.274(1.0); 7.263(1.3); 7.261(1.1); 7.251(0.7); 7.187(0.4); 7.178(2.3); 7.175(1.5); 7.170(2.6); 7.166(1.4); 7.162(1.8); 7.154(0.3); 5.272(0.9); 5.260(1.2); 5.248(0.9); 5.239(0.8); 5.227(1.1); 5.215(0.8); 4.722(0.5); 4.711(0.5); 4.212(0.6); 4.200(1.9); 4.189(2.0); 4.177(0.6); 3.946(1.9); 3.918(2.2); 3.793(2.1); 3.765(2.5); 3.708(1.2); 3.464(3.7); 3.436(3.1); 3.319(23.7); 2.891(16.0); 2.732(12.6); 2.731(12.7); 2.614(0.8); 2.611 (0.5); 2.582(0.7); 2.523(1.3); 2.520(1.7); 2.517(1.9); 2.508(41.6); 2.505(89.2); 2.502(122.0); 2.499(87.5); 2.496(40.9); 2.389(0.6); 2.386(0.8); 2.383(0.6); 1.909(0.3); 1.658(12.0); 1.582(10.7); 1.477(2.4); 1.466(2.4); 1.408(6.1); 1.397(6.1); 1.374(5.6); 1.362(5.6); 1.333(0.5); 1.321(0.5); 1.291(0.5); 1.279(0.5); 1.268(0.6); 1.255(3.1); 1.244(5.6); 1.232(3.3); 1.206(0.5); 1.194(0.8); 1.182(0.4); 1.056(0.3); 0.000(3.8)
Example 295: $^1$H-NMR(601.6 MHz, DMSO):
19.276(1.5); 9.007(3.8); 9.003(4.2); 9.001(4.6); 8.997(4.6); 8.775(2.4); 8.771(2.3); 8.761(2.8); 8.757(2.7); 8.450(2.5); 8.436(2.4); 8.235(2.5); 8.232(2.8); 8.217(3.1); 8.214(3.3); 8.187(3.1); 8.184(1.6); 8.173(2.7); 8.169(2.3); 8.165(2.3); 8.162(2.0); 8.150(3.0); 8.147(2.8); 8.083(2.7); 8.073(3.2); 8.069(2.2); 8.058(2.3); 7.953(1.7); 7.633(1.4); 7.628(1.8); 7.624(1.6); 7.620(1.8); 7.605(0.3); 7.580(1.4); 7.476(1.9); 7.471(2.0); 7.468(2.0); 7.463(2.1); 7.398(2.2); 7.393(2.4); 7.390(2.3); 7.385(2.4); 7.287(1.9); 7.285(1.5); 7.282(1.8); 7.248(1.6); 7.246(1.6); 7.240(1.5); 7.237(1.5); 7.211(1.5); 7.209(2.3); 7.207(1.8); 7.204(2.2); 7.202(1.4); 7.117(2.0); 7.115(1.9); 7.109(1.9); 7.107(1.9); 7.028(2.4); 7.026(2.3); 7.020(2.3); 7.018(2.2); 5.077(0.9); 5.063(1.4); 5.051(1.4); 5.036(0.7); 4.510(1.1); 4.498(1.0); 4.487(0.3); 4.202(1.2); 4.190(3.8); 4.179(3.8); 4.167(1.3); 3.941(2.5); 3.913(2.8); 3.900(3.0); 3.872(3.4); 3.699(2.8); 3.480(3.8); 3.452(3.4); 3.319(27.7); 2.891(14.6); 2.732(11.8); 2.731(11.3); 2.613(1.1); 2.610(0.8); 2.523(1.9); 2.520(2.4); 2.517(2.3); 2.508(57.9); 2.505(125.9); 2.502(176.8); 2.499(127.8); 2.496(59.8); 2.389(0.8); 2.386(1.1); 2.383(0.8); 1.909(0.7); 1.827(0.4); 1.646(16.0); 1.602(13.5); 1.503(5.8); 1.491(5.8); 1.446(7.9); 1.434(7.9); 1.406(6.7); 1.394(6.7); 1.377(0.6); 1.366(0.5); 1.348(0.4); 1.337(0.5); 1.327(0.4); 1.252(5.1); 1.240(10.7); 1.229(5.2); 1.186(0.6); 1.174(1.2); 1.162(0.6); 1.056(0.5); 0.000(6.1)
Example 296: $^1$H-NMR(601.6 MHz, DMSO):
19.276(0.5); 9.005(2.5); 9.001(4.4); 8.997(3.1); 8.775(1.7); 8.771(1.6); 8.753(2.0); 8.749(1.9); 8.663(1.1); 8.650(1.1); 8.624(1.2); 8.611(1.2); 8.219(1.8); 8.216(1.9); 8.199(2.1); 8.196(2.3); 8.174(1.2); 8.171(1.0); 8.160(1.6); 8.156(1.7); 8.155(1.7); 8.152(1.2); 8.140(2.0); 8.137(1.8); 8.079(1.9); 8.073(1.5); 8.065(1.4); 8.058(1.6); 7.953(1.2); 5.186(0.8); 5.174(1.1); 5.161(0.9); 5.151(0.8); 5.139(1.0); 5.127(0.7); 4.753(0.5); 4.742(0.5); 4.237(0.7); 4.225(2.1); 4.213(2.1); 4.202(0.7); 3.910(1.7); 3.882(1.9); 3.806(2.0); 3.778(2.3); 3.732(1.2); 3.462(2.3); 3.454(1.9); 3.434(2.0); 3.426(1.7); 3.319(14.4); 2.891(10.7); 2.731(8.4); 2.639(2.6); 2.617(0.5); 2.614(0.8); 2.611(0.6); 2.604(6.0); 2.598(2.7); 2.552(0.8); 2.535(12.4); 2.528(1.4); 2.523(1.5); 2.520(1.7); 2.517(1.7); 2.508(39.3); 2.505(84.6); 2.502(115.7); 2.499(82.0); 2.496(37.7); 2.492(6.0); 2.427(15.1); 2.389(0.5); 2.386(0.7); 2.383(0.5); 2.322(6.2); 2.256(13.4); 2.252(1.6); 2.238(0.7); 2.235(0.5); 2.229(0.5); 2.198(0.4); 2.170(16.0); 2.161(1.0); 1.909(0.4); 1.776(0.5); 1.613(11.2); 1.550(9.3); 1.496(2.1);

| NMR Peak Lists Table 1 |
|---|
| 1.485(2.1); 1.444(5.3); 1.433(5.3); 1.416(4.5); 1.404(4.5); 1.377(0.5); 1.365(0.5); 1.263(3.3); 1.251(6.6); 1.240(3.4); 1.225(1.1); 1.213(0.5); 1.208(0.4); 1.197(0.3); 1.056(0.5); 0.000(3.9)<br>Example 297: $^1$H-NMR(601.6 MHz, DMSO):<br>19.275(0.5); 9.005(3.7); 9.002(3.8); 8.765(2.8); 8.761(2.7); 8.327(0.7); 8.317(1.4); 8.308(0.7); 8.217(2.9); 8.214(3.2); 8.170(1.8); 8.167(1.6); 8.156(2.7); 8.152(2.3); 8.078(2.9); 8.064(2.1); 8.003(0.3); 4.192(0.8); 4.180(2.3); 4.168(2.4); 4.157(0.8); 3.865(2.7); 3.837(3.1); 3.690(2.9); 3.485(3.0); 3.477(0.4); 3.456(2.7); 3.325(2.5); 3.167(0.5); 3.156(0.9); 3.144(1.4); 3.134(1.4); 3.130(1.4); 3.119(1.5); 3.108(1.1); 3.097(0.7); 3.010(0.7); 2.891(1.2); 2.731(0.9); 2.614(0.6); 2.523(0.9); 2.520(1.2); 2.517(1.4); 2.508(30.4); 2.505(64.7); 2.502(88.1); 2.499(62.9); 2.496(29.1); 2.424(1.1); 2.386(0.8); 2.353(0.8); 2.307(1.1); 2.274(6.3); 1.640(0.6); 1.629(1.7); 1.613(16.0); 1.594(0.8); 1.249(2.6); 1.237(5.3); 1.225(2.6); 1.156(0.4); 1.145(0.8); 1.133(0.4); 1.056(0.4); 0.000(2.6)<br>Example 298: $^1$H-NMR(300.2 MHz, CDCl3):<br>8.933(2.4); 8.926(2.4); 8.315(1.9); 8.308(1.9); 8.189(0.9); 8.183(0.9); 8.159(1.7); 8.153(1.8); 8.099(2.2); 8.069(1.1); 7.812(2.1); 7.806(2.0); 7.436(5.2); 7.373(1.4); 7.280(1.5); 3.967(1.9); 3.910(2.3); 3.833(16.0); 3.332(2.2); 3.275(1.9); 1.899(2.2); 1.753(11.4); 1.515(15.6); 1.260(0.4); 0.880(0.4); 0.000(0.8)<br>Example 299: $^1$H-NMR(300.2 MHz, CDCl3):<br>8.944(2.0); 8.936(2.0); 8.329(1.5); 8.322(1.5); 8.187(0.7); 8.181(0.7); 8.157(1.5); 8.151(1.6); 8.108(1.9); 8.079(0.9); 7.821(1.6); 7.815(1.6); 7.268(4.9); 6.946(1.1); 5.302(0.6); 4.089(8.0); 3.973(1.6); 3.916(1.9); 3.337(14.9); 3.306(0.3); 3.302(0.4); 3.278(1.6); 1.747(9.5); 1.690(6.4); 1.655(16.0); 0.000(3.4)<br>Example 300: $^1$H-NMR(499.9 MHz, CDCl3):<br>8.938(2.4); 8.934(2.6); 8.314(2.2); 8.310(2.4); 8.156(1.0); 8.152(1.1); 8.138(1.8); 8.134(2.0); 8.097(2.6); 8.079(1.4); 7.806(2.4); 7.803(2.6); 7.264(4.6); 7.057(0.5); 7.047(0.9); 5.296(1.7); 4.191(0.4); 4.186(0.4); 4.179(0.4); 4.176(0.4); 4.159(0.5); 4.155(0.9); 4.150(0.8); 4.144(0.9); 4.138(0.3); 4.089(0.9); 4.081(3.2); 4.077(7.7); 4.057(0.4); 4.053(0.5); 4.047(0.4); 4.043(0.5); 3.954(2.3); 3.920(2.6); 3.355(2.6); 3.345(16.0); 3.321(2.2); 1.776(13.5); 1.764(0.3); 1.636(6.5); 1.265(0.4); 1.257(0.5); 0.881(0.5); 0.000(3.2)<br>Example 301: $^1$H-NMR(300.2 MHz, CDCl3):<br>8.945(4.1); 8.937(4.3); 8.328(3.2); 8.321(3.2); 8.178(1.4); 8.171(1.4); 8.148(3.5); 8.142(3.7); 8.110(4.3); 8.080(1.7); 7.818(3.4); 7.813(3.4); 7.276(4.0); 7.113(1.9); 5.304(2.8); 4.032(1.8); 4.000(1.8); 3.974(2.2); 3.942(2.2); 3.397(2.2); 3.389(2.2); 3.340(1.9); 3.332(1.9); 2.174(0.6); 1.800(16.0); 1.797(15.2); 1.778(11.3); 1.744(11.5); 1.719(0.4); 1.564(0.6); 1.315(0.5); 1.308(0.7); 1.301(0.8); 1.293(0.9); 1.289(1.0); 1.279(1.2); 1.272(1.0); 1.267(1.3); 1.263(1.2); 1.260(1.2); 1.256(1.4); 1.245(0.6); 1.236(0.5); 0.880(0.5); 0.786(0.5); 0.777(0.7); 0.764(1.1); 0.760(0.8); 0.756(0.7); 0.748(1.9); 0.744(2.5); 0.739(1.6); 0.731(1.6); 0.717(5.8); 0.693(6.0); 0.668(0.3); 0.000(2.3)<br>Example 302: $^1$H-NMR(400.0 MHz, DMSO):<br>9.058(1.8); 8.389(0.5); 8.307(0.9); 8.302(1.2); 8.288(0.7); 8.284(0.4); 8.266(0.9); 8.261(0.7); 8.177(1.1); 8.155(0.7); 7.408(1.8); 4.081(1.4); 4.066(1.4); 3.963(0.5); 3.945(1.6); 3.927(1.7); 3.903(16.0); 3.896(0.9); 3.852(0.9); 3.500(0.9); 3.457(0.8); 3.331(33.6); 2.512(17.9); 2.507(35.1); 2.503(45.3); 2.498(32.4); 2.494(15.5); 2.348(0.3); 2.171(0.5); 2.049(6.9); 1.615(5.0); 1.603(0.5); 1.266(2.0); 1.248(4.3); 1.230(2.0)<br>Example 303: $^1$H-NMR(400.0 MHz, DMSO):<br>9.064(3.8); 8.311(2.8); 8.305(2.0); 8.283(1.8); 8.278(1.4); 8.183(2.2); 8.161(1.6); 7.917(1.0); 7.897(1.0); 3.934(0.5); 3.917(1.0); 3.908(16.0); 3.898(0.9); 3.881(0.6); 3.866(2.3); 3.478(2.1); 3.435(1.8); 3.334(83.0); 2.681(0.3); 2.677(0.5); 2.673(0.3); 2.517(30.4); 2.513(57.5); 2.508(73.0); 2.504(53.3); 2.339(0.3); 2.335(0.4); 1.607(11.0); 1.113(6.3); 1.096(6.2); 1.068(6.4); 1.052(6.3)<br>Example 304: $^1$H-NMR(300.2 MHz, CDCl3):<br>9.049(2.5); 9.042(2.5); 8.128(0.5); 8.123(0.5); 8.099(3.0); 8.093(3.9); 8.088(4.1); 8.060(2.8); 8.055(2.6); 7.866(2.5); 7.862(2.6); 7.276(3.1); 6.921(1.1); 6.884(1.2); 6.862(1.3); 6.825(1.3); 6.735(0.7); 6.709(0.8); 6.040(2.8); 5.981(2.5); 5.531(2.8); 5.494(2.6); 4.079(0.6); 4.057(0.9); 4.052(0.7); 4.035(0.8); 4.030(0.9); 4.013(0.4); 4.009(0.7); 3.982(2.8); 3.925(3.3); 3.360(3.1); 3.303(2.6); 1.927(1.8); 1.756(16.0); 1.335(0.7); 1.313(0.7); 1.256(0.5); 1.215(8.3); 1.193(8.3); 1.154(8.4); 1.132(8.3); 1.111(0.4); 0.000(1.7)<br>Example 305: $^1$H-NMR(300.2 MHz, CDCl3):<br>8.939(2.1); 8.932(2.2); 8.320(1.6); 8.313(1.6); 8.184(0.8); 8.178(0.8); 8.154(1.7); 8.148(1.7); 8.100(2.0); 8.070(1.0); 7.811(1.8); 7.805(1.7); 7.270(3.5); 7.165(0.6); 7.136(0.6); 5.302(0.6); 4.196(0.5); 4.182(0.5); 4.178(0.4); 4.167(0.5); 3.972(1.8); 3.915(2.2); 3.545(0.6); 3.530(0.6); 3.513(1.5); 3.498(1.4); 3.479(1.6); 3.475(0.9); 3.460(1.9); 3.448(1.0); 3.443(1.6); 3.428(1.8); 3.403(1.4); 3.381(15.9); 3.372(1.3); 3.354(2.5); 3.297(2.0); 3.286(16.0); 1.769(10.6); 1.731(1.9); 0.000(2.3)<br>Example 306: $^1$H-NMR(300.2 MHz, CDCl3):<br>9.570(2.6); 8.948(3.2); 8.941(3.2); 8.319(2.7); 8.312(2.6); 8.159(0.9); 8.153(0.8); 8.129(2.8); 8.123(2.9); 8.104(3.5); 8.074(1.0); 7.803(2.8); 7.798(2.6); 7.271(4.0); 5.303(2.0); 4.588(5.5); 4.580(5.5); 4.017(2.5); 3.960(2.9); 3.402(3.0); 3.344(2.7); 3.010(0.3); 2.547(1.7); 2.539(3.5); 2.531(1.7); 1.826(16.0); 1.768(0.6); 1.729(2.9); 1.255(0.4); 0.000(2.5)<br>Example 307: $^1$H-NMR(499.9 MHz, CDCl3):<br>8.939(2.9); 8.935(3.0); 8.316(2.7); 8.312(2.8); 8.159(1.2); 8.155(1.2); 8.141(2.2); 8.137(2.3); 8.101(3.2); 8.083(1.7); 7.814(3.0); 7.810(3.0); 7.264(5.1); 6.787(0.9); 6.771(1.0); 3.980(0.9); 3.965(1.2); 3.957(1.7); 3.952(3.8); 3.940(1.5); 3.935(1.4); 3.917(4.0); 3.506(0.7); 3.501(0.8); 3.482(1.5); 3.478(1.6); 3.472(0.9); 3.467(0.9); 3.459(0.9); 3.454(0.9); 3.448(1.6); 3.444(1.6); 3.425(0.8); 3.421(0.8); 3.345(2.9); 3.311(2.7); 1.949(0.5); 1.945(0.7); 1.941(0.7); 1.937(0.6); 1.929(0.4); 1.924(0.7); 1.919(0.9); 1.915(0.9); 1.911(0.7); 1.840(0.6); 1.836(0.7); 1.832(0.7); 1.828(0.6); 1.820(0.4); 1.815(0.7); 1.811(0.9); 1.806(0.9); 1.802(0.7); 1.763(16.0); 1.643(5.0); 1.581(0.4); 1.572(0.4); 1.559(0.8); 1.550(0.8); 1.534(1.0); 1.526(1.1); 1.512(1.1); 1.503(1.1); 1.487(0.8); 1.478(0.8); 1.464(0.4); 1.455(0.4); 1.303(0.4); 1.289(0.5); 1.266(1.4); 0.895(0.9); 0.881(2.1); 0.867(1.1); 0.000(3.4)<br>Example 308: $^1$H-NMR(300.2 MHz, CDCl3):<br>9.049(2.7); 9.042(2.6); 8.080(6.3); 8.076(6.4); 8.060(2.5); 8.054(2.3); 7.860(3.0); 7.280(2.9); 7.253(3.9); 6.981(0.5); 6.964(0.9); 6.946(0.6); 6.921(1.0); 6.884(1.1); 6.862(1.2); 6.825(1.2); 6.043(2.6); 5.984(2.2); 5.534(2.5); 5.497(2.4); 5.300(0.6); 4.368(0.7); 4.349(0.7); 4.319(1.5); 4.300(1.5); 4.235(1.5); 4.218(1.5); 4.186(0.8); 4.169(0.7); 4.075(1.3); 4.051(3.9); 4.027(4.0); 4.005(3.0); 3.948(2.8); 3.384(2.6); 3.327(2.2); 2.192(16.0); 1.779(13.6); 1.443(4.7); 1.418(9.8); 1.394(4.7); 1.258(0.3); 0.077(4.9); 0.000(1.6)<br>Example 309: $^1$H-NMR(300.2 MHz, CDCl3):<br>8.947(3.9); 8.939(4.0); 8.329(2.9); 8.322(2.8); 8.177(1.2); 8.171(1.2); 8.148(3.1); 8.142(3.1); 8.109(3.7); 8.080(1.5); 7.821(3.2); 7.816(3.1); 7.265(15.6); 6.958(0.4); 6.729(0.3); 6.710(0.4); 6.699(0.4); 4.148(0.4); 4.133(0.6); 4.118(0.4); 3.984(2.0); 3.981(1.6); 3.970(1.3); 3.926(2.5); 3.913(1.4); 3.876(0.4); 3.866(0.5); 3.850(0.3); 3.834(0.5); 3.822(0.5); 3.813(0.4); 3.796(0.4); 3.661(0.5); 3.649(0.5); 3.621(1.1); 3.610(1.0); 3.598(0.9); 3.581(1.2); 3.569(0.8); 3.538(0.8); |

NMR Peak Lists Table 1

3.521(0.5); 3.506(0.3); 3.499(0.6); 3.466(0.7); 3.460(0.5); 3.433(0.4); 3.427(0.6); 3.376(1.3); 3.371(1.2); 3.364(1.2); 3.361(1.2); 3.318(1.1); 3.314(1.0); 3.307(1.0); 3.303(1.0); 3.130(0.4); 3.090(0.8); 3.054(0.9); 3.015(0.4); 1.794(5.3); 1.785(9.8); 1.780(7.4); 1.765(0.9); 1.758(0.8); 1.749(0.9); 1.733(0.7); 1.719(0.5); 1.705(0.3); 1.691(0.5); 1.678(0.5); 1.665(0.7); 1.650(0.7); 1.624(16.0); 1.601(0.6); 1.584(0.4); 1.576(0.5); 1.562(0.5); 1.520(0.4); 1.266(1.0); 1.005(2.5); 0.981(2.4); 0.903(0.4); 0.888(2.6); 0.882(1.5); 0.866(2.5); 0.849(2.6); 0.826(2.4); 0.698(2.7); 0.676(2.6); 0.011(0.3); 0.000(10.4); −0.011(0.5)
Example 310: $^1$H-NMR(400.0 MHz, DMSO):
9.009(7.2); 9.004(7.5); 8.986(1.6); 8.971(1.9); 8.966(2.0); 8.951(1.6); 8.774(5.1); 8.244(5.4); 8.239(6.2); 8.203(1.9); 8.198(3.1); 8.193(1.5); 8.180(2.7); 8.175(4.7); 8.170(2.4); 8.091(4.6); 8.069(3.1); 7.729(4.2); 7.721(4.8); 7.662(4.3); 7.654(4.8); 7.615(4.9); 7.607(4.2); 7.511(4.8); 7.503(4.3); 5.257(1.2); 5.236(2.1); 5.218(2.2); 5.198(1.3); 3.976(2.5); 3.933(3.0); 3.917(2.5); 3.874(3.0); 3.559(2.9); 3.529(2.9); 3.515(2.5); 3.485(2.5); 3.357(0.4); 3.329(144.0); 3.307(0.4); 2.892(1.3); 2.732(1.0); 2.677(0.5); 2.672(0.6); 2.668(0.5); 2.550(0.5); 2.536(0.5); 2.526(2.0); 2.521(3.1); 2.512(36.6); 2.508(73.4); 2.503(96.5); 2.499(69.1); 2.494(32.7); 2.335(0.5); 2.330(0.6); 2.325(0.4); 1.677(16.0); 1.671(16.0); 1.582(7.8); 1.564(7.8); 1.552(8.0); 1.534(7.9); 1.233(0.4)
Example 311: $^1$H-NMR(400.0 MHz, DMSO):
9.007(3.0); 9.001(6.1); 8.995(3.6); 8.774(2.1); 8.768(2.1); 8.759(2.5); 8.753(2.3); 8.232(2.1); 8.228(2.3); 8.212(2.5); 8.207(2.7); 8.186(1.3); 8.181(1.0); 8.163(1.8); 8.159(1.7); 8.147(1.4); 8.143(1.1); 8.125(2.2); 8.120(2.0); 8.085(2.3); 8.066(3.1); 8.044(1.7); 8.029(1.3); 8.006(1.5); 7.999(1.3); 7.976(1.1); 7.954(1.4); 7.548(3.9); 7.474(4.6); 4.711(0.4); 4.695(1.0); 4.689(1.0); 4.673(1.7); 4.656(1.0); 4.651(0.9); 4.635(0.4); 4.019(1.0); 4.001(3.2); 3.982(3.2); 3.964(1.1); 3.947(1.2); 3.929(3.8); 3.911(4.1); 3.903(2.9); 3.893(1.4); 3.860(3.3); 3.491(0.5); 3.472(2.3); 3.453(1.8); 3.429(2.0); 3.329(120.2); 2.892(10.7); 2.733(8.9); 2.677(0.5); 2.672(0.6); 2.668(0.5); 2.526(2.2); 2.512(39.2); 2.508(77.1); 2.503(100.0); 2.499(71.4); 2.494(33.9); 2.335(0.5); 2.330(0.6); 2.325(0.5); 2.079(13.6); 1.917(16.0); 1.817(0.4); 1.801(0.7); 1.796(0.5); 1.780(1.0); 1.760(1.3); 1.741(1.2); 1.730(0.8); 1.724(0.8); 1.711(1.1); 1.696(1.1); 1.690(0.9); 1.679(0.9); 1.656(11.9); 1.581(10.3); 1.339(3.9); 1.321(8.6); 1.303(3.9); 1.254(4.7); 1.235(10.4); 1.217(4.5); 0.870(2.8); 0.852(6.3); 0.834(2.7); 0.753(2.4); 0.735(5.2); 0.716(2.2)
Example 312: $^1$H-NMR(300.2 MHz, CDCl3):
8.947(2.2); 8.942(2.7); 8.940(2.7); 8.935(2.3); 8.333(1.5); 8.326(1.5); 8.319(1.6); 8.311(1.5); 8.180(0.7); 8.174(0.7); 8.151(1.5); 8.144(1.7); 8.136(0.5); 8.112(2.3); 8.106(3.5); 8.090(2.2); 8.078(0.9); 8.061(0.6); 7.825(1.6); 7.819(1.5); 7.794(1.6); 7.789(1.5); 7.265(16.1); 7.254(2.8); 7.199(2.7); 6.896(0.6); 6.869(0.7); 6.857(0.7); 6.828(0.6); 5.060(0.5); 5.032(0.9); 5.009(0.9); 4.981(0.5); 4.122(0.8); 4.097(2.4); 4.073(2.5); 4.048(0.9); 4.036(0.9); 4.011(3.1); 3.987(2.6); 3.962(2.5); 3.951(1.9); 3.905(1.9); 3.358(3.2); 3.300(2.7); 2.241(10.4); 2.041(10.4); 1.785(9.2); 1.753(9.2); 1.637(16.0); 1.507(4.3); 1.496(3.5); 1.484(4.4); 1.472(6.8); 1.448(3.3); 1.438(4.4); 1.416(4.6); 1.411(4.0); 1.386(6.7); 1.362(3.1); 0.011(0.5); 0.000(12.7); −0.011(0.5)
Example 313: $^1$H-NMR(400.0 MHz, DMSO):
9.017(5.0); 9.011(5.2); 8.787(4.4); 8.781(4.3); 8.639(2.7); 8.610(2.3); 8.259(2.7); 8.255(2.9); 8.249(2.2); 8.245(2.3); 8.192(2.0); 8.172(2.8); 8.170(3.0); 8.094(4.9); 8.072(3.1); 7.960(1.9); 3.988(2.0); 3.968(1.6); 3.944(2.4); 3.924(1.9); 3.521(3.7); 3.478(3.2); 3.410(0.3); 3.337(351.7); 3.301(0.5); 2.899(12.9); 2.755(0.5); 2.739(11.5); 2.679(1.3); 2.514(150.3); 2.510(188.9); 2.506(135.6); 2.473(1.6); 2.455(2.0); 2.437(2.2); 2.418(1.6); 2.401(0.8); 2.383(0.6); 2.364(0.5); 2.336(1.2); 2.053(0.5); 2.031(1.0); 2.015(1.2); 1.997(1.0); 1.981(0.9); 1.959(0.6); 1.941(0.6); 1.927(0.9); 1.921(0.8); 1.908(1.3); 1.896(0.8); 1.888(1.0); 1.875(0.8); 1.748(0.5); 1.727(1.4); 1.710(2.0); 1.688(1.6); 1.670(1.2); 1.644(16.0); 1.370(0.6); 1.361(0.3); 1.349(0.9); 1.316(0.8); 1.304(0.4); 1.293(0.7); 1.241(0.9); 1.147(6.0); 1.130(5.8); 1.099(7.3); 1.082(7.1)
Example 314: $^1$H-NMR(400.0 MHz, DMSO):
8.954(4.1); 8.949(4.2); 8.608(2.9); 8.603(2.8); 8.235(3.0); 8.230(3.3); 8.167(2.6); 8.162(2.6); 8.145(2.8); 8.140(2.5); 8.074(3.4); 8.052(2.1); 7.954(1.1); 4.589(7.4); 3.922(2.8); 3.879(3.3); 3.466(3.2); 3.423(2.8); 3.338(126.3); 2.893(8.8); 2.733(7.2); 2.725(0.6); 2.718(0.7); 2.714(0.6); 2.706(1.2); 2.696(0.9); 2.693(0.8); 2.690(0.6); 2.686(0.6); 2.678(0.8); 2.674(0.4); 2.668(0.4); 2.527(1.0); 2.522(1.6); 2.514(18.1); 2.509(36.1); 2.504(47.1); 2.500(33.7); 2.495(15.9); 1.587(16.0); 0.624(0.5); 0.612(0.8); 0.603(1.2); 0.598(1.7); 0.595(2.4); 0.589(1.6); 0.585(1.8); 0.580(1.2); 0.576(1.9); 0.571(1.8); 0.566(0.8); 0.560(1.5); 0.556(2.1); 0.549(3.4); 0.542(2.9); 0.533(0.9); 0.524(0.4)
Example 315: $^1$H-NMR(400.0 MHz, DMSO):
9.009(8.2); 9.004(8.4); 8.770(2.9); 8.765(2.8); 8.756(3.2); 8.750(3.0); 8.234(2.8); 8.229(3.2); 8.189(1.9); 8.184(1.5); 8.174(3.2); 8.168(4.4); 8.162(2.6); 8.131(2.5); 8.126(1.7); 8.113(2.6); 8.109(4.2); 8.104(3.3); 8.094(2.0); 8.088(3.5); 8.066(5.9); 8.044(1.9); 7.954(0.3); 7.116(2.4); 7.111(0.8); 7.105(0.4); 7.099(1.1); 7.094(4.4); 7.084(0.4); 7.078(0.9); 7.072(3.2); 6.950(3.3); 6.944(1.0); 6.939(3.4); 6.933(1.6); 6.927(2.5); 6.922(0.9); 6.916(2.3); 6.875(2.3); 6.869(0.8); 6.858(1.1); 6.852(4.7); 6.842(0.6); 6.837(1.0); 6.831(3.9); 6.822(0.4); 6.792(0.4); 6.782(3.9); 6.776(1.2); 6.771(4.1); 6.765(1.6); 6.759(2.4); 6.754(0.9); 6.748(2.2); 4.160(0.7); 4.140(1.0); 4.136(1.7); 4.116(1.7); 4.102(1.6); 4.090(2.1); 4.077(1.0); 4.064(2.8); 4.057(2.3); 4.044(4.0); 4.032(0.5); 3.884(2.4); 3.840(2.9); 3.772(2.6); 3.729(3.3); 3.612(0.4); 3.603(0.8); 3.591(1.0); 3.582(1.2); 3.572(1.2); 3.560(1.2); 3.555(0.9); 3.542(0.7); 3.538(0.7); 3.520(0.4); 3.500(3.1); 3.493(3.5); 3.456(2.7); 3.450(2.7); 3.394(0.4); 3.337(369.7); 3.304(0.5); 3.285(0.4); 2.892(2.8); 2.733(2.2); 2.682(0.3); 2.677(0.6); 2.673(0.9); 2.668(0.6); 2.526(3.0); 2.521(4.5); 2.513(52.7); 2.508(105.7); 2.504(138.6); 2.499(98.7); 2.495(46.2); 2.335(0.6); 2.331(0.9); 2.326(0.6); 1.626(16.0); 1.590(14.5); 1.233(0.6); 1.105(0.4); 1.096(0.5); 1.084(0.9); 1.072(0.7); 1.063(1.0); 1.054(0.7); 1.042(0.7); 1.034(1.0); 1.022(0.7); 1.014(0.9); 1.001(0.5); 0.993(0.4); 0.501(0.7); 0.481(1.2); 0.471(0.6); 0.467(0.6); 0.461(0.5); 0.456(0.7); 0.451(0.5); 0.432(0.9); 0.415(1.5); 0.412(1.6); 0.401(1.4); 0.390(0.9); 0.380(0.7); 0.313(0.9); 0.309(0.7); 0.301(1.2); 0.293(3.8); 0.281(3.1); 0.270(1.2); 0.234(0.3); 0.221(0.4); 0.207(1.9); 0.199(2.6); 0.192(1.7)
Example 316: $^1$H-NMR(400.0 MHz, DMSO):
8.959(6.6); 8.954(6.7); 8.615(5.0); 8.610(4.8); 8.243(5.1); 8.239(5.6); 8.182(1.5); 8.175(2.0); 8.170(1.5); 8.159(2.3); 8.152(3.1); 8.147(2.5); 8.082(5.4); 8.060(3.4); 7.850(2.5); 7.828(2.6); 4.593(13.2); 3.940(0.4); 3.934(0.7); 3.918(1.0); 3.906(2.8); 3.896(1.1); 3.887(0.7); 3.875(3.1); 3.863(2.8); 3.832(3.1); 3.474(2.5); 3.442(2.6); 3.431(2.2); 3.377(0.4); 3.341(252.1); 3.300(0.4); 2.897(2.2); 2.737(1.8); 2.682(0.4); 2.678(0.6); 2.673(0.4); 2.531(2.2); 2.518(35.6); 2.513(70.5); 2.509(92.0); 2.504(65.9); 2.500(31.3); 2.340(0.5); 2.335(0.6); 2.331(0.4); 1.609(16.0); 1.599(13.2); 1.573(0.6); 1.556(0.7); 1.540(1.2); 1.531(0.6); 1.519(0.8); 1.509(0.9); 1.495(0.5); 1.486(0.8); 1.471(0.7); 1.466(0.6); 1.452(1.2); 1.437(1.3); 1.428(2.0); 1.413(0.9); 1.406(1.1); 1.397(0.5); 1.392(0.5); 1.237(0.4); 1.205(0.4); 1.193(0.7); 1.186(0.8); 1.173(1.4); 1.158(1.2); 1.144(1.6); 1.131(0.8); 1.120(0.3); 1.070(8.1); 1.053(8.0); 1.019(7.0); 1.003(6.9); 0.873(7.2); 0.867(7.7); 0.857(7.6); 0.850(6.8); 0.755(7.8); 0.739(7.9); 0.731(7.6); 0.715(7.0)

| NMR Peak Lists Table 1 |
| --- |

Example 317: ¹H-NMR(400.0 MHz, DMSO):
9.003(3.9); 8.998(4.1); 8.768(2.9); 8.762(2.7); 8.215(2.8); 8.211(3.2); 8.169(2.6); 8.164(2.4); 8.147(2.8); 8.142(2.5); 8.076(3.3); 8.054(2.0); 3.913(2.7); 3.869(3.2); 3.458(3.1); 3.414(2.7); 3.370(0.5); 3.334(185.0); 3.304(0.5); 2.892(0.4); 2.733(0.4); 2.724(0.6); 2.717(0.6); 2.705(1.1); 2.695(0.9); 2.692(0.8); 2.689(0.7); 2.684(0.6); 2.677(0.9); 2.672(0.6); 2.667(0.5); 2.526(1.7); 2.521(2.7); 2.512(29.8); 2.508(58.9); 2.503(76.8); 2.499(54.5); 2.494(25.4); 2.334(0.3); 2.330(0.5); 2.325(0.3); 1.586(16.0); 1.233(0.4); 0.623(0.5); 0.611(0.8); 0.602(1.2); 0.597(1.6); 0.594(2.4); 0.588(1.5); 0.584(1.7); 0.579(1.1); 0.575(1.8); 0.569(1.6); 0.565(0.8); 0.558(1.4); 0.554(2.1); 0.548(3.2); 0.540(2.9); 0.531(0.9); 0.522(0.4)

Example 318: ¹H-NMR(400.0 MHz, DMSO):
8.960(8.7); 8.955(8.7); 8.612(3.0); 8.607(3.0); 8.599(3.3); 8.594(3.0); 8.315(0.4); 8.254(3.0); 8.249(3.2); 8.196(3.3); 8.191(3.6); 8.183(1.6); 8.166(2.7); 8.161(2.5); 8.130(3.1); 8.125(1.8); 8.114(2.7); 8.108(4.8); 8.103(3.4); 8.092(2.3); 8.086(3.6); 8.064(6.0); 8.042(2.0); 7.954(0.7); 7.117(2.6); 7.111(0.9); 7.105(0.5); 7.099(1.2); 7.094(4.6); 7.084(0.5); 7.078(1.0); 7.072(3.4); 7.062(0.3); 6.961(0.4); 6.951(3.5); 6.945(1.2); 6.940(3.6); 6.934(1.7); 6.928(2.6); 6.923(1.0); 6.917(2.4); 6.873(2.3); 6.867(0.8); 6.856(1.2); 6.850(4.7); 6.840(0.6); 6.835(1.0); 6.828(4.0); 6.819(0.4); 6.793(0.4); 6.783(4.0); 6.777(1.2); 6.772(4.1); 6.766(1.6); 6.760(2.3); 6.755(0.9); 6.749(2.1); 4.591(16.0); 4.161(0.8); 4.141(1.1); 4.136(1.7); 4.117(1.7); 4.103(1.6); 4.090(2.1); 4.078(1.0); 4.064(2.9); 4.058(2.4); 4.045(1.4); 4.033(0.5); 3.893(2.5); 3.849(3.0); 3.782(2.6); 3.739(3.3); 3.624(0.4); 3.612(0.5); 3.603(0.9); 3.591(1.0); 3.583(1.3); 3.573(1.2); 3.561(1.3); 3.543(0.8); 3.539(0.7); 3.520(0.5); 3.507(3.2); 3.500(3.5); 3.464(2.7); 3.457(2.8); 3.413(0.3); 3.398(0.5); 3.392(0.4); 3.386(0.6); 3.336(424.1); 3.303(0.7); 2.892(5.7); 2.733(4.7); 2.732(4.5); 2.682(0.3); 2.678(0.7); 2.673(0.9); 2.668(0.7); 2.526(3.3); 2.521(5.1); 2.513(54.6); 2.509(107.3); 2.504(139.2); 2.499(98.4); 2.495(45.5); 2.335(0.6); 2.331(0.9); 2.326(0.6); 1.625(15.9); 1.589(14.6); 1.233(0.6); 1.105(0.4); 1.097(0.5); 1.085(1.0); 1.073(0.8); 1.064(1.0); 1.052(0.8); 1.047(0.7); 1.043(0.8); 1.035(1.0); 1.023(0.7); 1.014(1.0); 1.002(0.6); 0.994(0.4); 0.502(0.7); 0.481(1.2); 0.472(0.7); 0.467(0.6); 0.457(0.7); 0.452(0.5); 0.432(0.9); 0.412(1.7); 0.401(1.5); 0.391(0.9); 0.381(0.8); 0.314(0.9); 0.310(0.8); 0.303(1.3); 0.293(4.1); 0.282(3.3); 0.271(1.3); 0.235(0.4); 0.222(0.4); 0.209(2.1); 0.200(2.7)

Example 319: ¹H-NMR(400.0 MHz, DMSO):
9.009(1.1); 9.004(1.1); 8.768(0.8); 8.762(0.7); 8.236(0.8); 8.232(0.9); 8.186(0.5); 8.181(0.4); 8.163(0.7); 8.159(0.6); 8.082(0.9); 8.060(0.6); 7.146(0.7); 3.893(0.7); 3.850(0.9); 3.456(0.9); 3.413(0.7); 3.340(31.3); 2.897(0.7); 2.737(0.5); 2.531(0.3); 2.518(5.6); 2.513(11.1); 2.509(14.4); 2.504(10.3); 2.499(4.8); 1.600(4.4); 1.293(16.0)

Example 320: ¹H-NMR(400.0 MHz, DMSO):
8.961(4.1); 8.956(4.0); 8.613(3.0); 8.608(2.9); 8.262(3.1); 8.258(3.3); 8.178(1.8); 8.174(1.5); 8.156(2.7); 8.152(2.5); 8.080(3.4); 8.058(2.2); 6.963(3.1); 4.595(7.2); 3.902(2.6); 3.859(3.2); 3.476(3.1); 3.432(2.6); 3.340(125.1); 2.897(2.1); 2.738(1.7); 2.678(0.3); 2.531(1.2); 2.518(21.0); 2.513(40.8); 2.509(52.4); 2.504(37.2); 2.500(17.6); 2.335(0.5); 2.331(0.7); 2.314(1.2); 2.297(1.7); 2.279(1.3); 2.262(0.5); 1.693(0.3); 1.620(15.7); 1.237(0.8); 1.229(0.8); 1.216(16.0); 1.201(15.8); 0.821(8.7); 0.804(8.5); 0.768(8.5); 0.751(8.3)

Example 321: ¹H-NMR(400.0 MHz, DMSO):
9.008(6.3); 9.003(6.6); 8.774(4.8); 8.768(4.5); 8.224(4.8); 8.219(5.4); 8.183(1.6); 8.177(2.1); 8.172(1.4); 8.161(2.4); 8.155(3.2); 8.150(2.4); 8.085(4.9); 8.063(3.1); 7.959(0.6); 7.855(2.3); 7.833(2.3); 3.940(0.4); 3.934(0.6); 3.918(1.0); 3.910(0.9); 3.899(2.9); 3.879(0.8); 3.867(2.8); 3.855(2.8); 3.824(3.0); 3.478(3.0); 3.466(2.5); 3.435(2.6); 3.423(2.3); 3.371(0.5); 3.338(228.9); 2.897(4.9); 2.738(3.7); 2.737(3.8); 2.682(0.4); 2.678(0.6); 2.673(0.4); 2.531(1.9); 2.526(3.1); 2.518(35.8); 2.513(71.9); 2.509(94.3); 2.504(67.2); 2.500(31.6); 2.340(0.5); 2.335(0.6); 2.331(0.4); 1.610(16.0); 1.600(13.2); 1.573(0.5); 1.557(0.6); 1.540(1.1); 1.531(0.6); 1.519(0.7); 1.509(0.9); 1.495(0.5); 1.486(0.8); 1.472(0.6); 1.466(0.6); 1.452(1.2); 1.437(1.2); 1.428(1.7); 1.411(0.8); 1.406(1.0); 1.392(0.5); 1.300(2.5); 1.237(0.5); 1.205(0.4); 1.193(0.6); 1.186(0.8); 1.173(1.3); 1.158(1.2); 1.144(1.5); 1.131(0.8); 1.070(7.7); 1.053(7.6); 1.020(6.9); 1.003(6.8); 0.873(7.0); 0.867(7.4); 0.857(7.3); 0.850(6.6); 0.755(7.3); 0.739(7.4); 0.731(7.1); 0.715(6.6)

Example 322: ¹H-NMR(400.0 MHz, DMSO):
8.962(1.1); 8.957(1.1); 8.612(0.8); 8.607(0.8); 8.259(0.8); 8.254(0.9); 8.185(0.5); 8.180(0.4); 8.163(0.7); 8.158(0.7); 8.082(0.9); 8.059(0.6); 7.144(0.8); 4.598(2.0); 3.903(0.7); 3.860(0.9); 3.466(0.9); 3.423(0.7); 3.339(24.5); 2.898(0.9); 2.739(0.7); 2.528(0.4); 2.519(4.7); 2.515(9.4); 2.510(12.4); 2.505(8.9); 2.501(4.3); 1.601(4.4); 1.295(16.0)

Example 323: ¹H-NMR(400.0 MHz, DMSO):
9.008(4.2); 9.002(4.3); 8.768(3.1); 8.763(2.9); 8.232(0.9); 8.221(3.9); 8.217(4.9); 8.203(0.8); 8.179(1.9); 8.174(1.5); 8.157(2.8); 8.152(2.5); 8.082(3.4); 8.060(2.2); 4.010(1.8); 3.986(5.7); 3.963(5.9); 3.939(2.0); 3.887(2.7); 3.843(3.2); 3.568(2.4); 3.552(5.1); 3.536(2.4); 3.487(3.2); 3.443(2.7); 3.340(159.7); 3.310(0.4); 3.218(0.4); 3.202(0.9); 3.184(1.4); 3.169(1.4); 3.156(1.4); 3.141(1.4); 3.124(0.9); 3.108(0.4); 2.897(0.5); 2.738(0.4); 2.678(0.4); 2.531(1.2); 2.518(22.7); 2.513(44.9); 2.509(58.4); 2.504(41.4); 2.500(19.4); 2.335(0.4); 1.737(0.7); 1.721(2.3); 1.704(3.5); 1.688(2.2); 1.671(0.6); 1.613(16.0)

Example 324: ¹H-NMR(400.0 MHz, DMSO):
9.747(0.9); 9.727(1.0); 9.679(1.0); 9.659(1.0); 8.970(2.0); 8.964(2.8); 8.957(2.2); 8.621(1.5); 8.616(1.6); 8.610(1.7); 8.605(1.5); 8.273(1.5); 8.268(1.6); 8.257(1.6); 8.252(1.7); 8.204(0.9); 8.199(0.7); 8.181(1.3); 8.177(1.3); 8.174(1.0); 8.169(0.9); 8.151(1.4); 8.146(1.3); 8.100(1.6); 8.092(0.6); 8.084(2.0); 8.077(1.2); 8.071(0.7); 8.068(0.6); 8.062(1.2); 7.958(2.1); 7.545(0.6); 7.526(0.5); 7.503(0.3); 7.491(0.9); 7.486(1.3); 7.468(2.1); 7.466(2.2); 7.458(1.2); 7.453(1.3); 7.449(1.4); 7.438(2.6); 7.432(2.7); 7.428(1.6); 7.424(1.3); 7.417(1.0); 7.407(2.9); 7.402(1.7); 7.398(0.7); 7.392(1.0); 7.385(1.7); 7.381(1.3); 7.376(0.7); 7.371(0.5); 7.364(0.9); 6.243(1.3); 6.221(2.2); 6.199(1.3); 4.600(3.8); 4.596(4.2); 3.953(1.3); 3.947(1.4); 3.909(1.6); 3.904(1.7); 3.582(1.6); 3.577(1.7); 3.539(1.3); 3.534(1.4); 3.340(190.5); 3.321(1.0); 2.897(16.0); 2.738(13.0); 2.737(13.0); 2.682(0.3); 2.678(0.5); 2.673(0.3); 2.531(1.4); 2.518(27.5); 2.513(54.8); 2.509(71.7); 2.504(51.2); 2.499(24.2); 2.340(0.3); 2.335(0.5); 2.331(0.3); 1.667(7.5); 1.653(0.8); 1.626(7.1); 1.237(0.5)

Example 325: ¹H-NMR(400.0 MHz, DMSO):
9.006(4.1); 9.000(4.2); 8.766(2.9); 8.760(2.7); 8.238(2.9); 8.233(3.2); 8.176(1.8); 8.171(1.5); 8.154(2.7); 8.149(2.5); 8.077(3.3); 8.055(2.1); 7.954(0.3); 6.961(2.6); 3.889(2.7); 3.846(3.2); 3.464(3.1); 3.420(2.7); 3.334(126.5); 2.892(2.9); 2.733(2.2); 2.732(2.3); 2.673(0.3); 2.526(1.1); 2.522(1.7); 2.513(21.2); 2.509(42.2); 2.504(55.1); 2.499(38.9); 2.495(18.0); 2.330(0.5); 2.327(0.6); 2.310(1.2); 2.293(1.7); 2.275(1.2); 2.258(0.5); 1.616(16.0); 1.232(0.5); 1.211(15.7); 1.196(15.5); 0.817(8.7); 0.799(8.5); 0.763(8.5); 0.746(8.3)

Example 326: ¹H-NMR(400.0 MHz, DMSO):
8.954(4.3); 8.949(4.3); 8.605(3.1); 8.599(3.0); 8.237(3.2); 8.232(3.6); 8.226(1.0); 8.210(1.7); 8.196(0.8); 8.173(1.9); 8.168(1.6); 8.151(2.8); 8.146(2.6); 8.076(3.5); 8.054(2.2); 4.589(7.6); 4.005(1.9); 3.981(6.0); 3.958(6.2); 3.934(2.1); 3.891(2.7); 3.848(3.3); 3.563(2.4); 3.547(5.3); 3.532(2.5); 3.490(3.2); 3.447(2.7); 3.334(143.1); 3.309(0.4); 3.213(0.4); 3.197(0.9); 3.180(1.5); 3.164(1.4); 3.152(1.4); 3.137(1.5); 3.120(0.9); 3.104(0.4); 2.673(0.4); 2.526(1.3); 2.513(22.3);

-continued

NMR Peak Lists Table 1

2.509(43.9); 2.504(57.1); 2.499(40.5); 2.495(19.0); 2.331(0.4); 1.733(0.7); 1.716(2.4); 1.700(3.6); 1.683(2.3); 1.667(0.6); 1.607(16.0)
Example 327: $^1$H-NMR(400.0 MHz, DMSO):
9.007(3.4); 9.001(3.5); 8.772(2.4); 8.766(2.3); 8.681(1.3); 8.661(1.3); 8.226(2.2); 8.222(2.8); 8.179(1.3); 8.174(1.0); 8.157(2.0); 8.152(1.7); 8.140(0.4); 8.083(2.7); 8.061(1.7); 5.002(1.0); 4.984(1.2); 4.965(0.9); 3.932(2.1); 3.888(2.5); 3.504(2.2); 3.461(1.8); 3.327(59.0); 3.304(15.3); 3.263(2.6); 3.075(16.0); 2.922(2.7); 2.892(1.8); 2.732(1.4); 2.672 (0.3); 2.525(1.3); 2.512(20.9); 2.508(40.8); 2.503(52.8); 2.499(38.0); 2.494(18.2); 2.330(0.3); 1.635(2.0); 1.616(10.6); 1.411(1.0); 1.394(1.0); 1.373(5.8); 1.356(5.7)
Example 328: $^1$H-NMR(400.0 MHz, DMSO):
9.002(5.9); 8.996(6.0); 8.768(5.0); 8.762(4.7); 8.218(4.8); 8.179(2.4); 8.175(2.0); 8.157(3.5); 8.153(3.2); 8.078(5.3); 8.056(3.4); 7.954(0.4); 7.852(1.1); 7.830(1.3); 7.822(1.5); 7.799(1.4); 3.898(2.0); 3.873(2.5); 3.855(2.3); 3.830(2.9); 3.798(0.4); 3.783(0.9); 3.776(0.8); 3.767(1.0); 3.761(1.1); 3.746(0.9); 3.731(0.4); 3.475(2.9); 3.460(2.3); 3.432(2.4); 3.417(2.0); 3.331(190.6); 2.892(2.8); 2.732(2.3); 2.677(0.4); 2.673(0.6); 2.668(0.5); 2.526(2.1); 2.513(35.8); 2.508 (71.1); 2.504(93.2); 2.499(66.9); 2.495(31.7); 2.335(0.4); 2.331(0.6); 2.326(0.4); 1.617(15.2); 1.607(11.8); 1.524(0.8); 1.507(1.0); 1.491(1.5); 1.474(1.1); 1.457(0.5); 1.450(0.4); 1.437(0.3); 1.422(0.5); 1.417(0.7); 1.410(0.6); 1.403(1.0); 1.389(1.4); 1.382(1.0); 1.373(1.7); 1.358(1.5); 1.349(1.6); 1.342(1.5); 1.334(0.8); 1.326(1.1); 1.316(0.4); 1.309(0.6); 1.233(0.5); 1.147(1.0); 1.128(1.9); 1.109(1.7); 1.090(1.0); 1.081(7.5); 1.064(7.4); 1.036(6.1); 1.019(6.1); 0.996(0.8); 0.988(0.8); 0.979(1.2); 0.971(1.4); 0.962(1.0); 0.956(1.2); 0.948(1.0); 0.940(0.6); 0.930(0.6); 0.852(16.0); 0.836(15.1); 0.662(9.7); 0.645(9.8); 0.639(10.1); 0.622(9.1)
Example 329: $^1$H-NMR(400.0 MHz, DMSO):
8.965(5.2); 8.960(4.7); 8.948(1.2); 8.938(1.0); 8.918(1.0); 8.616(3.1); 8.257(3.2); 8.196(1.2); 8.193(1.5); 8.189(1.0); 8.174(1.7); 8.171(2.3); 8.167(1.6); 8.091(3.8); 8.069(2.5); 7.959(1.2); 5.207(0.8); 5.189(1.1); 5.174(1.0); 5.170(0.9); 5.156(1.2); 5.137(0.9); 4.598(8.4); 3.924(1.5); 3.896(1.4); 3.881(1.8); 3.853(1.8); 3.568(1.7); 3.547(1.8); 3.525(1.4); 3.504(1.5); 3.336(116.2); 3.069(0.4); 3.051(1.0); 3.034(1.4); 3.017(1.1); 2.999(0.4); 2.969(0.4); 2.952(1.0); 2.934(1.3); 2.917(1.0); 2.897(10.2); 2.738(8.2); 2.678(0.4); 2.557(0.5); 2.543(0.4); 2.531(1.3); 2.518(26.0); 2.513(51.9); 2.509(68.0); 2.504(48.4); 2.500(22.8); 2.335(0.4); 1.652(9.8); 1.645(9.0); 1.558(4.6); 1.540(5.7); 1.537(6.1); 1.519 (5.0); 1.248(16.0); 1.231(15.7); 1.132(10.9); 1.115(10.6)
Example 330: $^1$H-NMR(400.0 MHz, DMSO):
8.956(4.7); 8.954(4.8); 8.951(5.2); 8.949(4.4); 8.609(3.2); 8.605(5.3); 8.253(3.0); 8.248(3.4); 8.240(2.8); 8.235(3.0); 8.188(1.9); 8.183(1.7); 8.180(1.9); 8.175(1.5); 8.166(2.8); 8.161(2.7); 8.158(2.7); 8.153(2.3); 8.082(3.5); 8.077(3.2); 8.060(2.3); 8.055(2.1); 7.983(1.4); 7.970(1.6); 7.962(1.6); 7.949(1.5); 4.590(12.1); 3.888(3.4); 3.887(3.3); 3.845(4.1); 3.843(4.0); 3.489(3.2); 3.478(2.9); 3.446(2.7); 3.435(2.5); 3.333(175.0); 3.309(0.5); 3.299(0.4); 3.282(0.6); 3.274(0.8); 3.265(0.8); 3.261(1.2); 3.257(1.0); 3.253(1.3); 3.244(1.2); 3.236(1.3); 3.232(0.8); 3.223(0.7); 3.215(0.6); 2.892(3.8); 2.734(2.9); 2.733(2.9); 2.678(0.4); 2.673(0.5); 2.669(0.4); 2.527(1.8); 2.522(2.7); 2.513(31.4); 2.509(63.3); 2.504 (83.3); 2.500(59.7); 2.495(28.2); 2.336(0.4); 2.331(0.5); 2.327(0.4); 1.611(14.8); 1.598(16.0); 1.233(0.5); 1.172(8.5); 1.156(8.4); 1.124(7.9); 1.107(7.7); 1.033(0.4); 1.025(0.5); 1.012(1.0); 1.004(0.6); 1.000(0.7); 0.992(1.1); 0.980(0.7); 0.974(0.7); 0.971(0.7); 0.962(1.2); 0.953(0.7); 0.949(0.7); 0.941(1.2); 0.929(0.6); 0.921(0.4); 0.439(0.3); 0.435(0.4); 0.426(0.8); 0.417(0.8); 0.413(0.8); 0.405(0.9); 0.396(0.5); 0.392(0.9); 0.383(0.9); 0.379(0.6); 0.375(0.7); 0.370(1.3); 0.361(1.4); 0.357(1.2); 0.350(1.5); 0.341(1.2); 0.336(0.9); 0.331(1.0); 0.327(0.7); 0.319(0.4); 0.309(0.3); 0.280(0.5); 0.269(0.9); 0.256(1.6); 0.246(1.9); 0.236(1.8); 0.228(0.6); 0.223(1.2); 0.215(0.5); 0.210(0.4); 0.167(0.5); 0.154(1.0); 0.144(1.3); 0.138(1.2); 0.131(1.3); 0.125(1.5); 0.115(1.4); 0.112(0.9); 0.103(1.3); 0.094(0.8); 0.091(1.3); 0.082(1.2); 0.069(0.9); 0.059(0.5)
Example 331: $^1$H-NMR(400.0 MHz, DMSO):
9.009(4.7); 9.003(4.9); 8.965(1.1); 8.945(1.2); 8.935(1.2); 8.915(1.1); 8.773(2.9); 8.770(3.0); 8.767(2.8); 8.231(3.5); 8.193(1.3); 8.190(1.6); 8.185(1.0); 8.171(1.9); 8.167(2.4); 8.166(2.3); 8.088(3.9); 8.065(2.6); 7.953(1.1); 5.202(0.8); 5.183(1.1); 5.169(1.0); 5.164(1.0); 5.150(1.2); 5.132(0.8); 3.910(1.5); 3.882(1.6); 3.867(1.8); 3.839(1.9); 3.554(1.9); 3.534(1.8); 3.511(1.6); 3.490(1.5); 3.329(128.0); 3.223(0.3); 3.220(0.4); 3.064(0.4); 3.046(1.0); 3.029(1.4); 3.012(1.1); 2.994(0.4); 2.966(0.4); 2.949(1.0); 2.931(1.4); 2.914(1.1); 2.892(9.4); 2.732(7.6); 2.677(0.4); 2.672(0.5); 2.668(0.4); 2.526(1.5); 2.521(2.3); 2.512(28.2); 2.508(56.5); 2.503(73.9); 2.499(53.1); 2.494(25.3); 2.335(0.3); 2.330(0.5); 2.326(0.3); 1.648(9.8); 1.640(10.0); 1.552(5.0); 1.534(6.1); 1.531(6.2); 1.513(4.9); 1.243(16.0); 1.226(15.6); 1.129(13.8); 1.112(13.6)
Example 332: $^1$H-NMR(400.0 MHz, DMSO):
9.006(4.6); 9.003(4.1); 9.000(4.9); 8.997(3.8); 8.767(3.2); 8.763(4.8); 8.232(2.9); 8.228(3.3); 8.219(2.3); 8.215(2.6); 8.190(1.9); 8.185(1.6); 8.181(1.6); 8.176(1.2); 8.167(2.8); 8.162(2.6); 8.159(2.4); 8.154(2.0); 8.084(3.4); 8.079(2.8); 8.062(2.3); 8.057(1.8); 7.987(1.1); 7.973(1.5); 7.966(1.4); 7.952(1.4); 3.879(3.7); 3.836(4.4); 3.481(3.2); 3.470(2.5); 3.437(2.7); 3.426(2.2); 3.330(142.1); 3.307(0.4); 3.282(0.5); 3.273(0.7); 3.265(0.7); 3.260(1.1); 3.256(0.9); 3.252(1.2); 3.244(1.1); 3.235(1.2); 3.231(0.8); 3.222(0.7); 3.214(0.6); 2.892(3.7); 2.733(2.6); 2.673(0.6); 2.668(0.4); 2.526(1.7); 2.521(2.8); 2.513(34.9); 2.508(69.5); 2.504(90.6); 2.499(64.0); 2.495(29.7); 2.335(0.4); 2.330(0.6); 2.326(0.4); 1.612(13.1); 1.598(16.0); 1.233(0.4); 1.172(8.4); 1.155(8.2); 1.124(6.8); 1.107(6.7); 1.024(0.4); 1.011(0.9); 1.003(0.5); 0.999(0.6); 0.991(0.9); 0.981(0.7); 0.973(0.7); 0.961(1.2); 0.952(0.7); 0.948(0.7); 0.940(1.1); 0.928(0.6); 0.920(0.4); 0.426(0.7); 0.416(0.7); 0.413(0.7); 0.404(0.8); 0.396(0.5); 0.391(0.8); 0.382(0.9); 0.370(1.2); 0.361(1.3); 0.349(1.4); 0.340(1.1); 0.336(0.8); 0.331(0.8); 0.327(0.7); 0.278(0.5); 0.268(0.9); 0.265(0.7); 0.255(1.5); 0.245(1.8); 0.235(1.8); 0.222(1.1); 0.214(0.5); 0.209(0.4); 0.166(0.4); 0.154(0.9); 0.143(1.2); 0.136(1.2); 0.131(1.1); 0.123(1.5); 0.114(1.3); 0.111(0.9); 0.102(1.2); 0.090(1.3); 0.081(1.2); 0.068(0.9); 0.058(0.5)
Example 333: $^1$H-NMR(400.0 MHz, DMSO):
8.957(2.7); 8.952(5.4); 8.946(3.0); 8.672(1.0); 8.653(1.1); 8.633(1.2); 8.615(2.6); 8.612(2.8); 8.594(2.2); 8.589(2.1); 8.240(1.9); 8.236(2.0); 8.219(2.2); 8.215(2.4); 8.179(1.1); 8.174(0.9); 8.160(1.5); 8.156(2.2); 8.152(1.6); 8.138(1.9); 8.133(1.8); 8.080(2.2); 8.074(2.6); 8.058(1.4); 8.052(1.5); 7.954(1.9); 7.628(0.4); 7.625(0.4); 7.598(0.4); 5.193(0.8); 5.175(1.2); 5.158(1.2); 5.141(1.2); 5.122(0.7); 4.592(5.0); 4.588(5.5); 3.927(1.5); 3.884(1.8); 3.823(1.8); 3.780(2.2); 3.477(2.3); 3.470(1.9); 3.434(1.9); 3.427(1.7); 3.330(133.6); 3.306(0.4); 2.892(15.4); 2.732(12.4); 2.677(0.4); 2.673 (0.5); 2.668(0.4); 2.536(12.5); 2.526(1.9); 2.513(31.6); 2.508(62.4); 2.503(81.2); 2.499(57.8); 2.494(27.2); 2.425 (14.8); 2.335(0.4); 2.330(0.6); 2.326(0.4); 2.257(13.2); 2.171(16.0); 1.613(10.7); 1.550(8.9); 1.448(5.2); 1.430(5.2); 1.419(4.6); 1.402(4.4); 1.233(0.4)
Example 334: $^1$H-NMR(400.0 MHz, DMSO):
8.988(1.8); 8.965(7.4); 8.960(6.6); 8.621(5.8); 8.269(6.3); 8.266(6.2); 8.205(2.1); 8.201(2.7); 8.183(2.9); 8.179(4.0); 8.095(5.2); 8.073(3.4); 7.959(2.6); 7.734(2.9); 7.726(3.2); 7.667(3.2); 7.659(3.5); 7.633(0.8); 7.620(3.7); 7.611(2.9); 7.603(0.6); 7.580(0.4); 7.573(0.5); 7.555(0.5); 7.516(3.5); 7.508(3.0); 5.279(0.3); 5.262(1.4); 5.242(2.4); 5.224(2.4);

-continued

NMR Peak Lists Table 1

5.204(1.2); 4.598(8.9); 3.990(2.1); 3.946(2.5); 3.930(2.3); 3.887(2.8); 3.571(2.7); 3.542(2.5); 3.528(2.3); 3.499(2.1); 3.336(123.4); 2.897(16.0); 2.737(14.4); 2.677(0.8); 2.565(1.4); 2.551(2.7); 2.512(98.4); 2.508(113.5); 2.335(0.7); 1.681(15.9); 1.675(15.7); 1.658(0.7); 1.587(7.7); 1.569(7.8); 1.556(7.3); 1.539(7.0); 1.238(0.6)
Example 335: $^1$H-NMR(400.0 MHz, DMSO):
8.960(3.7); 8.956(6.4); 8.951(3.7); 8.754(1.5); 8.735(2.6); 8.716(1.4); 8.618(2.6); 8.613(2.6); 8.599(2.6); 8.594(2.5); 8.517(4.4); 8.513(2.7); 8.506(2.8); 8.502(4.6); 8.408(4.5); 8.404(2.8); 8.397(2.8); 8.393(4.6); 8.258(2.6); 8.254(2.8); 8.232(2.6); 8.228(2.9); 8.198(1.6); 8.192(2.4); 8.187(1.4); 8.176(2.4); 8.172(3.6); 8.165(2.1); 8.089(5.4); 8.067(3.6); 7.954(2.1); 7.356(4.0); 7.352(2.6); 7.344(2.5); 7.341(3.8); 7.268(4.0); 7.265(2.6); 7.256(2.5); 7.253(3.8); 4.979(0.9); 4.960(1.2); 4.941(0.9); 4.931(0.9); 4.913(1.3); 4.894(0.9); 4.592(6.3); 4.587(6.2); 3.961(2.2); 3.917(2.5); 3.866(2.2); 3.823(2.7); 3.500(3.0); 3.496(2.9); 3.457(2.5); 3.452(2.5); 3.367(0.6); 3.334(182.7); 2.892(16.0); 2.733(13.1); 2.678 (0.4); 2.673(0.6); 2.669(0.5); 2.526(2.3); 2.513(37.0); 2.509(72.6); 2.504(94.3); 2.499(68.3); 2.495(33.4); 2.335(0.4); 2.331(0.6); 2.326(0.4); 1.655(13.0); 1.610(12.7); 1.443(6.7); 1.425(6.7); 1.408(6.8); 1.390(6.6); 1.233(0.5)
Example 336: $^1$H-NMR(400.0 MHz, DMSO):
8.959(3.9); 8.953(7.3); 8.947(4.3); 8.616(2.9); 8.611(2.9); 8.602(3.2); 8.597(3.1); 8.460(3.0); 8.439(3.0); 8.256(2.9); 8.251(3.2); 8.237(3.2); 8.233(3.5); 8.192(1.7); 8.187(1.4); 8.169(4.2); 8.165(3.7); 8.147(2.7); 8.143(2.5); 8.084(3.2); 8.074(3.7); 8.062(2.2); 8.051(2.3); 7.954(0.8); 7.480(1.9); 7.473(2.1); 7.468(2.1); 7.461(2.1); 7.401(2.1); 7.394(2.3); 7.389(2.3); 7.381(2.4); 7.289(2.2); 7.286(1.8); 7.282(2.1); 7.210(2.5); 7.207(2.0); 7.203(2.3); 7.121(2.2); 7.118(2.2); 7.109(2.1); 7.106(2.1); 7.032(2.5); 7.029(2.5); 7.020(2.4); 7.017(2.3); 5.086(1.1); 5.069(1.9); 5.049(1.8); 5.031(1.1); 4.593(7.0); 4.588(7.6); 3.959(2.4); 3.916(3.9); 3.875(3.2); 3.495(5.4); 3.452(4.5); 3.356(0.4); 3.329(119.6); 2.892 (6.3); 2.733(5.2); 2.677(0.5); 2.673(0.6); 2.668(0.4); 2.526(2.1); 2.513(36.9); 2.508(73.5); 2.504(96.4); 2.499(69.5); 2.495(33.4); 2.335(0.5); 2.330(0.6); 2.326(0.4); 1.647(16.0); 1.603(14.2); 1.450(8.0); 1.433(8.0); 1.410(7.4); 1.393(7.3); 1.233(0.6)
Example 337: $^1$H-NMR(400.0 MHz, DMSO):
9.007(3.7); 9.002(6.0); 8.997(4.0); 8.774(2.8); 8.768(2.7); 8.755(4.3); 8.750(3.5); 8.736(2.8); 8.716(1.5); 8.516(4.3); 8.512(2.7); 8.504(2.7); 8.500(4.4); 8.407(4.8); 8.403(2.9); 8.396(3.0); 8.392(4.9); 8.313(0.7); 8.236(2.7); 8.231(3.1); 8.211(2.7); 8.206(3.6); 8.199(2.1); 8.193(2.7); 8.188(1.4); 8.177(2.7); 8.171(3.7); 8.165(2.5); 8.089(6.1); 8.067(4.0); 7.954(0.6); 7.354(4.2); 7.350(2.6); 7.342(2.5); 7.338(4.1); 7.266(4.6); 7.263(2.8); 7.255(2.8); 7.251(4.4); 4.978(1.0); 4.960(1.4); 4.941(1.0); 4.930(1.0); 4.911(1.4); 4.893(0.9); 3.952(2.5); 3.909(2.9); 3.858(2.7); 3.815(3.3); 3.490(3.4); 3.485(3.0); 3.447(3.0); 3.442(2.6); 3.331(171.4); 2.893(4.9); 2.733(3.9); 2.678(0.6); 2.673(0.8); 2.669(0.6); 2.526 (2.4); 2.522(3.9); 2.513(47.0); 2.509(94.4); 2.504(123.9); 2.499(87.8); 2.495(40.9); 2.335(0.6); 2.331(0.8); 2.326(0.6); 1.657(16.0); 1.611(14.4); 1.443(7.9); 1.425(7.9); 1.408(7.4); 1.390(7.2); 1.234(0.5); 0.000(0.7)
Example 338: $^1$H-NMR(300.2 MHz, CDCl3):
8.969(3.0); 8.966(2.9); 8.962(3.3); 8.959(2.5); 8.272(3.3); 8.183(0.9); 8.177(0.9); 8.170(0.7); 8.164(0.7); 8.153(2.2); 8.147(2.4); 8.140(1.8); 8.134(1.9); 8.114(2.8); 8.106(2.3); 8.085(1.1); 8.076(0.8); 7.853(2.2); 7.847(2.3); 7.841(1.9); 7.835(1.7); 7.271(7.3); 7.263(0.7); 7.255(1.0); 7.244(0.9); 7.228(0.9); 4.863(0.8); 4.840(1.3); 4.817(0.9); 4.414(1.3); 4.408(1.4); 4.380(2.6); 4.374(2.3); 4.346(1.6); 4.341(1.5); 4.304(0.9); 4.300(0.4); 4.291(0.9); 4.272(1.2); 4.269(1.1); 4.264(0.7); 4.260(1.1); 4.255(1.2); 4.237(1.0); 4.228(0.5); 4.224(1.0); 4.158(0.7); 4.134(2.0); 4.110(2.1); 4.086(0.7); 3.998(2.2); 3.964(1.8); 3.941(2.6); 3.907(2.1); 3.381(3.5); 3.334(7.6); 3.324(3.1); 3.021(0.9); 3.017(1.1); 3.015(1.1); 3.012(0.9); 2.986(1.8); 2.980(1.8); 2.959(0.3); 2.954(0.8); 2.951(0.9); 2.947(1.0); 2.944(0.8); 2.907(0.6); 2.904(0.6); 2.885(0.6); 2.882(0.6); 2.876(0.7); 2.873(1.0); 2.869(0.7); 2.853(0.7); 2.850(1.1); 2.846(0.7); 2.840(0.6); 2.837(0.6); 2.818(0.6); 2.815(0.5); 2.046(9.4); 1.781(14.1); 1.778(16.0); 1.728(6.1); 1.506(5.3); 1.483(5.3); 1.445(7.0); 1.422(6.9); 1.284(2.7); 1.260(5.3); 1.236(2.6); 0.000(5.9)
Example 339: $^1$H-NMR(400.0 MHz, DMSO):
8.963(2.1); 8.958(2.1); 8.950(1.7); 8.945(1.7); 8.751(0.8); 8.731(0.8); 8.708(0.6); 8.688(0.6); 8.622(1.5); 8.617(1.4); 8.585(1.2); 8.580(1.1); 8.261(1.5); 8.257(1.6); 8.204(1.0); 8.199(0.8); 8.182(2.4); 8.177(1.5); 8.137(0.8); 8.116(0.9); 8.112(0.8); 8.107(0.5); 8.093(1.8); 8.090(1.6); 8.085(1.3); 8.071(1.2); 8.054(1.7); 8.038(0.7); 8.032(0.8); 7.954(2.5); 7.940(1.0); 7.936(0.9); 7.865(0.6); 7.845(0.9); 7.841(1.5); 7.819(1.1); 7.749(0.8); 7.729(0.9); 7.626(0.8); 7.610(1.2); 7.580(0.4); 7.576(0.4); 7.563(0.9); 7.559(0.8); 7.555(0.4); 7.542(1.4); 7.538(1.5); 7.528(1.2); 7.521(1.0); 7.518(1.1); 7.510(2.1); 7.505(0.8); 7.494(1.3); 7.429(0.6); 7.425(0.6); 7.409(1.3); 7.389(0.6); 7.386(0.7); 7.372(1.1); 7.352(1.0); 7.334(0.6); 5.768(0.4); 5.751(0.7); 5.734(0.8); 5.716(0.5); 4.594(3.6); 4.585(2.9); 3.974(1.2); 3.930(1.5); 3.841(1.0); 3.798(1.2); 3.493(1.7); 3.490(1.5); 3.450(1.5); 3.447(1.2); 3.332(99.1); 2.891(16.0); 2.733(12.8); 2.732 (12.3); 2.672(0.4); 2.526(1.2); 2.521(1.9); 2.512(22.6); 2.508(44.9); 2.503(58.4); 2.499(41.5); 2.494(19.3); 2.330(0.4); 1.680(5.8); 1.584(7.4); 1.574(2.9); 1.556(2.7); 1.531(3.4); 1.513(3.4); 1.485(0.4); 1.468(0.4); 1.441(0.4); 1.424(0.4)
Example 340: $^1$H-NMR(400.0 MHz, DMSO):
9.012(1.9); 9.006(2.0); 8.999(2.6); 8.993(2.6); 8.781(1.3); 8.775(1.3); 8.755(0.7); 8.744(2.0); 8.738(2.2); 8.712(0.9); 8.692(0.9); 8.241(1.3); 8.236(1.5); 8.206(0.9); 8.201(0.6); 8.184(1.2); 8.179(1.1); 8.165(1.8); 8.161(2.0); 8.136(0.7); 8.113(1.4); 8.109(0.8); 8.095(1.6); 8.091(2.1); 8.086(1.7); 8.073(1.0); 8.054(1.6); 8.034(1.4); 7.954(2.4); 7.940(0.9); 7.936(0.8); 7.866(0.9); 7.847(1.2); 7.842(1.5); 7.819(0.9); 7.751(1.1); 7.730(1.3); 7.625(0.7); 7.609(1.0); 7.576(0.3); 7.563(0.7); 7.559(0.7); 7.555(0.3); 7.542(1.2); 7.538(1.3); 7.528(1.0); 7.521(0.8); 7.518(0.8); 7.510(2.0); 7.501(0.4); 7.492(1.5); 7.446(0.3); 7.441(0.4); 7.429(1.0); 7.425(0.9); 7.421(0.5); 7.410(1.5); 7.407(1.4); 7.392(0.9); 7.389(1.0); 7.373(1.5); 7.353(1.4); 7.334(0.9); 5.767(0.6); 5.750(0.9); 5.733(0.6); 3.965(1.1); 3.832(1.5); 3.789(1.8); 3.482(2.3); 3.439(1.9); 3.332(138.3); 2.891(16.0); 2.733(13.2); 2.677(0.3); 2.672(0.5); 2.668(0.4); 2.526(1.4); 2.521(2.3); 2.512(28.5); 2.508(56.8); 2.503(74.2); 2.499(52.7); 2.494(24.8); 2.335(0.4); 2.330(0.5); 2.325(0.3); 1.681(8.9); 1.585(6.6); 1.573(4.1); 1.556(4.0); 1.531(3.0); 1.513(3.0); 1.233(0.6)
Example 341: $^1$H-NMR(300.2 MHz, CDCl3):
8.972(6.3); 8.966(6.6); 8.283(5.8); 8.277(5.8); 8.177(1.8); 8.147(4.7); 8.115(7.1); 8.086(2.7); 7.844(5.9); 7.265(18.3); 6.911(0.7); 6.880(0.7); 6.821(1.2); 6.804(0.9); 6.791(1.3); 5.302(0.4); 4.018(0.6); 3.997(2.1); 3.989(2.6); 3.969(2.5); 3.951(3.1); 3.940(2.5); 3.932(3.5); 3.912(2.5); 3.905(2.5); 3.894(2.9); 3.879(2.4); 3.852(1.9); 3.827(1.6); 3.813(0.7); 3.801(2.4); 3.775(2.3); 3.757(1.7); 3.729(1.1); 3.714(0.9); 3.700(1.4); 3.686(0.7); 3.670(2.6); 3.645(2.0); 3.624(1.6); 3.597(1.7); 3.573(0.9); 3.520(1.1); 3.497(1.5); 3.468(1.6); 3.454(0.9); 3.441(0.7); 3.430(1.0); 3.402(0.8); 3.376(1.8); 3.363(3.4); 3.352(2.1); 3.329(11.5); 3.319(2.2); 3.306(3.1); 3.295(1.8); 2.369(0.4); 2.356(0.4); 2.343(0.7); 2.331(0.8); 2.318(0.9); 2.304(1.1); 2.293(0.8); 2.279(1.2); 2.269(0.9); 2.254(1.0); 2.243(0.8); 2.229(0.6); 2.217(0.4); 2.077(0.5); 2.066(0.8); 2.047(0.7); 2.034(0.5); 2.022(0.9); 2.005(0.8); 1.996(0.8); 1.980(1.0); 1.966(0.6); 1.953(0.7); 1.938(0.5); 1.863(0.3); 1.850(0.7); 1.832(0.4); 1.822(0.6); 1.805(0.6); 1.773(16.0); 1.767(13.4); 1.757(10.7); 1.731(1.0); 1.715(0.7); 1.704(0.5); 1.689(0.6); 1.669(0.8); 1.634(11.2); 1.601(0.9); 1.596(0.9); 1.580(1.0); 1.568(0.9); 1.554(1.2); 1.540(0.8); 1.528(0.7); 1.514(0.6); 1.238(5.5); 1.215(5.4); 1.190(4.3); 1.168(8.3); 1.147(4.8); 1.124(3.7); 1.101(3.6); 0.010(0.7); 0.000(14.6)

NMR Peak Lists Table 1

Example 342: ¹H-NMR(400.0 MHz, DMSO):
8.960(4.3); 8.955(4.6); 8.951(4.6); 8.946(4.3); 8.683(1.8); 8.662(2.0); 8.653(1.9); 8.632(1.8); 8.617(3.3); 8.613(3.1); 8.590(3.2); 8.585(3.1); 8.256(3.5); 8.252(3.5); 8.216(3.1); 8.211(3.6); 8.196(1.9); 8.192(1.6); 8.174(2.8); 8.170(4.2); 8.165(1.7); 8.148(2.8); 8.143(2.5); 8.087(3.5); 8.074(3.7); 8.065(2.5); 8.052(2.3); 7.954(0.4); 7.497(4.6); 7.480(1.9); 7.475(6.0); 7.468(0.7); 7.425(0.6); 7.418(4.8); 7.414(1.7); 7.401(1.8); 7.397(5.9); 7.390(0.8); 7.332(3.8); 7.312(3.1); 7.227(3.7); 7.207(3.1); 5.029(1.0); 5.010(1.4); 4.991(1.2); 4.985(1.2); 4.966(1.5); 4.947(1.1); 4.593(7.0); 4.585(7.0); 3.954(2.7); 3.911(3.2); 3.845(2.8); 3.802(3.3); 3.486(3.9); 3.483(4.0); 3.443(3.3); 3.440(3.4); 3.330(143.4); 3.309(0.5); 2.892(3.1); 2.733(2.5); 2.678(0.6); 2.673(0.7); 2.668(0.5); 2.526(2.4); 2.513(43.9); 2.509(88.1); 2.504(115.8); 2.499(83.1); 2.495(39.7); 2.335(0.6); 2.331(0.7); 2.326(0.5); 1.646(16.0); 1.579(16.0); 1.442(7.5); 1.424(7.6); 1.406(7.8); 1.388(7.6); 1.321(0.3); 1.304(0.6); 1.287(0.3); 1.233(0.5)
Example 343: ¹H-NMR(400.0 MHz, DMSO):
8.959(6.1); 8.954(6.3); 8.757(1.3); 8.736(2.2); 8.715(1.3); 8.618(2.3); 8.611(3.3); 8.604(2.3); 8.259(2.5); 8.254(3.1); 8.246(2.5); 8.182(2.3); 8.177(2.0); 8.160(3.5); 8.155(3.2); 8.083(4.6); 8.061(3.0); 7.954(2.0); 4.651(0.6); 4.632(1.0); 4.614(1.0); 4.592(10.0); 3.958(2.0); 3.915(2.8); 3.912(2.7); 3.869(2.5); 3.552(2.5); 3.535(2.3); 3.509(2.1); 3.492(2.0); 3.328(113.1); 3.305(0.3); 2.892(16.0); 2.733(13.0); 2.677(0.4); 2.673(0.5); 2.668(0.4); 2.526(1.6); 2.521(2.5); 2.513(30.5); 2.508(61.2); 2.504(80.6); 2.499(58.1); 2.495(27.8); 2.335(0.4); 2.330(0.5); 2.326(0.4); 1.642(12.3); 1.616(11.6); 1.330(5.3); 1.312(5.4); 1.299(5.3); 1.281(5.1); 1.233(0.6)
Example 344: ¹H-NMR(400.0 MHz, DMSO):
9.009(3.5); 9.003(4.1); 9.001(5.0); 8.995(4.8); 8.777(2.4); 8.771(2.2); 8.750(3.2); 8.744(3.0); 8.685(1.3); 8.665(1.5); 8.655(1.8); 8.635(1.7); 8.236(2.2); 8.231(2.6); 8.196(3.6); 8.192(4.1); 8.176(3.2); 8.171(3.9); 8.166(1.5); 8.149(3.1); 8.144(2.6); 8.089(2.6); 8.076(3.7); 8.067(1.8); 8.053(2.3); 7.954(1.4); 7.502(0.4); 7.495(3.2); 7.491(1.1); 7.479(1.3); 7.474(4.2); 7.467(0.5); 7.424(0.6); 7.417(4.6); 7.412(1.6); 7.400(1.7); 7.396(5.7); 7.389(0.6); 7.383(1.1); 7.332(2.7); 7.312(2.1); 7.227(3.6); 7.207(2.9); 5.028(1.0); 5.009(1.3); 4.990(1.1); 4.984(0.9); 4.965(1.1); 4.946(0.7); 3.945(2.0); 3.902(2.3); 3.836(2.7); 3.793(3.4); 3.475(3.9); 3.432(3.3); 3.331(229.3); 3.307(0.8); 2.892(11.6); 2.732(9.3); 2.677 (0.6); 2.673(0.8); 2.668(0.6); 2.526(2.9); 2.513(50.2); 2.508(98.9); 2.504(128.5); 2.499(90.9); 2.494(42.3); 2.335(0.7); 2.330(0.8); 2.326(0.6); 1.646(16.0); 1.579(11.5); 1.568(0.7); 1.441(7.4); 1.423(7.4); 1.405(5.5); 1.387(5.5); 1.233(0.7)
Example 345: ¹H-NMR(400.0 MHz, DMSO):
9.008(7.0); 9.002(7.2); 8.777(2.5); 8.769(3.9); 8.762(4.0); 8.738(2.3); 8.718(1.2); 8.239(3.2); 8.234(3.8); 8.226(2.7); 8.183(2.6); 8.179(2.2); 8.161(4.0); 8.157(3.5); 8.086(5.4); 8.063(3.4); 4.651(0.7); 4.633(1.2); 4.613(1.2); 4.595(0.8); 3.950(2.0); 3.907(2.9); 3.903(3.0); 3.860(3.2); 3.544(3.1); 3.526(2.4); 3.501(2.6); 3.483(2.0); 3.329(122.0); 2.892(1.6); 2.733(1.3); 2.677(0.5); 2.673(0.6); 2.668(0.5); 2.526(2.1); 2.513(37.8); 2.508(73.4); 2.504(94.5); 2.499(67.9); 2.495(32.7); 2.335(0.4); 2.331(0.6); 2.326(0.4); 1.643(16.0); 1.617(12.3); 1.330(6.9); 1.312(6.9); 1.299(5.6); 1.281 (5.4); 1.233(0.5)
Example 346: ¹H-NMR(400.0 MHz, DMSO):
8.959(2.0); 8.953(2.5); 8.952(2.7); 8.946(2.3); 8.645(0.8); 8.625(0.9); 8.615(1.8); 8.611(2.2); 8.592(2.4); 8.588(1.9); 8.253(1.4); 8.249(1.5); 8.214(1.6); 8.209(1.8); 8.194(0.9); 8.189(0.8); 8.171(1.4); 8.169(1.5); 8.167(1.5); 8.147(1.5); 8.142(1.4); 8.086(1.6); 8.076(1.9); 8.063(1.1); 8.054(1.2); 7.954(0.6); 7.384(16.0); 7.327(0.5); 7.322(1.0); 7.316(0.5); 7.307(0.8); 7.300(4.9); 7.289(5.5); 7.282(0.8); 7.273(0.5); 7.267(1.0); 4.983(0.5); 4.965(0.7); 4.945(0.6); 4.937(0.6); 4.918(0.7); 4.899(0.5); 4.592(3.7); 4.585(4.0); 3.947(1.2); 3.904(1.4); 3.832(1.4); 3.789(1.7); 3.477(2.0); 3.434(1.7); 3.332(107.1); 2.892(5.1); 2.732(4.1); 2.673(0.4); 2.526(1.1); 2.521(1.8); 2.513(22.0); 2.508(44.0); 2.504(57.6); 2.499(40.9); 2.495(19.2); 2.330(0.4); 1.640(8.1); 1.567(6.8); 1.424(3.9); 1.406(3.9); 1.388(3.4); 1.370(3.3)
Example 347: ¹H-NMR(400.0 MHz, DMSO):
8.958(2.9); 8.952(5.0); 8.946(3.2); 8.614(2.1); 8.609(2.1); 8.600(2.4); 8.595(2.3); 8.252(2.1); 8.248(2.3); 8.232(2.4); 8.228(2.5); 8.184(1.2); 8.179(1.0); 8.162(1.8); 8.157(1.7); 8.146(1.3); 8.141(1.1); 8.123(2.1); 8.119(2.0); 8.083(2.3); 8.064(3.0); 8.042(1.7); 8.025(1.3); 8.002(1.5); 7.994(1.3); 7.971(1.7); 7.954(1.5); 7.628(0.3); 7.549(4.2); 7.473(4.5); 4.711(0.4); 4.695(1.0); 4.689(1.0); 4.673(1.7); 4.657(1.0); 4.651(0.9); 4.636(0.4); 4.592(5.1); 4.588(5.6); 4.019(0.4); 4.001(3.3); 3.983(3.3); 3.964(1.1); 3.946(1.2); 3.928(3.8); 3.910(6.1); 3.892(1.3); 3.869(2.8); 3.867(2.9); 3.504(2.0); 3.479(2.2); 3.461(1.7); 3.436(1.9); 3.328(105.4); 2.892(12.2); 2.733(9.9); 2.677(0.4); 2.672(0.6); 2.668(0.4); 2.526 (2.0); 2.512(36.3); 2.508(71.3); 2.503(92.9); 2.499(66.6); 2.494(31.6); 2.335(0.4); 2.330(0.6); 2.326(0.4); 2.080(14.1); 1.920(16.0); 1.817(0.4); 1.801(0.7); 1.780(1.0); 1.776(0.8); 1.760(1.3); 1.741(1.2); 1.730(0.9); 1.724(0.8); 1.712(1.2); 1.696(1.1); 1.691(0.9); 1.679(0.9); 1.655(11.4); 1.581(10.3); 1.339(4.1); 1.321(8.9); 1.303(4.0); 1.251(4.7); 1.233 (10.3); 1.215(4.5); 0.870(2.8); 0.852(6.2); 0.834(2.6); 0.754(2.4); 0.736(5.4); 0.717(2.2)
Example 348: ¹H-NMR(400.0 MHz, DMSO):
9.013(2.1); 9.006(4.0); 9.000(3.0); 8.780(1.6); 8.774(1.6); 8.756(2.1); 8.750(2.0); 8.653(0.8); 8.633(0.9); 8.619(1.2); 8.599(1.1); 8.238(1.4); 8.233(1.6); 8.199(2.5); 8.195(2.9); 8.178(1.6); 8.175(2.1); 8.153(2.0); 8.148(1.7); 8.092(1.7); 8.083(2.5); 8.070(1.2); 8.061(1.6); 7.959(1.6); 7.388(16.0); 7.352(0.8); 7.337(0.8); 7.327(1.2); 7.321(0.6); 7.311(1.0); 7.305(6.4); 7.294(7.0); 7.288(0.9); 7.278(0.6); 7.272(1.2); 4.988(1.7); 4.969(0.9); 4.950(0.8); 4.941(0.6); 4.922(0.7); 4.903(0.5); 3.944(1.2); 3.901(1.5); 3.829(1.8); 3.786(2.2); 3.474(2.7); 3.431(2.3); 3.335(145.3); 2.897(13.3); 2.738 (10.8); 2.682(0.4); 2.678(0.5); 2.673(0.4); 2.531(1.7); 2.526(2.7); 2.518(31.0); 2.513(61.2); 2.509(79.9); 2.504(56.9); 2.500(26.8); 2.340(0.4); 2.335(0.5); 2.331(0.4); 1.646(10.7); 1.572(7.7); 1.561(0.6); 1.428(5.1); 1.411(5.1); 1.393 (3.6); 1.375(3.5); 1.239(0.4); 1.205(0.6)
Example 349: ¹H-NMR(400.0 MHz, DMSO):
8.965(2.1); 8.960(2.4); 8.956(3.0); 8.951(2.9); 8.796(0.9); 8.776(1.0); 8.759(1.2); 8.738(1.2); 8.627(1.7); 8.622(1.6); 8.596(2.3); 8.591(2.2); 8.261(1.7); 8.257(1.8); 8.215(2.2); 8.211(2.6); 8.204(1.1); 8.200(0.9); 8.188(1.5); 8.183(2.2); 8.177(1.3); 8.166(2.0); 8.161(1.7); 8.094(1.9); 8.087(2.6); 8.072(1.3); 8.065(1.7); 7.959(2.1); 7.573(0.9); 7.569(0.9); 7.554(1.1); 7.550(1.0); 7.426(1.2); 7.418(1.9); 7.415(2.1); 7.409(0.8); 7.402(1.6); 7.398(1.5); 7.395(1.6); 7.379(0.6); 7.376(0.6); 7.360(1.4); 7.351(1.4); 7.345(1.0); 7.339(1.7); 7.328(1.7); 7.288(0.9); 7.284(0.8); 7.269(1.0); 7.265(0.9); 7.250(0.5); 7.246(0.4); 7.198(0.4); 7.186(2.9); 7.179(1.5); 7.174(2.1); 7.169(1.4); 7.162(2.3); 5.284(0.9); 5.266(1.3); 5.247(1.1); 5.233(1.0); 5.215(0.6); 4.597(3.8); 4.589(5.1); 3.968(1.4); 3.925(1.6); 3.815(1.8); 3.772(2.3); 3.484(3.7); 3.441(3.1); 3.335(127.6); 2.897(16.0); 2.738(13.8); 2.682(0.4); 2.678(0.5); 2.673(0.4); 2.531(1.6); 2.517(31.6); 2.513(61.4); 2.508(79.0); 2.504(56.7); 2.500(27.1); 2.340(0.4); 2.335(0.5); 2.331(0.4); 1.663(11.1); 1.586(8.0); 1.417(5.7); 1.399(5.7); 1.382(4.3); 1.364(4.2); 1.238(0.5)
Example 350: ¹H-NMR(400.0 MHz, DMSO):
8.965(3.7); 8.959(3.9); 8.955(4.2); 8.950(4.2); 8.623(2.9); 8.618(2.8); 8.596(3.3); 8.591(3.2); 8.570(1.6); 8.550(1.8); 8.538(1.8); 8.517(1.8); 8.262(2.8); 8.257(3.1); 8.224(3.2); 8.220(3.6); 8.203(1.6); 8.198(1.4); 8.180(2.7); 8.177(3.3); 8.156(2.7); 8.151(2.5); 8.092(3.1); 8.080(3.7); 8.070(2.2); 8.058(2.3); 7.378(1.3); 7.374(1.9); 7.357(4.8); 7.344(3.7); 7.326(4.2); 7.307(1.8); 7.295(2.1); 7.292(3.0); 7.273(5.0); 7.248(0.9); 7.245(1.6); 7.238(3.1); 7.233(1.6); 7.227(2.2);

-continued

NMR Peak Lists Table 1

7.220(5.3); 7.210(1.0); 7.200(2.5); 7.160(1.8); 7.147(0.7); 7.142(2.3); 7.136(0.5); 7.124(0.7); 5.000(1.1); 4.981(1.5); 4.962(1.3); 4.939(1.4); 4.920(1.0); 4.597(7.2); 4.590(8.0); 3.961(2.3); 3.918(2.7); 3.859(2.7); 3.816(3.3); 3.486(5.8); 3.443(4.9); 3.337(144.1); 3.336(147.4); 3.313(0.5); 2.897(1.4); 2.738(1.2); 2.683(0.5); 2.678(0.6); 2.674(0.5); 2.518(38.7); 2.513(74.9); 2.509(97.4); 2.504(70.9); 2.500(34.8); 2.340(0.5); 2.335(0.6); 2.331(0.5); 1.660(16.0); 1.581(13.9); 1.441(8.2); 1.423(8.2); 1.405(7.2); 1.388(7.1); 1.238(0.5)

Example 351: $^1$H-NMR(300.2 MHz, CDCl3):
8.974(3.2); 8.968(4.6); 8.962(3.1); 8.288(2.2); 8.282(2.2); 8.273(2.3); 8.267(2.1); 8.186(1.0); 8.179(0.9); 8.156(2.4); 8.150(2.7); 8.142(0.8); 8.118(5.1); 8.113(3.5); 8.100(3.4); 8.088(1.3); 8.071(0.8); 7.857(2.3); 7.852(2.3); 7.827(2.2); 7.822(2.1); 7.265(22.3); 7.254(4.2); 7.197(3.8); 6.914(0.4); 6.905(0.8); 6.877(1.0); 6.864(1.0); 6.835(0.9); 5.061(0.8); 5.032(1.3); 5.009(1.3); 4.981(0.8); 4.122(1.2); 4.097(3.7); 4.073(3.9); 4.049(1.3); 4.032(1.3); 4.017(2.6); 4.008(3.8); 3.983(3.8); 3.970(2.6); 3.960(4.0); 3.913(2.8); 3.368(5.0); 3.332(6.1); 3.326(5.9); 3.311(4.3); 2.242(16.0); 2.046(15.5); 1.786(13.2); 1.754(13.8); 1.657(13.5); 1.507(6.3); 1.497(5.4); 1.484(6.4); 1.472(10.8); 1.448(5.2); 1.439(6.6); 1.416 (6.5); 1.406(5.2); 1.382(10.0); 1.357(4.6); 1.260(0.5); 1.254(0.5); 0.011(0.6); 0.009(0.3); 0.000(17.9); −0.011(0.8)

Example 352: $^1$H-NMR(400.0 MHz, DMSO):
8.957(5.3); 8.952(5.4); 8.737(1.2); 8.717(1.2); 8.678(1.0); 8.658(1.0); 8.610(3.2); 8.246(2.0); 8.242(3.9); 8.237(2.4); 8.177(1.1); 8.172(0.9); 8.161(1.3); 8.155(2.4); 8.150(1.5); 8.139(1.4); 8.134(1.8); 8.079(3.5); 8.057(2.1); 5.022(0.9); 5.002(1.5); 4.984(1.6); 4.965(0.8); 4.592(8.2); 4.325(1.2); 4.307(4.0); 4.289(4.0); 4.281(0.6); 4.271(1.3); 4.263(0.5); 3.940(3.1); 3.897(3.6); 3.515(2.6); 3.472(2.1); 3.470(2.0); 3.330(32.5); 3.304(14.9); 3.262(15.8); 3.076(14.1); 2.924(16.0); 2.892(0.9); 2.733(0.7); 2.677(0.4); 2.672(0.5); 2.668(0.4); 2.537(0.4); 2.526(1.7); 2.521(2.6); 2.512 (32.3); 2.508(65.2); 2.503(85.7); 2.499(61.0); 2.494(28.7); 2.335(0.4); 2.330(0.6); 2.325(0.4); 1.633(10.4); 1.615(8.6); 1.411(5.5); 1.394(5.4); 1.373(4.8); 1.356(4.7); 1.295(4.3); 1.282(0.9); 1.277(9.0); 1.264(1.4); 1.259(4.3); 1.246(0.7); 1.234(0.5)

Example 353: $^1$H-NMR(400.0 MHz, DMSO):
9.004(3.2); 8.998(3.4); 8.763(2.2); 8.758(2.1); 8.295(0.6); 8.281(1.1); 8.266(0.6); 8.212(2.2); 8.208(2.5); 8.172(1.5); 8.167(1.1); 8.150(2.2); 8.145(1.9); 8.077(2.6); 8.055(1.6); 7.954(2.0); 3.869(2.1); 3.825(2.5); 3.503(2.4); 3.459(2.0); 3.328(59.7); 3.278(0.4); 3.263(0.7); 3.246(1.1); 3.230(1.2); 3.211(1.2); 3.196(1.1); 3.178(0.8); 3.164(0.4); 2.892 (16.0); 2.770(1.3); 2.763(3.0); 2.757(1.4); 2.733(13.2); 2.732(12.7); 2.526(1.0); 2.521(1.5); 2.512(16.9); 2.508(34.0); 2.503(44.6); 2.499(32.0); 2.494(15.1); 2.347(1.2); 2.340(1.3); 2.329(2.7); 2.322(2.6); 2.311(1.2); 2.304(1.1); 1.609(12.4)

Example 354: $^1$H-NMR(400.0 MHz, DMSO):
9.330(1.1); 9.307(1.2); 9.265(1.4); 9.241(1.4); 8.970(2.6); 8.964(2.7); 8.949(3.2); 8.943(3.2); 8.630(2.0); 8.625(2.0); 8.595(2.4); 8.590(2.3); 8.288(2.0); 8.283(2.1); 8.228(2.5); 8.224(2.6); 8.211(1.3); 8.206(1.1); 8.189(1.7); 8.184(1.6); 8.145(1.3); 8.140(1.1); 8.123(2.1); 8.118(2.0); 8.100(2.1); 8.077(1.5); 8.057(2.6); 8.035(1.6); 7.958(2.0); 7.512(1.8); 7.495(1.0); 7.475(1.1); 7.449(3.5); 7.430(1.4); 7.382(0.5); 7.375(0.4); 7.361(0.6); 7.350(0.4); 7.338(1.7); 7.319(2.0); 7.300(2.1); 7.283(2.1); 7.272(1.2); 7.262(1.3); 7.241(1.4); 7.222(1.6); 7.199(1.8); 7.180(1.1); 5.800(1.0); 5.777(1.5); 5.755(1.1); 4.599(4.8); 4.587(5.7); 4.013(1.6); 3.980(2.1); 3.970(2.0); 3.936(2.3); 3.561(1.9); 3.536(2.3); 3.518(1.7); 3.493(2.0); 3.340(248.5); 2.897(16.0); 2.738(13.5); 2.723(0.3); 2.682(0.5); 2.678(0.7); 2.673(0.5); 2.518(42.2); 2.513(79.9); 2.509(102.4); 2.504(74.7); 2.500(38.1); 2.359(2.5); 2.340(9.8); 2.308(2.2); 2.281(11.2); 1.707(11.3); 1.616(9.3); 1.293(0.7); 1.238(0.4)

Example 355: $^1$H-NMR(400.0 MHz, DMSO):
8.961(3.9); 8.955(4.0); 8.611(3.1); 8.606(3.0); 8.300(0.8); 8.285(1.6); 8.270(0.8); 8.239(3.1); 8.235(3.4); 8.176(1.7); 8.172(1.5); 8.154(2.7); 8.150(2.5); 8.082(3.5); 8.060(2.2); 7.634(0.5); 7.631(0.4); 7.622(0.4); 7.605(0.4); 7.574(0.3); 4.597(7.1); 3.884(2.7); 3.841(3.3); 3.517(3.1); 3.474(2.6); 3.335(48.8); 3.286(0.5); 3.270(0.9); 3.253(1.5); 3.237(1.6); 3.218(1.6); 3.203(1.5); 3.185(1.0); 3.171(0.5); 2.778(1.7); 2.772(3.8); 2.765(1.8); 2.532(0.8); 2.519(17.2); 2.515 (34.4); 2.510(45.2); 2.505(32.7); 2.501(15.8); 2.354(1.6); 2.347(1.7); 2.336(3.6); 2.329(3.4); 2.318(1.6); 2.311 (1.4); 1.615(16.0)

Example 356: $^1$H-NMR(400.0 MHz, DMSO):
9.750(1.8); 9.729(1.9); 9.681(2.0); 9.660(2.0); 9.019(4.1); 9.013(6.9); 9.006(4.6); 8.780(3.1); 8.775(3.2); 8.769(3.4); 8.763(3.1); 8.252(3.0); 8.248(3.4); 8.237(3.3); 8.232(3.6); 8.205(1.4); 8.200(1.5); 8.183(2.7); 8.178(2.7); 8.175(2.2); 8.170(1.6); 8.153(2.8); 8.148(2.6); 8.102(3.4); 8.085(3.8); 8.080(2.4); 8.063(2.3); 7.958(0.8); 7.490(1.5); 7.486(2.1); 7.466(4.4); 7.458(2.5); 7.453(2.6); 7.449(2.9); 7.438(5.5); 7.432(5.6); 7.428(3.4); 7.424(2.7); 7.418(2.0); 7.413(3.4); 7.408(6.0); 7.403(3.5); 7.398(1.5); 7.393(2.0); 7.386(3.6); 7.381(2.7); 7.377(1.5); 7.372(0.9); 7.364(1.9); 7.355(0.3); 7.350(0.3); 7.347(0.4); 6.243(2.6); 6.221(4.1); 6.200(2.7); 3.945(2.8); 3.939(2.9); 3.901(3.4); 3.895(3.5); 3.574(3.4); 3.569(3.5); 3.531(2.8); 3.526(2.9); 3.339(262.9); 3.301(0.4); 2.897(6.0); 2.737(4.9); 2.682(0.6); 2.678(0.8); 2.673 (0.6); 2.531(2.7); 2.518(47.5); 2.513(93.1); 2.509(120.7); 2.504(86.4); 2.500(41.1); 2.340(0.6); 2.335(0.8); 2.331 (0.6); 1.669(16.0); 1.627(15.2); 1.239(0.5)

Example 357: $^1$H-NMR(400.0 MHz, DMSO):
9.498(0.9); 9.473(0.9); 9.440(1.1); 9.416(1.1); 8.966(2.1); 8.961(2.2); 8.946(2.6); 8.941(2.7); 8.626(1.6); 8.621(1.5); 8.594(1.9); 8.589(1.8); 8.287(1.5); 8.282(1.6); 8.229(1.9); 8.224(2.1); 8.208(0.8); 8.203(0.8); 8.186(1.3); 8.181(1.2); 8.147(1.1); 8.142(0.9); 8.124(1.7); 8.120(1.6); 8.095(1.7); 8.073(1.2); 8.056(2.2); 8.033(1.4); 7.954(1.9); 7.921(1.4); 7.877(1.8); 7.687(0.7); 7.669(0.9); 7.644(0.9); 7.627(1.1); 7.610(0.4); 7.528(0.5); 7.525(0.6); 7.519(0.6); 7.514(1.1); 7.505(0.5); 7.494(1.4); 7.490(2.1); 7.484(2.1); 7.476(1.1); 7.470(0.8); 7.465(1.8); 7.460(1.8); 7.455(2.3); 7.449(2.3); 7.431(1.8); 7.411(0.6); 5.962(0.5); 5.953(0.5); 5.940(0.8); 5.931(0.7); 5.917(0.6); 5.908(0.5); 4.595(3.6); 4.584(4.4); 4.013(1.3); 3.984(1.6); 3.969(1.5); 3.941(1.9); 3.564(1.5); 3.539(1.9); 3.520(1.3); 3.496(1.6); 3.365(0.4); 3.334 (196.0); 2.892(16.0); 2.733(12.8); 2.678(0.4); 2.673(0.6); 2.669(0.4); 2.527(1.5); 2.522(2.5); 2.513(33.5); 2.509 (67.2); 2.504(88.0); 2.500(62.7); 2.495(29.4); 2.336(0.4); 2.331(0.5); 2.326(0.4); 1.699(9.4); 1.620(7.3); 1.233(0.4)

Example 358: $^1$H-NMR(400.0 MHz, DMSO):
9.329(1.1); 9.305(1.2); 9.264(1.3); 9.240(1.4); 9.014(3.0); 9.008(3.2); 8.993(3.6); 8.987(3.7); 8.784(2.1); 8.778(2.0); 8.750(2.5); 8.744(2.4); 8.263(2.1); 8.258(2.3); 8.208(1.6); 8.203(3.6); 8.198(2.8); 8.186(1.9); 8.181(1.7); 8.142(1.5); 8.137(1.2); 8.120(2.3); 8.115(2.2); 8.096(1.3); 8.074(1.6); 8.054(2.9); 8.032(1.7); 7.954(1.6); 7.506(1.8); 7.489(0.9); 7.469(1.1); 7.444(3.5); 7.425(1.3); 7.333(1.0); 7.314(2.1); 7.295(2.0); 7.278(1.9); 7.258(1.1); 7.236(1.3); 7.217(0.9); 7.195(1.6); 7.176(1.0); 5.794(1.0); 5.772(1.5); 5.750(1.0); 4.000(1.8); 3.967(2.2); 3.957(2.2); 3.924(2.5); 3.548(2.1); 3.523(2.5); 3.505(1.9); 3.480(2.2); 3.335(270.2); 3.312(1.0); 2.892(16.0); 2.733(12.5); 2.732(12.6); 2.677(0.5); 2.673(0.7); 2.668(0.5); 2.526(2.0); 2.521(3.2); 2.513(40.7); 2.508(81.8); 2.504(107.2); 2.499(76.0); 2.495(35.6); 2.335(10.4); 2.277(11.9); 1.703(12.6); 1.613(10.6); 1.288(0.8); 1.233(0.4)

-continued

NMR Peak Lists Table 1

Example 359: $^1$H-NMR(400.0 MHz, DMSO):
8.969(3.8); 8.963(4.0); 8.959(3.3); 8.953(3.3); 8.610(5.3); 8.605(5.1); 8.227(2.4); 8.223(2.7); 8.175(1.4); 8.170(1.1);
8.153(2.1); 8.148(2.0); 8.135(1.0); 8.130(1.3); 8.118(1.7); 8.113(2.7); 8.108(4.4); 8.100(5.8); 8.088(4.5); 8.083(3.7);
8.067(1.5); 8.060(1.8); 7.958(0.4); 7.156(1.9); 7.138(2.8); 7.135(2.9); 7.116(2.2); 6.933(2.0); 6.914(3.1); 6.912(3.2);
6.893(2.4); 6.725(3.1); 6.705(2.9); 6.583(3.9); 6.562(4.7); 6.543(0.9); 6.206(1.1); 6.187(2.1); 6.170(1.0); 4.601(7.0);
4.593(5.9); 3.832(1.9); 3.789(2.3); 3.739(0.4); 3.714(0.9); 3.698(1.0); 3.674(1.1); 3.652(1.0); 3.638(1.0); 3.617(0.9);
3.476(0.4); 3.464(0.7); 3.453(1.0); 3.442(2.1); 3.428(3.7); 3.409(2.4); 3.395(2.3); 3.384(2.7); 3.378(1.4); 3.363(2.1);
3.339(275.3); 3.324(5.4); 3.280(0.7); 2.938(0.6); 2.919(1.1); 2.900(14.2); 2.789(16.0); 2.738(2.8); 2.682(0.6); 2.678
(0.7); 2.673(0.5); 2.531(2.2); 2.517(43.8); 2.513(85.7); 2.508(110.8); 2.504(79.4); 2.500(37.8); 2.340(0.5); 2.335(0.7);
2.331(0.5); 1.545(13.5); 1.386(11.2); 1.238(0.6); 1.114(0.4); 1.103(0.7); 1.092(0.7); 1.082(0.8); 1.071(0.5); 1.061(0.5);
1.056(0.5); 1.044(0.7); 1.033(0.6); 1.023(0.7); 1.012(0.4); 0.509(0.5); 0.488(1.0); 0.466(0.7); 0.439(0.5); 0.436(0.5);
0.412(1.3); 0.398(0.9); 0.388(1.3); 0.363(0.5); 0.287(0.6); 0.263(0.9); 0.240(0.5); 0.237(0.5); 0.223(0.3); 0.201(2.5);
0.105(1.7); 0.098(2.2)
Example 360: $^1$H-NMR(400.0 MHz, DMSO):
9.504(1.0); 9.480(1.1); 9.446(1.3); 9.422(1.3); 9.020(2.5); 9.014(2.6); 9.000(3.0); 8.994(3.2); 8.789(1.8); 8.783(1.7);
8.758(2.2); 8.752(2.1); 8.271(1.8); 8.266(2.0); 8.213(3.1); 8.209(3.2); 8.192(1.6); 8.187(1.5); 8.153(1.3); 8.148(1.1);
8.131(2.0); 8.126(1.8); 8.102(2.0); 8.080(1.4); 8.062(2.5); 8.040(1.6); 7.959(2.0); 7.924(1.7); 7.881(2.0); 7.691(0.8);
7.673(1.0); 7.649(1.0); 7.632(1.2); 7.515(0.5); 7.510(0.4); 7.499(1.3); 7.495(2.0); 7.489(2.2); 7.481(0.8); 7.476(0.6);
7.470(1.7); 7.465(1.7); 7.460(2.5); 7.454(2.5); 7.436(1.9); 7.416(0.6); 5.966(0.6); 5.957(0.6); 5.945(0.9); 5.935(0.9);
5.922(0.7); 5.912(0.6); 4.008(1.5); 3.982(1.8); 3.965(1.8); 3.938(2.2); 3.790(2.4); 3.536(2.1); 3.517(1.5); 3.492(1.9);
3.339(216.7); 3.307(0.4); 2.897(16.0); 2.738(12.9); 2.737(13.3); 2.682(0.5); 2.678(0.6); 2.673(0.4); 2.531(1.8);
2.518(35.6); 2.513(72.0); 2.509(94.7); 2.504(68.7); 2.500(33.1); 2.340(0.5); 2.335(0.6); 2.331(0.4); 1.705(10.7);
1.626(8.8); 1.238(0.4)
Example 361: $^1$H-NMR(400.0 MHz, DMSO):
8.958(3.9); 8.952(6.9); 8.947(3.4); 8.614(2.9); 8.608(4.9); 8.603(2.5); 8.253(2.8); 8.249(3.1); 8.229(2.3); 8.224(2.6);
8.188(7.1); 8.182(1.7); 8.171(1.5); 8.165(3.2); 8.160(2.4); 8.149(2.2); 8.144(2.0); 8.084(3.2); 8.075(2.8); 8.062(2.2);
8.053(1.8); 7.954(2.0); 7.832(1.4); 7.811(1.7); 7.794(1.2); 4.591(9.9); 3.882(2.5); 3.839(3.2); 3.830(2.3); 3.787(2.7);
3.505(5.2); 3.498(5.8); 3.462(6.3); 3.454(6.9); 3.426(5.5); 3.413(5.6); 3.404(5.3); 3.395(5.6); 3.392(5.7); 3.383(5.4);
3.371(5.0); 3.352(4.2); 3.341(3.8); 3.331(3.4); 3.320(3.1); 3.309(2.5); 3.298(2.2); 3.087(0.4); 3.076(0.4); 3.062(0.4);
3.038(0.3); 2.892(16.0); 2.839(1.1); 2.816(1.1); 2.809(1.3); 2.786(1.2); 2.733(13.0); 2.720(0.9); 2.697(0.9); 2.689(1.2);
2.683(0.4); 2.678(0.7); 2.673(0.9); 2.667(1.3); 2.552(1.0); 2.540(1.3); 2.526(2.6); 2.521(4.8); 2.513(46.6); 2.508(93.0);
2.504(121.4); 2.499(87.5); 2.495(43.1); 2.474(2.6); 2.455(2.3); 2.438(1.7); 2.382(1.2); 2.375(1.2); 2.360(1.8); 2.349
(0.9); 2.341(0.8); 2.335(0.9); 2.331(1.1); 2.326(0.8); 2.322(0.5); 2.296(0.8); 2.285(1.7); 2.270(1.2); 2.263(1.1);
1.674(0.4); 1.657(2.4); 1.641(5.2); 1.632(14.2); 1.600(14.5); 1.574(0.4); 1.399(0.4); 1.381(1.8); 1.373(2.1); 1.365(3.3);
1.357(2.1); 1.349(1.7); 1.331(0.4); 1.233(0.6); 0.991(0.4); 0.979(0.8); 0.971(0.6); 0.967(0.6); 0.959(0.9); 0.951(0.6);
0.943(0.7); 0.939(0.7); 0.931(1.0); 0.923(0.7); 0.919(0.8); 0.911(1.1); 0.898(0.6); 0.890(0.4); 0.447(0.3); 0.439(0.6);
0.426(0.7); 0.416(0.7); 0.404(0.5); 0.393(0.5); 0.382(0.4); 0.378(0.4); 0.369(0.8); 0.361(0.9); 0.356(1.0); 0.349(1.2);
0.340(1.1); 0.335(0.9); 0.319(0.7); 0.311(0.3); 0.307(0.3); 0.297(0.4); 0.292(0.4); 0.279(0.6); 0.269(0.8); 0.256(1.0);
0.245(0.8); 0.240(0.8); 0.236(0.7); 0.226(0.8); 0.216(0.8); 0.205(0.9); 0.193(0.8); 0.183(1.0); 0.170(1.2); 0.164(1.3);
0.157(1.4); 0.152(1.1); 0.147(1.1); 0.134(0.5); 0.111(0.5); 0.098(0.9); 0.088(1.1); 0.075(0.9); 0.065(0.5)
Example 362: $^1$H-NMR(400.0 MHz, DMSO):
9.012(3.8); 9.006(4.1); 9.003(1.9); 8.997(1.6); 8.765(3.6); 8.759(3.5); 8.203(1.0); 8.198(1.3); 8.171(0.7); 8.167(0.5);
8.149(1.1); 8.144(0.9); 8.129(1.0); 8.125(1.1); 8.114(1.5); 8.107(2.9); 8.102(3.9); 8.091(1.9); 8.085(4.5); 8.079(4.9);
8.063(1.4); 8.057(0.9); 7.953(0.7); 7.150(0.8); 7.132(1.2); 7.129(1.3); 7.110(1.0); 6.928(2.0); 6.910(2.9); 6.906(3.1);
6.888(2.4); 6.719(1.4); 6.699(1.2); 6.578(3.5); 6.556(3.6); 6.537(0.4); 6.200(1.1); 6.182(2.1); 6.164(1.0); 3.819(0.9);
3.775(1.1); 3.708(0.4); 3.692(0.5); 3.668(0.8); 3.647(0.9); 3.633(0.9); 3.612(0.8); 3.459(0.5); 3.448(0.7); 3.437(1.3);
3.426(1.5); 3.414(1.8); 3.403(1.7); 3.389(1.7); 3.381(1.0); 3.371(1.6); 3.363(1.7); 3.358(2.0); 3.332(241.8); 3.320(6.1);
3.307(4.3); 3.264(0.7); 2.894(7.0); 2.892(7.6); 2.782(16.0); 2.732(4.5); 2.677(0.5); 2.672(0.7); 2.668(0.6); 2.525(2.2);
2.512(42.6); 2.508(85.8); 2.503(112.9); 2.499(81.0); 2.494(38.4); 2.334(0.5); 2.330(0.7); 2.325(0.5); 1.540(13.5);
1.382(5.3); 1.233(0.8); 1.109(0.4); 1.098(0.7); 1.086(0.6); 1.076(0.7); 1.064(0.5); 1.056(0.7); 1.038(0.3); 0.504(0.4);
0.484(0.9); 0.461(0.6); 0.407(0.8); 0.380(1.0); 0.357(0.5); 0.256(0.4); 0.230(0.4); 0.195(2.4); 0.188(1.9); 0.092(0.9)
Example 363: $^1$H-NMR(400.0 MHz, DMSO):
8.953(1.7); 8.948(1.7); 8.605(1.2); 8.600(1.1); 8.298(0.6); 8.236(1.2); 8.232(1.3); 8.212(0.7); 8.174(0.7); 8.169(0.6);
8.152(1.1); 8.147(1.0); 8.076(1.3); 8.054(0.9); 4.589(2.9); 3.879(1.1); 3.835(1.3); 3.529(0.4); 3.488(1.8); 3.445(2.3);
3.413(1.7); 3.390(1.5); 3.148(0.5); 3.131(1.1); 3.116(1.1); 3.099(0.5); 2.526(0.4); 2.522(0.7); 2.513(9.3); 2.508(18.8);
2.504(24.7); 2.499(17.7); 2.495(8.3); 2.233(0.8); 2.215(1.7); 2.198(1.0); 2.101(16.0); 1.607(6.2); 1.591(0.3);
1.574(0.9); 1.556(1.2); 1.539(0.8)
Example 364: $^1$H-NMR(400.0 MHz, DMSO):
9.007(3.6); 9.001(7.2); 8.996(3.9); 8.772(2.9); 8.768(4.9); 8.763(2.9); 8.233(2.4); 8.229(2.7); 8.209(2.6); 8.204(3.0);
8.188(1.7); 8.181(7.9); 8.173(1.9); 8.166(2.5); 8.161(2.1); 8.151(2.5); 8.146(2.2); 8.086(2.8); 8.078(3.2); 8.064(1.9);
8.056(2.0); 7.953(1.2); 7.836(1.2); 7.821(1.5); 7.814(1.4); 7.799(1.3); 3.873(2.3); 3.830(2.8); 3.820(2.6); 3.777(3.1);
3.739(0.4); 3.717(0.4); 3.498(5.5); 3.490(5.5); 3.455(7.0); 3.447(7.3); 3.403(7.7); 3.396(7.7); 3.392(7.7); 3.383(7.4);
3.371(7.0); 3.352(5.9); 3.341(5.3); 3.331(4.7); 3.319(4.1); 3.297(2.8); 3.062(0.4); 3.049(0.3); 3.040(0.4); 2.892(10.5);
2.840(0.9); 2.817(1.0); 2.810(1.2); 2.787(1.0); 2.749(0.4); 2.732(8.3); 2.721(1.0); 2.698(1.0); 2.690(1.3); 2.682(0.5);
2.677(0.8); 2.673(1.1); 2.668(1.7); 2.553(1.1); 2.541(1.3); 2.526(3.3); 2.521(5.1); 2.513(51.2); 2.508(101.4); 2.504
(132.1); 2.499(95.0); 2.494(45.8); 2.476(2.3); 2.457(1.8); 2.452(1.6); 2.439(1.3); 2.383(1.2); 2.377(1.5); 2.361(1.9);
2.350(0.9); 2.335(0.9); 2.330(1.0); 2.326(0.8); 2.321(0.5); 2.297(0.8); 2.286(1.8); 2.271(1.3); 2.265(1.2); 1.657(2.1);
1.641(4.5); 1.632(16.0); 1.601(12.8); 1.400(0.4); 1.382(2.1); 1.374(2.4); 1.367(3.9); 1.358(2.4); 1.350(2.0); 1.333(0.4);
1.233(0.6); 0.999(0.3); 0.991(0.5); 0.979(0.9); 0.967(0.6); 0.958(0.9); 0.950(0.6); 0.946(0.7); 0.938(0.7); 0.930(0.9);
0.922(0.6); 0.918(0.7); 0.910(0.9); 0.898(0.5); 0.890(0.3); 0.447(0.4); 0.439(0.7); 0.426(0.8); 0.416(0.8); 0.408(0.5);
0.404(0.5); 0.394(0.5); 0.382(0.4); 0.378(0.4); 0.369(0.7); 0.361(0.8); 0.353(0.9); 0.349(1.1); 0.340(1.1); 0.330(0.9);
0.319(0.8); 0.311(0.4); 0.307(0.4); 0.297(0.4); 0.292(0.4); 0.278(0.6); 0.269(0.9); 0.256(1.1); 0.245(0.8); 0.235(0.6);
0.225(0.7); 0.217(0.7); 0.204(0.7); 0.192(0.6); 0.187(0.6); 0.177(1.1); 0.169(1.1); 0.164(1.4); 0.155(1.4); 0.142(1.0);
0.132(0.4); 0.110(0.4); 0.098(0.8); 0.087(0.9); 0.074(0.8); 0.064(0.4)
Example 365: $^1$H-NMR(300.2 MHz, CDCl3):
8.968(4.1); 8.961(4.1); 8.278(3.2); 8.272(3.1); 8.190(1.4); 8.183(1.5); 8.160(3.1); 8.154(3.2); 8.111(3.5); 8.082(1.6);
7.845(3.2); 7.267(7.7); 7.007(0.7); 6.993(0.8); 6.980(0.8); 6.967(0.7); 5.302(1.1); 4.157(0.5); 4.150(0.4); 4.140(0.7);

NMR Peak Lists Table 1

4.134(0.8); 4.129(0.7); 4.118(0.8); 4.112(0.8); 4.106(0.7); 4.096(0.5); 4.090(0.6); 3.982(1.9); 3.977(2.2); 3.924(2.3); 3.920(2.6); 3.390(2.5); 3.381(14.1); 3.371(2.7); 3.359(4.0); 3.329(8.6); 3.309(3.7); 3.302(3.8); 3.281(16.0); 1.766 (11.4); 1.761(12.7); 1.686(1.5); 1.237(6.0); 1.214(6.0); 1.170(5.2); 1.148(5.2); 0.000(6.2); −0.011(0.4)
Example 366: $^1$H-NMR(400.0 MHz, DMSO):
8.956(2.2); 8.950(2.2); 8.608(1.6); 8.603(1.5); 8.241(1.6); 8.237(1.7); 8.173(1.0); 8.168(0.8); 8.151(1.5); 8.146(1.3); 8.114(0.4); 8.100(0.8); 8.078(1.9); 8.056(1.1); 4.591(3.8); 4.457(0.8); 4.443(2.0); 4.429(0.8); 3.874(1.4); 3.831(1.7); 3.519(1.6); 3.476(1.3); 3.334(62.3); 3.223(16.0); 3.220(15.9); 3.213(1.2); 3.205(1.5); 3.198(1.4); 3.191(0.8); 3.184 (0.8); 2.892(1.4); 2.733(1.1); 2.732(1.1); 2.526(0.6); 2.513(10.7); 2.509(20.8); 2.504(26.8); 2.499(19.0); 2.495(8.8); 1.613(8.2)
Example 367: $^1$H-NMR(400.0 MHz, DMSO):
8.953(4.7); 8.951(5.3); 8.948(5.0); 8.946(5.0); 8.609(5.5); 8.604(5.3); 8.239(5.5); 8.175(3.0); 8.171(2.5); 8.153(4.4); 8.148(4.1); 8.075(6.2); 8.053(4.0); 7.841(1.4); 7.819(1.5); 7.806(1.5); 7.784(1.5); 4.589(7.1); 4.586(7.7); 3.906(2.4); 3.880(2.7); 3.862(2.8); 3.837(3.3); 3.810(1.0); 3.803(0.8); 3.793(1.3); 3.777(1.0); 3.758(0.5); 3.484(3.0); 3.468(2.7); 3.441(2.6); 3.424(2.4); 3.332(194.9); 2.678(0.5); 2.673(0.7); 2.669(0.5); 2.526(2.0); 2.522(3.1); 2.513(38.6); 2.509 (78.2); 2.504(103.2); 2.499(73.9); 2.495(34.9); 2.335(0.5); 2.331(0.6); 2.326(0.5); 1.621(16.0); 1.602(14.0); 1.529 (0.4); 1.507(0.5); 1.493(0.6); 1.481(0.4); 1.473(0.4); 1.387(1.0); 1.379(1.0); 1.371(1.0); 1.366(1.0); 1.348(1.0); 1.334(0.9); 1.314(0.6); 1.299(0.5); 1.288(0.7); 1.280(0.8); 1.231(6.4); 1.120(0.4); 1.101(0.7); 1.071(9.4); 1.054 (9.7); 1.030(8.6); 1.013(7.9); 1.001(0.9); 0.995(0.7); 0.980(1.3); 0.963(2.0); 0.954(1.3); 0.946(2.2); 0.932(2.3); 0.922(1.4); 0.916(1.4); 0.904(0.7); 0.895(0.6); 0.862(2.4); 0.845(7.4); 0.828(2.8); 0.556(3.8); 0.538(9.0); 0.521(4.1)
Example 368: $^1$H-NMR(300.2 MHz, CDCl3):
8.941(3.2); 8.933(3.3); 8.322(2.4); 8.314(2.3); 8.178(1.1); 8.172(1.1); 8.148(2.5); 8.142(2.6); 8.101(3.0); 8.071(1.3); 7.811(2.6); 7.805(2.6); 7.267(7.1); 6.806(0.7); 6.780(0.7); 4.204(0.5); 4.181(1.0); 4.157(1.0); 4.134(0.6); 3.976(2.7); 3.919(3.2); 3.344(3.0); 3.287(2.6); 2.050(0.4); 2.033(0.5); 2.011(0.8); 2.000(0.4); 1.986(0.8); 1.968(0.8); 1.944(0.6); 1.931(0.4); 1.924(0.4); 1.757(16.0); 1.735(0.6); 1.707(0.9); 1.683(1.2); 1.669(5.5); 1.648(0.9); 1.638(1.1); 1.633(1.2); 1.623(0.9); 1.611(1.4); 1.598(0.9); 1.587(0.8); 1.582(0.9); 1.554(0.5); 1.480(0.5); 1.476(0.5); 1.459(0.6); 1.456(0.6); 1.437(0.6); 1.416(0.6); 1.398(0.6); 1.375(0.6); 1.352(0.5); 1.333(0.4); 0.000(4.9)
Example 369: $^1$H-NMR(400.0 MHz, DMSO):
8.958(5.0); 8.952(5.1); 8.613(4.5); 8.609(4.3); 8.244(4.5); 8.182(2.5); 8.177(2.1); 8.160(3.7); 8.155(3.4); 8.081(5.1); 8.059(3.3); 7.853(1.2); 7.831(1.3); 7.822(1.3); 7.800(1.2); 4.594(10.9); 3.911(1.9); 3.887(2.1); 3.868(2.3); 3.844(2.5); 3.803(0.4); 3.788(0.8); 3.781(0.7); 3.772(1.0); 3.767(1.0); 3.758(0.7); 3.750(0.8); 3.736(0.4); 3.487(2.5); 3.473(2.2); 3.444(2.1); 3.430(1.9); 3.337(154.6); 3.310(0.4); 2.897(1.3); 2.738(1.0); 2.682(0.4); 2.678(0.5); 2.673(0.4); 2.531(1.8); 2.518(31.7); 2.513(62.1); 2.509(80.3); 2.504(57.5); 2.500(27.6); 2.340(0.3); 2.335(0.5); 2.331(0.4); 1.621(13.0); 1.611(11.5); 1.528(0.8); 1.512(1.0); 1.495(1.6); 1.479(1.2); 1.463(0.6); 1.455(0.4); 1.446(0.4); 1.441(0.4); 1.427(0.5); 1.422(0.7); 1.414(0.6); 1.408(1.0); 1.393(1.4); 1.387(1.0); 1.378(1.6); 1.362(1.5); 1.354(1.5); 1.346(1.4); 1.338(0.7); 1.329(1.0); 1.321(0.4); 1.313(0.5); 1.237(0.4); 1.152(1.1); 1.133(2.0); 1.114(1.8); 1.095(1.0); 1.085(6.6); 1.069(6.5); 1.040(6.2); 1.024(6.1); 1.001(0.7); 0.993(0.8); 0.983(1.1); 0.975(1.3); 0.967(1.0); 0.961(1.1); 0.953(0.9); 0.944(0.6); 0.935(0.5); 0.857(16.0); 0.840(15.2); 0.664(8.6); 0.648(8.8); 0.642(9.0); 0.626(8.1)
Example 370: $^1$H-NMR(400.0 MHz, DMSO):
9.002(6.3); 8.996(6.4); 8.769(4.6); 8.763(4.3); 8.223(3.3); 8.219(5.1); 8.177(3.0); 8.172(2.3); 8.155(4.4); 8.150(3.9); 8.077(5.6); 8.055(3.7); 7.845(1.0); 7.823(1.1); 7.810(1.5); 7.787(1.4); 3.897(1.9); 3.870(2.6); 3.854(2.2); 3.827(3.5); 3.810(0.9); 3.802(0.7); 3.793(1.2); 3.779(0.8); 3.776(0.8); 3.757(0.4); 3.509(0.5); 3.477(3.1); 3.459(2.2); 3.434(2.6); 3.416(1.9); 3.330(184.0); 3.308(0.6); 2.677(0.5); 2.673(0.6); 2.668(0.5); 2.526(2.0); 2.521(3.2); 2.513(38.9); 2.508 (78.0); 2.504(102.1); 2.499(72.2); 2.495(33.6); 2.335(0.5); 2.330(0.7); 2.326(0.5); 1.621(16.0); 1.603(11.0); 1.528(0.4); 1.507(0.4); 1.493(0.5); 1.473(0.4); 1.427(0.3); 1.393(0.9); 1.387(0.9); 1.378(0.9); 1.370(0.9); 1.366(0.9); 1.348(0.9); 1.334(0.9); 1.314(0.6); 1.299(0.6); 1.279(0.7); 1.232(5.5); 1.120(0.4); 1.101(0.7); 1.071(9.1); 1.054(9.4); 1.029(6.9); 1.013(6.1); 1.005(1.0); 0.999(0.8); 0.984(1.2); 0.977(1.1); 0.966(2.0); 0.950(1.9); 0.939(1.7); 0.933(2.0); 0.923(1.3); 0.917(1.3); 0.906(0.8); 0.895(0.6); 0.862(1.9); 0.846(5.8); 0.828(2.1); 0.561(3.7); 0.544(8.7); 0.526(4.1)
Example 371: $^1$H-NMR(300.2 MHz, CDCl3):
8.923(3.3); 8.916(3.3); 8.298(2.7); 8.291(2.6); 8.171(1.2); 8.165(1.2); 8.141(2.5); 8.135(2.6); 8.086(3.2); 8.056(1.6); 7.791(3.0); 7.785(2.9); 7.297(1.3); 7.244(1.0); 7.225(0.6); 3.978(2.7); 3.921(3.2); 3.567(0.5); 3.552(0.8); 3.547(0.6); 3.526(2.4); 3.521(4.6); 3.510(5.8); 3.506(5.1); 3.497(2.9); 3.492(2.8); 3.482(4.2); 3.458(1.6); 3.447(1.3); 3.426(1.1); 3.421(0.8); 3.412(0.5); 3.402(0.6); 3.397(0.6); 3.394(0.7); 3.380(0.4); 3.364(3.3); 3.307(2.6); 2.149(2.2); 1.783(16.0); 1.213(5.4); 1.189(10.8); 1.166(5.3); 0.000(0.7)
Example 372: $^1$H-NMR(499.9 MHz, CDCl3):
8.854(3.0); 8.850(3.1); 8.240(2.7); 8.236(2.8); 8.085(1.3); 8.082(1.3); 8.067(2.1); 8.064(2.2); 8.017(3.0); 7.999(1.8); 7.743(3.0); 7.740(3.0); 7.197(2.2); 6.445(0.9); 6.425(0.9); 3.918(2.7); 3.884(3.0); 3.265(2.9); 3.231(2.7); 3.124(0.5); 3.103(1.5); 3.082(1.6); 3.061(0.5); 1.724(16.0); 1.709(1.5); 1.674(0.8); 1.669(0.7); 1.644(0.6); 1.638(0.7); 1.634(0.6); 1.626(0.4); 1.617(0.6); 1.612(0.8); 1.607(0.7); 1.600(0.5); 1.593(0.7); 1.587(0.8); 1.580(0.6); 1.574(0.6); 1.567(0.7); 1.560(0.9); 1.554(0.7); 1.283(0.3); 1.275(0.6); 1.265(0.6); 1.262(0.6); 1.252(0.6); 1.244(0.6); 1.239(0.7); 1.231(0.8); 1.219(0.7); 1.211(1.0); 1.204(1.3); 1.197(1.1); 1.185(1.0); 1.178(1.2); 1.171(0.7); 1.159(0.3); 1.152(0.4); 1.065(0.4); 1.058(0.4); 1.039(0.8); 1.032(0.8); 1.012(1.0); 1.008(0.8); 0.993(0.9); 0.987(1.0); 0.968(0.7); 0.962(0.7); 0.864(8.2); 0.851(7.9); 0.643(7.8); 0.630(7.7); 0.000(3.5); −0.076(1.2)
Example 373: $^1$H-NMR(300.2 MHz, CDCl3):
8.945(1.2); 8.937(1.2); 8.924(1.2); 8.324(1.1); 8.317(0.9); 8.162(0.3); 8.132(1.0); 8.126(0.9); 8.104(1.2); 8.074(0.4); 7.801(1.2); 7.273(0.9); 4.017(0.8); 3.959(1.0); 3.384(0.9); 3.327(0.8); 1.826(5.0); 1.774(1.1); 1.281(16.0); 0.000(0.5)
Example 374: $^1$H-NMR(300.2 MHz, CDCl3):
8.937(4.9); 8.929(5.0); 8.319(3.6); 8.311(3.5); 8.184(1.3); 8.182(1.3); 8.178(1.3); 8.154(2.6); 8.152(2.7); 8.148(2.8); 8.100(2.8); 8.098(2.9); 8.070(1.4); 8.068(1.4); 7.814(2.2); 7.807(3.2); 7.799(2.1); 7.273(5.7); 7.028(0.6); 6.997(1.1); 6.966(0.7); 4.155(0.5); 4.149(0.5); 4.143(0.5); 4.133(0.7); 4.129(0.8); 4.117(0.7); 4.106(0.9); 4.094(0.5); 4.091(0.5); 4.086(0.5); 4.079(0.5); 3.982(2.1); 3.967(2.1); 3.924(2.5); 3.910(2.4); 3.569(0.5); 3.561(0.5); 3.549(0.6); 3.546(0.5); 3.538(1.7); 3.526(1.7); 3.514(1.8); 3.502(1.7); 3.494(0.6); 3.491(0.7); 3.479(0.6); 3.471(0.4); 3.462(0.4); 3.450(1.3); 3.427(4.6); 3.420(2.6); 3.415(2.3); 3.404(5.8); 3.388(0.6); 3.380(1.4); 3.372(0.6); 3.360(4.4); 3.349(5.6); 3.345(4.9); 3.292(3.9); 3.010(0.4); 1.799(6.9); 1.767(16.0); 1.765(15.4); 1.255(0.5); 1.240(7.3); 1.237(6.0); 1.217(7.6); 1.214(9.6); 1.190(4.1); 1.176(6.7); 1.154(6.6); 1.112(4.1); 1.089(8.1); 1.065(3.8); 0.000(3.4)

-continued

NMR Peak Lists Table 1

Example 375: ¹H-NMR(499.9 MHz, CDCl3):
9.274(2.5); 9.247(2.4); 8.944(5.0); 8.940(4.9); 8.317(4.4); 8.149(1.3); 8.146(1.9); 8.142(1.1); 8.131(2.8); 8.128(4.3); 8.125(2.6); 8.102(5.8); 8.084(2.5); 7.803(5.0); 7.800(4.8); 7.265(10.5); 4.001(3.7); 3.967(4.1); 3.364(2.8); 3.358(2.9); 3.337(0.6); 3.330(2.7); 3.324(3.3); 3.312(1.2); 3.309(1.5); 3.296(1.4); 3.292(1.1); 3.279(1.0); 1.814(16.0); 1.806(15.8); 1.764(0.4); 1.646(10.7); 1.335(8.4); 1.326(9.6); 1.322(9.0); 1.313(8.5); 1.304(0.6); 1.289(0.7); 1.266(2.0); 0.970(0.4); 0.963(0.5); 0.959(0.6); 0.953(1.1); 0.943(1.2); 0.936(1.2); 0.926(1.1); 0.920(0.6); 0.917(0.5); 0.909(0.5); 0.895(1.4); 0.881(3.4); 0.867(1.6); 0.645(0.3); 0.636(0.7); 0.634(0.5); 0.627(1.0); 0.625(0.9); 0.618(1.4); 0.610(1.2); 0.607(1.1); 0.603(1.0); 0.600(1.0); 0.595(0.6); 0.591(0.8); 0.583(0.4); 0.523(0.4); 0.511(0.9); 0.506(0.7); 0.502(1.0); 0.499(0.9); 0.494(1.4); 0.489(0.9); 0.485(1.5); 0.476(0.7); 0.472(0.9); 0.468(0.8); 0.464(0.9); 0.455(1.1); 0.446(1.0); 0.436(1.0); 0.426(0.7); 0.408(0.4); 0.398(0.8); 0.389(0.9); 0.379(1.0); 0.368(0.7); 0.110(0.4); 0.100(0.8); 0.091(0.9); 0.079(1.2); 0.070(1.4); 0.060(1.1); 0.050(0.9); 0.049(0.9); 0.039(0.7); 0.006(0.3); 0.000(6.4)
Example 376: ¹H-NMR(400.1 MHz, CDCl3):
9.703(0.3); 9.694(0.3); 8.972(0.5); 8.966(0.5); 8.956(0.5); 8.949(6.2); 8.944(6.1); 8.399(0.4); 8.393(0.4); 8.365(0.4); 8.360(0.4); 8.348(4.5); 8.343(4.4); 8.213(0.5); 8.208(0.4); 8.165(1.8); 8.160(1.7); 8.143(5.6); 8.138(5.7); 8.132(0.7); 8.122(6.5); 8.100(1.9); 8.045(0.4); 8.040(0.4); 7.928(4.6); 7.924(4.5); 7.88(0.4); 7.264(52.8); 6.609(1.1); 6.588(1.1); 5.302(5.9); 4.752(5.5); 4.743(5.5); 4.199(0.8); 4.191(0.7); 4.181(2.2); 4.173(2.1); 4.163(2.2); 4.155(2.2); 4.145(0.7); 4.136(0.7); 4.132(0.5); 4.114(0.5); 4.103(0.5); 4.087(1.1); 4.070(1.6); 4.067(1.3); 4.054(1.3); 4.050(1.6); 4.034(1.1); 4.017(0.4); 3.104(0.7); 2.915(0.6); 2.841(0.5); 2.047(1.8); 1.649(0.4); 1.608(6.2); 1.535(1.1); 1.528(0.4); 1.519(1.1); 1.511(0.4); 1.489(15.7); 1.471(15.8); 1.332(2.9); 1.316(3.1); 1.304(0.6); 1.290(1.3); 1.278(1.3); 1.271(1.9); 1.261(3.6); 1.256(2.4); 1.246(0.9); 1.243(1.3); 1.240(1.1); 1.229(0.5); 1.223(1.0); 1.207(16.0); 1.191(15.2); 1.131(0.6); 1.120(15.3); 1.103(15.2); 0.963(0.4); 0.947(0.4); 0.899(1.4); 0.882(4.3); 0.864(1.8); 0.008(1.3); 0.000(36.2); −0.009(1.2)
Example 377: ¹H-NMR(300.2 MHz, CDCl3):
8.929(4.3); 8.921(4.5); 8.311(3.2); 8.304(3.2); 8.181(0.9); 8.176(1.4); 8.170(1.0); 8.152(1.8); 8.146(2.9); 8.141(2.0); 8.093(3.3); 8.064(1.7); 7.807(3.3); 7.802(3.3); 7.287(2.4); 6.977(1.1); 3.984(2.2); 3.979(2.3); 3.966(0.7); 3.959(0.8); 3.956(0.8); 3.936(0.9); 3.927(2.8); 3.922(2.9); 3.909(0.6); 3.466(1.2); 3.452(0.4); 3.434(1.6); 3.420(1.7); 3.414(1.9); 3.400(1.8); 3.382(1.6); 3.379(2.0); 3.371(16.0); 3.364(4.2); 3.354(2.5); 3.341(1.1); 3.327(1.4); 3.313(1.5); 3.306(2.1); 3.297(2.3); 3.281(0.8); 3.275(0.3); 3.260(14.8); 3.012(0.4); 2.017(1.7); 1.783(15.2); 1.771(1.9); 1.695(0.4); 1.691(0.3); 1.670(0.7); 1.654(0.4); 1.649(0.6); 1.645(0.6); 1.633(0.5); 1.629(0.5); 1.624(0.7); 1.608(0.8); 1.598(0.7); 1.587(0.7); 1.583(0.7); 1.573(0.8); 1.562(0.7); 1.547(0.7); 1.524(0.9); 1.500(0.9); 1.473(0.6); 1.453(0.4); 1.255(0.4); 0.975(2.5); 0.950(5.4); 0.926(2.3); 0.917(0.5); 0.892(0.4); 0.842(2.8); 0.817(5.8); 0.792(2.4); 0.000(1.2)
Example 378: ¹H-NMR(300.2 MHz, CDCl3):
8.890(2.5); 8.884(2.5); 8.127(2.7); 8.121(2.4); 8.108(0.8); 8.103(0.8); 8.079(2.6); 8.073(3.1); 8.066(3.7); 8.036(0.6); 7.795(2.7); 7.285(2.1); 7.250(4.1); 6.971(0.7); 6.954(1.2); 6.938(0.7); 4.365(0.8); 4.346(0.8); 4.316(1.6); 4.297(1.6); 4.229(1.6); 4.213(1.6); 4.180(0.8); 4.163(0.8); 4.073(1.3); 4.049(3.8); 4.025(3.9); 3.997(2.8); 3.940(2.5); 3.376(2.3); 3.319(2.0); 2.189(16.0); 2.140(13.3); 2.062(1.1); 2.044(1.0); 1.775(12.8); 1.441(4.2); 1.417(8.6); 1.393(4.2); 1.303 (0.7); 1.261(3.7); 1.258(3.7); 1.234(0.7); 0.901(1.2); 0.880(3.3); 0.856(1.4); 0.000(1.2)
Example 379: ¹H-NMR(499.9 MHz, CDCl3):
9.232(2.6); 9.228(2.7); 8.332(2.6); 8.072(6.6); 8.071(6.1); 7.889(3.1); 7.591(2.6); 7.589(2.7); 7.273(2.9); 7.248(4.2); 6.963(0.6); 6.953(1.1); 6.942(0.7); 6.904(2.4); 6.897(2.6); 6.574(1.8); 6.571(2.0); 6.567(1.9); 6.564(1.8); 4.351(0.9); 4.340(0.9); 4.321(1.5); 4.310(1.5); 4.230(1.5); 4.220(1.6); 4.200(1.0); 4.190(1.0); 4.126(0.4); 4.112(0.4); 4.056(1.3); 4.041(4.0); 4.027(4.1); 4.012(1.5); 3.996(2.6); 3.962(2.8); 3.374(2.6); 3.340(2.4); 2.194(16.0); 2.187(1.6); 2.038(1.7); 1.780(14.1); 1.430(4.6); 1.415(9.5); 1.400(4.7); 1.269(0.6); 1.255(1.2); 1.241(0.5); 0.000(1.6)
Example 380: ¹H-NMR(499.9 MHz, DMSO):
8.993(3.5); 8.988(3.6); 8.755(3.0); 8.751(3.0); 8.207(2.9); 8.203(3.4); 8.170(1.8); 8.166(1.6); 8.152(2.4); 8.148(2.3); 8.072(3.2); 8.055(2.2); 7.554(1.5); 7.388(1.5); 5.747(0.8); 3.889(2.7); 3.854(3.1); 3.435(2.9); 3.401(2.6); 3.302(55.3); 2.511(1.1); 2.508(2.3); 2.504(3.3); 2.500(2.6); 2.497(1.4); 1.629(0.4); 1.611(16.0); 1.231(0.7)
Example 381: ¹H-NMR(300.2 MHz, CDCl3):
8.895(2.5); 8.888(2.6); 8.133(2.7); 8.129(2.6); 8.113(0.5); 8.104(2.6); 8.098(2.8); 8.079(3.0); 8.049(0.9); 7.808(2.4); 7.802(2.3); 7.271(5.7); 6.718(0.8); 6.692(0.8); 4.075(0.4); 4.053(0.9); 4.049(0.7); 4.031(0.8); 4.027(0.9); 4.005(0.7); 3.982(0.5); 3.975(2.7); 3.917(3.1); 3.354(2.8); 3.296(2.4); 2.142(16.0); 1.752(15.2); 1.332(1.0); 1.310(1.0); 1.256(1.4); 1.236(0.3); 1.212(8.2); 1.190(8.1); 1.151(8.4); 1.129(8.2); 0.881(0.5); 0.856(0.4); 0.073(0.4); 0.000(2.9)
Example 382: ¹H-NMR(300.2 MHz, CDCl3):
9.243(3.0); 9.236(3.1); 8.354(2.5); 8.347(2.5); 8.131(0.5); 8.126(0.4); 8.102(3.5); 8.096(5.2); 8.093(4.4); 8.063(0.5); 7.902(2.7); 7.603(2.4); 7.601(2.6); 7.597(2.7); 7.595(2.5); 7.267(3.3); 6.919(2.3); 6.917(2.4); 6.907(2.5); 6.906(2.5); 6.733(0.8); 6.706(0.8); 6.586(2.3); 6.580(2.3); 6.575(2.3); 6.569(2.2); 5.301(0.3); 4.082(0.6); 4.060(0.9); 4.055(0.7); 4.038(0.8); 4.033(0.9); 4.016(0.4); 4.012(0.7); 3.991(2.9); 3.934(3.3); 3.372(3.0); 3.314(2.6); 1.761(16.0); 1.742(0.7); 1.725(2.1); 1.341(0.6); 1.319(0.6); 1.283(0.4); 1.263(1.2); 1.217(8.4); 1.195(8.3); 1.158(8.5); 1.136(8.4); 0.903(0.4); 0.881(1.4); 0.858(0.5); 0.000(4.7)
Example 383: ¹H-NMR(400.0 MHz, DMSO):
9.257(2.1); 9.252(2.2); 8.986(1.9); 8.451(2.2); 8.448(2.4); 8.403(0.6); 8.388(1.2); 8.373(0.6); 8.319(1.1); 8.314(1.0); 8.297(1.5); 8.292(1.6); 8.207(2.2); 8.184(1.5); 7.411(3.8); 4.090(2.4); 4.075(2.4); 3.963(1.1); 3.945(3.3); 3.927(3.4); 3.917(2.0); 3.908(16.0); 3.874(2.0); 3.512(2.0); 3.469(1.7); 3.341(77.1); 3.174(0.4); 2.682(0.4); 2.677(0.5); 2.673(0.4); 2.512(71.1); 2.508(89.7); 2.504(66.8); 2.339(0.4); 2.335(0.5); 2.330(0.4); 2.176(0.9); 2.055(13.6); 1.625(10.3); 1.613(1.0); 1.262(3.8); 1.244(7.8); 1.226(3.6); 1.218(0.7)
Example 384: ¹H-NMR(400.0 MHz, DMSO):
9.251(2.4); 9.246(2.5); 8.982(2.0); 8.450(2.5); 8.445(2.6); 8.326(1.3); 8.322(1.2); 8.316(0.3); 8.304(1.9); 8.299(1.8); 8.204(2.6); 8.181(1.9); 7.905(1.1); 7.885(1.1); 3.933(0.7); 3.920(2.7); 3.903(16.0); 3.877(3.0); 3.480(2.7); 3.436(2.3); 3.331(147.8); 2.677(0.4); 2.672(0.5); 2.668(0.4); 2.543(0.5); 2.512(34.4); 2.508(66.1); 2.504(84.8); 2.499(61.1); 2.494(29.7); 2.335(0.4); 2.330(0.5); 2.326(0.4); 1.606(13.9); 1.111(7.8); 1.095(7.6); 1.066(7.9); 1.049(7.8)
Example 385: ¹H-NMR(400.0 MHz, DMSO):
9.009(2.1); 9.004(2.2); 8.804(1.8); 8.799(1.7); 8.384(0.5); 8.370(0.9); 8.352(2.0); 8.348(1.8); 8.170(0.8); 8.166(0.7); 8.148(1.3); 8.144(1.2); 8.082(1.8); 8.059(1.1); 7.287(3.0); 4.182(1.1); 4.164(1.1); 4.100(0.4); 4.085(0.4); 4.064(0.9); 4.048(0.9); 4.013(1.0); 3.999(0.9); 3.977(0.5); 3.963(0.4); 3.903(16.0); 3.870(0.8); 3.851(2.4); 3.833(2.5); 3.815(0.8); 3.334(62.6); 3.169(0.4); 2.677(0.4); 2.673(0.5); 2.508(60.4); 2.503(74.5); 2.499(54.4); 2.330(0.4); 2.099(0.6); 1.975(10.6); 1.505(7.6); 1.488(0.6); 1.235(0.3); 1.205(3.8); 1.187(3.7); 1.152(3.1); 1.134(6.1); 1.116(2.8)

NMR Peak Lists Table 1

Example 386: ¹H-NMR(400.0 MHz, DMSO):
9.010(1.6); 9.004(1.7); 8.774(1.1); 8.768(1.0); 8.357(0.6); 8.232(1.0); 8.227(1.2); 8.168(0.6); 8.163(0.5); 8.146(1.0); 8.141(1.0); 8.083(1.2); 8.060(0.7); 7.427(1.9); 4.098(0.7); 4.083(0.8); 4.063(0.6); 3.966(0.6); 3.948(1.7); 3.930(1.7); 3.912(0.7); 3.903(16.0); 3.806(2.6); 3.795(0.4); 3.548(7.1); 3.535(0.9); 3.338(48.4); 3.172(0.6); 3.169(0.6); 3.132(1.1); 3.076(1.2); 3.036(0.6); 2.672(0.3); 2.525(1.2); 2.512(21.6); 2.507(43.0); 2.503(56.1); 2.498(40.1); 2.494(19.1); 2.329(0.3); 2.178(0.9); 2.063(7.2); 1.272(2.1); 1.254(4.6); 1.236(2.3); 1.219(0.5)

Example 387: ¹H-NMR(400.0 MHz, DMSO):
9.010(2.2); 9.005(2.2); 8.776(1.5); 8.771(1.4); 8.235(1.5); 8.230(1.6); 8.178(0.8); 8.174(0.7); 8.156(1.3); 8.151(1.2); 8.087(1.7); 8.065(1.0); 7.871(0.8); 7.851(0.8); 3.945(0.3); 3.929(0.5); 3.925(0.4); 3.903(16.0); 3.892(0.4); 3.846(0.5); 3.802(2.0); 3.784(1.9); 3.740(0.4); 3.587(10.6); 3.565(0.4); 3.328(76.2); 3.157(1.0); 3.117(1.7); 3.045(1.7); 3.006(1.0); 2.672(0.4); 2.525(1.3); 2.512(26.3); 2.507(51.1); 2.503(65.8); 2.498(47.5); 2.494(23.2); 2.330(0.4); 1.337(0.4); 1.113(4.4); 1.096(4.5); 1.080(0.9); 1.074(4.5); 1.064(0.8); 1.057(4.5); 1.009(0.9); 0.993(0.9)

Example 388: ¹H-NMR(300.2 MHz, CDCl3):
9.162(2.5); 8.948(3.2); 8.941(3.4); 8.324(2.4); 8.317(2.4); 8.159(0.9); 8.153(0.8); 8.130(2.8); 8.124(2.9); 8.104(3.4); 8.074(1.0); 7.802(2.5); 7.797(2.4); 7.268(6.8); 4.211(0.5); 4.190(1.2); 4.169(1.7); 4.149(1.3); 4.128(0.5); 4.015(2.6); 3.957(3.1); 3.385(3.0); 3.328(2.5); 1.817(16.0); 1.674(3.5); 1.268(9.8); 1.263(10.0); 1.247(9.4); 1.243(9.3); 0.903(0.3); 0.881(1.1); 0.858(0.4); 0.000(4.7)

Example 389: ¹H-NMR(300.2 MHz, CDCl3):
9.330(2.5); 8.947(3.2); 8.940(3.3); 8.319(2.4); 8.311(2.4); 8.157(0.9); 8.151(0.8); 8.127(2.8); 8.121(2.9); 8.102(3.4); 8.072(1.0); 7.800(2.6); 7.795(2.5); 7.270(4.9); 5.303(1.2); 4.035(0.9); 4.031(0.9); 4.017(2.9); 4.011(3.0); 4.008(2.9); 3.988(2.9); 3.984(2.8); 3.960(3.6); 3.389(3.0); 3.331(2.5); 1.813(16.0); 1.719(2.7); 1.305(5.2); 1.281(10.8); 1.258(5.7); 0.881(0.9); 0.858(0.4); 0.000(3.3)

Example 390: ¹H-NMR(300.2 MHz, CDCl3):
8.935(4.3); 8.927(4.4); 8.315(3.3); 8.308(3.2); 8.181(1.6); 8.175(1.6); 8.152(3.2); 8.145(3.4); 8.096(3.4); 8.066(1.7); 7.805(3.4); 7.276(3.9); 7.010(0.7); 6.996(0.8); 6.985(0.8); 6.970(0.7); 4.159(0.5); 4.153(0.4); 4.143(0.7); 4.137(0.8); 4.131(0.7); 4.121(0.8); 4.115(0.8); 4.109(0.7); 4.099(0.5); 4.093(0.6); 3.974(2.1); 3.970(2.1); 3.917(2.5); 3.912(2.6); 3.393(2.4); 3.389(3.0); 3.382(15.6); 3.374(2.8); 3.351(3.9); 3.342(0.7); 3.328(3.7); 3.313(3.6); 3.294(3.5); 3.282(16.0); 1.845(2.4); 1.782(0.6); 1.767(12.1); 1.762(12.5); 1.255(0.6); 1.238(6.0); 1.216(5.9); 1.172(5.7); 1.150(5.7); 0.000(2.5)

Example 391: ¹H-NMR(300.2 MHz, CDCl3):
8.940(3.2); 8.932(3.3); 8.319(2.3); 8.312(2.3); 8.179(1.2); 8.173(1.2); 8.149(2.4); 8.143(2.5); 8.097(2.9); 8.068(1.4); 7.805(2.6); 7.799(2.6); 7.268(6.7); 7.221(0.8); 7.204(0.5); 3.974(2.7); 3.917(3.2); 3.593(0.6); 3.573(1.4); 3.552(2.0); 3.532(1.8); 3.522(0.8); 3.511(1.5); 3.502(1.2); 3.498(1.3); 3.491(3.8); 3.485(3.4); 3.481(2.3); 3.465(2.1); 3.454(1.0); 3.440(0.9); 3.422(0.8); 3.418(0.5); 3.404(0.9); 3.392(0.5); 3.379(0.6); 3.355(3.2); 3.346(0.4); 3.298(2.6); 1.777(15.9); 1.696(3.6); 1.260(0.9); 1.171(0.3); 1.158(8.5); 1.138(16.0); 1.117(8.6); 0.881(0.9); 0.858(0.4); 0.000(4.8)

Example 392: ¹H-NMR(300.2 MHz, CDCl3):
8.931(2.0); 8.923(2.1); 8.306(1.5); 8.299(1.5); 8.174(0.8); 8.167(0.8); 8.144(1.6); 8.138(1.7); 8.091(1.9); 8.061(0.9); 7.797(1.7); 7.791(1.7); 7.282(1.5); 7.202(0.5); 7.185(0.3); 3.976(1.8); 3.919(2.1); 3.571(0.4); 3.551(0.4); 3.536(0.3); 3.524(0.5); 3.519(0.6); 3.503(0.5); 3.496(0.7); 3.488(2.0); 3.472(2.7); 3.457(2.1); 3.445(0.6); 3.436(0.4); 3.425(0.6); 3.419(0.6); 3.404(0.4); 3.387(0.5); 3.371(0.5); 3.361(2.7); 3.353(16.0); 3.304(1.7); 1.932(0.8); 1.779(10.4); 1.260(0.4); 0.000(0.9)

Example 393: ¹H-NMR(400.1 MHz, DMSO):
9.026(5.9); 9.020(6.3); 8.812(5.0); 8.806(4.9); 8.300(5.1); 8.122(0.9); 8.099(8.0); 8.097(8.4); 8.092(6.1); 8.074(0.9); 8.070(1.0); 8.046(2.3); 8.025(2.3); 4.131(0.9); 4.112(3.7); 4.094(3.7); 4.075(1.0); 4.040(0.4); 4.024(1.0); 4.007(1.5); 4.003(1.3); 3.990(1.3); 3.987(1.6); 3.970(1.1); 3.953(0.5); 3.669(0.4); 3.652(1.6); 3.646(0.9); 3.634(1.8); 3.628(2.5); 3.611(2.5); 3.593(0.8); 3.574(0.7); 3.557(2.4); 3.539(2.5); 3.533(1.7); 3.498(0.5); 3.314(28.6); 2.682(0.5); 2.677(0.7); 2.672(0.5); 2.558(0.5); 2.530(2.2); 2.517(41.3); 2.512(83.7); 2.508(114.1); 2.503(86.0); 2.499(45.7); 2.339(0.6); 2.335(0.8); 2.330(0.6); 1.564(0.7); 1.284(12.7); 1.265(12.9); 1.184(7.2); 1.166(16.0); 1.157(14.1); 1.149(9.4); 1.141(14.6); 1.134(14.7); 1.117(13.6); 1.089(0.9)

Example 394: ¹H-NMR(300.2 MHz, CDCl3):
8.899(1.5); 8.895(1.5); 8.144(2.4); 8.138(2.3); 8.113(0.4); 8.107(0.4); 8.083(3.1); 8.078(4.5); 8.045(0.4); 7.800(2.5); 7.272(5.2); 7.251(3.2); 6.955(0.6); 6.938(1.0); 6.921(0.6); 4.366(0.7); 4.347(0.7); 4.316(1.5); 4.297(1.5); 4.227(1.5); 4.210(1.5); 4.177(0.8); 4.160(0.8); 4.082(1.2); 4.057(3.7); 4.033(3.8); 4.008(1.4); 3.995(2.4); 3.938(2.7); 3.377(2.6); 3.319(2.2); 2.546(1.2); 2.521(3.6); 2.496(3.8); 2.471(1.3); 2.192(16.0); 2.172(0.5); 1.842(0.4); 1.775(13.6); 1.445(4.7); 1.421(9.8); 1.396(4.6); 1.325(4.8); 1.300(10.0); 1.275(4.5); 1.257(0.7); 0.074(7.6); 0.062(0.4); 0.000(2.4)

Example 395: ¹H-NMR(400.0 MHz, DMSO):
9.002(3.0); 8.997(3.1); 8.800(2.3); 8.794(2.2); 8.221(2.2); 8.217(2.5); 8.182(1.3); 8.177(1.0); 8.160(1.9); 8.155(1.7); 8.076(2.4); 8.053(1.6); 7.877(1.2); 7.856(1.2); 3.942(1.9); 3.918(0.7); 3.908(1.6); 3.899(2.9); 3.882(0.8); 3.865(0.5); 3.372(2.2); 3.334(130.2); 3.304(0.4); 2.682(0.4); 2.677(0.6); 2.673(0.4); 2.517(37.8); 2.513(73.9); 2.508(95.9); 2.504(69.9); 2.499(34.7); 2.339(0.4); 2.335(0.6); 2.331(0.4); 1.512(0.9); 1.476(2.9); 1.451(2.9); 1.415(0.9); 1.117(6.3); 1.100(6.3); 1.052(6.4); 1.036(6.4); 0.079(2.4); 0.071(52.9); 0.063(2.3)

Example 396: ¹H-NMR(499.9 MHz, CDCl3):
8.942(2.4); 8.938(2.5); 8.345(2.0); 8.341(1.9); 8.192(1.1); 8.188(1.1); 8.174(1.7); 8.170(1.7); 8.112(2.2); 8.094(1.4); 7.913(2.2); 7.910(2.2); 7.266(2.9); 5.297(0.5); 4.650(2.4); 4.612(2.5); 3.477(2.5); 3.440(2.3); 3.357(16.0); 3.292(13.5); 3.038(13.4); 0.074(0.5); 0.000(1.5)

Example 397: ¹H-NMR(400.1 MHz, DMSO):
9.035(7.5); 9.029(7.7); 8.810(5.5); 8.805(5.1); 8.456(5.8); 8.451(5.8); 8.199(4.6); 8.194(3.5); 8.181(3.1); 8.177(6.1); 8.172(5.3); 8.115(6.3); 8.093(3.7); 4.097(0.4); 4.081(1.2); 4.064(1.8); 4.061(1.5); 4.047(1.5); 4.044(1.9); 4.027(1.4); 4.010(0.5); 3.679(2.8); 3.668(3.4); 3.655(3.4); 3.643(3.1); 3.314(37.3); 2.681(0.7); 2.677(1.0); 2.672(0.7); 2.557(0.5); 2.530(2.4); 2.525(4.0); 2.517(56.9); 2.512(116.4); 2.508(157.4); 2.503(110.2); 2.499(50.8); 2.462(0.6); 2.458(0.7); 2.344(0.4); 2.339(0.7); 2.334(1.0); 2.330(0.7); 2.018(3.1); 2.005(3.2); 1.994(3.6); 1.981(3.0); 1.175(15.7); 1.158(15.6); 1.133(16.0); 1.117(15.9); 0.864(3.6); 0.852(5.5); 0.840(3.1)

Example 398: ¹H-NMR(400.1 MHz, DMSO):
9.034(10.8); 9.028(11.2); 8.813(8.0); 8.807(7.5); 8.450(11.6); 8.445(11.0); 8.188(4.3); 8.184(4.0); 8.166(7.5); 8.161(7.4); 8.112(9.3); 8.090(5.2); 4.045(0.5); 4.027(0.6); 3.690(4.1); 3.678(4.9); 3.665(4.9); 3.654(4.4); 3.314(60.8); 2.833(0.6); 2.821(1.2); 2.817(1.3); 2.812(1.4); 2.805(3.0); 2.793(2.8); 2.788(1.8); 2.781(1.1); 2.777(1.7); 2.765(0.6); 2.686(0.5); 2.681(1.1); 2.677(1.5); 2.672(1.1); 2.558(1.2); 2.553(1.0); 2.530(3.8); 2.517(88.2); 2.512(181.7); 2.508(246.8); 2.503(174.6); 2.499(81.7); 2.457(0.9); 2.339(1.2); 2.334(1.6); 2.330(1.1); 2.025(4.4); 2.012(4.6);

NMR Peak Lists Table 1

2.001(4.8); 1.995(3.0); 1.988(4.3); 1.250(0.5); 1.199(0.7); 1.181(1.3); 1.164(0.7); 0.872(4.9); 0.860(8.0); 0.848(4.8); 0.678(0.4); 0.671(1.2); 0.651(10.5); 0.647(5.6); 0.633(16.0); 0.627(10.3); 0.622(4.7); 0.618(7.7); 0.608(1.7); 0.596(0.8); 0.581(0.5)
Example 399: $^1$H-NMR(400.1 MHz, DMSO):
9.032(3.2); 9.026(3.3); 8.806(2.3); 8.801(2.2); 8.705(0.7); 8.690(1.4); 8.676(0.7); 8.452(2.5); 8.447(2.5); 8.190(1.3); 8.185(1.2); 8.168(2.1); 8.163(2.1); 8.108(2.6); 8.086(1.5); 7.490(4.3); 4.178(1.7); 4.169(1.9); 4.164(1.9); 4.154(1.7); 4.063(0.6); 4.045(1.9); 4.027(1.9); 4.010(1.7); 3.992(3.9); 3.974(3.9); 3.956(1.3); 3.694(1.1); 3.682(1.4); 3.669(1.4); 3.658(1.2); 3.315(17.8); 2.677(0.4); 2.530(1.1); 2.517(24.6); 2.512(49.8); 2.508(67.1); 2.503(47.0); 2.499(21.8); 2.462(0.3); 2.458(0.3); 2.334(0.4); 2.135(16.0); 2.029(1.2); 2.016(1.3); 2.004(1.4); 1.995(8.6); 1.322(4.8); 1.304(10.3); 1.286(4.6); 1.199(2.3); 1.181(4.6); 1.164(2.2); 0.881(1.3); 0.869(2.2); 0.857(1.2)
Example 400: $^1$H-NMR(400.1 MHz, DMSO):
9.035(3.5); 9.032(3.6); 8.809(3.7); 8.462(4.9); 8.438(1.3); 8.199(1.7); 8.177(2.9); 8.117(3.5); 8.095(2.1); 4.201(1.1); 4.188(1.7); 4.174(1.3); 4.159(0.5); 3.992(1.3); 3.972(2.1); 3.956(1.5); 3.734(1.5); 3.715(3.0); 3.704(2.5); 3.691(2.0); 3.680(1.7); 3.392(0.6); 3.374(0.7); 3.358(1.0); 3.342(0.7); 3.333(1.4); 3.314(23.1); 3.277(1.1); 3.262(0.9); 3.244(0.6); 3.229(0.4); 2.676(0.8); 2.507(133.4); 2.333(0.9); 2.036(1.2); 2.023(1.4); 2.012(1.4); 1.995(1.9); 1.347(12.2); 1.284(0.4); 1.258(16.0); 1.200(0.4); 1.182(0.5); 0.918(1.4); 0.906(2.8); 0.894(1.6); 0.865(0.5)
Example 401: $^1$H-NMR(400.1 MHz, DMSO):
9.035(4.7); 9.029(5.0); 8.810(3.3); 8.804(3.2); 8.458(3.5); 8.454(3.8); 8.416(1.0); 8.402(1.9); 8.387(1.0); 8.198(1.9); 8.193(1.9); 8.175(3.2); 8.171(3.3); 8.113(3.8); 8.091(2.3); 3.681(1.7); 3.670(2.1); 3.657(2.1); 3.645(1.9); 3.436(2.3); 3.419(8.1); 3.415(4.4); 3.401(11.2); 3.384(5.9); 3.365(0.3); 3.315(20.7); 3.300(1.3); 3.282(1.9); 3.264(2.0); 3.247(1.9); 3.229(1.0); 3.214(0.5); 2.681(0.3); 2.677(0.5); 2.672(0.4); 2.530(1.3); 2.526(2.1); 2.517(26.6); 2.512(56.1); 2.508(77.9); 2.503(57.8); 2.499(29.6); 2.339(0.4); 2.335(0.5); 2.330(0.4); 2.021(1.9); 2.008(2.0); 1.996(2.1); 1.984(1.8); 1.759(0.7); 1.742(2.4); 1.726(3.7); 1.709(2.4); 1.692(0.8); 1.251(0.5); 1.134(7.6); 1.116(16.0); 1.099(7.6); 0.882(2.1); 0.871(3.4); 0.865(1.3); 0.858(2.1); 0.847(0.4)
Example 402: $^1$H-NMR(400.1 MHz, CDCl3):
8.951(0.8); 8.945(0.8); 8.933(6.1); 8.927(6.0); 8.374(0.6); 8.369(0.6); 8.323(4.6); 8.317(4.4); 8.179(0.7); 8.175(1.1); 8.171(1.0); 8.167(0.9); 8.163(0.8); 8.153(2.2); 8.149(2.2); 8.131(4.6); 8.126(4.7); 8.096(5.7); 8.074(2.5); 7.833(5.0); 7.829(4.7); 7.343(1.3); 7.283(3.3); 6.698(1.3); 6.679(1.2); 5.303(0.4); 4.267(5.0); 4.225(6.0); 4.123(0.5); 4.106(1.3); 4.090(1.8); 4.086(1.4); 4.073(1.5); 4.070(1.8); 4.057(0.8); 4.054(1.3); 4.037(0.5); 3.849(5.9); 3.806(4.9); 3.751(0.4); 3.734(1.0); 3.716(1.0); 3.699(0.4); 3.489(1.4); 2.813(13.6); 2.011(0.4); 1.352(0.3); 1.337(3.5); 1.320(3.3); 1.261(2.8); 1.256(16.0); 1.240(15.9); 1.226(1.5); 1.190(16.0); 1.174(15.8); 0.000(2.0)
Example 403: $^1$H-NMR(400.1 MHz, DMSO):
9.030(6.5); 9.025(6.8); 8.800(5.0); 8.794(4.7); 8.380(5.2); 8.375(5.4); 8.195(2.7); 8.190(2.5); 8.172(4.5); 8.168(4.4); 8.124(2.6); 8.108(6.8); 8.086(3.5); 5.759(0.7); 4.071(0.4); 4.054(1.1); 4.045(0.5); 4.038(1.6); 4.034(1.4); 4.021(1.4); 4.017(1.6); 4.001(1.1); 3.984(0.4); 3.750(6.3); 3.726(6.5); 3.366(0.4); 3.317(160.8); 3.267(0.6); 2.681(0.5); 2.676(0.7); 2.672(0.5); 2.557(0.3); 2.530(2.1); 2.516(45.0); 2.512(89.8); 2.507(120.0); 2.503(85.4); 2.499(40.9); 2.467(0.7); 2.462(0.8); 2.458(2.8); 2.339(0.6); 2.334(0.8); 2.330(0.6); 2.258(0.6); 2.242(2.4); 2.233(0.8); 2.227(2.5); 2.218(2.4); 2.211(0.8); 2.202(2.4); 2.187(0.7); 1.994(0.7); 1.240(0.5); 1.181(0.5); 1.159(13.7); 1.142(13.7); 1.123(14.2); 1.107 (14.1); 0.864(0.3); 0.807(16.0); 0.791(15.8)
Example 404: $^1$H-NMR(400.0 MHz, DMSO):
8.890(4.3); 8.344(2.3); 8.339(2.7); 8.305(1.5); 8.301(1.2); 8.283(2.1); 8.278(1.8); 8.187(2.6); 8.165(1.8); 7.909(1.2); 7.888(1.2); 5.037(6.8); 3.929(0.6); 3.912(3.1); 3.903(16.0); 3.896(0.9); 3.892(0.9); 3.876(0.8); 3.869(2.6); 3.480(2.4); 3.437(2.1); 3.330(127.3); 2.677(0.4); 2.672(0.5); 2.668(0.4); 2.542(0.4); 2.526(1.8); 2.512(33.9); 2.508(66.8); 2.503(86.4); 2.499(62.1); 2.494(30.0); 2.335(0.4); 2.330(0.5); 2.326(0.4); 1.601(13.1); 1.108(7.6); 1.091(7.5); 1.063 (7.8); 1.046(7.7)
Example 405: $^1$H-NMR(499.9 MHz, CDCl3):
9.000(1.7); 8.329(2.2); 8.325(2.2); 8.153(1.2); 8.150(1.3); 8.136(2.0); 8.132(2.1); 8.075(2.2); 8.057(1.5); 7.877(2.6); 7.874(2.6); 7.200(2.6); 7.181(2.9); 6.859(0.6); 6.849(1.1); 6.838(0.7); 5.921(0.8); 5.906(0.9); 5.854(0.8); 5.839(0.9); 5.217(3.8); 4.275(0.9); 4.264(1.0); 4.246(1.5); 4.234(1.5); 4.152(1.6); 4.141(1.6); 4.122(1.1); 4.112(1.0); 4.048(0.4); 4.034(0.4); 3.986(1.3); 3.971(3.8); 3.956(3.9); 3.942(1.4); 3.924(2.8); 3.890(3.0); 3.291(2.8); 3.256(2.6); 2.120(0.3); 2.108(16.0); 2.086(2.9); 1.960(1.8); 1.705(15.2); 1.359(4.6); 1.344(9.7); 1.330(4.8); 1.192(0.6); 1.177(1.4); 1.163(0.6); 0.000(6.5); −0.007(0.4); −0.080(1.4)
Example 406: $^1$H-NMR(300.2 MHz, CDCl3):
8.978(2.3); 8.971(2.3); 8.300(1.6); 8.293(1.6); 8.203(0.8); 8.196(0.8); 8.173(1.8); 8.167(1.9); 8.131(2.2); 8.102(0.9); 7.899(1.9); 7.893(1.8); 7.264(7.7); 6.669(0.4); 6.644(0.4); 4.185(0.5); 4.163(0.7); 4.158(0.6); 4.141(0.6); 4.136(0.8); 4.115(0.5); 4.111(0.5); 3.994(1.9); 3.934(2.5); 3.565(2.6); 3.504(2.0); 3.406(16.0); 3.328(4.4); 2.046(1.7); 1.614(2.0); 1.284(0.6); 1.262(6.5); 1.239(9.6); 1.216(6.1); 0.070(0.9); 0.000(6.5)
Example 407: $^1$H-NMR(400.1 MHz, DMSO):
8.972(8.9); 8.967(8.9); 8.835(2.4); 8.821(4.7); 8.807(2.4); 8.595(7.9); 8.590(7.6); 8.322(8.1); 8.318(8.2); 8.193(3.9); 8.189(3.5); 8.171(6.1); 8.167(5.8); 8.103(8.2); 8.081(5.1); 5.755(4.3); 4.591(16.0); 3.984(0.6); 3.977(0.7); 3.968(1.0); 3.958(5.5); 3.940(4.1); 3.934(4.8); 3.926(6.7); 3.921(7.1); 3.912(11.3); 3.885(0.7); 3.879(0.7); 3.871(0.6); 3.864(0.6); 3.773(7.9); 3.727(5.1); 3.340(0.4); 3.315(10.4); 3.291(47.2); 3.115(4.4); 3.109(8.8); 3.103(4.1); 2.673(0.3); 2.508(41.5); 2.504(52.4); 2.500(38.4); 0.000(0.5)
Example 408: $^1$H-NMR(400.1 MHz, DMSO):
8.970(4.9); 8.965(5.0); 8.596(3.7); 8.591(3.5); 8.349(1.0); 8.334(2.0); 8.313(4.0); 8.308(4.1); 8.191(2.0); 8.186(1.8); 8.169(3.2); 8.164(3.1); 8.101(4.1); 8.079(2.5); 5.756(0.4); 4.591(9.3); 3.951(2.8); 3.905(4.0); 3.736(3.9); 3.690(2.8); 3.459(0.4); 3.431(2.7); 3.414(8.1); 3.408(4.0); 3.396(9.3); 3.392(8.4); 3.378(4.7); 3.282(26.3); 3.256(1.0); 3.238(2.0); 3.227(2.2); 3.224(2.2); 3.212(2.1); 3.195(1.0); 2.527(0.4); 2.514(8.8); 2.509(17.6); 2.505(23.5); 2.500(16.6); 2.496 (7.8); 1.746(0.8); 1.730(2.7); 1.713(4.1); 1.697(2.6); 1.681(0.7); 1.128(7.8); 1.111(16.0); 1.093(7.5)
Example 409: $^1$H-NMR(400.1 MHz, DMSO):
8.974(3.3); 8.969(3.4); 8.598(2.9); 8.593(2.6); 8.583(1.5); 8.568(0.7); 8.314(2.3); 8.310(2.5); 8.192(1.3); 8.187(1.2); 8.170(2.1); 8.165(2.1); 8.103(2.6); 8.081(1.6); 7.473(4.2); 5.760(9.4); 4.595(6.0); 4.151(1.6); 4.137(2.8); 4.123(1.6); 4.101(0.4); 4.086(0.3); 3.946(1.8); 3.931(2.3); 3.913(4.0); 3.900(3.0); 3.896(2.8); 3.744(2.4); 3.698(1.7); 3.457(0.3); 3.439(0.9); 3.432(1.0); 3.265(17.5); 2.530(0.5); 2.526(0.7); 2.517(7.6); 2.512(15.6); 2.508(21.5); 2.503(15.5); 2.499 (7.7); 2.459(0.3); 2.131(16.0); 1.742(1.3); 1.724(2.5); 1.706(2.5); 1.688(1.4); 1.670(0.4); 0.827(4.5); 0.809(9.6); 0.790(4.2)

NMR Peak Lists Table 1

Example 410: ¹H-NMR(300.2 MHz, CDCl3):
8.952(2.5); 8.944(2.5); 8.471(0.6); 8.451(0.6); 8.333(2.6); 8.327(2.5); 8.196(1.0); 8.190(1.1); 8.166(2.2); 8.160(2.3); 8.119(2.9); 8.089(1.3); 7.856(2.8); 7.852(2.7); 7.265(6.4); 5.302(1.3); 4.682(0.6); 4.660(0.9); 4.634(0.9); 4.612(0.6); 4.210(2.2); 4.149(2.8); 3.763(2.9); 3.702(2.2); 3.420(16.0); 1.602(1.6); 1.366(7.4); 1.344(8.4); 1.336(8.6); 1.314(7.5); 1.255(0.4); 0.000(4.3)
Example 411: ¹H-NMR(400.0 MHz, DMSO):
8.771(4.4); 8.382(0.7); 8.368(1.4); 8.353(0.7); 8.280(2.4); 8.276(2.7); 8.198(1.4); 8.194(1.3); 8.176(1.7); 8.172(1.7); 8.017(2.5); 7.994(2.0); 7.403(4.4); 4.868(5.8); 4.078(3.3); 4.063(3.2); 3.960(1.3); 3.954(0.4); 3.942(3.8); 3.924(3.9); 3.903(10.3); 3.883(1.9); 3.840(2.3); 3.488(2.3); 3.445(1.9); 3.330(170.4); 2.676(0.5); 2.672(0.7); 2.667(0.5); 2.507 (88.7); 2.503(114.4); 2.498(82.5); 2.334(0.5); 2.330(0.7); 2.325(0.5); 2.169(1.0); 2.049(16.0); 1.604(11.6); 1.592(1.2); 1.260(4.4); 1.242(9.3); 1.224(4.3); 1.216(0.7); 0.000(4.0)
Example 412: ¹H-NMR(400.0 MHz, DMSO):
8.678(3.7); 8.671(3.7); 8.122(3.2); 8.118(3.2); 7.983(1.5); 7.961(4.3); 7.942(3.1); 7.938(2.8); 7.920(1.1); 7.916(1.1); 7.875(1.4); 7.855(1.4); 7.819(2.8); 7.812(2.7); 4.128(2.7); 4.112(5.6); 4.095(2.7); 3.929(0.8); 3.912(1.2); 3.903(10.1); 3.896(1.1); 3.892(1.2); 3.878(3.1); 3.835(3.1); 3.453(3.1); 3.410(2.7); 3.371(0.8); 3.336(284.3); 2.677(0.5); 2.672(0.7); 2.668(0.5); 2.542(0.4); 2.512(44.2); 2.508(86.7); 2.503(112.0); 2.499(80.9); 2.334(0.5); 2.330(0.7); 2.326(0.5); 1.879(0.3); 1.861(1.4); 1.844(2.9); 1.826(3.0); 1.808(1.5); 1.791(0.4); 1.587(16.0); 1.108(9.1); 1.091(9.0); 1.063(9.6); 1.056(6.2); 1.046(9.7); 1.038(11.2); 1.019(4.8); 0.000(6.2)
Example 413: ¹H-NMR(400.0 MHz, DMSO):
9.007(3.2); 9.001(3.3); 8.798(2.5); 8.793(2.4); 8.365(0.7); 8.351(1.3); 8.336(0.7); 8.324(0.4); 8.220(2.4); 8.216(2.8); 8.172(1.3); 8.168(1.1); 8.150(2.0); 8.145(1.9); 8.077(2.7); 8.054(1.7); 7.404(4.4); 7.211(0.3); 4.130(0.7); 4.115(0.7); 4.094(1.3); 4.079(1.2); 4.016(1.3); 4.002(1.3); 3.979(0.8); 3.966(0.9); 3.950(1.5); 3.940(2.1); 3.932(4.1); 3.910(14.4); 3.896(3.3); 3.395(2.3); 3.379(0.6); 3.339(173.8); 3.176(0.6); 2.683(0.6); 2.679(0.8); 2.675(0.6); 2.549(0.4); 2.532(2.5); 2.519(53.9); 2.515(106.3); 2.510(138.3); 2.506(100.1); 2.341(0.6); 2.337(0.8); 2.332(0.6); 2.178(1.1); 2.057(16.0); 1.507(0.8); 1.471(3.0); 1.452(2.9); 1.416(0.8); 1.249(4.5); 1.231(9.5); 1.212(4.4); 1.207(0.9); 0.881(0.4); 0.035(2.5); 0.027(53.5); 0.019(2.9); 0.013(4.4); 0.007(7.9); −0.001(0.4)
Example 414: ¹H-NMR(400.1 MHz, DMSO):
9.017(15.5); 9.011(16.0); 8.753(10.6); 8.748(10.1); 8.544(4.7); 8.524(4.8); 8.286(10.9); 8.282(11.4); 8.191(6.4); 8.186(5.6); 8.168(10.1); 8.164(9.6); 8.101(12.1); 8.079(7.5); 7.737(0.5); 5.755(13.6); 4.337(0.5); 4.316(2.1); 4.296(4.1); 4.275(4.2); 4.254(2.3); 4.233(0.5); 3.946(9.0); 3.900(12.4); 3.705(12.1); 3.659(9.0); 3.455(0.4); 3.316(80.4); 3.296(0.8); 3.278(85.6); 3.096(0.4); 2.513(5.0); 2.509(10.4); 2.504(14.2); 2.500(9.9); 2.495(4.5); 2.177(0.7); 2.169(1.5); 2.157(5.0); 2.152(6.0); 2.144(4.7); 2.137(8.9); 2.131(10.8); 2.117(5.9); 2.109(7.6); 2.090(2.6); 2.084(2.3); 2.071(0.5); 2.063(0.5); 2.056(0.6); 1.686(0.3); 1.670(2.6); 1.658(2.3); 1.647(4.7); 1.637(3.1); 1.627(5.9); 1.607(2.7); 1.603(3.1); 1.582(1.1); 1.072(0.5); 0.000(7.8)
Example 415: ¹H-NMR(400.0 MHz, DMSO):
9.020(3.7); 9.014(3.6); 8.755(3.0); 8.750(2.8); 8.283(3.0); 8.279(3.2); 8.193(1.5); 8.188(1.3); 8.171(2.3); 8.166(2.2); 8.101(3.2); 8.079(2.0); 8.040(1.3); 8.020(1.3); 4.002(0.7); 3.986(1.0); 3.966(1.0); 3.949(0.7); 3.903(9.2); 3.897(2.4); 3.851(3.0); 3.813(0.5); 3.693(3.0); 3.647(2.1); 3.597(1.0); 3.592(0.6); 3.579(1.1); 3.574(1.5); 3.557(1.4); 3.539(0.5); 3.525(0.5); 3.507(1.5); 3.490(1.6); 3.485(1.1); 3.472(0.6); 3.467(1.0); 3.449(0.4); 3.333(251.9); 3.175(0.5); 3.163(0.5); 2.676(0.5); 2.672(0.7); 2.668(0.5); 2.507(86.6); 2.503(111.8); 2.499(82.3); 2.334(0.5); 2.330(0.7); 2.326(0.5); 1.235 (0.6); 1.182(4.2); 1.164(9.0); 1.148(11.6); 1.132(16.0); 1.116(8.2); 0.000(3.4)
Example 416: ¹H-NMR(400.0 MHz, DMSO):
9.019(3.2); 9.014(3.3); 8.752(2.5); 8.746(2.5); 8.545(0.7); 8.530(1.3); 8.516(0.6); 8.316(0.4); 8.284(2.5); 8.280(2.7); 8.187(1.3); 8.183(1.1); 8.165(2.0); 8.160(1.9); 8.098(2.7); 8.075(1.7); 7.479(4.4); 7.269(0.4); 4.140(3.1); 4.125(3.0); 4.015(1.5); 3.997(4.0); 3.978(3.9); 3.960(1.3); 3.913(1.8); 3.903(12.3); 3.867(2.4); 3.717(2.4); 3.671(1.6); 3.572(0.8); 3.567(0.5); 3.554(0.9); 3.549(1.3); 3.532(1.2); 3.514(0.4); 3.497(0.4); 3.479(1.3); 3.462(1.3); 3.457(1.0); 3.444(0.5); 3.439(0.9); 3.371(0.5); 3.330(150.0); 3.169(0.9); 2.676(0.6); 2.671(0.8); 2.667(0.6); 2.542(0.5); 2.524(2.7); 2.511(53.7); 2.507(105.7); 2.503(136.9); 2.498(98.4); 2.334(0.6); 2.329(0.8); 2.325(0.6); 2.234(1.3); 2.160(0.3); 2.123(16.0); 1.319(4.5); 1.301(9.6); 1.283(4.4); 1.260(0.8); 1.242(0.5); 1.235(0.4); 1.166(3.5); 1.148(7.4); 1.131(3.4); 0.000(5.2)
Example 417: ¹H-NMR(400.0 MHz, DMSO):
8.670(3.0); 8.662(3.0); 8.368(0.6); 8.353(1.2); 8.339(0.6); 8.316(0.3); 8.118(2.4); 8.113(2.5); 7.979(1.3); 7.957(3.2); 7.931(2.2); 7.927(2.1); 7.909(0.9); 7.905(0.9); 7.805(2.2); 7.798(2.1); 7.396(4.2); 4.236(1.0); 4.219(3.5); 4.201(3.5); 4.184(1.1); 4.084(1.8); 4.075(2.1); 4.069(2.0); 4.061(1.9); 3.953(1.4); 3.935(3.8); 3.917(3.9); 3.903(11.6); 3.873(1.9); 3.829(2.3); 3.482(2.3); 3.439(1.9); 3.371(0.5); 3.364(0.6); 3.331(147.7); 3.169(0.5); 2.676(0.5); 2.671(0.7); 2.667(0.5); 2.542(0.4); 2.525(2.1); 2.511(44.5); 2.507(89.5); 2.502(117.1); 2.498(84.2); 2.494(40.9); 2.334(0.5); 2.329(0.7); 2.325(0.5); 2.167(1.0); 2.047(16.0); 1.601(11.6); 1.589(1.1); 1.449(3.7); 1.432(7.8); 1.414(3.5); 1.253(4.6); 1.235(9.9); 1.217(4.5); 0.874(0.3); 0.000(6.1)
Example 418: ¹H-NMR(400.0 MHz, DMSO):
8.679(3.1); 8.672(3.0); 8.369(0.7); 8.354(1.3); 8.340(0.6); 8.316(0.3); 8.118(2.5); 8.114(2.6); 7.980(1.3); 7.958(3.2); 7.931(2.2); 7.926(2.1); 7.909(0.9); 7.904(0.9); 7.817(2.2); 7.809(2.2); 7.397(4.3); 4.128(2.2); 4.111(4.6); 4.095(2.3); 4.084(2.0); 4.076(2.1); 4.070(2.1); 4.062(2.0); 3.953(1.4); 3.935(3.9); 3.917(3.9); 3.903(11.5); 3.871(1.9); 3.828(2.3); 3.481(2.3); 3.438(1.9); 3.378(0.3); 3.371(0.5); 3.331(198.0); 3.169(0.6); 2.676(0.5); 2.671(0.7); 2.667(0.5); 2.542(0.4); 2.525(2.1); 2.511(45.4); 2.507(89.4); 2.503(115.3); 2.498(82.3); 2.494(39.6); 2.334(0.5); 2.329(0.7); 2.325(0.5); 2.168(1.1); 2.047(16.0); 1.861(1.2); 1.844(2.4); 1.825(2.4); 1.808(1.3); 1.602(11.6); 1.590(1.1); 1.254(4.4); 1.236(9.5); 1.218(4.3); 1.195(0.3); 1.056(4.3); 1.037(8.8); 1.019(3.9); 0.000(4.1)
Example 419: ¹H-NMR(400.0 MHz, DMSO):
9.002(3.1); 8.997(3.3); 8.858(2.6); 8.853(2.4); 8.135(2.7); 8.131(2.8); 8.092(1.7); 8.070(2.8); 8.001(2.0); 7.996(1.9); 7.979(1.3); 7.974(1.2); 7.873(1.2); 7.853(1.2); 5.513(5.9); 4.008(0.6); 3.992(0.9); 3.973(0.9); 3.956(0.6); 3.903(8.3); 3.487(16.0); 3.370(0.4); 3.331(167.5); 3.174(1.2); 3.163(1.1); 2.676(0.4); 2.672(0.6); 2.667(0.4); 2.507(76.2); 2.503(97.7); 2.498(71.4); 2.334(0.5); 2.330(0.6); 2.325(0.4); 1.437(12.7); 1.151(7.3); 1.135(7.3); 1.106(7.2); 1.089(7.1); 0.000(2.7)
Example 420: ¹H-NMR(400.1 MHz, CDCl3):
8.943(0.3); 7.262(5.9); 5.299(3.3); 4.149(1.2); 4.131(3.5); 4.113(3.6); 4.095(1.2); 2.044(16.0); 1.994(2.1); 1.572(2.0); 1.322(0.4); 1.304(0.8); 1.287(1.1); 1.277(5.7); 1.264(4.2); 1.259(10.9); 1.241(5.5); 1.225(1.0); 1.187(0.8); 1.170(0.8); 0.899(1.9); 0.882(5.9); 0.864(2.4); 0.069(5.5); 0.000(3.3)

NMR Peak Lists Table 1

Example 421: $^1$H-NMR(400.0 MHz, DMSO):
9.956(0.6); 8.879(1.1); 8.873(1.2); 8.541(0.5); 8.339(0.6); 8.130(1.1); 8.126(1.1); 7.951(1.6); 7.946(1.3); 7.939(1.5); 7.398(1.9); 4.080(1.0); 4.076(0.9); 4.065(0.9); 4.061(0.9); 3.954(0.5); 3.936(1.6); 3.918(1.7); 3.900(0.6); 3.883(0.8); 3.839(0.9); 3.484(0.9); 3.440(0.8); 3.334(145.7); 2.891(4.7); 2.731(3.9); 2.525(0.9); 2.511(19.8); 2.507(39.7); 2.503(51.7); 2.498(37.0); 2.494(17.7); 2.049(7.1); 1.607(0.5); 1.593(4.6); 1.527(16.0); 1.255(1.9); 1.237(4.1); 1.219(1.9); 0.000(3.8)

Example 422: $^1$H-NMR(300.2 MHz, CDCl3):
8.720(1.0); 8.711(1.1); 8.513(0.4); 8.002(2.6); 7.807(1.2); 7.281(1.1); 7.255(2.4); 6.970(0.6); 6.952(0.3); 5.300(0.5); 4.322(0.6); 4.303(0.6); 4.238(0.6); 4.221(0.7); 4.188(0.3); 4.171(0.3); 4.075(0.5); 4.051(1.6); 4.026(1.6); 4.002(0.6); 3.965(0.8); 3.908(0.9); 3.367(0.9); 3.310(0.8); 2.192(6.6); 2.049(0.4); 2.021(0.6); 1.775(5.0); 1.559(16.0); 1.441(1.9); 1.417(3.8); 1.392(1.8); 1.260(0.4); 0.000(0.6)

Example 423: $^1$H-NMR(400.0 MHz, DMSO):
9.038(4.8); 9.033(4.8); 8.757(4.0); 8.752(3.8); 8.545(3.8); 8.319(2.2); 8.299(2.0); 8.249(2.1); 8.244(1.9); 8.226(2.8); 8.222(2.6); 8.105(4.0); 8.083(2.9); 5.479(0.5); 5.455(1.7); 5.431(1.8); 5.407(0.6); 3.904(16.0); 3.886(0.9); 3.869(1.3); 3.849(1.3); 3.832(0.9); 3.815(0.3); 3.329(211.6); 3.176(0.7); 3.163(0.7); 2.677(0.8); 2.672(1.0); 2.668(0.7); 2.508 (133.5); 2.503(164.8); 2.499(118.0); 2.334(0.8); 2.330(1.0); 2.325(0.7); 1.733(9.6); 1.235(0.4); 1.092(10.8); 1.076(10.6); 0.994(11.0); 0.977(10.9); 0.000(5.8)

Example 424: $^1$H-NMR(300.2 MHz, CDCl3):
8.935(3.1); 8.927(3.1); 8.319(2.4); 8.312(2.4); 8.169(1.1); 8.163(1.0); 8.139(2.3); 8.133(2.4); 8.093(3.0); 8.064(1.3); 7.813(2.6); 7.808(2.5); 7.280(2.2); 7.250(4.2); 7.040(0.6); 7.022(1.1); 7.005(0.6); 4.376(0.8); 4.357(0.8); 4.327(1.5); 4.308(1.5); 4.232(1.5); 4.215(1.5); 4.183(0.8); 4.165(0.8); 3.960(2.4); 3.936(3.8); 3.912(2.6); 3.902(2.3); 3.845(2.7); 3.523(2.5); 3.466(1.9); 2.199(16.0); 2.107(0.7); 2.083(0.7); 2.059(1.3); 2.035(1.3); 1.972(1.3); 1.949(2.2); 1.924(0.8); 1.901(0.7); 1.874(0.4); 1.849(1.4); 1.825(2.5); 1.801(2.6); 1.777(1.5); 1.752(0.4); 1.257(1.1); 0.903(4.8); 0.878(9.8); 0.854(4.9); 0.837(0.7); 0.830(0.7); 0.812(0.4); 0.533(0.3); 0.522(0.4); 0.507(1.1); 0.503(1.0); 0.481(0.7); 0.476(0.8); 0.439(1.0); 0.409(1.1); 0.395(0.4); 0.379(0.4); 0.213(0.7); 0.197(2.4); 0.182(2.5); 0.166(0.6); 0.000(1.6)

Example 425: $^1$H-NMR(300.2 MHz, CDCl3):
8.944(3.1); 8.936(3.1); 8.328(2.3); 8.321(2.2); 8.174(1.1); 8.168(1.0); 8.144(2.4); 8.138(2.4); 8.100(2.9); 8.070(1.2); 7.819(2.5); 7.813(2.4); 7.264(13.4); 7.007(0.5); 6.990(1.0); 6.973(0.5); 5.301(0.4); 4.370(0.7); 4.351(0.8); 4.320(1.5); 4.302(1.5); 4.230(1.5); 4.213(1.5); 4.180(0.8); 4.163(0.8); 4.082(1.3); 4.057(3.9); 4.033(3.9); 4.009(1.3); 3.900(2.1); 3.842(2.8); 3.523(2.5); 3.466(1.9); 2.199(16.0); 2.101(0.6); 2.077(0.7); 2.053(1.3); 2.046(0.5); 2.029(1.3); 1.976(1.2); 1.954(1.3); 1.928(0.6); 1.906(0.6); 1.636(3.4); 1.448(4.9); 1.423(10.1); 1.399(4.7); 1.283(0.4); 1.260(1.2); 0.904(0.5); 0.898(0.5); 0.882(1.5); 0.855(0.9); 0.838(0.5); 0.830(0.5); 0.524(0.3); 0.508(1.1); 0.481(0.8); 0.477(0.8); 0.435(1.0); 0.408(1.2); 0.394(0.4); 0.377(0.3); 0.211(0.6); 0.196(2.3); 0.181(2.5); 0.166(0.6); 0.011(0.4); 0.000(9.9); −0.011(0.5)

Example 426: $^1$H-NMR(300.2 MHz, CDCl3):
8.922(4.8); 8.914(4.8); 8.303(3.8); 8.296(3.7); 8.189(2.1); 8.182(2.1); 8.159(3.4); 8.153(3.5); 8.086(4.3); 8.057(2.5); 7.804(4.1); 7.798(4.0); 7.782(0.5); 7.776(0.4); 7.539(0.9); 7.521(1.6); 7.503(0.9); 7.283(2.4); 3.887(3.3); 3.830(4.3); 3.544(0.8); 3.536(2.2); 3.529(2.7); 3.516(5.9); 3.510(4.7); 3.492(12.9); 3.478(3.1); 3.468(7.8); 3.458(2.5); 3.445(3.0); 3.435(3.7); 3.380(0.6); 3.358(1.4); 3.341(1.5); 3.337(1.2); 3.319(1.1); 3.300(1.9); 3.295(0.9); 3.274(0.4); 2.093(1.0); 2.069(1.1); 2.045(2.2); 2.021(2.3); 2.002(1.7); 1.975(2.1); 1.953(2.3); 1.927(1.0); 1.905(1.0); 1.851(0.9); 1.830(2.9); 1.810(3.8); 1.790(2.7); 1.769(0.9); 1.298(0.6); 1.278(7.8); 1.255(16.0); 1.232(7.3); 0.931(0.4); 0.914(0.8); 0.908(0.7); 0.891(1.2); 0.875(0.9); 0.867(0.9); 0.851(0.6); 0.842(0.4); 0.566(0.4); 0.561(0.4); 0.556(0.5); 0.528(2.1); 0.499(3.2); 0.469(1.9); 0.438(0.5); 0.434(0.5); 0.220(3.6); 0.216(3.5); 0.204(3.6); 0.200(3.3); 0.000(1.7)

Example 427: $^1$H-NMR(300.2 MHz, CDCl3):
8.944(0.9); 8.931(15.1); 8.923(15.5); 8.336(0.6); 8.312(12.1); 8.305(11.9); 8.173(5.6); 8.167(5.6); 8.143(11.5); 8.137 (12.0); 8.091(14.5); 8.061(6.9); 7.808(13.3); 7.802(13.0); 7.783(0.9); 7.777(0.8); 7.735(0.4); 7.729(0.4); 7.707(0.3); 7.283(7.3); 7.008(5.6); 6.997(5.8); 3.911(11.5); 3.853(14.8); 3.485(13.3); 3.427(10.4); 2.796(0.9); 2.783(2.6); 2.771 (4.1); 2.759(6.0); 2.747(6.1); 2.735(4.3); 2.723(2.9); 2.710(1.1); 2.059(1.8); 2.034(1.9); 2.011(8.6); 1.987(16.0); 1.966(9.1); 1.937(3.6); 1.918(2.0); 1.302(0.7); 1.255(3.1); 0.934(0.4); 0.917(0.9); 0.907(1.4); 0.891(2.9); 0.879(4.1); 0.867(4.6); 0.855(3.8); 0.847(4.2); 0.843(4.2); 0.823(7.7); 0.816(9.0); 0.810(8.3); 0.806(7.2); 0.800(6.4); 0.792(8.3); 0.787(8.3); 0.782(7.6); 0.762(2.2); 0.758(2.3); 0.750(1.3); 0.738(1.7); 0.623(1.5); 0.611(2.4); 0.599(1.5); 0.594(1.5); 0.589(3.0); 0.576(7.0); 0.574(7.5); 0.559(10.2); 0.550(6.0); 0.544(7.6); 0.537(8.1); 0.528(6.6); 0.525(6.9); 0.509(4.4); 0.498(6.6); 0.492(7.7); 0.480(3.6); 0.472(3.6); 0.462(5.2); 0.433(2.3); 0.399(0.5); 0.257(0.9); 0.249(0.9); 0.241(1.4); 0.229(3.7); 0.217(13.6); 0.201(13.3); 0.189(3.8); 0.178(1.5); 0.161(0.9); 0.078(0.6); 0.000(5.3); −0.011(0.3)

Example 428: $^1$H-NMR(300.2 MHz, DMSO):
8.957(2.2); 8.950(2.2); 8.607(1.6); 8.600(1.5); 8.241(1.6); 8.235(1.8); 8.178(0.9); 8.171(0.7); 8.148(1.5); 8.142(1.4); 8.101(0.5); 8.080(2.7); 8.063(0.6); 8.051(1.1); 4.595(4.1); 3.887(1.3); 3.829(1.6); 3.511(1.6); 3.453(1.3); 3.382(0.7); 3.377(0.7); 3.359(2.3); 3.340(2.1); 3.322(13.9); 3.291(0.6); 3.275(1.2); 3.258(1.2); 3.255(1.3); 3.235(1.0); 3.211(16.0); 2.514(3.4); 2.508(7.0); 2.502(9.6); 2.496(7.0); 2.490(3.4); 1.603(8.2); 0.011(0.4); 0.000(9.4); −0.011(0.4)

Example 429: $^1$H-NMR(400.1 MHz, CDCl3):
8.974(2.4); 8.969(2.4); 8.293(2.0); 8.288(1.9); 8.188(0.9); 8.183(0.9); 8.166(1.9); 8.161(1.9); 8.126(2.4); 8.104(1.1); 7.891(2.2); 7.887(2.1); 7.264(6.0); 6.953(0.5); 6.933(0.5); 5.299(1.2); 4.486(0.4); 4.466(0.8); 4.445(0.8); 4.425(0.4); 3.984(2.1); 3.939(2.6); 3.543(2.6); 3.498(2.2); 3.402(16.0); 3.325(4.7); 2.425(0.5); 2.417(0.6); 2.415(0.6); 2.406(0.6); 2.400(0.8); 2.393(0.9); 2.388(0.7); 2.382(0.6); 2.375(0.6); 2.369(0.5); 2.358(0.3); 2.000(0.5); 1.995(0.6); 1.992(0.6); 1.973(0.9); 1.969(1.0); 1.947(0.8); 1.940(0.5); 1.803(0.7); 1.793(0.6); 1.786(0.9); 1.777(0.8); 1.771(0.9); 1.760(1.2); 1.750(0.5); 1.741(0.6); 1.734(0.5); 1.630(2.9); 0.000(3.8)

Example 430: $^1$H-NMR(300.2 MHz, CDCl3):
8.685(1.0); 8.676(1.1); 8.023(1.9); 8.019(2.2); 7.824(1.0); 7.264(3.7); 6.844(0.6); 3.942(0.8); 3.885(0.9); 3.341(0.9); 3.284(0.8); 1.749(4.7); 1.630(2.1); 1.567(16.0); 1.211(2.5); 1.189(2.5); 1.152(2.6); 1.130(2.6); 0.000(3.4)

Example 431: $^1$H-NMR(601.6 MHz, DMSO):
9.194(4.2); 8.402(0.7); 8.392(1.5); 8.382(0.8); 8.265(0.9); 8.261(2.2); 8.257(2.9); 8.254(3.0); 8.249(2.5); 8.246(1.4); 8.132(2.2); 8.125(0.4); 8.117(1.8); 7.407(4.2); 4.077(3.3); 4.067(3.4); 3.952(1.3); 3.940(3.9); 3.928(3.9); 3.916(1.3); 3.875(2.0); 3.847(2.3); 3.484(2.4); 3.455(2.4); 3.445(0.6); 3.424(0.7); 3.418(1.0); 3.411(1.3); 3.402(1.7); 3.366(1905.4); 3.337(2.9); 3.332(2.9); 3.327(1.9); 3.309(0.7); 3.289(0.3); 2.619(0.9); 2.616(1.2); 2.613(0.9); 2.544(26.1); 2.525(2.1); 2.522(2.7); 2.519(2.9); 2.510(63.3); 2.507(135.7); 2.504(189.7); 2.501(144.8); 2.499(72.2); 2.391(0.8); 2.389(1.2); 2.386(0.9); 2.168(0.9); 2.046(16.0); 1.610(11.6); 1.599(0.9); 1.257(4.5); 1.245(9.6); 1.233(4.6); 1.215(0.6); 0.000(5.8)

-continued

NMR Peak Lists Table 1

Example 432: $^1$H-NMR(400.0 MHz, DMSO):
9.102(4.3); 8.380(0.6); 8.365(1.3); 8.351(0.6); 8.316(0.3); 8.216(2.2); 8.212(2.6); 8.178(1.4); 8.173(1.2); 8.156(1.7); 8.151(1.6); 7.979(2.3); 7.957(1.9); 7.401(4.3); 4.077(3.2); 4.062(3.2); 3.960(1.2); 3.942(3.7); 3.924(3.8); 3.903(12.1); 3.866(1.8); 3.823(2.2); 3.470(2.2); 3.426(1.9); 3.331(170.4); 3.169(0.4); 2.676(0.6); 2.672(0.8); 2.667(0.6); 2.511 (50.1); 2.507(99.3); 2.503(129.5); 2.498(93.3); 2.494(45.4); 2.334(0.6); 2.329(0.8); 2.325(0.6); 2.168(0.6); 2.047 (16.0); 1.602(11.3); 1.261(4.4); 1.243(9.3); 1.225(4.3); 1.216(0.4); 0.000(5.0)
Example 433: $^1$H-NMR(400.0 MHz, DMSO):
9.002(2.8); 8.996(2.9); 8.715(2.2); 8.710(2.2); 8.371(0.7); 8.358(1.3); 8.344(0.7); 8.314(0.8); 8.059(1.4); 8.037(2.5); 8.000(2.8); 7.983(2.1); 7.978(1.5); 7.961(1.1); 7.956(1.0); 7.480(3.9); 5.531(5.2); 4.128(2.2); 4.117(2.3); 4.091(0.5); 3.991(1.1); 3.973(3.2); 3.955(3.3); 3.937(1.1); 3.902(16.0); 3.481(14.3); 3.405(0.3); 3.384(0.5); 3.332(306.5); 3.176 (1.6); 3.163(1.5); 2.672(1.0); 2.668(0.8); 2.507(131.1); 2.503(170.1); 2.498(125.8); 2.349(0.4); 2.330(1.0); 2.325(0.8); 2.090(14.6); 1.433(10.7); 1.366(0.3); 1.298(0.4); 1.275(4.2); 1.257(8.8); 1.238(5.2); 1.189(0.5); 1.175(0.6); 0.853(0.4); 0.000(5.7)
Example 434: $^1$H-NMR(499.9 MHz, CDCl3):
8.940(2.9); 8.935(2.9); 8.611(1.9); 8.310(2.4); 8.307(2.3); 8.160(1.2); 8.156(1.2); 8.142(2.0); 8.138(2.0); 8.092(2.6); 8.075(1.5); 7.910(4.2); 7.807(2.7); 7.804(2.6); 7.484(4.2); 7.274(3.3); 4.039(2.3); 4.005(2.6); 3.947(0.3); 3.868(16.0); 3.433(2.4); 3.399(2.2); 2.965(0.8); 2.890(0.7); 2.807(0.7); 1.866(0.4); 1.852(12.7); 1.240(0.5); 1.181(0.6); 0.075(1.4); 0.000(2.9)
Example 435: $^1$H-NMR(300.2 MHz, CDCl3):
8.532(2.7); 8.523(2.7); 7.961(1.7); 7.932(3.1); 7.862(2.3); 7.856(2.4); 7.833(1.4); 7.826(1.4); 7.638(3.1); 7.633(2.9); 7.284(1.4); 7.193(2.7); 7.184(2.6); 6.759(1.0); 6.733(1.0); 4.134(1.3); 4.111(1.0); 4.096(0.8); 4.073(1.0); 4.051(1.2); 4.047(1.0); 4.029(1.0); 4.025(1.1); 4.003(0.8); 3.981(0.4); 3.945(2.7); 3.888(3.2); 3.331(3.1); 3.273(2.6); 2.047(0.9); 1.741(16.0); 1.282(0.4); 1.258(0.9); 1.235(0.4); 1.208(8.6); 1.186(8.6); 1.148(8.7); 1.126(8.6); 0.000(0.9)
Example 436: $^1$H-NMR(300.2 MHz, CDCl3):
9.061(2.4); 9.054(2.5); 8.546(1.8); 8.540(1.8); 8.187(1.0); 8.181(1.0); 8.158(1.7); 8.151(1.8); 8.082(2.1); 8.052(1.2); 7.816(2.0); 7.810(2.0); 7.283(1.1); 6.703(0.5); 6.677(0.5); 4.188(0.5); 4.166(0.7); 4.162(0.5); 4.144(0.6); 4.140(0.7); 4.118(0.5); 3.987(2.0); 3.927(2.5); 3.554(2.5); 3.493(2.0); 3.403(16.0); 1.929(0.5); 1.283(0.6); 1.265(7.9); 1.242(10.2); 1.219(6.4); 0.901(0.7); 0.879(2.2); 0.856(0.8); 0.000(0.9)
Example 437: $^1$H-NMR(499.9 MHz, CDCl3):
9.071(2.8); 9.067(2.9); 8.560(2.5); 8.557(2.4); 8.178(1.3); 8.174(1.3); 8.160(1.9); 8.156(1.9); 8.086(2.4); 8.068(1.7); 7.819(2.6); 7.816(2.6); 7.343(3.9); 7.279(2.6); 6.917(0.6); 6.907(1.1); 6.897(0.6); 4.399(0.4); 4.388(0.4); 4.369(1.9); 4.357(3.4); 4.346(1.9); 4.327(0.4); 4.316(0.4); 4.144(0.3); 4.130(0.9); 4.106(1.1); 4.101(0.6); 4.091(3.2); 4.077(3.3); 4.062(1.1); 4.010(2.2); 3.974(2.5); 3.548(2.5); 3.512(2.2); 3.387(16.0); 2.260(14.7); 2.052(4.0); 1.897(0.4); 1.476(4.2); 1.462(8.6); 1.447(4.2); 1.277(1.1); 1.262(2.2); 1.248(1.2); 0.000(2.0)
Example 438: $^1$H-NMR(300.2 MHz, DMSO):
8.955(3.8); 8.595(4.0); 8.370(2.4); 8.352(1.5); 8.245(4.3); 8.169(1.9); 8.139(3.1); 8.075(3.6); 8.045(2.1); 7.405(5.0); 4.597(5.1); 4.091(4.6); 4.072(4.6); 3.968(1.7); 3.944(4.4); 3.920(4.5); 3.896(1.9); 3.841(2.1); 3.782(2.8); 3.524(2.6); 3.466(1.9); 3.332(13.6); 2.892(0.5); 2.734(0.5); 2.505(7.2); 2.062(16.0); 2.024(1.8); 2.001(2.0); 1.975(1.9); 1.936(1.7); 1.912(1.7); 1.889(1.2); 1.866(0.8); 1.258(4.7); 1.234(9.1); 1.210(4.8); 0.903(4.2); 0.879(7.6); 0.855(4.0); 0.000(1.1)
Example 439: $^1$H-NMR(300.2 MHz, DMSO):
8.955(7.7); 8.598(8.5); 8.527(0.4); 8.244(9.1); 8.195(6.6); 8.179(7.7); 8.143(7.0); 8.075(7.3); 8.046(4.3); 7.962(0.4); 4.598(9.7); 3.881(4.2); 3.823(5.7); 3.498(5.3); 3.439(4.3); 3.340(13.5); 2.895(0.8); 2.716(3.7); 2.702(3.7); 2.509(7.3); 2.025(1.5); 2.001(2.7); 1.979(3.9); 1.955(4.1); 1.927(4.1); 1.901(3.8); 1.879(2.8); 1.856(1.7); 0.922(9.0); 0.898(16.0); 0.875(8.8); 0.589(10.7); 0.568(11.8); 0.424(0.6); 0.355(0.4); 0.308(0.4); 0.286(0.4); 0.000(1.2)
Example 440: $^1$H-NMR(300.2 MHz, CDCl3):
8.963(5.0); 8.957(4.9); 8.274(4.0); 8.268(3.7); 8.192(1.9); 8.186(1.8); 8.163(3.6); 8.156(3.7); 8.104(4.6); 8.074(2.3); 7.838(4.4); 7.832(4.2); 7.461(0.9); 7.444(1.5); 7.427(0.9); 7.268(8.6); 3.891(3.8); 3.862(0.4); 3.833(4.6); 3.544(1.1); 3.532(2.3); 3.524(3.7); 3.513(6.0); 3.505(4.8); 3.490(9.2); 3.479(2.9); 3.467(8.3); 3.458(2.5); 3.443(2.9); 3.438(1.1); 3.380(4.4); 3.351(1.7); 3.327(11.0); 3.312(1.6); 3.306(1.3); 3.288(1.1); 2.243(1.1); 2.219(1.5); 2.196(1.9); 2.171(1.7); 2.147(0.5); 2.080(0.6); 2.046(0.5); 2.021(1.6); 1.997(2.0); 1.973(1.6); 1.949(1.2); 1.925(0.4); 1.840(1.2); 1.820(3.4); 1.800(4.6); 1.780(3.6); 1.759(1.4); 1.276(7.9); 1.253(16.0); 1.230(7.7); 1.063(5.6); 1.039(11.8); 1.014(5.1); 0.000(7.3); −0.011(0.4)
Example 441: $^1$H-NMR(300.2 MHz, CDCl3):
8.966(8.1); 8.959(8.3); 8.272(6.0); 8.266(6.0); 8.185(1.5); 8.179(2.8); 8.173(1.6); 8.155(3.5); 8.149(6.5); 8.143(3.7); 8.129(0.3); 8.108(5.6); 8.078(2.4); 7.838(6.6); 7.273(9.8); 7.250(1.4); 7.231(1.4); 7.212(1.2); 7.193(0.8); 4.290(0.4); 4.274(0.7); 4.269(0.9); 4.256(1.5); 4.247(1.2); 4.239(2.0); 4.226(1.5); 4.219(1.9); 4.207(1.3); 4.199(0.7); 4.186(0.6); 4.134(0.8); 4.110(0.9); 4.086(0.3); 4.066(2.1); 4.044(2.0); 4.038(2.7); 4.018(3.4); 3.997(2.1); 3.990(2.7); 3.969(2.1); 3.888(3.3); 3.877(3.4); 3.862(0.5); 3.830(4.1); 3.819(4.2); 3.690(2.3); 3.681(2.8); 3.670(2.2); 3.662(2.2); 3.641(2.0); 3.602(3.0); 3.589(1.3); 3.581(3.3); 3.574(2.7); 3.566(1.2); 3.558(2.7); 3.553(2.6); 3.545(1.9); 3.542(2.0); 3.537(2.1); 3.525(1.5); 3.519(1.4); 3.439(1.3); 3.420(5.3); 3.415(5.9); 3.410(2.3); 3.395(2.3); 3.376(2.1); 3.368(1.6); 3.362(4.3); 3.358(3.7); 3.349(1.8); 3.333(15.8); 2.804(0.5); 2.260(1.1); 2.253(1.0); 2.235(1.5); 2.228(1.4); 2.212(1.8); 2.205(1.8); 2.187(1.7); 2.180(1.6); 2.163(0.6); 2.156(0.5); 2.069(0.6); 2.046(5.7); 2.021(2.9); 1.997(2.3); 1.973(1.6); 1.949(0.5); 1.771(5.9); 1.480(15.5); 1.399(15.7); 1.339(15.6); 1.317(16.0); 1.284(1.4); 1.260(2.5); 1.236(1.2); 1.083(5.0); 1.077 (5.4); 1.059(11.0); 1.052(11.2); 1.034(5.0); 1.027(4.9); 0.000(7.3); −0.011(0.4)
Example 442: $^1$H-NMR(400.1 MHz, CDCl3):
8.970(2.3); 8.965(2.3); 8.291(1.8); 8.286(1.8); 8.178(0.8); 8.174(0.8); 8.156(1.9); 8.151(1.9); 8.121(2.3); 8.099(1.0); 7.896(2.0); 7.891(1.9); 7.338(3.2); 7.273(3.3); 6.906(0.4); 6.893(0.7); 6.880(0.4); 4.366(1.7); 4.356(1.9); 4.352(1.9); 4.342(1.7); 4.108(1.1); 4.089(3.3); 4.071(3.3); 4.053(1.1); 4.025(2.0); 3.979(2.4); 3.560(2.4); 3.515(2.1); 3.387(16.0); 3.333(4.8); 2.259(13.6); 1.477(4.1); 1.459(8.6); 1.441(4.1); 0.000(1.7)
Example 443: $^1$H-NMR(300.2 MHz, CDCl3):
8.958(2.7); 8.951(2.7); 8.682(0.8); 8.260(2.3); 8.254(2.3); 8.143(0.7); 8.137(0.7); 8.113(2.3); 8.108(2.5); 8.090(3.2); 8.060(0.9); 7.840(2.5); 7.835(2.5); 7.404(3.9); 7.286(1.1); 4.706(0.7); 4.689(0.7); 4.654(1.5); 4.637(1.5); 4.561(1.5); 4.546(1.5); 4.509(0.8); 4.494(0.7); 4.454(2.2); 4.396(2.5); 4.132(0.4); 4.108(0.4); 3.778(16.0); 3.556(2.3); 3.498(2.1); 3.345(5.1); 2.203(14.3); 2.045(1.6); 1.932(12.3); 1.282(0.5); 1.258(1.1); 1.235(0.5); 0.000(0.8)
Example 444: $^1$H-NMR(300.2 MHz, CDCl3):
8.968(6.5); 8.961(6.5); 8.270(5.4); 8.264(5.1); 8.180(2.2); 8.174(2.2); 8.151(5.0); 8.145(5.1); 8.130(0.4); 8.110(6.7); 8.080(2.8); 7.841(5.7); 7.835(5.5); 7.270(7.2); 7.138(1.2); 7.122(2.1); 7.104(1.3); 4.203(1.1); 4.195(1.2); 4.184(1.2);

| NMR Peak Lists Table 1 |
|---|
| 4.176(1.2); 4.145(2.4); 4.136(2.7); 4.126(2.5); 4.117(2.4); 4.044(2.4); 4.035(2.6); 4.027(2.6); 4.018(2.5); 3.985(1.2); 3.977(1.3); 3.968(1.2); 3.960(1.2); 3.902(5.1); 3.862(0.4); 3.844(6.3); 3.414(5.8); 3.356(4.7); 3.332(12.4); 2.283(0.4); 2.254(4.1); 2.245(7.3); 2.237(4.8); 2.211(2.7); 2.186(2.4); 2.161(0.8); 2.080(2.6); 2.070(0.7); 2.046(3.3); 2.021(2.7); 1.998(2.1); 1.974(1.5); 1.949(0.5); 1.722(1.3); 1.284(0.5); 1.260(0.9); 1.236(0.4); 1.097(0.7); 1.080(7.6); 1.055(16.0); 1.030(7.0); 0.000(5.7) |
| Example 445: $^1$H-NMR(300.2 MHz, CDCl3): |
| 8.972(2.8); 8.965(2.9); 8.280(2.1); 8.273(2.1); 8.171(0.8); 8.165(0.8); 8.142(2.2); 8.136(2.4); 8.109(2.9); 8.079(1.0); 7.845(2.3); 7.839(2.3); 7.264(14.1); 7.237(3.9); 6.955(0.5); 6.938(0.9); 6.920(0.5); 4.392(0.8); 4.373(0.8); 4.343(1.3); 4.323(1.3); 4.215(1.3); 4.199(1.4); 4.166(0.8); 4.149(0.8); 3.960(2.3); 3.936(3.6); 3.912(4.4); 3.854(2.6); 3.408(2.4); 3.350(2.0); 3.329(5.6); 2.253(0.6); 2.228(0.8); 2.205(1.3); 2.194(16.0); 2.181(1.3); 2.156(0.3); 2.046(0.4); 2.036(0.9); 2.011(1.1); 1.988(0.9); 1.964(0.7); 1.850(1.3); 1.825(2.4); 1.802(2.4); 1.777(1.4); 1.753(0.4); 1.620(4.5); 1.050(2.9); 1.026(6.5); 1.001(2.7); 0.902(4.2); 0.877(8.7); 0.853(3.9); 0.011(0.4); 0.000(11.6); −0.011(0.5) |
| Example 446: $^1$H-NMR(300.2 MHz, CDCl3): |
| 8.969(6.2); 8.963(6.1); 8.280(5.2); 8.274(5.0); 8.191(2.4); 8.185(2.4); 8.175(1.1); 8.162(4.7); 8.155(4.9); 8.114(6.2); 8.084(2.9); 7.849(5.8); 7.844(5.5); 7.263(36.7); 6.730(1.7); 6.702(1.8); 6.435(0.4); 5.301(0.4); 4.129(0.5); 4.107(1.3); 4.085(1.9); 4.063(1.7); 4.058(1.9); 4.036(1.3); 4.014(0.6); 3.899(4.8); 3.863(0.6); 3.841(5.9); 3.377(5.5); 3.325(12.2); 3.320(6.8); 3.009(0.3); 2.267(0.4); 2.242(1.5); 2.217(2.0); 2.194(2.5); 2.170(2.2); 2.145(0.8); 2.080(1.1); 2.032(0.7); 2.008(2.2); 1.984(2.6); 1.961(2.1); 1.936(1.6); 1.913(0.6); 1.648(1.3); 1.418(0.5); 1.393(0.9); 1.367(0.6); 1.293(0.4); 1.253(0.9); 1.218(16.0); 1.196(15.8); 1.159(16.0); 1.137(15.7); 1.096(0.6); 1.058(7.5); 1.034(15.3); 1.009(7.0); 0.000(27.5) |
| Example 447: $^1$H-NMR(300.2 MHz, CDCl3): |
| 8.969(6.8); 8.962(6.8); 8.276(5.3); 8.270(5.0); 8.189(2.3); 8.183(2.6); 8.159(5.1); 8.153(5.2); 8.112(6.6); 8.083(3.0); 7.842(5.7); 7.836(5.4); 7.608(0.4); 7.262(71.5); 7.214(0.3); 7.016(1.7); 6.991(1.8); 6.911(0.4); 4.415(1.1); 4.388(2.1); 4.360(2.1); 4.333(1.1); 3.884(5.1); 3.863(0.5); 3.844(0.3); 3.827(6.3); 3.375(5.8); 3.343(0.6); 3.324(13.4); 3.317(6.0); 2.414(0.7); 2.400(1.1); 2.389(1.3); 2.376(1.2); 2.364(1.4); 2.353(1.3); 2.339(1.1); 2.319(1.3); 2.307(1.3); 2.297(1.3); 2.284(1.1); 2.271(1.0); 2.261(0.7); 2.247(0.8); 2.223(1.6); 2.198(2.1); 2.176(2.7); 2.151(2.4); 2.126(0.9); 2.079(1.2); 2.056(0.3); 2.034(0.8); 2.009(2.3); 1.985(2.8); 1.962(3.4); 1.937(3.2); 1.930(2.9); 1.902(2.9); 1.875(1.7); 1.865(1.8); 1.839(0.9); 1.796(0.4); 1.776(1.5); 1.754(2.6); 1.741(2.2); 1.730(3.0); 1.719(3.4); 1.695(1.6); 1.684(1.4); 1.661(0.8); 1.574(2.0); 1.393(0.6); 1.368(0.3); 1.255(0.5); 1.171(0.4); 1.096(0.3); 1.054(7.6); 1.029(16.0); 1.004(7.0); 0.011(3.0); 0.000(67.5); −0.011(3.1) |
| Example 448: $^1$H-NMR(300.2 MHz, CDCl3): |
| 9.076(2.5); 9.069(2.6); 8.567(1.8); 8.561(1.9); 8.199(1.0); 8.193(1.0); 8.169(1.8); 8.163(1.9); 8.095(2.1); 8.065(1.2); 7.822(2.0); 7.816(2.0); 7.607(0.4); 7.585(0.6); 7.262(28.0); 3.979(1.9); 3.919(2.5); 3.596(1.8); 3.577(3.7); 3.558(2.3); 3.540(3.4); 3.515(4.8); 3.492(5.0); 3.480(2.8); 3.469(1.7); 3.457(0.7); 3.432(0.3); 3.424(0.5); 3.405(16.0); 1.889(0.5); 1.869(1.5); 1.850(2.1); 1.831(1.5); 1.811(0.5); 1.274(4.0); 1.251(8.2); 1.227(3.9); 0.011(1.0); 0.000(26.8); −0.011(1.1) |
| Example 449: $^1$H-NMR(300.2 MHz, CDCl3): |
| 9.078(2.9); 9.071(2.9); 8.565(2.4); 8.559(2.4); 8.186(1.1); 8.179(1.1); 8.156(2.0); 8.150(2.1); 8.096(2.7); 8.067(1.4); 7.825(2.6); 7.820(2.4); 7.313(3.9); 7.264(10.6); 6.860(0.9); 4.367(1.9); 4.354(2.4); 4.349(2.4); 4.337(2.0); 4.013(2.1); 3.998(2.3); 3.975(3.8); 3.952(4.1); 3.552(2.7); 3.519(0.5); 3.491(2.1); 3.385(16.0); 3.355(0.4); 2.958(0.6); 2.885(0.5); 2.254(14.8); 2.093(0.3); 1.892(1.3); 1.867(2.5); 1.843(2.5); 1.819(1.5); 1.795(0.4); 0.943(3.9); 0.918(7.9); 0.893(3.7); 0.000(9.9) |
| Example 450: $^1$H-NMR(300.2 MHz, CDCl3): |
| 9.079(2.9); 9.073(2.8); 8.567(2.6); 8.561(2.5); 8.189(1.1); 8.182(1.2); 8.159(2.2); 8.153(2.1); 8.098(2.8); 8.068(1.4); 7.824(2.8); 7.819(2.5); 7.262(31.0); 6.849(1.0); 4.006(2.1); 3.945(2.7); 3.553(0.4); 3.538(2.8); 3.519(0.7); 3.501(0.5); 3.477(2.2); 3.425(0.4); 3.387(16.0); 2.958(0.4); 2.886(0.5); 2.873(0.5); 2.861(0.8); 2.849(1.1); 2.837(1.1); 2.825(0.8); 2.813(0.5); 1.580(2.2); 0.894(0.7); 0.870(2.6); 0.853(2.3); 0.847(2.1); 0.830(1.0); 0.637(0.9); 0.620(2.2); 0.612(2.4); 0.606(2.3); 0.584(0.7); 0.000(29.7) |
| Example 451: $^1$H-NMR(300.2 MHz, CDCl3): |
| 8.966(2.6); 8.959(2.6); 8.803(0.7); 8.267(2.1); 8.152(0.7); 8.146(0.6); 8.122(2.2); 8.116(2.3); 8.097(3.0); 8.068(0.9); 7.846(2.2); 7.841(2.2); 7.478(3.3); 7.414(3.4); 7.272(2.4); 4.769(0.7); 4.752(0.7); 4.718(1.4); 4.701(1.3); 4.617(1.4); 4.601(1.4); 4.566(0.7); 4.550(0.7); 4.440(2.2); 4.382(2.5); 4.133(0.4); 4.110(0.5); 3.882(16.0); 3.559(2.3); 3.501(2.1); 3.335(5.0); 2.046(2.0); 1.928(12.3); 1.789(0.5); 1.283(0.6); 1.259(1.2); 1.235(0.5); 0.000(2.1) |
| Example 452: $^1$H-NMR(300.2 MHz, CDCl3): |
| 8.532(2.1); 8.524(2.1); 7.962(1.7); 7.933(2.6); 7.842(2.0); 7.837(2.1); 7.813(1.3); 7.807(1.3); 7.653(3.0); 7.648(2.8); 7.274(2.6); 7.240(4.4); 7.205(2.6); 7.196(2.6); 6.983(0.8); 6.966(1.3); 6.950(0.8); 5.299(2.2); 4.357(0.8); 4.338(0.8); 4.308(1.7); 4.289(1.7); 4.229(1.8); 4.212(1.8); 4.179(0.9); 4.162(0.9); 4.133(0.4); 4.067(2.5); 4.042(4.5); 4.018(4.3); 3.994(1.6); 3.971(2.5); 3.914(2.8); 3.357(2.6); 3.300(2.2); 2.293(0.5); 2.188(16.0); 2.046(0.5); 1.764(13.9); 1.458(0.4); 1.435(4.7); 1.410(9.0); 1.386(4.5); 1.283(0.4); 1.258(1.4); 1.235(0.4); 0.880(0.3); 0.854(0.4); 0.074(1.1); 0.000(1.8) |
| Example 453: $^1$H-NMR(300.2 MHz, CDCl3): |
| 8.966(5.9); 8.959(6.0); 8.276(4.9); 8.270(4.8); 8.187(1.4); 8.184(1.7); 8.182(1.7); 8.179(1.5); 8.158(3.0); 8.155(3.6); 8.152(3.7); 8.149(3.2); 8.109(3.7); 8.106(3.7); 8.104(3.7); 8.079(1.7); 8.074(1.7); 7.841(5.3); 7.270(8.8); 7.232(1.0); 7.196(1.3); 7.166(1.0); 4.371(0.6); 4.350(1.7); 4.328(1.5); 4.322(1.5); 4.300(1.3); 4.280(0.6); 4.205(1.5); 4.181(4.7); 4.157(5.3); 4.134(3.4); 4.110(2.1); 4.087(0.8); 4.078(1.6); 4.054(4.8); 4.030(4.9); 4.006(1.7); 3.983(2.6); 3.959(2.7); 3.926(3.1); 3.902(3.2); 3.353(4.0); 3.350(3.9); 3.330(12.1); 3.295(3.4); 3.293(3.3); 2.958(0.4); 2.886(0.3); 2.804(0.5); 2.560(5.1); 2.540(5.1); 2.490(5.2); 2.470(5.1); 2.046(9.0); 1.760(16.0); 1.749(16.0); 1.717(1.6); 1.311(5.3); 1.294(8.7); 1.288(12.1); 1.272(8.5); 1.264(6.7); 1.260(6.4); 1.238(9.2); 1.215(8.0); 1.190(5.5); 1.166(10.9); 1.142(5.3); 0.000(8.4); −0.011(0.4) |
| Example 454: $^1$H-NMR(300.2 MHz, CDCl3): |
| 9.060(2.8); 9.054(2.9); 8.528(2.7); 8.522(2.6); 8.174(1.2); 8.168(1.2); 8.144(2.2); 8.138(2.2); 8.073(2.9); 8.043(1.6); 7.760(2.9); 7.755(2.8); 7.272(2.2); 7.007(0.9); 6.981(0.9); 4.402(0.6); 4.375(1.1); 4.347(1.1); 4.320(0.6); 3.954(2.4); 3.897(2.9); 3.333(2.8); 3.276(2.4); 2.403(0.4); 2.391(0.6); 2.378(0.7); 2.367(0.7); 2.354(0.9); 2.341(0.7); 2.329(0.7); 2.316(0.8); 2.303(0.7); 2.293(0.7); 2.278(0.6); 2.267(0.5); 2.259(0.4); 1.971(0.8); 1.959(0.4); 1.940(1.2); 1.930(0.9); 1.926(0.9); 1.905(1.0); 1.902(1.0); 1.894(1.2); 1.875(0.6); 1.862(0.8); 1.829(0.5); 1.768(2.3); 1.752(16.0); 1.725(1.9); 1.713(1.9); 1.690(0.9); 1.678(0.7); 1.654(0.4); 0.000(1.6) |
| Example 455: $^1$H-NMR(300.2 MHz, CDCl3): |
| 9.071(2.8); 9.064(2.9); 8.543(2.2); 8.537(2.2); 8.158(1.0); 8.152(1.0); 8.129(2.1); 8.123(2.5); 8.076(2.7); 8.046(1.3); 7.769(2.4); 7.764(2.4); 7.265(8.2); 7.231(3.9); 6.932(0.5); 6.915(0.9); 6.898(0.5); 5.301(9.9); 4.365(0.7); 4.346(0.7); |

NMR Peak Lists Table 1

4.316(1.5); 4.297(1.5); 4.226(1.5); 4.209(1.5); 4.176(0.8); 4.160(0.8); 3.986(2.4); 3.960(2.3); 3.937(3.8); 3.929(3.3); 3.913(2.5); 3.361(2.6); 3.303(2.2); 2.185(16.0); 1.851(1.3); 1.827(2.5); 1.803(2.6); 1.776(14.5); 1.754(0.6); 0.905(4.3); 0.880(8.7); 0.855(3.9); 0.000(7.6); −0.011(0.3)
Example 456: $^1$H-NMR(300.2 MHz, CDCl3):
9.058(3.0); 9.051(3.0); 8.531(2.7); 8.525(2.7); 8.180(1.3); 8.174(1.4); 8.151(2.3); 8.145(2.3); 8.067(2.9); 8.037(1.7); 7.758(3.0); 7.752(2.9); 7.470(0.6); 7.455(1.0); 7.438(0.6); 7.274(2.5); 3.958(2.6); 3.901(3.1); 3.547(0.6); 3.535(1.4); 3.523(1.9); 3.514(3.6); 3.506(2.4); 3.503(2.3); 3.496(2.6); 3.490(6.2); 3.467(5.9); 3.444(2.9); 3.424(1.3); 3.404(0.6); 3.383(0.5); 3.362(1.1); 3.344(1.4); 3.335(3.3); 3.323(0.9); 3.317(0.8); 3.299(0.6); 3.277(2.8); 1.837(0.7); 1.818(2.5); 1.797(2.5); 1.764(16.0); 1.277(5.1); 1.254(10.3); 1.230(5.0); 0.000(2.0)
Example 457: $^1$H-NMR(300.2 MHz, CDCl3):
8.972(2.8); 8.965(2.9); 8.297(2.6); 8.291(2.6); 8.217(1.2); 8.211(1.3); 8.188(2.4); 8.182(2.6); 8.125(3.1); 8.095(1.6); 7 904(2.0); 7.269(4.4); 5.302(16.0); 4.142(0.6); 4.122(0.8) 4.105(1.2); 4.086(0.7); 4.019(1.0); 3.952(0.6); 3.891(0.6); 3.730(0.4); 3.714(0.4); 3.690(0.4); 3.552(3.3); 3.535(3.6); 3.493(2.1); 3.330(6.3); 1.833(3.1); 0.000(4.0)
Example 458: $^1$H-NMR(300.2 MHz, CDCl3):
8.969(3.2); 8.963(3.2); 8.278(2.7); 8.271(2.6); 8.186(1.1); 8.180(1.1); 8.156(2.5); 8.150(2.5); 8.111(3.3); 8.081(1.4); 7.843(2.9); 7.837(2.8); 7.263(12.6); 7.201(1.0); 7.184(0.6); 3.985(2.7); 3.927(3.2); 3.558(0.5); 3.543(0.8); 3.525(1.9); 3.512(4.7); 3.501(8.2); 3.487(2.8); 3.479(4.7); 3.464(0.8); 3.455(1.6); 3.436(1.3); 3.415(1.0); 3.410(0.9); 3.401(0.6); 3.383(0.7); 3.368(3.3); 3.325(6.2); 3.310(2.7); 1.778(16.0); 1.604(2.7); 1.213(5.2); 1.190(10.3); 1.167(5.0); 0.000 (11.7); −0.011(0.6)
Example 459: $^1$H-NMR(300.2 MHz, CDCl3):
8.971(2.1); 8.964(2.2); 8.280(1.7); 8.274(1.7); 8.190(0.7); 8.184(0.8); 8.161(1.6); 8.155(1.7); 8.113(2.2); 8.083(1.0); 7.848(1.8); 7.842(1.8); 7.262(19.5); 7.165(0.6); 7.135(0.6); 4.194(0.5); 4.179(0.5); 4.164(0.5); 3.980(1.8); 3.922(2.1); 3.543(0.6); 3.528(0.6); 3.511(1.5); 3.496(1.4); 3.477(1.5); 3.458(1.8); 3.446(0.9); 3.441(1.5); 3.426(1.7); 3.400(1.4); 3.380(16.0); 3.368(1.3); 3.362(2.4); 3.355(1.2); 3.349(0.9); 3.334(1.0); 3.324(4.2); 3.305(1.9); 3.286(15.1); 1.782 (0.7); 1.767(10.3); 1.568(3.9); 0.011(0.7); 0.000(18.3); −0.011(0.8)
Example 460: $^1$H-NMR(300.2 MHz, CDCl3):
8.947(3.1); 8.940(3.2); 8.261(2.5); 8.255(2.5); 8.228(1.4); 8.222(1.5); 8.199(2.1); 8.193(2.2); 8.082(2.8); 8.052(1.8); 7.853(2.9); 7.848(2.8); 7.607(0.4); 7.261(58.6); 4.567(2.1); 4.539(3.7); 4.510(2.8); 4.088(2.8); 4.032(3.2); 3.942(3.1); 3.912(3.7); 3.884(2.3); 3.331(3.3); 3.308(6.2); 3.275(2.7); 2.958(0.4); 2.884(0.3); 2.077(0.3); 2.065(0.3); 1.850(0.7); 1.772(16.0); 1.734(0.5); 1.568(3.2); 1.252(0.5); 0.011(1.9); 0.000(54.7); −0.011(2.6)
Example 461: $^1$H-NMR(300.2 MHz, CDCl3):
8.967(2.9); 8.960(3.0); 8.272(2.4); 8.266(2.4); 8.164(0.8); 8.158(0.8); 8.134(2.3); 8.129(2.6); 8.104(3.2); 8.074(1.1); 7.839(2.5); 7.834(2.6); 7.279(2.7); 7.272(4.1); 6.938(0.5); 6.921(1.0); 6.904(0.6); 4.407(0.4); 4.384(1.1); 4.372(0.9); 4.362(1.6); 4.354(1.0); 4.340(1.2); 4.323(1.7); 4.304(1.6); 4.233(1.5); 4.216(1.6); 4.183(0.8); 4.167(0.8); 4.157(0.5); 4.133(1.2); 4.109(1.2); 4.086(0.4); 4.008(2.3); 3.951(2.7); 3.381(2.6); 3.338(5.8); 3.324(2.3); 2.199(1.9); 2.191(16.0); 2.045(5.2); 1.784(13.3); 1.463(1.1); 1.450(14.4); 1.428(14.2); 1.283(1.4); 1.259(2.8); 1.235(1.4); 0.000(1.9)
Example 462: $^1$H-NMR(300.2 MHz, CDCl3):
8.973(2.6); 8.966(2.6); 8.538(1.5); 8.279(2.1); 8.273(2.1); 8.181(0.8); 8.175(0.8); 8.151(2.1); 8.145(2.3); 8.117(2.8); 8.088(1.0); 7.895(3.8); 7.857(2.3); 7.852(2.3); 7.475(3.7); 7.473(3.7); 7.262(20.0); 4.056(2.2); 3.999(2.6); 3.866(16.0); 3.450(2.5); 3.392(2.1); 3.326(5.0); 2.958(0.4); 1.849(12.6); 1.583(12.3); 0.011(0.8); 0.000(18.3); −0.011(0.9)
Example 463: $^1$H-NMR(300.2 MHz, CDCl3):
8.967(2.3); 8.960(2.3); 8.277(2.0); 8.271(2.0); 8.197(0.9); 8.190(0.9); 8.167(1.8); 8.161(1.8); 8.113(2.4); 8.083(1.2); 7.850(2.2); 7.844(2.2); 7.435(5.2); 7.366(1.4); 7.272(2.1); 4.134(0.5); 4.110(0.5); 3.976(2.0); 3.918(2.3); 3.833(16.0); 3.339(2.8); 3.334(4.9); 3.282(1.9); 2.066(0.3); 2.046(2.1); 1.778(0.5); 1.768(0.8); 1.752(11.5); 1.513(15.7); 1.417(0.3); 1.387(0.4); 1.283(0.6); 1.260(1.1); 1.236(0.6); 0.000(1.7)
Example 464: $^1$H-NMR(300.2 MHz, CDCl3):
8.972(3.3); 8.966(3.4); 8.281(2.6); 8.275(2.6); 8.159(0.9); 8.153(0.8); 8.129(2.8); 8.123(3.0); 8.104(3.8); 8.075(1.0); 7.838(2.8); 7.833(2.8); 7.378(4.8); 7.262(29.2); 6.911(0.7); 6.895(1.1); 6.879(0.6); 4.357(0.9); 4.339(0.8); 4.308(2.0); 4.290(2.0); 4.240(2.0); 4.223(2.0); 4.190(0.9); 4.173(0.9); 4.093(1.5); 4.069(4.8); 4.045(4.9); 4.021(1.7); 3.998(2.8); 3.941(3.2); 3.376(3.1); 3.327(6.6); 3.319(2.9); 2.657(1.1); 2.631(3.6); 2.606(3.7); 2.580(1.3); 1.775(16.0); 1.580(9.0); 1.454(5.0); 1.430(10.6); 1.406(4.9); 1.136(4.4); 1.110(9.7); 1.085(4.2); 0.011(1.0); 0.000(27.0); −0.011(1.2)
Example 465: $^1$H-NMR(300.2 MHz, CDCl3):
8.968(1.7); 8.962(1.8); 8.278(1.3); 8.272(1.3); 8.191(0.6); 8.185(0.6); 8.162(1.3); 8.156(1.4); 8.116(1.7); 8.086(0.7); 7.850(1.5); 7.844(1.4); 7.274(1.7); 6.951(1.1); 4.090(7.2); 3.982(1.4); 3.924(1.7); 3.346(2.1); 3.337(16.0); 3.288(1.4); 2.047(0.5); 1.803(0.5); 1.749(8.2); 1.658(12.4); 0.000(1.4)
Example 466: $^1$H-NMR(300.2 MHz, CDCl3):
8.993(0.4); 8.986(0.5); 8.971(2.5); 8.965(2.6); 8.353(0.3); 8.347(0.3); 8.298(2.3); 8.293(2.2); 8.252(0.4); 8.249(0.5); 8.220(1.3); 8.214(1.3); 8.191(1.6); 8.185(1.7); 8.126(2.6); 8.097(1.4); 7.917(1.0); 7.321(0.9); 7.275(2.6); 5.303(1.5); 3.931(2.4); 3.856(16.0); 3.540(3.0); 3.481(1.0); 3.346(1.6); 3.335(4.8); 1.895(0.4); 1.885(0.4); 1.865(0.6); 1.840(0.7); 1.823(0.6); 1.814(0.4); 1.797(0.4); 1.781(1.1); 1.681(0.4); 1.669(0.3); 1.658(0.6); 1.647(0.4); 1.634(0.7); 1.624(0.4); 1.611(0.5); 1.601(0.3); 1.588(0.4); 1.420(1.1); 1.398(1.1); 1.359(1.7); 1.339(5.0); 1.317(3.9); 1.260(0.3); 1.001(2.4); 0.985(2.4); 0.977(3.9); 0.960(1.3); 0.952(1.8); 0.000(1.7)
Example 467: $^1$H-NMR(300.2 MHz, CDCl3):
8.994(0.7); 8.987(0.8); 8.976(5.4); 8.969(5.5); 8.358(0.5); 8.351(0.5); 8.305(3.9); 8.299(3.8); 8.242(0.9); 8.236(0.6); 8.216(1.1); 8.212(2.4); 8.206(2.6); 8.183(3.9); 8.176(4.2); 8.128(4.9); 8.098(2.4); 7.939(4.3); 7.933(4.1); 7.265(17.7); 7.138(1.3); 5.301(1.3); 4.684(0.6); 4.620(0.5); 4.595(0.4); 3.521(0.5); 3.493(0.9); 3.362(0.6); 3.337(16.0); 3.329(13.1); 2.411(0.4); 1.616(5.3); 1.437(3.6); 1.414(4.4); 1.377(1.5); 1.357(13.5); 1.334(12.7); 1.254(1.0); 1.229 (0.3); 1.046(0.3); 0.895(2.6); 0.881(2.5); 0.871(2.8); 0.829(1.0); 0.808(0.9); 0.682(0.4); 0.325(0.4); 0.309(0.3); 0.071(0.4); 0.011(0.5); 0.000(15.6); −0.011(0.7)
Example 468: $^1$H-NMR(300.2 MHz, CDCl3):
8.991(0.4); 8.977(2.2); 8.971(2.2); 8.301(1.7); 8.295(1.7); 8.219(1.1); 8.213(1.4); 8.190(1.5); 8.184(1.7); 8.131(2.1); 8.101(1.1); 7.922(1.1); 7.315(0.8); 7.264(10.1); 5.302(1.0); 3.946(2.2); 3.866(16.0); 3.524(2.6); 3.464(1.8); 3.399(0.4); 3.337(0.8); 3.328(4.3); 1.601(3.0); 1.415(1.8); 1.393(1.9); 1.363(2.2); 1.343(7.0); 1.321(5.3); 1.284(0.4); 1.260(0.6); 1.255(0.6); 0.882(0.3); 0.000(8.8); −0.011(0.4)
Example 469: $^1$H-NMR(300.2 MHz, CDCl3):
8.985(2.9); 8.978(3.0); 8.310(2.4); 8.304(2.4); 8.209(0.8); 8.203(0.9); 8.180(1.9); 8.174(2.1); 8.162(0.5); 8.139(3.2); 8.109(1.3); 7.951(2.7); 7.946(2.6); 7.263(10.4); 6.356(0.4); 6.181(0.5); 6.166(0.9); 6.151(0.5); 5.975(0.4); 4.846(0.6);

NMR Peak Lists Table 1

4.824(0.8); 4.802(0.6); 4.760(0.5); 4.697(0.5); 4.658(2.2); 4.595(2.4); 3.622(0.5); 3.608(0.5); 3.578(0.6); 3.573(0.5); 3.565(0.9); 3.549(0.4); 3.529(0.5); 3.513(2.8); 3.479(0.9); 3.462(0.5); 3.450(2.2); 3.416(0.6); 3.362(16.0); 3.342(3.2); 3.334(6.2); 1.582(3.1); 1.339(1.3); 1.333(1.3); 1.316(1.4); 1.310(1.3); 1.293(5.1); 1.271(5.2); 1.251(4.9); 1.228(4.7); 0.000(9.3); −0.011(0.4)

Example 470: $^1$H-NMR(300.2 MHz, CDCl3):
8.972(5.5); 8.965(5.5); 8.281(4.1); 8.275(4.0); 8.183(1.7); 8.176(1.7); 8.153(4.5); 8.147(4.6); 8.117(5.3); 8.087(2.0); 7.852(4.6); 7.847(4.4); 7.270(9.3); 6.997(0.4); 6.966(0.6); 6.933(0.4); 6.739(0.4); 6.720(0.5); 6.709(0.5); 6.691(0.5); 4.158(1.4); 4.149(0.7); 4.134(4.2); 4.110(3.7); 4.087(1.3); 3.994(2.7); 3.980(1.6); 3.966(0.7); 3.952(0.5); 3.936(3.3); 3.922(2.3); 3.907(0.8); 3.881(0.6); 3.867(0.8); 3.851(0.5); 3.835(0.6); 3.813(0.6); 3.797(0.5); 3.759(0.4); 3.700(0.4); 3.687(0.4); 3.661(0.5); 3.650(0.6); 3.636(0.6); 3.621(1.6); 3.610(1.4); 3.599(1.1); 3.581(1.6); 3.569(1.1); 3.551(0.5); 3.539(1.2); 3.522(0.8); 3.512(0.4); 3.506(0.4); 3.499(0.7); 3.483(0.4); 3.473(0.5); 3.466(0.9); 3.460(0.6); 3.434(0.7); 3.427(1.0); 3.387(1.7); 3.382(1.9); 3.375(2.0); 3.372(1.7); 3.333(11.4); 3.325(2.0); 3.318(1.8); 3.314(1.5); 3.130(0.6); 3.091(1.1); 3.054(1.1); 3.015(0.4); 2.047(16.0); 2.010(0.3); 2.000(0.4); 1.796(9.0); 1.786(13.3); 1.782(8.3); 1.765(1.3); 1.760(1.2); 1.748(1.4); 1.733(1.0); 1.720(0.8); 1.704(3.8); 1.693(0.9); 1.680(0.7); 1.667(0.9); 1.651(1.0); 1.633(0.7); 1.623(0.5); 1.610(0.5); 1.602(0.5); 1.587(0.5); 1.578(0.4); 1.564(0.6); 1.522(0.6); 1.507(0.4); 1.481(0.4); 1.284(4.3); 1.260(8.7); 1.236(4.2); 1.033(0.4); 1.006(3.4); 0.982(3.3); 0.948(0.3); 0.889(4.0); 0.867(4.2); 0.852(3.8); 0.828(3.5); 0.701(2.7); 0.679(2.6); 0.663(0.4); 0.000(7.9); −0.011(0.4)

Example 471: $^1$H-NMR(300.2 MHz, CDCl3):
9.311(2.9); 9.282(2.7); 8.976(5.4); 8.969(5.7); 8.280(4.1); 8.274(4.2); 8.172(1.0); 8.168(1.1); 8.166(1.1); 8.163(0.9); 8.142(3.2); 8.138(3.8); 8.136(4.1); 8.133(3.5); 8.117(6.6); 8.087(1.9); 8.022(0.5); 7.834(4.7); 7.829(4.8); 7.270(8.8); 4.135(0.7); 4.111(0.8); 4.026(4.3); 3.969(5.1); 3.393(2.8); 3.387(3.2); 3.347(0.5); 3.334(12.5); 3.318(0.9); 3.311(1.4); 3.306(1.3); 3.297(1.2); 3.291(1.3); 3.281(1.3); 3.276(1.2); 3.260(1.1); 3.239(0.4); 2.959(3.9); 2.885(3.3); 2.047(3.4); 1.820(16.0); 1.812(15.3); 1.768(0.4); 1.709(4.2); 1.344(8.6); 1.335(8.6); 1.323(8.9); 1.314(8.4); 1.284(1.1); 1.260(2.0); 1.236(1.0); 0.988(0.3); 0.977(0.6); 0.960(0.9); 0.948(1.1); 0.934(1.2); 0.919(1.0); 0.905(0.9); 0.893(0.5); 0.651(0.5); 0.640(0.8); 0.625(1.3); 0.620(1.1); 0.615(0.9); 0.609(1.1); 0.595(1.3); 0.581(0.7); 0.570(0.5); 0.540(0.4); 0.526(0.6); 0.522(0.7); 0.510(1.1); 0.498(1.0); 0.494(1.5); 0.481(1.8); 0.465(1.6); 0.457(1.3); 0.451(1.5); 0.437(1.1); 0.433(1.1); 0.420(0.8); 0.406(0.8); 0.392(1.0); 0.376(1.0); 0.359(0.7); 0.342(0.4); 0.120(0.4); 0.105(0.6); 0.097(0.5); 0.089(1.2); 0.073(1.6); 0.058(1.3); 0.054(1.2); 0.042(0.9); 0.039(0.9); 0.023(0.7); 0.008(0.5); 0.000(7.2); −0.011(0.4)

Example 472: $^1$H-NMR(400.0 MHz, DMSO):
8.886(4.3); 8.353(0.7); 8.338(1.3); 8.324(0.7); 8.316(0.4); 8.094(2.3); 8.090(2.6); 8.048(1.4); 8.044(1.2); 8.026(1.7); 8.022(1.5); 7.815(2.4); 7.793(2.0); 7.397(4.4); 4.092(0.5); 4.076(2.8); 4.059(2.8); 4.039(14.9); 4.004(0.7); 3.957(1.3); 3.939(3.7); 3.921(3.8); 3.903(9.7); 3.841(1.7); 3.797(2.1); 3.446(2.1); 3.403(1.9); 3.332(162.8); 2.672(0.7); 2.507(92.0); 2.503(116.9); 2.499(87.2); 2.330(0.7); 2.325(0.5); 2.166(0.5); 2.046(16.0); 1.591(11.5); 1.259(4.4); 1.241(9.1); 1.223(4.2); 0.000(2.9)

Example 473: $^1$H-NMR(300.2 MHz, CDCl3):
8.955(1.9); 8.949(1.9); 8.273(2.3); 8.267(2.3); 8.164(0.7); 8.159(0.8); 8.135(2.1); 8.129(2.2); 8.103(2.7); 8.073(1.0); 8.013(1.7); 7.875(2.3); 7.871(2.3); 7.462(0.5); 7.443(1.0); 7.424(0.5); 7.271(4.5); 4.024(1.3); 4.020(1.2); 3.964(1.6); 3.960(1.6); 3.918(0.6); 3.902(0.9); 3.885(0.7); 3.711(0.5); 3.697(0.5); 3.673(1.2); 3.659(1.1); 3.633(1.5); 3.615(1.5); 3.594(0.9); 3.574(2.5); 3.545(0.8); 3.526(0.6); 3.511(2.1); 3.490(0.7); 3.470(0.7); 3.459(0.6); 3.443(0.6); 3.400(16.0); 3.334(5.8); 2.962(11.8); 2.885(10.3); 2.756(0.3); 1.255(0.5); 0.000(2.1)

Example 474: $^1$H-NMR(300.2 MHz, CDCl3):
9.068(3.2); 9.061(3.3); 8.540(2.7); 8.534(2.6); 8.176(0.7); 8.169(1.2); 8.163(0.7); 8.146(1.3); 8.140(2.4); 8.133(1.4); 8.078(2.3); 8.049(1.2); 7.766(2.9); 7.264(9.6); 7.242(0.4); 7.220(0.7); 7.194(0.6); 7.173(0.4); 5.301(0.9); 4.257(0.5); 4.241(0.9); 4.228(0.9); 4.221(0.9); 4.208(0.7); 4.061(0.8); 4.039(0.8); 4.033(1.1); 4.011(1.5); 3.990(0.9); 3.984(1.1); 3.967(1.6); 3.963(1.1); 3.945(1.4); 3.910(1.7); 3.888(1.7); 3.680(0.9); 3.659(0.9); 3.652(0.9); 3.631(0.8); 3.587(0.9); 3.574(0.4); 3.566(1.1); 3.559(1.1); 3.538(1.0); 3.528(0.7); 3.515(1.1); 3.508(0.7); 3.499(0.8); 3.495(0.9); 3.477(0.6); 3.443(0.6); 3.431(0.7); 3.426(0.7); 3.414(0.8); 3.396(1.0); 3.377(1.0); 3.372(1.9); 3.358(1.7); 3.351(0.7); 3.331(0.3); 3.315(1.4); 3.301(1.4); 2.316(0.3); 2.264(0.4); 1.785(16.0); 1.481(6.6); 1.394(6.5); 1.339(6.7); 1.318(6.7); 1.284(0.5); 1.255(2.5); 1.228(0.3); 1.222(0.4); 0.880(0.5); 0.855(0.4); 0.071(0.7); 0.000(3.3)

Example 475: $^1$H-NMR(499.9 MHz, DMSO):
9.628(7.1); 9.506(0.8); 8.999(0.5); 8.995(0.6); 8.970(5.2); 8.966(4.9); 8.667(0.8); 8.618(6.3); 8.380(0.7); 8.357(0.4); 8.353(0.4); 8.339(0.4); 8.336(0.4); 8.278(4.6); 8.201(3.4); 8.198(3.2); 8.183(4.7); 8.180(4.6); 8.171(0.5); 8.096(4.5); 8.079(3.2); 7.742(0.7); 5.773(0.5); 4.643(1.2); 4.624(8.4); 4.601(0.5); 4.588(0.8); 4.575(1.6); 4.562(2.0); 4.549(1.5); 4.535(0.6); 4.426(0.4); 4.389(0.5); 3.921(0.4); 3.878(2.7); 3.841(3.4); 3.663(3.4); 3.627(2.5); 3.387(0.4); 3.367(20.7); 3.335(20.1); 3.288(2.4); 3.278(1.0); 3.191(0.5); 2.933(0.4); 2.690(2.0); 2.513(6.4); 2.509(8.7); 2.506(6.8); 2.024(0.4); 1.222(3.8); 1.209(3.1); 1.129(16.0); 1.116(15.8); 0.000(3.6)

Example 476: $^1$H-NMR(300.2 MHz, CDCl3):
8.979(2.3); 8.972(2.4); 8.300(1.7); 8.293(1.8); 8.197(0.6); 8.193(0.6); 8.191(0.6); 8.168(1.5); 8.164(1.5); 8.162(1.5); 8.132(2.3); 8.102(0.9); 7.899(1.9); 7.894(2.0); 7.267(5.2); 7.161(0.6); 4.314(0.4); 4.311(0.4); 4.300(0.7); 4.291(0.5); 4.280(0.6); 4.134(0.3); 4.116(0.6); 4.110(0.4); 4.098(0.8); 4.094(0.7); 4.087(0.9); 4.077(0.8); 4.070(0.9); 4.065(0.7); 4.048(0.7); 4.006(1.1); 3.996(1.0); 3.946(1.4); 3.936(1.2); 3.731(0.9); 3.728(0.8); 3.711(0.8); 3.708(0.8); 3.703(0.9); 3.700(0.8); 3.683(0.7); 3.680(0.7); 3.596(0.6); 3.590(1.6); 3.586(2.0); 3.577(0.6); 3.565(1.1); 3.552(0.7); 3.546(1.1); 3.530(1.4); 3.526(1.8); 3.513(0.5); 3.493(0.7); 3.473(0.4); 3.446(0.4); 3.424(16.0); 3.331(4.6); 2.046(1.5); 1.651(3.9); 1.487(4.3); 1.424(5.1); 1.364(4.3); 1.348(5.2); 1.284(0.5); 1.260(1.1); 1.236(0.5); 0.000(0.8)

Example 477: $^1$H-NMR(300.2 MHz, CDCl3):
8.936(2.6); 8.930(2.6); 8.323(2.8); 8.317(2.7); 8.162(0.9); 8.158(1.0); 8.133(2.4); 8.128(2.5); 8.099(3.1); 8.070(1.2); 7.845(2.9); 7.383(1.1); 7.266(5.1); 4.025(1.2); 4.021(1.2); 3.965(1.5); 3.961(1.5); 3.897(1.1); 3.712(0.6); 3.698(0.6); 3.672(1.3); 3.663(1.3); 3.631(1.6); 3.615(1.6); 3.592(1.2); 3.580(1.4); 3.563(3.0); 3.526(0.7); 3.503(2.3); 3.446(0.6); 3.403(16.0); 3.159(0.4); 2.962(0.6); 2.885(0.6); 1.255(1.5); 0.000(3.2)

Example 478: $^1$H-NMR(300.2 MHz, CDCl3):
8.955(2.5); 8.947(2.6); 8.563(0.6); 8.337(2.1); 8.330(2.1); 8.295(0.5); 8.183(0.7); 8.177(0.7); 8.153(2.0); 8.147(2.1); 8.119(2.4); 8.090(0.9); 8.081(0.4); 8.076(0.5); 7.859(2.2); 7.854(2.2); 7.409(3.5); 7.264(9.2); 5.301(0.8); 4.743(0.4); 4.726(0.4); 4.691(1.6); 4.674(1.6); 4.657(1.6); 4.641(1.6); 4.605(0.4); 4.589(0.4); 4.267(2.0); 4.206(2.5); 4.143(1.0); 4.118(2.9); 4.094(2.9); 4.070(1.0); 3.765(2.6); 3.705(2.1); 3.414(16.0); 2.260(12.7); 1.503(3.8); 1.479(7.9); 1.455(3.7); 1.256(0.5); 0.071(9.7); 0.000(5.4)

| NMR Peak Lists Table 1 |
| --- |

Example 479: $^1$H-NMR(300.2 MHz, CDCl3):
8.934(3.3); 8.927(3.4); 8.306(3.2); 8.300(3.1); 8.156(1.1); 8.150(1.1); 8.126(2.8); 8.120(2.8); 8.089(3.7); 8.060(1.5); 7.800(3.4); 7.795(3.3); 7.292(1.6); 7.282(2.0); 7.276(2.1); 7.268(3.7); 7.208(0.8); 7.191(1.3); 7.173(0.8); 7.132(2.4); 7.126(2.2); 6.997(2.2); 6.995(2.1); 6.981(2.1); 5.297(0.9); 4.577(0.9); 4.556(0.9); 4.527(1.6); 4.506(1.6); 4.426(1.7); 4.408(1.7); 4.376(0.9); 4.358(0.9); 4.007(2.6); 3.950(3.0); 3.378(3.0); 3.321(2.5); 1.849(0.4); 1.796(16.0); 0.076(2.8); 0.000(1.8)
Example 481: $^1$H-NMR(400.0 MHz, DMSO):
11.360(2.6); 9.119(3.1); 9.114(3.1); 8.933(2.7); 8.929(2.6); 8.225(2.7); 8.221(2.8); 8.169(1.3); 8.164(1.1); 8.147(2.2); 8.142(2.0); 8.087(2.8); 8.065(1.7); 4.098(1.9); 4.053(2.5); 3.783(2.6); 3.739(2.0); 3.331(28.8); 2.892(0.6); 2.733(0.6); 2.508(28.0); 2.504(35.1); 2.499(25.7); 2.030(16.0); 0.008(0.3); 0.000(8.6); −0.008(0.3)
Example 482: $^1$H-NMR(400.0 MHz, DMSO):
9.029(5.5); 9.024(5.6); 8.766(4.3); 8.760(4.0); 8.313(2.1); 8.297(5.3); 8.293(6.4); 8.183(2.1); 8.178(1.9); 8.160(3.6); 8.156(3.5); 8.104(4.8); 8.082(2.8); 6.662(1.2); 6.527(2.6); 6.392(1.5); 4.104(0.4); 4.091(0.4); 4.016(0.4); 3.999(1.0); 3.983(1.5); 3.966(1.3); 3.962(1.5); 3.942(5.7); 3.934(5.9); 3.903(16.0); 3.889(0.6); 3.835(0.5); 3.462(0.5); 3.330 (191.9); 3.176(1.6); 3.163(1.5); 2.677(0.6); 2.672(0.8); 2.668(0.6); 2.512(50.5); 2.508(99.6); 2.503(128.9); 2.499 (92.2); 2.494(44.3); 2.334(0.6); 2.330(0.8); 2.325(0.6); 1.121(12.1); 1.104(15.4); 1.101(15.6); 1.084(12.2); 0.000(5.0)
Example 483: $^1$H-NMR(300.2 MHz, CDCl3):
9.808(0.9); 8.963(3.3); 8.956(3.4); 8.495(3.1); 8.452(3.0); 8.269(2.5); 8.263(2.5); 8.179(1.2); 8.173(1.2); 8.150(2.5); 8.143(2.6); 8.097(3.2); 8.067(1.5); 7.859(2.8); 7.853(2.7); 7.267(6.5); 5.019(0.5); 5.003(0.5); 4.962(1.4); 4.945(1.4); 4.897(1.4); 4.881(1.5); 4.839(0.6); 4.824(0.6); 4.455(2.8); 4.437(3.0); 4.134(0.5); 4.110(0.6); 3.588(3.0); 3.530(2.7); 3.328(6.4); 2.577(13.4); 2.047(2.5); 1.969(16.0); 1.677(2.7); 1.284(0.7); 1.260(1.6); 1.236(0.7); 0.000(5.3)
Example 484: $^1$H-NMR(300.2 MHz, CDCl3):
9.078(2.6); 9.071(2.6); 8.565(2.0); 8.559(2.0); 8.194(1.0); 8.188(1.0); 8.164(1.8); 8.158(1.9); 8.099(2.3); 8.069(1.3); 7.821(2.1); 7.815(2.1); 7.261(33.9); 6.947(0.5); 6.923(0.5); 6.910(0.4); 4.498(0.4); 4.471(0.8); 4.442(0.8); 4.415(0.4); 3.978(2.0); 3.918(2.6); 3.553(0.4); 3.533(2.6); 3.519(0.5); 3.473(2.0); 3.423(0.4); 3.399(16.0); 2.803(0.6); 2.427(0.6); 2.416(0.7); 2.403(0.9); 2.391(1.0); 2.379(0.8); 2.367(0.6); 2.093(0.4); 2.003(0.7); 1.968(1.0); 1.938(0.9); 1.911(0.4); 1.811(0.5); 1.795(1.0); 1.781(0.9); 1.770(1.1); 1.759(1.3); 1.736(0.7); 1.725(0.6); 1.575(0.8); 0.011(1.1); 0.000(32.5); −0.011(1.8)
Example 485: $^1$H-NMR(300.2 MHz, CDCl3):
9.080(2.7); 9.074(2.8); 8.567(2.2); 8.562(2.2); 8.194(0.9); 8.190(0.9); 8.164(1.6); 8.160(1.6); 8.101(2.4); 8.072(1.3); 7.828(2.5); 7.822(2.3); 7.262(20.2); 7.152(0.8); 4.310(0.6); 4.299(0.8); 4.289(0.7); 4.279(0.7); 4.270(0.3); 4.115(0.6); 4.097(0.9); 4.093(0.8); 4.087(0.9); 4.075(0.7); 4.069(1.1); 4.047(0.6); 3.991(1.1); 3.980(1.1); 3.931(1.5); 3.920(1.4); 3.729(1.0); 3.706(1.1); 3.700(1.1); 3.680(0.9); 3.610(0.3); 3.595(0.6); 3.583(0.7); 3.571(2.2); 3.568(2.2); 3.552(1.2); 3.545(1.5); 3.531(0.9); 3.524(0.8); 3.518(0.9); 3.511(1.9); 3.492(0.9); 3.472(0.5); 3.465(0.4); 3.445(0.6); 3.421(16.0); 2.113(0.4); 2.093(0.4); 1.574(3.3); 1.487(5.4); 1.422(5.3); 1.387(0.5); 1.364(5.6); 1.348(5.6); 0.011(1.0); 0.000(19.1); −0.011(1.1)
Example 486: $^1$H-NMR(400.0 MHz, DMSO):
9.044(4.1); 8.384(0.7); 8.369(1.4); 8.355(0.7); 8.315(0.4); 8.189(2.8); 8.179(1.7); 8.174(1.0); 8.157(2.6); 8.152(3.0); 8.046(2.3); 8.024(1.7); 7.815(1.4); 7.406(4.3); 4.080(3.4); 4.065(3.4); 3.962(1.3); 3.954(0.4); 3.944(4.0); 3.926(4.0); 3.903(14.6); 3.878(1.7); 3.835(2.0); 3.486(2.1); 3.443(1.9); 3.399(0.4); 3.387(0.6); 3.378(0.9); 3.336(360.2); 3.169 (3.1); 2.676(0.6); 2.672(0.8); 2.667(0.6); 2.542(0.5); 2.525(2.6); 2.511(51.7); 2.507(102.6); 2.503(133.1); 2.498(95.2); 2.494(45.5); 2.334(0.6); 2.329(0.8); 2.325(0.6); 2.170(0.7); 2.049(16.0); 2.041(1.4); 1.607(10.7); 1.596(0.9); 1.565 (0.6); 1.264(4.8); 1.246(10.2); 1.235(0.7); 1.228(4.7); 1.218(0.6); 0.874(0.4); 0.000(2.9)
Example 487: $^1$H-NMR(400.0 MHz, DMSO):
8.889(4.8); 8.098(2.7); 8.094(2.9); 8.060(1.6); 8.056(1.3); 8.039(1.9); 8.034(1.6); 7.862(1.4); 7.841(1.4); 7.817(2.6); 7.795(2.2); 4.093(0.4); 4.040(16.0); 3.922(0.7); 3.903(11.1); 3.886(1.0); 3.869(0.7); 3.847(2.1); 3.804(2.5); 3.418 (2.5); 3.375(2.6); 3.333(285.0); 3.299(0.5); 2.676(0.6); 2.672(0.8); 2.507(106.0); 2.503(133.7); 2.499(98.0); 2.334 (0.6); 2.330(0.8); 2.325(0.6); 1.575(13.0); 1.103(7.5); 1.087(7.5); 1.060(7.7); 1.043(7.6); 0.000(2.9)
Example 488: $^1$H-NMR(400.0 MHz, DMSO):
9.104(5.8); 8.316(0.4); 8.219(3.1); 8.215(3.6); 8.190(2.0); 8.186(1.5); 8.168(2.2); 8.164(1.9); 7.981(3.1); 7.958(2.5); 7.887(1.6); 7.867(1.5); 3.925(0.8); 3.903(13.6); 3.889(1.3); 3.874(3.2); 3.856(0.4); 3.830(3.0); 3.443(3.1); 3.399(2.8); 3.334(406.0); 3.175(0.4); 3.163(0.4); 2.676(0.7); 2.672(1.0); 2.668(0.8); 2.507(128.7); 2.503(165.5); 2.499(122.3); 2.334(0.7); 2.330(1.0); 2.326(0.7); 1.588(16.0); 1.105(9.2); 1.088(9.2); 1.060(9.3); 1.044(9.2); 0.000(3.9)
Example 489: $^1$H-NMR(300.2 MHz, CDCl3):
8.945(3.2); 8.937(3.4); 8.602(5.1); 8.320(3.1); 8.313(2.9); 8.152(1.0); 8.146(1.0); 8.122(2.8); 8.117(3.0); 8.097(3.8); 8.068(1.3); 7.803(3.2); 7.800(3.2); 7.268(4.7); 7.254(0.9); 7.234(1.3); 7.216(0.8); 5.301(0.5); 4.696(0.8); 4.675(0.8); 4.645(1.8); 4.624(1.7); 4.567(1.8); 4.548(1.8); 4.516(0.8); 4.497(0.8); 3.981(2.5); 3.924(2.9); 3.384(2.8); 3.326(2.4); 2.958(0.4); 2.884(0.4); 2.440(16.0); 2.046(0.8); 1.780(15.2); 1.755(0.8); 1.701(0.5); 1.259(0.7); 1.235(0.5); 0.073(1.3); 0.000(3.9)
Example 490: $^1$H-NMR(300.2 MHz, DMSO):
9.195(0.9); 9.174(2.0); 9.154(1.0); 9.005(4.3); 8.997(4.7); 8.759(3.3); 8.752(3.2); 8.234(3.1); 8.228(3.7); 8.198(2.0); 8.191(1.4); 8.168(3.0); 8.162(2.7); 8.088(3.7); 8.059(2.2); 7.698(4.5); 7.687(5.4); 7.572(5.8); 7.561(4.9); 5.765(1.9); 4.596(5.1); 4.576(5.1); 3.936(2.4); 3.878(3.2); 3.580(3.0); 3.522(2.3); 3.344(2.5); 2.524(0.6); 2.518(1.3); 2.512(1.8); 2.506(1.3); 2.500(0.6); 1.687(16.0); 0.000(1.3); −0.040(0.8)
Example 491: $^1$H-NMR(300.2 MHz, CDCl3):
8.939(3.0); 8.931(3.3); 8.312(2.7); 8.304(3.5); 8.178(1.0); 8.172(1.0); 8.149(2.3); 8.142(2.4); 8.103(2.9); 8.073(1.3); 7.915(4.5); 7.820(2.5); 7.815(2.5); 7.278(2.1); 4.099(1.2); 4.075(3.8); 4.054(3.5); 4.051(4.4); 4.026(1.4); 3.997(2.8); 3.443(2.6); 3.386(2.2); 2.249(16.0); 2.046(0.9); 1.864(13.5); 1.458(4.5); 1.434(9.5); 1.409(4.4); 1.259(0.7); 1.235 (0.4); 0.078(1.3); 0.000(1.8)
Example 492: $^1$H-NMR(400.0 MHz, DMSO):
8.513(4.3); 8.353(0.7); 8.339(1.3); 8.324(0.7); 8.316(0.4); 8.138(2.4); 8.133(2.6); 8.054(1.4); 8.050(1.3); 8.032(1.7); 8.028(1.5); 7.819(2.4); 7.797(2.0); 7.397(4.2); 4.562(5.6); 4.092(0.6); 4.076(2.5); 4.054(16.0); 3.957(1.2); 3.939(3.6); 3.921(3.7); 3.903(15.2); 3.852(1.8); 3.809(2.1); 3.459(2.2); 3.416(1.9); 3.371(0.4); 3.330(142.8); 3.169(0.5); 2.672 (0.7); 2.542(0.5); 2.507(92.9); 2.502(117.8); 2.498(84.2); 2.329(0.7); 2.168(1.0); 2.047(15.2); 1.591(11.0); 1.580(1.2); 1.258(4.2); 1.240(8.8); 1.222(4.1); 0.919(0.4); 0.000(4.5)

NMR Peak Lists Table 1

Example 493: $^1$H-NMR(400.0 MHz, DMSO):
8.889(3.9); 8.403(0.7); 8.389(1.3); 8.374(0.7); 8.341(2.2); 8.337(2.5); 8.316(0.5); 8.294(1.2); 8.289(1.1); 8.271(1.8); 8.267(1.7); 8.187(2.4); 8.165(1.6); 7.407(4.3); 5.038(5.8); 4.081(2.8); 4.066(3.4); 3.962(1.2); 3.954(0.4); 3.944(3.7); 3.926(3.8); 3.903(15.9); 3.861(2.1); 3.508(2.2); 3.464(1.9); 3.364(0.4); 3.331(192.2); 3.169(0.7); 2.676(0.5); 2.672(0.7); 2.667(0.5); 2.525(1.9); 2.511(47.0); 2.507(92.8); 2.503(120.1); 2.498(87.6); 2.494(43.8); 2.334(0.6); 2.330(0.8); 2.325(0.6); 2.171(0.8); 2.049(16.0); 1.614(11.2); 1.263(4.3); 1.245(9.2); 1.234(1.0); 1.227(4.3); 1.217(0.7); 0.874(0.4); 0.000(4.3)
Example 494: $^1$H-NMR(300.2 MHz, CDCl3):
8.952(2.7); 8.944(2.9); 8.339(2.0); 8.332(2.0); 8.206(1.0); 8.199(1.0); 8.176(2.0); 8.170(2.1); 8.122(2.5); 8.092(1.3); 7.951(1.6); 7.845(2.2); 7.839(2.2); 7.270(3.9); 5.300(1.1); 4.061(2.1); 4.028(0.9); 4.004(5.1); 3.979(2.8); 3.955(0.9); 3.437(2.4); 3.380(2.0); 2.095(14.9); 2.089(16.0); 2.046(0.8); 1.889(12.4); 1.831(0.7); 1.755(0.7); 1.385(3.7); 1.361 (8.2); 1.337(3.6); 1.259(0.6); 0.000(3.5)
Example 495: $^1$H-NMR(300.2 MHz, CDCl3):
8.935(3.3); 8.928(3.4); 8.295(2.4); 8.288(2.4); 8.150(0.9); 8.144(0.9); 8.120(2.7); 8.114(2.8); 8.090(3.3); 8.060(1.1); 7.794(2.6); 7.788(2.5); 7.310(0.5); 7.288(0.8); 7.276(2.0); 7.267(0.5); 4.117(0.5); 4.093(0.5); 4.087(0.6); 4.073(0.3); 4.067(0.8); 4.063(0.6); 4.043(0.7); 4.038(0.8); 4.013(0.7); 3.982(2.9); 3.925(3.3); 3.873(0.6); 3.853(0.8); 3.844(0.7); 3.824(1.1); 3.803(0.5); 3.794(0.7); 3.774(0.4); 3.409(3.1); 3.352(2.6); 2.047(0.8); 1.802(16.0); 1.260(0.5); 0.079(1.9); 0.000(1.3)
Example 496: $^1$H-NMR(300.2 MHz, CDCl3):
8.942(1.8); 8.935(1.8); 8.321(1.7); 8.314(1.7); 8.293(2.2); 8.287(2.1); 8.193(0.7); 8.187(0.7); 8.163(1.4); 8.157(1.4); 8.107(1.8); 8.077(0.9); 7.816(1.8); 7.811(1.7); 7.378(1.2); 7.268(2.0); 6.264(2.2); 6.258(2.1); 3.949(1.4); 3.892(1.7); 3.324(1.7); 3.267(1.4); 1.752(16.0); 1.743(10.0); 0.000(1.7)
Example 497: $^1$H-NMR(300.2 MHz, CDCl3):
9.256(0.7); 8.914(3.2); 8.906(3.3); 8.299(2.4); 8.292(2.3); 8.219(1.5); 8.212(1.4); 8.189(2.1); 8.183(2.1); 8.069(2.6); 8.039(1.8); 7.816(2.8); 7.811(2.7); 7.264(12.5); 5.302(1.4); 4.569(2.2); 4.541(3.9); 4.511(2.9); 4.078(2.7); 4.022(3.1); 3.950(3.1); 3.924(2.3); 3.920(3.6); 3.893(2.2); 3.320(3.0); 3.263(2.6); 2.958(0.3); 2.046(0.9); 1.769(16.0); 1.616(2.0); 1.260(0.7); 0.011(0.4); 0.000(10.1); −0.011(0.4)
Example 498: $^1$H-NMR(300.2 MHz, CDCl3):
8.953(2.5); 8.946(2.5); 8.347(1.8); 8.339(1.7); 8.195(0.7); 8.193(0.7); 8.189(0.7); 8.165(1.4); 8.163(1.4); 8.159(1.5); 8.122(2.2); 8.093(0.9); 7.866(2.0); 7.861(1.9); 7.266(5.7); 7.159(0.6); 5.302(0.5); 4.318(0.4); 4.311(0.4); 4.301(0.7); 4.291(0.5); 4.280(0.6); 4.116(0.7); 4.098(0.7); 4.094(0.7); 4.088(0.8); 4.077(0.6); 4.070(0.9); 4.066(0.7); 4.048(0.6); 3.999(1.0); 3.989(1.1); 3.939(1.3); 3.928(1.4); 3.731(0.9); 3.728(0.9); 3.711(0.8); 3.708(0.9); 3.702(0.9); 3.700(0.8); 3.682(0.7); 3.679(0.7); 3.596(0.4); 3.578(2.0); 3.575(1.9); 3.565(1.3); 3.552(0.8); 3.546(1.2); 3.533(0.7); 3.526(0.7); 3.518(1.4); 3.515(1.5); 3.493(0.6); 3.474(0.4); 3.447(0.4); 3.423(16.0); 3.179(0.3); 2.804(0.4); 1.487(4.8); 1.423(4.5); 1.365(4.8); 1.349(4.7); 0.000(4.9)
Example 499: $^1$H-NMR(300.2 MHz, CDCl3):
9.081(2.2); 9.074(2.3); 8.566(1.9); 8.560(1.8); 8.191(0.9); 8.185(0.9); 8.162(1.8); 8.155(1.9); 8.102(2.2); 8.073(1.1); 7.827(2.1); 7.821(2.0); 7.263(9.4); 7.019(0.6); 4.190(1.1); 4.182(1.2); 4.172(1.2); 4.163(1.6); 4.162(1.5); 4.153(1.2); 4.143(1.2); 4.135(1.6); 4.110(0.6); 4.085(0.3); 4.004(2.0); 3.944(2.6); 3.564(2.6); 3.504(2.1); 3.417(16.0); 2.303(1.3); 2.295(2.7); 2.286(1.3); 2.046(2.4); 1.589(5.9); 1.284(0.7); 1.260(1.4); 1.236(0.7); 0.000(8.1); −0.011(0.3)
Example 500: $^1$H-NMR(300.2 MHz, CDCl3):
8.941(2.0); 8.934(2.0); 8.320(1.8); 8.314(1.7); 8.183(0.8); 8.177(0.8); 8.153(1.5); 8.147(1.5); 8.102(2.0); 8.072(0.9); 7.809(1.9); 7.804(1.9); 7.261(31.6); 7.010(0.7); 6.985(0.7); 4.414(0.4); 4.387(0.8); 4.359(0.7); 4.332(0.4); 3.875(1.5); 3.817(1.8); 3.364(1.7); 3.306(1.4); 2.388(0.6); 2.377(0.5); 2.362(0.6); 2.333(0.5); 2.319(0.5); 2.306(0.6); 2.287(0.5); 2.222(0.5); 2.198(0.7); 2.174(0.9); 2.149(0.8); 2.123(0.3); 2.079(0.3); 2.008(0.8); 1.983(1.0); 1.960(1.2); 1.935(1.2); 1.902(1.1); 1.873(0.7); 1.838(0.4); 1.775(0.6); 1.755(1.0); 1.742(0.9); 1.731(1.2); 1.720(1.3); 1.695(0.6); 1.686(0.5); 1.553(16.0); 1.252(0.4); 1.052(2.4); 1.028(4.7); 1.003(2.2); 0.000(29.9)
Example 501: $^1$H-NMR(300.2 MHz, CDCl3):
8.943(1.6); 8.936(1.6); 8.322(1.4); 8.316(1.3); 8.176(0.6); 8.169(0.7); 8.153(0.7); 8.146(1.3); 8.139(0.8); 8.100(1.1); 8.069(0.5); 7.810(1.4); 7.261(27.5); 7.230(0.5); 7.210(0.4); 7.196(0.4); 4.253(0.4); 4.236(0.4); 4.224(0.3); 4.217(0.4); 4.065(0.4); 4.043(0.4); 4.037(0.5); 4.016(0.8); 3.994(0.5); 3.988(0.6); 3.966(0.4); 3.877(0.7); 3.866(0.7); 3.819(0.9); 3.808(0.9); 3.687(0.5); 3.666(0.5); 3.659(0.4); 3.638(0.4); 3.597(0.6); 3.587(0.4); 3.576(0.6); 3.568(0.7); 3.555(0.5); 3.547(0.6); 3.541(0.5); 3.533(0.6); 3.521(0.4); 3.418(0.4); 3.407(1.2); 3.393(0.6); 3.374(0.4); 3.346(1.0); 2.233(0.3); 2.210(0.4); 2.202(0.4); 2.185(0.3); 2.042(0.5); 2.018(0.6); 1.994(0.5); 1.970(0.4); 1.555(16.0); 1.479(3.3); 1.397(3.4); 1.339(3.2); 1.316(3.5); 1.081(1.1); 1.074(1.2); 1.056(2.3); 1.050(2.4); 1.032(1.1); 1.025(1.1); 0.011(1.1); 0.000(25.5); −0.011(1.3)
Example 502: $^1$H-NMR(300.2 MHz, CDCl3):
8.946(3.0); 8.938(3.0); 8.324(2.2); 8.317(2.1); 8.166(0.9); 8.160(0.9); 8.136(2.4); 8.130(2.5); 8.099(2.8); 8.069(1.1); 7.812(2.4); 7.807(2.2); 7.262(23.1); 7.237(3.9); 6.945(0.5); 6.928(0.9); 6.911(0.6); 5.301(1.9); 4.391(0.8); 4.372(0.8); 4.342(1.4); 4.323(1.3); 4.216(1.4); 4.199(1.4); 4.166(0.8); 4.150(0.8); 3.961(2.3); 3.938(3.6); 3.914(2.5); 3.902(2.3); 3.844(2.7); 3.397(2.4); 3.339(2.0); 2.251(0.6); 2.226(0.8); 2.203(1.5); 2.193(16.0); 2.179(1.3); 2.154(0.9); 2.034(0.9); 2.010(1.1); 1.986(0.9); 1.962(0.6); 1.852(1.3); 1.827(2.4); 1.804(2.4); 1.779(1.4); 1.755(0.4); 1.587(6.1); 1.049(3.1); 1.024(6.7); 0.999(2.8); 0.904(4.3); 0.879(9.0); 0.855(4.0); 0.070(0.9); 0.011(0.6); 0.000(19.8); −0.011(0.8)
Example 503: $^1$H-NMR(300.2 MHz, CDCl3):
8.974(2.2); 8.967(2.3); 8.280(1.8); 8.274(1.7); 8.180(0.7); 8.174(0.7); 8.150(1.8); 8.144(1.9); 8.116(2.4); 8.086(0.9); 7.843(1.9); 7.837(1.8); 7.263(12.1); 7.068(0.4); 7.052(0.6); 4.164(0.4); 4.156(0.8); 4.148(0.7); 4.138(0.8); 4.097(0.9); 4.089(3.0); 4.081(5.6); 4.039(0.4); 4.022(0.4); 3.979(1.9); 3.922(2.2); 3.382(2.2); 3.350(16.0); 3.327(5.3); 1.781(11.0); 0.011(0.4); 0.000(11.0); −0.011(0.5)
Example 504: $^1$H-NMR(300.2 MHz, CDCl3):
8.972(3.1); 8.965(3.1); 8.282(2.6); 8.276(2.5); 8.182(1.0); 8.176(0.9); 8.152(2.6); 8.146(2.6); 8.118(3.4); 8.089(1.2); 7.850(2.8); 7.845(2.7); 7.265(10.1); 6.814(0.9); 6.787(0.9); 4.000(1.0); 3.976(3.3); 3.963(2.0); 3.950(1.9); 3.918(3.9); 3.901(1.0); 3.524(0.7); 3.517(0.8); 3.485(1.9); 3.478(1.6); 3.451(1.6); 3.445(1.9); 3.413(0.8); 3.405(0.7); 3.375(2.9); 3.331(5.8); 3.317(2.6); 2.959(0.4); 2.886(0.3); 1.963(0.5); 1.956(0.6); 1.949(0.7); 1.942(0.5); 1.921(0.6); 1.914(0.8); 1.907(0.8); 1.900(0.6); 1.849(0.7); 1.840(0.7); 1.833(0.5); 1.804(0.9); 1.797(0.9); 1.790(0.8); 1.767(14.8); 1.638(16.0); 1.609(0.7); 1.593(0.5); 1.570(0.9); 1.564(0.9); 1.555(0.9); 1.549(0.8); 1.526(1.3); 1.519(1.0); 1.512(1.2); 1.488(0.7); 1.483(0.8); 1.473(0.7); 1.468(0.7); 1.445(0.3); 0.000(9.0); −0.011(0.5)

NMR Peak Lists Table 1

Example 505: ¹H-NMR(300.2 MHz, CDCl3):
9.464(2.4); 8.979(3.2); 8.973(3.3); 8.286(3.0); 8.280(2.9); 8.173(0.9); 8.167(0.8); 8.144(2.8); 8.138(2.9); 8.121(4.0); 8.091(1.1); 7.845(3.1); 7.841(2.9); 7.263(16.0); 5.301(0.4); 4.582(5.7); 4.574(5.8); 4.022(2.5); 3.965(2.9); 3.412(3.0); 3.355(2.5); 3.330(6.2); 2.910(0.4); 2.544(1.6); 2.536(3.4); 2.528(1.7); 2.077(0.4); 2.065(0.4); 1.850(0.4); 1.825(16.0); 1.805(1.6); 1.606(0.9); 1.253(0.7); 0.010(0.6); 0.000(13.9); −0.011(0.8)

Example 506: ¹H-NMR(300.2 MHz, CDCl3):
8.979(2.6); 8.973(2.6); 8.301(2.2); 8.295(2.1); 8.193(0.9); 8.187(0.9); 8.163(2.2); 8.157(2.3); 8.130(2.8); 8.100(1.0); 7.897(2.3); 7.891(2.2); 7.263(17.8); 6.854(0.8); 5.301(0.3); 4.105(0.5); 4.020(2.1); 3.960(2.6); 3.556(3.1); 3.520(0.5); 3.496(2.1); 3.439(0.4); 3.428(0.6); 3.391(16.0); 3.361(0.3); 3.327(5.1); 2.958(0.5); 2.886(0.5); 2.874(0.4); 2.862(0.7); 2.850(1.0); 2.837(1.0); 2.825(0.7); 2.813(0.5); 2.113(0.5); 2.095(0.5); 1.605(1.9); 1.284(0.4); 1.254(0.7); 0.893(0.6); 0.870(2.3); 0.853(2.1); 0.846(1.8); 0.841(1.0); 0.829(0.9); 0.638(0.7); 0.625(1.6); 0.621(1.9); 0.613(2.0); 0.608(1.8); 0.585(0.6); 0.322(0.5); 0.305(0.5); 0.011(0.7); 0.000(15.4); −0.011(0.9)

Example 507: ¹H-NMR(300.2 MHz, CDCl3):
8.934(5.9); 8.926(6.0); 8.314(4.6); 8.307(4.6); 8.179(1.3); 8.176(1.7); 8.170(1.4); 8.150(2.7); 8.146(3.5); 8.144(3.5); 8.140(2.9); 8.094(3.2); 8.088(3.4); 8.064(1.6); 8.059(1.7); 7.804(5.1); 7.278(4.4); 7.239(0.9); 7.204(1.3); 7.173(0.9); 5.304(10.8); 4.374(0.6); 4.353(1.2); 4.331(1.4); 4.325(1.4); 4.303(1.2); 4.283(0.6); 4.205(1.4); 4.181(4.5); 4.158(4.7); 4.134(1.8); 4.127(0.8); 4.080(1.5); 4.056(4.7); 4.032(4.9); 4.009(1.6); 3.975(2.4); 3.952(2.6); 3.918(2.8); 3.894(3.1); 3.344(3.9); 3.287(3.3); 2.805(9.5); 2.563(4.8); 2.543(4.8); 2.492(5.2); 2.473(5.1); 2.046(0.8); 1.760(16.0); 1.750(15.1); 1.312(5.1); 1.296(8.5); 1.288(11.5); 1.274(8.6); 1.264(7.4); 1.240(8.3); 1.218(7.5); 1.193(5.5); 1.169(10.8); 1.145(5.2); 1.133(0.8); 1.112(0.9); 1.094(0.4); 0.880(1.0); 0.857(0.4); 0.000(3.4)

Example 508: ¹H-NMR(300.2 MHz, CDCl3):
8.970(4.7); 8.963(4.8); 8.280(3.5); 8.274(3.5); 8.189(1.3); 8.183(1.3); 8.159(2.9); 8.155(2.8); 8.153(2.8); 8.109(3.0); 8.082(1.4); 7.851(2.1); 7.843(3.4); 7.836(2.4); 7.608(0.4); 7.262(56.7); 7.019(0.7); 6.989(1.1); 6.956(0.6); 6.911(0.4); 4.125(0.9); 4.102(0.9); 4.088(0.6); 4.076(0.6); 3.989(1.9); 3.974(2.3); 3.932(2.3); 3.917(2.8); 3.559(0.5); 3.547(0.6); 3.536(1.5); 3.524(1.6); 3.512(1.6); 3.500(1.6); 3.489(0.7); 3.477(0.5); 3.469(0.4); 3.458(0.4); 3.448(1.4); 3.425(5.9); 3.417(2.4); 3.411(2.2); 3.402(6.2); 3.378(1.7); 3.356(9.2); 3.341(4.8); 3.324(9.7); 3.299(3.9); 1.766(16.0); 1.763(14.2); 1.566(2.0); 1.237(8.7); 1.215(9.1); 1.213(10.1); 1.189(3.8); 1.174(6.0); 1.151(6.0); 1.112(4.6); 1.088(9.3); 1.065(4.5); 0.011(1.6); 0.000(46.0); −0.011(2.1)

Example 509: ¹H-NMR(300.2 MHz, CDCl3):
8.973(2.9); 8.966(3.0); 8.657(0.7); 8.277(2.2); 8.271(2.2); 8.161(0.8); 8.155(0.8); 8.131(2.4); 8.126(2.6); 8.105(3.1); 8.075(1.0); 7.860(2.4); 7.854(2.3); 7.346(3.8); 7.262(28.4); 5.301(0.6); 4.736(0.8); 4.719(0.8); 4.684(1.3); 4.667(1.3); 4.534(1.4); 4.519(1.4); 4.482(0.9); 4.467(0.9); 4.355(2.2); 4.297(2.6); 4.135(0.7); 4.092(3.8); 4.067(3.9); 4.043(1.4); 3.705(7.0); 3.589(2.3); 3.530(2.0); 3.330(5.5); 2.485(0.6); 2.461(0.8); 2.438(1.0); 2.414(0.9); 2.207(16.0); 2.188(1.2); 2.164(1.0); 2.140(0.8); 2.046(0.3); 1.627(1.8); 1.482(4.6); 1.457(9.6); 1.433(4.6); 1.267(0.5); 1.254(0.5); 1.017(2.9); 0.993(6.4); 0.968(2.8); 0.070(0.8); 0.011(0.6); 0.000(20.5); −0.011(1.0)

Example 510: ¹H-NMR(499.9 MHz, CDCl3):
8.940(2.5); 8.936(2.4); 8.331(2.0); 8.326(2.0); 8.164(1.0); 8.160(1.0); 8.146(1.9); 8.142(1.8); 8.106(2.3); 8.088(1.2); 7.856(2.3); 7.853(2.1); 7.268(2.6); 6.858(0.7); 3.997(2.2); 3.961(2.6); 3.527(2.6); 3.491(2.3); 3.386(16.0); 2.861(0.5); 2.854(0.7); 2.847(1.0); 2.840(1.0); 2.832(0.7); 2.825(0.5); 2.802(2.1); 1.254(0.5); 0.872(0.7); 0.865(1.0); 0.863(1.2); 0.859(1.9); 0.855(1.0); 0.849(1.7); 0.845(1.7); 0.841(0.8); 0.835(0.8); 0.628(0.8); 0.618(1.9); 0.615(1.8); 0.610(1.8); 0.608(1.6); 0.605(1.4); 0.597(0.6); 0.000(1.8)

Example 511: ¹H-NMR(300.2 MHz, CDCl3):
8.992(0.4); 8.978(2.5); 8.971(2.6); 8.398(0.3); 8.392(0.3); 8.353(3.2); 8.347(3.3); 8.290(1.9); 8.284(2.0); 8.213(0.3); 8.199(1.3); 8.193(0.9); 8.169(1.9); 8.163(2.1); 8.128(2.5); 8.099(1.0); 7.896(2.1); 7.891(2.1); 7.418(1.3); 7.306(0.7); 7.262(17.8); 6.415(0.3); 6.388(3.3); 6.383(3.3); 4.050(2.0); 3.990(2.5); 3.516(2.5); 3.455(2.1); 3.421(16.0); 3.334(0.7); 3.326(4.9); 2.957(0.6); 2.884(0.6); 2.804(0.8); 1.902(2.4); 1.824(10.7); 1.803(10.7); 1.587(0.3); 1.253(0.5); 0.011(0.5); 0.000(13.9); −0.011(0.7)

Example 513: ¹H-NMR(300.2 MHz, CDCl3):
9.058(0.8); 8.973(1.6); 8.966(1.6); 8.425(1.0); 8.407(1.0); 8.294(1.1); 8.287(1.1); 8.226(0.7); 8.219(0.7); 8.196(1.1); 8.190(1.2); 8.127(1.4); 8.097(0.8); 7.907(1.3); 7.901(1.2); 7.607(0.5); 7.282(0.3); 7.280(0.3); 7.279(0.4); 7.277(0.4); 7.276(0.4); 7.274(0.5); 7.273(0.6); 7.271(0.8); 7.270(1.1); 7.261(94.4); 7.250(1.4); 7.235(0.5); 7.218(1.5); 7.041(0.7); 7.024(0.7); 6.910(0.5); 4.019(1.2); 3.959(1.6); 3.837(0.6); 3.565(1.6); 3.505(1.3); 3.467(10.5); 3.319(3.1); 2.421(0.4); 2.389(5.8); 1.884(1.0); 1.808(13.7); 1.775(0.6); 1.543(16.0); 0.307(1.7); 0.011(2.3); 0.000(74.5); −0.011(2.9)

Example 514: ¹H-NMR(300.2 MHz, CDCl3):
8.976(3.7); 8.969(3.7); 8.297(2.9); 8.291(2.9); 8.202(1.6); 8.196(1.4); 8.173(3.1); 8.166(3.3); 8.129(3.5); 8.099(1.5); 7.899(3.1); 7.893(3.0); 7.266(13.0); 7.252(0.7); 7.245(0.8); 7.244(0.8); 4.470(0.3); 4.451(0.8); 4.441(0.5); 4.428(0.9); 4.422(0.9); 4.409(0.5); 4.404(0.6); 4.400(0.8); 4.381(0.4); 4.005(1.8); 3.996(1.6); 3.945(2.3); 3.936(2.1); 3.748(0.8); 3.724(12.9); 3.693(15.0); 3.557(2.5); 3.554(2.7); 3.497(2.0); 3.494(2.2); 3.411(16.0); 3.405(13.8); 3.339(0.4); 3.329(8.0); 2.804(0.6); 2.622(2.3); 2.602(3.3); 2.596(2.2); 2.581(2.0); 2.577(2.0); 2.046(1.4); 1.643(4.9); 1.338(5.5); 1.320(5.6); 1.315(6.2); 1.298(4.8); 1.284(0.6); 1.260(1.0); 1.236(0.4); 0.323(0.3); 0.306(0.4); 0.000(8.3); −0.011(0.3)

Example 515: ¹H-NMR(300.2 MHz, CDCl3):
9.088(0.8); 8.971(4.5); 8.964(4.6); 8.277(3.6); 8.271(3.6); 8.178(0.9); 8.173(1.5); 8.167(1.0); 8.149(2.2); 8.143(3.6); 8.138(2.4); 8.108(4.0); 8.077(1.6); 7.855(3.8); 7.262(40.2); 4.433(2.1); 4.423(0.6); 4.418(0.7); 4.406(2.8); 4.391(1.7); 4.375(3.1); 4.362(0.9); 4.348(2.5); 4.108(1.3); 4.086(1.3); 4.079(1.6); 4.057(1.5); 4.053(1.5); 4.031(1.4); 4.025(1.8); 4.003(1.5); 3.989(1.0); 3.979(1.1); 3.971(0.7); 3.959(1.2); 3.942(1.5); 3.931(0.9); 3.924(1.0); 3.912(0.8); 3.850(0.8); 3.831(1.4); 3.812(1.4); 3.801(1.2); 3.797(1.0); 3.784(1.3); 3.764(0.9); 3.752(1.9); 3.732(1.5); 3.723(1.3); 3.703(1.2); 3.621(1.3); 3.601(1.4); 3.593(1.4); 3.570(2.9); 3.559(2.3); 3.512(2.1); 3.501(2.1); 3.326(8.7); 2.370(1.0); 2.053(0.9); 2.046(0.7); 2.024(1.1); 1.949(16.0); 1.946(15.6); 1.787(0.4); 1.702(0.5); 1.680(0.4); 1.584(3.4); 1.525(9.8); 1.460(9.5); 1.396(0.4); 1.362(10.3); 1.352(10.6); 1.320(0.9); 1.284(1.0); 1.255(2.7); 0.881(0.6); 0.856(0.6); 0.011(1.0); 0.000(27.3); −0.011(1.4)

Example 516: ¹H-NMR(300.2 MHz, CDCl3):
8.993(0.3); 8.978(2.5); 8.971(2.5); 8.293(1.8); 8.286(1.7); 8.212(0.8); 8.208(1.3); 8.202(0.9); 8.178(1.9); 8.172(1.9); 8.131(2.3); 8.101(1.0); 7.899(2.0); 7.894(2.1); 7.878(1.3); 7.313(0.8); 7.275(0.4); 7.273(0.4); 7.272(0.5); 7.261(37.6); 6.814(2.6); 6.810(2.6); 4.008(1.9); 3.948(2.4); 3.547(2.5); 3.487(2.0); 3.448(16.0); 3.333(0.6); 3.324(4.7); 2.471(1.1); 2.468(1.1); 2.433(9.7); 2.429(9.7); 1.967(2.5); 1.879(13.8); 1.564(8.3); 0.011(0.8); 0.000(29.3); −0.009(1.0); −0.011(1.3)

NMR Peak Lists Table 1

Example 517: ¹H-NMR(300.2 MHz, CDCl3):
8.974(3.3); 8.967(3.3); 8.282(2.9); 8.277(2.9); 8.174(1.0); 8.168(1.0); 8.144(2.7); 8.139(2.8); 8.113(3.6); 8.084(1.3); 7.849(3.1); 7.844(3.1); 7.298(1.6); 7.288(2.1); 7.282(2.2); 7.272(3.0); 7.262(17.6); 7.162(1.3); 7.136(2.6); 6.999(2.2); 6.995(2.1); 6.982(2.0); 6.979(1.9); 4.578(0.8); 4.557(0.9); 4.528(1.6); 4.508(1.5); 4.423(1.6); 4.405(1.7); 4.373(0.9); 4.355(0.8); 4.018(2.6); 3.961(3.1); 3.393(3.1); 3.335(3.4); 3.328(6.2); 1.799(16.0); 1.767(0.5); 1.591(1.5); 0.000(13.2)
Example 518: ¹H-NMR(300.2 MHz, CDCl3):
8.973(3.3); 8.966(3.2); 8.283(2.7); 8.277(2.5); 8.213(1.3); 8.207(1.2); 8.183(2.4); 8.177(2.4); 8.122(3.1); 8.092(1.6); 7.862(2.9); 7.857(2.8); 7.728(2.1); 7.263(18.8); 6.732(3.6); 6.729(3.5); 3.984(2.6); 3.927(3.1); 3.338(3.1); 3.325(6.2); 3.281(2.6); 2.804(0.3); 2.385(13.4); 2.382(13.2); 1.814(14.3); 1.802(14.6); 1.774(16.0); 1.603(1.0); 0.011(0.6); 0.000(14.4); −0.011(0.9)
Example 519: ¹H-NMR(300.2 MHz, CDCl3):
8.941(5.2); 8.933(5.3); 8.326(4.1); 8.319(4.0); 8.192(2.0); 8.185(2.0); 8.162(3.8); 8.156(4.0); 8.101(4.9); 8.071(2.5); 7.857(4.7); 7.851(4.5); 7.265(11.1); 6.628(1.3); 6.603(1.3); 5.307(6.2); 5.105(4.1); 4.190(4.4); 4.133(5.3); 4.115(0.6); 4.093(1.1); 4.071(1.6); 4.066(1.3); 4.049(1.4); 4.044(1.5); 4.022(1.1); 4.000(0.4); 3.507(4.9); 3.450(4.3); 2.046(0.8); 1.910(16.0); 1.909(15.8); 1.634(3.4); 1.284(0.3); 1.260(0.8); 1.236(0.5); 1.206(13.8); 1.184(13.9); 1.170(14.2); 1.148(13.7); 0.071(2.9); 0.011(0.4); 0.000(8.2); −0.011(0.4)
Example 520: ¹H-NMR(300.2 MHz, CDCl3):
8.936(4.5); 8.928(4.7); 8.320(3.1); 8.313(3.0); 8.194(1.8); 8.188(1.8); 8.164(3.2); 8.158(3.4); 8.093(3.8); 8.063(2.1); 7.849(3.5); 7.843(3.5); 7.407(0.6); 7.390(1.1); 7.373(0.7); 7.267(8.7); 5.318(4.8); 5.101(2.6); 5.098(3.1); 5.097(3.1); 5.094(2.7); 4.197(3.6); 4.140(4.2); 3.542(0.4); 3.530(2.1); 3.525(2.5); 3.514(3.0); 3.510(4.1); 3.506(4.3); 3.498(5.7); 3.494(6.9); 3.491(7.1); 3.486(3.1); 3.471(6.1); 3.468(5.1); 3.448(2.6); 3.442(4.2); 3.430(0.7); 3.385(0.6); 3.368(0.8); 3.364(1.4); 3.347(1.4); 3.343(1.0); 3.325(0.9); 3.319(0.8); 3.302(0.8); 3.298(0.5); 3.280(0.4); 2.804(0.6); 1.921(9.3); 1.918(12.0); 1.916(12.1); 1.914(9.6); 1.837(0.9); 1.816(2.7); 1.797(3.6); 1.777(2.7); 1.756(0.9); 1.704(0.4); 1.432 (0.7); 1.278(7.6); 1.255(16.0); 1.232(7.4); 1.217(1.0); 0.073(1.6); 0.000(6.4)
Example 521: ¹H-NMR(300.2 MHz, CDCl3):
8.945(3.0); 8.938(3.0); 8.328(2.2); 8.321(2.1); 8.177(1.0); 8.171(1.0); 8.147(2.2); 8.141(2.3); 8.101(2.8); 8.071(1.2); 7.855(2.4); 7.849(2.3); 7.268(6.8); 7.232(3.9); 6.879(0.5); 6.861(0.9); 6.844(0.5); 5.304(3.2); 5.103(2.1); 5.102(2.1); 4.384(0.8); 4.365(0.8); 4.335(1.4); 4.315(1.4); 4.230(1.5); 4.212(3.2); 4.180(0.8); 4.164(0.9); 4.155(2.7); 3.961(2.4); 3.937(3.8); 3.913(2.5); 3.526(2.5); 3.469(2.2); 2.957(1.6); 2.884(1.4); 2.804(5.8); 2.489(1.7); 2.185(16.0); 2.009(2.9); 1.906(8.5); 1.875(0.5); 1.850(1.4); 1.826(2.5); 1.802(2.5); 1.778(1.5); 1.754(0.5); 1.720(0.5); 1.254(0.4); 0.932(0.5); 0.902(4.4); 0.878(8.8); 0.853(4.0); 0.072(1.4); 0.000(4.8)
Example 522: ¹H-NMR(300.2 MHz, CDCl3):
8.941(6.5); 8.934(4.7); 8.323(4.8); 8.316(4.7); 8.188(1.3); 8.181(2.4); 8.175(1.4); 8.158(2.6); 8.152(4.9); 8.146(2.8); 8.100(5.2); 8.071(2.5); 7.850(4.9); 7.845(4.6); 7.267(12.2); 7.190(0.5); 7.171(1.0); 7.152(0.6); 7.127(0.6); 7.108(0.8); 7.088(0.5); 5.351(3.5); 5.329(3.8); 5.125(4.5); 5.123(4.3); 4.267(0.5); 4.261(0.7); 4.248(1.2); 4.239(0.9); 4.232(1.5); 4.226(1.0); 4.218(1.1); 4.212(1.4); 4.199(1.1); 4.191(3.0); 4.178(0.5); 4.163(2.7); 4.134(3.1); 4.107(3.2); 4.048(1.5); 4.026(1.6); 4.019(2.0); 4.011(1.8); 3.998(1.6); 3.989(1.7); 3.982(2.1); 3.961(1.6); 3.647(1.7); 3.626(1.7); 3.619(1.6); 3.604(1.3); 3.598(1.7); 3.585(2.6); 3.571(0.9); 3.563(2.4); 3.557(3.7); 3.544(4.6); 3.535(3.1); 3.525(4.0); 3.519(1.3); 3.487(2.7); 3.468(2.5); 3.445(1.0); 3.432(1.2); 3.429(1.3); 3.424(1.2); 3.416(1.4); 3.405(1.6); 3.399(0.6); 3.385(1.5); 3.377(0.8); 3.369(0.6); 3.358(1.0); 3.338(0.6); 2.074(0.3); 2.069(0.4); 2.046(0.4); 2.009(8.2); 1.933(16.0); 1.930 (15.4); 1.668(1.4); 1.455(11.9); 1.441(12.8); 1.340(13.7); 1.335(14.3); 1.260(0.6); 1.255(0.5); 1.217(0.5); 0.073(0.7); 0.000(9.2); −0.011(0.4)
Example 523: ¹H-NMR(300.2 MHz, CDCl3):
8.939(5.8); 8.932(5.9); 8.320(3.9); 8.314(3.9); 8.187(2.2); 8.181(2.2); 8.158(4.2); 8.151(4.4); 8.099(5.0); 8.069(2.5); 7.848(4.5); 7.842(4.3); 7.266(12.6); 6.925(1.2); 6.898(1.2); 5.301(6.3); 5.299(4.6); 5.104(3.4); 5.101(3.8); 5.099(3.8); 5.096(3.4); 4.400(0.9); 4.373(1.6); 4.345(1.7); 4.318(0.9); 4.175(4.7); 4.118(5.4); 3.498(5.2); 3.441(4.5); 2.410(0.4); 2.405(0.3); 2.401(0.5); 2.397(0.5); 2.387(0.8); 2.375(1.1); 2.364(1.1); 2.362(1.2); 2.351(1.3); 2.348(1.3); 2.339(1.6); 2.326(1.4); 2.313(1.5); 2.302(1.1); 2.289(1.0); 2.284(0.7); 2.277(0.8); 2.266(0.6); 2.010(0.5); 1.988(0.4); 1.984(0.4); 1.979(0.5); 1.949(1.7); 1.942(1.0); 1.910(13.4); 1.908(16.0); 1.906(15.8); 1.903(12.3); 1.894(2.1); 1.886(2.4); 1.876 (1.3); 1.857(1.0); 1.848(0.8); 1.797(0.4); 1.788(0.4); 1.775(1.3); 1.773(1.3); 1.760(1.6); 1.754(2.2); 1.749(1.4); 1.744(1.5); 1.742(1.5); 1.730(2.4); 1.719(3.0); 1.704(1.3); 1.694(1.6); 1.684(1.5); 1.660(0.9); 1.648(0.4); 1.255(1.4); 1.237(0.4); 1.218(0.4); 1.169(0.4); 0.084(0.4); 0.072(9.1); 0.059(0.5); 0.000(9.0); −0.011(0.4)
Example 524: ¹H-NMR(499.9 MHz, CDCl3):
8.934(4.9); 8.929(5.3); 8.919(0.3); 8.309(4.2); 8.304(4.2); 8.163(2.3); 8.160(2.3); 8.146(3.6); 8.142(3.8); 8.092(4.7); 8.074(3.0); 7.845(4.6); 7.842(4.7); 7.266(4.3); 7.018(0.9); 7.009(1.6); 6.999(1.0); 5.333(6.2); 5.124(4.1); 5.123(4.2); 4.174(5.4); 4.168(1.5); 4.162(1.3); 4.157(1.3); 4.140(5.6); 4.133(2.3); 4.127(2.1); 4.122(2.0); 4.032(1.8); 4.026(2.0); 4.021(2.0); 4.016(2.0); 3.996(1.2); 3.991(1.3); 3.986(1.3); 3.981(1.2); 3.517(4.9); 3.483(4.5); 2.246(2.7); 2.241(5.5); 2.236(2.9); 2.068(1.1); 2.063(1.2); 1.921(16.0); 1.691(1.4); 1.422(0.5); 1.286(0.6); 1.257(1.5); 1.114(0.8); 0.894(0.4); 0.881(1.0); 0.866(0.6); 0.000(2.3)
Example 525: ¹H-NMR(300.2 MHz, CDCl3):
8.963(4.9); 8.956(5.1); 8.269(3.7); 8.262(3.7); 8.177(1.6); 8.171(1.6); 8.148(4.1); 8.142(4.3); 8.110(5.2); 8.081(2.0); 7.840(4.0); 7.835(3.9); 7.293(2.3); 7.136(2.7); 4.156(1.0); 4.133(3.0); 4.109(3.1); 4.085(1.1); 4.039(2.1); 4.008(2.2); 3.982(2.5); 3.950(2.5); 3.409(2.6); 3.401(2.6); 3.358(6.6); 3.355(6.6); 3.344(2.4); 2.046(14.1); 2.014(2.2); 1.833(0.6); 1.802(16.0); 1.798(15.1); 1.779(12.5); 1.762(0.9); 1.748(13.5); 1.723(0.5); 1.324(0.6); 1.317(0.8); 1.311(0.8); 1.308 (0.7); 1.302(1.1); 1.300(1.1); 1.289(1.4); 1.283(4.6); 1.277(1.2); 1.266(1.1); 1.259(8.0); 1.248(0.5); 1.245(0.6); 1.235(3.8); 0.806(0.3); 0.787(0.7); 0.778(0.8); 0.775(0.6); 0.765(1.4); 0.758(0.8); 0.748(2.3); 0.744(3.0); 0.739(1.9); 0.730(2.2); 0.717(7.1); 0.708(2.8); 0.690(5.6); 0.667(0.3); 0.000(1.4)
Example 526: ¹H-NMR(300.2 MHz, CDCl3):
8.969(3.7); 8.962(3.7); 8.281(3.1); 8.275(3.0); 8.193(0.8); 8.186(1.2); 8.179(0.8); 8.164(1.7); 8.157(2.6); 8.150(1.7); 8.112(3.9); 8.082(1.7); 7.846(3.1); 7.264(18.3); 6.961(1.0); 6.932(1.0); 3.989(2.0); 3.984(2.0); 3.960(0.6); 3.951(0.8); 3.932(3.0); 3.927(2.8); 3.902(0.4); 3.461(0.5); 3.447(0.4); 3.429(1.5); 3.415(1.6); 3.408(1.9); 3.394(1.8); 3.368(16.0); 3.359(4.0); 3.346(0.6); 3.339(0.8); 3.325(6.9); 3.319(2.0); 3.310(2.2); 3.303(2.6); 3.286(0.9); 3.272(0.9); 3.258(14.8); 2.958(0.4); 2.886(0.4); 1.778(15.8); 1.713(0.3); 1.692(0.5); 1.667(0.9); 1.642(1.3); 1.622(2.0); 1.605(1.4); 1.593(1.0); 1.584(0.9); 1.580(0.9); 1.567(1.0); 1.559(0.8); 1.543(0.8); 1.520(0.9); 1.495(0.9); 1.468(0.6); 1.448(0.4); 1.253(0.4); 0.972(2.6); 0.948(5.5); 0.923(2.3); 0.839(2.6); 0.815(5.4); 0.790(2.3); 0.011(0.4); 0.000(13.1); −0.011(0.7)

-continued

NMR Peak Lists Table 1

Example 527: $^1$H-NMR(400.0 MHz, DMSO):
8.970(5.9); 8.965(5.9); 8.616(5.0); 8.611(4.7); 8.256(5.2); 8.252(5.2); 8.164(2.3); 8.160(1.9); 8.142(4.4); 8.138(4.0); 8.099(5.8); 8.077(2.9); 4.603(10.3); 4.061(3.4); 4.016(5.1); 3.876(1.1); 3.866(5.5); 3.860(2.8); 3.843(3.2); 3.826(2.9); 3.821(3.7); 3.810(1.0); 3.693(4.0); 3.678(4.9); 3.575(5.5); 3.560(4.3); 3.329(92.3); 2.891(0.5); 2.732(0.4); 2.676(0.4); 2.672(0.5); 2.668(0.4); 2.507(70.1); 2.503(87.0); 2.499(61.7); 2.334(0.4); 2.330(0.5); 2.326(0.4); 1.234(0.3); 1.212 (15.8); 1.196(15.9); 1.184(16.0); 1.168(15.6); 0.008(0.8); 0.000(19.3); −0.008(0.8)
Example 528: $^1$H-NMR(400.0 MHz, DMSO):
9.018(5.5); 9.012(5.5); 8.775(4.8); 8.770(4.4); 8.231(5.0); 8.228(5.1); 8.164(2.2); 8.160(1.8); 8.142(4.3); 8.138(3.8); 8.099(5.7); 8.077(2.8); 4.051(3.4); 4.006(5.1); 3.877(0.9); 3.859(6.6); 3.843(3.2); 3.827(2.4); 3.813(3.8); 3.696(4.1); 3.680(5.1); 3.577(5.6); 3.562(4.4); 3.331(40.1); 2.509(33.9); 2.504(43.3); 2.500(31.3); 1.214(15.9); 1.197(15.9); 1.186(16.0); 1.169(15.6); 0.008(0.4); 0.000(10.3); −0.009(0.4)
Example 529: $^1$H-NMR(400.0 MHz, DMSO):
9.021(6.2); 9.015(6.3); 8.766(5.0); 8.761(4.7); 8.316(0.9); 8.283(5.1); 8.278(5.2); 8.182(2.6); 8.178(2.3); 8.160(4.3); 8.155(4.1); 8.100(5.6); 8.077(3.3); 7.952(0.4); 3.999(1.0); 3.983(3.6); 3.967(3.7); 3.952(1.0); 3.812(2.8); 3.781(1.1); 3.766(7.1); 3.748(3.1); 3.731(2.4); 3.714(1.0); 3.698(6.2); 3.652(2.9); 3.393(4.0); 3.329(577.2); 2.891(3.3); 2.731(2.8); 2.676(1.9); 2.671(2.5); 2.667(1.8); 2.541(1.6); 2.524(7.9); 2.511(153.0); 2.507(300.3); 2.502(388.2); 2.498(278.1); 2.493(133.9); 2.333(1.7); 2.329(2.4); 2.324(1.7); 1.639(0.6); 1.371(12.4); 1.355(12.3); 1.295(16.0); 1.279(15.8); 1.235(0.9); 1.218(16.0); 1.201(15.8); 1.174(0.3); 1.104(0.4); 1.095(0.4); 1.087(0.4); 1.079(0.5); 0.845(0.4); 0.146 (0.4); 0.008(3.5); 0.000(94.6); −0.008(3.7); −0.150(0.5)
Example 530: $^1$H-NMR(300.2 MHz, CDCl3):
8.983(3.1); 8.977(5.9); 8.971(4.1); 8.385(2.2); 8.377(2.2); 8.291(4.6); 8.274(2.7); 8.267(2.7); 8.195(1.0); 8.189(1.0); 8.165(2.6); 8.159(3.0); 8.133(3.6); 8.125(4.3); 8.120(6.4); 8.103(1.5); 7.862(3.0); 7.857(2.8); 7.802(2.8); 7.627(1.3); 7.619(1.3); 7.607(0.8); 7.600(1.5); 7.591(1.5); 7.541(0.3); 7.520(1.5); 7.513(1.3); 7.492(1.6); 7.485(1.6); 7.342(2.5); 7.313(2.1); 7.261(125.1); 7.190(2.8); 7.162(3.2); 7.130(1.3); 6.910(0.8); 5.091(1.2); 5.067(2.3); 5.044(2.3); 5.020(1.2); 4.996(0.3); 4.003(2.7); 3.946(2.9); 3.876(2.6); 3.819(3.1); 3.375(3.0); 3.360(3.2); 3.333(6.2); 3.325(7.2); 3.317(3.0); 3.303(2.7); 2.802(1.3); 2.077(0.9); 2.065(1.0); 1.926(0.5); 1.849(1.5); 1.792(15.9); 1.767(1.5); 1.714(16.0); 1.621(1.1); 1.567(8.1); 1.543(8.0); 1.521(7.7); 1.497(7.6); 1.427(0.5); 1.387(0.8); 1.366(0.7); 1.253(0.7); 0.196(0.4); 0.011(3.9); 0.000(107.6); −0.011(4.9); −0.198(0.5)
Example 531: $^1$H-NMR(300.2 MHz, CDCl3):
8.927(3.1); 8.919(3.1); 8.313(2.3); 8.306(2.2); 8.169(1.1); 8.163(1.1); 8.139(2.2); 8.133(2.3); 8.089(2.8); 8.059(1.3); 7.848(2.5); 7.842(2.4); 7.296(1.2); 7.259(3.9); 6.932(0.5); 6.915(1.0); 6.898(0.6); 5.309(3.3); 5.106(2.2); 5.104(2.2); 4.387(0.7); 4.368(0.7); 4.337(1.4); 4.318(1.4); 4.243(1.5); 4.226(1.6); 4.215(2.4); 4.194(0.8); 4.177(0.8); 4.159(2.6); 4.078(1.3); 4.054(3.9); 4.029(4.0); 4.005(1.3); 3.533(2.5); 3.476(2.2); 2.805(0.7); 2.211(1.9); 2.187(16.0); 1.911(8.6); 1.909(8.5); 1.444(4.7); 1.419(9.9); 1.395(4.7); 0.000(0.7)
Example 532: $^1$H-NMR(300.2 MHz, CDCl3):
8.971(3.0); 8.964(2.9); 8.279(2.5); 8.273(2.4); 8.183(1.1); 8.177(1.0); 8.153(2.5); 8.147(2.4); 8.112(3.1); 8.083(1.3); 7.844(2.8); 7.838(2.6); 7.262(21.0); 6.847(0.8); 3.989(2.7); 3.932(3.2); 3.410(0.4); 3.390(0.7); 3.363(3.5); 3.346(1.2); 3.341(1.3); 3.325(6.2); 3.305(3.3); 3.285(1.1); 3.279(1.0); 3.260(1.1); 3.240(0.6); 3.236(0.6); 3.216(0.4); 1.771(16.0); 1.579(2.9); 1.191(4.8); 1.167(9.6); 1.143(4.7); 0.010(0.9); 0.000(16.8); −0.011(1.0)
Example 533: $^1$H-NMR(300.2 MHz, CDCl3):
8.943(3.0); 8.936(3.0); 8.323(2.8); 8.316(2.6); 8.178(1.1); 8.172(1.1); 8.148(2.4); 8.142(2.5); 8.102(3.2); 8.072(1.4); 7.810(3.0); 7.805(2.9); 7.262(22.0); 6.842(0.9); 3.980(2.6); 3.923(3.1); 3.411(0.4); 3.391(0.7); 3.366(1.4); 3.352(3.3); 3.322(1.0); 3.302(1.3); 3.295(2.9); 3.284(1.2); 3.279(1.1); 3.260(1.1); 3.236(0.6); 3.215(0.4); 2.958(0.3); 1.771(16.0); 1.566(4.5); 1.253(0.5); 1.192(4.6); 1.167(9.2); 1.143(4.5); 0.000(17.6)
Example 534: $^1$H-NMR(300.2 MHz, CDCl3):
8.971(2.8); 8.964(2.8); 8.300(1.8); 8.276(2.4); 8.270(2.3); 8.186(0.9); 8.180(0.9); 8.156(2.2); 8.150(2.4); 8.118(3.0); 8.088(1.2); 7.913(4.5); 7.860(2.5); 7.855(2.5); 7.272(3.8); 4.134(0.7); 4.110(0.8); 4.099(1.2); 4.086(0.5); 4.075(3.9); 4.063(2.6); 4.050(4.0); 4.026(1.4); 4.006(2.8); 3.453(2.6); 3.396(2.2); 3.333(5.6); 2.249(16.0); 2.046(3.3); 1.863 (13.4); 1.783(3.0); 1.458(4.4); 1.434(9.4); 1.409(4.3); 1.283(0.9); 1.259(1.8); 1.236(0.9); 0.000(2.6)
Example 535: $^1$H-NMR(400.0 MHz, DMSO):
9.022(2.9); 9.016(3.0); 8.744(2.2); 8.738(2.1); 8.282(2.3); 8.277(2.3); 8.178(1.2); 8.173(1.0); 8.156(2.0); 8.151(1.9); 8.142(1.1); 8.121(1.1); 8.094(2.5); 8.072(1.5); 4.169(1.9); 4.122(2.3); 4.004(0.5); 3.987(0.7); 3.967(0.7); 3.950(0.5); 3.903(8.1); 3.787(2.3); 3.740(2.0); 3.329(141.5); 2.676(0.4); 2.672(0.6); 2.667(0.4); 2.542(0.4); 2.512(38.8); 2.507 (75.6); 2.503(97.0); 2.498(68.8); 2.494(32.7); 2.334(0.4); 2.330(0.6); 2.325(0.4); 2.176(16.0); 1.235(0.3); 1.146(6.3); 1.130(6.3); 1.113(6.5); 1.097(6.4); 0.000(3.6)
Example 536: $^1$H-NMR(300.2 MHz, CDCl3):
8.969(2.9); 8.962(3.0); 8.276(2.2); 8.269(2.3); 8.176(1.0); 8.170(1.0); 8.146(2.4); 8.140(2.5); 8.108(3.0); 8.079(1.3); 7.838(2.6); 7.832(2.5); 7.265(9.5); 6.909(0.6); 6.894(0.6); 4.134(0.8); 4.110(0.8); 3.992(2.7); 3.935(3.2); 3.368(3.0); 3.327(5.8); 3.310(3.0); 2.860(9.7); 2.844(9.7); 2.046(3.4); 1.777(16.0); 1.702(0.9); 1.641(8.4); 1.294(0.3); 1.284(1.1); 1.272(0.4); 1.260(2.4); 1.236(1.4); 1.230(0.7); 1.207(0.4); 0.000(6.5)
Example 537: $^1$H-NMR(300.2 MHz, CDCl3):
8.944(2.0); 8.936(2.0); 8.323(1.4); 8.316(1.3); 8.173(0.7); 8.166(0.7); 8.143(1.6); 8.137(1.6); 8.100(1.8); 8.070(0.8); 7.806(1.6); 7.800(1.5); 7.262(28.8); 7.254(0.6); 7.253(0.5); 7.251(0.4); 6.911(0.3); 6.893(0.4); 6.879(0.3); 3.983(1.8); 3.926(2.1); 3.357(1.9); 3.300(1.6); 2.860(6.5); 2.843(6.5); 2.047(0.5); 1.776(10.5); 1.560(16.0); 1.260(0.3); 0.011(0.7); 0.000(22.4); −0.008(0.6); −0.009(0.6); −0.011(0.9)
Example 538: $^1$H-NMR(300.2 MHz, CDCl3):
8.982(3.1); 8.975(3.3); 8.249(2.7); 8.242(2.7); 8.013(1.6); 8.010(2.0); 8.007(2.1); 8.004(1.7); 7.678(2.1); 7.672(2.1); 7.262(32.8); 7.253(0.7); 7.252(0.6); 7.250(0.5); 7.249(0.4); 7.247(0.4); 7.244(0.3); 7.225(3.9); 6.935(0.5); 6.918(0.9); 6.901(0.5); 4.360(0.7); 4.341(0.7); 4.311(1.4); 4.291(1.4); 4.226(1.5); 4.209(1.5); 4.176(0.7); 4.160(0.7); 3.988(2.4); 3.956(2.4); 3.931(6.0); 3.908(2.5); 3.365(2.6); 3.315(5.9); 3.308(2.6); 2.796(10.0); 2.186(16.0); 2.076(0.3); 2.065(0.4); 1.872(0.4); 1.848(1.4); 1.823(2.5); 1.799(2.7); 1.774(14.7); 1.751(0.6); 1.577(3.7); 1.253(0.3); 0.901(4.4); 0.877(9.2); 0.852(4.0); 0.011(0.9); 0.009(0.5); 0.000(26.8); −0.008(0.9); −0.010(0.7); −0.011(1.0)
Example 539: $^1$H-NMR(300.2 MHz, CDCl3):
8.946(3.3); 8.938(3.4); 8.285(2.9); 8.277(2.9); 8.001(1.6); 7.998(2.0); 7.995(2.1); 7.992(1.6); 7.640(2.1); 7.634(2.0); 7.264(15.1); 7.227(3.8); 6.931(0.5); 6.913(0.9); 6.897(0.5); 5.301(0.6); 4.360(0.7); 4.341(0.7); 4.311(1.4); 4.292(1.4); 4.227(1.4); 4.210(1.5); 4.177(0.7); 4.160(0.7); 3.977(2.4); 3.957(2.4); 3.934(3.6); 3.920(3.0); 3.910(2.6); 3.354(2.6);

NMR Peak Lists Table 1

3.297(2.2); 2.804(0.4); 2.785(10.0); 2.184(16.0); 2.076(0.4); 2.065(0.4); 1.874(0.3); 1.849(1.4); 1.842(0.5); 1.825(2.4); 1.801(2.5); 1.773(14.2); 1.753(0.7); 1.615(0.3); 0.903(4.4); 0.879(9.1); 0.854(4.0); 0.011(0.4); 0.000(12.0); −0.011(0.5)
Example 540: $^1$H-NMR(300.2 MHz, CDCl3):
8.979(3.6); 8.972(3.7); 8.431(2.9); 8.391(2.9); 8.247(3.3); 8.240(3.1); 8.030(2.4); 8.027(2.4); 7.754(0.6); 7.737(1.1); 7.719(0.6); 7.681(2.5); 7.675(2.5); 7.262(47.4); 7.251(0.9); 4.679(0.6); 4.660(0.6); 4.625(1.4); 4.606(1.4); 4.558(1.5); 4.540(1.5); 4.505(0.6); 4.487(0.6); 4.002(2.7); 3.945(3.2); 3.389(3.1); 3.332(2.7); 3.313(6.8); 2.795(11.9); 2.546(13.5); 2.076(0.4); 2.065(0.4); 1.843(0.3); 1.825(0.4); 1.800(16.0); 1.569(4.0); 1.253(0.6); 0.011(1.6); 0.000(37.7); −0.009(0.9); −0.011(1.3)
Example 541: $^1$H-NMR(300.2 MHz, CDCl3):
8.979(3.9); 8.972(3.9); 8.247(3.8); 8.240(3.6); 8.027(2.0); 8.023(2.2); 7.674(3.0); 7.263(22.5); 7.226(0.9); 7.201(0.9); 7.181(0.5); 4.259(0.5); 4.254(0.6); 4.238(1.2); 4.225(1.2); 4.218(1.1); 4.206(0.8); 4.059(1.0); 4.037(1.0); 4.031(1.2); 4.015(1.2); 4.009(1.1); 3.994(1.1); 3.987(1.3); 3.967(2.1); 3.948(1.6); 3.911(1.8); 3.890(1.9); 3.678(1.0); 3.658(1.0); 3.650(1.0); 3.629(0.9); 3.591(1.1); 3.583(0.6); 3.570(1.5); 3.563(1.6); 3.551(0.7); 3.542(1.3); 3.524(0.9); 3.515(1.1); 3.504(0.8); 3.498(0.8); 3.492(0.8); 3.475(0.6); 3.439(0.7); 3.427(0.8); 3.422(0.8); 3.410(0.8); 3.402(0.8); 3.392(0.6); 3.376(2.4); 3.363(2.7); 3.336(1.0); 3.313(7.7); 3.306(2.2); 2.798(13.4); 2.076(0.3); 2.065(0.4); 1.781(16.0); 1.587(0.7); 1.483(7.5); 1.404(7.7); 1.339(7.7); 1.324(8.1); 0.011(1.0); 0.000(17.8); −0.011(1.0)
Example 542: $^1$H-NMR(300.2 MHz, CDCl3):
8.945(3.6); 8.937(3.8); 8.431(2.9); 8.392(2.8); 8.285(3.3); 8.277(3.3); 8.020(2.4); 8.017(2.5); 7.732(1.0); 7.646(2.5); 7.640(2.4); 7.607(0.5); 7.261(77.8); 6.910(0.5); 4.678(0.6); 4.659(0.6); 4.625(1.4); 4.606(1.4); 4.558(1.5); 4.540(1.5); 4.505(0.6); 4.487(0.6); 3.992(2.8); 3.935(3.2); 3.378(3.0); 3.320(2.6); 2.786(11.9); 2.547(13.1); 2.065(0.4); 1.799 (16.0); 1.569(4.2); 1.251(0.8); 0.011(2.2); 0.000(62.4); −0.011(2.8)
Example 543: $^1$H-NMR(300.2 MHz, CDCl3):
8.943(4.0); 8.935(4.0); 8.283(3.9); 8.275(3.8); 8.019(1.6); 8.016(1.8); 8.012(2.1); 8.008(1.8); 8.006(1.6); 7.637(2.8); 7.263(18.2); 7.242(0.5); 7.222(0.8); 7.200(0.7); 7.177(0.4); 4.259(0.5); 4.238(1.1); 4.226(1.1); 4.219(1.0); 4.206(0.8); 4.198(0.4); 4.059(1.0); 4.037(0.9); 4.031(1.2); 4.015(1.2); 4.009(1.0); 3.993(1.0); 3.987(1.2); 3.965(1.1); 3.958(1.6); 3.938(1.6); 3.900(1.9); 3.880(1.9); 3.678(1.0); 3.658(1.0); 3.650(1.0); 3.629(0.9); 3.589(1.1); 3.581(0.5); 3.568(1.5); 3.561(1.7); 3.545(0.6); 3.540(1.3); 3.535(0.8); 3.522(0.9); 3.515(1.2); 3.502(0.8); 3.499(0.8); 3.492(0.7); 3.476(0.6); 3.439(0.6); 3.426(0.7); 3.421(0.7); 3.409(0.7); 3.404(0.7); 3.392(0.5); 3.384(1.1); 3.374(0.6); 3.365(2.5); 3.352(1.9); 3.338(0.8); 3.318(0.5); 3.308(1.6); 3.294(1.5); 2.958(0.4); 2.886(0.4); 2.804(0.7); 2.788(13.1); 2.077(0.3); 2.065(0.4); 1.780(16.0); 1.759(0.6); 1.610(0.4); 1.483(7.2); 1.403(7.4); 1.340(7.3); 1.324(7.7); 0.011(0.6); 0.000(14.6); −0.011(0.7)
Example 544: $^1$H-NMR(300.2 MHz, CDCl3):
9.039(3.4); 9.032(3.3); 8.347(3.3); 8.340(3.1); 8.312(3.5); 8.306(3.4); 7.701(3.2); 7.696(3.0); 7.268(5.3); 6.971(0.9); 6.944(0.9); 4.398(0.6); 4.370(1.0); 4.343(1.1); 4.316(0.6); 3.940(2.5); 3.883(3.0); 3.310(2.8); 3.253(2.4); 2.405(0.3); 2.393(0.5); 2.381(0.7); 2.371(0.6); 2.357(0.8); 2.344(0.7); 2.332(0.7); 2.328(0.6); 2.319(0.8); 2.307(0.7); 2.296(0.7); 2.282(0.6); 2.271(0.5); 2.263(0.3); 2.047(0.8); 1.974(0.7); 1.960(0.3); 1.943(1.1); 1.927(0.8); 1.913(0.8); 1.908(0.9); 1.896(1.2); 1.878(0.5); 1.864(0.8); 1.860(0.8); 1.830(0.5); 1.773(1.4); 1.756(16.0); 1.730(1.9); 1.719(2.0); 1.704(1.1); 1.695(1.2); 1.684(1.1); 1.660(0.5); 1.260(0.4); 0.072(1.5); 0.000(3.9)
Example 545: $^1$H-NMR(300.2 MHz, CDCl3):
9.039(4.3); 9.032(4.3); 8.348(3.6); 8.341(3.5); 8.306(2.4); 8.299(2.5); 8.292(2.3); 7.707(2.4); 7.703(3.1); 7.699(2.3); 7.271(5.7); 7.197(0.7); 7.174(0.7); 7.152(0.4); 4.268(0.5); 4.263(0.5); 4.255(0.5); 4.247(1.3); 4.235(1.0); 4.229(0.9); 4.214(0.7); 4.066(1.0); 4.044(0.9); 4.038(1.2); 4.016(1.8); 3.994(0.9); 3.988(1.2); 3.966(0.9); 3.953(1.6); 3.932(1.5); 3.896(1.9); 3.874(1.8); 3.682(1.1); 3.662(1.1); 3.654(1.0); 3.634(0.9); 3.587(1.0); 3.575(0.4); 3.566(1.2); 3.558(1.2); 3.543(0.7); 3.538(1.2); 3.528(0.7); 3.522(0.5); 3.514(1.0); 3.508(0.7); 3.497(1.1); 3.492(0.8); 3.475(0.6); 3.447(0.6); 3.434(0.7); 3.429(0.8); 3.420(0.8); 3.417(0.8); 3.400(1.1); 3.387(0.4); 3.382(0.8); 3.374(0.5); 3.370(0.4); 3.352(2.0); 3.339(1.9); 3.295(1.4); 3.281(1.5); 2.047(0.7); 1.791(16.0); 1.682(0.8); 1.488(7.1); 1.410(6.6); 1.344(7.2); 1.323(6.7); 1.260(0.5); 0.073(1.4); 0.000(4.0)
Example 546: $^1$H-NMR(300.2 MHz, CDCl3):
9.029(3.6); 9.022(3.6); 8.344(3.3); 8.337(3.3); 8.304(3.7); 8.298(3.7); 7.705(3.3); 7.699(3.2); 7.278(2.5); 6.683(0.9); 6.657(0.9); 4.135(0.4); 4.111(0.7); 4.078(0.7); 4.056(1.0); 4.052(0.8); 4.034(0.8); 4.030(1.0); 4.008(0.7); 3.954(2.7); 3.897(3.2); 3.319(3.0); 3.262(2.6); 2.048(1.7); 1.761(16.0); 1.285(0.5); 1.261(1.0); 1.237(0.7); 1.221(8.4); 1.199(8.4); 1.161(8.5); 1.139(8.4); 0.075(1.7); 0.000(1.7)
Example 547: $^1$H-NMR(300.2 MHz, CDCl3):
9.028(3.8); 9.021(3.9); 8.343(3.3); 8.336(3.3); 8.309(3.9); 8.303(4.0); 7.694(3.1); 7.688(3.1); 7.495(0.5); 7.477(0.9); 7.460(0.5); 7.278(3.0); 3.945(2.8); 3.888(3.2); 3.559(0.5); 3.547(1.3); 3.536(1.6); 3.526(3.4); 3.516(1.9); 3.508(2.1); 3.503(6.1); 3.498(2.0); 3.480(5.8); 3.474(1.1); 3.469(0.9); 3.457(2.0); 3.449(1.2); 3.427(1.2); 3.407(0.5); 3.387(0.5); 3.367(0.9); 3.349(0.9); 3.327(0.7); 3.321(0.7); 3.312(3.1); 3.304(0.7); 3.255(2.6); 2.805(0.4); 1.842(0.5); 1.820(1.7); 1.802(2.2); 1.799(2.2); 1.781(2.0); 1.768(16.0); 1.291(5.6); 1.280(0.3); 1.268(11.5); 1.244(5.5); 0.075 (2.0); 0.000(2.2)
Example 548: $^1$H-NMR(300.2 MHz, DMSO):
9.069(4.4); 9.062(4.4); 8.685(4.1); 8.679(3.9); 8.261(3.5); 8.256(7.3); 8.250(6.0); 7.905(1.8); 7.878(1.8); 4.689(7.6); 3.964(0.3); 3.941(0.8); 3.913(3.3); 3.897(1.2); 3.893(1.3); 3.870(1.0); 3.855(3.3); 3.474(3.1); 3.416(2.5); 3.334(6.0); 2.894(0.4); 2.734(0.4); 2.512(4.7); 2.506(6.2); 2.500(4.6); 1.596(16.0); 1.566(0.8); 1.113(9.4); 1.091(9.7); 1.072 (10.1); 1.050(9.8); 0.000(5.1)
Example 549: $^1$H-NMR(300.2 MHz, DMSO):
9.067(3.9); 9.061(3.8); 8.682(4.1); 8.676(3.9); 8.379(1.9); 8.352(1.9); 8.251(6.4); 8.243(5.5); 4.689(6.4); 4.658(0.5); 4.271(0.7); 4.244(1.4); 4.216(1.4); 4.189(0.8); 3.912(2.3); 3.854(2.9); 3.464(2.7); 3.406(2.2); 3.334(8.5); 2.893(1.0); 2.771(0.4); 2.734(1.0); 2.691(0.7); 2.511(5.4); 2.506(6.6); 2.132(1.4); 2.104(3.0); 2.072(3.8); 2.039(2.6); 2.008(1.0); 1.641(1.2); 1.591(16.0); 1.557(1.6); 1.525(0.5); 1.415(0.9); 0.000(4.1)
Example 550: $^1$H-NMR(300.2 MHz, CDCl3):
9.054(3.8); 9.047(3.8); 8.317(3.9); 8.311(3.9); 8.286(3.2); 8.280(3.1); 7.729(3.2); 7.724(3.1); 7.499(0.5); 7.481(1.0); 7.464(0.6); 7.281(3.3); 3.955(2.8); 3.897(3.2); 3.558(0.5); 3.545(1.4); 3.535(1.7); 3.526(3.4); 3.518(2.2); 3.515(2.0); 3.507(2.4); 3.503(6.3); 3.497(2.1); 3.479(5.9); 3.472(1.1); 3.468(1.0); 3.456(2.1); 3.448(1.3); 3.426(1.2); 3.406(0.5); 3.387(7.1); 3.367(1.1); 3.349(1.0); 3.325(3.5); 3.304(0.6); 3.282(0.3); 3.267(2.6); 2.961(1.6); 2.886(1.3); 2.885(1.3); 2.805(7.6); 1.842(0.6); 1.820(1.7); 1.802(2.2); 1.799(2.2); 1.781(2.1); 1.769(16.0); 1.291(5.8); 1.267(11.8); 1.244 (5.6); 0.076(1.7); 0.000(2.1)

NMR Peak Lists Table 1

Example 551: $^1$H-NMR(300.2 MHz, CDCl3):
8.975(3.3); 8.968(3.4); 8.246(2.9); 8.239(3.0); 8.033(2.2); 8.030(2.3); 8.026(1.9); 7.671(2.2); 7.665(2.3); 7.423(0.9); 7.404(0.5); 7.262(23.1); 5.301(3.6); 3.960(2.7); 3.903(3.2); 3.540(0.4); 3.528(1.4); 3.520(1.7); 3.514(2.3); 3.508(2.3); 3.502(2.3); 3.490(6.9); 3.481(2.0); 3.467(5.9); 3.444(2.4); 3.418(1.3); 3.398(0.6); 3.378(0.6); 3.357(1.0); 3.336(3.9); 3.310(7.0); 3.293(0.7); 3.279(2.7); 2.958(0.5); 2.885(0.5); 2.796(11.4); 2.065(0.3); 1.842(0.3); 1.833(0.6); 1.813(1.8); 1.792(2.3); 1.773(2.0); 1.758(16.0); 1.586(1.6); 1.276(5.4); 1.253(11.3); 1.230(5.3); 0.070(0.4); 0.011(0.6); 0.008(0.4); 0.000(18.8); −0.011(0.8)

Example 552: $^1$H-NMR(300.2 MHz, CDCl3):
8.939(3.5); 8.931(3.6); 8.281(3.2); 8.273(3.1); 8.024(1.7); 8.021(2.3); 8.018(2.3); 8.015(1.8); 7.634(2.2); 7.628(2.2); 7.442(0.5); 7.425(0.8); 7.407(0.5); 7.263(16.7); 5.301(3.7); 3.950(2.7); 3.893(3.2); 3.542(0.4); 3.530(1.3); 3.521(1.5); 3.515(2.3); 3.512(2.0); 3.509(2.8); 3.503(2.1); 3.501(1.9); 3.491(6.8); 3.482(1.8); 3.468(5.8); 3.445(2.3); 3.441(1.4); 3.419(1.2); 3.399(5.1); 3.378(0.5); 3.357(0.9); 3.339(1.0); 3.335(0.9); 3.325(3.1); 3.317(0.9); 3.311(0.7); 3.293(0.5); 3.267(2.6); 2.786(10.9); 1.834(0.5); 1.813(1.6); 1.794(2.1); 1.792(2.1); 1.774(1.7); 1.757(16.0); 1.600(0.4); 1.277(5.4); 1.254(11.4); 1.231(5.3); 0.011(0.4); 0.000(13.4); −0.011(0.5)

Example 553: $^1$H-NMR(499.9 MHz, CDCl3):
9.035(3.2); 9.030(3.2); 8.342(3.1); 8.338(2.9); 8.278(3.2); 8.274(3.2); 7.705(2.9); 7.701(2.8); 7.268(4.6); 7.252(3.9); 6.883(0.5); 6.873(0.9); 6.862(0.5); 4.352(0.9); 4.341(0.9); 4.323(1.4); 4.311(1.4); 4.217(1.4); 4.207(1.4); 4.188(0.9); 4.177(0.9); 4.068(1.3); 4.053(4.0); 4.039(4.0); 4.024(1.3); 3.955(2.5); 3.921(2.8); 3.321(2.7); 3.286(2.4); 2.953(1.1); 2.910(0.7); 2.880(0.9); 2.802(4.0); 2.192(16.0); 2.075(0.5); 2.064(0.6); 2.039(0.4); 1.847(0.4); 1.789(0.4); 1.775(14.4); 1.762(0.5); 1.759(0.3); 1.677(0.3); 1.443(4.8); 1.429(9.8); 1.414(4.7); 1.257(0.4); 0.073(2.0); 0.000(3.3)

Example 554: $^1$H-NMR(499.9 MHz, CDCl3):
9.036(3.0); 9.032(3.3); 8.343(3.0); 8.338(3.0); 8.278(3.1); 8.275(3.2); 7.705(2.8); 7.702(2.9); 7.268(4.5); 7.231(4.0); 6.887(0.5); 6.877(0.9); 6.867(0.5); 4.350(0.9); 4.339(0.9); 4.320(1.4); 4.309(1.4); 4.217(1.4); 4.207(1.4); 4.187(0.9); 4.177(0.9); 3.954(3.5); 3.939(4.0); 3.924(2.8); 3.921(3.2); 3.320(2.6); 3.285(2.4); 2.953(0.8); 2.910(0.4); 2.880(0.7); 2.802(2.8); 2.484(0.3); 2.190(16.0); 2.075(0.5); 2.064(0.6); 2.039(0.5); 1.857(0.4); 1.846(0.6); 1.842(1.5); 1.827(2.7); 1.813(2.7); 1.799(1.6); 1.788(0.3); 1.784(0.7); 1.774(14.3); 1.257(0.5); 0.900(4.5); 0.886(8.9); 0.871(4.2); 0.073(1.3); 0.000(3.3)

Example 555: $^1$H-NMR(300.2 MHz, CDCl3):
9.068(3.3); 9.062(3.4); 8.297(5.0); 8.291(4.8); 7.744(2.7); 7.739(2.8); 7.269(7.9); 7.259(3.8); 6.906(0.5); 6.889(0.9); 6.872(0.5); 5.302(1.7); 4.374(0.7); 4.355(0.7); 4.324(1.4); 4.305(1.4); 4.223(1.4); 4.207(1.5); 4.174(0.8); 4.157(0.8); 4.089(1.0); 4.065(3.1); 4.041(3.2); 4.016(1.1); 3.982(2.4); 3.925(2.8); 3.381(5.9); 3.351(2.6); 3.293(2.3); 2.805(0.8); 2.195(16.0); 2.046(0.4); 1.780(13.7); 1.686(5.1); 1.456(5.1); 1.432(10.8); 1.408(5.0); 1.260(0.4); 0.000(5.6)

Example 556: $^1$H-NMR(300.2 MHz, CDCl3):
9.071(3.2); 9.064(3.2); 8.298(5.3); 8.293(5.0); 7.745(2.9); 7.740(2.8); 7.267(9.2); 7.237(3.9); 6.908(0.5); 6.891(0.9); 6.875(0.5); 5.302(1.2); 4.372(0.8); 4.353(0.8); 4.322(1.5); 4.303(1.5); 4.223(1.5); 4.206(1.5); 4.173(0.8); 4.157(0.8); 3.982(2.5); 3.968(2.0); 3.945(3.2); 3.925(3.6); 3.380(5.9); 3.350(2.7); 3.292(2.3); 2.805(0.6); 2.193(16.0); 1.858(1.4); 1.834(2.5); 1.810(2.6); 1.780(14.0); 1.762(0.7); 1.655(5.6); 0.911(4.5); 0.886(9.1); 0.861(4.1); 0.000(6.8)

Example 557: $^1$H-NMR(499.9 MHz, CDCl3):
8.945(5.5); 8.940(6.0); 8.319(5.5); 8.315(5.5); 8.164(2.2); 8.160(2.3); 8.158(1.2); 8.154(1.1); 8.146(4.0); 8.143(4.3); 8.140(2.1); 8.136(1.7); 8.103(5.0); 8.099(2.2); 8.086(2.8); 8.081(1.3); 7.847(4.9); 7.843(6.0); 7.262(13.8); 6.742(1.7); 6.727(1.7); 4.248(0.6); 4.234(0.9); 4.221(0.6); 4.130(0.4); 4.116(1.1); 4.100(1.4); 4.090(1.6); 4.087(1.7); 4.080(0.9); 4.077(1.2); 4.074(1.3); 4.067(0.7); 4.064(0.8); 4.061(0.7); 4.051(0.5); 3.982(0.5); 3.970(1.6); 3.965(0.7); 3.957(1.8); 3.952(1.9); 3.944(0.8); 3.939(1.8); 3.926(0.7); 3.919(1.5); 3.888(3.8); 3.884(2.3); 3.853(5.9); 3.757(6.2); 3.722(3.8); 3.694(2.0); 3.659(1.5); 3.395(4.2); 3.377(4.1); 2.803(0.9); 2.759(1.2); 2.745(1.2); 1.612(6.0); 1.329(14.3); 1.316(14.6); 1.304(1.5); 1.289(1.6); 1.281(5.9); 1.268(7.5); 1.234(14.9); 1.221(16.0); 1.205(5.5); 1.178(14.8); 1.170(6.7); 1.165(15.3); 1.157(5.9); 0.895(2.0); 0.882(5.3); 0.867(2.5); 0.006(0.4); 0.000(10.0); −0.007(0.6)

Example 558: $^1$H-NMR(499.9 MHz, CDCl3):
8.945(6.2); 8.941(7.2); 8.938(3.4); 8.312(5.2); 8.308(6.3); 8.150(2.3); 8.147(2.4); 8.141(1.3); 8.138(1.3); 8.133(4.7); 8.129(4.9); 8.124(2.3); 8.120(2.2); 8.111(0.4); 8.099(5.7); 8.093(2.7); 8.081(2.8); 8.075(1.5); 8.012(0.3); 7.838(5.3); 7.834(5.3); 7.828(2.5); 7.824(2.3); 7.733(0.4); 7.262(18.0); 7.144(1.8); 7.133(2.2); 7.123(1.2); 5.296(2.0); 4.280(0.4); 4.267(0.7); 4.253(0.9); 4.239(0.8); 4.181(0.7); 4.178(1.5); 4.173(1.4); 4.170(0.9); 4.166(1.5); 4.161(1.3); 4.146(1.1); 4.143(2.7); 4.137(2.5); 4.135(1.5); 4.131(2.6); 4.126(2.4); 4.114(0.4); 4.063(2.7); 4.058(2.5); 4.052(3.1); 4.047(3.3); 4.037(2.9); 4.034(2.4); 4.027(2.3); 4.022(3.3); 4.017(1.9); 4.012(1.6); 4.002(0.7); 3.996(0.7); 3.991(0.7); 3.986(0.6); 3.982(0.3); 3.930(1.8); 3.895(2.5); 3.863(3.3); 3.828(7.2); 3.776(7.6); 3.741(3.5); 3.723(2.8); 3.688(2.0); 3.091(4.0); 3.075(3.9); 2.802(14.1); 2.603(1.4); 2.588(1.4); 2.264(3.3); 2.258(6.8); 2.256(2.5); 2.253(3.9); 2.251(3.3); 2.246(1.5); 2.089(0.4); 2.079(1.2); 2.069(1.2); 2.046(0.5); 2.040(1.6); 1.617(7.8); 1.559(0.4); 1.546(0.4); 1.496(0.5); 1.483(0.5); 1.344(16.0); 1.332(16.0); 1.314(6.7); 1.301(6.8); 1.278(0.6); 1.271(1.2); 1.266(1.4); 1.256(2.3); 1.242(0.7); 0.895(0.8); 0.882(2.1); 0.867(1.0); 0.006(0.5); 0.000(13.1); −0.007(0.7)

Example 559: $^1$H-NMR(300.2 MHz, CDCl3):
8.951(3.2); 8.948(1.8); 8.943(3.4); 8.324(2.7); 8.317(2.6); 8.155(0.8); 8.149(0.8); 8.146(0.4); 8.140(0.3); 8.125(2.5); 8.119(2.8); 8.116(1.4); 8.110(1.2); 8.100(3.2); 8.070(0.9); 8.064(0.4); 7.837(2.3); 7.831(2.6); 7.268(10.0); 7.259(4.3); 6.991(0.7); 6.973(1.0); 6.956(0.5); 4.418(0.7); 4.399(1.0); 4.379(0.3); 4.369(1.3); 4.349(0.8); 4.329(0.4); 4.252(0.4); 4.237(1.4); 4.230(0.6); 4.221(1.6); 4.206(0.5); 4.188(0.8); 4.172(0.9); 4.029(0.8); 4.022(0.3); 4.008(0.9); 4.001(1.0); 3.979(1.1); 3.971(2.4); 3.947(4.4); 3.924(2.5); 3.898(1.2); 3.888(1.0); 3.839(3.1); 3.788(3.2); 3.729(1.9); 3.669(0.6); 3.311(2.8); 3.282(2.7); 2.788(0.8); 2.764(0.8); 2.201(16.0); 1.859(1.5); 1.834(2.8); 1.810(2.8); 1.786(1.6); 1.762(0.4); 1.701(4.9); 1.327(6.2); 1.306(6.2); 1.275(2.1); 0.910(4.6); 0.885(9.4); 0.860(4.2); 0.000(7.2)

Example 560: $^1$H-NMR(400.1 MHz, CDCl3):
8.945(5.9); 8.939(6.4); 8.312(5.1); 8.161(1.2); 8.156(2.2); 8.152(1.5); 8.147(0.8); 8.139(2.5); 8.134(4.7); 8.129(3.3); 8.125(1.5); 8.119(1.0); 8.098(4.5); 8.091(1.7); 8.076(2.1); 8.069(0.7); 7.834(5.1); 7.830(5.1); 7.822(1.7); 7.268(12.4); 7.252(1.2); 7.241(1.0); 7.223(0.5); 4.290(0.4); 4.281(0.7); 4.275(0.8); 4.266(1.8); 4.251(2.2); 4.242(1.2); 4.237(1.6); 4.227(1.0); 4.222(0.7); 4.212(0.4); 4.073(1.6); 4.068(0.9); 4.056(2.0); 4.051(3.2); 4.047(1.3); 4.043(1.3); 4.035(2.5); 4.030(3.0); 4.023(1.7); 4.013(2.2); 4.008(2.3); 4.001(0.9); 3.992(1.5); 3.985(0.7); 3.953(0.7); 3.910(1.5); 3.885(1.7); 3.866(1.1); 3.862(1.4); 3.841(3.3); 3.818(3.4); 3.772(3.7); 3.766(3.7); 3.728(3.4); 3.722(2.7); 3.711(1.6); 3.697(2.6); 3.690(1.6); 3.686(0.7); 3.679(1.3); 3.675(1.5); 3.664(0.5); 3.653(0.8); 3.622(1.9); 3.615(0.8); 3.606(2.2); 3.600(2.5); 3.593(1.2); 3.589(1.0); 3.585(2.6); 3.578(1.3); 3.571(1.2); 3.568(1.2); 3.562(0.8); 3.558(1.2); 3.554(1.1); 3.549(1.2); 3.543(1.0); 3.534(1.1); 3.527(0.4); 3.521(0.3); 3.437(1.0); 3.434(1.1); 3.428(1.3); 3.425(1.4); 3.419(1.8); 3.404(1.2); 3.399(0.9); 3.393(1.0); 3.390(1.0); 3.384(1.3); 3.374(0.5); 3.369(0.6); 3.296(2.6); 3.275(3.0); 3.271(2.8); 3.251(2.4);

-continued

NMR Peak Lists Table 1

2.819(0.8); 2.804(9.7); 2.782(0.7); 2.763(0.7); 1.713(7.8); 1.482(12.5); 1.382(11.7); 1.368(4.2); 1.347(12.6); 1.340 (12.9); 1.332(13.6); 1.326(3.8); 1.310(16.0); 1.303(5.0); 1.295(2.9); 1.263(0.7); 0.881(0.8); 0.864(0.4); 0.000(8.5)
Example 561: $^1$H-NMR(300.2 MHz, CDCl3):
9.041(3.7); 9.034(3.6); 8.435(3.4); 8.399(3.5); 8.351(3.7); 8.343(3.6); 8.310(3.9); 8.304(3.8); 7.761(0.8); 7.743(1.4); 7.725(1.0); 7.710(3.8); 7.705(3.6); 7.268(8.0); 4.675(0.6); 4.656(0.6); 4.621(1.7); 4.603(1.7); 4.569(1.7); 4.551(1.7); 4.515(0.6); 4.498(0.6); 3.985(2.7); 3.928(3.2); 3.364(3.0); 3.306(2.6); 2.960(0.7); 2.886(0.6); 2.551(14.5); 1.809 (16.0); 1.678(5.8); 0.000(5.7)
Example 562: $^1$H-NMR(300.2 MHz, CDCl3):
8.950(3.1); 8.946(1.8); 8.942(3.3); 8.322(2.6); 8.314(2.6); 8.153(0.8); 8.147(0.8); 8.142(0.4); 8.136(0.4); 8.123(2.5); 8.117(2.7); 8.113(1.3); 8.107(1.2); 8.098(3.1); 8.091(1.3); 8.069(0.9); 8.061(0.4); 7.836(2.2); 7.830(2.5); 7.278(4.3); 7.269(8.2); 6.987(0.8); 6.969(1.0); 6.951(0.5); 4.414(0.7); 4.394(1.2); 4.374(0.3); 4.364(1.3); 4.345(1.7); 4.325(0.5); 4.254(0.5); 4.245(1.4); 4.229(1.8); 4.213(0.6); 4.195(0.8); 4.179(1.0); 4.091(1.2); 4.067(3.7); 4.055(0.5); 4.043(3.9); 4.034(1.1); 4.026(0.6); 4.018(1.5); 4.012(1.2); 4.005(1.0); 3.984(0.9); 3.947(0.6); 3.895(1.1); 3.888(1.0); 3.837(3.1); 3.788(3.3); 3.729(1.9); 3.670(0.6); 3.325(2.5); 3.297(2.3); 2.835(0.7); 2.811(0.7); 2.201(16.0); 2.046(1.0); 1.733(3.2); 1.455(5.1); 1.431(10.7); 1.406(5.1); 1.331(6.3); 1.310(6.3); 1.278(2.2); 1.257(2.4); 1.236(0.4); 0.000(5.9)
Example 563: $^1$H-NMR(400.1 MHz, CDCl3):
9.039(3.9); 9.034(3.9); 8.444(2.9); 8.441(3.2); 8.393(3.1); 8.281(4.0); 8.276(4.1); 8.266(3.4); 8.261(3.3); 7.797(0.7); 7.784(1.2); 7.770(0.7); 7.726(3.4); 7.721(3.3); 7.288(2.2); 5.304(0.5); 4.670(0.6); 4.656(0.6); 4.630(1.5); 4.616(1.5); 4.574(1.5); 4.561(1.5); 4.534(0.6); 4.521(0.6); 3.988(2.8); 3.945(3.2); 3.391(7.1); 3.368(3.1); 3.325(2.7); 2.542(14.1); 2.045(0.5); 1.810(16.0); 1.259(0.4); 0.000(1.5)
Example 564: $^1$H-NMR(400.1 MHz, CDCl3):
9.060(4.3); 9.055(4.3); 8.306(2.4); 8.302(2.6); 8.299(2.7); 8.295(2.5); 8.285(3.5); 8.280(3.4); 7.741(2.2); 7.737(3.8); 7.733(2.2); 7.271(5.2); 7.212(0.4); 7.197(0.7); 7.184(0.6); 7.171(0.6); 7.156(0.3); 5.301(0.4); 4.256(0.6); 4.247(0.8); 4.241(0.9); 4.232(1.0); 4.227(0.8); 4.218(0.7); 4.057(1.0); 4.041(1.0); 4.036(1.2); 4.020(1.0); 4.009(1.1); 3.992(1.1); 3.988(1.3); 3.971(1.0); 3.952(1.7); 3.931(1.8); 3.910(1.9); 3.889(2.1); 3.676(1.1); 3.660(1.1); 3.654(1.0); 3.639(0.9); 3.582(1.2); 3.567(1.2); 3.561(1.3); 3.553(0.5); 3.545(1.4); 3.539(0.5); 3.532(0.4); 3.528(0.9); 3.518(0.7); 3.516(0.6); 3.512(0.8); 3.510(0.8); 3.504(0.7); 3.497(0.7); 3.493(0.7); 3.481(0.6); 3.440(0.7); 3.431(0.7); 3.427(0.7); 3.418(0.7); 3.411(0.7); 3.405(0.5); 3.396(1.3); 3.379(8.1); 3.361(0.7); 3.353(2.0); 3.346(0.6); 3.340(1.9); 3.310(1.7); 3.297(1.6); 2.044(0.6); 1.789(16.0); 1.681(3.2); 1.486(7.4); 1.410(7.7); 1.342(7.4); 1.322(7.8); 1.259(0.6); 0.000(3.8)
Example 565: $^1$H-NMR(400.1 MHz, CDCl3):
8.936(4.1); 8.931(4.5); 8.927(1.7); 8.310(2.7); 8.304(3.5); 8.300(1.2); 8.165(1.6); 8.160(1.6); 8.154(0.7); 8.149(0.7); 8.143(2.9); 8.138(3.0); 8.131(1.2); 8.127(1.1); 8.089(3.2); 8.079(1.3); 8.066(1.9); 8.057(0.7); 7.826(3.1); 7.822(3.1); 7.815(1.3); 7.810(1.1); 7.587(1.2); 7.575(0.7); 7.274(4.7); 4.267(0.4); 4.250(0.5); 4.234(0.4); 4.004(1.0); 3.999(0.5); 3.988(1.1); 3.983(1.2); 3.972(0.5); 3.967(1.1); 3.951(0.3); 3.925(0.9); 3.881(1.2); 3.872(1.9); 3.828(4.0); 3.764(4.3); 3.720(2.1); 3.687(1.3); 3.643(1.0); 3.558(0.7); 3.549(1.7); 3.544(1.2); 3.538(2.6); 3.535(3.0); 3.532(2.9); 3.526(2.6); 3.520(6.2); 3.510(3.7); 3.499(4.1); 3.492(6.1); 3.488(3.0); 3.487(3.2); 3.474(6.1); 3.471(2.8); 3.457(2.2); 3.453(1.0); 3.393(0.5); 3.378(1.1); 3.365(1.3); 3.349(0.9); 3.344(0.9); 3.330(1.0); 3.315(0.5); 3.046(0.8); 3.028(0.7); 2.804(1.4); 1.836(2.5); 1.826(2.3); 1.813(2.6); 1.810(2.6); 1.806(1.5); 1.797(2.2); 1.789(1.1); 1.782(0.8); 1.774(0.4); 1.336(9.1); 1.320(9.1); 1.304(0.5); 1.292(3.3); 1.276(3.9); 1.272(8.5); 1.254(16.0); 1.237(7.7); 0.881(0.8); 0.863(0.3); 0.000(3.5)
Example 566: $^1$H-NMR(400.1 MHz, CDCl3):
9.031(3.5); 9.025(3.6); 8.336(3.2); 8.331(3.1); 8.287(3.6); 8.282(3.6); 7.697(3.1); 7.693(3.0); 7.271(3.2); 7.084(0.5); 7.071(0.9); 7.058(0.5); 4.156(0.5); 4.150(0.5); 4.142(0.5); 4.136(0.5); 4.112(1.3); 4.106(1.4); 4.098(1.3); 4.092(1.3); 4.056(1.3); 4.050(1.3); 4.043(1.3); 4.037(1.3); 4.012(0.5); 4.006(0.6); 3.999(0.5); 3.993(0.5); 3.948(2.8); 3.905(3.2); 3.341(3.0); 3.298(2.7); 2.264(1.8); 2.257(3.6); 2.251(1.7); 2.080(0.9); 2.071(1.1); 1.852(0.7); 1.787(16.0); 0.880(0.4); 0.000(2.2)
Example 567: $^1$H-NMR(400.1 MHz, CDCl3):
8.938(3.8); 8.933(4.5); 8.928(1.4); 8.474(3.8); 8.376(3.8); 8.373(3.6); 8.305(2.6); 8.300(3.3); 8.294(1.0); 8.153(1.3); 8.148(1.3); 8.134(0.7); 8.130(2.9); 8.126(2.8); 8.112(0.9); 8.107(0.9); 8.087(3.2); 8.074(1.2); 8.064(1.6); 8.052(0.5); 7.832(3.5); 7.828(3.5); 7.818(1.9); 7.815(1.9); 7.802(0.6); 7.270(7.1); 4.774(1.2); 4.759(0.8); 4.734(1.2); 4.718(1.2); 4.698(0.4); 4.682(0.4); 4.548(1.4); 4.535(1.4); 4.508(1.0); 4.495(1.0); 4.265(0.3); 4.148(0.4); 4.134(0.8); 4.130(1.2); 4.118(1.1); 4.112(1.2); 4.102(0.8); 4.095(0.4); 3.899(0.6); 3.855(1.2); 3.850(0.8); 3.806(4.7); 3.793(4.5); 3.778(1.3); 3.749(0.7); 3.735(0.7); 3.654(1.2); 3.636(1.1); 3.115(0.4); 3.096(0.4); 2.544(16.0); 2.044(3.7); 1.770(2.8); 1.334(8.1); 1.318(8.1); 1.309(2.9); 1.293(2.6); 1.276(1.1); 1.258(2.1); 1.240(1.0); 0.000(5.3)
Example 568: $^1$H-NMR(300.2 MHz, CDCl3):
8.947(7.7); 8.945(5.3); 8.940(8.2); 8.319(6.8); 8.311(6.8); 8.175(2.3); 8.169(2.5); 8.160(1.3); 8.154(0.5); 8.145(5.5); 8.139(6.3); 8.130(3.0); 8.105(6.8); 8.099(3.9); 8.075(2.8); 8.069(1.5); 7.837(5.6); 7.830(7.4); 7.268(18.0); 7.059(2.2); 7.032(2.3); 5.409(0.4); 4.425(1.1); 4.414(0.6); 4.398(2.0); 4.388(1.2); 4.371(2.1); 4.360(1.1); 4.344(1.1); 4.333(0.6); 4.251(0.7); 4.229(1.0); 4.208(0.7); 4.158(0.4); 4.134(1.1); 4.111(1.1); 4.087(0.4); 4.019(0.4); 3.998(1.4); 3.977(1.7); 3.970(1.8); 3.948(1.6); 3.933(2.2); 3.886(3.1); 3.875(3.1); 3.828(7.5); 3.763(8.0); 3.704(3.6); 3.698(3.6); 3.640(2.1); 3.362(3.2); 3.333(3.0); 3.047(0.5); 2.834(1.0); 2.810(1.0); 2.729(1.1); 2.437(0.6); 2.424(0.8); 2.414(1.2); 2.401(1.7); 2.389(1.6); 2.377(1.9); 2.365(2.0); 2.358(1.4); 2.353(1.8); 2.340(1.9); 2.328(1.8); 2.318(1.7); 2.305(1.5); 2.292(1.3); 2.282(0.9); 2.273(0.6); 2.265(0.5); 2.047(5.0); 2.019(0.5); 1.985(1.4); 1.981(1.2); 1.955(2.9); 1.924(3.3); 1.901(2.0); 1.894(2.1); 1.890(2.2); 1.875(0.6); 1.864(1.0); 1.821(0.3); 1.811(0.5); 1.801(1.5); 1.797(1.5); 1.792(1.3); 1.784(2.3); 1.780(2.7); 1.771(2.7); 1.766(2.6); 1.756(3.6); 1.745(4.3); 1.735(2.3); 1.731(1.7); 1.721(2.1); 1.710(2.0); 1.700(1.4); 1.686(3.2); 1.649(0.3); 1.327(16.0); 1.306(16.0); 1.284(8.7); 1.263(7.9); 1.260(5.7); 1.236(1.6); 0.011(0.4); 0.000 (12.9); −0.011(0.6)
Example 569: $^1$H-NMR(400.1 MHz, CDCl3):
9.068(3.4); 9.063(3.4); 8.309(3.5); 8.305(3.6); 8.298(0.4); 8.291(3.0); 8.286(2.9); 7.744(3.0); 7.739(3.0); 7.263(10.5); 7.055(0.5); 7.043(0.8); 7.030(0.5); 5.300(0.4); 4.153(0.5); 4.146(0.6); 4.139(0.6); 4.132(0.5); 4.109(1.3); 4.102(1.3); 4.095(1.3); 4.088(1.2); 4.048(1.3); 4.042(1.3); 4.035(1.3); 4.029(1.3); 4.004(0.6); 3.998(0.6); 3.991(0.6); 3.985(0.5); 3.955(2.8); 3.912(3.2); 3.374(6.2); 3.349(3.0); 3.306(2.7); 2.258(1.8); 2.252(3.6); 2.245(1.8); 2.079(0.6); 2.069(0.7); 1.850(0.5); 1.785(16.0); 1.580(4.1); 0.882(0.5); 0.000(7.5)
Example 570: $^1$H-NMR(400.0 MHz, DMSO):
9.021(2.9); 9.015(3.0); 8.743(2.3); 8.738(2.3); 8.640(0.6); 8.626(1.2); 8.611(0.6); 8.315(0.4); 8.276(2.3); 8.272(2.5); 8.167(1.1); 8.163(1.0); 8.145(1.8); 8.141(1.8); 8.091(2.6); 8.069(1.5); 7.458(4.1); 4.163(1.9); 4.153(0.5); 4.130(1.7); 4.116(4.8); 4.101(1.6); 4.079(0.4); 3.989(1.2); 3.971(3.5); 3.953(3.5); 3.935(1.2); 3.903(13.7); 3.819(2.2); 3.773(1.8); 3.401(0.4); 3.378(0.8); 3.336(293.8); 2.676(0.6); 2.672(0.8); 2.668(0.6); 2.507(103.2); 2.503(133.8); 2.499(97.5);

NMR Peak Lists Table 1

2.334(0.6); 2.330(0.8); 2.326(0.6); 2.218(0.9); 2.112(16.0); 2.104(15.5); 1.336(0.6); 1.287(4.1); 1.269(8.7); 1.251(4.3); 1.234(1.1); 1.225(0.7); 1.177(0.6); 0.000(4.3)
Example 571: ¹H-NMR(300.2 MHz, CDCl3):
9.051(2.8); 9.044(2.9); 8.377(2.5); 8.370(2.5); 8.314(2.8); 8.308(2.9); 7.771(2.3); 7.765(2.3); 7.336(3.2); 7.269(6.3); 6.877(0.4); 6.859(0.7); 6.843(0.4); 4.366(1.9); 4.359(1.9); 4.348(1.9); 4.341(1.9); 4.134(0.4); 4.121(0.8); 4.110(0.5); 4.097(2.5); 4.087(0.4); 4.073(2.5); 4.048(0.9); 4.024(2.0); 3.964(2.4); 3.511(2.4); 3.451(2.0); 3.381(16.0); 2.961(0.4); 2.887(0.4); 2.885(0.4); 2.258(13.2); 2.046(1.5); 1.676(1.9); 1.487(4.1); 1.463(8.6); 1.438(4.1); 1.284(0.5); 1.260(1.0); 1.236(0.4); 0.072(1.1); 0.000(4.8)
Example 572: ¹H-NMR(300.2 MHz, CDCl3):
9.046(2.9); 9.039(3.0); 8.375(2.7); 8.368(2.6); 8.308(3.0); 8.302(3.0); 7.769(2.6); 7.763(2.5); 7.320(3.6); 7.273(4.0); 6.889(0.5); 6.872(0.8); 6.855(0.5); 4.368(1.8); 4.357(2.1); 4.350(2.1); 4.339(1.9); 4.134(0.5); 4.110(0.5); 4.019(2.1); 4.002(1.9); 3.978(3.1); 3.958(3.2); 3.955(2.6); 3.515(2.5); 3.455(2.0); 3.380(16.0); 2.255(14.0); 2.047(2.1); 1.893(1.2); 1.869(2.2); 1.845(2.2); 1.821(1.3); 1.796(0.4); 1.746(1.8); 1.284(0.7); 1.260(1.5); 1.236(0.6); 0.944(3.8); 0.920(7.8); 0.895(3.6); 0.881(0.5); 0.073(1.3); 0.000(2.7)
Example 573: ¹H-NMR(300.2 MHz, CDCl3):
9.055(2.9); 9.048(3.0); 8.380(2.1); 8.373(2.1); 8.329(1.7); 8.325(2.1); 8.323(2.1); 8.319(1.8); 7.771(2.4); 7.766(2.4); 7.267(6.9); 7.151(0.6); 4.322(0.4); 4.314(0.5); 4.304(0.7); 4.294(0.5); 4.283(0.6); 4.118(0.6); 4.101(0.7); 4.096(0.7); 4.090(0.8); 4.079(0.7); 4.073(0.9); 4.068(0.7); 4.051(0.6); 3.990(1.1); 3.983(1.1); 3.930(1.4); 3.923(1.4); 3.731(0.8); 3.726(0.8); 3.711(0.8); 3.706(0.9); 3.702(0.9); 3.698(0.8); 3.682(0.7); 3.678(0.7); 3.594(0.5); 3.582(0.5); 3.575(0.5); 3.562(0.9); 3.552(0.7); 3.544(1.0); 3.536(2.2); 3.534(2.3); 3.523(0.6); 3.514(0.5); 3.494(0.7); 3.474(1.8); 3.448(0.4); 3.418(16.0); 2.809(0.4); 1.627(7.0); 1.488(4.7); 1.429(4.7); 1.367(4.7); 1.352(4.8); 1.266(0.6); 0.881(0.7); 0.000(4.5)
Example 574: ¹H-NMR(300.2 MHz, CDCl3):
9.049(2.8); 9.041(2.8); 8.376(2.3); 8.369(2.3); 8.325(2.8); 8.319(2.8); 7.769(2.2); 7.763(2.2); 7.269(4.6); 6.663(0.4); 6.638(0.5); 4.182(0.4); 4.160(0.6); 4.155(0.5); 4.138(0.5); 4.133(0.6); 4.111(0.5); 3.986(1.9); 3.926(2.4); 3.510(2.5); 3.450(2.0); 3.400(16.0); 3.353(0.5); 3.292(0.4); 3.042(0.4); 1.651(5.6); 1.264(6.6); 1.243(11.4); 1.221(6.0); 0.881(0.9); 0.000(2.9)
Example 575: ¹H-NMR(300.2 MHz, CDCl3):
8.982(3.3); 8.975(3.3); 8.248(2.9); 8.242(2.9); 8.026(2.3); 8.023(2.2); 8.019(1.8); 7.678(2.3); 7.672(2.3); 7.261(43.2); 7.086(0.5); 7.069(0.9); 4.169(0.5); 4.160(0.5); 4.150(0.5); 4.142(0.5); 4.110(1.3); 4.102(1.3); 4.092(1.3); 4.083(1.3); 4.043(1.3); 4.035(1.4); 4.026(1.4); 4.018(1.4); 3.985(0.5); 3.976(0.9); 3.970(2.9); 3.959(0.6); 3.913(3.3); 3.374(3.1); 3.313(6.8); 2.801(11.1); 2.253(1.8); 2.244(3.7); 2.236(1.9); 1.779(16.0); 1.555(10.4); 0.011(1.2); 0.000(41.2); −0.011(1.8)
Example 576: ¹H-NMR(300.2 MHz, CDCl3):
8.980(3.3); 8.973(3.3); 8.251(3.0); 8.244(3.0); 8.032(2.4); 8.029(2.4); 7.682(2.4); 7.677(2.3); 7.261(37.0); 6.707(0.8); 6.683(0.8); 4.072(0.6); 4.050(0.9); 4.046(0.7); 4.029(0.8); 4.024(0.9); 4.002(0.7); 3.980(0.3); 3.964(2.7); 3.907(3.2); 3.340(3.0); 3.312(6.1); 3.283(2.6); 2.801(11.8); 2.065(0.4); 1.842(0.4); 1.828(0.4); 1.750(16.0); 1.698(0.4); 1.649(0.4); 1.211(8.3); 1.189(8.2); 1.148(8.3); 1.126(8.2); 0.011(1.3); 0.000(35.7); −0.011(1.7)
Example 577: ¹H-NMR(300.2 MHz, CDCl3):
8.944(3.4); 8.936(3.4); 8.281(3.4); 8.273(3.2); 8.011(2.7); 8.009(2.6); 7.638(2.8); 7.633(2.7); 7.263(10.0); 7.073(1.0); 4.169(0.5); 4.160(0.5); 4.150(0.5); 4.142(0.5); 4.110(1.3); 4.102(1.4); 4.092(1.3); 4.083(1.3); 4.046(1.3); 4.037(1.4); 4.029(1.4); 4.020(1.3); 3.987(0.5); 3.979(0.6); 3.970(0.7); 3.960(2.9); 3.903(3.1); 3.362(3.0); 3.305(2.5); 2.958(0.4); 2.886(0.3); 2.804(0.9); 2.788(12.7); 2.255(1.8); 2.246(3.5); 2.238(1.8); 1.778(16.0); 1.723(0.3); 1.711(0.5); 0.000(9.5)
Example 578: ¹H-NMR(300.2 MHz, CDCl3):
8.943(4.0); 8.936(3.2); 8.287(4.0); 8.280(3.2); 8.018(3.7); 7.645(4.0); 7.263(8.3); 6.713(1.3); 6.687(1.2); 4.072(0.8); 4.050(1.3); 4.028(1.2); 4.002(0.8); 3.981(0.5); 3.953(2.6); 3.896(3.1); 3.330(3.1); 3.272(2.5); 2.791(15.1); 2.076(0.4); 2.065(0.3); 1.841(0.4); 1.824(0.8); 1.749(16.0); 1.212(8.8); 1.190(8.4); 1.149(8.9); 1.127(8.5); 0.000(8.0)
Example 579: ¹H-NMR(300.2 MHz, DMSO):
9.182(3.4); 9.174(3.6); 8.926(0.7); 8.907(1.5); 8.893(3.4); 8.886(3.6); 8.355(1.8); 8.349(4.2); 8.343(5.3); 8.337(2.2); 5.813(2.3); 4.028(1.6); 3.999(1.3); 3.990(2.1); 3.980(2.2); 3.967(3.5); 3.835(2.4); 3.773(1.4); 3.389(8.0); 3.348(16.0); 3.185(1.4); 3.177(3.1); 3.169(1.3); 2.572(0.7); 2.566(1.4); 2.560(2.0); 2.554(1.4); 2.548(0.7); 2.134(0.4); 0.000(2.2)
Example 580: ¹H-NMR(300.2 MHz, DMSO):
9.139(3.5); 9.132(3.7); 9.036(0.7); 9.017(1.4); 8.997(0.7); 8.856(3.1); 8.849(3.0); 8.478(2.9); 8.456(3.2); 8.452(2.4); 8.317(1.8); 8.311(4.1); 8.304(5.3); 8.298(2.3); 4.487(2.6); 4.467(2.5); 4.016(1.9); 3.955(2.8); 3.801(2.3); 3.739(1.5); 3.332(11.1); 3.320(16.0); 2.518(1.3); 2.512(2.8); 2.506(3.9); 2.500(2.9); 2.493(1.6); 2.478(11.4); 0.000(1.3)
Example 581: ¹H-NMR(300.2 MHz, CDCl3):
9.050(3.0); 9.043(3.0); 8.376(2.4); 8.368(2.3); 8.335(0.4); 8.328(0.6); 8.324(2.8); 8.318(2.8); 7.762(2.2); 7.756(2.2); 7.267(6.1); 6.951(0.5); 6.924(0.5); 4.495(0.4); 4.468(0.7); 4.441(0.7); 4.414(0.4); 3.986(1.9); 3.925(2.4); 3.496(2.4); 3.436(2.0); 3.396(16.0); 3.353(1.6); 3.291(1.4); 3.042(1.3); 2.428(0.6); 2.418(0.6); 2.405(0.9); 2.393(0.8); 2.380(0.9); 2.366(0.6); 2.354(0.4); 2.016(0.4); 2.012(0.6); 2.008(0.6); 1.982(0.9); 1.977(0.9); 1.972(0.8); 1.947(0.7); 1.943(0.7); 1.937(0.5); 1.819(0.4); 1.815(0.4); 1.798(0.9); 1.785(0.7); 1.774(1.0); 1.762(1.2); 1.748(0.4); 1.740(0.5); 1.728(0.5); 1.616(3.1); 0.000(4.6)
Example 582: ¹H-NMR(499.9 MHz, CDCl3):
9.041(2.7); 9.037(2.7); 8.368(2.7); 8.364(2.7); 8.318(2.9); 8.315(2.8); 7.761(2.7); 7.757(2.7); 7.561(0.8); 7.266(3.5); 3.963(2.3); 3.927(2.6); 3.587(2.1); 3.576(4.3); 3.565(2.3); 3.535(0.5); 3.527(1.4); 3.523(0.7); 3.519(0.9); 3.513(4.1); 3.507(1.7); 3.499(4.8); 3.488(4.2); 3.476(1.4); 3.464(0.7); 3.460(0.5); 3.452(2.4); 3.400(16.0); 1.873(0.6); 1.861(1.9); 1.850(2.5); 1.838(1.8); 1.826(0.6); 1.639(3.0); 1.264(4.3); 1.250(8.3); 1.236(4.1); 0.072(0.5); 0.000(2.5)
Example 583: ¹H-NMR(300.2 MHz, CDCl3):
8.943(3.2); 8.935(3.4); 8.282(3.0); 8.275(3.0); 8.019(2.2); 8.016(2.3); 8.013(1.9); 7.638(2.2); 7.632(2.2); 7.262(25.4); 6.998(0.7); 6.971(0.7); 4.394(0.5); 4.368(0.9); 4.339(0.9); 4.312(0.5); 3.943(2.5); 3.886(3.0); 3.324(2.9); 3.266(2.4); 2.802(0.8); 2.790(11.1); 2.389(0.4); 2.376(0.6); 2.364(0.5); 2.352(0.7); 2.339(0.5); 2.326(0.5); 2.313(0.6); 2.300(0.6); 2.288(0.6); 2.275(0.5); 2.264(0.4); 1.965(0.6); 1.933(1.0); 1.916(0.7); 1.899(0.8); 1.883(1.0); 1.869(0.5); 1.854(0.7); 1.850(0.7); 1.821(0.5); 1.764(1.2); 1.746(1.2); 1.723(1.7); 1.712(1.9); 1.693(0.8); 1.688(1.0); 1.677(0.9); 1.652(0.6); 1.637(0.5); 1.617(0.6); 0.011(0.8); 0.000(24.3); −0.011(1.2)
Example 584: ¹H-NMR(300.2 MHz, CDCl3):
8.980(3.2); 8.973(3.3); 8.247(2.8); 8.240(2.7); 8.031(2.1); 8.028(2.2); 7.675(2.2); 7.669(2.1); 7.607(0.4); 7.261(62.5); 7.004(0.7); 6.977(0.8); 6.910(0.4); 4.394(0.5); 4.367(0.9); 4.340(0.9); 4.313(0.5); 3.953(2.5); 3.896(3.0); 3.335(2.9); 3.312(6.0); 3.278(2.4); 2.801(10.9); 2.386(0.5); 2.377(0.6); 2.366(0.5); 2.349(0.6); 2.339(0.5); 2.326(0.5); 2.313(0.6);

| NMR Peak Lists Table 1 |
| --- |
| 2.299(0.6); 2.290(0.6); 2.275(0.5); 1.966(0.6); 1.935(1.0); 1.916(0.7); 1.905(0.7); 1.899(0.8); 1.886(1.0); 1.870(0.5); 1.850(0.7); 1.829(0.4); 1.821(0.6); 1.765(1.2); 1.747(16.0); 1.722(1.7); 1.711(1.9); 1.688(1.1); 1.676(1.1); 1.652(1.0); 1.604(1.3); 1.591(1.2); 1.487(0.4); 0.011(1.8); 0.000(59.8); −0.011(2.7) |
| Example 585: $^1$H-NMR(300.2 MHz, CDCl3): |
| 8.946(3.5); 8.939(3.6); 8.285(3.8); 8.280(3.8); 7.998(3.8); 7.639(4.0); 7.263(14.3); 7.249(6.3); 6.909(1.8); 4.361(1.0); 4.343(1.0); 4.312(2.0); 4.293(2.0); 4.226(2.0); 4.210(2.0); 4.177(1.0); 4.160(1.0); 4.079(1.7); 4.055(4.3); 4.031(4.4); 4.007(1.9); 3.978(2.6); 3.921(2.9); 3.355(2.8); 3.298(2.4); 2.786(14.9); 2.729(0.5); 2.187(16.0); 1.773(15.0); 1.660 (0.9); 1.612(3.6); 1.449(4.8); 1.424(8.7); 1.400(4.6); 0.000(12.9) |
| Example 586: $^1$H-NMR(300.2 MHz, CDCl3): |
| 8.981(3.2); 8.974(3.3); 8.249(2.8); 8.242(2.7); 8.014(1.6); 8.010(2.0); 8.007(2.1); 8.004(1.6); 7.678(2.1); 7.672(2.0); 7.264(17.3); 7.256(0.6); 7.248(3.8); 6.934(0.5); 6.917(0.8); 6.900(0.5); 5.301(12.5); 4.362(0.7); 4.343(0.7); 4.312(1.4); 4.293(1.4); 4.227(1.5); 4.210(1.5); 4.177(0.7); 4.161(0.7); 4.078(1.2); 4.054(3.9); 4.029(4.0); 4.005(1.4); 3.988(2.4); 3.931(2.8); 3.366(2.6); 3.317(6.0); 3.309(2.7); 2.958(0.4); 2.884(0.3); 2.795(10.1); 2.188(16.0); 1.774(13.7); 1.758 (0.7); 1.749(0.5); 1.663(0.4); 1.621(2.2); 1.447(5.0); 1.422(10.6); 1.398(4.9); 0.011(0.5); 0.000(16.3); −0.008(0.5); −0.009(0.4); −0.011(0.6) |
| Example 587: $^1$H-NMR(499.9 MHz, MeOD): |
| 8.955(3.5); 8.677(3.2); 8.610(1.0); 8.255(1.8); 8.238(2.1); 8.166(3.2); 8.125(0.4); 8.082(2.0); 8.065(1.8); 4.810(20.5); 4.328(1.6); 4.293(1.7); 3.795(1.8); 3.760(1.6); 3.544(2.3); 3.534(4.0); 3.523(3.7); 3.509(4.6); 3.495(4.5); 3.481(1.9); 3.471(0.9); 3.458(0.9); 3.444(1.2); 3.432(1.2); 3.417(0.8); 3.402(1.1); 3.390(1.3); 3.377(1.0); 3.363(0.9); 3.334(43.4); 3.016(1.1); 2.885(1.0); 2.365(16.0); 1.856(2.1); 1.844(3.0); 1.832(2.2); 1.537(0.6); 1.403(0.6); 1.226(4.4); 1.212(8.7); 1.199(4.4) |
| Example 588: $^1$H-NMR(300.2 MHz, CDCl3): |
| 8.951(2.4); 8.944(2.5); 8.330(2.0); 8.323(1.9); 8.160(0.7); 8.154(0.7); 8.131(2.1); 8.125(2.2); 8.104(2.6); 8.075(0.8); 7.860(2.1); 7.855(2.0); 7.273(1.9); 7.154(0.6); 7.127(0.7); 5.300(0.4); 4.474(0.4); 4.447(0.8); 4.420(0.8); 4.393(0.9); 4.335(2.0); 4.276(2.4); 3.704(2.4); 3.645(2.0); 2.438(0.4); 2.427(0.5); 2.423(0.5); 2.416(0.5); 2.413(0.5); 2.402(0.6); 2.398(0.6); 2.388(0.7); 2.371(16.0); 2.356(0.8); 2.353(0.8); 2.344(0.6); 2.339(0.6); 2.328(0.5); 2.316(0.4); 2.030(0.7); 2.000(1.2); 1.996(1.3); 1.966(1.3); 1.936(0.7); 1.931(0.8); 1.815(0.6); 1.801(0.7); 1.794(1.0); 1.781(0.9); 1.770(1.1); 1.759(1.5); 1.746(0.6); 1.735(0.7); 1.724(0.5); 1.254(0.4); 0.000(1.4) |
| Example 589: $^1$H-NMR(300.2 MHz, CDCl3): |
| 8.950(3.0); 8.946(2.0); 8.942(2.8); 8.480(2.3); 8.412(2.3); 8.331(2.8); 8.325(2.2); 8.156(1.0); 8.150(0.9); 8.126(2.8); 8.121(3.0); 8.099(2.9); 8.069(0.9); 8.012(0.5); 7.994(0.9); 7.977(0.5); 7.864(2.9); 7.860(2.8); 7.277(3.8); 4.773(0.5); 4.754(0.5); 4.720(1.0); 4.700(1.0); 4.622(1.0); 4.605(1.0); 4.569(0.5); 4.551(0.5); 4.365(2.0); 4.349(0.8); 4.306(2.4); 4.290(1.0); 3.762(2.9); 3.704(2.4); 2.719(0.4); 2.628(0.8); 2.563(10.3); 2.493(0.6); 2.431(6.2); 2.399(16.0); 1.867(1.1); 1.254(0.4); 0.000(2.5) |
| Example 590: $^1$H-NMR(300.2 MHz, CDCl3): |
| 8.957(1.7); 8.951(1.7); 8.340(2.3); 8.333(2.3); 8.144(0.4); 8.139(0.4); 8.114(2.5); 8.109(3.3); 8.104(3.3); 8.074(0.5); 7.857(2.5); 7.315(2.6); 7.268(5.4); 7.072(0.5); 7.055(0.9); 7.038(0.6); 5.302(0.7); 4.454(0.7); 4.434(0.7); 4.404(1.3); 4.385(1.3); 4.347(2.0); 4.289(2.9); 4.276(1.5); 4.244(0.8); 4.227(0.7); 4.106(0.9); 4.082(2.5); 4.057(2.6); 4.033(0.9); 3.724(2.3); 3.665(2.0); 2.349(16.0); 2.227(12.2); 1.704(1.0); 1.468(3.6); 1.443(7.3); 1.419(3.5); 1.254(0.4); 0.073(8.8); 0.000(3.7) |
| Example 591: $^1$H-NMR(300.2 MHz, CDCl3): |
| 8.958(2.2); 8.950(2.3); 8.340(1.9); 8.333(1.9); 8.145(0.4); 8.139(0.3); 8.115(2.2); 8.109(2.7); 8.103(2.9); 8.074(0.4); 7.857(2.0); 7.295(3.1); 7.268(5.3); 7.080(0.4); 7.062(0.7); 7.045(0.4); 4.459(0.6); 4.439(0.6); 4.409(1.1); 4.390(1.1); 4.348(1.9); 4.289(2.5); 4.268(1.2); 4.236(0.7); 4.219(0.7); 3.985(1.8); 3.961(2.9); 3.937(1.9); 3.722(2.1); 3.663(1.8); 2.344(16.0); 2.227(12.5); 1.871(1.0); 1.847(1.9); 1.823(1.9); 1.799(1.1); 1.700(0.6); 1.254(0.6); 0.918(3.4); 0.893(7.1); 0.869(3.2); 0.073(11.4); 0.000(3.7) |
| Example 592: $^1$H-NMR(300.2 MHz, CDCl3): |
| 9.073(2.1); 9.067(2.1); 8.318(3.0); 8.313(2.9); 7.805(1.7); 7.800(1.7); 7.350(0.3); 7.336(2.3); 7.269(4.9); 6.880(0.4); 6.863(0.5); 4.366(1.5); 4.359(1.6); 4.349(1.4); 4.341(1.3); 4.134(0.4); 4.120(0.8); 4.110(0.6); 4.095(2.2); 4.087(0.5); 4.071(2.2); 4.047(0.8); 4.031(1.5); 3.971(1.8); 3.525(1.8); 3.464(1.5); 3.406(0.7); 3.398(1.1); 3.383(16.0); 2.959(0.4); 2.886(0.4); 2.884(0.4); 2.271(1.0); 2.259(9.8); 2.046(1.6); 1.688(3.2); 1.494(0.3); 1.487(3.3); 1.476(0.6); 1.470(0.7); 1.462(6.9); 1.446(0.4); 1.438(3.2); 1.284(0.5); 1.260(1.0); 1.236(0.4); 0.000(4.3) |
| Example 593: $^1$H-NMR(300.2 MHz, CDCl3): |
| 9.070(2.4); 9.063(2.4); 8.314(4.4); 8.308(4.1); 7.803(2.1); 7.797(2.1); 7.334(0.3); 7.320(2.9); 7.272(4.1); 7.256(0.3); 6.889(0.4); 6.872(0.7); 6.855(0.4); 4.339(1.6); 4.356(1.9); 4.351(1.8); 4.339(1.5); 4.134(0.4); 4.110(0.4); 4.027(1.7); 4.003(1.4); 3.979(2.5); 3.967(2.5); 3.955(1.6); 3.527(2.1); 3.467(1.7); 3.407(1.2); 3.382(16.0); 2.961(0.6); 2.886(0.5); 2.268(1.0); 2.255(11.5); 2.046(1.6); 1.893(1.0); 1.869(1.9); 1.845(1.9); 1.821(1.1); 1.724(1.6); 1.284(0.5); 1.260(1.1); 1.236(0.5); 0.944(3.3); 0.920(6.7); 0.895(3.1); 0.881(0.3); 0.000(3.4) |
| Example 594: $^1$H-NMR(300.2 MHz, CDCl3): |
| 9.080(3.1); 9.073(2.7); 8.336(2.4); 8.332(2.9); 8.330(2.7); 8.326(2.6); 8.321(2.7); 8.315(2.2); 7.807(2.8); 7.801(2.4); 7.266(8.1); 7.151(0.8); 4.321(0.5); 4.314(0.6); 4.303(0.9); 4.294(0.7); 4.283(0.6); 4.118(0.7); 4.101(0.9); 4.095(0.8); 4.089(0.9); 4.079(0.8); 4.072(1.0); 4.067(0.7); 4.051(0.6); 3.998(1.3); 3.991(1.1); 3.937(1.6); 3.931(1.4); 3.731(0.9); 3.726(0.8); 3.711(1.0); 3.706(1.1); 3.703(1.0); 3.698(0.8); 3.683(0.8); 3.677(0.6); 3.594(0.5); 3.583(0.6); 3.575(0.6); 3.563(1.2); 3.547(3.0); 3.533(0.8); 3.524(0.6); 3.514(0.5); 3.493(1.1); 3.487(1.8); 3.475(0.5); 3.448(0.4); 3.420(16.0); 3.380(5.0); 2.808(0.7); 1.607(8.1); 1.489(5.3); 1.431(5.2); 1.367(5.8); 1.353(5.4); 1.267(2.1); 0.904(0.7); 0.882(2.0); 0.859(0.8); 0.011(0.8); 0.000(6.9) |
| Example 595: $^1$H-NMR(300.2 MHz, CDCl3): |
| 9.074(2.5); 9.067(2.6); 8.333(2.7); 8.327(2.8); 8.316(2.2); 8.310(2.2); 7.803(2.1); 7.797(2.1); 7.268(5.2); 6.661(0.4); 6.635(0.5); 4.183(0.4); 4.161(0.6); 4.156(0.5); 4.139(0.5); 4.134(0.7); 4.112(0.5); 3.993(1.9); 3.933(2.4); 3.522(2.5); 3.461(2.0); 3.401(16.0); 3.380(4.7); 2.806(1.8); 1.634(3.6); 1.264(7.3); 1.242(11.7); 1.221(6.0); 0.903(0.5); 0.881(1.8); 0.858(0.6); 0.000(4.3) |
| Example 596: $^1$H-NMR(300.2 MHz, CDCl3): |
| 9.070(2.8); 9.064(2.8); 8.515(2.1); 8.511(2.2); 8.427(2.2); 8.328(2.9); 8.322(3.0); 8.314(2.5); 8.307(2.4); 7.804(2.4); 7.798(2.4); 7.763(0.5); 7.746(0.8); 7.727(0.4); 7.272(4.5); 4.696(1.3); 4.677(2.4); 4.658(1.3); 4.134(0.9); 4.110(0.9); 4.086(0.4); 4.032(1.9); 3.972(2.4); 3.559(2.4); 3.499(2.0); 3.452(0.4); 3.428(16.0); 3.410(0.3); 3.385(5.0); 2.597(0.4); 2.577(10.2); 2.047(4.2); 1.720(3.9); 1.284(1.2); 1.260(2.4); 1.236(1.1); 0.000(3.6) |

NMR Peak Lists Table 1

Example 597: ¹H-NMR(300.2 MHz, CDCl3):
9.074(2.7); 9.068(2.7); 8.330(2.9); 8.324(2.9); 8.316(2.5); 8.309(2.4); 7.797(2.5); 7.791(2.4); 7.267(5.5); 6.952(0.6); 6.926(0.6); 4.496(0.4); 4.469(0.8); 4.441(0.8); 4.414(0.4); 3.992(2.0); 3.931(2.5); 3.509(2.6); 3.449(2.1); 3.398(16.0); 3.379(5.2); 2.428(0.6); 2.419(0.7); 2.405(1.0); 2.393(1.0); 2.380(1.0); 2.367(0.7); 2.357(0.4); 2.047(0.3); 2.011(0.7); 2.007(0.6); 1.982(1.0); 1.977(1.0); 1.972(0.9); 1.946(0.8); 1.943(0.8); 1.937(0.6); 1.818(0.5); 1.815(0.5); 1.798(0.9); 1.785(0.8); 1.773(1.1); 1.762(1.3); 1.748(0.4); 1.739(0.5); 1.727(0.5); 1.618(4.8); 1.260(0.5); 0.882(0.6); 0.000(4.5)
Example 598: ¹H-NMR(300.2 MHz, CDCl3):
9.079(2.6); 9.072(2.6); 8.327(2.9); 8.320(4.5); 8.313(2.2); 7.805(2.2); 7.799(2.1); 7.266(7.0); 7.038(0.3); 7.023(0.6); 7.008(0.4); 4.193(1.1); 4.184(1.2); 4.174(1.1); 4.165(1.3); 4.162(1.3); 4.154(1.2); 4.145(1.2); 4.136(1.2); 4.021(0.4); 4.014(2.0); 3.954(2.4); 3.541(2.5); 3.481(2.0); 3.416(16.0); 3.382(4.6); 2.309(1.4); 2.300(2.9); 2.292(1.4); 2.047(0.9); 1.608(3.4); 1.284(0.5); 1.279(0.4); 1.260(1.2); 1.236(0.3); 0.882(1.0); 0.858(0.4); 0.000(5.6)
Example 599: ¹H-NMR(300.2 MHz, CDCl3):
9.067(2.5); 9.061(2.4); 8.334(2.6); 8.328(2.6); 8.316(2.2); 8.309(2.1); 7.798(2.2); 7.792(2.1); 7.628(0.3); 7.612(0.6); 7.596(0.4); 7.273(3.6); 3.991(1.9); 3.931(2.4); 3.601(1.8); 3.583(3.4); 3.564(2.0); 3.544(1.3); 3.535(0.6); 3.520(6.2); 3.497(5.6); 3.478(1.4); 3.474(1.9); 3.459(2.5); 3.404(16.0); 3.382(5.0); 2.808(3.0); 2.047(1.5); 1.892(0.4); 1.872(1.4); 1.853(1.8); 1.834(1.3); 1.814(0.4); 1.715(2.0); 1.306(0.6); 1.283(1.7); 1.279(5.0); 1.265(4.0); 1.260(4.9); 1.256(10.5); 1.232(4.1); 0.903(1.3); 0.881(4.6); 0.858(1.6); 0.000(2.8)
Example 600: ¹H-NMR(300.2 MHz, CDCl3):
8.954(3.0); 8.947(2.9); 8.308(3.0); 8.300(2.8); 8.028(2.5); 7.691(2.6); 7.313(4.1); 7.263(23.2); 6.856(1.0); 4.365(2.2); 4.353(2.7); 4.347(2.6); 4.336(2.2); 4.012(2.3); 3.999(2.5); 3.975(4.0); 3.951(5.1); 3.541(2.7); 3.481(2.2); 3.380(16.0); 2.798(11.2); 2.254(14.9); 1.917(0.4); 1.892(1.4); 1.868(2.6); 1.844(2.7); 1.820(1.5); 1.795(0.5); 1.589(13.0); 1.255 (0.4); 0.944(4.1); 0.919(8.0); 0.894(3.8); 0.000(17.5)
Example 601: ¹H-NMR(300.2 MHz, CDCl3):
8.954(3.0); 8.946(2.9); 8.513(2.7); 8.424(2.8); 8.307(3.0); 8.300(2.9); 8.042(2.6); 7.719(1.2); 7.692(3.0); 7.263(20.8); 4.727(0.3); 4.694(1.7); 4.674(2.8); 4.654(1.7); 4.618(0.4); 4.601(0.4); 4.021(2.0); 3.961(2.6); 3.569(2.6); 3.509(2.3); 3.473(0.3); 3.424(16.0); 2.800(11.4); 2.577(11.9); 1.598(10.0); 1.253(0.4); 0.000(15.1)
Example 602: ¹H-NMR(300.2 MHz, CDCl3):
8.950(2.6); 8.942(2.6); 8.307(2.4); 8.300(2.3); 8.046(1.4); 8.043(1.7); 8.040(1.7); 8.037(1.3); 7.685(1.7); 7.680(1.7); 7.572(0.6); 7.262(20.4); 5.301(2.1); 3.981(1.9); 3.921(2.4); 3.595(1.9); 3.576(3.6); 3.557(2.3); 3.540(1.5); 3.528(2.8); 3.517(4.4); 3.493(5.8); 3.469(3.0); 3.455(0.6); 3.448(0.3); 3.399(16.0); 2.797(8.4); 1.889(0.5); 1.869(1.5); 1.850(1.9); 1.831(1.4); 1.811(0.4); 1.573(7.5); 1.276(3.9); 1.253(8.1); 1.229(3.8); 0.070(0.5); 0.011(0.5); 0.000(14.5); −0.011(0.5)
Example 603: ¹H-NMR(499.9 MHz, DMSO):
8.948(3.5); 8.944(3.4); 8.598(3.4); 8.595(3.2); 8.231(3.6); 8.228(3.6); 8.165(1.8); 8.162(1.6); 8.148(2.5); 8.144(2.2); 8.070(3.2); 8.053(2.3); 7.893(1.7); 7.877(1.7); 4.560(5.8); 3.896(2.5); 3.861(2.9); 3.535(0.8); 3.527(0.9); 3.519(0.9); 3.488(0.4); 3.467(2.9); 3.433(2.5); 3.291(19.2); 2.716(1.1); 2.692(1.6); 2.684(1.5); 2.659(1.2); 2.505(5.5); 2.502(6.8); 2.498(5.3); 2.118(15.1); 1.909(0.6); 1.903(0.7); 1.881(1.8); 1.864(1.6); 1.859(1.5); 1.831(0.7); 1.655(0.7); 1.648(0.8); 1.630(1.7); 1.623(2.2); 1.614(1.9); 1.598(16.0); 1.574(2.5); 1.568(2.7); 1.558(3.2); 1.551(3.2); 1.541(1.7); 1.533(1.1); 0.000(2.1)
Example 604: ¹H-NMR(400.1 MHz, DMSO):
9.007(3.1); 9.002(3.2); 8.753(2.7); 8.748(2.4); 8.474(0.7); 8.459(1.4); 8.444(0.7); 8.249(2.5); 8.245(2.6); 8.168(1.3); 8.163(1.2); 8.145(2.1); 8.141(2.0); 8.079(2.7); 8.057(1.7); 7.401(4.3); 6.230(1.4); 6.204(1.5); 6.187(1.6); 6.161(1.7); 5.755(0.8); 5.420(2.1); 5.418(2.2); 5.377(1.9); 5.375(1.9); 5.325(2.1); 5.322(2.1); 5.298(2.0); 5.296(1.9); 4.094(3.5); 4.079(3.5); 4.024(2.0); 3.981(2.5); 3.960(1.3); 3.942(3.9); 3.924(3.9); 3.906(1.3); 3.646(2.3); 3.603(1.9); 3.316(16.5); 2.892(0.7); 2.733(0.6); 2.525(0.5); 2.512(10.8); 2.508(21.5); 2.503(28.8); 2.499(20.5); 2.494(9.7); 2.125(0.6); 2.056(16.0); 1.911(0.4); 1.297(0.4); 1.260(4.6); 1.242(9.8); 1.224(4.5)
Example 605: ¹H-NMR(300.2 MHz, CDCl3):
8.955(2.9); 8.947(2.9); 8.308(2.7); 8.300(2.8); 8.028(2.2); 7.690(2.3); 7.330(3.6); 7.261(41.1); 6.849(0.9); 4.364(2.2); 4.357(2.3); 4.345(2.3); 4.339(2.2); 4.117(1.1); 4.093(3.5); 4.068(3.6); 4.044(1.3); 4.017(2.1); 3.957(2.5); 3.538(2.6); 3.509(0.6); 3.495(0.4); 3.478(2.1); 3.443(0.5); 3.380(16.0); 2.798(10.3); 2.257(14.2); 1.559(7.3); 1.486(4.1); 1.461 (8.4); 1.437(4.1); 0.011(2.1); 0.000(33.3); −0.011(1.8)
Example 606: ¹H-NMR(300.2 MHz, CDCl3):
8.955(2.5); 8.948(2.5); 8.309(2.1); 8.301(2.1); 8.039(1.5); 7.691(1.6); 7.685(1.6); 7.261(34.2); 7.252(0.8); 7.248(0.5); 7.246(0.4); 7.243(0.3); 7.148(0.5); 4.317(0.3); 4.310(0.4); 4.299(0.6); 4.289(0.5); 4.278(0.5); 4.114(0.6); 4.098(0.7); 4.092(0.6); 4.086(0.8); 4.077(0.6); 4.070(0.8); 4.064(0.6); 4.048(0.6); 3.988(1.0); 3.978(1.0); 3.928(1.2); 3.918(1.2); 3.730(0.7); 3.726(0.7); 3.710(0.7); 3.705(0.8); 3.702(0.8); 3.697(0.7); 3.682(0.6); 3.677(0.6); 3.595(0.4); 3.583(0.4); 3.576(0.5); 3.561(2.2); 3.557(1.7); 3.550(0.8); 3.545(1.1); 3.531(0.6); 3.524(0.6); 3.510(0.6); 3.501(1.2); 3.497(1.3); 3.490(0.7); 3.470(0.4); 3.443(0.3); 3.415(16.0); 2.801(8.0); 1.555(5.7); 1.487(4.2); 1.426(4.2); 1.365(4.3); 1.351(4.3); 0.011(0.9); 0.000(28.7); −0.011(1.2)
Example 607: ¹H-NMR(300.2 MHz, CDCl3):
8.958(2.5); 8.950(2.7); 8.310(2.4); 8.302(2.4); 8.037(1.8); 8.034(1.8); 7.691(1.9); 7.686(1.8); 7.261(54.7); 7.019(0.4); 7.004(0.6); 4.189(1.1); 4.180(1.2); 4.171(1.2); 4.162(1.5); 4.151(1.2); 4.142(1.2); 4.133(1.2); 4.100(0.4); 4.003(1.9); 3.942(2.6); 3.553(2.6); 3.492(2.3); 3.412(16.0); 2.803(8.9); 2.301(1.3); 2.293(2.7); 2.284(1.4); 1.548(9.9); 0.011(1.7); 0.000(44.4); −0.011(2.3)
Example 608: ¹H-NMR(300.2 MHz, CDCl3):
8.953(2.5); 8.946(2.6); 8.306(2.3); 8.298(2.3); 8.041(1.3); 8.038(1.7); 8.035(1.7); 8.032(1.3); 7.684(1.7); 7.678(1.6); 7.276(0.4); 7.273(0.5); 7.261(57.1); 6.948(0.4); 6.922(0.5); 6.910(0.5); 4.498(0.4); 4.470(0.7); 4.442(0.7); 4.415(0.4); 3.978(1.9); 3.918(2.4); 3.522(2.5); 3.461(1.9); 3.394(16.0); 2.800(8.1); 2.426(0.6); 2.416(0.6); 2.403(0.8); 2.391(0.8); 2.377(0.7); 2.365(0.6); 2.351(0.4); 2.002(0.6); 1.973(0.8); 1.967(0.8); 1.936(0.7); 1.810(0.5); 1.794(0.9); 1.780(0.7); 1.769(1.0); 1.758(1.2); 1.735(0.5); 1.723(0.4); 1.548(2.9); 0.011(1.4); 0.000(45.4); −0.011(2.0)
Example 609: ¹H-NMR(300.2 MHz, CDCl3):
8.987(2.5); 8.980(2.5); 8.268(2.1); 8.261(2.1); 8.054(1.3); 8.050(1.6); 8.047(1.7); 8.044(1.3); 7.726(1.6); 7.720(1.6); 7.262(18.4); 6.665(0.4); 6.639(0.4); 4.183(0.4); 4.161(0.6); 4.156(0.5); 4.139(0.5); 4.134(0.6); 4.112(0.5); 3.985(1.9); 3.924(2.4); 3.548(2.5); 3.488(2.0); 3.399(16.0); 3.313(4.5); 2.810(7.9); 1.335(0.4); 1.313(0.4); 1.260(5.9); 1.237(9.6); 1.215(5.9); 0.011(0.5); 0.000(14.9); −0.009(0.4); −0.011(0.6)
Example 610: ¹H-NMR(300.2 MHz, CDCl3):
8.988(2.5); 8.981(2.6); 8.269(2.0); 8.262(2.1); 8.047(1.6); 7.726(1.8); 7.720(1.8); 7.263(15.6); 7.154(0.6); 4.317(0.4); 4.309(0.4); 4.299(0.7); 4.290(0.5); 4.279(0.6); 4.114(0.6); 4.099(0.7); 4.093(0.7); 4.086(0.8); 4.077(0.6); 4.070(0.9);

| NMR Peak Lists Table 1 |
|---|
| 4.064(0.7); 4.048(0.6); 3.996(1.0); 3.986(1.0); 3.936(1.3); 3.926(1.3); 3.731(0.8); 3.726(0.8); 3.711(0.7); 3.706(0.9); 3.703(0.9); 3.698(0.7); 3.683(0.7); 3.678(0.7); 3.596(0.4); 3.584(0.5); 3.574(1.7); 3.570(1.7); 3.564(1.3); 3.550(0.8); 3.545(1.2); 3.531(0.6); 3.525(0.6); 3.514(1.3); 3.510(1.7); 3.490(0.6); 3.470(0.4); 3.443(0.4); 3.417(16.0); 3.315(4.7); 2.809(8.5); 1.582(2.8); 1.487(4.5); 1.427(4.5); 1.364(4.5); 1.351(4.6); 0.011(0.4); 0.000(12.4); −0.011(0.6) |
| Example 611: $^1$H-NMR(300.2 MHz, CDCl3): |
| 8.990(2.4); 8.983(2.4); 8.269(2.1); 8.262(2.1); 8.048(1.3); 8.045(1.6); 8.042(1.6); 8.039(1.3); 7.726(1.7); 7.720(1.6); 7.262(19.0); 7.014(0.6); 4.189(1.1); 4.181(1.2); 4.171(1.2); 4.162(1.5); 4.160(1.4); 4.151(1.2); 4.142(1.2); 4.134(1.1); 4.011(1.9); 3.950(2.5); 3.566(2.5); 3.505(2.0); 3.429(0.7); 3.413(16.0); 3.374(0.5); 3.316(4.7); 3.297(0.5); 3.271(0.4); 2.810(8.1); 2.301(1.3); 2.293(2.8); 2.284(1.3); 1.621(0.6); 0.011(0.5); 0.000(14.8); −0.011(0.6) |
| Example 612: $^1$H-NMR(300.2 MHz, CDCl3): |
| 8.984(2.4); 8.977(2.5); 8.269(2.1); 8.262(2.2); 8.056(1.2); 8.053(1.6); 8.050(1.7); 8.047(1.4); 7.721(1.6); 7.715(1.6); 7.567(0.6); 7.263(20.5); 5.301(1.8); 3.989(1.9); 3.929(2.4); 3.594(1.8); 3.575(3.6); 3.557(2.2); 3.541(3.5); 3.533(0.8); 3.516(4.4); 3.493(5.8); 3.481(2.4); 3.475(1.6); 3.470(1.9); 3.455(0.6); 3.401(16.0); 3.311(4.6); 2.807(8.0); 1.890(0.5); 1.869(1.4); 1.850(1.9); 1.831(1.4); 1.811(0.4); 1.575(7.5); 1.276(4.0); 1.253(8.1); 1.229(3.8); 0.011(0.5); 0.000(15.3); −0.011(0.6) |
| Example 613: $^1$H-NMR(300.2 MHz, CDCl3): |
| 8.949(2.5); 8.941(2.6); 8.303(2.3); 8.295(2.2); 8.041(1.3); 8.037(1.6); 8.034(1.6); 8.031(1.3); 7.689(1.6); 7.683(1.6); 7.266(5.7); 6.670(0.4); 6.644(0.4); 4.184(0.5); 4.162(0.7); 4.157(0.5); 4.140(0.6); 4.135(0.8); 4.113(0.5); 3.979(1.9); 3.919(2.5); 3.537(2.5); 3.477(2.0); 3.398(16.0); 2.797(7.9); 2.047(0.8); 1.627(6.6); 1.261(6.3); 1.238(10.3); 1.216(6.0); 0.000(3.9) |
| Example 614: $^1$H-NMR(300.2 MHz, CDCl3): |
| 8.988(2.7); 8.981(2.8); 8.268(2.4); 8.261(2.5); 8.039(2.0); 8.037(2.0); 7.726(2.1); 7.721(2.0); 7.331(3.5); 7.263(19.3); 6.859(0.8); 6.841(0.5); 4.364(1.9); 4.357(2.0); 4.346(2.0); 4.339(2.0); 4.117(1.1); 4.093(3.4); 4.068(3.5); 4.044(1.2); 4.025(2.0); 3.964(2.5); 3.552(2.5); 3.509(0.4); 3.492(2.1); 3.444(0.4); 3.382(16.0); 3.316(5.2); 3.296(0.3); 2.958(0.4); 2.885(0.3); 2.806(9.6); 2.257(14.0); 1.597(6.2); 1.485(4.1); 1.461(8.6); 1.437(4.1); 0.011(0.4); 0.000(15.1); −0.011(0.8) |
| Example 615: $^1$H-NMR(300.2 MHz, CDCl3): |
| 8.989(2.6); 8.982(2.7); 8.269(2.3); 8.262(2.3); 8.040(1.8); 8.037(1.8); 7.726(1.8); 7.721(1.8); 7.312(3.3); 7.262(29.3); 6.874(0.4); 6.857(0.7); 4.366(1.6); 4.353(1.9); 4.348(1.9); 4.335(1.7); 4.020(2.0); 3.975(3.1); 3.959(2.6); 3.951(2.3); 3.554(2.4); 3.494(2.0); 3.382(16.0); 3.315(4.9); 2.958(0.3); 2.807(8.6); 2.254(13.6); 1.892(1.1); 1.868(2.1); 1.844(2.1); 1.820(1.2); 1.580(11.4); 1.252(0.4); 0.943(3.7); 0.933(0.4); 0.919(7.6); 0.894(3.4); 0.011(0.8); 0.000(23.4); −0.011(1.0) |
| Example 616: $^1$H-NMR(300.2 MHz, CDCl3): |
| 8.986(2.7); 8.979(2.7); 8.513(2.1); 8.509(2.2); 8.424(2.2); 8.267(2.5); 8.260(2.4); 8.051(2.0); 8.048(2.0); 7.727(2.6); 7.722(2.7); 7.264(14.6); 4.694(1.3); 4.674(2.3); 4.654(1.3); 4.029(2.0); 3.969(2.5); 3.582(2.5); 3.522(2.0); 3.425(16.0); 3.316(5.0); 2.808(9.3); 2.576(10.2); 1.637(2.0); 0.011(0.4); 0.000(11.5); −0.011(0.6) |
| Example 617: $^1$H-NMR(300.2 MHz, CDCl3): |
| 8.988(2.5); 8.981(2.6); 8.268(2.2); 8.261(2.2); 8.048(1.7); 8.045(1.8); 8.041(1.4); 7.720(1.8); 7.715(1.7); 7.607(0.4); 7.261(59.5); 6.951(0.5); 6.928(0.5); 6.911(0.5); 4.498(0.4); 4.470(0.8); 4.442(0.7); 4.414(0.4); 3.985(1.9); 3.924(2.5); 3.535(2.6); 3.475(2.0); 3.396(16.0); 3.312(4.8); 2.809(8.5); 2.426(2.1); 2.416(0.7); 2.403(0.8); 2.391(0.9); 2.378(0.7); 2.365(0.6); 2.002(0.6); 1.967(0.9); 1.937(0.8); 1.810(0.5); 1.793(1.0); 1.781(0.8); 1.769(1.1); 1.758(1.3); 1.735(0.6); 1.723(0.5); 1.568(3.8); 0.011(1.6); 0.000(47.1); −0.011(2.1) |
| Example 618: $^1$H-NMR(400.1 MHz, DMSO): |
| 8.982(3.0); 8.977(3.1); 8.782(0.7); 8.767(1.4); 8.753(0.7); 8.606(2.3); 8.601(2.3); 8.321(2.3); 8.316(2.5); 8.174(1.2); 8.169(1.0); 8.152(2.1); 8.147(2.1); 8.102(2.7); 8.080(1.5); 7.435(4.3); 6.687(0.6); 6.552(1.3); 6.417(0.8); 4.604(5.8); 4.183(0.4); 4.168(0.4); 4.147(1.5); 4.132(1.6); 4.125(1.6); 4.111(1.5); 4.088(0.4); 4.074(0.4); 3.988(1.3); 3.970(4.3); 3.960(5.6); 3.952(4.7); 3.934(1.3); 3.318(29.7); 2.677(0.4); 2.558(0.4); 2.531(1.0); 2.517(22.9); 2.513(47.3); 2.508(64.4); 2.504(46.1); 2.499(21.9); 2.335(0.4); 2.084(16.0); 1.292(4.7); 1.273(10.0); 1.255(4.5); 0.944(0.6) |
| Example 619: $^1$H-NMR(400.1 MHz, DMSO): |
| 8.983(4.0); 8.978(4.1); 8.610(3.0); 8.550(0.5); 8.536(1.2); 8.527(1.2); 8.512(0.6); 8.316(3.2); 8.178(1.2); 8.175(1.1); 8.156(2.2); 8.153(2.2); 8.107(3.7); 8.085(2.0); 6.687(0.5); 6.676(0.5); 6.553(1.0); 6.541(1.0); 6.418(0.6); 6.406(0.6); 4.603(8.0); 4.158(0.8); 4.143(1.6); 4.128(1.5); 4.115(0.8); 3.976(5.7); 3.944(1.0); 3.929(1.8); 3.923(1.3); 3.913(1.1); 3.908(2.0); 3.892(0.9); 3.687(1.0); 3.672(1.1); 3.667(1.8); 3.653(1.4); 3.646(1.0); 3.632(0.9); 3.318(14.8); 3.309(0.9); 3.296(1.8); 3.281(2.2); 3.271(1.8); 3.265(0.9); 3.256(0.7); 3.238(0.3); 2.530(0.4); 2.517(11.0); 2.513(22.6); 2.508(30.8); 2.504(22.2); 2.499(10.6); 1.298(16.0); 1.234(8.1); 1.225(8.4) |
| Example 620: $^1$H-NMR(400.1 MHz, DMSO): |
| 8.982(4.7); 8.977(4.8); 8.611(3.5); 8.606(3.4); 8.512(1.0); 8.498(1.9); 8.483(1.0); 8.319(3.5); 8.314(3.7); 8.179(1.8); 8.175(1.6); 8.157(3.2); 8.152(3.1); 8.106(4.1); 8.084(2.2); 6.668(1.0); 6.533(2.0); 6.398(1.2); 4.604(8.8); 3.957(7.5); 3.395(2.3); 3.378(7.6); 3.369(3.5); 3.360(8.3); 3.353(7.4); 3.343(3.1); 3.337(3.5); 3.316(25.4); 3.271(0.6); 3.255(1.1); 3.238(1.6); 3.222(1.4); 3.199(1.4); 3.184(1.5); 3.167(1.0); 3.152(0.5); 2.677(0.2); 2.558(0.4); 2.530(0.9); 2.526(1.5); 2.517(20.7); 2.513(42.7); 2.508(58.1); 2.504(41.3); 2.499(19.4); 2.335(0.4); 1.719(0.7); 1.702(2.5); 1.686(3.9); 1.670(2.4); 1.653(0.7); 1.099(7.7); 1.082(16.0); 1.064(7.5) |
| Example 621: $^1$H-NMR(400.1 MHz, DMSO): |
| 8.983(5.9); 8.978(6.0); 8.611(4.4); 8.606(4.2); 8.324(4.5); 8.319(4.8); 8.296(2.3); 8.276(2.2); 8.186(2.3); 8.181(2.2); 8.164(4.0); 8.159(4.0); 8.108(5.1); 8.086(2.9); 7.634(0.4); 7.604(0.5); 6.663(1.3); 6.528(2.7); 6.393(1.7); 4.605(10.9); 4.022(0.4); 4.005(1.2); 4.002(1.1); 3.989(1.6); 3.985(1.4); 3.968(1.9); 3.956(6.2); 3.948(6.4); 3.903(0.6); 3.365(0.4); 3.316(74.3); 2.682(0.7); 2.677(1.0); 2.673(0.7); 2.562(0.5); 2.558(0.8); 2.553(0.7); 2.531(3.9); 2.526(5.5); 2.517(58.5); 2.513(121.5); 2.508(167.3); 2.504(122.6); 2.499(62.4); 2.414(0.9); 2.410(0.8); 2.340(0.9); 2.335(1.2); 2.331(0.9); 1.995(0.6); 1.241(0.5); 1.182(0.4); 1.129(12.6); 1.112(15.1); 1.109(16.0); 1.092(13.4); 1.045(0.5) |
| Example 622: $^1$H-NMR(400.1 MHz, DMSO): |
| 9.115(3.4); 9.110(3.7); 8.914(2.4); 8.910(2.4); 8.781(0.7); 8.766(1.4); 8.752(0.7); 8.249(2.3); 8.245(2.7); 8.159(1.4); 8.154(1.3); 8.137(2.1); 8.132(2.1); 8.064(2.6); 8.042(1.7); 7.434(4.2); 7.225(0.4); 6.688(0.6); 6.553(1.3); 6.418(0.8); 4.183(0.4); 4.168(0.4); 4.146(1.5); 4.131(1.5); 4.123(1.6); 4.108(1.6); 4.086(0.5); 4.072(0.5); 3.995(0.5); 3.988(1.3); 3.977(0.7); 3.970(4.0); 3.952(4.4); 3.940(5.5); 3.934(2.9); 3.317(41.4); 2.677(0.4); 2.531(1.5); 2.526(2.3); 2.517(23.5); 2.513(49.1); 2.508(68.0); 2.504(49.7); 2.499(25.1); 2.340(0.4); 2.335(0.5); 2.331(0.4); 2.197(1.5); 2.082(16.0); 1.995(0.9); 1.293(4.8); 1.274(10.7); 1.256(5.1); 1.239(1.2); 1.221(0.5); 1.182(0.5) |

-continued

NMR Peak Lists Table 1

Example 623: ¹H-NMR(400.1 MHz, DMSO):
9.116(4.3); 9.111(4.5); 8.921(3.0); 8.919(3.1); 8.916(2.9); 8.549(0.5); 8.534(1.2); 8.525(1.2); 8.510(0.5); 8.245(3.2); 8.163(1.4); 8.160(1.3); 8.140(2.2); 8.138(2.1); 8.069(3.7); 8.047(2.5); 6.688(2.3); 6.676(0.5); 6.554(1.0); 6.542(1.0); 6.419(0.6); 6.407(0.6); 4.156(0.8); 4.142(1.6); 4.127(1.5); 4.113(0.8); 3.955(5.7); 3.942(1.4); 3.927(1.8); 3.921(1.4); 3.912(1.1); 3.906(2.1); 3.891(0.9); 3.685(1.1); 3.671(1.1); 3.665(1.7); 3.650(1.3); 3.645(1.0); 3.631(0.8); 3.317(19.2); 3.308(0.9); 3.294(1.9); 3.280(2.3); 3.269(1.8); 3.253(0.7); 3.236(0.4); 3.183(0.4); 3.170(0.4); 3.136(0.4); 2.943(0.4); 2.530(0.6); 2.517(14.9); 2.513(30.7); 2.508(41.6); 2.504(29.8); 2.499(14.2); 2.080(0.6); 1.297(16.0); 1.234(8.4); 1.224(7.9)

Example 624: ¹H-NMR(400.1 MHz, DMSO):
9.113(4.8); 9.107(5.0); 8.916(3.7); 8.911(3.5); 8.511(1.0); 8.497(2.0); 8.482(1.0); 8.244(3.6); 8.240(3.9); 8.163(2.1); 8.158(1.8); 8.141(3.1); 8.136(2.9); 8.066(4.0); 8.043(2.6); 6.669(1.0); 6.555(2.1); 6.400(1.3); 3.937(7.4); 3.394(2.4); 3.376(7.7); 3.367(3.6); 3.359(8.3); 3.351(7.5); 3.341(3.2); 3.336(3.6); 3.317(14.6); 3.271(0.6); 3.255(1.1); 3.238(1.6); 3.223(1.4); 3.215(0.7); 3.205(0.7); 3.198(1.4); 3.183(1.6); 3.165(1.0); 3.150(0.6); 2.530(0.5); 2.517(10.6); 2.513(21.8); 2.508(29.6); 2.504(20.9); 2.499(9.7); 1.718(0.7); 1.701(2.6); 1.685(4.0); 1.669(2.5); 1.652(0.7); 1.235(0.4); 1.098(7.8); 1.081(16.0); 1.063(7.5)

Example 625: ¹H-NMR(400.1 MHz, DMSO):
9.116(5.7); 9.110(6.1); 8.918(4.4); 8.913(4.2); 8.296(2.2); 8.275(2.3); 8.251(4.4); 8.247(4.8); 8.170(2.5); 8.165(2.3); 8.148(3.8); 8.143(3.7); 8.069(4.7); 8.046(3.1); 6.664(1.2); 6.529(2.6); 6.394(1.6); 4.021(0.4); 4.004(1.0); 3.988(1.6); 3.984(1.7); 3.971(1.3); 3.967(1.6); 3.951(1.4); 3.937(5.5); 3.928(5.9); 3.883(0.7); 3.317(34.5); 2.898(1.1); 2.738(0.9); 2.682(0.3); 2.677(0.5); 2.673(0.3); 2.531(1.4); 2.517(26.4); 2.513(54.6); 2.508(75.1); 2.504(55.4); 2.499(28.4); 2.340(0.5); 2.335(0.4); 2.331(0.4); 1.127(12.3); 1.111(15.1); 1.108(16.0); 1.091(13.1)

Example 626: ¹H-NMR(400.1 MHz, DMSO):
9.033(3.3); 9.027(3.4); 8.785(0.7); 8.765(2.9); 8.759(2.8); 8.300(2.4); 8.296(2.6); 8.176(1.2); 8.172(1.1); 8.154(2.2); 8.150(2.2); 8.104(2.8); 8.082(1.6); 7.435(4.2); 6.689(0.7); 6.555(1.4); 6.420(0.8); 4.184(0.4); 4.170(0.5); 4.148(1.5); 4.133(1.6); 4.124(1.6); 4.110(1.6); 4.088(0.5); 4.073(0.5); 3.995(0.4); 3.989(1.3); 3.971(4.1); 3.952(9.3); 3.935(1.7); 3.317(32.9); 2.898(0.6); 2.739(0.5); 2.677(0.4); 2.531(1.6); 2.526(2.3); 2.517(19.7); 2.513(40.1); 2.508(54.7); 2.504(39.6); 2.499(19.8); 2.335(0.4); 2.198(1.0); 2.084(16.0); 1.916(0.5); 1.293(4.7); 1.275(10.3); 1.257(4.9); 1.239(0.8); 1.221(0.4)

Example 627: ¹H-NMR(400.1 MHz, DMSO):
9.034(4.4); 9.028(4.6); 8.773(2.8); 8.770(2.8); 8.767(2.8); 8.553(0.5); 8.539(1.2); 8.529(1.2); 8.515(0.5); 8.296(3.2); 8.180(1.3); 8.177(1.2); 8.158(2.3); 8.155(2.3); 8.153(2.1); 8.110(3.8); 8.087(2.1); 6.690(0.5); 6.678(0.5); 6.556(1.0); 6.544(1.0); 6.421(0.6); 6.409(0.4); 4.157(0.8); 4.143(1.6); 4.128(1.5); 4.115(0.8); 3.966(5.7); 3.944(1.1); 3.929(1.8); 3.923(1.4); 3.913(1.1); 3.908(2.1); 3.892(1.0); 3.687(1.1); 3.672(1.1); 3.667(1.8); 3.653(1.4); 3.652(1.3); 3.646(1.1); 3.632(0.9); 3.317(17.5); 3.309(1.0); 3.296(1.8); 3.281(2.3); 3.270(1.8); 3.265(1.0); 3.255(0.7); 3.237(0.4); 2.531(0.5); 2.526(0.9); 2.517(13.9); 2.513(29.0); 2.508(39.9); 2.504(28.5); 2.499(13.5); 1.298(16.0); 1.235(8.3); 1.225(8.4)

Example 628: ¹H-NMR(400.1 MHz, DMSO):
9.032(4.8); 9.026(5.0); 8.770(3.5); 8.764(3.3); 8.514(0.9); 8.500(1.9); 8.486(0.9); 8.297(3.6); 8.293(3.8); 8.181(1.9); 8.176(1.6); 8.159(3.3); 8.154(3.2); 8.108(4.2); 8.085(2.3); 6.670(1.0); 6.536(2.1); 6.401(1.3); 3.948(7.4); 3.395(2.3); 3.378(7.7); 3.369(3.4); 3.360(8.3); 3.353(7.4); 3.343(3.1); 3.337(3.5); 3.318(42.4); 3.272(0.6); 3.268(0.4); 3.256(1.1); 3.239(1.6); 3.223(1.4); 3.216(0.7); 3.206(0.7); 3.199(1.3); 3.184(1.5); 3.166(1.0); 3.151(0.5); 2.531(0.7); 2.517(16.1); 2.513(33.2); 2.508(45.2); 2.504(31.9); 2.499(14.8); 2.458(0.4); 1.719(0.7); 1.702(2.6); 1.686(3.9); 1.670(2.5); 1.653(0.7); 1.099(7.8); 1.082(16.0); 1.064(7.5)

Example 629: ¹H-NMR(300.2 MHz, CDCl3):
8.941(2.0); 8.324(2.1); 8.182(0.8); 8.152(1.7); 8.108(2.0); 8.080(0.9); 7.818(2.2); 7.327(0.3); 7.261(27.2); 6.927(1.5); 3.991(1.4); 3.935(1.6); 3.337(1.6); 3.280(1.3); 2.954(0.4); 2.882(0.4); 2.330(2.9); 1.755(8.4); 1.700(0.4); 1.652(13.7); 1.596(0.5); 1.551(16.0); 1.498(0.4); 0.000(21.4)

Example 630: ¹H-NMR(400.1 MHz, CDCl3):
8.963(0.4); 8.957(0.5); 8.945(7.0); 8.939(6.9); 8.328(5.2); 8.323(4.9); 8.186(0.6); 8.179(0.4); 8.176(0.4); 8.156(2.3); 8.151(2.2); 8.133(5.5); 8.129(5.6); 8.105(6.7); 8.083(2.6); 7.827(5.5); 7.823(5.2); 7.332(5.9); 7.269(10.7); 6.972(1.3); 6.953(1.3); 5.300(0.3); 4.416(1.1); 4.396(2.0); 4.375(2.0); 4.355(1.1); 4.248(5.8); 4.205(7.1); 3.840(6.8); 3.797(5.7); 3.750(0.8); 3.732(2.4); 3.715(2.5); 3.697(0.8); 3.490(2.2); 2.957(0.8); 2.884(0.7); 2.799(16.0); 2.702(0.3); 2.433(0.4); 2.431(0.4); 2.425(0.8); 2.414(0.9); 2.412(0.8); 2.405(1.3); 2.397(1.2); 2.386(1.2); 2.379(1.0); 2.372(0.5); 2.367(0.8); 2.358(0.8); 2.346(0.9); 2.337(1.1); 2.332(0.8); 2.328(1.2); 2.318(1.3); 2.310(1.0); 2.308(1.0); 2.300(1.1); 2.293(0.5); 2.288(0.4); 2.281(0.4); 2.044(0.6); 2.042(0.5); 2.019(1.5); 2.007(0.5); 1.994(2.2); 1.985(0.8); 1.971(1.5); 1.968(1.6); 1.966(1.5); 1.960(1.6); 1.944(0.9); 1.935(2.3); 1.912(1.6); 1.909(1.5); 1.907(1.4); 1.886(0.9); 1.846(0.3); 1.835(0.4); 1.827(0.4); 1.820(0.4); 1.812(0.5); 1.804(0.7); 1.799(0.7); 1.781(2.0); 1.778(1.9); 1.776(2.0); 1.771(1.3); 1.769(1.3); 1.763(3.1); 1.755(3.6); 1.748(1.7); 1.746(1.6); 1.744(1.7); 1.737(3.3); 1.730(1.7); 1.718(1.7); 1.711(1.7); 1.701(0.5); 1.692(0.9); 1.683(0.6); 1.664(0.4); 1.261(2.8); 1.255(0.4); 1.244(5.3); 1.226(2.6); 0.073(0.4); 0.000(6.7)

Example 631: ¹H-NMR(400.1 MHz, CDCl3):
8.948(0.3); 8.940(3.0); 8.934(3.0); 8.329(2.3); 8.323(2.3); 8.171(0.6); 8.136(0.8); 8.132(0.7); 8.114(2.5); 8.110(2.6); 8.097(3.2); 8.075(0.9); 7.830(2.4); 7.826(2.3); 7.361(0.4); 7.293(4.0); 7.285(2.4); 6.962(0.5); 6.949(0.8); 6.936(0.5); 4.415(0.8); 4.400(0.8); 4.377(1.4); 4.363(1.4); 4.288(2.4); 4.275(1.5); 4.262(1.5); 4.246(2.9); 4.238(1.0); 4.225(0.9); 4.081(1.3); 4.063(4.0); 4.045(4.0); 4.026(1.3); 3.860(2.7); 3.818(2.3); 3.745(0.4); 3.728(1.1); 3.710(1.1); 3.693(0.4); 3.480(4.3); 2.819(7.0); 2.292(1.2); 2.211(16.0); 1.485(0.3); 1.467(0.7); 1.450(5.0); 1.431(9.9); 1.413(4.7); 1.257(1.2); 1.240(2.1); 1.222(1.1); 0.000(1.3)

Example 632: ¹H-NMR(400.1 MHz, CDCl3):
9.034(0.4); 9.028(0.4); 8.934(4.8); 8.929(4.8); 8.381(0.4); 8.326(3.6); 8.320(3.4); 8.187(0.3); 8.181(0.5); 8.171(0.4); 8.160(2.0); 8.156(2.0); 8.138(3.4); 8.133(3.5); 8.094(4.3); 8.072(2.1); 7.823(3.9); 7.819(3.7); 7.586(1.1); 7.329(0.4); 7.279(3.2); 4.255(3.9); 4.213(4.7); 3.841(4.6); 3.799(3.8); 3.590(0.5); 3.575(0.7); 3.571(0.6); 3.566(1.8); 3.562(0.9); 3.554(3.8); 3.550(2.6); 3.542(2.6); 3.538(3.6); 3.529(1.8); 3.526(4.2); 3.513(1.9); 3.508(8.0); 3.496(2.1); 3.491(8.1); 3.479(1.8); 3.473(2.8); 3.465(0.8); 3.442(0.7); 3.428(1.4); 3.425(0.9); 3.415(1.1); 3.411(1.4); 3.397(0.9); 3.394(0.8); 3.380(0.6); 3.377(0.5); 3.363(0.4); 2.802(10.9); 1.866(0.6); 1.858(0.7); 1.851(1.3); 1.841(1.6); 1.836(2.0); 1.829(2.1); 1.814(1.3); 1.806(0.7); 1.799(0.6); 1.322(0.6); 1.284(7.9); 1.267(16.0); 1.249(7.8); 1.242(0.6); 0.000(1.8)

Example 633: ¹H-NMR(400.1 MHz, CDCl3):
8.946(0.3); 8.931(3.9); 8.925(3.8); 8.469(3.8); 8.390(3.9); 8.317(3.4); 8.312(3.2); 8.178(0.4); 8.142(1.3); 8.138(1.3); 8.120(2.9); 8.116(2.9); 8.089(3.8); 8.066(1.6); 7.900(0.9); 7.888(1.5); 7.875(0.9); 7.827(3.6); 7.823(3.4); 7.287(2.0); 5.304(0.9); 4.711(0.7); 4.697(0.7); 4.671(1.8); 4.657(1.8); 4.624(1.8); 4.611(1.8); 4.584(0.7); 4.570(0.7); 4.303(2.8);

| NMR Peak Lists Table 1 |
|---|

4.261(3.4); 3.886(3.4); 3.843(2.8); 3.730(0.9); 3.712(0.9); 3.695(0.3); 3.482(3.5); 2.852(7.3); 2.587(0.7); 2.546(16.0); 2.041(0.5); 2.011(0.5); 1.257(1.1); 1.240(1.9); 1.222(1.0); 0.000(1.1)
Example 634: $^1$H-NMR(400.0 MHz, DMSO):
9.448(2.8); 8.960(3.2); 8.955(3.4); 8.620(2.4); 8.615(2.3); 8.272(2.4); 8.267(2.6); 8.204(1.4); 8.199(1.2); 8.182(2.0); 8.177(1.9); 8.090(2.6); 8.068(1.8); 7.954(0.5); 7.356(5.1); 4.595(5.9); 4.033(1.2); 4.015(5.3); 3.997(3.9); 3.979(1.3); 3.971(2.4); 3.559(2.3); 3.515(2.0); 3.337(130.6); 2.892(4.2); 2.732(3.4); 2.526(0.9); 2.513(18.2); 2.508(36.9); 2.504(48.3); 2.499(34.3); 2.495(16.1); 2.105(16.0); 1.710(11.5); 1.623(0.4); 1.277(4.3); 1.259(9.5); 1.241(4.2); 0.008(0.4); 0.000(10.3); −0.009(0.3)
Example 635: $^1$H-NMR(400.0 MHz, DMSO):
8.957(3.0); 8.952(3.1); 8.607(2.4); 8.602(2.4); 8.384(0.7); 8.370(1.3); 8.355(0.7); 8.245(2.5); 8.241(2.6); 8.167(1.3); 8.162(1.1); 8.145(2.0); 8.140(1.9); 8.076(2.7); 8.054(1.7); 7.953(1.2); 7.363(4.5); 4.594(5.2); 4.451(0.9); 4.433(1.5); 4.416(1.0); 4.138(0.6); 4.123(0.6); 4.101(1.4); 4.086(1.3); 4.056(1.3); 4.042(1.4); 4.020(0.6); 4.005(0.6); 3.899(1.9); 3.856(2.3); 3.498(2.2); 3.454(1.9); 3.332(79.3); 2.892(8.6); 2.732(7.6); 2.672(0.4); 2.537(0.4); 2.525(1.0); 2.512(23.3); 2.508(45.8); 2.503(59.2); 2.499(42.6); 2.330(0.4); 2.042(16.0); 1.920(0.7); 1.907(1.0); 1.888(1.3); 1.876(1.0); 1.858 (0.5); 1.765(0.4); 1.748(0.9); 1.740(0.7); 1.731(1.3); 1.714(1.1); 1.699(0.8); 1.684(0.6); 1.672(0.5); 1.659(0.7); 1.652 (0.8); 1.641(1.2); 1.635(1.3); 1.630(1.6); 1.616(12.5); 1.588(0.4); 1.548(0.4); 1.547(0.3); 1.537(0.3); 1.527(0.6); 1.520(1.1); 1.509(1.2); 1.502(1.5); 1.490(1.1); 1.483(0.7); 0.008(0.5); 0.000(13.0); −0.009(0.5)
Example 636: $^1$H-NMR(400.0 MHz, DMSO):
9.007(3.1); 9.001(3.1); 8.767(2.5); 8.762(2.4); 8.388(0.7); 8.373(1.3); 8.358(0.7); 8.225(2.4); 8.221(2.7); 8.168(1.3); 8.164(1.1); 8.146(2.0); 8.142(1.8); 8.078(2.7); 8.056(1.7); 7.953(1.0); 7.365(4.5); 4.454(0.9); 4.436(1.5); 4.418(1.0); 4.137(0.6); 4.122(0.6); 4.100(1.4); 4.085(1.3); 4.057(1.3); 4.043(1.4); 4.020(0.6); 4.006(0.6); 3.890(2.0); 3.847(2.4); 3.490(2.3); 3.447(2.0); 3.332(86.0); 2.891(6.9); 2.732(6.0); 2.672(0.4); 2.512(23.4); 2.508(45.7); 2.503(59.0); 2.499(42.3); 2.330(0.4); 2.041(16.0); 1.922(0.7); 1.909(1.0); 1.890(1.3); 1.879(1.0); 1.862(0.4); 1.768(0.4); 1.750(0.9); 1.734(1.2); 1.717(1.0); 1.702(0.8); 1.686(0.6); 1.676(0.5); 1.663(0.6); 1.656(0.8); 1.646(1.2); 1.639(1.2); 1.634(1.4); 1.616(12.7); 1.592(0.4); 1.531(0.6); 1.523(1.0); 1.512(1.2); 1.506(1.5); 1.499(0.8); 1.493(1.1); 1.486(0.7); 1.477(0.4); 0.008(0.8); 0.000(18.9); −0.009(0.7)
Example 637: $^1$H-NMR(400.0 MHz, DMSO):
8.960(2.4); 8.954(2.5); 8.719(0.6); 8.705(1.1); 8.690(0.5); 8.613(1.9); 8.608(1.9); 8.258(1.9); 8.253(2.1); 8.190(1.2); 8.181(2.1); 8.174(2.1); 8.168(1.7); 8.163(1.5); 8.086(2.1); 8.064(1.4); 7.330(1.1); 7.323(1.0); 7.309(1.4); 7.301(1.3); 7.173(2.0); 7.151(1.6); 4.596(4.3); 4.351(2.3); 4.336(2.2); 3.936(1.6); 3.893(1.9); 3.774(16.0); 3.543(1.8); 3.500(1.5); 3.335(44.3); 2.892(1.6); 2.732(1.4); 2.564(0.5); 2.551(1.0); 2.538(0.5); 2.526(0.6); 2.512(12.9); 2.508(26.4); 2.504 (35.0); 2.499(25.5); 2.495(12.5); 1.663(9.5); 0.000(10.0); −0.008(0.4)
Example 638: $^1$H-NMR(400.0 MHz, DMSO):
8.954(3.1); 8.949(3.1); 8.601(2.5); 8.596(2.4); 8.438(0.7); 8.423(1.4); 8.409(0.7); 8.231(2.5); 8.226(2.7); 8.159(1.3); 8.155(1.2); 8.137(2.0); 8.133(1.9); 8.071(2.8); 8.048(1.7); 7.953(1.4); 7.262(4.7); 4.719(0.8); 4.698(1.3); 4.677(0.8); 4.593(5.6); 4.068(3.3); 4.053(3.3); 3.878(2.0); 3.834(2.4); 3.491(2.3); 3.448(2.0); 3.334(86.2); 2.891(9.8); 2.732(8.5); 2.672(0.3); 2.565(0.3); 2.551(0.6); 2.537(0.5); 2.526(1.0); 2.512(20.9); 2.508(41.4); 2.503(53.9); 2.499(38.7); 2.495(18.7); 2.461(0.9); 2.437(1.3); 2.432(1.5); 2.409(1.2); 2.391(0.4); 2.385(0.5); 2.330(0.3); 2.291(0.4); 2.271(0.9); 2.264(1.2); 2.258(1.2); 2.246(1.1); 2.237(0.9); 2.217(0.3); 2.138(16.0); 1.767(0.5); 1.753(1.2); 1.741(1.4); 1.728(2.2); 1.717(1.1); 1.703(1.0); 1.686(0.3); 1.592(12.0); 0.008(0.5); 0.000(13.9); −0.008(0.5)
Example 639: $^1$H-NMR(400.0 MHz, DMSO):
9.003(3.1); 8.998(3.2); 8.760(2.5); 8.754(2.4); 8.441(0.7); 8.427(1.3); 8.412(0.7); 8.210(2.4); 8.206(2.7); 8.161(1.3); 8.157(1.1); 8.139(2.1); 8.134(1.9); 8.073(2.8); 8.050(1.7); 7.953(1.3); 7.262(4.7); 4.719(0.8); 4.698(1.2); 4.677(0.8); 4.067(3.4); 4.052(3.4); 3.869(2.0); 3.826(2.4); 3.483(2.4); 3.440(2.0); 3.333(91.6); 2.892(9.3); 2.732(7.9); 2.672(0.4); 2.525(1.1); 2.512(21.8); 2.508(43.9); 2.503(57.7); 2.499(41.7); 2.461(0.9); 2.437(1.3); 2.433(1.5); 2.409(1.1); 2.385 (0.4); 2.330(0.4); 2.291(0.4); 2.272(0.9); 2.264(1.1); 2.259(1.2); 2.251(1.0); 2.246(1.0); 2.238(0.9); 2.138(16.0); 1.767 (0.5); 1.754(1.2); 1.742(1.3); 1.729(2.2); 1.717(1.1); 1.704(1.0); 1.592(12.3); 0.008(0.5); 0.000(15.0); −0.009(0.6)
Example 640: $^1$H-NMR(400.0 MHz, DMSO):
8.957(4.2); 8.951(4.3); 8.607(3.4); 8.602(3.2); 8.505(0.9); 8.491(1.9); 8.476(0.9); 8.243(3.4); 8.239(3.6); 8.172(1.8); 8.167(1.5); 8.149(2.8); 8.145(2.6); 8.078(3.7); 8.055(2.3); 7.953(1.6); 7.580(6.5); 4.595(7.7); 4.078(4.7); 4.063(4.7); 4.055(2.1); 4.036(5.4); 4.018(5.5); 4.000(1.8); 3.912(2.6); 3.868(3.2); 3.513(3.1); 3.470(2.7); 3.333(146.2); 2.891 (11.3); 2.733(9.6); 2.677(0.4); 2.672(0.5); 2.668(0.4); 2.525(1.5); 2.512(30.6); 2.508(60.3); 2.503(77.6); 2.499(55.1); 2.494(26.0); 2.334(0.4); 2.330(0.5); 2.326(0.3); 1.625(16.0); 1.276(6.2); 1.258(13.2); 1.240(6.1); 0.008(0.6); 0.000(16.0); −0.009(0.6)
Example 641: $^1$H-NMR(400.0 MHz, DMSO):
8.956(2.3); 8.951(2.4); 8.609(1.8); 8.604(1.7); 8.383(0.5); 8.369(1.0); 8.354(0.5); 8.242(1.8); 8.238(1.9); 8.169(1.0); 8.164(0.8); 8.147(1.5); 8.142(1.4); 8.076(2.0); 8.054(1.3); 7.522(3.3); 4.595(4.2); 4.119(2.0); 4.104(1.9); 4.030(0.9); 4.012(2.9); 3.994(3.0); 3.976(1.0); 3.913(1.5); 3.870(1.8); 3.510(1.7); 3.466(1.4); 3.333(66.6); 2.892(1.9); 2.732(1.6); 2.526(0.7); 2.512(14.9); 2.508(30.2); 2.503(39.6); 2.499(28.3); 2.494(13.5); 2.301(16.0); 1.626(8.7); 1.272(3.4); 1.254(7.2); 1.236(3.4); 0.000(4.7)
Example 642: $^1$H-NMR(400.0 MHz, DMSO):
9.006(3.9); 9.001(3.9); 8.767(3.5); 8.761(3.4); 8.507(1.0); 8.493(1.9); 8.478(1.0); 8.222(3.6); 8.219(3.8); 8.174(1.8); 8.169(1.4); 8.151(2.8); 8.147(2.4); 8.080(3.7); 8.058(2.3); 7.954(0.9); 7.582(6.2); 4.078(4.8); 4.064(4.9); 4.038(5.1); 4.020(5.1); 4.002(1.7); 3.903(2.6); 3.860(3.2); 3.505(3.1); 3.462(2.6); 3.335(185.3); 2.892(5.6); 2.733(5.1); 2.672(0.6); 2.508(70.9); 2.504(86.1); 2.330(0.5); 1.626(16.0); 1.279(5.5); 1.261(11.6); 1.243(5.5); 0.000(12.1)
Example 643: $^1$H-NMR(400.0 MHz, DMSO):
8.955(2.6); 8.950(2.7); 8.606(2.0); 8.601(1.9); 8.243(2.3); 8.238(2.5); 8.218(0.6); 8.170(1.1); 8.165(0.9); 8.148(1.7); 8.143(1.6); 8.075(2.2); 8.053(1.4); 7.954(0.6); 7.327(3.9); 4.594(4.6); 4.008(2.7); 3.994(2.7); 3.898(1.7); 3.882(1.1); 3.864(3.4); 3.855(2.2); 3.846(3.4); 3.828(1.1); 3.721(16.0); 3.496(1.9); 3.453(1.6); 3.332(72.7); 2.892(4.4); 2.733(3.6); 2.526(0.8); 2.512(16.6); 2.508(33.2); 2.503(43.3); 2.499(30.9); 2.494(14.8); 1.653(0.4); 1.612(9.7); 1.232(3.9); 1.214(8.2); 1.196(3.7); 0.008(0.4); 0.000(11.6); −0.009(0.4)
Example 644: $^1$H-NMR(400.0 MHz, DMSO):
9.005(2.4); 9.000(2.5); 8.768(2.0); 8.763(1.9); 8.385(0.5); 8.371(1.1); 8.356(0.5); 8.221(1.9); 8.217(2.2); 8.171(1.1); 8.166(0.9); 8.148(1.7); 8.144(1.5); 8.078(2.2); 8.056(1.4); 7.953(0.7); 7.523(3.6); 4.118(2.4); 4.104(2.4); 4.032(1.0); 4.014(3.0); 3.996(3.0); 3.978(1.0); 3.904(1.5); 3.860(1.8); 3.501(1.8); 3.458(1.5); 3.332(70.6); 2.891(4.6); 2.732(3.8); 2.508(36.2); 2.503(46.8); 2.499(34.2); 2.300(16.0); 1.655(0.5); 1.626(9.3); 1.275(3.4); 1.257(7.3); 1.239(3.4); 0.008 (0.5); 0.000(12.9); −0.008(0.6)

NMR Peak Lists Table 1

Example 645: ¹H-NMR(400.0 MHz, DMSO):
9.004(2.8); 8.999(2.9); 8.765(2.3); 8.759(2.2); 8.250(0.6); 8.236(1.4); 8.222(2.8); 8.218(2.8); 8.172(1.2); 8.167(1.0); 8.150(1.9); 8.145(1.7); 8.077(2.5); 8.054(1.6); 7.953(0.7); 7.328(4.3); 4.008(3.1); 3.993(3.1); 3.889(1.9); 3.884(1.4); 3.866(3.5); 3.847(5.0); 3.830(1.2); 3.721(16.0); 3.488(2.1); 3.445(1.8); 3.331(74.1); 2.891(5.3); 2.732(4.4); 2.507 (38.9); 2.503(50.6); 2.499(36.8); 1.654(0.5); 1.612(10.8); 1.234(4.0); 1.216(8.2); 1.198(3.8); 0.008(0.5); 0.000(12.8); −0.008(0.6)
Example 646: ¹H-NMR(400.0 MHz, DMSO):
8.957(3.8); 8.951(3.9); 8.606(3.1); 8.602(3.0); 8.364(0.8); 8.350(1.6); 8.336(0.8); 8.243(3.1); 8.239(3.4); 8.177(1.7); 8.173(1.4); 8.155(2.5); 8.150(2.4); 8.080(3.4); 8.057(2.2); 7.954(0.4); 4.595(7.0); 4.519(1.5); 4.506(3.0); 4.493(1.5); 4.400(1.4); 4.387(3.0); 4.374(1.5); 3.897(2.6); 3.853(3.2); 3.520(3.1); 3.476(2.8); 3.467(0.5); 3.453(0.9); 3.439(1.2); 3.423(1.0); 3.413(0.4); 3.409(0.5); 3.404(0.5); 3.400(0.4); 3.390(1.0); 3.376(1.1); 3.372(1.2); 3.358(1.2); 3.335(92.9); 3.313(0.3); 2.892(3.1); 2.733(2.7); 2.526(0.8); 2.513(17.4); 2.509(34.8); 2.504(45.5); 2.500(32.9); 2.495(16.0); 1.618(16.0); 0.000(7.1)
Example 647: ¹H-NMR(400.0 MHz, DMSO):
9.006(3.7); 9.000(3.8); 8.765(3.1); 8.760(2.9); 8.367(0.8); 8.352(1.5); 8.338(0.8); 8.222(3.0); 8.218(3.4); 8.179(1.7); 8.174(1.4); 8.157(2.5); 8.152(2.3); 8.081(3.3); 8.059(2.1); 4.518(1.4); 4.505(2.9); 4.492(1.5); 4.400(1.4); 4.387(2.9); 4.374(1.5); 3.888(2.6); 3.844(3.2); 3.511(3.1); 3.468(2.8); 3.453(0.9); 3.439(1.1); 3.435(1.1); 3.422(1.0); 3.412(0.4); 3.408(0.4); 3.403(0.5); 3.399(0.4); 3.390(0.9); 3.385(0.7); 3.375(1.0); 3.371(1.1); 3.357(1.1); 3.334(97.9); 2.892(0.9); 2.732(0.7); 2.526(0.9); 2.512(19.4); 2.508(38.5); 2.504(50.1); 2.499(36.1); 2.495(17.5); 1.618(16.0); 0.008(0.5); 0.000(14.1); −0.009(0.5)
Example 648: ¹H-NMR(400.0 MHz, DMSO):
9.064(4.1); 9.061(3.8); 9.014(3.8); 9.008(4.0); 8.998(0.8); 8.915(0.9); 8.900(1.8); 8.885(0.9); 8.778(3.4); 8.772(3.5); 8.700(3.7); 8.687(3.8); 8.248(3.3); 8.244(3.6); 8.213(0.7); 8.205(1.9); 8.200(1.5); 8.183(2.7); 8.178(2.6); 8.156(0.5); 8.151(0.4); 8.098(3.5); 8.076(2.5); 8.057(0.4); 7.954(0.9); 7.600(0.3); 7.427(0.3); 7.308(2.7); 7.295(2.2); 4.443(0.3); 4.428(0.4); 4.400(2.4); 4.386(3.8); 4.373(2.4); 4.345(0.4); 4.330(0.3); 3.943(2.6); 3.900(3.2); 3.891(0.6); 3.847(0.6); 3.562(3.1); 3.518(2.6); 3.441(0.6); 3.398(0.5); 3.331(119.9); 2.892(6.0); 2.732(5.3); 2.672(0.6); 2.668(0.4); 2.508 (71.1); 2.503(89.8); 2.499(65.1); 2.334(0.4); 2.330(0.6); 1.691(16.0); 1.605(2.9); 0.008(1.0); 0.000(24.6); −0.009(1.1)
Example 649: ¹H-NMR(400.0 MHz, DMSO):
8.959(1.7); 8.953(1.7); 8.615(1.4); 8.610(1.3); 8.480(0.4); 8.466(0.8); 8.451(0.4); 8.266(1.4); 8.261(1.5); 8.206(0.8); 8.201(0.7); 8.184(1.1); 8.179(1.0); 8.086(1.4); 8.064(1.0); 7.064(2.1); 4.595(2.9); 4.390(1.0); 4.375(1.7); 4.361(0.9); 3.937(1.1); 3.894(1.3); 3.560(1.3); 3.516(1.1); 3.336(64.1); 2.892(1.0); 2.733(0.8); 2.551(0.4); 2.526(0.6); 2.512(12.6); 2.508(24.7); 2.504(31.7); 2.499(22.6); 2.495(10.7); 2.273(16.0); 1.685(6.7); 0.000(4.8)
Example 650: ¹H-NMR(400.0 MHz, DMSO):
8.998(2.5); 8.993(2.5); 8.759(2.4); 8.339(0.8); 8.326(1.6); 8.314(0.8); 8.308(1.3); 8.236(2.6); 8.232(2.8); 8.190(1.5); 8.185(1.2); 8.168(2.1); 8.163(1.8); 8.076(2.9); 8.070(2.2); 8.057(2.8); 7.953(0.9); 7.412(1.5); 7.391(2.1); 7.302(1.5); 7.290(1.4); 7.281(1.1); 7.269(1.0); 4.404(2.0); 4.391(3.6); 4.378(1.9); 3.928(2.0); 3.885(2.4); 3.830(16.0); 3.554(2.9); 3.511(2.0); 3.361(3.8); 3.355(73.7); 3.350(116.5); 3.342(90.4); 3.338(126.1); 2.894(5.7); 2.735(5.0); 2.679(0.4); 2.674(0.5); 2.510(64.4); 2.505(82.6); 2.501(59.2); 2.336(0.4); 2.332(0.5); 2.327(0.3); 1.673(12.4); 1.234(0.4); 0.746 (0.3); 0.008(0.7); 0.000(15.7); −0.008(0.5)
Example 651: ¹H-NMR(400.0 MHz, DMSO):
8.956(3.1); 8.951(3.1); 8.609(2.3); 8.605(2.2); 8.340(0.7); 8.327(1.4); 8.315(0.7); 8.262(2.4); 8.258(2.6); 8.188(1.4); 8.183(1.2); 8.166(2.0); 8.161(1.8); 8.077(2.9); 8.071(1.9); 8.062(2.0); 8.059(2.2); 8.056(2.0); 7.954(0.8); 7.419(1.4); 7.416(1.4); 7.398(2.0); 7.395(1.8); 7.307(1.4); 7.295(1.4); 7.286(1.1); 7.274(1.0); 4.595(5.3); 4.404(1.8); 4.391(3.2); 4.378(1.7); 3.936(1.9); 3.893(2.3); 3.828(16.0); 3.566(2.2); 3.523(1.9); 3.334(64.6); 2.892(6.3); 2.733(5.3); 2.673(0.4); 2.565(0.2); 2.551(1.6); 2.537(0.9); 2.526(1.0); 2.512(24.5); 2.508(49.3); 2.503(64.1); 2.499(45.9); 2.494(22.0); 2.330(0.4); 1.670(11.7); 1.653(0.6); 0.008(0.4); 0.000(13.3); −0.008(0.5)
Example 652: ¹H-NMR(400.0 MHz, DMSO):
9.004(4.1); 8.999(4.4); 8.761(3.3); 8.755(3.1); 8.610(0.9); 8.595(1.8); 8.580(0.9); 8.217(3.2); 8.213(3.6); 8.170(1.8); 8.165(1.5); 8.148(2.7); 8.143(2.5); 8.076(3.6); 8.053(2.3); 7.606(5.3); 7.369(5.8); 6.417(0.4); 6.407(0.8); 6.398(0.4); 6.279(0.9); 6.269(1.8); 6.260(0.8); 6.141(0.4); 6.132(0.9); 6.122(0.4); 4.572(1.4); 4.563(1.5); 4.534(3.1); 4.525(3.0); 4.497(1.6); 4.487(1.5); 4.189(0.4); 4.174(0.5); 4.152(2.1); 4.137(3.8); 4.121(2.1); 4.100(0.5); 4.084(0.4); 3.886(2.6); 3.843(3.2); 3.501(3.1); 3.458(2.6); 3.335(166.3); 2.891(1.9); 2.732(1.6); 2.672(0.4); 2.525(1.2); 2.512(26.6); 2.508 (53.5); 2.503(70.2); 2.499(51.0); 2.494(25.0); 2.334(0.3); 2.330(0.4); 1.609(16.0); 0.008(0.5); 0.000(13.9); −0.009(0.6)
Example 653: ¹H-NMR(400.0 MHz, DMSO):
8.955(4.1); 8.950(4.1); 8.602(3.8); 8.597(4.1); 8.578(0.9); 8.238(3.4); 8.233(3.5); 8.168(1.8); 8.164(1.5); 8.146(2.7); 8.142(2.4); 8.074(3.6); 8.052(2.3); 7.954(0.4); 7.606(5.5); 7.371(5.9); 6.416(0.4); 6.407(0.9); 6.397(0.4); 6.279(0.9); 6.269(1.8); 6.260(0.9); 6.141(0.4); 6.132(0.9); 6.122(0.4); 4.593(7.0); 4.572(1.5); 4.562(1.5); 4.534(3.2); 4.525(3.1); 4.496(1.6); 4.487(1.5); 4.189(0.4); 4.174(0.5); 4.153(2.2); 4.138(4.0); 4.122(2.2); 4.101(0.5); 4.085(0.4); 3.895(2.6); 3.852(3.2); 3.510(3.1); 3.466(2.6); 3.366(0.4); 3.336(151.7); 2.892(3.0); 2.733(2.6); 2.673(0.4); 2.526(1.2); 2.512 (27.9); 2.508(54.2); 2.503(69.0); 2.499(49.2); 2.335(0.3); 2.330(0.4); 1.608(16.0); 1.234(0.3); 0.008(0.5); 0.000(13.1); −0.009(0.5)
Example 654: ¹H-NMR(400.0 MHz, DMSO):
9.128(0.9); 9.113(1.9); 9.098(0.9); 8.961(4.1); 8.956(4.6); 8.614(3.2); 8.609(3.2); 8.260(3.4); 8.256(3.7); 8.190(1.8); 8.185(1.6); 8.168(2.7); 8.163(2.5); 8.087(3.5); 8.077(0.4); 8.065(2.3); 7.953(0.6); 7.072(4.2); 7.069(4.3); 4.596(7.5); 4.514(5.0); 4.499(5.0); 3.916(2.6); 3.872(3.2); 3.570(3.1); 3.527(2.6); 3.337(126.5); 3.205(0.5); 2.892(4.8); 2.732(3.7); 2.673(0.4); 2.526(1.1); 2.513(22.7); 2.508(46.3); 2.504(61.0); 2.499(44.0); 2.495(21.3); 2.331(0.4); 2.281(15.2); 2.280(15.4); 1.666(16.0); 1.653(1.6); 1.622(0.5); 0.008(0.4); 0.000(12.1); −0.009(0.5)
Example 655: ¹H-NMR(400.0 MHz, DMSO):
9.131(0.9); 9.116(1.8); 9.100(0.9); 9.010(4.1); 9.004(4.4); 8.772(3.2); 8.767(3.1); 8.240(3.3); 8.235(3.7); 8.191(1.8); 8.187(1.5); 8.169(2.7); 8.164(2.4); 8.089(3.5); 8.067(2.3); 7.954(0.5); 7.072(4.1); 7.070(4.1); 4.514(5.0); 4.499(5.0); 3.907(2.6); 3.864(3.2); 3.563(3.1); 3.520(2.6); 3.333(58.7); 3.206(0.3); 2.892(3.8); 2.733(3.0); 2.526(0.8); 2.513(17.8); 2.508(36.0); 2.504(47.2); 2.499(33.9); 2.495(16.5); 2.282(15.4); 2.280(14.6); 1.668(16.0); 1.655(1.3); 0.008(0.5); 0.000(14.0); −0.009(0.5)
Example 656: ¹H-NMR(400.0 MHz, DMSO):
8.957(6.6); 8.952(6.8); 8.623(5.3); 8.618(5.2); 8.253(4.8); 8.249(5.2); 8.193(3.0); 8.188(2.6); 8.171(4.2); 8.166(3.9); 8.083(5.9); 8.061(4.0); 7.954(1.6); 4.592(12.2); 4.582(0.4); 4.427(1.1); 4.069(0.5); 4.034(0.6); 3.784(8.5); 3.457(2.8); 3.414(2.6); 3.376(0.4); 3.336(212.4); 3.307(0.4); 2.892(11.6); 2.733(10.1); 2.677(0.4); 2.673(0.6); 2.668(0.4); 2.565

| NMR Peak Lists Table 1 |
|---|
| (1.0); 2.552(2.1); 2.538(1.2); 2.526(1.8); 2.513(35.9); 2.508(71.8); 2.504(94.0); 2.500(67.8); 2.496(33.2); 2.335(0.4); 2.331(0.6); 2.327(0.4); 1.600(15.2); 1.577(0.8); 1.273(1.4); 1.260(13.8); 1.250(16.0); 1.244(15.1); 1.234(14.6); 0.008(0.6); 0.000(15.6); −0.008(0.6)<br>Example 657: $^1$H-NMR(400.0 MHz, DMSO):<br>9.451(2.8); 9.010(3.1); 9.004(3.6); 8.998(0.5); 8.779(2.5); 8.773(2.5); 8.764(0.3); 8.251(2.5); 8.247(2.8); 8.206(1.8); 8.201(1.2); 8.183(2.0); 8.179(1.9); 8.092(2.7); 8.080(0.4); 8.070(1.8); 7.953(0.7); 7.355(5.1); 4.033(1.2); 4.015(3.9); 4.005(2.3); 3.997(3.9); 3.979(1.3); 3.962(2.4); 3.551(2.3); 3.507(0.1); 3.334(97.1); 2.891(4.8); 2.732(4.1); 2.672(0.4); 2.526(1.0); 2.512(21.6); 2.508(43.4); 2.503(56.9); 2.499(41.4); 2.495(20.4); 2.330(0.4); 2.105(16.0); 1.711(12.1); 1.622(1.4); 1.276(4.2); 1.258(9.1); 1.240(4.1); 0.000(4.0)<br>Example 658: $^1$H-NMR(400.0 MHz, DMSO):<br>9.006(6.5); 9.000(6.7); 8.783(5.4); 8.777(5.1); 8.233(4.9); 8.230(5.4); 8.195(3.1); 8.190(2.4); 8.173(4.2); 8.168(3.7); 8.085(5.9); 8.062(3.9); 4.420(0.9); 4.068(0.5); 4.032(0.6); 3.783(8.8); 3.448(2.9); 3.405(2.7); 3.372(0.4); 3.335 (220.5); 2.892(1.5); 2.733(1.3); 2.677(0.5); 2.673(0.6); 2.668(0.5); 2.508(74.1); 2.504(96.0); 2.499(69.1); 2.335(0.4); 2.331(0.6); 1.601(15.5); 1.260(12.8); 1.249(16.0); 1.243(14.1); 1.233(14.4); 0.008(0.5); 0.000(14.5); −0.008(0.5)<br>Example 659: $^1$H-NMR(400.0 MHz, DMSO):<br>8.959(3.9); 8.953(3.9); 8.609(3.2); 8.604(3.1); 8.556(0.9); 8.540(1.7); 8.525(0.8); 8.246(3.2); 8.242(3.4); 8.177(1.7); 8.172(1.5); 8.154(2.7); 8.150(2.4); 8.082(3.5); 8.060(2.2); 7.954(1.6); 6.175(0.4); 6.165(0.7); 6.155(0.3); 6.035(0.8); 6.025(1.6); 6.014(0.7); 5.895(0.4); 5.885(0.8); 5.874(0.4); 4.596(6.7); 3.898(2.6); 3.855(3.2); 3.551(3.7); 3.536(0.7); 3.522(0.9); 3.508(3.6); 3.499(1.3); 3.489(0.8); 3.475(0.7); 3.469(0.6); 3.460(0.9); 3.450(0.4); 3.336(102.5); 3.206(0.6); 2.892(10.9); 2.733(9.3); 2.673(0.3); 2.509(40.5); 2.504(51.1); 2.500(36.2); 1.653(1.5); 1.626(16.0); 0.000(5.5)<br>Example 660: $^1$H-NMR(400.0 MHz, DMSO):<br>9.008(3.9); 9.002(4.1); 8.768(3.1); 8.762(2.9); 8.557(0.8); 8.542(1.6); 8.527(0.8); 8.234(0.4); 8.226(3.0); 8.221(3.4); 8.178(1.8); 8.173(1.5); 8.156(2.7); 8.151(2.5); 8.084(3.4); 8.062(2.2); 7.954(1.9); 6.175(0.4); 6.164(0.7); 6.154(0.3); 6.034(0.7); 6.024(1.6); 6.014(0.7); 5.894(0.4); 5.884(0.8); 5.873(0.4); 3.889(2.6); 3.845(3.2); 3.559(0.4); 3.543(3.7); 3.522(0.9); 3.512(1.3); 3.499(3.5); 3.488(0.8); 3.474(0.7); 3.469(0.6); 3.464(0.6); 3.459(0.7); 3.450(0.6); 3.335(143.0); 3.205(0.5); 2.892(13.7); 2.732(11.2); 2.673(0.4); 2.512(21.9); 2.508(44.1); 2.504(57.9); 2.499(42.0); 2.495(20.8); 2.331(0.4); 1.655(1.4); 1.626(16.0); 0.000(6.8)<br>Example 661: $^1$H-NMR(400.0 MHz, DMSO):<br>8.955(3.1); 8.950(3.2); 8.603(2.4); 8.598(2.3); 8.409(0.7); 8.395(1.3); 8.380(0.7); 8.239(2.4); 8.234(2.6); 8.163(1.3); 8.158(1.2); 8.141(2.0); 8.136(1.9); 8.081(0.3); 8.072(2.7); 8.050(1.7); 7.953(0.8); 7.351(4.4); 6.641(0.5); 4.594(5.7); 4.122(0.5); 4.107(0.5); 4.085(1.5); 4.070(1.5); 4.060(1.5); 4.046(1.5); 4.024(0.5); 4.009(0.4); 3.886(2.0); 3.872(2.0); 3.854(3.8); 3.843(2.7); 3.836(2.2); 3.499(2.3); 3.455(1.9); 3.333(80.2); 2.892(5.7); 2.762(0.4); 2.732(4.7); 2.673(0.3); 2.564(0.4); 2.551(0.9); 2.537(0.6); 2.526(1.1); 2.512(20.1); 2.508(40.7); 2.503(53.5); 2.499(38.5); 2.495(18.6); 2.330(0.3); 2.051(16.0); 1.628(0.7); 1.609(13.0); 1.592(2.1); 1.573(1.5); 1.555(0.6); 1.210(0.7); 1.207(0.6); 1.189(1.5); 1.171(2.1); 1.154(1.4); 1.137(0.4); 1.134(0.3); 1.115(0.7); 1.103(0.9); 1.096(1.4); 1.087(0.8); 1.079(1.6); 1.065(0.7); 1.058(0.9); 0.785(4.4); 0.768(8.7); 0.749(3.9); 0.008(0.4); 0.000(10.6); −0.009(0.4)<br>Example 662: $^1$H-NMR(400.0 MHz, DMSO):<br>9.006(3.2); 9.000(3.3); 8.763(2.6); 8.757(2.4); 8.412(0.7); 8.398(1.4); 8.383(0.7); 8.218(2.5); 8.214(2.7); 8.165(1.4); 8.160(1.2); 8.143(2.2); 8.138(2.0); 8.075(2.8); 8.052(1.7); 7.953(0.6); 7.351(4.5); 4.121(0.5); 4.106(0.5); 4.084(1.5); 4.069(1.6); 4.061(1.6); 4.046(1.6); 4.024(0.5); 4.009(0.4); 3.877(2.5); 3.872(2.4); 3.854(3.9); 3.834(3.5); 3.491(2.4); 3.448(2.0); 3.332(92.4); 2.892(4.0); 2.732(3.4); 2.672(0.4); 2.512(23.0); 2.508(44.7); 2.503(57.5); 2.499(41.3); 2.330(0.4); 2.050(16.0); 1.628(0.7); 1.609(13.6); 1.592(2.2); 1.574(1.6); 1.556(0.6); 1.211(0.7); 1.191(1.6); 1.173(2.1); 1.155(1.4); 1.139(0.4); 1.116(0.7); 1.103(0.9); 1.098(1.4); 1.088(0.8); 1.080(1.7); 1.067(0.7); 1.059(0.9); 0.787(4.5); 0.770(8.8); 0.751(3.9); 0.008(0.3); 0.000(8.5)<br>Example 663: $^1$H-NMR(400.0 MHz, DMSO):<br>8.955(3.0); 8.950(3.0); 8.604(2.6); 8.600(2.6); 8.403(0.7); 8.388(1.5); 8.374(0.8); 8.238(2.7); 8.234(2.9); 8.175(0.4); 8.164(1.3); 8.159(1.2); 8.141(2.1); 8.137(1.9); 8.073(2.9); 8.051(1.8); 7.953(0.9); 7.360(4.7); 6.640(0.7); 4.594(5.5); 4.120(0.4); 4.104(0.4); 4.083(1.7); 4.067(2.5); 4.050(1.7); 4.028(0.4); 4.014(0.4); 3.887(4.1); 3.869(4.4); 3.851(2.5); 3.844(2.6); 3.498(2.4); 3.454(2.0); 3.335(97.7); 2.892(5.9); 2.732(5.3); 2.672(0.3); 2.565(0.7); 2.551(1.5); 2.537(0.9); 2.508(44.5); 2.503(56.9); 2.499(41.6); 2.330(0.4); 2.049(16.0); 1.608(12.5); 1.582(2.5); 1.563(1.8); 1.545(0.7); 1.152(1.2); 1.134(2.1); 1.115(2.2); 1.096(1.3); 1.078(0.4); 0.797(4.4); 0.778(8.5); 0.760(3.6); 0.000(4.9)<br>Example 664: $^1$H-NMR(400.0 MHz, DMSO):<br>9.005(3.5); 8.999(3.7); 8.764(2.5); 8.758(2.4); 8.406(0.7); 8.392(1.3); 8.377(0.7); 8.217(2.5); 8.212(2.7); 8.166(1.4); 8.162(1.1); 8.155(0.4); 8.144(2.1); 8.139(1.9); 8.076(2.9); 8.054(1.8); 7.953(0.7); 7.360(4.5); 4.121(0.4); 4.105(0.4); 4.084(1.6); 4.067(2.4); 4.051(1.6); 4.029(0.4); 4.014(0.4); 3.887(2.2); 3.869(4.3); 3.852(2.2); 3.835(2.5); 3.491(2.5); 3.447(2.3); 3.417(0.4); 3.406(0.6); 3.398(0.7); 3.353(322.2); 3.205(0.7); 2.892(5.3); 2.733(4.0); 2.674(0.4); 2.527(1.1); 2.513(22.8); 2.509(44.9); 2.505(58.3); 2.500(41.8); 2.496(20.1); 2.331(0.4); 2.048(16.0); 1.655(1.7); 1.609(12.3); 1.583(2.2); 1.565(1.6); 1.546(0.6); 1.154(1.1); 1.135(2.0); 1.117(2.0); 1.098(1.2); 0.799(4.4); 0.781(8.7); 0.762(3.5); 0.000(5.4)<br>Example 665: $^1$H-NMR(400.0 MHz, DMSO):<br>8.956(8.7); 8.951(8.7); 8.625(6.2); 8.621(5.8); 8.251(5.3); 8.197(2.4); 8.193(3.1); 8.175(3.3); 8.170(4.5); 8.082(7.1); 8.060(4.9); 7.954(2.2); 6.536(0.5); 4.591(15.0); 4.119(0.9); 4.107(0.9); 4.047(0.7); 4.045(0.7); 3.770(4.8); 3.466(1.4); 3.459(1.3); 3.424(1.3); 3.388(0.4); 3.336(272.7); 2.892(16.0); 2.733(13.3); 2.732(13.2); 2.678(0.5); 2.673(0.7); 2.669(0.5); 2.552(0.6); 2.526(2.1); 2.513(42.2); 2.509(83.9); 2.504(108.9); 2.500(77.2); 2.495(36.4); 2.335(0.5); 2.331(0.7); 2.326(0.5); 1.794(0.6); 1.776(1.0); 1.760(1.4); 1.741(1.5); 1.721(1.2); 1.704(0.5); 1.615(8.7); 1.584(2.8); 1.566(2.5); 1.549(1.7); 1.532(1.0); 1.514(0.3); 1.273(0.7); 1.256(15.9); 1.239(15.5); 0.904(3.2); 0.894(4.7); 0.886(6.4); 0.876(7.7); 0.868(3.5); 0.858(3.4); 0.008(0.9); 0.000(25.1); −0.009(0.9)<br>Example 666: $^1$H-NMR(400.0 MHz, DMSO):<br>9.006(8.1); 9.000(8.4); 8.979(0.4); 8.785(5.9); 8.780(5.6); 8.231(5.4); 8.199(2.4); 8.195(3.0); 8.177(3.2); 8.173(4.4); 8.119(0.3); 8.115(0.4); 8.084(7.0); 8.062(4.7); 8.047(0.3); 8.022(0.4); 7.954(2.2); 4.430(0.8); 4.122(0.8); 4.061(0.7); 4.042(0.7); 3.770(4.8); 3.546(0.3); 3.458(1.4); 3.415(1.3); 3.374(0.8); 3.302(0.5); 2.892(16.0); 2.733(13.6); 2.678(0.6); 2.673(0.7); 2.669(0.5); 2.565(0.3); 2.552(0.7); 2.538(0.6); 2.526(2.1); 2.513(45.6); 2.508(91.7); 2.504(120.3); 2.500(86.9); 2.495(42.3); 2.335(0.6); 2.331(0.8); 2.326(0.6); 1.794(0.6); 1.775(1.0); 1.759(1.3); 1.740(1.5); 1.721(1.1); 1.705(0.5); 1.616(8.7); 1.608(8.4); 1.583(2.7); 1.566(2.5); 1.549(1.7); 1.531 (1.0); 1.513(0.3); 1.256(15.0); 1.239(14.8); 0.903(3.1); 0.894(4.5); 0.885(6.1); 0.876(7.6); 0.868(3.5); 0.857(3.3); 0.008(0.7); 0.000(22.8); −0.008(0.9) |

-continued

NMR Peak Lists Table 1

Example 667: ¹H-NMR(400.0 MHz, DMSO):
8.960(4.2); 8.955(4.4); 8.767(1.0); 8.752(1.9); 8.737(1.0); 8.613(3.4); 8.608(3.4); 8.259(3.3); 8.255(3.5); 8.195(1.9); 8.191(1.6); 8.173(2.8); 8.169(2.5); 8.088(3.6); 8.079(0.4); 8.065(2.4); 7.954(1.5); 7.625(1.7); 7.605(3.6); 7.586(2.0); 7.100(2.7); 7.081(2.5); 7.007(2.6); 6.988(2.5); 6.536(0.5); 4.596(7.5); 4.390(2.3); 4.380(2.7); 4.375(2.7); 4.366(2.3); 3.947(2.7); 3.903(3.3); 3.561(3.1); 3.517(2.6); 3.334(100.5); 2.952(0.6); 2.934(1.5); 2.917(2.0); 2.900(1.8); 2.892 (10.6); 2.883(0.8); 2.733(8.9); 2.677(0.4); 2.672(0.5); 2.668(0.4); 2.550(0.5); 2.536(0.4); 2.526(1.4); 2.512(31.5); 2.508 (62.4); 2.503(80.8); 2.499(57.5); 2.495(27.5); 2.335(0.4); 2.330(0.5); 2.326(0.4); 1.691(16.0); 1.624(1.2); 1.283(0.6); 1.266(0.6); 1.259(0.4); 1.243(0.4); 1.234(0.6); 1.212(0.4); 1.167(12.4); 1.158(12.8); 1.150(12.5); 1.141(12.2); 1.115(0.4); 1.098(0.3); 0.008(0.7); 0.000(23.2); −0.009(0.9)
Example 668: ¹H-NMR(400.0 MHz, DMSO):
9.012(3.8); 9.006(3.9); 8.778(3.1); 8.773(3.0); 8.723(7.6); 8.711(7.7); 8.565(0.9); 8.550(1.7); 8.536(0.9); 8.317(0.7); 8.245(3.0); 8.241(3.4); 8.201(1.8); 8.196(1.4); 8.179(2.5); 8.174(2.2); 8.092(3.3); 8.069(2.2); 7.953(0.4); 7.378(1.7); 7.366(3.2); 7.353(1.6); 6.537(0.4); 4.503(2.6); 4.496(2.7); 4.488(2.7); 4.482(2.6); 3.917(2.6); 3.874(3.2); 3.554(3.1); 3.511(2.6); 3.427(0.4); 3.384(1.0); 3.367(2.1); 3.332(1000.7); 3.284(0.5); 2.891(3.0); 2.731(2.6); 2.676(2.1); 2.671 (2.8); 2.667(2.0); 2.511(169.6); 2.507(331.5); 2.502(429.4); 2.498(307.8); 2.494(148.9); 2.333(2.0); 2.329(2.6); 2.325(1.9); 1.689(0.4); 1.670(16.0); 1.234(1.6); 0.146(0.4); 0.008(3.1); 0.000(73.3); −0.008(2.7); −0.150(0.4)
Example 669: ¹H-NMR(400.0 MHz, DMSO):
9.008(1.8); 9.003(1.8); 8.774(1.3); 8.768(1.3); 8.484(0.4); 8.469(0.8); 8.455(0.4); 8.245(1.3); 8.240(1.5); 8.208(0.9); 8.204(0.7); 8.186(1.1); 8.181(1.0); 8.089(1.4); 8.067(1.0); 7.064(2.1); 4.389(0.9); 4.375(1.6); 4.361(0.9); 3.926(1.1); 3.883(1.4); 3.553(1.3); 3.509(1.1); 3.335(56.8); 2.892(0.7); 2.732(0.6); 2.526(0.4); 2.512(10.3); 2.508(21.0); 2.504(27.5); 2.499(19.6); 2.495(9.3); 2.273(16.0); 1.685(6.9); 0.000(3.4)
Example 670: ¹H-NMR(400.0 MHz, DMSO):
9.064(3.7); 9.061(3.6); 8.964(3.7); 8.959(3.7); 8.914(1.0); 8.899(1.7); 8.884(0.8); 8.700(3.6); 8.687(3.6); 8.618(2.9); 8.613(2.8); 8.269(3.0); 8.264(3.1); 8.204(1.7); 8.199(1.5); 8.181(2.4); 8.177(2.2); 8.096(3.2); 8.074(2.2); 7.954(2.2); 7.309(2.0); 7.296(1.9); 4.598(6.6); 4.444(0.3); 4.428(0.4); 4.400(2.3); 4.387(3.2); 4.374(2.2); 4.346(0.4); 4.330(0.3); 3.953(2.4); 3.909(2.9); 3.570(2.8); 3.526(2.4); 3.337(194.5); 2.892(16.0); 2.748(0.9); 2.732(13.5); 2.677(0.4); 2.673 (0.5); 2.668(0.4); 2.526(1.5); 2.513(31.2); 2.508(62.8); 2.504(82.2); 2.499(58.9); 2.495(28.2); 2.335(0.4); 2.331(0.5); 2.326(0.4); 1.720(0.3); 1.701(1.1); 1.690(14.3); 1.605(0.7); 1.233(0.4); 0.008(0.6); 0.000(18.3); −0.008(0.7)
Example 671: ¹H-NMR(400.0 MHz, DMSO):
9.012(3.0); 9.006(3.1); 8.788(0.6); 8.770(2.9); 8.763(2.6); 8.288(2.5); 8.274(2.6); 8.244(2.2); 8.240(2.5); 8.196(1.3); 8.191(1.1); 8.174(1.9); 8.169(1.8); 8.089(2.5); 8.067(1.7); 6.822(1.3); 6.816(1.4); 6.808(1.2); 6.801(1.4); 6.712(2.3); 6.706(2.1); 4.364(1.5); 4.349(2.7); 4.335(1.5); 3.952(1.9); 3.909(2.3); 3.665(16.0); 3.546(2.2); 3.503(1.9); 3.333(39.3); 2.892(1.8); 2.733(1.6); 2.526(0.7); 2.513(14.4); 2.508(29.0); 2.504(38.0); 2.499(27.2); 2.495(13.0); 1.689(11.5); 0.008(0.4); 0.000(11.9); −0.009(0.4)
Example 672: ¹H-NMR(400.0 MHz, DMSO):
8.962(2.8); 8.957(2.7); 8.763(0.6); 8.748(1.3); 8.733(0.6); 8.614(2.2); 8.609(2.1); 8.262(2.2); 8.258(2.4); 8.194(1.2); 8.190(1.0); 8.172(1.7); 8.167(1.6); 8.090(2.4); 8.068(1.6); 7.953(1.0); 7.612(1.3); 7.592(1.9); 7.573(1.4); 6.775(1.9); 6.757(1.8); 6.637(2.0); 6.617(1.9); 4.597(5.1); 4.333(1.8); 4.315(1.8); 3.990(0.4); 3.952(1.7); 3.909(2.1); 3.862(0.5); 3.764(16.0); 3.753(0.6); 3.556(2.1); 3.513(1.7); 3.333(107.5); 2.891(6.7); 2.732(5.8); 2.672(0.4); 2.525(1.1); 2.512 (23.7); 2.508(47.4); 2.503(62.1); 2.499(44.9); 2.330(0.4); 1.690(10.5); 0.008(0.5); 0.000(15.6); −0.008(0.6)
Example 673: ¹H-NMR(400.0 MHz, DMSO):
9.009(2.4); 9.003(2.8); 8.772(2.2); 8.767(2.3); 8.721(0.6); 8.707(1.1); 8.692(0.6); 8.237(2.1); 8.233(2.3); 8.211(0.4); 8.206(0.4); 8.191(1.2); 8.187(1.1); 8.181(2.1); 8.173(2.5); 8.170(2.2); 8.165(1.6); 8.088(2.2); 8.081(0.4); 8.066(1.5); 7.954(0.9); 7.330(1.0); 7.322(1.0); 7.308(1.3); 7.301(1.3); 7.172(2.1); 7.150(1.6); 6.536(0.3); 4.351(2.4); 4.335(2.3); 3.927(1.7); 3.883(2.0); 3.775(16.0); 3.640(0.4); 3.572(0.4); 3.567(0.5); 3.535(1.9); 3.492(1.6); 3.334(73.4); 3.188 (0.4); 2.892(5.7); 2.732(5.0); 2.508(38.7); 2.504(50.1); 2.499(36.9); 1.663(10.1); 1.625(1.3); 1.605(0.4); 0.008(0.4); 0.000(12.2); −0.008(0.5)
Example 674: ¹H-NMR(400.0 MHz, DMSO):
9.010(2.6); 9.005(2.7); 8.772(2.3); 8.766(2.5); 8.750(1.1); 8.735(0.5); 8.241(2.1); 8.237(2.3); 8.196(1.2); 8.191(1.0); 8.174(1.7); 8.169(1.5); 8.092(2.3); 8.069(1.5); 7.954(0.7); 7.611(1.3); 7.592(1.8); 7.573(1.4); 6.775(1.8); 6.757(1.7); 6.637(1.9); 6.617(1.8); 4.334(1.8); 4.316(1.8); 3.943(1.8); 3.900(2.1); 3.763(16.0); 3.548(2.0); 3.505(1.7); 3.334 (67.0); 2.892(5.3); 2.733(4.6); 2.526(0.8); 2.512(16.4); 2.508(32.4); 2.504(42.1); 2.499(30.1); 2.495(14.6); 1.692(10.4); 0.008(0.5); 0.000(12.9); −0.008(0.5)
Example 675: ¹H-NMR(400.0 MHz, DMSO):
8.954(3.3); 8.949(3.3); 8.602(2.5); 8.597(2.3); 8.443(0.6); 8.429(1.3); 8.414(0.6); 8.232(2.4); 8.228(2.7); 8.160(1.3); 8.156(1.1); 8.138(2.1); 8.133(1.9); 8.072(2.7); 8.050(1.6); 7.953(1.1); 7.145(4.7); 4.594(6.0); 4.068(3.1); 4.053(3.1); 3.878(1.9); 3.835(2.3); 3.494(2.3); 3.450(1.9); 3.415(0.4); 3.403(0.7); 3.397(0.7); 3.387(1.5); 3.379(0.8); 3.375(0.8); 3.371(0.7); 3.360(0.6); 3.333(91.1); 2.892(8.7); 2.732(7.3); 2.672(0.3); 2.526(1.0); 2.512(20.1); 2.508(40.8); 2.503 (53.6); 2.499(38.3); 2.494(18.2); 2.330(0.3); 2.245(16.0); 2.029(0.6); 1.623(0.7); 1.607(0.7); 1.594(11.7); 0.925(4.2); 0.920(5.0); 0.907(1.8); 0.903(2.9); 0.008(0.5); 0.000(14.8); −0.008(0.5)
Example 676: ¹H-NMR(400.0 MHz, DMSO):
9.003(3.6); 8.998(3.7); 8.760(2.6); 8.755(2.3); 8.446(0.7); 8.432(1.3); 8.417(0.6); 8.211(2.6); 8.207(2.8); 8.162(1.4); 8.157(1.1); 8.146(0.5); 8.140(2.2); 8.135(2.0); 8.074(2.7); 8.051(1.7); 7.953(1.1); 7.144(4.7); 4.067(3.3); 4.052(3.3); 3.870(2.0); 3.826(2.4); 3.485(2.4); 3.442(2.0); 3.415(0.4); 3.403(0.7); 3.397(0.8); 3.387(1.6); 3.379(0.8); 3.375(0.9); 3.371(0.8); 3.360(0.8); 3.334(113.9); 2.892(8.6); 2.7324(7.1); 2.7316(7.1); 2.672(0.4); 2.526(1.3); 2.512(23.3); 2.508(46.1); 2.503(59.9); 2.499(42.7); 2.494(20.2); 2.330(0.4); 2.245(16.0); 2.028(1.0); 1.624(1.1); 1.607(1.1); 1.595(12.1); 0.925(4.4); 0.921(5.0); 0.918(4.2); 0.908(1.9); 0.904(2.9); 0.008(0.7); 0.000(16.2); −0.009(0.6)
Example 677: ¹H-NMR(400.0 MHz, DMSO):
9.010(3.1); 9.004(3.1); 8.769(2.5); 8.763(2.3); 8.636(0.7); 8.621(1.3); 8.606(0.6); 8.335(2.4); 8.320(2.5); 8.238(2.4); 8.234(2.6); 8.192(1.4); 8.187(1.1); 8.170(2.0); 8.165(1.8); 8.106(4.0); 8.088(2.6); 8.066(1.7); 7.008(2.6); 6.994(2.5); 4.288(2.4); 4.273(2.4); 3.928(2.0); 3.884(2.4); 3.829(16.0); 3.529(2.1); 3.486(1.9); 3.333(49.7); 2.891(0.7); 2.733 (0.6); 2.508(39.7); 2.503(50.7); 2.499(36.2); 2.495(17.5); 1.663(11.7); 0.008(0.5); 0.000(12.6); −0.009(0.5)
Example 678: ¹H-NMR(400.0 MHz, DMSO):
9.012(2.9); 9.006(3.1); 8.999(0.3); 8.908(0.7); 8.892(1.4); 8.877(0.7); 8.771(2.4); 8.765(2.3); 8.238(2.5); 8.234(2.8); 8.195(1.4); 8.190(1.1); 8.173(2.0); 8.168(1.8); 8.094(2.6); 8.072(1.7); 8.033(2.4); 8.020(2.4); 7.954(1.0); 6.823(1.6); 6.821(1.6); 6.810(1.6); 6.808(1.5); 6.565(3.0); 4.272(3.0); 4.256(3.0); 3.914(1.9); 3.871(2.3); 3.754(16.0); 3.536(2.3);

NMR Peak Lists Table 1

3.493(1.9); 3.360(0.5); 3.334(98.7); 3.206(0.4); 2.892(7.0); 2.733(5.7); 2.508(38.9); 2.504(49.9); 2.499(36.0); 1.662(11.7); 0.008(0.4); 0.000(11.4); −0.008(0.5)
Example 679: $^1$H-NMR(400.0 MHz, DMSO):
8.961(3.2); 8.956(3.2); 8.652(0.7); 8.637(1.5); 8.622(0.8); 8.610(2.8); 8.606(2.7); 8.378(2.0); 8.364(2.0); 8.258(2.7); 8.254(2.9); 8.190(1.4); 8.186(1.3); 8.168(2.1); 8.163(2.0); 8.132(3.5); 8.087(2.7); 8.065(1.8); 7.954(0.5); 7.070(2.3); 7.056(2.2); 4.596(5.4); 4.296(3.2); 4.281(3.2); 4.128(0.5); 4.081(0.5); 3.937(2.0); 3.893(2.5); 3.855(16.0); 3.540(2.4); 3.496(2.0); 3.338(18.9); 2.892(2.9); 2.733(2.6); 2.673(0.3); 2.508(45.7); 2.504(57.5); 2.499(42.2); 2.331(0.4); 1.663(12.0); 1.636(0.4); 0.008(0.5); 0.000(11.4)
Example 680: $^1$H-NMR(400.0 MHz, DMSO):
9.014(2.7); 9.008(2.8); 8.776(2.4); 8.770(2.7); 8.752(0.6); 8.277(4.2); 8.249(2.1); 8.245(2.3); 8.207(1.3); 8.203(1.0); 8.185(1.8); 8.180(1.6); 8.100(2.6); 8.096(2.6); 8.084(2.5); 8.078(1.7); 7.108(1.7); 6.996(1.7); 4.277(2.1); 4.262(2.0); 3.940(1.7); 3.896(16.0); 3.549(2.0); 3.506(1.7); 3.334(13.8); 2.892(0.9); 2.733(0.8); 2.549(0.4); 2.526(0.7); 2.513 (13.8); 2.508(27.4); 2.504(35.4); 2.499(25.3); 2.495(12.2); 1.693(10.2); 0.008(0.5); 0.000(13.2); −0.009(0.5)
Example 681: $^1$H-NMR(400.0 MHz, DMSO):
8.963(2.9); 8.958(3.0); 8.906(0.6); 8.891(1.3); 8.875(0.6); 8.612(2.2); 8.607(2.2); 8.258(2.3); 8.254(2.5); 8.193(1.3); 8.189(1.1); 8.171(1.9); 8.167(1.7); 8.092(2.5); 8.070(1.6); 8.033(2.2); 8.020(2.3); 7.954(1.6); 6.824(1.5); 6.821(1.5); 6.811(1.4); 6.808(1.5); 6.565(2.7); 4.595(5.3); 4.272(2.9); 4.256(2.7); 3.923(1.8); 3.880(2.2); 3.753(16.0); 3.544(2.1); 3.501(1.8); 3.336(100.4); 2.892(8.7); 2.732(7.1); 2.526(0.7); 2.513(16.7); 2.508(34.1); 2.504(44.9); 2.499(32.3); 2.495(15.5); 1.661(10.9); 0.008(0.3); 0.000(9.9); −0.009(0.4)
Example 682: $^1$H-NMR(400.0 MHz, DMSO):
9.006(2.0); 9.001(2.1); 8.895(0.6); 8.880(1.2); 8.865(0.6); 8.766(2.3); 8.761(2.3); 8.313(0.3); 8.225(2.3); 8.185(1.2); 8.181(1.0); 8.163(1.7); 8.158(1.5); 8.084(2.2); 8.073(0.4); 8.062(1.5); 7.953(0.7); 7.472(2.2); 7.449(2.6); 7.171(2.0); 7.148(1.7); 4.559(0.3); 4.544(0.3); 4.520(1.5); 4.504(2.6); 4.488(1.5); 3.985(16.0); 3.918(1.7); 3.875(2.1); 3.536(1.9); 3.492(1.5); 3.335(142.0); 2.893(4.4); 2.733(3.9); 2.677(0.4); 2.673(0.5); 2.508(56.8); 2.504(73.0); 2.500(54.2); 2.335(0.3); 2.330(0.4); 1.649(10.4); 1.595(0.7); 0.008(0.8); 0.000(17.3)
Example 683: $^1$H-NMR(400.0 MHz, DMSO):
8.965(3.0); 8.959(3.0); 8.777(0.7); 8.762(1.4); 8.747(0.7); 8.617(2.4); 8.613(2.3); 8.274(4.8); 8.266(2.7); 8.206(1.4); 8.201(1.1); 8.184(2.0); 8.179(1.8); 8.099(2.8); 8.092(2.4); 8.080(2.5); 7.954(0.9); 7.005(1.9); 6.993(1.9); 4.597(5.1); 4.276(2.5); 4.261(2.4); 3.949(1.9); 3.905(2.7); 3.896(16.0); 3.557(2.2); 3.514(1.9); 3.335(72.5); 2.892(6.1); 2.733(5.3); 2.526(0.9); 2.508(35.1); 2.504(44.8); 2.499(31.6); 2.495(14.9); 1.692(11.2); 0.008(0.5); 0.000(13.4); −0.009(0.5)
Example 684: $^1$H-NMR(400.0 MHz, DMSO):
8.962(2.9); 8.957(3.0); 8.787(0.6); 8.773(1.3); 8.758(0.6); 8.611(2.3); 8.606(2.2); 8.289(2.6); 8.275(2.7); 8.266(2.4); 8.261(2.5); 8.194(1.3); 8.189(1.1); 8.172(1.9); 8.167(1.8); 8.088(2.5); 8.065(1.7); 7.953(0.4); 6.823(1.3); 6.817(1.4); 6.809(1.2); 6.803(1.4); 6.713(2.3); 6.707(2.1); 4.597(5.0); 4.364(1.5); 4.350(2.8); 4.335(1.5); 3.961(1.9); 3.918(2.3); 3.664(16.0); 3.553(2.2); 3.510(1.8); 3.334(45.9); 2.892(3.0); 2.733(2.6); 2.551(0.4); 2.512(19.2); 2.508(38.3); 2.503(49.8); 2.499(35.8); 2.495(17.3); 1.688(11.3); 0.008(0.5); 0.000(13.8); −0.008(0.5)
Example 685: $^1$H-NMR(400.0 MHz, DMSO):
9.012(2.8); 9.006(3.0); 8.773(2.3); 8.768(2.4); 8.696(0.6); 8.681(1.2); 8.665(0.6); 8.242(2.3); 8.238(2.6); 8.198(1.3); 8.194(1.0); 8.176(2.0); 8.171(1.7); 8.094(2.5); 8.072(1.7); 8.022(1.2); 8.018(1.3); 8.010(1.3); 8.005(1.2); 7.954(0.6); 7.389(1.1); 7.386(1.1); 7.371(1.2); 6.905(1.4); 6.893(1.4); 6.887(1.4); 6.875(1.3); 4.239(2.6); 4.224(2.5); 3.934(1.8); 3.891(2.3); 3.862(16.0); 3.536(2.1); 3.493(1.8); 3.334(54.6); 2.892(4.5); 2.733(3.9); 2.508(33.5); 2.504(42.5); 2.499(30.1); 1.678(10.9); 1.655(0.5); 1.618(0.7); 0.008(0.4); 0.000(11.4); −0.009(0.4)
Example 686: $^1$H-NMR(400.0 MHz, DMSO):
9.005(2.5); 8.999(2.6); 8.811(0.5); 8.796(1.0); 8.780(0.6); 8.760(1.9); 8.754(1.8); 8.216(1.8); 8.212(2.0); 8.172(1.1); 8.168(0.8); 8.150(1.6); 8.146(1.4); 8.078(2.2); 8.056(1.4); 8.023(1.6); 8.017(1.6); 7.593(1.1); 7.587(1.0); 7.571(1.1); 7.565(1.1); 6.746(1.9); 6.724(1.8); 4.238(1.3); 4.229(1.4); 4.222(1.4); 4.214(1.3); 3.890(1.5); 3.846(1.9); 3.788(16.0); 3.509(1.8); 3.465(1.5); 3.336(54.2); 2.892(1.3); 2.733(0.9); 2.527(0.5); 2.513(10.1); 2.509(20.3); 2.505(26.5); 2.500(18.9); 2.496(9.1); 1.656(0.8); 1.614(9.2); 0.000(6.6)
Example 687: $^1$H-NMR(400.0 MHz, DMSO):
8.962(2.8); 8.957(2.8); 8.693(0.6); 8.678(1.2); 8.663(0.6); 8.614(2.2); 8.609(2.1); 8.263(2.2); 8.259(2.4); 8.197(1.2); 8.192(1.0); 8.175(1.8); 8.170(1.7); 8.092(2.4); 8.070(1.6); 8.021(1.2); 8.017(1.3); 8.009(1.3); 8.005(1.2); 7.389(1.1); 7.385(1.1); 7.371(1.2); 7.367(1.1); 6.905(1.4); 6.892(1.4); 6.887(1.4); 6.874(1.3); 4.596(4.9); 4.239(2.5); 4.224(2.5); 3.943(1.7); 3.899(2.2); 3.863(16.0); 3.544(2.0); 3.501(1.7); 3.334(68.3); 2.892(1.9); 2.733(1.5); 2.512(15.1); 2.508 (29.6); 2.504(38.1); 2.499(27.2); 2.495(13.1); 1.677(10.5); 0.008(0.4); 0.000(10.2); −0.009(0.4)
Example 688: $^1$H-NMR(400.0 MHz, DMSO):
8.956(2.5); 8.951(2.6); 8.809(0.5); 8.793(1.1); 8.778(0.5); 8.602(1.9); 8.597(1.8); 8.238(1.9); 8.233(2.0); 8.171(1.0); 8.166(0.9); 8.149(1.6); 8.144(1.5); 8.077(2.2); 8.054(1.4); 8.023(1.6); 8.017(1.6); 7.593(1.1); 7.587(1.0); 7.572(1.2); 7.566(1.1); 6.745(1.9); 6.724(1.8); 4.594(4.7); 4.237(1.3); 4.230(1.4); 4.222(1.4); 4.214(1.4); 3.898(1.5); 3.855(1.8); 3.788(16.0); 3.516(1.8); 3.473(1.5); 3.334(48.8); 2.892(2.6); 2.733(2.0); 2.527(0.5); 2.513(10.8); 2.509(21.9); 2.504(28.9); 2.500(20.9); 2.495(10.1); 1.654(0.8); 1.613(9.0); 0.000(8.7); −0.008(0.3)
Example 689: $^1$H-NMR(400.0 MHz, DMSO):
8.961(3.5); 8.956(3.5); 8.823(0.9); 8.808(1.7); 8.794(0.8); 8.608(3.1); 8.604(3.0); 8.375(1.9); 8.362(2.0); 8.348(3.2); 8.247(3.1); 8.243(3.4); 8.179(1.6); 8.174(1.4); 8.157(2.4); 8.152(2.3); 8.084(3.4); 8.062(2.1); 7.953(0.9); 7.315(2.0); 7.302(1.9); 4.596(5.8); 4.363(4.0); 4.348(3.9); 3.926(2.4); 3.883(2.9); 3.535(3.0); 3.491(2.7); 3.348(9.0); 2.892(5.3); 2.732(4.7); 2.673(0.4); 2.565(1.5); 2.551(3.0); 2.537(1.7); 2.508(51.0); 2.504(65.1); 2.499(47.8); 2.325(16.0); 1.646(14.4); 1.273(0.5); 1.258(0.8); 1.243(0.8); 0.000(10.4)
Example 690: $^1$H-NMR(400.0 MHz, DMSO):
8.964(4.2); 8.959(4.3); 8.871(0.9); 8.856(1.8); 8.840(0.9); 8.617(3.2); 8.613(3.2); 8.317(0.3); 8.298(3.5); 8.274(2.2); 8.265(4.2); 8.261(5.5); 8.201(1.9); 8.196(1.7); 8.179(2.8); 8.174(2.6); 8.097(3.6); 8.075(2.5); 7.954(1.8); 7.053(2.3); 7.040(2.2); 6.538(0.4); 4.597(7.7); 4.287(4.0); 4.272(4.0); 3.943(2.6); 3.900(3.2); 3.554(3.1); 3.511(2.6); 3.340(84.8); 2.892(13.4); 2.872(0.6); 2.748(0.4); 2.732(11.2); 2.677(0.4); 2.673(0.6); 2.668(0.4); 2.551(1.4); 2.526(1.4); 2.513 (28.9); 2.508(58.9); 2.504(77.7); 2.499(55.6); 2.495(26.5); 2.335(0.4); 2.331(0.6); 2.326(0.4); 2.234(16.0); 2.194 (0.5); 1.685(15.8); 1.654(0.4); 1.233(0.3); 0.008(0.5); 0.000(15.8); −0.009(0.5)
Example 691: $^1$H-NMR(400.0 MHz, DMSO):
9.015(3.7); 9.009(3.7); 8.951(0.8); 8.936(1.7); 8.920(0.8); 8.774(3.2); 8.769(3.0); 8.385(2.4); 8.372(2.4); 8.246(3.1); 8.242(3.4); 8.205(1.8); 8.200(1.4); 8.183(2.5); 8.178(2.2); 8.099(3.3); 8.077(2.2); 7.954(0.9); 7.147(3.5); 7.129(1.6); 4.330(3.7); 4.315(3.7); 3.924(2.4); 3.881(3.0); 3.548(3.0); 3.505(2.6); 3.446(0.6); 3.341(18.3); 3.208(0.3); 2.892(6.4);

-continued

NMR Peak Lists Table 1

2.733(5.8); 2.677(0.4); 2.673(0.5); 2.668(0.4); 2.565(1.1); 2.551(2.2); 2.537(1.3); 2.508(56.4); 2.504(71.4); 2.499 (51.2); 2.385(16.0); 2.334(0.4); 2.331(0.4); 1.678(14.8); 1.274(0.3); 1.259(0.6); 1.243(0.6); 0.008(0.7); 0.000(15.7)
Example 692: $^1$H-NMR(400.0 MHz, DMSO):
8.975(1.0); 8.966(4.6); 8.961(5.8); 8.945(0.9); 8.615(3.2); 8.610(3.1); 8.431(2.2); 8.418(2.3); 8.267(3.2); 8.262(3.5); 8.204(1.9); 8.199(1.6); 8.181(2.7); 8.177(2.5); 8.098(3.5); 8.076(2.4); 7.953(1.5); 7.226(3.5); 7.210(1.5); 4.600(7.4); 4.359(3.7); 4.344(3.7); 3.934(2.6); 3.891(3.2); 3.560(3.2); 3.517(2.8); 3.343(13.7); 2.892(10.4); 2.747(0.4); 2.732(8.7); 2.677(0.4); 2.673(0.5); 2.668(0.4); 2.579(0.3); 2.565(2.0); 2.537(2.3); 2.526(1.6); 2.512(30.9); 2.508(62.2); 2.504(81.3); 2.499(58.0); 2.495(27.5); 2.420(16.0); 2.335(0.4); 2.330(0.5); 2.326(0.4); 1.679(15.5); 1.273(0.4); 1.259(0.6); 1.243(0.7); 1.234(0.4); 0.008(0.7); 0.000(18.5); −0.009(0.6)
Example 693: $^1$H-NMR(400.0 MHz, DMSO):
9.010(4.3); 9.004(4.8); 9.000(1.1); 8.787(0.8); 8.781(0.9); 8.772(3.8); 8.767(4.0); 8.754(1.9); 8.739(0.9); 8.238(3.8); 8.234(4.1); 8.197(1.9); 8.192(1.5); 8.175(3.0); 8.170(2.6); 8.154(0.6); 8.150(0.5); 8.090(3.6); 8.079(0.9); 8.067(2.4); 8.057(0.5); 7.954(1.1); 7.624(1.8); 7.605(3.8); 7.586(2.1); 7.100(2.7); 7.081(2.5); 7.006(2.6); 6.987(2.5); 6.536(0.6); 4.389(2.3); 4.380(2.5); 4.374(2.5); 4.366(2.3); 4.312(0.6); 4.268(0.6); 3.937(2.6); 3.894(3.2); 3.553(3.1); 3.510(2.7); 3.450(0.7); 3.406(0.7); 3.336(209.6); 3.205(1.6); 2.952(0.6); 2.935(1.5); 2.918(2.0); 2.900(2.1); 2.892(9.5); 2.884 (1.0); 2.732(6.7); 2.677(0.4); 2.673(0.5); 2.668(0.4); 2.543(0.3); 2.526(1.4); 2.512(32.8); 2.508(66.2); 2.504(86.9); 2.499(62.6); 2.495(30.4); 2.335(0.4); 2.330(0.5); 2.326(0.4); 1.692(16.0); 1.655(4.1); 1.323(1.0); 1.305(1.0); 1.282(1.0); 1.265(1.1); 1.234(0.5); 1.168(11.9); 1.159(12.2); 1.150(12.1); 1.142(11.8); 1.092(0.3); 0.008(0.5); 0.000(14.5); −0.008(0.6)
Example 694: $^1$H-NMR(400.0 MHz, DMSO):
8.959(2.4); 8.953(2.5); 8.895(0.5); 8.880(1.1); 8.865(0.5); 8.609(1.9); 8.604(1.9); 8.251(1.9); 8.246(2.1); 8.183(1.1); 8.179(0.9); 8.161(1.6); 8.157(1.5); 8.083(2.1); 8.061(1.4); 7.474(2.3); 7.451(2.6); 7.174(2.6); 7.151(2.3); 4.596(4.2); 4.520(1.4); 4.505(2.5); 4.490(1.4); 3.984(16.0); 3.927(1.5); 3.884(1.9); 3.546(1.8); 3.503(1.5); 3.335(58.0); 2.892(1.3); 2.732(1.1); 2.513(12.3); 2.509(24.8); 2.504(32.6); 2.500(23.5); 2.495(11.3); 1.648(9.2); 0.000(5.6)
Example 695: $^1$H-NMR(400.0 MHz, DMSO):
9.005(2.9); 9.000(2.9); 8.867(0.6); 8.852(1.2); 8.838(0.6); 8.768(1.1); 8.760(2.5); 8.754(2.0); 8.473(7.7); 8.214(2.4); 8.210(2.9); 8.171(1.4); 8.166(1.0); 8.149(2.1); 8.144(1.7); 8.079(2.9); 8.056(1.8); 7.954(1.3); 4.251(1.8); 4.244(1.9); 4.236(1.9); 4.230(1.7); 3.938(0.6); 3.891(1.8); 3.860(16.0); 3.848(2.3); 3.510(2.3); 3.466(2.0); 3.336(70.7); 2.892(8.4); 2.732(7.4); 2.672(0.4); 2.508(50.4); 2.504(60.4); 2.499(43.9); 2.331(0.4); 1.620(4.4); 1.607(9.8); 0.000(9.2); −0.009(0.7)
Example 696: $^1$H-NMR(400.0 MHz, DMSO):
8.956(2.3); 8.951(2.7); 8.947(1.1); 8.866(0.5); 8.851(1.0); 8.836(0.5); 8.607(0.8); 8.601(2.1); 8.595(1.7); 8.474(7.2); 8.235(1.7); 8.230(1.9); 8.224(0.8); 8.219(0.8); 8.170(1.1); 8.165(0.9); 8.147(1.8); 8.143(1.5); 8.076(2.5); 8.054(1.6); 7.954(0.6); 4.593(4.2); 4.252(1.3); 4.246(1.4); 4.237(1.3); 4.230(1.3); 3.946(0.6); 3.901(1.8); 3.860(16.0); 3.518(1.7); 3.498(0.6); 3.475(1.4); 3.455(0.5); 3.339(26.2); 2.892(4.7); 2.733(4.0); 2.527(0.7); 2.513(15.4); 2.509(31.2); 2.504 (40.9); 2.500(29.3); 2.495(14.1); 1.607(9.0); 0.000(7.2)
Example 697: $^1$H-NMR(400.0 MHz, DMSO):
9.010(3.6); 9.005(3.7); 8.773(3.4); 8.767(3.9); 8.749(0.8); 8.244(2.9); 8.240(3.3); 8.201(1.8); 8.196(1.5); 8.179(2.5); 8.174(2.3); 8.092(3.2); 8.070(2.2); 7.953(0.9); 7.595(1.4); 7.576(2.8); 7.557(1.6); 7.085(2.1); 7.065(2.0); 6.986(2.1); 6.967(1.9); 4.360(3.9); 4.345(3.9); 3.940(2.4); 3.897(2.8); 3.544(2.8); 3.501(2.3); 3.338(107.8); 2.892(6.1); 2.732(5.2); 2.673(0.5); 2.668(0.3); 2.551(4.5); 2.512(27.3); 2.508(54.4); 2.504(71.3); 2.499(52.0); 2.394(16.0); 2.371(0.7); 2.335(0.3); 2.330(0.5); 1.700(0.6); 1.683(14.3); 0.008(0.5); 0.000(14.4); −0.008(0.6)
Example 698: $^1$H-NMR(400.0 MHz, DMSO):
8.961(3.7); 8.956(3.7); 8.779(0.8); 8.764(1.6); 8.748(0.8); 8.614(2.9); 8.609(2.8); 8.264(2.9); 8.260(3.2); 8.199(1.7); 8.194(1.4); 8.177(2.4); 8.172(2.2); 8.090(3.2); 8.068(2.1); 7.954(1.0); 7.597(1.2); 7.578(2.5); 7.558(1.4); 7.086(2.0); 7.067(1.8); 6.989(1.9); 6.970(1.8); 4.596(6.8); 4.361(3.9); 4.346(3.8); 3.950(2.4); 3.907(2.9); 3.552(2.8); 3.509(2.4); 3.337(86.6); 2.892(7.3); 2.732(6.3); 2.673(0.4); 2.565(0.7); 2.551(1.6); 2.537(0.9); 2.526(1.2); 2.513(21.9); 2.508(44.2); 2.504(58.1); 2.499(41.9); 2.495(20.3); 2.395(16.0); 2.371(0.3); 2.330(0.4); 1.683(14.4); 0.008(0.5); 0.000(15.6); −0.009(0.6)
Example 699: $^1$H-NMR(400.0 MHz, DMSO):
9.044(5.0); 9.010(4.2); 9.004(5.3); 8.999(1.7); 8.960(0.9); 8.945(1.7); 8.929(0.8); 8.766(4.2); 8.760(3.0); 8.665(11.6); 8.317(0.8); 8.226(3.2); 8.221(3.8); 8.214(1.5); 8.179(2.3); 8.175(1.9); 8.157(3.4); 8.153(3.0); 8.084(3.6); 8.062(2.3); 7.953(0.9); 7.599(0.6); 7.424(0.6); 6.534(1.3); 4.341(2.9); 4.324(2.8); 3.889(1.1); 3.865(3.2); 3.846(1.2); 3.526(3.2); 3.482(2.7); 3.448(0.6); 3.441(1.3); 3.412(0.4); 3.398(1.4); 3.332(804.0); 2.891(6.6); 2.732(5.5); 2.680 (0.9); 2.676(1.8); 2.672(2.5); 2.667(1.8); 2.546(2.3); 2.542(2.3); 2.525(7.4); 2.511(147.8); 2.507(295.8); 2.502(384.1); 2.498(272.1); 2.493(127.5); 2.338(0.8); 2.334(1.7); 2.329(2.4); 2.325(1.7); 1.627(16.0); 1.604(6.2); 1.235(1.4); 0.146(0.5); 0.008(3.9); 0.000(115.0); −0.009(3.9); −0.149(0.5)
Example 700: $^1$H-NMR(400.0 MHz, DMSO):
9.010(4.3); 9.004(4.4); 8.815(0.8); 8.801(1.7); 8.786(0.9); 8.768(3.2); 8.762(3.0); 8.352(2.3); 8.339(2.9); 8.333(4.1); 8.228(3.1); 8.224(3.4); 8.181(1.9); 8.176(1.5); 8.158(2.8); 8.154(2.6); 8.086(3.5); 8.064(2.2); 7.953(0.4); 7.273(1.9); 7.261(1.8); 4.355(3.7); 4.340(3.7); 3.918(2.6); 3.874(3.2); 3.525(3.2); 3.482(2.8); 3.458(0.4); 3.446(0.5); 3.341(6.7); 2.892(3.1); 2.733(2.7); 2.672(0.4); 2.668(0.3); 2.565(1.1); 2.551(2.2); 2.537(1.2); 2.526(1.1); 2.512(26.0); 2.508(52.8); 2.503(68.9); 2.499(49.0); 2.494(23.0); 2.334(0.4); 2.330(0.5); 2.325(0.4); 2.308(16.0); 1.646(15.7); 1.273(0.5); 1.259(0.7); 1.243(0.8); 0.008(0.6); 0.000(19.5); −0.009(0.7)
Example 701: $^1$H-NMR(400.0 MHz, DMSO):
10.300(3.7); 9.447(1.5); 9.006(4.9); 9.001(4.2); 8.773(4.5); 8.769(3.6); 8.243(4.7); 8.239(3.9); 8.190(2.3); 8.185(1.6); 8.168(3.5); 8.163(2.5); 8.085(3.7); 8.063(2.4); 7.955(6.4); 7.579(6.5); 7.190(2.8); 4.089(1.5); 4.071(4.8); 4.053(4.8); 4.035(1.6); 4.010(2.6); 3.994(1.0); 3.967(3.1); 3.951(1.2); 3.897(0.6); 3.879(1.8); 3.861(1.9); 3.846(9.8); 3.571(3.0); 3.549(1.2); 3.527(2.5); 3.506(1.0); 3.332(116.5); 2.892(1.1); 2.733(1.0); 2.673(0.5); 2.668(0.4); 2.508(68.0); 2.504 (84.2); 2.499(60.5); 2.330(0.5); 2.326(0.4); 1.701(8.0); 1.695(16.0); 1.323(5.5); 1.305(11.8); 1.287(5.3); 1.259(2.1); 1.241(4.5); 1.223(2.0); 0.008(0.6); 0.000(15.8); −0.008(0.7)
Example 702: $^1$H-NMR(400.0 MHz, DMSO):
9.014(3.8); 9.009(3.9); 8.872(0.9); 8.857(1.8); 8.842(0.9); 8.778(3.3); 8.773(3.3); 8.553(0.4); 8.532(0.4); 8.520(0.4); 8.492(0.5); 8.478(0.6); 8.466(0.4); 8.454(0.7); 8.443(0.6); 8.405(0.3); 8.363(0.7); 8.349(1.1); 8.336(1.2); 8.317(0.8); 8.296(4.0); 8.272(2.3); 8.259(2.4); 8.246(3.6); 8.243(3.7); 8.203(2.0); 8.198(1.8); 8.181(2.8); 8.176(2.5); 8.161(0.6); 8.100(3.5); 8.078(2.5); 7.954(2.0); 7.928(0.6); 7.911(0.8); 7.861(4.1); 7.840(4.3); 7.559(3.7); 7.538(4.5); 7.495(0.5); 7.454(0.7); 7.446(0.7); 7.438(0.7); 7.431(0.7); 7.376(2.0); 7.358(3.5); 7.357(3.5); 7.338(2.6); 7.307(3.3); 7.304(2.9);

-continued

NMR Peak Lists Table 1

7.287(3.7); 7.269(1.8); 7.169(0.7); 7.157(0.5); 7.048(2.4); 7.036(2.4); 4.470(0.3); 4.455(0.4); 4.304(1.2); 4.286(4.7); 4.270(4.2); 3.934(2.6); 3.891(3.4); 3.733(0.4); 3.707(0.3); 3.672(0.4); 3.547(3.9); 3.503(4.0); 3.348(16.8); 3.062(0.6); 3.040(0.5); 3.020(0.4); 3.007(0.4); 2.987(0.5); 2.969(0.3); 2.928(0.6); 2.919(0.5); 2.892(13.0); 2.866(0.6); 2.748(0.5); 2.733(11.2); 2.677(0.8); 2.673(1.0); 2.668(0.7); 2.508(119.7); 2.504(150.4); 2.499(110.0); 2.428(1.4); 2.409(0.5); 2.385(0.6); 2.367(0.6); 2.342(1.4); 2.331(2.8); 2.315(1.8); 2.292(0.7); 2.282(0.6); 2.267(0.9); 2.256(3.9); 2.232(16.0); 2.193(0.6); 2.178(0.4); 2.173(0.4); 2.111(0.4); 2.071(0.4); 1.915(0.7); 1.839(0.3); 1.685(15.5); 1.646(0.4); 1.606(0.8); 1.585(0.6); 1.341(0.7); 1.325(0.6); 1.247(0.4); 1.234(0.8); 1.206(1.9); 1.190(1.8); 0.008(0.7); 0.000(22.2); −0.008(1.2)

Example 703: $^1$H-NMR(400.0 MHz, DMSO):
8.954(5.0); 8.949(4.0); 8.910(0.4); 8.893(0.7); 8.878(0.3); 8.604(4.6); 8.245(1.6); 8.232(3.9); 8.176(2.3); 8.171(1.7); 8.154(3.4); 8.149(2.7); 8.127(1.1); 8.120(1.1); 8.077(3.9); 8.055(2.6); 8.045(1.4); 7.954(0.8); 7.598(2.3); 7.425(2.2); 7.180(1.0); 4.592(7.2); 4.323(1.5); 4.307(1.4); 3.927(0.9); 3.900(2.6); 3.884(1.1); 3.857(3.1); 3.709(7.3); 3.533(1.0); 3.490(0.9); 3.449(3.1); 3.406(2.6); 3.334(101.7); 2.892(4.7); 2.732(4.1); 2.673(0.4); 2.504(67.8); 2.330(0.4); 1.647(5.3); 1.605(16.0); 0.000(12.7)

Example 704: $^1$H-NMR(400.0 MHz, DMSO):
9.043(5.1); 8.958(5.2); 8.954(7.0); 8.949(3.8); 8.943(2.0); 8.927(0.9); 8.665(11.8); 8.605(5.3); 8.317(1.0); 8.245(3.5); 8.240(4.7); 8.233(2.9); 8.176(2.5); 8.173(2.3); 8.155(3.9); 8.151(3.8); 8.081(4.1); 8.059(2.6); 7.952(1.0); 7.595(1.4); 7.423(1.4); 6.535(1.5); 4.595(8.6); 4.340(3.3); 4.325(3.2); 3.917(2.7); 3.897(2.1); 3.874(3.3); 3.854(2.5); 3.533(3.2); 3.490(2.7); 3.472(0.4); 3.449(2.7); 3.405(2.5); 3.332(1168.5); 3.272(0.4); 2.891(7.3); 2.747(0.6); 2.732(6.3); 2.676 (2.8); 2.671(3.8); 2.667(2.8); 2.542(2.2); 2.524(10.8); 2.507(454.0); 2.502(587.7); 2.498(425.6); 2.333(2.6); 2.329(3.6); 2.325(2.7); 1.782(0.5); 1.626(16.0); 1.603(12.4); 1.234(2.2); 0.146(0.6); 0.008(5.1); 0.000(152.1); −0.009(6.2); −0.150(0.6)

Example 705: $^1$H-NMR(400.0 MHz, DMSO):
9.010(1.7); 9.004(5.3); 8.998(4.0); 8.894(0.6); 8.770(3.1); 8.764(4.0); 8.230(1.2); 8.226(1.4); 8.217(3.0); 8.212(3.4); 8.183(0.8); 8.178(2.3); 8.173(1.5); 8.161(1.2); 8.156(3.5); 8.151(2.4); 8.127(1.1); 8.120(1.1); 8.079(3.4); 8.057(2.2); 8.044(1.2); 8.040(1.2); 7.953(1.3); 7.600(1.6); 7.425(1.6); 7.184(0.7); 7.180(0.9); 7.174(0.6); 4.321(1.4); 4.306(1.4); 3.917(1.0); 3.890(2.7); 3.874(1.2); 3.847(3.1); 3.710(9.5); 3.565(3.1); 3.525(1.9); 3.482(1.1); 3.441(3.1); 3.398(2.6); 3.330(152.3); 2.891(9.6); 2.732(8.0); 2.676(0.5); 2.672(0.7); 2.667(0.5); 2.525(1.6); 2.512(42.2); 2.507(85.4); 2.503(111.7); 2.498(79.9); 2.494(38.1); 2.334(0.6); 2.330(0.7); 2.325(0.6); 1.806(0.4); 1.792(0.4); 1.765(0.5); 1.753 (0.4); 1.647(5.9); 1.605(16.0); 1.234(0.6); 0.941(0.8); 0.747(1.2); 0.008(1.2); 0.000(38.1); −0.009(1.4)

Example 706: $^1$H-NMR(400.0 MHz, DMSO):
10.298(2.6); 9.444(2.5); 8.961(2.9); 8.956(4.9); 8.952(3.2); 8.614(4.1); 8.263(4.3); 8.226(0.3); 8.192(1.4); 8.188(2.1); 8.183(1.3); 8.169(2.1); 8.165(3.2); 8.161(1.9); 8.088(2.5); 8.083(2.7); 8.069(1.6); 8.061(1.7); 7.955(6.0); 7.579(4.4); 7.190(4.9); 6.536(0.8); 4.596(8.8); 4.089(1.1); 4.071(3.3); 4.053(3.4); 4.035(1.1); 4.019(1.8); 4.003(1.6); 3.976(2.1); 3.960(1.9); 3.905(0.3); 3.897(1.0); 3.879(3.0); 3.861(3.2); 3.847(16.0); 3.578(2.0); 3.557(1.8); 3.535(1.8); 3.525(0.4); 3.514(1.6); 3.333(110.2); 2.892(13.0); 2.732(11.1); 2.677(0.4); 2.673(0.5); 2.668(0.3); 2.551(1.1); 2.538(0.8); 2.526 (1.5); 2.512(30.8); 2.508(60.3); 2.504(77.6); 2.499(55.6); 2.495(26.8); 2.335(0.4); 2.330(0.5); 2.326(0.4); 1.700 (10.6); 1.694(11.2); 1.624(1.4); 1.323(3.8); 1.305(8.0); 1.287(3.7); 1.259(3.5); 1.241(7.3); 1.223(3.3); 0.008(0.6); 0.000(16.1); −0.008(0.6)

Example 710: $^1$H-NMR(499.9 MHz, CDCl3):
9.039(0.7); 9.035(0.7); 8.945(2.9); 8.941(3.1); 8.396(0.7); 8.392(0.7); 8.334(2.6); 8.330(2.7); 8.196(0.5); 8.179(0.9); 8.171(0.9); 8.169(0.9); 8.141(1.0); 8.138(1.0); 8.123(2.3); 8.120(2.5); 8.099(3.1); 8.081(1.8); 7.893(0.4); 7.889(0.5); 7.876(0.4); 7.872(0.4); 7.827(2.8); 7.824(2.9); 7.285(2.6); 7.280(4.5); 6.973(0.7); 6.963(1.2); 6.953(0.7); 4.417(1.0); 4.405(1.0); 4.387(1.4); 4.376(1.4); 4.287(2.3); 4.266(1.5); 4.254(3.3); 4.236(1.1); 4.226(1.0); 3.966(2.5); 3.952(4.2); 3.938(2.6); 3.869(2.7); 3.835(2.3); 3.733(0.5); 3.719(0.5); 3.487(3.0); 2.827(5.7); 2.292(0.8); 2.211(16.0); 1.863(0.4); 1.848(1.5); 1.834(2.8); 1.819(2.8); 1.805(1.5); 1.790(0.4); 1.259(0.5); 1.245(1.0); 1.231(0.5); 0.927(0.4); 0.912(0.4); 0.904(4.2); 0.889(8.4); 0.875(4.1); 0.000(1.4)

Example 711: $^1$H-NMR(400.1 MHz, DMSO):
8.953(2.4); 8.949(2.3); 8.605(2.5); 8.237(2.5); 8.172(1.1); 8.150(1.7); 8.077(2.2); 8.055(1.4); 7.774(1.3); 7.753(1.2); 4.583(3.6); 3.918(0.6); 3.900(1.0); 3.889(1.8); 3.871(0.9); 3.846(1.5); 3.828(0.6); 3.486(1.6); 3.443(1.3); 3.315(16.0); 2.503(6.2); 2.344(0.6); 2.325(0.7); 2.314(0.9); 2.295(0.8); 2.238(0.4); 2.219(0.4); 2.192(0.9); 2.174(1.1); 2.161(1.3); 2.138(16.0); 2.094(0.3); 2.042(6.2); 1.596(7.6); 1.083(1.6); 1.066(1.6); 1.034(4.0); 1.018(4.0); 0.000(2.9)

Example 712: $^1$H-NMR(400.1 MHz, DMSO):
9.102(4.6); 9.097(4.8); 8.904(3.5); 8.899(3.3); 8.239(3.4); 8.234(3.7); 8.175(2.3); 8.170(2.3); 8.165(1.9); 8.153(3.3); 8.148(3.7); 8.061(3.6); 8.039(2.5); 7.738(0.5); 3.920(2.5); 3.874(3.7); 3.704(3.6); 3.658(2.6); 3.617(0.5); 3.603(0.7); 3.595(0.6); 3.582(0.7); 3.571(0.4); 3.308(61.4); 3.274(24.8); 2.747(1.6); 2.719(1.8); 2.510(9.2); 2.505(19.3); 2.501 (26.6); 2.496(18.8); 2.492(8.8); 2.169(0.8); 2.140(16.0); 1.926(0.9); 1.899(1.7); 1.878(0.9); 1.871(1.0); 1.649(3.0); 1.641(2.8); 1.634(2.7); 1.626(3.1); 1.597(0.9); 0.008(1.3); 0.000(39.6); −0.009(1.4)

Example 713: $^1$H-NMR(300.2 MHz, CDCl3):
8.944(3.1); 8.936(3.2); 8.325(2.4); 8.318(2.4); 8.176(1.1); 8.170(1.1); 8.147(2.5); 8.141(2.6); 8.102(3.0); 8.072(1.3); 7.810(2.6); 7.804(2.6); 7.262(33.5); 6.853(0.7); 5.301(0.4); 3.977(2.7); 3.920(3.2); 3.362(0.6); 3.350(3.1); 3.342(1.2); 3.318(1.4); 3.293(3.2); 3.273(0.6); 3.262(0.5); 3.239(1.0); 3.220(1.2); 3.196(0.6); 3.176(0.5); 1.771(16.0); 1.572(1.3); 1.560(1.3); 1.536(1.7); 1.526(0.8); 1.513(2.1); 1.509(2.0); 1.502(1.2); 1.485(2.0); 1.461(0.8); 1.400(0.4); 1.377(1.3); 1.352(1.6); 1.325(1.7); 1.302(1.0); 1.278(0.4); 0.934(4.4); 0.910(8.9); 0.886(3.5); 0.011(1.0); 0.000(26.4); −0.011(1.2)

Example 714: $^1$H-NMR(400.1 MHz, DMSO):
9.003(4.3); 8.997(4.3); 8.762(3.6); 8.756(3.4); 8.510(0.9); 8.495(1.9); 8.481(0.9); 8.217(3.5); 8.213(4.0); 8.170(1.9); 8.165(1.6); 8.148(2.8); 8.143(2.6); 8.077(3.8); 8.055(2.4); 7.615(6.0); 7.412(0.8); 4.115(0.8); 4.103(4.7); 4.088(4.4); 4.073(0.8); 4.055(0.7); 4.034(1.7); 4.015(5.2); 3.997(5.2); 3.979(1.7); 3.896(2.8); 3.853(3.4); 3.564(2.6); 3.502(3.3); 3.458(2.7); 3.365(0.7); 3.316(88.6); 2.892(0.5); 2.691(0.6); 2.552(0.5); 2.507(36.4); 2.503(48.6); 2.498(35.3); 1.824(0.3); 1.781(0.4); 1.757(0.4); 1.731(0.3); 1.622(16.0); 1.607(0.9); 1.278(6.2); 1.260(13.1); 1.242(6.2); 1.229(0.4); 0.940(0.7); 0.750(1.1); 0.000(1.9)

Example 715: $^1$H-NMR(400.1 MHz, DMSO):
8.993(0.6); 8.987(0.6); 8.971(5.2); 8.966(5.2); 8.724(1.3); 8.710(2.6); 8.695(1.3); 8.667(0.4); 8.598(4.6); 8.594(4.6); 8.313(5.1); 8.309(5.0); 8.296(0.4); 8.291(0.3); 8.191(2.5); 8.187(2.4); 8.169(3.7); 8.165(3.7); 8.103(4.8); 8.080(2.9); 7.821(0.4); 7.778(0.5); 7.735(0.4); 7.704(8.1); 7.502(0.8); 4.603(1.0); 4.591(9.7); 4.301(0.3); 4.201(0.5); 4.186(0.5); 4.178(0.5); 4.164(3.8); 4.154(3.9); 4.150(4.0); 4.140(3.6); 4.122(1.0); 4.118(0.7); 4.104(1.2); 4.092(2.3); 4.087(1.1); 4.074(6.8); 4.056(6.8); 4.038(2.3); 3.959(3.1); 3.913(4.6); 3.753(4.3); 3.707(3.0); 3.346(0.4); 3.319(76.6); 3.279(26.4);

-continued

NMR Peak Lists Table 1

2.892(0.7); 2.733(0.4); 2.691(0.7); 2.508(35.9); 2.504(46.8); 2.499(34.2); 2.454(0.4); 1.358(0.5); 1.344(7.5); 1.326 (16.0); 1.308(8.4); 1.289(0.9); 1.285(0.6); 1.267(0.4); 1.260(0.3); 0.281(0.3); 0.000(0.4)
Example 716: $^1$H-NMR(400.1 MHz, DMSO):
9.006(4.0); 9.001(4.1); 8.884(0.9); 8.869(1.9); 8.854(0.9); 8.764(3.3); 8.758(3.1); 8.545(2.0); 8.541(2.7); 8.539(2.8); 8.535(2.8); 8.500(6.7); 8.493(2.9); 8.235(3.2); 8.230(3.6); 8.192(1.9); 8.188(1.5); 8.170(2.7); 8.165(2.4); 8.088(3.4); 8.066(2.3); 4.478(4.6); 4.463(4.5); 3.937(2.6); 3.894(3.2); 3.545(3.1); 3.502(2.6); 3.319(39.2); 2.691(0.4); 2.513(10.6); 2.509(20.1); 2.505(26.3); 2.500(18.8); 1.672(16.0)
Example 717: $^1$H-NMR(499.9 MHz, CDCl3):
9.216(2.1); 8.940(2.6); 8.935(2.7); 8.328(2.4); 8.325(2.5); 8.180(1.3); 8.176(1.5); 8.171(2.1); 8.162(2.0); 8.158(2.3); 8.155(2.4); 8.099(2.3); 8.082(1.5); 7.841(2.6); 7.838(2.6); 7.760(1.2); 7.744(2.0); 7.728(1.2); 7.641(3.0); 7.627(3.5); 7.624(2.7); 7.489(0.6); 7.474(1.7); 7.459(1.5); 7.429(2.5); 7.414(3.3); 7.400(1.3); 7.270(4.9); 7.121(2.0); 7.106(1.9); 5.344(7.7); 5.305(0.9); 5.284(0.4); 4.130(0.7); 4.115(0.7); 4.078(2.1); 4.044(2.3); 3.453(2.2); 3.419(2.0); 3.342(0.9); 3.148(16.0); 3.094(0.8); 3.010(0.8); 2.621(0.9); 2.052(3.0); 1.882(11.6); 1.771(1.1); 1.744(1.5); 1.698(0.9); 1.357(1.3); 1.343(1.3); 1.299(0.5); 1.285(0.6); 1.276(1.4); 1.262(3.2); 1.248(1.5); 1.226(0.6); 1.212(0.5); 0.894(1.0); 0.881(2.5); 0.866(1.2); 0.000(3.1)
Example 718: $^1$H-NMR(400.1 MHz, DMSO):
9.043(1.3); 9.028(2.6); 9.013(1.4); 8.996(0.8); 8.991(0.8); 8.974(5.4); 8.968(5.5); 8.711(0.5); 8.708(0.5); 8.669(0.5); 8.664(0.5); 8.636(0.7); 8.630(0.9); 8.624(0.8); 8.620(0.8); 8.601(16.0); 8.597(11.6); 8.579(1.0); 8.572(0.8); 8.552(4.0); 8.548(3.9); 8.330(4.4); 8.326(4.6); 8.317(0.8); 8.312(0.6); 8.204(2.4); 8.199(2.2); 8.182(3.6); 8.177(3.5); 8.108(4.5); 8.086(3.0); 7.822(1.0); 4.682(0.6); 4.667(0.6); 4.605(1.1); 4.592(9.8); 4.566(0.4); 4.581(5.8); 4.526(5.7); 4.021(3.1); 3.975(4.4); 3.804(4.3); 3.757(3.1); 3.378(0.3); 3.368(0.9); 3.328(30.2); 3.319(76.6); 3.277(0.6); 3.266(0.8); 2.892(0.7); 2.734(0.6); 2.691(0.4); 2.553(0.6); 2.549(0.7); 2.513(17.2); 2.509(33.0); 2.504(43.5); 2.500(32.0); 2.495(16.5); 2.452(0.7); 2.448(0.7); 0.000(0.4)
Example 719: $^1$H-NMR(400.0 MHz, DMSO):
9.150(0.8); 9.136(1.4); 9.122(0.7); 9.052(3.1); 9.047(3.1); 8.778(2.8); 8.773(2.8); 8.319(3.1); 8.171(0.8); 8.167(0.8); 8.149(2.4); 8.145(2.5); 8.126(3.5); 8.104(1.2); 7.499(4.6); 7.265(0.4); 4.599(2.0); 4.554(2.6); 4.271(2.5); 4.227(2.0); 4.207(0.6); 4.192(0.6); 4.170(1.6); 4.155(1.6); 4.136(1.6); 4.122(1.7); 4.099(0.7); 4.085(0.6); 3.999(1.3); 3.980(3.9); 3.962(3.9); 3.944(1.3); 3.904(6.1); 3.333(383.7); 3.174(0.6); 2.672(1.7); 2.506(229.6); 2.502(292.1); 2.499(224.1); 2.329(1.8); 2.215(1.2); 2.100(16.0); 1.296(4.4); 1.278(8.9); 1.260(4.7); 1.242(1.4); 1.226(0.6); 0.854 (0.3); 0.146(0.3); 0.008(2.8); 0.000(69.2); −0.150(0.4)
Example 720: $^1$H-NMR(400.1 MHz, DMSO):
9.032(3.8); 9.026(3.9); 8.792(3.2); 8.786(3.1); 8.245(3.1); 8.240(3.5); 8.203(1.8); 8.198(1.5); 8.181(2.7); 8.176(2.5); 8.166(1.0); 8.151(1.7); 8.136(0.9); 8.107(3.4); 8.085(2.2); 3.913(2.6); 3.870(3.1); 3.595(4.9); 3.507(3.2); 3.464(2.6); 3.396(0.7); 3.345(96.5); 3.229(1.4); 3.212(3.3); 3.196(3.3); 3.179(1.4); 2.933(1.8); 2.584(0.4); 2.538(39.0); 2.533(50.8); 2.529(36.9); 2.360(0.3); 1.858(0.6); 1.799(0.8); 1.640(16.0); 1.483(0.4); 1.464(0.3); 1.387(0.9); 1.380(0.9); 1.370(2.1); 1.363(2.1); 1.352(2.1); 1.345(2.1); 1.335(0.9); 1.328(0.9); 0.972(1.3); 0.779(2.1); 0.667(0.3); 0.661(0.4); 0.647(0.7); 0.642(0.7); 0.630(1.1); 0.622(0.7); 0.618(0.7); 0.610(0.8); 0.598(0.4); 0.593(0.3); 0.369(1.1); 0.362(1.8); 0.358(2.4); 0.352(1.8); 0.349(2.0); 0.338(2.0); 0.329(1.0); 0.012(1.1); 0.003(2.7); 0.000(3.3); −0.009(3.2); −0.021(1.0)
Example 721: $^1$H-NMR(300.2 MHz, CDCl3):
9.111(1.6); 8.961(2.5); 8.953(2.6); 8.357(1.8); 8.350(1.8); 8.237(1.5); 8.217(1.0); 8.211(2.4); 8.188(1.8); 8.181(1.9); 8.139(2.3); 8.110(1.0); 7.907(2.0); 7.901(1.9); 7.817(1.0); 7.790(1.6); 7.764(1.0); 7.660(1.5); 7.655(2.1); 7.650(1.1); 7.640(0.8); 7.633(2.7); 7.627(2.2); 7.488(1.2); 7.480(0.4); 7.470(1.0); 7.465(1.5); 7.460(0.8); 7.456(0.6); 7.448(2.5); 7.444(1.1); 7.430(1.2); 7.428(1.1); 7.424(2.4); 7.407(0.4); 7.401(0.8); 7.395(0.5); 7.265(6.1); 7.178(1.6); 7.154(1.5); 5.358(6.5); 5.300(2.8); 4.173(1.8); 4.113(2.1); 3.620(2.1); 3.560(1.8); 3.493(14.6); 3.132(16.0); 1.643(1.7); 0.074(1.5); 0.000(4.4)
Example 722: $^1$H-NMR(300.2 MHz, CDCl3):
8.952(2.3); 8.944(2.4); 8.349(2.2); 8.342(2.2); 8.177(0.7); 8.171(0.7); 8.147(2.1); 8.142(2.2); 8.118(2.8); 8.088(0.9); 7.839(2.3); 7.834(2.3); 7.267(5.4); 6.886(0.5); 6.867(0.8); 6.848(0.5); 6.809(1.0); 6.795(0.4); 6.781(3.6); 6.765(1.5); 6.759(2.7); 6.752(3.0); 6.746(2.3); 6.737(1.0); 3.879(16.0); 3.858(0.4); 3.830(15.8); 3.823(3.7); 3.653(0.6); 3.645(0.5); 3.630(1.4); 3.623(1.4); 3.609(1.4); 3.602(1.5); 3.586(0.8); 3.580(0.7); 3.517(2.6); 3.457(2.0); 3.348(15.7); 2.862(1.0); 2.857(1.0); 2.840(1.9); 2.833(1.9); 2.817(0.9); 2.810(0.9); 1.654(5.6); 0.000(4.1)
Example 723: $^1$H-NMR(400.1 MHz, DMSO):
9.006(4.1); 9.001(3.9); 8.765(4.4); 8.217(6.2); 8.175(2.3); 8.153(3.2); 8.082(3.7); 8.060(2.3); 3.882(2.6); 3.839(3.2); 3.766(1.7); 3.747(2.9); 3.730(1.9); 3.672(1.4); 3.652(2.7); 3.640(2.9); 3.632(2.6); 3.620(2.6); 3.569(9.1); 3.551(7.9); 3.531(4.5); 3.512(2.0); 3.487(3.6); 3.444(2.9); 3.321(66.8); 3.184(1.6); 3.177(1.9); 3.166(2.7); 3.159(2.7); 3.146(2.6); 3.139(2.9); 3.123(3.5); 3.115(3.4); 3.066(0.6); 3.050(0.6); 2.901(0.5); 2.695(0.5); 2.677(0.5); 2.605(0.4); 2.508(54.5); 2.334(0.5); 2.090(0.8); 2.073(1.5); 2.055(2.0); 2.037(1.7); 2.019(1.1); 1.964(1.7); 1.951(1.8); 1.946(1.9); 1.938(1.8); 1.927(1.6); 1.834(1.2); 1.771(1.4); 1.614(16.0); 1.519(2.2); 1.502(4.4); 1.485(4.2); 1.468(2.1); 1.419(1.4); 1.412(1.5); 1.401(1.6); 1.392(1.7); 1.383(1.5); 1.372(1.3); 1.245(0.4); 1.177(0.4); 1.170(0.4); 0.947(2.1); 0.754(3.5)
Example 724: $^1$H-NMR(300.2 MHz, CDCl3):
8.944(3.0); 8.936(3.1); 8.325(2.5); 8.318(2.5); 8.177(1.1); 8.171(1.1); 8.147(2.4); 8.141(2.5); 8.102(3.2); 8.072(1.4); 7.811(2.8); 7.806(2.8); 7.262(34.5); 6.911(0.4); 6.878(0.9); 3.981(2.6); 3.924(3.2); 3.353(3.2); 3.330(0.6); 3.309(1.1); 3.296(2.7); 3.285(1.5); 3.264(1.2); 3.241(0.6); 3.233(0.6); 3.209(1.1); 3.190(1.3); 3.166(0.9); 3.146(0.6); 1.775(16.0); 1.610(0.4); 1.584(1.9); 1.565(17.6); 1.536(3.6); 1.512(1.9); 1.488(0.5); 1.254(0.5); 0.940(4.6); 0.916(9.0); 0.891(4.1); 0.011(1.1); 0.000(27.5); −0.011(1.6)
Example 725: $^1$H-NMR(300.2 MHz, CDCl3):
8.943(3.1); 8.936(3.2); 8.324(2.5); 8.317(2.5); 8.178(1.1); 8.172(1.1); 8.148(2.5); 8.142(2.5); 8.103(3.2); 8.073(1.4); 7.815(2.7); 7.810(2.6); 7.266(7.2); 7.044(0.5); 7.026(0.8); 7.006(0.5); 4.839(1.8); 4.835(2.4); 4.830(1.9); 4.807(2.4); 4.004(2.7); 3.946(3.2); 3.917(0.4); 3.896(0.4); 3.864(1.1); 3.843(1.1); 3.809(1.1); 3.789(1.1); 3.756(0.4); 3.736(0.4); 3.373(3.0); 3.316(2.6); 1.805(16.0); 1.768(0.7); 1.716(9.3); 0.000(5.6)
Example 726: $^1$H-NMR(300.2 MHz, CDCl3):
8.955(3.0); 8.948(3.3); 8.337(2.8); 8.330(2.9); 8.174(1.0); 8.169(1.0); 8.145(2.8); 8.139(2.9); 8.116(3.7); 8.086(1.3); 7.817(3.3); 7.263(16.7); 6.938(2.0); 4.015(2.6); 3.957(3.1); 3.392(3.0); 3.334(2.6); 1.803(1.2); 1.781(16.0); 1.754 (15.1); 1.714(14.9); 1.603(1.5); 1.535(0.5); 1.481(0.5); 1.410(0.4); 1.253(0.4); 0.000(13.3)
Example 727: $^1$H-NMR(300.2 MHz, CDCl3):
8.946(2.9); 8.939(3.1); 8.331(2.5); 8.323(2.5); 8.182(1.0); 8.176(1.1); 8.153(2.3); 8.147(2.5); 8.107(3.1); 8.078(1.3); 7.826(2.8); 7.820(2.8); 7.262(36.1); 6.861(1.7); 3.981(2.5); 3.924(3.0); 3.325(2.8); 3.268(2.4); 2.370(6.5); 2.224(0.8);

| NMR Peak Lists Table 1 |
| --- |

2.200(1.0); 2.178(1.2); 2.154(1.4); 2.126(1.2); 2.105(1.2); 2.080(1.1); 1.857(0.4); 1.840(1.0); 1.832(1.2); 1.816(1.4); 1.807(1.4); 1.794(1.2); 1.786(1.4); 1.769(16.0); 1.563(13.8); 1.252(0.8); 1.002(3.7); 0.978(7.9); 0.953(3.5); 0.923(3.8); 0.899(7.9); 0.874(3.5); 0.000(28.5)

Example 728: $^1$H-NMR(300.2 MHz, CDCl3):
8.945(3.2); 8.940(3.9); 8.321(3.9); 8.164(1.5); 8.134(3.4); 8.102(3.9); 8.072(1.6); 7.805(4.2); 7.608(0.4); 7.321(0.4); 7.262(42.3); 7.198(0.4); 3.985(2.6); 3.927(3.0); 3.352(3.1); 3.294(2.6); 2.958(0.4); 2.885(0.4); 2.113(5.7); 1.805(0.6); 1.743(16.0); 1.562(29.3); 1.333(0.5); 1.290(4.9); 1.254(1.2); 1.217(0.4); 1.172(0.4); 1.110(1.9); 1.097(4.7); 1.075(1.4); 1.050(0.3); 0.000(31.9); −0.057(0.4)

Example 729: $^1$H-NMR(400.1 MHz, DMSO):
9.036(0.4); 8.951(1.0); 8.946(1.0); 8.928(8.5); 8.923(8.6); 8.622(0.7); 8.617(0.7); 8.579(0.8); 8.574(0.9); 8.554(6.6); 8.549(6.4); 8.299(1.8); 8.285(4.0); 8.269(8.4); 8.265(8.0); 8.150(3.6); 8.145(3.9); 8.128(5.6); 8.123(5.9); 8.059(7.3); 8.037(4.5); 7.693(2.1); 4.562(1.9); 4.547(16.0); 3.902(5.0); 3.856(7.2); 3.689(7.1); 3.643(5.0); 3.333(0.8); 3.317(0.6); 3.281(164.9); 3.240(47.5); 3.223(2.1); 3.206(3.7); 3.191(5.5); 3.176(3.7); 3.159(1.9); 3.144(0.7); 3.126(0.3); 2.486(0.7); 2.473(18.3); 2.469(37.3); 2.464(50.4); 2.460(36.0); 2.455(17.1); 1.949(0.4); 1.436(0.8); 1.418(0.8); 1.374(2.7); 1.356(7.8); 1.338(7.9); 1.321(2.7); 0.666(0.5); 0.660(0.6); 0.646(1.3); 0.641(1.2); 0.637(1.0); 0.629(2.1); 0.621(1.1); 0.616(1.3); 0.609(1.5); 0.597(0.8); 0.591(0.6); 0.396(0.8); 0.392(0.8); 0.386(0.4); 0.378(2.3); 0.368(6.3); 0.364(6.7); 0.358(2.8); 0.355(2.9); 0.348(6.2); 0.344(5.9); 0.335(2.1); 0.240(0.4); 0.041(0.9); 0.029(0.9); 0.013(2.2); 0.003(6.2); 0.000(7.1); −0.009(6.7); −0.012(6.2); −0.023(2.0)

Example 730: $^1$H-NMR(300.2 MHz, CDCl3):
8.947(3.0); 8.940(3.2); 8.326(2.7); 8.319(2.7); 8.168(0.9); 8.162(1.0); 8.138(2.5); 8.132(2.7); 8.106(3.5); 8.077(1.3); 7.817(2.9); 7.813(2.9); 7.294(0.6); 7.275(1.3); 7.262(32.5); 3.966(2.6); 3.909(3.2); 3.656(0.7); 3.634(0.9); 3.610(1.6); 3.589(1.5); 3.567(0.6); 3.556(0.5); 3.534(1.2); 3.512(1.4); 3.490(1.0); 3.467(0.6); 3.389(3.0); 3.331(2.6); 2.715(0.4); 2.681(1.4); 2.659(3.0); 2.639(3.1); 2.618(1.3); 2.583(0.5); 1.793(16.0); 1.767(0.6); 1.578(5.0); 1.252(0.6); 0.000(24.7); −0.011(1.2)

Example 731: $^1$H-NMR(300.2 MHz, CDCl3):
8.954(4.9); 8.947(5.1); 8.328(4.8); 8.321(3.2); 8.170(0.6); 8.160(0.9); 8.154(0.8); 8.141(2.1); 8.135(2.7); 8.130(3.3); 8.124(3.8); 8.118(3.8); 8.110(4.4); 8.088(1.0); 8.080(1.1); 7.811(3.4); 7.262(34.3); 7.180(1.9); 7.152(2.0); 4.812(0.5); 4.784(1.5); 4.760(2.4); 4.734(1.8); 4.707(0.7); 3.966(3.4); 3.908(4.4); 3.423(2.2); 3.397(3.0); 3.365(1.9); 3.339(2.5); 1.979(0.4); 1.954(0.9); 1.929(1.5); 1.911(1.6); 1.899(1.8); 1.887(1.3); 1.874(2.7); 1.848(2.8); 1.824(2.1); 1.810(16.0); 1.772(11.6); 1.725(0.3); 1.578(2.9); 1.252(0.8); 1.159(3.1); 1.135(6.2); 1.110(2.8); 1.075(4.2); 1.051(8.6); 1.026(3.8); 0.000(27.0)

Example 732: $^1$H-NMR(300.2 MHz, CDCl3):
8.954(3.2); 8.948(3.1); 8.334(3.2); 8.328(3.0); 8.184(1.2); 8.156(2.7); 8.150(2.7); 8.119(3.7); 8.089(1.4); 7.825(3.4); 7.608(0.4); 7.403(2.4); 7.262(61.3); 6.911(0.4); 4.934(2.6); 4.921(3.0); 4.912(3.7); 4.900(3.5); 4.801(3.4); 4.788(3.6); 4.779(3.0); 4.766(2.5); 3.989(2.5); 3.932(3.1); 3.394(3.1); 3.336(2.5); 2.568(6.0); 1.795(16.0); 1.738(0.3); 1.602(0.5); 1.557(56.3); 1.516(0.6); 1.485(0.4); 1.253(1.1); 0.000(47.6)

Example 733: $^1$H-NMR(300.2 MHz, CDCl3):
8.949(2.8); 8.941(3.5); 8.931(1.7); 8.332(2.7); 8.325(4.0); 8.212(1.0); 8.207(1.1); 8.183(2.4); 8.177(2.5); 8.155(1.3); 8.149(1.3); 8.121(2.9); 8.096(2.0); 8.068(0.9); 7.865(2.7); 7.860(2.7); 7.829(0.5); 7.812(1.4); 7.808(1.4); 7.267(7.3); 4.255(2.3); 4.200(2.7); 4.157(0.7); 4.134(2.7); 4.110(2.0); 4.085(0.9); 4.079(1.3); 3.602(2.6); 3.546(2.3); 3.383(1.2); 3.339(0.6); 3.327(1.1); 3.008(0.5); 2.958(1.2); 2.885(1.1); 2.420(16.0); 2.312(1.3); 2.235(0.8); 2.046(8.5); 2.014(13.8); 1.998(7.2); 1.849(6.3); 1.829(1.4); 1.803(0.5); 1.767(1.5); 1.685(0.7); 1.283(2.3); 1.259(4.6); 1.236(2.3); 0.072(2.9); 0.000(5.6)

Example 734: $^1$H-NMR(400.1 MHz, DMSO):
8.965(3.1); 8.959(3.1); 8.603(2.4); 8.598(2.3); 8.475(0.7); 8.460(1.4); 8.446(0.7); 8.277(2.4); 8.272(2.6); 8.172(1.3); 8.167(1.2); 8.150(2.0); 8.145(2.0); 8.084(2.7); 8.062(1.6); 7.405(4.3); 6.235(1.4); 6.208(1.6); 6.192(1.6); 6.165(1.7); 5.427(2.1); 5.424(2.1); 5.383(1.9); 5.381(1.9); 5.329(2.1); 5.327(2.0); 5.302(2.0); 5.300(1.9); 4.591(5.9); 4.098(3.4); 4.084(3.4); 4.037(2.0); 3.993(2.4); 3.964(1.3); 3.946(3.9); 3.928(3.9); 3.910(1.3); 3.660(2.3); 3.617(1.9); 3.375(0.4); 3.324(122.8); 3.273(0.4); 2.530(0.6); 2.517(15.4); 2.513(31.3); 2.508(42.2); 2.504(29.9); 2.499(14.1); 2.181(0.4); 2.129(0.4); 2.061(16.0); 1.263(4.6); 1.245(9.9); 1.227(4.5)

Example 735: $^1$H-NMR(400.1 MHz, DMSO):
8.976(0.5); 8.967(4.9); 8.962(5.0); 8.606(4.0); 8.601(3.9); 8.278(4.1); 8.262(0.8); 8.247(1.5); 8.227(1.5); 8.212(0.7); 8.177(1.8); 8.174(1.7); 8.155(2.7); 8.151(2.6); 8.088(4.4); 8.066(2.7); 6.231(1.2); 6.214(1.5); 6.205(1.4); 6.198(1.5); 6.188(1.5); 6.171(1.5); 6.162(1.4); 5.473(1.9); 5.471(2.1); 5.467(2.1); 5.465(2.1); 5.430(1.7); 5.428(1.8); 5.424(1.9); 5.422(1.9); 5.355(3.5); 5.353(3.5); 5.329(3.3); 5.327(3.3); 4.592(9.4); 4.143(1.0); 4.138(0.9); 4.129(1.6); 4.124(1.4); 4.114(1.2); 4.110(1.0); 4.100(0.5); 4.094(0.4); 4.039(1.7); 4.022(1.7); 3.996(2.1); 3.979(2.1); 3.919(1.1); 3.904(2.2); 3.898(1.6); 3.888(1.4); 3.883(2.5); 3.868(1.2); 3.686(2.1); 3.676(2.1); 3.670(1.7); 3.656(1.4); 3.649(1.4); 3.643(1.9); 3.633(2.2); 3.624(1.6); 3.610(1.4); 3.604(1.3); 3.589(1.2); 3.421(0.6); 3.371(0.7); 3.360(0.4); 3.322(415.2); 3.292(4.0); 3.272(4.2); 3.257(3.7); 3.243(2.0); 3.228(1.1); 3.213(1.4); 3.197(1.0); 3.180(0.7); 3.164(0.5); 2.682(0.6); 2.678(0.8); 2.673(0.7); 2.531(3.1); 2.517(50.0); 2.513(103.0); 2.509(142.2); 2.504(106.1); 2.500(55.0); 2.340(0.8); 2.335(1.0); 2.331(0.8); 1.340(0.5); 1.295(16.0); 1.254(1.0); 1.225(10.9); 1.220(11.5); 0.819(0.4); 0.803(0.4)

Example 736: $^1$H-NMR(400.1 MHz, DMSO):
8.965(4.3); 8.960(4.3); 8.606(4.2); 8.601(4.0); 8.280(4.3); 8.275(4.5); 8.248(1.2); 8.233(2.3); 8.219(1.2); 8.180(2.2); 8.175(1.9); 8.158(3.3); 8.153(3.1); 8.087(4.5); 8.065(2.8); 6.233(2.2); 6.207(2.5); 6.190(2.6); 6.164(2.7); 5.452(3.6); 5.409(3.2); 5.343(3.5); 5.317(3.3); 4.591(9.3); 4.032(3.4); 3.988(4.1); 3.649(4.0); 3.606(3.2); 3.420(0.8); 3.415(0.4); 3.397(0.5); 3.391(0.5); 3.374(3.5); 3.357(8.2); 3.349(4.7); 3.339(10.9); 3.333(14.1); 3.322(496.4); 3.273(1.8); 3.253(0.3); 3.246(0.4); 3.230(0.7); 3.214(1.4); 3.197(2.0); 3.182(2.0); 3.168(1.9); 3.154(0.8); 3.136(1.2); 3.121(0.7); 2.677(1.1); 2.673(0.8); 2.560(0.4); 2.517(68.6); 2.513(137.7); 2.508(185.5); 2.504(134.5); 2.465(1.1); 2.340(0.9); 2.335(1.2); 2.331(0.9); 1.695(1.0); 1.679(3.1); 1.662(4.6); 1.646(3.0); 1.629(0.8); 1.133(0.4); 1.115(0.7); 1.098(0.4); 1.085(7.9); 1.068(16.0); 1.050(7.7); 0.811(0.5); 0.795(0.5)

Example 737: $^1$H-NMR(400.1 MHz, DMSO):
8.979(0.4); 8.974(0.5); 8.965(5.9); 8.960(5.9); 8.606(4.7); 8.602(4.5); 8.282(4.9); 8.278(5.0); 8.184(2.6); 8.179(2.3); 8.162(4.0); 8.157(3.7); 8.087(5.3); 8.064(3.3); 7.983(2.3); 7.962(2.2); 6.233(2.7); 6.206(3.0); 6.189(3.2); 6.163(3.2); 5.446(4.1); 5.444(4.2); 5.403(3.7); 5.401(3.9); 5.336(4.2); 5.334(4.1); 5.310(3.8); 5.307(3.8); 4.591(11.1); 4.040(4.2); 3.996(5.0); 3.973(0.4); 3.957(1.1); 3.941(1.6); 3.921(1.6); 3.904(1.1); 3.888(0.5); 3.642(4.8); 3.599(4.0); 3.421(1.7); 3.373(1.5); 3.370(1.1); 3.357(0.6); 3.321(950.6); 3.289(1.5); 3.271(2.4); 3.251(0.4); 3.198(0.4); 2.682(1.4); 2.677(2.0); 2.673(1.5); 2.608(0.4); 2.561(0.6); 2.530(4.7); 2.517(121.4); 2.513(248.9); 2.508(337.4); 2.504(242.9); 2.499(116.6);

| NMR Peak Lists Table 1 |
|---|
| 2.464(1.8); 2.459(1.8); 2.380(0.4); 2.340(1.7); 2.335(2.2); 2.331(1.6); 1.160(0.5); 1.144(0.6); 1.123(0.6); 1.107(14.1); 1.090(15.1); 1.085(16.0); 1.069(14.2); 0.810(0.6); 0.795(0.6)<br>Example 738: $^1$H-NMR(400.1 MHz, DMSO):<br>9.105(0.4); 9.098(3.3); 9.092(3.4); 8.912(2.5); 8.907(2.4); 8.473(0.7); 8.458(1.4); 8.443(0.7); 8.205(2.3); 8.201(2.7); 8.157(1.5); 8.152(1.3); 8.135(2.1); 8.130(1.9); 8.046(2.6); 8.024(1.8); 7.404(4.2); 6.233(1.4); 6.206(1.6); 6.189(1.7); 6.163(1.7); 5.760(0.4); 5.421(2.1); 5.419(2.1); 5.378(1.9); 5.376(2.0); 5.327(2.1); 5.325(2.0); 5.300(2.0); 5.298(1.9); 4.097(3.4); 4.082(3.4); 4.018(2.0); 3.975(2.5); 3.965(1.4); 3.947(3.9); 3.929(3.9); 3.910(1.3); 3.611(2.2); 3.598(1.9); 3.373(0.5); 3.323(196.7); 3.273(0.5); 2.677(0.4); 2.530(1.3); 2.517(24.2); 2.513(49.0); 2.508(66.2); 2.504(46.9); 2.499(22.0); 2.340(0.3); 2.335(0.4); 2.179(1.1); 2.128(0.8); 2.059(16.0); 1.302(0.5); 1.265(4.7); 1.247(10.2); 1.240 (0.8); 1.229(4.6); 1.222(0.9); 1.204(0.3); 0.800(0.3); 0.784(0.3)<br>Example 739: $^1$H-NMR(400.1 MHz, DMSO):<br>9.110(0.4); 9.100(5.0); 9.094(5.4); 8.914(3.8); 8.909(3.8); 8.259(0.6); 8.244(1.3); 8.224(1.4); 8.206(4.2); 8.172(0.3); 8.162(1.8); 8.159(1.7); 8.140(2.6); 8.137(2.5); 8.135(2.3); 8.050(4.0); 8.028(2.7); 6.239(1.2); 6.230(1.3); 6.213(1.4); 6.203(1.4); 6.196(1.5); 6.186(1.5); 6.170(1.5); 6.160(1.5); 5.469(1.8); 5.467(2.0); 5.463(2.0); 5.461(2.0); 5.426(1.6); 5.423(1.9); 5.420(1.8); 5.417(1.8); 5.354(3.4); 5.352(3.5); 5.327(3.2); 5.325(3.3); 4.142(0.9); 4.136(0.9); 4.127(1.5); 4.123(1.3); 4.113(1.1); 4.108(1.0); 4.099(0.4); 4.093(0.4); 4.021(1.6); 4.004(1.6); 3.978(2.0); 3.961(2.1); 3.917(1.1); 3.902(1.9); 3.897(1.6); 3.887(1.3); 3.882(2.2); 3.867(1.2); 3.668(2.6); 3.657(2.3); 3.648(1.4); 3.634(1.3); 3.623(2.9); 3.614(1.9); 3.609(1.6); 3.602(1.3); 3.588(1.1); 3.422(0.5); 3.372(1.1); 3.343(0.6); 3.322(450.1); 3.290(4.2); 3.272(3.6); 3.271(3.7); 3.255(3.9); 3.241(2.3); 3.227(1.3); 3.211(1.5); 3.195(1.1); 3.177(0.9); 3.162(0.5); 2.682(0.6); 2.678(0.9); 2.673(0.6); 2.559(0.3); 2.531(1.8); 2.526(3.1); 2.518(45.8); 2.513(98.1); 2.509(137.6); 2.504(103.5); 2.500(53.7); 2.340(0.8); 2.335(1.0); 2.331(0.8); 1.339(0.6); 1.293(16.0); 1.254(1.1); 1.225(10.3); 1.220(10.6); 0.812(0.4); 0.797(0.4)<br>Example 740: $^1$H-NMR(400.1 MHz, DMSO):<br>9.113(0.3); 9.107(0.5); 9.097(5.0); 9.092(5.1); 8.913(4.2); 8.909(4.0); 8.330(0.4); 8.245(1.2); 8.231(2.3); 8.216(1.4); 8.207(4.2); 8.202(4.6); 8.165(2.5); 8.160(2.1); 8.142(3.3); 8.138(3.0); 8.087(4.3); 8.026(2.9); 6.231(2.2); 6.205(2.5); 6.188(2.6); 6.162(2.6); 5.449(3.6); 5.447(3.4); 5.406(3.2); 5.404(3.1); 5.342(3.5); 5.340(3.4); 5.315(3.3); 5.313(3.1); 4.013(3.3); 3.970(4.0); 3.630(3.9); 3.587(3.2); 3.414(0.4); 3.396(0.5); 3.390(0.4); 3.374(1.9); 3.369(1.1); 3.356(8.4); 3.348(4.7); 3.338(10.5); 3.332(13.3); 3.321(322.9); 3.272(2.4); 3.246(0.5); 3.229(0.8); 3.222(0.8); 3.213(1.3); 3.197(2.0); 3.181(2.0); 3.166(2.0); 3.152(1.9); 3.135(1.2); 3.119(0.6); 2.898(0.6); 2.738(0.4); 2.682(0.5); 2.677(0.7); 2.673(0.5); 2.547(0.3); 2.530(1.9); 2.513(90.8); 2.508(120.9); 2.504(87.6); 2.459(1.2); 2.339(0.6); 2.335(0.8); 2.331(0.6); 1.694(1.0); 1.677(3.1); 1.661(4.5); 1.645(2.9); 1.628(0.8); 1.132(0.4); 1.114(0.8); 1.097(0.5); 1.085(7.8); 1.067(16.0); 1.050(7.7); 0.805(0.6); 0.789(0.6)<br>Example 741: $^1$H-NMR(400.1 MHz, DMSO):<br>9.114(0.4); 9.108(0.5); 9.097(6.1); 9.092(6.3); 8.914(4.9); 8.909(4.5); 8.210(4.7); 8.205(5.3); 8.169(3.0); 8.164(2.3); 8.147(4.1); 8.142(3.6); 8.048(5.2); 8.026(3.6); 7.980(2.3); 7.960(2.3); 6.230(2.8); 6.204(3.1); 6.187(3.3); 6.161(3.3); 5.442(4.2); 5.439(4.4); 5.399(3.7); 5.396(3.9); 5.334(4.2); 5.332(4.2); 5.308(3.9); 5.306(4.0); 4.096(0.6); 4.082(0.6); 4.021(4.2); 3.978(5.1); 3.956(1.1); 3.940(1.6); 3.923(1.4); 3.919(1.6); 3.886(0.4); 3.623(4.8); 3.580(4.0); 3.370(0.6); 3.361(0.4); 3.322(548.7); 3.272(4.0); 3.266(0.6); 3.222(0.5); 3.183(2.2); 3.170(2.1); 2.682(0.5); 2.677(1.1); 2.673(0.8); 2.531(2.6); 2.517(64.2); 2.513(131.5); 2.508(178.3); 2.504(127.8); 2.499(60.9); 2.463(1.5); 2.458(1.7); 2.414(0.3); 2.340(0.8); 2.335(1.1); 2.331(0.9); 1.159(0.7); 1.142(0.7); 1.123(0.8); 1.105(14.4); 1.089(15.2); 1.084(16.0); 1.067(14.2); 0.803(0.8); 0.788(0.8)<br>Example 742: $^1$H-NMR(400.1 MHz, DMSO):<br>9.026(0.4); 9.016(5.4); 9.010(5.6); 8.763(4.0); 8.757(3.9); 8.256(4.3); 8.229(1.5); 8.213(0.7); 8.179(1.6); 8.178(1.8); 8.175(1.7); 8.157(2.5); 8.156(2.8); 8.153(2.7); 8.151(2.4); 8.089(4.4); 8.067(2.7); 6.241(1.3); 6.232(1.3); 6.215(1.5); 6.205(1.5); 6.198(1.6); 6.189(1.6); 6.172(1.6); 6.162(1.6); 5.472(2.0); 5.470(2.2); 5.466(2.1); 5.464(2.1); 5.429(1.8); 5.427(2.0); 5.423(1.9); 5.421(1.9); 5.356(3.7); 5.354(3.7); 5.330(3.5); 5.327(3.5); 4.143(1.0); 4.137(0.9); 4.129(1.6); 4.123(1.3); 4.114(1.2); 4.109(1.0); 4.100(0.4); 4.094(0.4); 4.031(1.8); 4.014(1.7); 3.987(2.2); 3.971(2.2); 3.918(1.2); 3.903(2.1); 3.897(1.7); 3.888(1.4); 3.883(2.4); 3.867(1.3); 3.677(2.2); 3.668(2.6); 3.656(1.5); 3.649(1.4); 3.634(2.8); 3.624(3.2); 3.610(1.5); 3.603(1.4); 3.589(1.2); 3.373(1.9); 3.323(294.1); 3.291(2.9); 3.276(2.2); 3.271(2.1); 3.257(3.2); 3.242(1.6); 3.228(0.9); 3.224(0.6); 3.213(1.3); 3.197(0.9); 3.179(0.7); 3.164(0.4); 2.682(0.4); 2.679(0.3); 2.564(0.4); 2.559(0.5); 2.531(1.7); 2.526(2.7); 2.517(29.0); 2.513(60.0); 2.508(82.5); 2.504(60.1); 2.499(30.5); 2.340(0.4); 2.335(0.6); 2.331(0.4); 1.342(0.6); 1.294(16.0); 1.254(1.0); 1.225(10.8); 1.220(11.0); 0.816(0.4); 0.801(0.4)<br>Example 743: $^1$H-NMR(400.1 MHz, DMSO):<br>9.015(4.9); 9.009(5.0); 8.764(3.9); 8.758(3.6); 8.259(4.1); 8.254(4.6); 8.235(2.1); 8.221(1.0); 8.182(2.1); 8.177(1.9); 8.160(3.3); 8.155(3.1); 8.089(4.2); 8.066(2.6); 6.234(2.2); 6.207(2.5); 6.190(2.6); 6.164(2.7); 5.453(3.3); 5.451(3.5); 5.410(3.0); 5.407(3.1); 5.345(3.3); 5.342(3.3); 5.318(3.1); 5.316(3.2); 4.023(3.2); 3.980(3.9); 3.641(3.8); 3.598(3.2); 3.422(0.4); 3.374(2.6); 3.357(8.1); 3.349(4.1); 3.339(9.7); 3.333(11.4); 3.322(346.0); 3.273(1.3); 3.248(0.3); 3.230(0.7); 3.215(1.2); 3.197(1.8); 3.182(1.8); 3.168(1.8); 3.153(1.8); 3.136(1.1); 3.121(0.6); 2.682(0.4); 2.677(0.6); 2.673(0.5); 2.531(1.4); 2.517(36.5); 2.513(75.4); 2.508(102.7); 2.504(74.0); 2.499(35.5); 2.459(0.7); 2.339(0.5); 2.335(0.7); 2.331(0.5); 1.695(0.9); 1.678(2.8); 1.662(4.2); 1.646(2.7); 1.629(0.7); 1.115(0.3); 1.085(7.8); 1.068(16.0); 1.050(7.6)<br>Example 744: $^1$H-NMR(400.1 MHz, DMSO):<br>9.029(0.4); 9.024(0.5); 9.013(6.0); 9.007(6.3); 8.761(4.5); 8.756(4.4); 8.260(4.6); 8.255(5.0); 8.185(2.7); 8.180(2.4); 8.173(0.5); 8.163(4.1); 8.158(3.9); 8.108(0.4); 8.087(5.2); 8.065(3.3); 7.986(2.1); 7.965(2.2); 6.233(2.8); 6.206(3.2); 6.190(3.4); 6.163(3.4); 5.445(4.2); 5.443(4.3); 5.402(3.8); 5.400(3.9); 5.337(4.1); 5.335(4.0); 5.311(3.9); 5.308(3.8); 4.032(4.1); 3.989(5.0); 3.974(0.6); 3.958(1.1); 3.941(1.6); 3.938(1.3); 3.925(1.4); 3.921(1.6); 3.904(1.2); 3.888(0.5); 3.726(0.3); 3.633(4.7); 3.590(4.0); 3.322(245.0); 3.273(1.6); 2.682(0.3); 2.677(0.5); 2.673(0.3); 2.531(1.8); 2.517 (27.1); 2.513(55.5); 2.508(75.9); 2.504(55.4); 2.499(28.1); 2.340(0.4); 2.335(0.5); 2.331(0.4); 1.160(0.7); 1.143(0.7); 1.124(0.9); 1.106(14.0); 1.090(15.1); 1.085(16.0); 1.069(14.3); 0.807(0.8); 0.792(0.8)<br>Example 745: $^1$H-NMR(400.0 MHz, DMSO):<br>9.128(5.8); 8.393(0.9); 8.378(1.7); 8.365(0.9); 8.326(3.5); 8.243(1.3); 8.240(1.3); 8.222(2.3); 8.218(2.4); 8.170(3.4); 8.147(1.9); 7.414(4.8); 7.308(0.5); 7.204(0.3); 4.108(0.4); 4.081(4.3); 4.067(4.2); 3.974(0.4); 3.963(1.4); 3.945(4.1); 3.927(4.7); 3.904(7.4); 3.879(2.6); 3.609(2.6); 3.565(2.0); 3.331(337.6); 3.173(0.9); 3.161(0.9); 2.671(2.0); 2.502 (329.9); 2.329(2.0); 2.174(1.1); 2.166(0.4); 2.056(16.0); 1.606(12.8); 1.298(0.3); 1.264(4.5); 1.245(9.2); 1.227(4.7); 1.199(0.4); 0.000(57.1)<br>Example 746: $^1$H-NMR(400.0 MHz, DMSO):<br>9.124(2.4); 8.583(4.5); 8.568(1.7); 8.556(2.0); 8.551(2.1); 8.329(2.3); 8.316(0.9); 8.300(0.3); 8.291(0.4); 8.284(0.4); 8.258(1.0); 8.254(1.0); 8.236(1.5); 8.232(1.6); 8.169(2.4); 8.165(2.3); 8.158(2.6); 8.148(3.9); 7.941(1.3); 7.930(2.4); 7.923(2.5); 7.919(2.5); 7.912(2.7); 7.909(2.7); 7.901(2.6); 7.874(0.9); 7.679(1.5); 7.660(2.9); 7.653(2.5); 7.593(1.2); |

-continued

NMR Peak Lists Table 1

7.570(2.5); 7.548(2.1); 7.526(1.7); 7.504(2.3); 7.490(2.5); 7.472(1.9); 7.457(0.7); 7.347(1.4); 7.324(4.0); 7.308(4.9); 7.290(4.4); 7.273(1.6); 4.056(0.8); 4.038(2.4); 4.020(2.4); 4.002(0.9); 3.930(2.0); 3.921(1.0); 3.902(4.2); 3.886(3.0); 3.604(0.5); 3.579(1.5); 3.536(1.4); 3.486(11.1); 3.475(16.0); 3.464(10.4); 3.380(21.1); 3.331(239.7); 3.177(1.3); 3.164(1.2); 2.677(1.4); 2.673(1.8); 2.668(1.4); 2.612(0.4); 2.508(213.5); 2.504(271.9); 2.499(196.0); 2.335(2.0); 2.330(2.7); 2.326(2.8); 2.299(11.2); 1.989(6.0); 1.984(5.2); 1.649(0.6); 1.595(10.8); 1.298(0.4); 1.260(0.8); 1.233(1.5); 1.195(3.1); 1.177(6.1); 1.159(3.2); 1.113(6.7); 1.096(6.6); 1.070(7.0); 1.054(6.9); 0.854(0.4); 0.000(39.8); −0.059(8.1); −0.150(0.4)
Example 747: $^1$H-NMR(400.0 MHz, DMSO):
9.054(6.7); 9.049(7.0); 8.783(5.6); 8.778(5.2); 8.666(2.2); 8.645(2.2); 8.331(5.6); 8.327(5.7); 8.185(2.1); 8.181(1.9); 8.163(5.1); 8.159(5.0); 8.134(6.8); 8.112(2.7); 7.744(0.4); 4.582(4.4); 4.537(5.6); 4.274(5.7); 4.230(4.5); 4.005(0.5); 3.989(1.3); 3.972(1.9); 3.953(1.9); 3.936(1.3); 3.919(0.5); 3.904(0.7); 3.331(402.6); 3.174(0.8); 3.161(0.8); 2.676(1.8); 2.671(2.5); 2.667(1.8); 2.541(1.4); 2.511(168.0); 2.507(326.3); 2.502(419.5); 2.498(301.6); 2.333(1.9); 2.329(2.6); 2.325(1.9); 1.299(0.4); 1.272(0.5); 1.235(2.0); 1.211(1.3); 1.194(1.2); 1.160(15.8); 1.143(15.7); 1.116(16.0); 1.100 (15.9); 1.008(0.4); 0.854(0.6); 0.837(0.4); 0.146(0.5); 0.008(4.2); 0.000(108.0); −0.008(4.3); −0.150(0.5)
Example 748: $^1$H-NMR(300.2 MHz, CDCl3):
8.948(2.2); 8.941(2.7); 8.937(3.6); 8.929(3.5); 8.338(1.6); 8.327(2.7); 8.318(2.5); 8.220(0.9); 8.214(0.9); 8.190(2.0); 8.184(2.3); 8.159(2.3); 8.152(2.5); 8.122(2.0); 8.096(3.4); 8.067(1.6); 8.017(1.5); 8.000(0.6); 7.993(0.4); 7.874(1.8); 7.868(1.8); 7.815(2.6); 7.809(2.7); 7.270(11.4); 4.867(0.5); 4.293(1.9); 4.237(2.2); 4.142(2.6); 4.085(3.0); 3.599(4.7); 3.543(1.9); 3.381(3.0); 3.339(0.3); 3.324(2.6); 3.294(0.4); 3.271(0.9); 3.254(0.8); 3.248(0.5); 3.230(0.8); 3.206(0.3); 3.153(0.4); 3.130(0.9); 3.107(1.2); 3.083(0.9); 3.060(0.4); 2.959(13.1); 2.884(11.1); 2.693(0.4); 2.670(0.9); 2.646(1.3); 2.623(1.0); 2.599(0.4); 2.371(0.3); 2.348(0.4); 2.322(0.4); 2.229(6.0); 2.188(0.5); 2.007(10.7); 1.894(0.7); 1.849(16.0); 1.784(0.7); 1.767(1.0); 1.761(0.7); 1.735(0.7); 1.730(0.7); 1.712(0.5); 1.356(7.6); 1.352(7.8); 1.333(7.5); 1.329(7.7); 1.303(0.4); 1.299(0.4); 1.276(0.4); 1.263(1.1); 1.253(1.1); 1.240(10.6); 1.222(10.6); 1.217(10.9); 1.198(9.3); 1.183(0.7); 1.160(0.4); 1.026(0.7); 0.848(0.8); 0.073(0.9); 0.000(8.6); −0.011(0.4)
Example 749: $^1$H-NMR(300.2 MHz, CDCl3):
8.949(0.8); 8.941(0.9); 8.937(0.9); 8.929(0.8); 8.341(0.6); 8.334(0.7); 8.326(0.6); 8.319(0.6); 8.224(0.3); 8.218(0.3); 8.194(0.6); 8.188(0.8); 8.180(0.3); 8.157(0.5); 8.151(0.6); 8.124(0.8); 8.095(1.0); 8.066(0.4); 8.017(0.5); 7.879(0.7); 7.873(0.7); 7.814(0.6); 7.809(0.6); 7.269(3.3); 4.309(0.7); 4.253(0.8); 4.143(0.6); 4.087(0.7); 3.602(1.0); 3.592(1.1); 3.536(0.7); 3.373(0.7); 3.316(0.6); 2.959(4.1); 2.885(3.5); 2.228(1.8); 2.000(4.1); 1.848(3.8); 1.818(0.5); 1.371(16.0); 1.314(0.8); 1.264(13.9); 1.239(1.2); 1.229(0.6); 1.216(0.4); 1.194(0.4); 0.000(2.5)
Example 750: $^1$H-NMR(300.2 MHz, CDCl3):
8.948(2.7); 8.939(4.6); 8.930(3.7); 8.336(2.8); 8.326(4.5); 8.318(3.7); 8.208(1.0); 8.203(1.0); 8.179(3.0); 8.174(3.2); 8.150(2.4); 8.145(2.6); 8.119(2.7); 8.092(4.3); 8.064(1.8); 8.019(1.4); 7.810(2.4); 7.804(3.5); 7.281(0.8); 7.269(9.3); 7.247(0.4); 4.793(2.2); 4.239(2.0); 4.183(2.4); 4.128(2.7); 4.111(0.9); 4.084(0.5); 4.071(2.9); 3.734(0.4); 3.719(0.5); 3.703(0.5); 3.603(7.0); 3.569(2.8); 3.525(0.3); 3.513(2.1); 3.374(2.9); 3.339(0.5); 3.330(0.5); 3.318(2.6); 3.294(0.4); 3.272(0.8); 3.254(0.7); 3.231(0.6); 3.008(0.4); 2.959(7.9); 2.936(0.3); 2.895(0.8); 2.885(7.4); 2.862(0.4); 2.410(0.4); 2.346(0.5); 2.290(1.5); 2.230(3.9); 2.189(0.4); 2.120(0.7); 2.110(0.5); 2.099(1.2); 2.076(0.9); 2.047(3.3); 1.976(12.5); 1.954(0.9); 1.936(0.8); 1.906(0.7); 1.886(0.6); 1.840(16.0); 1.818(2.1); 1.803(1.4); 1.768(1.1); 1.710(5.3); 1.631(0.4); 1.605(0.8); 1.596(0.7); 1.586(1.5); 1.560(0.9); 1.540(0.5); 1.284(0.9); 1.261(2.0); 1.238(1.7); 1.216(0.8); 1.070(3.6); 1.055(4.0); 1.042(6.5); 0.886(6.7); 0.858(5.1); 0.073(0.7); 0.012(0.8); 0.000(7.1); −0.022(0.3)
Example 751: $^1$H-NMR(300.2 MHz, CDCl3):
9.311(1.1); 9.306(1.1); 8.960(1.6); 8.952(1.9); 8.946(3.6); 8.939(3.6); 8.927(2.7); 8.922(2.5); 8.762(0.8); 8.757(0.9); 8.746(1.0); 8.739(2.2); 8.733(1.8); 8.723(1.9); 8.717(1.8); 8.381(0.5); 8.374(2.9); 8.368(0.6); 8.349(1.3); 8.338(2.9); 8.331(2.8); 8.237(0.6); 8.231(0.6); 8.208(2.3); 8.202(2.4); 8.179(2.4); 8.172(2.5); 8.140(1.5); 8.113(3.5); 8.084(1.7); 8.059(1.1); 8.052(1.6); 8.046(1.1); 8.032(1.2); 8.025(1.9); 8.019(1.8); 7.909(1.4); 7.903(1.3); 7.843(3.1); 7.837(3.0); 7.447(0.6); 7.431(0.6); 7.421(0.6); 7.404(0.6); 7.390(1.3); 7.373(1.4); 7.363(1.3); 7.347(1.3); 7.267(15.8); 5.352(1.8); 5.302(0.9); 4.390(1.3); 4.334(1.5); 4.187(2.7); 4.157(0.9); 4.131(4.2); 4.109(2.7); 4.085(0.9); 3.733(0.8); 3.717(1.0); 3.702(0.8); 3.686(1.6); 3.630(1.5); 3.601(4.7); 3.440(3.1); 3.383(2.7); 3.293(0.4); 3.270(0.8); 3.253(0.7); 3.248(0.4); 3.230(0.6); 2.957(9.5); 2.882(8.3); 2.424(0.5); 2.407(0.7); 2.345(0.4); 2.289(3.6); 2.228(4.2); 2.098(7.2); 2.046(11.5); 1.910(16.0); 1.817(0.8); 1.760(0.4); 1.735(0.5); 1.701(7.0); 1.283(3.0); 1.260(6.4); 1.236(3.4); 1.215(0.9); 1.023(0.9); 0.848(1.2); 0.071(1.0); 0.000(12.2); −0.011(0.7)
Example 752: $^1$H-NMR(300.2 MHz, CDCl3):
8.931(3.2); 8.924(3.2); 8.323(2.6); 8.199(1.3); 8.193(1.3); 8.170(2.3); 8.164(2.4); 8.091(2.6); 8.061(1.5); 7.858(2.9); 7.263(18.3); 5.301(2.1); 4.540(1.8); 4.482(2.0); 3.837(0.3); 3.831(0.3); 3.382(0.9); 3.358(1.6); 3.333(1.1); 3.302(9.0); 3.279(0.5); 3.265(1.5); 3.253(1.7); 3.207(1.2); 3.195(1.5); 2.962(7.4); 1.761(16.0); 1.731(0.6); 1.707(0.5); 1.698(0.5); 1.690(0.5); 1.673(0.6); 1.615(3.7); 1.591(2.1); 1.581(1.6); 1.565(0.9); 1.557(0.8); 1.014(1.7); 0.990(3.3); 0.965(1.5); 0.926(2.2); 0.902(4.2); 0.877(1.9); 0.071(0.7); 0.011(0.5); 0.000(13.1); −0.011(0.7)
Example 753: $^1$H-NMR(300.2 MHz, CDCl3):
8.942(3.1); 8.935(3.2); 8.325(3.0); 8.318(2.9); 8.177(1.2); 8.171(1.2); 8.147(2.6); 8.141(2.7); 8.102(3.5); 8.072(1.5); 7.812(3.2); 7.808(3.2); 7.264(12.8); 6.927(1.1); 3.984(2.6); 3.926(3.0); 3.354(3.0); 3.297(2.5); 3.213(0.5); 3.191(1.0); 3.169(1.5); 3.147(1.8); 3.125(1.0); 3.079(1.0); 3.058(1.6); 3.036(1.4); 3.013(0.9); 2.993(0.6); 1.838(0.6); 1.815(1.3); 1.782(16.0); 1.748(0.9); 1.726(0.4); 1.612(3.2); 1.253(0.7); 0.918(9.9); 0.910(10.4); 0.896(10.0); 0.888(9.8); 0.000(9.6)
Example 754: $^1$H-NMR(400.0 MHz, DMSO):
9.010(4.0); 9.004(4.0); 8.771(3.9); 8.766(4.0); 8.746(2.0); 8.732(1.0); 8.330(3.4); 8.239(3.9); 8.236(3.8); 8.196(2.1); 8.191(1.5); 8.174(2.9); 8.169(2.4); 8.091(3.5); 8.068(2.4); 7.954(1.2); 7.563(1.8); 7.558(1.7); 7.543(2.0); 7.538(1.8); 7.135(2.9); 7.115(2.7); 4.377(4.3); 4.362(4.2); 3.934(2.6); 3.891(3.2); 3.542(3.0); 3.498(2.5); 3.340(92.6); 2.892(7.1); 2.733(6.3); 2.674(0.3); 2.592(1.4); 2.573(4.0); 2.554(4.2); 2.535(1.8); 2.509(46.3); 2.505(54.5); 2.500(39.3); 2.331(0.3); 1.674(16.0); 1.608(0.5); 1.161(5.7); 1.142(11.6); 1.123(5.4); 0.000(5.7)
Example 755: $^1$H-NMR(400.0 MHz, DMSO):
8.964(4.2); 8.959(4.2); 8.950(0.5); 8.809(1.0); 8.794(1.9); 8.779(0.9); 8.614(3.5); 8.609(3.5); 8.335(3.1); 8.322(3.2); 8.282(3.5); 8.277(3.6); 8.210(1.9); 8.206(1.6); 8.188(2.6); 8.184(2.4); 8.094(3.5); 8.072(2.5); 7.954(1.4); 7.054(2.1); 7.042(2.0); 6.947(3.8); 4.598(7.4); 4.449(0.8); 4.433(0.8); 4.408(1.7); 4.393(1.7); 4.344(1.7); 4.329(1.7); 4.303(0.8); 4.288(0.8); 3.958(2.6); 3.915(3.2); 3.561(3.0); 3.517(2.7); 3.339(90.1); 2.892(9.2); 2.733(7.9); 2.673(0.3); 2.509(42.5); 2.505(53.8); 2.500(38.8); 2.418(1.4); 2.399(4.2); 2.380(4.3); 2.361(1.5); 2.331(0.4); 1.699(16.0); 1.622(1.1); 0.955(5.9); 0.936(12.2); 0.917(5.7); 0.000(5.0)

-continued

NMR Peak Lists Table 1

Example 756: ¹H-NMR(400.0 MHz, DMSO):
9.009(4.1); 9.004(4.3); 8.771(4.1); 8.766(4.9); 8.749(1.0); 8.240(3.4); 8.236(3.8); 8.199(1.9); 8.195(1.6); 8.177(2.7); 8.173(2.5); 8.090(3.5); 8.068(2.4); 7.954(0.8); 7.615(1.8); 7.596(1.7); 7.577(2.0); 7.089(2.7); 7.070(2.5); 7.003(2.6); 6.984(2.5); 4.377(4.1); 4.362(4.1); 3.940(2.6); 3.897(3.2); 3.549(3.1); 3.506(2.6); 3.341(118.3); 2.892(5.4); 2.733(4.7); 2.689(1.6); 2.670(4.9); 2.651(4.8); 2.632(1.6); 2.509(37.6); 2.505(48.1); 2.500(35.6); 1.689(16.0); 1.656(0.3); 1.169(6.1); 1.150(12.5); 1.131(5.9); 0.000(5.0)
Example 757: ¹H-NMR(400.0 MHz, DMSO):
8.961(4.1); 8.956(4.2); 8.759(1.0); 8.744(2.0); 8.730(1.0); 8.613(3.5); 8.608(3.4); 8.330(3.1); 8.326(3.1); 8.261(3.5); 8.257(3.8); 8.195(1.8); 8.190(1.6); 8.172(2.7); 8.168(2.5); 8.089(3.6); 8.067(2.4); 7.955(0.5); 7.563(1.7); 7.557(1.7); 7.543(1.9); 7.537(1.9); 7.135(2.9); 7.115(2.7); 4.597(7.5); 4.378(4.3); 4.363(4.2); 3.944(2.6); 3.900(3.2); 3.550(3.1); 3.506(2.6); 3.341(82.0); 2.892(3.4); 2.733(3.0); 2.592(1.3); 2.573(4.1); 2.554(4.2); 2.535(1.7); 2.509(32.4); 2.505 (41.4); 2.501(30.6); 1.674(16.0); 1.655(0.5); 1.160(5.8); 1.142(12.0); 1.123(5.6); 0.000(4.2)
Example 758: ¹H-NMR(400.0 MHz, DMSO):
9.008(4.1); 9.002(4.1); 8.890(0.9); 8.876(1.8); 8.861(0.9); 8.766(3.5); 8.760(3.2); 8.735(2.9); 8.723(2.9); 8.244(3.4); 8.240(3.7); 8.201(1.9); 8.196(1.5); 8.179(2.7); 8.174(2.3); 8.088(3.5); 8.065(2.4); 7.955(2.0); 7.721(2.2); 7.718(2.2); 7.708(2.1); 7.582(4.1); 4.479(4.5); 4.464(4.5); 3.942(2.6); 3.899(3.2); 3.550(3.1); 3.507(2.6); 3.340(82.3); 2.893(13.2); 2.734(11.5); 2.509(36.1); 2.505(44.8); 2.501(31.9); 1.684(16.0); 1.656(0.3); 0.000(5.7)
Example 759: ¹H-NMR(400.0 MHz, DMSO):
8.961(4.3); 8.956(4.3); 8.778(1.0); 8.763(2.0); 8.748(1.0); 8.614(3.4); 8.609(3.3); 8.262(3.4); 8.258(3.6); 8.198(1.9); 8.194(1.6); 8.176(2.8); 8.171(2.5); 8.089(3.6); 8.067(2.4); 7.955(1.1); 7.615(1.8); 7.596(3.8); 7.577(2.1); 7.089(2.7); 7.070(2.5); 7.004(2.6); 6.985(2.5); 4.598(7.6); 4.378(3.9); 4.363(3.8); 3.950(2.7); 3.907(3.2); 3.557(3.1); 3.514(2.6); 3.342(104.7); 2.892(7.5); 2.733(6.5); 2.689(1.6); 2.670(5.0); 2.651(4.9); 2.632(1.7); 2.514(17.7); 2.510(33.5); 2.505(42.5); 2.501(30.4); 2.497(14.7); 1.689(16.0); 1.168(6.6); 1.149(13.6); 1.130(6.3); 0.000(4.8)
Example 760: ¹H-NMR(400.0 MHz, DMSO):
9.015(4.0); 9.009(4.1); 8.842(1.0); 8.828(1.8); 8.813(0.9); 8.773(3.5); 8.768(3.4); 8.339(3.2); 8.326(3.2); 8.262(3.4); 8.258(3.7); 8.213(1.9); 8.208(1.7); 8.191(2.6); 8.186(2.3); 8.095(3.5); 8.073(2.4); 7.954(1.3); 7.074(2.1); 7.063(1.9); 7.061(2.0); 6.956(3.8); 4.467(0.9); 4.451(0.9); 4.426(1.6); 4.410(1.6); 4.328(1.6); 4.314(1.6); 4.287(1.0); 4.273(0.9); 3.954(2.6); 3.910(3.1); 3.555(3.0); 3.512(2.6); 3.339(119.8); 2.892(8.2); 2.733(7.3); 2.674(0.4); 2.648(0.5); 2.631(1.2); 2.613(1.7); 2.596(1.3); 2.579(0.5); 2.509(46.5); 2.504(59.2); 2.500(43.2); 2.331(0.4); 1.706(16.0); 1.619(0.8); 0.967(10.7); 0.957(11.4); 0.949(11.1); 0.940(10.5); 0.000(6.0)
Example 761: ¹H-NMR(400.0 MHz, DMSO):
8.959(4.0); 8.954(4.0); 8.888(1.0); 8.874(2.1); 8.859(1.0); 8.735(3.1); 8.723(3.2); 8.609(3.6); 8.605(3.5); 8.265(3.6); 8.261(3.9); 8.199(1.8); 8.195(1.6); 8.177(2.6); 8.173(2.4); 8.086(3.6); 8.064(2.5); 7.954(1.9); 7.718(2.4); 7.706(2.3); 7.584(4.4); 4.595(7.0); 4.479(4.8); 4.464(4.7); 3.951(2.6); 3.908(3.2); 3.558(3.1); 3.515(2.6); 3.384(0.3); 3.343(126.1); 3.306(0.4); 2.893(11.9); 2.733(10.7); 2.509(40.3); 2.505(50.8); 2.501(38.2); 1.683(16.0); 1.654(0.4); 0.000(4.7)
Example 762: ¹H-NMR(400.0 MHz, DMSO):
9.013(3.8); 9.008(4.1); 8.810(1.0); 8.795(2.0); 8.773(3.8); 8.768(3.7); 8.335(3.1); 8.322(3.2); 8.254(3.9); 8.212(1.9); 8.208(1.7); 8.190(2.5); 8.186(2.5); 8.096(3.5); 8.074(2.4); 7.954(1.1); 7.056(2.2); 7.044(2.2); 6.949(4.0); 4.448(0.8); 4.432(0.9); 4.407(1.8); 4.391(1.8); 4.345(1.7); 4.331(1.8); 4.305(0.9); 4.290(0.8); 3.947(2.6); 3.904(3.1); 3.554(3.1); 3.510(2.6); 3.420(0.4); 3.353(248.8); 2.892(6.3); 2.733(5.7); 2.675(0.4); 2.509(42.2); 2.505(55.1); 2.501(43.5); 2.423(1.5); 2.405(4.3); 2.386(4.4); 2.367(1.6); 2.332(0.4); 1.700(16.0); 0.961(5.7); 0.942(11.5); 0.923(5.5); 0.000(4.5)
Example 763: ¹H-NMR(400.0 MHz, DMSO):
8.955(3.5); 8.950(3.5); 8.610(3.0); 8.605(2.9); 8.246(3.1); 8.242(3.2); 8.178(1.6); 8.173(1.3); 8.156(2.3); 8.151(2.2); 8.113(0.8); 8.097(1.5); 8.079(3.7); 8.056(2.1); 7.955(0.6); 4.592(5.9); 3.908(2.3); 3.865(2.8); 3.512(2.7); 3.468(2.3); 3.347(131.9); 3.138(0.3); 3.122(0.4); 3.105(2.4); 3.097(2.5); 3.089(2.6); 3.081(2.3); 3.064(0.4); 2.893(3.6); 2.734(3.2); 2.510(28.8); 2.506(36.0); 2.502(26.4); 1.918(0.3); 1.895(1.0); 1.875(1.6); 1.854(1.6); 1.830(0.7); 1.779(0.4); 1.774(0.4); 1.762(0.6); 1.757(0.7); 1.751(0.6); 1.740(0.7); 1.735(0.9); 1.729(0.5); 1.712(0.6); 1.701(0.4); 1.696(0.4); 1.687(0.6); 1.678(0.6); 1.673(0.7); 1.664(1.1); 1.643(14.6); 1.622(0.6); 1.533(1.2); 1.519(1.3); 1.510(1.7); 1.505(1.6); 1.490(1.6); 1.482(1.1); 1.468(0.7); 1.001(16.0); 0.000(1.9)
Example 764: ¹H-NMR(400.0 MHz, DMSO):
9.005(3.8); 8.999(3.8); 8.764(3.6); 8.759(3.3); 8.449(1.0); 8.434(1.8); 8.419(0.9); 8.216(3.5); 8.213(3.8); 8.175(1.8); 8.170(1.4); 8.153(2.7); 8.148(2.3); 8.080(3.6); 8.058(2.3); 3.880(2.6); 3.837(3.2); 3.502(3.1); 3.459(2.6); 3.350(174.8); 3.302(0.6); 3.287(0.8); 3.270(1.0); 3.255(1.3); 3.241(0.7); 3.207(0.7); 3.194(1.3); 3.179(0.9); 3.160(0.7); 3.146(0.4); 2.893(0.8); 2.734(0.8); 2.574(0.8); 2.559(1.1); 2.553(1.2); 2.539(2.0); 2.510(35.8); 2.506(43.3); 2.371(0.4); 2.352(0.8); 2.319(2.1); 2.295(2.1); 2.263(0.6); 1.617(16.0); 0.000(1.2)
Example 765: ¹H-NMR(400.0 MHz, DMSO):
9.006(3.9); 9.000(3.9); 8.765(3.5); 8.760(3.3); 8.731(1.8); 8.713(1.9); 8.216(3.4); 8.212(3.8); 8.177(1.8); 8.173(1.4); 8.155(2.7); 8.151(2.4); 8.081(3.6); 8.059(2.3); 4.138(0.3); 4.120(0.7); 4.102(1.0); 4.083(0.8); 4.068(0.4); 3.901(2.6); 3.858(3.2); 3.498(3.1); 3.454(2.6); 3.342(133.2); 3.305(0.4); 2.892(0.9); 2.869(0.4); 2.858(0.8); 2.844(0.9); 2.837(1.3); 2.824(1.6); 2.811(1.9); 2.803(1.7); 2.790(2.2); 2.779(1.6); 2.759(1.6); 2.745(1.0); 2.733(1.5); 2.713(0.5); 2.679(0.3); 2.674(0.3); 2.509(36.3); 2.505(45.1); 2.501(33.2); 1.607(16.0); 0.000(4.0)
Example 766: ¹H-NMR(400.0 MHz, DMSO):
8.955(5.6); 8.950(5.9); 8.606(4.9); 8.601(4.8); 8.377(0.8); 8.363(2.0); 8.350(2.0); 8.336(0.8); 8.233(5.0); 8.176(2.4); 8.172(2.1); 8.154(3.5); 8.150(3.4); 8.078(5.1); 8.055(3.3); 7.954(1.6); 4.592(9.4); 4.460(0.7); 4.455(1.2); 4.450(0.8); 4.439(1.0); 4.434(2.0); 4.429(2.0); 4.413(0.9); 4.407(1.4); 4.402(0.8); 4.248(1.3); 4.243(1.6); 4.239(1.7); 4.234(1.6); 4.227(1.6); 4.222(1.8); 4.218(1.6); 4.213(1.4); 4.121(0.7); 4.105(0.9); 4.096(1.4); 4.079(1.5); 4.075(1.5); 4.071(1.0); 4.058(1.3); 4.054(1.0); 4.049(0.8); 4.032(0.6); 3.898(2.0); 3.889(2.0); 3.855(2.3); 3.845(2.5); 3.501(3.4); 3.458(2.9); 3.437(0.3); 3.347(242.9); 3.321(3.9); 3.304(2.2); 3.288(2.1); 3.272(1.5); 3.264(1.4); 3.258(1.3); 3.248(1.3); 3.238(1.8); 3.214(2.5); 3.206(1.1); 3.191(1.3); 3.182(1.4); 3.159(0.7); 2.893(10.5); 2.733(9.2); 2.674(0.4); 2.509(54.5); 2.505(70.3); 2.501(52.0); 2.332(0.4); 1.987(0.4); 1.978(0.6); 1.969(0.8); 1.960(1.0); 1.951(1.0); 1.943(1.2); 1.934(1.1); 1.925(0.9); 1.915(0.6); 1.907(0.3); 1.816(0.6); 1.797(1.2); 1.781(1.6); 1.761(1.4); 1.745(0.8); 1.726(0.4); 1.610(16.0); 0.000(2.9)
Example 767: ¹H-NMR(400.0 MHz, DMSO):
9.004(3.4); 8.998(3.5); 8.768(2.9); 8.762(2.8); 8.225(2.9); 8.221(3.2); 8.179(1.6); 8.175(1.3); 8.157(2.3); 8.153(2.2); 8.118(0.7); 8.102(1.4); 8.080(3.4); 8.058(2.0); 3.899(2.3); 3.856(2.8); 3.504(2.7); 3.461(2.3); 3.349(135.4); 3.138(0.3); 3.121(0.4); 3.105(2.3); 3.095(2.5); 3.088(2.5); 3.080(2.4); 3.063(0.4); 2.893(0.5); 2.734(0.4); 2.510(26.6); 2.506(34.3); 2.502(25.3); 1.895(1.0); 1.874(1.5); 1.853(1.5); 1.828(0.7); 1.778(0.4); 1.773(0.4); 1.761(0.5); 1.756(0.7); 1.750(0.6);

NMR Peak Lists Table 1

1.739(0.6); 1.734(0.9); 1.728(0.5); 1.716(0.4); 1.711(0.6); 1.699(0.4); 1.695(0.4); 1.685(0.6); 1.676(0.5); 1.671(0.6); 1.661(1.1); 1.644(14.8); 1.625(0.6); 1.620(0.5); 1.532(1.2); 1.518(1.2); 1.509(1.6); 1.503(1.6); 1.488(1.5); 1.480(1.1); 1.466(0.7); 1.000(16.0); 0.000(2.0)
Example 768: $^1$H-NMR(400.0 MHz, DMSO):
11.386(0.8); 8.960(4.3); 8.955(4.3); 8.820(1.1); 8.804(2.1); 8.789(1.0); 8.612(3.6); 8.607(3.4); 8.261(3.5); 8.257(3.8); 8.189(1.9); 8.185(1.6); 8.167(2.8); 8.163(2.6); 8.086(3.7); 8.064(2.5); 7.954(1.0); 7.262(2.5); 7.243(2.7); 6.038(8.1); 6.023(2.6); 4.594(7.4); 4.108(3.9); 4.092(3.9); 3.919(2.7); 3.876(3.2); 3.549(3.1); 3.505(2.6); 3.351(175.9); 2.892(6.7); 2.733(5.8); 2.510(33.8); 2.506(43.3); 2.501(31.4); 1.658(16.0); 0.000(1.9)
Example 769: $^1$H-NMR(400.0 MHz, DMSO):
9.014(4.4); 9.008(4.5); 8.897(1.0); 8.881(1.9); 8.866(1.0); 8.771(3.5); 8.241(4.0); 8.200(1.7); 8.178(2.5); 8.091(3.6); 8.069(2.4); 7.986(3.4); 7.973(3.5); 7.954(1.6); 6.761(2.5); 6.749(2.5); 6.545(0.3); 6.436(3.4); 4.979(0.8); 4.963(1.7); 4.948(1.7); 4.933(0.8); 4.318(0.6); 4.302(0.6); 4.277(1.7); 4.262(1.7); 4.237(1.7); 4.222(1.8); 4.197(0.7); 4.181(0.6); 3.917(1.9); 3.874(2.4); 3.872(2.3); 3.541(3.2); 3.498(2.7); 3.347(226.5); 3.303(0.5); 2.892(9.8); 2.733(8.7); 2.674(0.4); 2.509(46.8); 2.505(59.1); 2.501(43.3); 2.332(0.4); 1.672(16.0); 1.520(0.4); 1.501(1.0); 1.483(1.6); 1.467(1.7); 1.451 (1.9); 1.435(1.6); 1.418(1.0); 1.400(0.4); 1.129(6.0); 1.113(6.1); 1.103(6.1); 1.088(5.9); 0.797(2.8); 0.779(5.8); 0.760(2.6); 0.744(2.9); 0.726(5.8); 0.707(2.6); 0.000(2.1)
Example 770: $^1$H-NMR(400.0 MHz, DMSO):
8.964(4.3); 8.959(4.6); 8.895(1.1); 8.880(2.1); 8.865(1.1); 8.610(4.0); 8.260(4.2); 8.199(1.8); 8.196(1.8); 8.177(2.6); 8.174(2.6); 8.089(3.6); 8.067(2.5); 7.985(3.5); 7.972(3.6); 7.954(2.1); 6.761(2.7); 6.748(2.7); 6.437(4.0); 4.977(0.9); 4.962(1.8); 4.946(1.8); 4.931(0.9); 4.593(7.8); 4.318(0.7); 4.302(0.7); 4.278(1.8); 4.262(1.8); 4.237(1.8); 4.222(1.9); 4.196(0.7); 4.181(0.7); 3.924(2.0); 3.881(2.5); 3.548(3.1); 3.504(2.6); 3.350(290.1); 3.298(0.4); 2.892(12.2); 2.733 (10.9); 2.674(0.4); 2.509(49.4); 2.505(64.4); 2.501(51.3); 2.332(0.4); 1.671(16.0); 1.519(0.4); 1.501(1.0); 1.483(1.7); 1.467(1.9); 1.452(2.0); 1.435(1.6); 1.417(1.0); 1.400(0.4); 1.129(5.7); 1.114(5.8); 1.100(5.8); 1.085(5.6); 0.796(2.7); 0.778(5.5); 0.759(2.5); 0.740(2.7); 0.722(5.4); 0.703(2.5); 0.000(1.4)
Example 771: $^1$H-NMR(400.0 MHz, DMSO):
9.013(4.3); 9.007(4.4); 8.844(1.0); 8.828(2.0); 8.813(1.0); 8.766(3.5); 8.760(3.3); 8.238(3.5); 8.234(3.8); 8.185(1.9); 8.180(1.6); 8.163(2.8); 8.158(2.6); 8.084(3.7); 8.062(2.4); 7.954(0.6); 7.837(3.2); 7.824(3.3); 6.616(2.6); 6.611(2.5); 6.400(2.4); 6.387(2.4); 6.366(4.1); 4.248(0.4); 4.233(0.5); 4.208(1.8); 4.191(2.6); 4.173(1.9); 4.148(0.5); 4.133(0.4); 3.933(2.6); 3.890(3.2); 3.539(3.1); 3.496(2.6); 3.394(0.5); 3.350(225.8); 3.318(0.8); 2.892(3.8); 2.733(3.3); 2.674(0.3); 2.513(21.6); 2.509(41.6); 2.505(53.1); 2.500(38.1); 2.216(0.9); 2.208(1.1); 2.201(1.2); 2.192(0.9); 2.185(0.6); 1.681(16.0); 0.475(0.4); 0.462(1.0); 0.457(1.1); 0.451(1.4); 0.438(2.1); 0.435(2.3); 0.422(1.5); 0.410(1.0); 0.397(0.4); 0.296(1.2); 0.287(3.2); 0.279(3.4); 0.000(1.9)
Example 772: $^1$H-NMR(400.0 MHz, DMSO):
9.065(1.0); 9.050(2.1); 9.035(1.0); 8.965(4.0); 8.960(4.1); 8.664(2.8); 8.651(2.9); 8.610(3.5); 8.606(3.5); 8.258(3.5); 8.254(3.8); 8.197(1.8); 8.192(1.6); 8.174(2.7); 8.170(2.5); 8.094(3.7); 8.072(2.4); 7.955(2.0); 7.679(4.2); 7.538(2.1); 7.526(2.1); 4.597(7.2); 4.438(4.3); 4.423(4.3); 3.934(2.6); 3.891(3.2); 3.561(3.1); 3.518(2.6); 3.349(208.4); 2.893 (12.2); 2.734(11.0); 2.510(40.6); 2.506(51.7); 2.502(38.3); 2.333(0.3); 1.677(16.0); 0.000(1.6)
Example 773: $^1$H-NMR(400.0 MHz, DMSO):
9.013(4.1); 9.007(4.1); 8.890(1.0); 8.875(2.0); 8.859(1.0); 8.773(3.6); 8.767(3.4); 8.241(3.6); 8.237(3.9); 8.200(1.9); 8.196(1.5); 8.178(2.7); 8.174(2.4); 8.094(3.6); 8.072(2.4); 7.997(3.4); 7.984(3.4); 7.954(1.6); 6.766(2.4); 6.754(2.3); 6.442(4.5); 5.163(0.6); 5.147(1.2); 5.132(2.2); 5.116(1.6); 5.101(0.6); 4.303(0.4); 4.287(0.4); 4.263(2.1); 4.247(3.8); 4.232(2.1); 4.206(0.4); 4.191(0.4); 3.916(2.6); 3.873(3.2); 3.538(3.1); 3.495(2.6); 3.345(214.6); 2.892(10.0); 2.733 (9.0); 2.674(0.4); 2.509(49.6); 2.505(61.3); 2.501(45.1); 2.331(0.4); 1.668(16.0); 1.175(10.4); 1.159(10.7); 1.148(10.7); 1.133(10.3); 0.000(2.9)
Example 774: $^1$H-NMR(400.0 MHz, DMSO):
8.963(4.2); 8.958(4.2); 8.888(1.0); 8.872(2.1); 8.857(1.0); 8.614(3.6); 8.609(3.4); 8.262(3.5); 8.257(3.8); 8.199(1.9); 8.195(1.6); 8.177(2.7); 8.173(2.5); 8.092(3.7); 8.070(2.5); 7.997(3.4); 7.984(3.5); 7.954(1.9); 6.768(2.3); 6.755(2.3); 6.442(4.4); 5.160(0.6); 5.145(1.7); 5.130(2.3); 5.114(1.7); 5.099(0.6); 4.594(7.7); 4.303(0.4); 4.287(0.4); 4.263(2.0); 4.247(3.6); 4.231(2.0); 4.206(0.4); 4.191(0.4); 3.924(2.6); 3.881(3.2); 3.546(3.1); 3.502(2.6); 3.346(247.9); 2.892(12.7); 2.733(11.1); 2.678(0.3); 2.674(0.4); 2.509(55.6); 2.504(70.3); 2.500(51.1); 2.331(0.4); 1.666(16.0); 1.312(0.5); 1.297(0.4); 1.268(0.5); 1.253(0.5); 1.233(0.3); 1.173(10.7); 1.158(10.8); 1.145(10.8); 1.129(10.6); 0.000(2.1)
Example 775: $^1$H-NMR(400.0 MHz, DMSO):
11.383(0.8); 9.008(4.3); 9.003(4.4); 8.821(1.0); 8.806(2.1); 8.790(1.0); 8.768(3.5); 8.763(3.4); 8.239(3.4); 8.235(3.8); 8.191(1.9); 8.186(1.6); 8.168(2.8); 8.164(2.5); 8.087(3.7); 8.065(2.4); 7.954(0.9); 7.261(2.6); 7.243(2.7); 6.037(7.9); 6.021(2.5); 4.107(3.8); 4.091(3.8); 3.911(2.6); 3.867(3.2); 3.540(3.2); 3.497(2.6); 3.346(156.7); 2.892(6.0); 2.733(5.3); 2.510(35.3); 2.505(45.2); 2.501(32.5); 1.658(16.0); 0.000(3.6)
Example 776: $^1$H-NMR(400.0 MHz, DMSO):
8.966(4.4); 8.961(4.4); 8.600(3.5); 8.596(3.4); 8.344(1.0); 8.330(1.9); 8.315(1.0); 8.189(3.3); 8.185(4.0); 8.171(2.1); 8.166(1.3); 8.149(3.1); 8.144(2.6); 8.092(3.8); 8.070(2.2); 7.955(0.4); 7.678(3.5); 7.401(2.1); 7.381(2.7); 7.259(2.0); 7.238(1.5); 4.596(7.4); 3.705(2.5); 3.662(3.3); 3.511(0.7); 3.494(1.1); 3.478(1.3); 3.461(1.2); 3.443(3.6); 3.400(3.1); 3.377(2.5); 3.352(225.4); 3.003(0.5); 2.986(1.1); 2.969(2.6); 2.953(2.3); 2.935(1.0); 2.918(0.4); 2.893(2.4); 2.734(2.0); 2.511(38.8); 2.506(49.9); 2.502(36.1); 1.550(16.0); 0.000(2.2)
Example 777: $^1$H-NMR(400.0 MHz, DMSO):
9.585(2.6); 9.569(2.4); 9.004(5.6); 8.998(5.7); 8.773(3.0); 8.767(5.1); 8.761(2.9); 8.213(5.4); 8.178(2.8); 8.174(2.3); 8.156(4.2); 8.152(3.8); 8.082(5.4); 8.060(3.4); 4.787(0.4); 3.914(2.9); 3.871(3.5); 3.492(4.7); 3.449(4.0); 3.350(297.6); 3.278(0.3); 2.893(2.2); 2.734(1.9); 2.674(0.5); 2.510(57.2); 2.506(72.0); 2.501(52.8); 2.337(0.4); 2.332(0.5); 2.116(0.7); 2.100(1.1); 2.094(1.0); 2.084(1.2); 2.078(1.2); 2.068(1.0); 2.062(1.1); 2.046(0.8); 1.657(0.8); 1.635(16.0); 1.631(15.0); 1.016(6.7); 1.004(8.9); 1.000(8.3); 0.988(6.9); 0.965(1.4); 0.636(0.5); 0.625(0.8); 0.614(1.0); 0.603(1.3); 0.592(1.1); 0.581(1.0); 0.570(0.6); 0.559(0.4); 0.405(0.4); 0.396(0.7); 0.385(0.8); 0.375(0.8); 0.366(0.5); 0.363(0.5); 0.353(0.5); 0.346(0.4); 0.333(1.0); 0.321(1.4); 0.313(1.6); 0.300(1.7); 0.293(1.5); 0.283(1.4); 0.275(1.1); 0.262(0.9); 0.250(0.3); 0.201(0.4); 0.188(0.9); 0.179(1.3); 0.171(1.5); 0.166(1.4); 0.159(1.6); 0.148(0.9); 0.136(0.3); 0.000(2.6); −0.009(0.9); −0.019(1.3); −0.030(1.5); −0.038(1.4); −0.051(1.1); −0.061(0.7)
Example 778: $^1$H-NMR(400.0 MHz, DMSO):
8.958(4.2); 8.952(4.2); 8.610(3.4); 8.606(3.3); 8.252(3.4); 8.248(3.6); 8.191(1.9); 8.187(1.6); 8.169(2.7); 8.165(2.4); 8.085(3.6); 8.063(2.4); 8.033(1.7); 8.011(1.7); 7.955(0.6); 4.593(7.2); 3.876(2.6); 3.833(3.2); 3.496(3.1); 3.453(2.6); 3.382(0.5); 3.350(159.4); 2.894(3.6); 2.774(0.7); 2.753(1.9); 2.734(4.4); 2.710(0.7); 2.511(30.1); 2.506(38.1); 2.502(27.4); 1.616(16.0); 1.137(0.4); 1.129(0.6); 1.117(1.2); 1.109(0.8); 1.105(0.8); 1.096(1.2); 1.084(0.8); 1.078(0.8);

NMR Peak Lists Table 1

1.071(0.7); 1.058(1.2); 1.051(0.7); 1.046(0.8); 1.038(1.2); 1.026(0.7); 1.018(0.5); 0.475(0.5); 0.471(0.5); 0.462(1.1); 0.454(1.0); 0.450(1.1); 0.441(1.4); 0.433(0.6); 0.429(0.7); 0.420(0.6); 0.415(0.5); 0.408(0.6); 0.404(0.6); 0.395(1.0); 0.390(0.9); 0.383(1.0); 0.373(1.4); 0.361(0.7); 0.354(0.9); 0.346(0.8); 0.343(0.8); 0.335(1.2); 0.323(1.1); 0.314(1.1); 0.301(0.6); 0.292(0.5); 0.280(0.5); 0.268(0.7); 0.258(1.1); 0.245(1.8); 0.236(1.9); 0.230(1.8); 0.225(1.8); 0.217(2.1); 0.210(2.6); 0.206(2.2); 0.200(1.7); 0.191(2.5); 0.175(1.6); 0.164(1.2); 0.152(0.5); 0.123(0.7); 0.110(0.9); 0.105(1.0); 0.100(1.3); 0.087(1.3); 0.079(0.7); 0.074(0.5); 0.000(1.5)
Example 779: $^1$H-NMR(400.0 MHz, DMSO):
9.015(4.0); 9.010(4.1); 8.759(3.5); 8.754(3.4); 8.346(1.0); 8.332(1.9); 8.317(1.1); 8.169(7.7); 8.148(3.2); 8.144(2.3); 8.094(3.1); 8.071(1.8); 7.678(3.6); 7.401(2.1); 7.381(2.8); 7.263(2.1); 7.243(1.6); 3.701(2.5); 3.657(3.3); 3.508(0.7); 3.491(1.1); 3.475(1.3); 3.459(1.2); 3.436(3.4); 3.410(0.6); 3.393(3.6); 3.380(2.0); 3.349(191.3); 3.003(0.5); 2.985(1.1); 2.969(2.7); 2.952(2.4); 2.935(1.1); 2.918(0.4); 2.893(0.9); 2.734(0.8); 2.510(39.6); 2.506(49.4); 2.502(36.1); 1.551(16.0); 0.000(2.6)
Example 780: $^1$H-NMR(400.0 MHz, DMSO):
9.583(2.3); 9.566(2.0); 8.955(5.6); 8.950(5.7); 8.609(4.9); 8.233(5.3); 8.177(2.8); 8.172(2.4); 8.155(4.0); 8.150(3.8); 8.080(5.4); 8.058(3.5); 4.770(0.7); 4.592(10.1); 3.923(2.9); 3.880(3.5); 3.499(4.6); 3.456(4.0); 3.424(0.4); 3.414(0.6); 3.350(344.4); 2.893(2.0); 2.733(1.5); 2.674(0.5); 2.510(67.0); 2.505(86.1); 2.501(63.5); 2.336(0.4); 2.332(0.5); 2.115(0.7); 2.100(1.0); 2.094(0.9); 2.083(1.1); 2.078(1.1); 2.067(1.0); 2.062(1.1); 2.046(0.8); 1.653(1.6); 1.633(16.0); 1.630(15.0); 1.233(0.4); 1.016(6.5); 1.003(9.0); 1.000(8.4); 0.988(7.1); 0.965(0.5); 0.634(0.5); 0.625(0.8); 0.614(1.1); 0.603(1.3); 0.592(1.1); 0.581(1.0); 0.571(0.6); 0.560(0.4); 0.405(0.4); 0.397(0.7); 0.387(0.8); 0.376(0.8); 0.364(0.5); 0.354(0.5); 0.335(0.9); 0.322(1.3); 0.315(1.4); 0.302(1.6); 0.296(1.7); 0.284(1.4); 0.275(1.1); 0.262(0.9); 0.251(0.4); 0.202(0.5); 0.190(0.9); 0.181(1.3); 0.172(1.5); 0.160(1.7); 0.149(0.9); 0.137(0.3); 0.000(3.4); −0.008(0.9); −0.019(1.3); −0.030(1.4); −0.037(1.4); −0.049(1.2); −0.061(0.7)
Example 781: $^1$H-NMR(400.0 MHz, DMSO):
9.008(3.4); 9.002(3.5); 8.788(2.8); 8.783(2.7); 8.251(2.8); 8.247(3.0); 8.178(1.5); 8.174(1.3); 8.156(2.3); 8.151(2.1); 8.081(3.0); 8.059(1.9); 4.336(2.4); 4.292(2.7); 3.813(0.5); 3.733(0.5); 3.693(0.5); 3.638(1.8); 3.624(1.9); 3.610(1.8); 3.534(1.2); 3.474(2.8); 3.430(2.5); 3.402(0.3); 3.349(244.8); 2.892(1.1); 2.733(0.9); 2.674(0.3); 2.509(43.1); 2.505(55.1); 2.500(40.2); 2.331(0.3); 1.664(16.0); 0.000(3.3)
Example 782: $^1$H-NMR(400.0 MHz, DMSO):
8.956(4.2); 8.951(4.1); 8.653(1.0); 8.639(2.0); 8.624(1.1); 8.603(3.7); 8.599(3.5); 8.236(3.7); 8.233(3.8); 8.169(1.8); 8.164(1.5); 8.146(2.8); 8.142(2.6); 8.074(3.7); 8.052(2.3); 7.663(5.5); 7.423(6.1); 5.075(1.3); 5.052(4.0); 5.029(4.2); 5.006(1.4); 4.593(6.6); 4.202(0.5); 4.187(0.6); 4.165(2.2); 4.148(3.2); 4.131(2.2); 4.109(0.5); 4.094(0.5); 3.895(2.6); 3.852(3.2); 3.514(3.1); 3.471(2.6); 3.351(182.1); 3.306(0.4); 2.893(1.9); 2.734(1.6); 2.510(38.5); 2.505(47.5); 2.501(35.0); 1.610(16.0); 0.000(1.2)
Example 783: $^1$H-NMR(400.0 MHz, DMSO):
9.006(3.7); 9.000(3.8); 8.768(3.4); 8.762(3.3); 8.231(3.4); 8.227(3.8); 8.192(1.8); 8.188(1.5); 8.170(2.6); 8.165(2.3); 8.086(3.5); 8.063(2.4); 8.036(1.7); 8.013(1.7); 3.867(2.6); 3.824(3.1); 3.487(3.5); 3.444(2.6); 3.345(128.4); 2.893(1.7); 2.773(0.7); 2.752(2.0); 2.732(2.7); 2.709(0.7); 2.510(32.0); 2.506(40.9); 2.502(30.9); 1.616(16.0); 1.136(0.4); 1.128(0.6); 1.116(1.2); 1.104(0.9); 1.096(1.2); 1.083(0.8); 1.076(0.8); 1.070(0.7); 1.057(1.1); 1.045(0.8); 1.037(1.1); 1.025(0.7); 1.017(0.5); 0.471(0.5); 0.461(1.1); 0.450(1.1); 0.440(1.3); 0.432(0.7); 0.428(0.7); 0.419(0.6); 0.415(0.5); 0.407(0.6); 0.394(1.0); 0.389(1.0); 0.382(1.0); 0.373(1.4); 0.361(0.6); 0.353(0.9); 0.343(0.8); 0.334(1.2); 0.322(1.1); 0.313(1.1); 0.300(0.6); 0.291(0.5); 0.279(0.5); 0.267(0.7); 0.257(1.1); 0.245(1.8); 0.235(1.9); 0.229(1.8); 0.224(1.8); 0.216(2.1); 0.209(2.6); 0.190(2.5); 0.174(1.7); 0.163(1.2); 0.150(0.5); 0.121(0.7); 0.108(0.9); 0.104(1.0); 0.099(1.3); 0.086(1.3); 0.078(0.7); 0.072(0.5); 0.000(2.2)
Example 784: $^1$H-NMR(400.0 MHz, DMSO):
8.958(3.4); 8.953(3.4); 8.628(3.1); 8.624(3.1); 8.271(3.2); 8.267(3.3); 8.176(1.5); 8.171(1.4); 8.153(2.3); 8.149(2.2); 8.079(3.2); 8.057(2.1); 4.596(6.1); 4.341(2.4); 4.298(2.7); 3.814(0.6); 3.734(0.6); 3.696(0.6); 3.639(2.1); 3.626(2.2); 3.611(2.1); 3.536(1.4); 3.484(2.9); 3.440(2.5); 3.342(94.1); 2.893(1.0); 2.734(0.9); 2.509(27.6); 2.505(34.3); 2.501(25.6); 1.663(16.0); 0.000(2.6)
Example 785: $^1$H-NMR(400.0 MHz, DMSO):
9.002(3.6); 8.997(3.8); 8.763(3.1); 8.757(3.0); 8.215(3.0); 8.211(3.4); 8.173(1.9); 8.168(1.9); 8.151(4.0); 8.146(3.2); 8.136(0.8); 8.077(3.3); 8.055(2.1); 3.872(2.5); 3.829(3.1); 3.482(3.0); 3.438(2.5); 3.348(135.6); 3.167(0.5); 3.151(1.4); 3.134(1.8); 3.129(1.4); 3.118(1.4); 3.113(1.9); 3.096(1.4); 3.079(0.5); 3.063(0.3); 2.893(0.7); 2.734(0.6); 2.511(25.6); 2.506(33.4); 2.502(24.5); 2.482(0.6); 2.463(1.0); 2.444(1.4); 2.425(1.1); 2.407(0.5); 1.920(0.4); 1.916(0.4); 1.910(0.6); 1.901(1.2); 1.889(1.3); 1.880(1.6); 1.869(1.2); 1.864(1.2); 1.850(0.5); 1.843(0.6); 1.791(0.3); 1.786(0.4); 1.766(1.2); 1.746(2.1); 1.734(1.3); 1.725(1.5); 1.714(1.0); 1.704(0.8); 1.688(0.3); 1.670(0.5); 1.662(0.7); 1.653(1.0); 1.644(1.5); 1.633(1.2); 1.623(1.8); 1.609(16.0); 0.000(1.7)
Example 786: $^1$H-NMR(400.0 MHz, DMSO):
8.957(4.0); 8.952(4.0); 8.730(1.9); 8.712(1.9); 8.607(3.5); 8.603(3.4); 8.237(3.5); 8.233(3.7); 8.176(1.8); 8.172(1.5); 8.154(2.7); 8.150(2.5); 8.080(3.6); 8.058(2.3); 7.954(0.7); 4.595(6.9); 4.139(0.3); 4.120(0.7); 4.102(1.0); 4.084(0.8); 4.067(0.4); 3.910(2.6); 3.866(3.2); 3.506(3.1); 3.463(2.7); 3.345(167.4); 3.308(0.4); 2.893(4.2); 2.868(0.4); 2.858(0.8); 2.844(1.0); 2.837(1.3); 2.823(1.7); 2.811(1.9); 2.803(1.7); 2.790(2.3); 2.779(1.7); 2.759(2.0); 2.743(1.1); 2.733(4.4); 2.713(0.5); 2.678(0.3); 2.674(0.3); 2.509(38.4); 2.505(47.9); 2.501(35.2); 1.606(16.0); 0.000(3.4)
Example 787: $^1$H-NMR(400.0 MHz, DMSO):
9.003(4.0); 8.997(4.0); 8.759(3.5); 8.753(3.4); 8.657(1.0); 8.643(2.0); 8.627(1.0); 8.214(3.6); 8.210(3.8); 8.169(1.8); 8.165(1.5); 8.147(2.7); 8.143(2.5); 8.075(3.6); 8.053(2.3); 7.955(0.9); 7.664(5.5); 7.424(6.1); 5.077(1.3); 5.054(4.0); 5.031(4.2); 5.008(1.4); 4.204(0.5); 4.189(0.6); 4.167(2.1); 4.151(2.6); 4.148(2.7); 4.132(2.1); 4.110(0.6); 4.095(0.5); 3.888(2.6); 3.845(3.2); 3.506(3.1); 3.463(2.6); 3.349(124.5); 2.893(2.5); 2.734(2.2); 2.510(26.9); 2.506(33.4); 2.502(25.0); 1.612(16.0); 0.000(2.3)
Example 788: $^1$H-NMR(400.0 MHz, DMSO):
8.954(3.7); 8.949(3.8); 8.605(3.3); 8.601(3.2); 8.237(3.3); 8.233(3.5); 8.172(1.8); 8.167(1.8); 8.149(3.9); 8.145(3.8); 8.132(0.9); 8.076(3.4); 8.054(2.2); 7.956(0.3); 4.592(6.7); 3.881(2.5); 3.838(3.0); 3.490(3.0); 3.446(2.5); 3.349(127.0); 3.185(0.3); 3.169(0.5); 3.152(1.4); 3.135(1.9); 3.130(1.5); 3.119(1.6); 3.114(2.0); 3.097(1.4); 3.080(0.5); 3.064(0.3); 2.894(2.0); 2.734(1.8); 2.511(25.4); 2.507(31.9); 2.502(23.5); 2.484(0.8); 2.464(1.1); 2.445(1.4); 2.426(1.1); 2.407(0.5); 1.921(0.4); 1.917(0.4); 1.911(0.6); 1.901(1.3); 1.891(1.4); 1.881(1.8); 1.870(1.3); 1.865(1.3); 1.844(0.7); 1.792(0.3); 1.786(0.4); 1.767(1.2); 1.747(2.2); 1.735(1.4); 1.726(1.6); 1.716(1.1); 1.706(0.9); 1.689(0.3); 1.671(0.6); 1.663(0.7); 1.654(1.0); 1.645(1.6); 1.635(1.4); 1.624(1.9); 1.609(16.0); 0.000(2.3)

NMR Peak Lists Table 1

Example 789: $^1$H-NMR(400.0 MHz, DMSO):
8.971(1.1); 8.958(5.6); 8.954(5.7); 8.941(1.1); 8.883(3.6); 8.878(3.6); 8.730(3.6); 8.725(3.6); 8.603(3.6); 8.599(3.5); 8.247(3.5); 8.243(3.8); 8.183(1.8); 8.178(1.6); 8.161(2.7); 8.156(2.5); 8.106(3.7); 8.082(3.7); 8.060(2.4); 7.955(2.0); 4.595(7.0); 4.389(3.5); 4.374(3.4); 3.924(2.6); 3.881(3.2); 3.539(3.1); 3.496(2.6); 3.347(132.9); 2.893(12.2); 2.734 (11.0); 2.510(34.5); 2.506(43.6); 2.502(32.2); 1.640(16.0); 0.000(2.6)

Example 790: $^1$H-NMR(400.0 MHz, DMSO):
9.012(1.2); 9.006(1.3); 8.799(0.6); 8.784(0.4); 8.775(1.1); 8.770(1.0); 8.236(1.0); 8.232(1.1); 8.194(0.6); 8.189(0.5); 8.172(0.8); 8.167(0.8); 8.094(1.1); 8.072(1.3); 8.065(0.7); 8.060(0.6); 7.954(0.5); 7.406(0.5); 7.390(0.6); 6.858(0.6); 6.846(0.6); 6.839(0.6); 6.827(0.5); 4.312(1.3); 4.297(1.2); 3.924(0.8); 3.881(1.0); 3.529(0.9); 3.486(0.8); 3.341(31.1); 2.892(3.5); 2.734(16.0); 2.509(12.3); 2.504(15.8); 2.500(11.7); 1.666(4.8); 0.000(2.0)

Example 791: $^1$H-NMR(400.0 MHz, DMSO):
8.959(4.5); 8.954(4.7); 8.942(2.1); 8.601(3.3); 8.425(2.9); 8.419(3.4); 8.333(3.5); 8.316(4.8); 8.246(3.7); 8.183(2.0); 8.156(2.5); 8.084(3.6); 8.061(2.4); 7.952(2.3); 7.529(1.3); 7.505(1.4); 4.595(6.6); 4.365(4.0); 4.349(3.8); 3.919(2.6); 3.876(3.1); 3.537(3.1); 3.493(3.1); 3.338(5656.0); 2.891(14.9); 2.731(13.3); 2.672(12.8); 2.507(1533.5); 2.502(1976.2); 2.498(1460.8); 2.329(12.0); 1.637(16.0); 1.232(1.2); 0.000(71.6)

Example 792: $^1$H-NMR(400.0 MHz, DMSO):
9.007(4.1); 9.001(4.2); 8.972(1.0); 8.957(2.0); 8.941(1.0); 8.883(3.5); 8.878(3.5); 8.761(3.5); 8.756(3.4); 8.729(3.5); 8.724(3.5); 8.226(3.4); 8.222(3.8); 8.184(1.9); 8.179(1.5); 8.162(2.7); 8.157(2.4); 8.104(3.6); 8.084(3.7); 8.061(2.4); 7.954(0.6); 4.388(3.4); 4.373(3.3); 3.914(2.6); 3.871(3.2); 3.530(3.1); 3.487(2.6); 3.344(158.7); 3.305(0.3); 2.893(4.0); 2.733(3.6); 2.509(40.9); 2.505(51.5); 2.501(37.5); 1.640(16.0); 0.000(3.1)

Example 793: $^1$H-NMR(400.0 MHz, DMSO):
8.961(4.1); 8.956(4.3); 8.891(0.9); 8.877(1.9); 8.862(0.9); 8.611(3.3); 8.606(3.2); 8.253(3.3); 8.248(3.6); 8.187(1.8); 8.183(1.5); 8.165(2.7); 8.161(2.5); 8.099(1.8); 8.088(5.2); 8.066(2.3); 7.955(0.4); 7.764(0.8); 7.760(0.8); 7.740(1.4); 7.720(0.9); 7.716(0.8); 7.303(1.1); 7.298(1.2); 7.290(1.2); 7.285(1.7); 7.280(1.2); 7.272(1.0); 7.268(1.0); 4.597(7.5); 4.382(0.3); 4.367(0.4); 4.343(2.0); 4.328(3.6); 4.313(1.9); 4.288(0.4); 4.273(0.4); 3.927(2.6); 3.883(3.2); 3.544(3.1); 3.501(2.6); 3.344(116.8); 2.893(3.0); 2.733(2.5); 2.510(30.7); 2.506(39.6); 2.501(28.7); 1.654(16.0); 0.000(4.0)

Example 794: $^1$H-NMR(400.0 MHz, DMSO):
9.008(4.0); 9.002(4.1); 8.963(0.9); 8.948(1.8); 8.933(0.9); 8.762(3.4); 8.757(3.2); 8.428(3.1); 8.421(3.1); 8.337(3.4); 8.228(3.3); 8.224(3.6); 8.185(1.8); 8.180(1.5); 8.163(2.7); 8.158(2.4); 8.085(3.5); 8.063(2.3); 7.955(0.3); 7.533(1.4); 7.508(1.4); 4.369(3.8); 4.354(3.7); 3.914(2.6); 3.871(3.2); 3.531(3.1); 3.487(2.5); 3.343(105.4); 2.893(2.2); 2.733(1.9); 2.510(33.6); 2.505(42.6); 2.501(30.9); 1.642(16.0); 0.000(3.8)

Example 795: $^1$H-NMR(400.0 MHz, DMSO):
8.963(4.2); 8.958(4.2); 8.653(1.0); 8.638(2.0); 8.614(3.7); 8.609(3.5); 8.260(3.6); 8.256(3.8); 8.195(1.9); 8.190(1.6); 8.173(2.8); 8.168(2.5); 8.092(3.7); 8.070(2.4); 8.000(2.0); 7.996(2.1); 7.988(2.1); 7.984(2.0); 7.955(0.5); 7.386(1.8); 7.371(1.9); 6.882(2.0); 6.870(2.1); 6.864(2.1); 6.852(1.9); 4.598(7.1); 4.344(1.8); 4.327(5.9); 4.309(5.9); 4.291(1.9); 4.237(4.2); 4.222(4.2); 3.938(2.6); 3.895(3.2); 3.546(3.1); 3.503(2.6); 3.341(79.0); 2.893(3.0); 2.734(2.6); 2.510(30.2); 2.505(38.4); 2.501(28.0); 1.676(16.0); 1.319(6.2); 1.302(12.8); 1.284(6.0); 0.000(5.0)

Example 796: $^1$H-NMR(400.0 MHz, DMSO):
9.010(3.7); 9.004(4.0); 8.892(0.9); 8.878(1.9); 8.863(0.9); 8.769(3.4); 8.764(3.2); 8.231(3.3); 8.227(3.7); 8.188(1.7); 8.184(1.4); 8.166(2.6); 8.162(2.4); 8.099(1.9); 8.089(5.1); 8.067(2.3); 7.760(0.8); 7.740(1.4); 7.720(0.9); 7.303(1.1); 7.298(1.1); 7.290(1.1); 7.285(1.7); 7.280(1.1); 7.272(1.0); 7.268(1.1); 4.382(0.4); 4.367(0.4); 4.342(2.0); 4.327(3.6); 4.312(2.0); 4.287(0.4); 4.271(0.4); 3.917(2.5); 3.874(3.1); 3.536(3.0); 3.492(2.5); 3.346(151.7); 3.206(0.3); 2.893(1.9); 2.733(1.5); 2.510(33.8); 2.505(43.5); 2.501(32.7); 1.655(16.0); 0.000(2.4)

Example 797: $^1$H-NMR(400.0 MHz, DMSO):
8.961(4.1); 8.956(4.1); 8.915(1.0); 8.901(2.1); 8.886(1.0); 8.705(4.4); 8.702(4.4); 8.611(3.5); 8.606(3.4); 8.368(4.4); 8.251(3.5); 8.248(3.7); 8.188(1.8); 8.183(1.6); 8.166(2.7); 8.161(2.5); 8.088(3.6); 8.066(2.4); 4.597(7.1); 4.473(3.5); 4.458(3.4); 4.456(3.4); 3.931(2.6); 3.888(3.2); 3.548(3.1); 3.505(2.6); 3.342(126.9); 2.893(0.9); 2.733(0.8); 2.510(36.6); 2.505(46.4); 2.501(34.2); 1.655(16.0); 0.000(5.1)

Example 798: $^1$H-NMR(400.0 MHz, DMSO):
9.011(4.0); 9.005(4.1); 8.772(3.5); 8.767(3.4); 8.655(1.0); 8.640(1.9); 8.625(1.0); 8.238(3.5); 8.234(3.8); 8.196(1.9); 8.192(1.5); 8.174(2.7); 8.169(2.4); 8.094(3.7); 8.072(2.4); 8.000(1.9); 7.996(2.0); 7.988(2.1); 7.984(1.9); 7.955(0.5); 7.388(1.8); 7.370(2.0); 6.882(2.0); 6.870(2.1); 6.864(2.0); 6.852(1.8); 4.343(1.8); 4.326(5.6); 4.308(5.6); 4.291(1.8); 4.237(4.3); 4.222(4.2); 3.928(2.6); 3.885(3.2); 3.538(3.1); 3.494(2.6); 3.342(100.2); 3.309(0.3); 2.893(3.0); 2.734(2.7); 2.509(34.6); 2.505(43.2); 2.501(31.5); 1.677(16.0); 1.318(5.9); 1.301(12.0); 1.283(5.7); 0.000(4.0)

Example 799: $^1$H-NMR(400.0 MHz, DMSO):
8.962(4.0); 8.957(4.1); 8.627(1.2); 8.613(5.1); 8.600(1.1); 8.539(4.0); 8.533(4.2); 8.404(3.5); 8.398(3.2); 8.262(3.4); 8.258(3.6); 8.192(1.8); 8.187(1.6); 8.170(2.6); 8.165(2.5); 8.088(3.6); 8.066(2.4); 7.954(0.9); 4.598(7.6); 4.579(0.4); 4.551(2.4); 4.538(4.2); 4.525(2.4); 4.496(0.4); 4.483(0.3); 3.916(2.5); 3.873(3.2); 3.567(3.1); 3.524(2.5); 3.343(80.9); 2.893(6.2); 2.733(5.5); 2.509(34.4); 2.505(43.9); 2.501(32.2); 1.669(16.0); 0.000(4.5)

Example 800: $^1$H-NMR(400.0 MHz, DMSO):
9.010(4.0); 9.005(4.0); 8.917(1.1); 8.902(2.2); 8.888(1.1); 8.769(3.7); 8.764(3.5); 8.704(4.5); 8.702(4.3); 8.368(4.6); 8.230(3.8); 8.227(4.0); 8.189(1.9); 8.185(1.5); 8.167(2.8); 8.162(2.5); 8.090(3.6); 8.068(2.3); 7.954(1.9); 4.472(3.7); 4.457(3.7); 3.921(2.6); 3.878(3.2); 3.540(3.1); 3.496(2.6); 3.341(146.2); 2.893(10.8); 2.733(9.8); 2.673(0.4); 2.509 (47.1); 2.505(56.6); 2.501(42.5); 2.332(0.4); 1.655(16.0); 0.000(3.8)

Example 801: $^1$H-NMR(400.0 MHz, DMSO):
8.963(2.8); 8.958(2.9); 8.872(0.7); 8.857(1.4); 8.842(0.7); 8.611(2.5); 8.606(2.4); 8.259(2.5); 8.255(2.6); 8.193(1.3); 8.188(1.1); 8.171(1.9); 8.166(1.7); 8.128(4.0); 8.089(2.5); 8.067(1.7); 8.025(4.1); 7.955(0.4); 4.597(5.0); 4.400(1.6); 4.387(2.5); 4.373(1.6); 3.957(1.8); 3.914(2.2); 3.794(16.0); 3.558(2.1); 3.514(1.8); 3.342(78.4); 2.893(2.2); 2.734(1.9); 2.510(23.9); 2.505(29.9); 2.501(21.9); 1.689(10.9); 0.000(2.8)

Example 802: $^1$H-NMR(400.0 MHz, DMSO):
9.010(3.6); 9.005(3.7); 8.772(3.6); 8.767(3.5); 8.631(1.1); 8.617(2.1); 8.604(1.1); 8.539(3.6); 8.533(3.8); 8.404(3.4); 8.399(3.2); 8.235(3.8); 8.193(1.8); 8.171(2.6); 8.168(2.4); 8.089(3.6); 8.067(2.4); 4.593(0.4); 4.580(0.4); 4.551(2.6); 4.538(4.5); 4.525(2.6); 4.497(0.4); 4.483(0.3); 3.908(2.5); 3.864(3.1); 3.560(3.1); 3.517(2.5); 3.343(71.1); 2.893(1.2); 2.734(1.1); 2.506(34.5); 1.671(16.0); 0.000(3.2)

Example 803: $^1$H-NMR(400.0 MHz, DMSO):
8.966(4.1); 8.960(4.1); 8.843(0.9); 8.828(1.8); 8.813(0.9); 8.614(3.4); 8.610(3.4); 8.339(3.2); 8.326(3.3); 8.284(3.4); 8.279(3.6); 8.212(2.0); 8.207(1.6); 8.190(2.6); 8.185(2.4); 8.094(3.5); 8.072(2.6); 7.955(1.4); 7.074(2.0); 7.072(2.1);

NMR Peak Lists Table 1

7.062(2.0); 7.059(2.0); 6.953(3.8); 4.598(6.7); 4.470(0.9); 4.454(1.0); 4.429(1.6); 4.413(1.6); 4.326(1.5); 4.312(1.6); 4.286(1.0); 4.271(0.9); 3.965(2.6); 3.922(3.1); 3.563(3.0); 3.520(2.6); 3.343(86.5); 2.893(9.5); 2.734(8.5); 2.639(0.5); 2.622(1.3); 2.605(1.7); 2.588(1.3); 2.570(0.6); 2.509(37.6); 2.505(47.9); 2.501(34.1); 1.706(16.0); 1.597(0.4); 0.959(11.4); 0.952(11.7); 0.942(11.4); 0.935(11.1); 0.000(4.8)
Example 804: $^1$H-NMR(400.0 MHz, DMSO):
9.011(2.8); 9.006(2.9); 8.874(0.7); 8.859(1.3); 8.844(0.6); 8.768(2.3); 8.763(2.2); 8.238(2.3); 8.233(2.5); 8.194(1.3); 8.190(1.0); 8.172(1.8); 8.167(1.7); 8.129(3.8); 8.090(2.4); 8.068(1.6); 8.024(4.0); 7.955(0.3); 4.400(1.5); 4.386(2.3); 4.373(1.5); 3.947(1.8); 3.904(2.2); 3.793(16.0); 3.550(2.1); 3.507(1.8); 3.341(73.8); 2.893(2.2); 2.733(1.9); 2.510 (23.5); 2.505(30.1); 2.501(21.9); 1.690(10.8); 0.000(3.7)
Example 805: $^1$H-NMR(400.0 MHz, DMSO):
9.067(0.9); 9.052(2.0); 9.036(1.0); 9.014(4.3); 9.008(4.4); 8.768(3.4); 8.763(3.2); 8.664(2.7); 8.651(2.7); 8.237(3.3); 8.233(3.7); 8.198(1.9); 8.193(1.5); 8.176(2.8); 8.171(2.5); 8.095(3.6); 8.073(2.4); 7.955(1.8); 7.679(3.9); 7.538(2.0); 7.526(1.9); 4.438(4.1); 4.423(4.0); 3.925(2.6); 3.881(3.2); 3.553(3.1); 3.510(2.6); 3.349(228.7); 3.312(0.4); 2.893 (12.1); 2.734(10.5); 2.514(20.5); 2.510(40.0); 2.506(51.4); 2.501(36.9); 2.497(17.9); 1.678(16.0); 0.000(1.6)
Example 806: $^1$H-NMR(400.0 MHz, DMSO):
8.960(1.1); 8.955(1.2); 8.940(0.4); 8.924(0.6); 8.909(0.3); 8.615(1.0); 8.611(1.0); 8.345(0.8); 8.332(0.9); 8.261(1.1); 8.201(0.5); 8.197(0.5); 8.179(0.7); 8.175(0.7); 8.092(0.9); 8.070(0.6); 7.953(1.0); 7.004(1.3); 6.996(1.0); 6.983(0.7); 4.590(1.8); 4.282(0.5); 4.267(0.5); 4.238(0.5); 4.224(0.5); 3.912(0.6); 3.868(0.8); 3.553(0.8); 3.510(0.7); 3.347(85.6); 2.892(6.1); 2.732(5.5); 2.508(17.0); 2.504(21.7); 2.500(17.8); 1.669(4.1); 1.352(16.0); 0.000(0.5)
Example 807: $^1$H-NMR(400.0 MHz, DMSO):
9.010(1.0); 9.004(1.1); 8.926(0.5); 8.775(0.8); 8.770(0.8); 8.346(0.7); 8.334(0.7); 8.246(0.8); 8.242(0.9); 8.203(0.5); 8.198(0.4); 8.181(0.7); 8.176(0.6); 8.094(0.9); 8.072(0.6); 7.954(0.4); 7.000(1.1); 6.983(0.5); 4.283(0.4); 4.267(0.4); 4.239(0.4); 4.224(0.4); 3.902(0.6); 3.859(0.8); 3.546(0.7); 3.503(0.6); 3.344(51.8); 2.892(3.0); 2.733(2.6); 2.513(5.8); 2.509(11.1); 2.505(14.2); 2.500(10.2); 2.496(4.9); 1.670(3.8); 1.355(16.0); 0.000(1.0)
Example 808: $^1$H-NMR(400.0 MHz, DMSO):
8.963(2.9); 8.957(2.9); 8.934(0.7); 8.918(1.4); 8.903(0.7); 8.611(2.5); 8.607(2.4); 8.298(2.2); 8.285(2.3); 8.261(2.5); 8.258(2.6); 8.198(1.3); 8.194(1.1); 8.176(1.9); 8.171(1.7); 8.093(2.5); 8.071(1.7); 7.954(1.3); 7.044(3.0); 6.936(1.6); 6.923(1.6); 4.595(4.8); 4.276(2.2); 4.260(2.2); 3.934(1.8); 3.891(2.2); 3.547(2.1); 3.504(1.8); 3.345(173.4); 3.298(0.3); 2.892(8.1); 2.733(7.3); 2.509(40.5); 2.504(50.9); 2.500(37.5); 2.398(16.0); 2.331(0.3); 1.669(11.0); 0.000(1.9)
Example 809: $^1$H-NMR(400.0 MHz, DMSO):
9.011(2.8); 9.006(2.9); 8.936(0.7); 8.921(1.4); 8.905(0.7); 8.769(2.4); 8.764(2.3); 8.298(2.2); 8.285(2.2); 8.240(2.4); 8.236(2.7); 8.200(1.3); 8.195(1.1); 8.177(1.9); 8.173(1.7); 8.094(2.5); 8.072(1.7); 7.954(1.3); 7.044(3.0); 6.935(1.6); 6.922(1.5); 4.276(2.2); 4.260(2.2); 3.925(1.8); 3.882(2.2); 3.540(2.1); 3.497(1.8); 3.345(140.9); 2.892(8.5); 2.733(7.5); 2.509(30.8); 2.505(39.4); 2.500(29.2); 2.399(16.0); 1.670(11.2); 0.000(1.8)
Example 810: $^1$H-NMR(400.0 MHz, DMSO):
8.965(1.8); 8.960(1.8); 8.863(0.4); 8.848(0.8); 8.833(0.4); 8.611(1.6); 8.607(1.5); 8.260(1.6); 8.257(1.7); 8.191(0.8); 8.187(0.7); 8.169(1.2); 8.165(1.1); 8.089(1.6); 8.067(1.0); 7.954(1.2); 7.928(1.4); 7.915(1.4); 6.425(1.0); 6.413(1.0); 6.370(1.5); 4.598(3.0); 4.253(0.7); 4.237(0.7); 4.205(0.7); 4.190(0.7); 3.955(1.1); 3.911(1.3); 3.541(1.3); 3.498(1.1); 3.345(64.9); 2.892(7.1); 2.867(16.0); 2.733(6.3); 2.509(21.1); 2.505(26.6); 2.500(19.9); 1.680(6.8); 0.000(1.2)
Example 811: $^1$H-NMR(400.0 MHz, DMSO):
9.015(1.9); 9.009(2.0); 8.885(0.4); 8.870(0.8); 8.854(0.4); 8.770(1.6); 8.764(1.5); 8.239(1.5); 8.235(1.7); 8.193(0.9); 8.188(0.7); 8.171(1.3); 8.166(1.1); 8.092(1.7); 8.069(1.1); 7.954(1.0); 7.926(1.5); 7.912(1.5); 6.460(0.8); 6.447(0.8); 6.421(1.1); 4.264(0.7); 4.248(0.7); 4.222(0.7); 4.207(0.7); 3.945(1.2); 3.902(1.4); 3.537(1.4); 3.494(1.2); 3.346(46.3); 2.890(16.0); 2.733(5.9); 2.509(18.3); 2.505(23.4); 2.500(16.9); 1.682(7.2); 0.000(1.3)
Example 812: $^1$H-NMR(400.0 MHz, DMSO):
8.996(1.1); 8.981(2.2); 8.964(5.0); 8.959(4.7); 8.612(3.7); 8.608(3.8); 8.257(4.1); 8.197(1.8); 8.193(1.7); 8.175(2.7); 8.171(2.7); 8.136(3.1); 8.124(3.2); 8.094(3.6); 8.072(2.4); 7.955(1.0); 7.190(2.0); 7.178(2.0); 6.933(4.0); 4.598(7.2); 4.374(3.8); 4.359(3.8); 3.940(2.6); 3.897(3.2); 3.555(3.1); 3.512(2.6); 3.347(156.8); 2.893(5.8); 2.734(5.3); 2.510 (37.1); 2.506(47.3); 2.502(37.5); 1.671(16.0); 0.000(2.3)
Example 813: $^1$H-NMR(400.0 MHz, DMSO):
9.012(4.1); 9.006(4.3); 8.998(1.1); 8.982(1.9); 8.967(0.9); 8.769(3.4); 8.764(3.2); 8.240(3.4); 8.236(3.7); 8.198(1.9); 8.194(1.5); 8.176(2.7); 8.172(2.4); 8.136(3.0); 8.123(3.0); 8.095(3.5); 8.073(2.3); 7.955(0.5); 7.189(1.7); 7.177(1.7); 6.932(3.6); 4.374(3.4); 4.359(3.2); 3.931(2.6); 3.887(3.2); 3.547(3.1); 3.503(2.6); 3.347(149.5); 2.893(3.5); 2.733(3.0); 2.510(34.5); 2.506(43.7); 2.501(31.7); 1.672(16.0); 0.000(1.8)
Example 814: $^1$H-NMR(400.0 MHz, DMSO):
8.964(4.3); 8.958(4.5); 8.953(1.4); 8.936(2.0); 8.921(1.0); 8.614(3.4); 8.610(3.4); 8.482(3.7); 8.478(3.7); 8.334(2.4); 8.322(2.5); 8.260(3.4); 8.255(3.7); 8.196(1.9); 8.191(1.6); 8.174(2.8); 8.170(2.5); 8.094(3.6); 8.072(2.4); 7.955(0.4); 7.249(1.4); 7.235(1.9); 7.220(1.4); 4.598(7.4); 4.445(0.4); 4.430(0.4); 4.404(1.9); 4.387(2.7); 4.369(1.9); 4.344(0.4); 4.329(0.4); 3.934(2.6); 3.891(3.3); 3.559(3.1); 3.515(2.6); 3.343(79.1); 2.893(2.9); 2.734(2.5); 2.510(32.1); 2.506 (41.1); 2.501(29.8); 1.671(16.0); 1.615(0.8); 0.000(4.8)
Example 815: $^1$H-NMR(400.0 MHz, DMSO):
11.647(1.4); 8.960(4.7); 8.955(4.8); 8.611(4.1); 8.607(3.9); 8.526(1.2); 8.511(2.4); 8.496(1.2); 8.260(3.7); 8.256(4.3); 8.193(1.9); 8.188(1.9); 8.171(2.8); 8.166(2.9); 8.088(4.2); 8.066(2.7); 7.970(0.3); 7.954(1.0); 7.263(1.7); 7.250(1.7); 7.126(1.7); 7.109(1.8); 6.821(0.3); 6.117(1.8); 6.100(3.4); 6.084(1.7); 4.596(8.3); 4.178(0.5); 4.166(0.3); 4.071(2.6); 4.063(2.6); 3.934(2.7); 3.890(3.3); 3.535(3.1); 3.492(2.6); 3.344(290.5); 2.892(6.3); 2.733(5.5); 2.677(0.4); 2.673 (0.5); 2.509(69.5); 2.504(87.9); 2.500(64.4); 2.335(0.4); 2.331(0.6); 2.327(0.4); 1.662(16.0); 1.527(8.8); 1.233(0.4); 0.000(5.3)
Example 816: $^1$H-NMR(400.0 MHz, DMSO):
11.403(1.0); 8.956(4.1); 8.951(4.3); 8.666(1.0); 8.651(2.0); 8.636(1.0); 8.603(3.5); 8.598(3.4); 8.235(3.4); 8.231(3.8); 8.168(1.8); 8.163(1.5); 8.146(2.7); 8.141(2.6); 8.076(3.7); 8.054(2.4); 7.953(0.9); 7.371(1.9); 7.364(2.0); 7.347(2.0); 7.341(2.1); 7.180(2.8); 7.175(2.7); 6.268(3.4); 6.244(3.2); 4.595(7.4); 4.062(0.5); 4.046(0.5); 4.025(2.0); 4.007(2.6); 3.990(2.0); 3.969(0.5); 3.953(0.5); 3.882(2.6); 3.839(3.2); 3.512(3.1); 3.469(2.7); 3.342(235.7); 2.892(5.8); 2.732(5.1); 2.673(0.5); 2.669(0.4); 2.509(56.8); 2.504(73.7); 2.500(54.2); 2.331(0.5); 2.327(0.3); 1.600(16.0); 0.000(7.8)
Example 817: $^1$H-NMR(400.0 MHz, DMSO):
11.404(1.0); 9.006(4.2); 9.000(4.3); 8.762(3.4); 8.757(3.3); 8.668(1.0); 8.653(1.9); 8.637(0.9); 8.214(3.4); 8.210(3.7); 8.170(1.9); 8.165(1.5); 8.147(2.8); 8.143(2.5); 8.078(3.7); 8.056(2.3); 7.954(0.9); 7.370(1.9); 7.363(2.0); 7.346(2.0); 7.340(2.1); 7.179(2.6); 7.174(2.5); 6.267(3.2); 6.244(3.1); 4.061(0.5); 4.046(0.5); 4.024(1.9); 4.007(2.5); 3.989(2.0);

NMR Peak Lists Table 1

3.967(0.5); 3.953(0.5); 3.873(2.6); 3.830(3.2); 3.504(3.2); 3.461(2.7); 3.342(335.4); 3.306(0.5); 2.892(6.0); 2.732(5.2); 2.677(0.5); 2.673(0.6); 2.668(0.5); 2.508(77.0); 2.504(98.2); 2.499(71.3); 2.335(0.5); 2.331(0.6); 2.326(0.4); 1.600 (16.0); 1.234(0.4); 0.008(0.5); 0.000(11.6); −0.008(0.6)

Example 818: $^1$H-NMR(400.0 MHz, DMSO):
8.963(1.5); 8.958(1.6); 8.814(0.4); 8.799(0.8); 8.784(0.4); 8.617(1.4); 8.613(1.3); 8.256(1.4); 8.252(1.5); 8.193(0.7); 8.188(0.6); 8.171(1.0); 8.166(1.0); 8.093(1.4); 8.071(1.7); 8.064(0.9); 8.060(0.8); 7.954(0.6); 7.412(0.7); 7.395(0.7); 6.860(0.7); 6.848(0.8); 6.842(0.7); 6.830(0.7); 4.596(2.7); 4.313(1.6); 4.298(1.6); 3.933(1.0); 3.890(1.2); 3.537(1.2); 3.494(1.0); 3.349(42.7); 2.892(3.9); 2.738(16.0); 2.552(0.4); 2.509(13.6); 2.505(17.4); 2.501(13.1); 1.666(6.0); 0.000(0.7)

Example 819: $^1$H-NMR(400.0 MHz, DMSO):
8.966(3.2); 8.961(3.1); 8.918(0.9); 8.903(1.7); 8.888(0.8); 8.609(3.0); 8.255(3.2); 8.185(1.5); 8.163(2.2); 8.159(2.0); 8.087(3.0); 8.065(1.9); 7.954(2.9); 7.863(2.4); 7.849(2.5); 6.583(1.4); 6.569(1.4); 6.535(2.8); 4.602(5.5); 4.248(2.7); 4.233(2.7); 3.930(1.9); 3.887(2.4); 3.562(2.4); 3.518(2.1); 3.344(40.4); 2.892(6.0); 2.733(14.8); 2.673(0.4); 2.552 (0.3); 2.504(56.3); 2.358(0.9); 2.335(0.7); 1.681(12.2); 0.610(1.7); 0.418(2.5); 0.411(2.5); 0.000(3.1)

Example 820: $^1$H-NMR(400.0 MHz, DMSO):
9.003(4.6); 8.997(4.7); 8.763(4.0); 8.758(3.8); 8.366(1.3); 8.352(1.9); 8.338(0.9); 8.211(4.2); 8.177(2.0); 8.173(1.7); 8.155(3.0); 8.151(2.7); 8.079(4.1); 8.056(2.7); 7.954(1.3); 4.461(0.8); 4.455(1.0); 4.439(1.1); 4.434(1.8); 4.429(1.5); 4.413(1.0); 4.407(1.1); 4.243(1.6); 4.233(1.7); 4.227(0.8); 4.222(1.8); 4.212(1.5); 4.121(0.8); 4.104(1.0); 4.095(1.6); 4.078(1.7); 4.070(1.0); 4.053(0.9); 3.889(0.7); 3.880(2.5); 3.846(0.9); 3.837(3.0); 3.494(3.2); 3.451(2.7); 3.373(1.7); 3.345(172.1); 3.324(3.2); 3.303(1.8); 3.288(1.7); 3.276(1.4); 3.272(1.4); 3.259(1.3); 3.238(1.7); 3.224(0.6); 3.214(1.9); 3.207(1.0); 3.192(1.2); 3.182(1.2); 3.160(0.7); 2.893(8.2); 2.733(7.2); 2.509(40.6); 2.505(52.0); 2.501(38.5); 1.987 (0.4); 1.978(0.6); 1.968(0.7); 1.961(0.9); 1.951(0.9); 1.942(1.0); 1.933(0.9); 1.925(0.6); 1.915(0.5); 1.817(0.5); 1.797(0.9); 1.781(1.3); 1.761(1.1); 1.745(0.7); 1.726(0.3); 1.611(16.0); 0.000(3.4)

Example 821: $^1$H-NMR(400.0 MHz, DMSO):
9.013(4.1); 9.007(4.2); 8.951(0.9); 8.936(1.9); 8.921(0.9); 8.774(3.3); 8.768(3.2); 8.481(3.8); 8.477(3.8); 8.333(2.4); 8.321(2.5); 8.239(3.3); 8.235(3.7); 8.197(1.9); 8.193(1.5); 8.175(2.7); 8.170(2.4); 8.096(3.5); 8.074(2.3); 7.954(0.9); 7.247(1.4); 7.232(1.9); 7.218(1.3); 4.444(0.4); 4.428(0.4); 4.403(1.9); 4.385(2.6); 4.367(1.8); 4.342(0.4); 4.327(0.4); 3.923(2.6); 3.880(3.2); 3.550(3.1); 3.507(2.6); 3.384(0.5); 3.344(209.6); 3.299(0.4); 2.892(5.9); 2.733(5.1); 2.674(0.4); 2.509(48.1); 2.505(61.5); 2.500(44.7); 2.331(0.4); 1.671(16.0); 0.000(4.8)

Example 825: $^1$H-NMR(400.0 MHz, DMSO):
9.005(3.7); 9.000(3.9); 8.955(2.6); 8.950(2.6); 8.765(3.2); 8.760(3.1); 8.732(1.7); 8.714(1.7); 8.606(2.2); 8.601(2.1); 8.447(0.6); 8.432(1.2); 8.417(0.6); 8.237(2.2); 8.233(2.4); 8.215(3.1); 8.178(1.9); 8.173(2.4); 8.169(1.2); 8.156(2.8); 8.151(3.9); 8.147(1.9); 8.081(4.1); 8.059(2.6); 4.592(4.6); 4.121(0.6); 4.103(0.9); 4.084(0.7); 3.902(2.5); 3.889(1.7); 3.858(3.1); 3.846(2.1); 3.510(2.1); 3.498(3.1); 3.466(1.8); 3.455(2.6); 3.388(0.6); 3.351(263.9); 3.303(0.7); 3.288(0.6); 3.272(0.7); 3.256(0.8); 3.241(0.5); 3.208(0.4); 3.194(0.8); 3.178(0.6); 3.161(0.4); 2.893(1.8); 2.871(0.4); 2.858(0.8); 2.846(0.8); 2.838(1.1); 2.825(1.4); 2.812(1.7); 2.804(1.6); 2.791(2.0); 2.780(1.5); 2.760(1.5); 2.746(0.8); 2.734(2.2); 2.714(0.5); 2.679(0.4); 2.675(0.4); 2.575(0.5); 2.560(0.7); 2.553(0.7); 2.539(1.2); 2.510(47.9); 2.506(61.0); 2.502(44.6); 2.354(0.5); 2.325(1.4); 2.295(1.2); 2.264(0.4); 1.616(11.5); 1.608(16.0); 0.000(3.4)

Example 833: $^1$H-NMR(400.0 MHz, DMSO):
11.648(0.9); 9.009(3.6); 9.004(3.6); 8.770(3.3); 8.528(1.0); 8.513(1.9); 8.498(1.0); 8.235(3.6); 8.194(1.4); 8.190(1.5); 8.172(2.0); 8.167(2.3); 8.090(3.3); 8.068(2.2); 7.970(0.7); 7.954(1.6); 7.366(0.5); 7.350(0.6); 7.263(1.1); 7.249(1.1); 7.125(1.2); 7.109(1.3); 6.833(0.5); 6.821(0.6); 6.815(0.6); 6.803(0.5); 6.117(1.1); 6.100(2.1); 6.084(1.1); 4.192(0.6); 4.179(1.0); 4.165(0.7); 4.077(1.7); 4.067(1.9); 4.057(1.6); 3.925(1.9); 3.881(2.3); 3.534(1.1); 3.527(2.1); 3.491(1.0); 3.484(1.8); 3.342(207.7); 2.892(8.6); 2.732(7.8); 2.673(0.5); 2.508(65.7); 2.504(79.4); 2.500(59.9); 2.330(0.5); 1.671(6.0); 1.663(10.8); 1.526(16.0); 1.234(0.3); 0.000(4.4)

Example 834: $^1$H-NMR(300.2 MHz, DMSO):
8.934(0.7); 8.927(0.8); 8.911(7.5); 8.904(7.8); 8.602(0.5); 8.596(0.6); 8.565(0.6); 8.559(0.6); 8.534(6.2); 8.528(6.1); 8.386(1.7); 8.366(3.4); 8.346(1.8); 8.274(0.4); 8.253(6.2); 8.247(6.8); 8.139(3.1); 8.132(3.0); 8.109(5.4); 8.103(5.4); 8.043(7.1); 8.014(4.0); 7.895(0.8); 7.688(1.3); 4.551(1.4); 4.536(14.4); 3.905(3.7); 3.844(6.1); 3.796(0.4); 3.769(3.2); 3.744(4.8); 3.719(3.4); 3.688(6.4); 3.667(1.8); 3.656(3.6); 3.640(3.7); 3.627(5.9); 3.613(2.6); 3.586(3.0); 3.576(1.7); 3.560(5.5); 3.544(1.6); 3.534(4.2); 3.509(1.8); 3.280(33.4); 3.224(38.4); 3.199(1.3); 3.182(3.3); 3.156(5.5); 3.131(5.6); 3.113(3.9); 3.103(5.0); 3.089(3.5); 3.079(3.1); 3.064(2.1); 3.054(1.0); 3.040(0.7); 2.832(5.2); 2.673(4.5); 2.451(3.9); 2.446(5.4); 2.440(4.1); 2.129(0.4); 2.104(0.9); 2.079(2.0); 2.055(2.7); 2.030(2.4); 2.006(1.8); 1.988(1.4); 1.980(1.5); 1.965(2.4); 1.950(1.5); 1.940(2.0); 1.930(1.8); 1.925(1.7); 1.915(0.9); 1.899(0.8); 1.577(0.5); 1.554(0.5); 1.520(2.2); 1.497(5.4); 1.474(5.0); 1.451(2.1); 1.438(1.2); 1.426(0.7); 1.413(2.3); 1.400(1.1); 1.388(2.4); 1.374(1.9); 1.362(1.0); 1.348(1.8); 1.323(0.7); 1.215(12.4); 1.201(14.9); 1.193(14.2); 1.180(16.0); 1.159(3.8); 1.139(0.8); 1.132(0.9); 1.115 (0.9); 1.091(0.5); 0.240(0.5); 0.220(0.4); −0.063(1.2)

Example 835: $^1$H-NMR(300.2 MHz, CDCl3):
8.935(0.9); 8.928(1.0); 8.311(0.7); 8.303(0.7); 8.165(0.3); 8.159(0.3); 8.135(0.7); 8.129(0.8); 8.087(0.9); 8.057(0.4); 8.025(0.5); 8.018(0.5); 8.008(0.5); 8.001(0.5); 7.786(0.8); 7.780(0.8); 7.439(0.2); 7.433(0.4); 7.415(0.4); 7.409(0.4); 7.265(2.7); 6.758(0.5); 6.741(0.5); 6.734(0.5); 6.717(0.5); 4.356(0.5); 4.338(0.9); 4.319(0.5); 3.955(0.8); 3.897(0.9); 3.353(0.9); 3.296(0.7); 2.958(0.7); 2.886(0.6); 2.884(0.6); 1.767(4.5); 1.655(0.5); 1.630(16.0); 0.000(2.0)

Example 836: $^1$H-NMR(400.1 MHz, DMSO):
9.540(0.3); 9.000(0.7); 8.995(0.8); 8.978(5.8); 8.973(5.6); 8.803(1.7); 8.789(3.2); 8.775(1.6); 8.672(0.6); 8.609(5.5); 8.606(5.3); 8.323(5.7); 8.320(5.7); 8.202(2.7); 8.198(2.8); 8.180(4.1); 8.112(5.2); 8.090(3.2); 7.965(0.7); 7.812(6.4); 7.796(1.2); 4.610(1.3); 4.597(9.7); 4.451(0.6); 4.437(0.6); 4.311(5.2); 4.297(5.1); 4.257(0.3); 4.221(2.3); 4.203(6.5); 4.184(6.5); 4.166(2.3); 3.968(3.1); 3.922(4.7); 3.768(4.6); 3.722(3.1); 3.369(0.6); 3.321(120.4); 3.293(28.4); 3.271(1.3); 3.244(0.4); 2.905(0.5); 2.897(1.1); 2.738(0.8); 2.696(0.4); 2.677(0.5); 2.508(88.6); 2.458(1.0); 2.335(0.6); 1.403(1.1); 1.389(8.1); 1.371(16.0); 1.353(7.7); 1.264(0.5); 1.250(0.4); 0.307(0.3)

Example 837: $^1$H-NMR(400.1 MHz, DMSO):
9.011(3.9); 9.006(3.9); 8.772(3.9); 8.767(3.6); 8.598(1.2); 8.584(2.3); 8.570(1.1); 8.226(4.1); 8.183(1.9); 8.179(1.7); 8.161(2.9); 8.157(2.5); 8.089(3.7); 8.067(2.4); 7.714(4.5); 4.296(0.6); 4.282(0.6); 4.258(2.3); 4.244(4.0); 4.230(2.2); 4.206(0.6); 4.191(0.5); 4.156(1.6); 4.138(4.4); 4.120(4.4); 4.102(1.5); 3.902(2.5); 3.859(3.1); 3.570(3.7); 3.519(3.5); 3.476(2.7); 3.320(61.7); 3.270(0.3); 2.906(1.3); 2.898(0.9); 2.738(0.6); 2.677(0.4); 2.508(52.7); 2.335(0.4); 1.834(0.5); 1.799(0.5); 1.762(0.6); 1.640(16.0); 1.612(0.6); 1.400(0.3); 1.315(5.4); 1.296(10.7); 1.278(5.3); 1.250(0.3); 0.948(1.0); 0.753(1.6)

-continued

NMR Peak Lists Table 1

Example 838: ¹H-NMR(400.1 MHz, DMSO):
8.978(7.2); 8.972(7.4); 8.713(5.6); 8.708(5.3); 8.303(1.5); 8.289(2.9); 8.274(1.5); 8.248(5.7); 8.244(6.0); 8.152(3.0); 8.147(2.7); 8.130(4.8); 8.125(4.6); 8.061(6.1); 8.039(3.8); 7.915(1.6); 8.897(4.2); 3.851(6.1); 3.678(6.0); 3.632(4.2); 3.277(62.0); 3.240(39.7); 3.224(1.9); 3.206(3.2); 3.191(4.6); 3.176(3.1); 3.159(1.6); 3.144(0.6); 2.853(12.3); 2.694 (10.0); 2.693(10.0); 2.651(16.0); 2.633(0.4); 2.486(0.8); 2.473(16.7); 2.468(33.5); 2.464(44.9); 2.459(32.4); 2.455 (15.6); 1.374(2.2); 1.356(6.5); 1.338(6.6); 1.321(2.3); 0.666(0.4); 0.659(0.5); 0.654(0.4); 0.646(1.1); 0.641(1.0); 0.637(0.9); 0.629(1.8); 0.621(1.0); 0.616(1.1); 0.609(1.2); 0.597(0.7); 0.591(0.5); 0.378(1.7); 0.369(5.2); 0.364(5.6); 0.358(2.4); 0.355(2.5); 0.348(5.2); 0.344(4.9); 0.335(1.7); 0.013(1.9); 0.003(5.3); 0.000(6.0); −0.009(5.7); −0.012(5.2); −0.023(1.7)
Example 839: ¹H-NMR(400.1 MHz, DMSO):
9.049(0.6); 9.043(0.6); 9.024(7.5); 9.019(7.6); 8.826(0.4); 8.821(0.4); 8.760(5.8); 8.754(5.6); 8.608(0.5); 8.603(0.5); 8.430(1.5); 8.415(3.0); 8.401(1.5); 8.337(0.3); 8.315(0.4); 8.310(0.6); 8.297(5.9); 8.293(6.2); 8.199(3.2); 8.195(3.2); 8.177(4.9); 8.173(5.0); 8.108(6.4); 8.086(4.0); 7.959(2.2); 7.739(1.0); 3.951(4.2); 3.905(6.1); 3.826(2.9); 3.807(4.5); 3.788(3.2); 3.738(2.2); 3.732(6.5); 3.718(3.5); 3.706(3.3); 3.697(2.2); 3.686(6.1); 3.642(2.3); 3.623(4.8); 3.603(3.6); 3.584(1.5); 3.374(0.7); 3.323(124.5); 3.287(39.5); 3.261(0.6); 3.242(2.8); 3.222(4.6); 3.214(1.3); 3.203(3.6); 3.196 (2.1); 3.186(3.1); 3.170(3.2); 3.158(1.9); 3.141(0.9); 3.125(0.4); 2.897(16.0); 2.738(13.1); 2.696(1.5); 2.678(0.4); 2.563 (0.4); 2.559(0.4); 2.531(1.1); 2.517(22.9); 2.513(46.1); 2.509(61.9); 2.504(44.5); 2.500(21.4); 2.335(0.4); 2.156(0.8); 2.138(1.9); 2.119(2.7); 2.101(2.3); 2.083(1.2); 2.066(0.4); 2.056(1.1); 2.044(1.1); 2.038(1.4); 2.026(2.2); 2.015(1.3); 2.008(2.0); 1.995(2.5); 1.989(0.9); 1.977(0.7); 1.595(0.3); 1.577(1.8); 1.561(4.2); 1.544(4.0); 1.540(3.7); 1.526(1.5); 1.511(0.4); 1.491(0.9); 1.472(2.0); 1.461(1.0); 1.453(1.9); 1.442(1.8); 1.433(0.8); 1.423(1.7); 1.404(0.6); 1.199(0.4); 1.181(0.7); 1.173(0.4); 1.163(0.4)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contain therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

The following Table 2 illustrates in a non limiting manner examples of compounds according to formula (II).

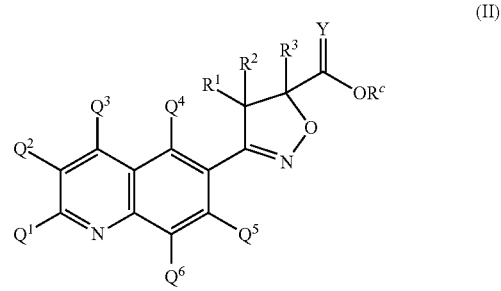

(II)

TABLE 2

| Ex-No | $Q^1$ | $Q^2$ | $Q^3$ | $Q^4$ | $Q^5$ | $Q^6$ | $R^1$ | $R^2$ | $R^3$ | Y | $R^c$ | Log P |
|---|---|---|---|---|---|---|---|---|---|---|---|---|
| II-01 | H | chloro | H | H | H | H | H | H | $CH_3$ | O | H | 1.87[a] |
| II-02 | H | bromo | H | H | fluoro | fluoro | H | H | $CH_3$ | O | H | 2.25[a] |
| II-03 | H | bromo | H | H | H | H | H | H | $CH_3$ | O | H | 1.94[a] |
| II-04 | H | bromo | H | H | H | H | H | H | methoxy | O | H | 1.73[a] |
| II-05 | H | H | H | H | methoxy | fluoro | H | H | $CH_3$ | O | H | 1.39[a] |
| II-06 | H | bromo | H | H | H | H | H | H | chloromethyl | O | H | 2.11[a] |
| II-07 | H | bromo | H | H | fluoro | H | H | H | $CH_3$ | O | H | 2.14[a] |
| II-08 | H | bromo | H | H | H | H | H | H | trifluoromethyl | O | H | 1.85[a] |
| II-09 | H | iodo | H | H | H | H | H | H | $CH_3$ | O | H | 2.05[a] |
| II-10 | H | ethynyl | H | H | H | H | H | H | $CH_3$ | O | H | 1.71[a] |
| II-11 | H | bromo | H | H | H | H | H | H | bromomethyl | O | H | 2.19[a] |

TABLE 2-continued

| Ex-No | Q¹ | Q² | Q³ | Q⁴ | Q⁵ | Q⁶ | R¹ | R² | R³ | Y | R^c | Log P |
|---|---|---|---|---|---|---|---|---|---|---|---|---|
| II-12 | H | bromo | H | H | H | H | H | H | phenyl | O | H | 2.76[a] |
| II-13 | H | bromo | H | H | fluoro | fluoro | H | H | trifluoromethyl | O | H | 2.01[a] |
| II-14 | H | bromo | H | H | H | H | H | H | trifluoromethyl | O | $CH_3$ | 3.4[a] |
| II-15 | H | bromo | H | H | H | H | H | $CH_3$ | $CH_3$ | O | $CH_3$ | 2.94[a] |
| II-16 | H | bromo | H | H | H | H | H | H | chloromethyl | O | $CH_3$ | 3.03[a] |
| II-17 | H | bromo | H | H | H | H | H | H | phenyl | O | $CH_3$ | 2.69[a] |
| II-18 | H | bromo | H | H | H | H | H | H | cyclopropyl | O | $CH_3$ | 3.27[a] |
| II-19 | H | bromo | H | H | H | H | H | H | 1-hydroxyethyl | O | $CH_3$ | 2.18[a] |
| II-20 | H | H | H | H | H | H | H | H | $CH_3$ | O | ethyl | 1.6[a] |
| II-21 | $CH_3$ | H | H | H | H | H | H | H | $CH_3$ | O | ethyl | |
| II-22 | H | bromo | H | H | fluoro | fluoro | H | H | trifluoromethyl | O | $CH_3$ | 3.72[a] |
| II-23 | H | chloro | H | H | H | H | H | H | $CH_3$ | O | $CH_3$ | 2.58[a] |
| II-24 | H | bromo | H | H | fluoro | fluoro | H | H | methoxy | O | $CH_3$ | 3.04[a] |
| II-25 | H | bromo | H | H | H | H | H | H | methoxy | O | $CH_3$ | 3.29[a] |
| II-26 | H | (trimethyl-silyl)ethynyl | H | H | H | H | H | H | $CH_3$ | O | $CH_3$ | 4.31[a] |
| II-27 | H | bromo | H | H | fluoro | fluoro | H | H | $CH_3$ | O | $CH_3$ | 3.06[a] |
| II-28 | H | bromo | H | H | H | H | H | $CH_3$ | ethoxy | O | ethyl | |
| II-29 | H | H | H | H | fluoro | fluoro | H | H | $CH_3$ | O | $CH_3$ | 2.11[a] |
| II-30 | H | iodo | H | H | H | H | H | H | $CH_3$ | O | $CH_3$ | 2.71[a] |
| II-31 | H | bromo | H | H | H | H | H | $CH_2CH_2CH_2$ |  | O | $CH_3$ | 3.23[a] |
| II-32 | H | bromo | H | H | H | H | H | $CH_2CH_2CH_2O$ |  | O | $CH_3$ | 2.80[a] |
| II-33 | H | bromo | H | H | H | H | H |  | $CH_3$ | O | $CH_3$ | 2.69[a] |
| II-34 | H | bromo | H | H | fluoro | H | H | H | $CH_3$ | O | $CH_3$ | 2.94[a] |
| II-35 | H | ethynyl | H | H | H | H | H | H | $CH_3$ | O | $CH_3$ | 2.35[a] |
| II-36 | H | Br | H | H | H | H | H | H | $CH_2F$ | O | H | 1.94[a] |
| II-37 | H | Br | H | H | H | H | H | H | Cyclopropyl | O | H | 2.43[a] |
| II-38 | OMe | Br | H | H | H | H | H | H | Me | O | H | 2.64[a] |
| II-39 | H | Br | H | H | H | H | H | H | (1E)-N-hydroxy-ethanimidoyl | O | Me | 2.58[a] |
| II-40 | H | Br | H | H | H | H | H | H | Ac | O | Me | 2.94[a] |
| II-41 | H | Br | H | H | H | H | $CH_2CH_2$ | H |  | O | Me | 2.71[a] |
| II-42 | H | Br | H | H | H | H | H | Et | Me | O | Et | 3.74[a] |
| II-43 | Cl | Br | H | H | H | H | H | H | Me | O | H | 2.57[a] |
| II-44 | Cl | Br | H | H | H | H | H | H | Me | O | Me | 3.74[a] |
| II-45 | OH | Br | H | H | H | H | H | H | Me | O | Me | 1.74[a] |
| II-46 | CN | Br | H | H | H | H | H | H | Me | O | H | 2.23[a] |
| II-47 | CN | Br | H | H | H | H | H | H | Me | O | Me | 3.02[a] |
| II-48 | H | Ethynyl | H | H | H | H | H | H | OMe | O | H | |
| II-49 | H | Br | H | H | H | H | H | OEt | Me | O | Et | 3.99[a] |
| II-50 | H | Br | H | H | H | H | H | H | 2-methoxy-2-oxoethyl | O | H | 1.98[a] |
| II-51 | H | Br | H | H | H | H | H |  | CH(Me) | O | Me | 3.09[a] |
| II-52 | H | Br | H | H | H | H | H | H | $CH_2OH$ | O | Me | 1.99[a] |
| II-53 | H | Br | H | H | H | H | H | $CH_2$ | $CH_2$ | O | Me | 2.77[a] |
| II-54 | H | Br | H | H | H | H | H | H | $CH_2SiMe_3$ | O | H | 3.42[a] |
| II-55 | Cl | Ethynyl | H | H | H | H | H | H | Me | O | H | 2.24[a] |
| II-56 | Cl | Ethynyl | H | H | H | H | H | H | Me | O | Me | 3.01[a] |
| II-57 | H | Br | H | H | H | H | H | H | OEt | O | Et | 2.53[a] |
| II-58 | H | Br | H | H | H | H | H | H | $CH_2SiMe_3$ | O | Et | 3.80[a] |
| II-59 | H | Br | H | H | H | H | H | H | Me | O | i-Pr | 3.53[a] |
| II-60 | Cl | I | H | H | H | H | H | H | Me | O | Me | 3.34 + 3.62[a] |
| II-61 | H | I | H | H | H | H | H | H | OMe | O | H | |
| II-62 | H | Br | H | H | H | H | H | H | $CH_2F$ | O | Et | 3.13[a] |
| II-63 | H | Br | H | H | H | H | H | H | Et | O | Et | 3.53[a] |
| II-64 | H | Br | H | H | H | H | H | H | Et | O | H | 2.30[a] |
| II-65 | H | Br | H | H | H | H | H | H | cyclopropylmethyl | O | Et | |
| II-66 | H | Br | H | H | H | H | H | H | cyclopropylmethyl | O | H | 2.70[a] |
| II-67 | H | (trimethyl-silyl)ethynyl | H | H | H | H | H | H | Et | O | Et | 5.19[a] |
| II-68 | CN | I | H | H | H | H | H | H | Me | O | Me | 3.02[a] |
| II-69 | H | Ethynyl | H | H | H | H | H | H | Et | O | H | 2.05[a] |
| II-70 | H | Br | H | H | H | H | H | H | 1-chlorovinyl | O | Me | 3.68[a] |
| II-71 | H | Ethynyl | H | H | H | H | H | H | OMe | O | 4-{[5-({[3-(3-ethynylquinolin-6-yl)-5-methoxy-4,5-dihydro-1,2-oxazol-5-yl]carbonyl}oxy)pentan-2-yl]amino}pentyl | 2.20[a] |
| II-72 | H | Br | H | H | H | H | H | H | prop-1-en-2-yl | O | Me | 3.44[a] |
| II-73 | H | Br | H | H | H | H | H | H | prop-1-en-2-yl | O | H | 2.52[a] |
| II-74 | H | Ethynyl | H | H | Me | H | H | H | Me | O | Me | 3.07[a] |
| II-75 | H | Ethynyl | H | H | H | Cl | H | H | Me | O | Me | 2.92[a] |
| II-76 | H | Ethynyl | H | H | H | Cl | H | H | Me | O | Me | 3.29[a] |
| II-77 | H | Br | H | H | H | H | H | H | 1-hydroxyethyl | O | H | 1.60 + 1.65[a] |
| II-78 | H | Ethynyl | H | H | H | Cl | H | H | Me | O | H | 2.20[a] |
| II-79 | H | Br | H | H | H | Cl | H | H | Me | O | H | 2.45[a] |
| II-80 | H | Br | H | H | H | Me | H | H | Me | O | Me | 3.55[a] |
| II-81 | H | Ethynyl | H | H | H | Me | H | H | Me | O | H | 2.30[a] |

TABLE 2-continued

| Ex-No | $Q^1$ | $Q^2$ | $Q^3$ | $Q^4$ | $Q^5$ | $Q^6$ | $R^1$ | $R^2$ | $R^3$ | Y | $R^c$ | Log P |
|---|---|---|---|---|---|---|---|---|---|---|---|---|
| II-82 | CN | I | H | H | H | H | H | H | Me | O | H | 2.24[a] |
| II-83 | Cl | I | H | H | H | H | H | H | Me | O | H | 2.59[a] |
| II-84 | H | Br | H | H | H | H | H | H | SMe | O | Me | 3.05[a] |
| II-85 | H | Br | H | H | H | Me | H | H | Me | O | H | 2.64[a] |
| II-86 | H | Ethynyl | H | H | H | Me | H | H | OMe | O | Et | 3.46[a] |
| II-87 | H | Br | H | H | H | Cl | H | H | OMe | O | Et | 3.69[a] |
| II-88 | H | Br | H | H | H | H | H | H | SMe | O | H | 2.01[a] |
| II-89 | H | Br | H | H | H | Cl | H | H | OMe | O | H | 2.19[a] |
| II-90 | H | Ethynyl | H | H | H | Cl | H | H | OMe | O | H | 1.95[a] |
| II-91 | H | Br | H | H | H | Me | H | H | OMe | O | Et | 3.99[a] |
| II-92 | H | Br | H | H | H | Me | H | H | OMe | O | H | 2.42[a] |
| II-93 | H | Ethynyl | H | H | H | Me | H | H | OMe | O | H | 2.07[a] |
| II-94 | H | Br | H | H | H | H | H | H | CN | O | H | 1.42[a] |
| II-95 | H | Br | Cl | H | H | H | H | H | Me | O | Me | 3.29[a] |
| II-96 | H | Br | Cl | H | H | H | H | H | Me | O | H | 2.34[a] |

Measurement of logP values was performed according EEC directive 79/831 Annex V.A8 by HPLC (High Performance Liquid Chromatography) on reversed phase columns with the following methods:
[a]Measurement of LC-MS was done at pH 2.7 with 0.1% formic acid in water and with acetonitrile (contains 0.1% formic acid) as eluent with a linear gradient from 10% acetonitrile to 95% acetonitrile. Calibration was done with not branched alkan2-ones (with 3 to 16 carbon atoms) with known logP-values (measurement of logP values using retention times with linear interpolation between successive alkanones). lambda-maX-values were determined using UV-spectra from 200 nm to 400 nm and the peak values of the chromatographic signals.

NMR-Peak Lists

1-NMR data of selected examples are written in form of 1-NMR-peak lists. To each signal peak are listed the δ-value in ppm and the signal intensit in round brackets. Between the δ-value-signal intensity pairs are semicolons as delimiters. The peak list of an example has therefore the form:

$\delta_1$ (intensity$_1$); $\delta_2$);......; $\delta_i$);......; $\delta_n$ (intensity$_n$)

NMR Peak List Table 2

Example II-01: 1H-NMR(400.0 MHz, DMSO):

8.937(2.1); 8.931(2.8); 8.927(1.7); 8.609(1.7); 8.604(2.3); 8.307(0.6); 8.304(0.4); 8.212(3.1); 8.163(1.4); 8.158(1.3); 8.141(2.5); 8.136(2.6); 8.092(2.7); 8.070(1.4); 7.952(1.9); 3.944(2.8); 3.901(3.3); 3.510(2.0); 3.467(1.9); 3.444(0.7); 3.338(42.4); 2.895(15.5); 2.736(12.5); 2.679(0.4); 2.674(0.6); 2.670(0.4); 2.528(1.7); 2.523(2.8); 2.514(34.6); 2.510(70.5); 2.505(92.7); 2.501(65.8); 2.496(30.7); 2.336(0.4); 2.332(0.6); 2.327(0.4); 1.624(16.0); 1.235(0.4); 0.000(3.3)

Example II-2, Solvent: DMSO, Spectrometer: 250, 13 MHz 9.1130 (3.21); 9.1043 (3.60); 8.8942 (2.14); 8.8873 (3.02); 8.8805 (2.19); 8.2676 (1.51); 8.2593 (1.72); 8.2392 (1.53); 8.2312 (1.65); 4.0220 (0.33); 3.9830 (1.55); 3.9170 (2.06); 3.5537 (2.05); 3.4839 (1.53); 3.3315 (0.90); 2.5247 (2.82); 2.5175 (5.89); 2.5103 (7.99); 2.5032 (5.81); 2.4960 (2.69); 1.9967 (1.26); 1.9176 (3.86); 1.6367 (16.00); 1.2105 (0.35); 1.1819 (0.68); 1.1536 (0.35)

Example II-03: 1H-NMR(300.2 MHz, DMSO):

13.312(0.7); 9.004(4.2); 8.996(4.5); 8.767(2.9); 8.760(2.8); 8.209(2.8); 8.204(3.4); 8.178(1.9); 8.172(1.3); 8149(31); 8.142(2.7); 8.082(3.5); 8.052(1.9); 4.042(0.5); 4.018(0.6); 3.949(2.5); 3.891(3.2); 3.523(3.1); 3.465(2.5); 3.329(1.2); 2.517(1.8); 2.511(3.9); 2.504(5.5); 2.498(4.0); 2.492(2.0); 1.991(2.4); 1.626(16.0); 1.199(0.7); 1.176(1.4); 1.152(0.7); 0.000(6.3)

Example II-04: 1H-NMR(300.2 MHz, DMSO):

9.018(3.0); 9.011(3.0); 8.750(2.6); 8.743(2.6); 8.281(2.7); 8.276(2.8); 8.191(1.2); 8.185(1.1); 8.161(2.3); 8.155(2.1); 8.100(2.9); 8.070(1.5); 4.012(1.7); 3.951(2.5); 3.727(2.5); 3.666(1.8); 3.349(16.0); 2.748(0.3); 2.697(0.8); 2.645(0.8); 2.615(0.4); 2.594(0.3); 2.513(2.6); 2.507(3.4); 2.501(2.6); 1.190(0.5); 0.000(2.3)

Example II-05, Solvent DMSO, Spectrometer: 250,13 MHz 8.9848 (1.82); 8.9787 (2.04); 8.9681 (2.03); 8.9619 (1.98); 8.4992 (0.98); 8.4938 (1.75); 8.4881 (1.06); 8.4659 (1.15); 8.4600 (1.89); 8.1420 (3.44); 8.1348 (3.52); 7.6235 (2.03); 7.6066 (1.94); 7.5901 (1.89); 7.5732 (1.89); 4.0499 (12.07); 4.0418 (11.84); 3.9542 (2.66); 3.8840 (3.45); 3.5176 (3.41); 3.4474 (2.65); 3.3573 (0.47); 2.5239 (0.74); 2.5171 (1.54); 2.5098 (2.11); 2.5026 (1.50); 2.4958 (0.68); 1.9937 (0.41); 1.9164 (2.41); 1.6192 (16.00)

Example II-06: 1H-NMR(400.0 MHz, DMSO):

9.010(4.0); 9.004(5.4); 9.001(4.0); 8.764(4.7); 8.307(1.6); 8.303(1.5); 8.299(1.1); 8.264(6.2); 8.178(3.1); 8174(2.8); 8156(4.8); 8.152(4.8); 8.087(5.0); 8.064(3.1); 7.952(2.2); 4.141(0.4); 4.110(12.8); 4.083(0.4); 4.024(4.8); 3.980(6.3); 3.754(5.9); 3.710(4.6); 3.669(0.4); 3.656(0.4); 3.651(0.4); 3.339(112.4); 3.165(0.8); 3.132(0.6); 3.106(0.5); 3.061(0.6); 3.040(0.3); 2.895(16.0); 2.878(0.4); 2.754(0.4); 2.736(13.1); 2.679(1.2); 2.674(1.6); 2.670(1.2); 2.564(1.8); 2.550(3.7); 2.536(2.7); 2.527(5.3); 2.514(100.0); 2.510(198.0); 2.505(257.0); 2.501(183.2); 2.496(86.4); 2.336(1.2); 2.332(1.6); 2.327(1.1); 1.330(0.4); 1.237(0.6); 0.057(0.4); 0.000(8.2)

Example II-08: 1H-NMR(400.0 MHz, DMSO):

9.032(3.5); 9.027(3.6); 8.738(2.9); 8.733(2.9); 8.336(3.2); 8.332(3.4); 8.310(0.8); 8.183(1.7); 8.178(1.5); 8.160(2.9); 8.156(2.9); 8.107(3.6); 8.085(2.0); 7.952(2.0); 4.282(1.1); 4.236(2.5); 4.176(2.2); 4.131(1.0); 3.788(0.3); 3.386(15.2); 3.148(0.9); 3.135(0.8); 3.078(0.5); 3.063(0.6); 3.003(0.4); 2.985(0.3); 2.893(16.0);

NMR Peak List Table 2

2.734(13.0); 2.678(0.6); 2.673(0.8); 2.669(0.6); 2.565(1.2); 2.551(2.5); 2.537(1.6); 2.526(2.6); 2.513(43.2); 2.509(87.1); 2.504(114.8); 2.500(83.1); 2.495(40.2); 2.336(0.6); 2.331(0.8); 2.326(0.6); 0.000(3.3)
Example II-09: 1H-NMR(400.1 MHz, DMSO):

9.091(4.2); 9.085(4.3); 8.921(3.2); 8.917(2.9); 8.158(5.7); 8.136(3.0); 8.131(2.1); 8.041(3.0); 8.019(2.1); 3.944(0.3); 3.931(2.8); 3.901(0.4); 3.888(3.3); 3.715(1.6); 3.525(0.4); 3.507(3.2); 3.464(2.7); 2.892(0.4); 2.513(4.5); 2.509(9.3); 2.504(12.5); 2.500(8.9); 2.495(4.2); 1.621(16.0); 0.000(8.2)
Example II-10: 1H-NMR(300.2 MHz, DMSO):

8.956(4.2); 8.949(4.4); 8.609(3.1); 8.602(3.0); 8.230(3.0); 8.224(3.5); 8.177(1.8); 8.170(1.4); 8.147(3.0); 8.141(2.7); 8.080(3.7); 8.051(2.0); 4.594(8.2); 3.955(2.6); 3.898(3.2); 3.526(3.0); 3.469(2.5); 3.327(2.2); 2.515(3.3); 2.509(7.3); 2.503(10.1); 2.497(7.4); 2.491(3.5); 1.621(16.0); 0.000(10.3); -0.011(0.4)
Example II-11: 1H-NMR(400.0 MHz, DMSO):

9.012(1.8); 9.006(2.3); 8.811(0.4); 8.805(0.5); 8.774(1.2); 8.768(1.5); 8.488(0.5); 8.483(0.6); 8.309(0.7); 8.306(0.4); 8.273(1.4); 8.269(1.9); 8.260(0.4); 8.255(0.6); 8.237(0.5); 8.233(0.7); 8.179(0.9); 8.174(1.0); 8156(1.7); 8.152(2.0); 8.132(0.4); 8.088(1.6); 8.065(1.0); 7.952(1.9); 6.892(0.7); 4.067(1.4); 4.023(1.8); 3.983(3.4); 3.737(1.7); 3.693(1.4); 3.503(0.6); 3.366(73.3); 2.894(16.0); 2.735(13.1); 2.679(0.6); 2.674(0.8); 2.669(0.6); 2.567(0.9); 2.553(2.0); 2.539(1.3); 2.527(2.4); 2.514(45.3); 2.509(90.2); 2.505(118.7); 2.500(84.4); 2.496(39.7); 2.336(0.5); 2.331(0.7); 2.327(0.5); 1.235(0.4); 0.000(3.6)
Example II-12: 1H-NMR(400.0 MHz, DMSO):

9.009(1.8); 9.003(1.8); 8.744(1.3); 8.739(1.2); 8.298(1.3); 8.293(1.3); 8.204(0.7); 8.199(0.7); 8.182(1.0); 8.177(1.0); 8.087(1.3); 8.064(0.9); 7.556(1.0); 7.553(1.5); 7.535(1.4); 7.469(0.4); 7.456(1.9); 7.452(0.9); 7.436(1.1); 7.406(0.8); 7.388(0.9); 4.425(1.0); 4.382(1.2); 3.918(1.1); 3.903(16.0); 3.875(0.9); 3.328(32.9); 2.676(0.4); 2.672(0.5); 2.667(0.4); 2.542(0.4); 2.512(33.1); 2.507(62.8); 2.503(79.8); 2.498(57.1); 2.494(27.5); 2.334(0.3); 2.329(0.5); 2.325(0.3)
Example II-13, Solvent: DMSO, Spectrometer: 250,13 MHz 9.2251 (0.54); 9.2176 (0.49); 9.1373 (15.12); 9.1287 (16.00); 9.0484 (0.47); 9.0397 (0.49); 8.9287 (0.50); 8.8410 (12.99); 8.7533 (0.47); 8.3657 (6.43); 8.3575 (6.98); 8.3374 (6.33); 8.3298 (6.50); 5.7684 (1.71); 4.3554 (3.63); 4.2819 (10.47); 4.2169 (12.28); 4.1434 (4.36); 4.0786 (0.57); 4.0502 (1.62); 4.0218 (1.57); 3.9930 (0.62); 2.6022 (0.54); 2.5277 (5.26); 2.5209 (11.27); 2.5137 (15.48); 2.5066 (11.09); 2.4999 (5.28); 2.4247 (0.46); 1.9978 (6.36); 1.9194 (8.93); 1.2109 (1.67); 1.1825 (3.29); 1.1539 (1.63)
Example II-14: 1H-NMR(400.0 MHz, DMSO):

9.048(2.6); 9.042(2.6); 8.760(2.0); 8.755(1.8); 8.346(2.0); 8.341(2.0); 8.179(0.9); 8.174(0.8); 8.157(2.0); 8152(1.9); 8.123(2.5); 8.101(1.1); 4.433(0.7); 4.387(1.9); 4.336(2.6); 4.290(1.1); 3.868(16.0); 3.333(107.1); 2.892(2.1); 2.732(1.7); 2.676(0.4); 2.672(0.5); 2.667(0.4); 2.525(1.6); 2.512(31.9); 2.507(62.3); 2.503(80.3); 2.498(57.1); 2.494(27.1); 2.334(0.4); 2.330(0.5); 2.325(0.4); 0.000(2.5)
Example II-15, Solvent: CDCl3, Spectrometer: 300,16 MHz 8.9393 (2.38); 8.9317 (2.39); 8.3478 (2.02); 8.3404 (1.93); 8.1673 (0.55); 8.1614 (0.48); 8.1376 (2.30); 8.1318 (2.50); 8.1203 (2.90); 8.0907 (0.62); 7.9161 (2.03); 7.9118 (1.96); 7.2755 (2.28); 3.8638 (16.00); 3.8291 (1.33); 3.8159 (0.58); 3.8105 (0.58); 3.7211 (1.29); 3.7076 (0.56); 3.6990 (0.37); 3.6832 (1.67); 3.6589 (1.71); 3.6347 (0.55); 3.3903 (0.37); 1.7444 (2.80); 1.6878 (12.03); 1.3802 (0.97); 1.2773 (6.31); 1.2530 (6.39); 1.1848 (0.95); 0.9560 (0.56); 0.9340 (0.55); -0.0002 (1.42)
Example II-16: 1H-NMR(400.0 MHz, DMSO):

9.022(2.8); 9.016(3.1); 8.783(2.4); 8.778(2.5); 8.270(2.6); 8.266(2.6); 8.173(1.2); 8.168(1.0); 8.151(2.1); 8.146(1.8); 8.096(2.6); 8.073(1.5); 4.199(0.9); 4.170(3.5); 4.154(3.5); 4.125(1.0); 4.116(0.9); 4.090(1.9); 4.046(2.5); 3.982(0.4); 3.903(16.0); 3.812(2.5); 3.794(15.4); 3.768(1.9); 3.755(0.4); 3.454(11.7); 3.370(2.4); 3.169(0.5); 2.676(0.4); 2.672(0.5); 2.668(0.4); 2.508(66.9); 2.503(85.6); 2.499(62.9); 2.334(0.4); 2.330(0.5); 2.325(0.4)
Example II-17: 1H-NMR(400.0 MHz, DMSO):

9.008(1.7); 9.003(2.7); 8.998(1.3); 8.739(1.5); 8.734(2.3); 8.308(0.6); 8.295(2.5); 8.199(1.3); 8.195(1.2); 8177(1.8); 8172(1.7); 8.088(2.1); 8.066(1.4); 7.953(0.4); 7.543(1.6); 7.539(2.3); 7.521(3.7); 7.483(1.5); 7.464(2.9); 7.445(1.7); 7.422(1.2); 7.420(1.2); 7.403(1.3); 7.386(0.4); 4.477(2.1); 4.433(2.5); 4.003(1.4); 3.997(1.1); 3.959(1.2); 3.953(1.0); 3.733(16.0); 3.407(0.4); 3.342(239.0); 3.339(189.5); 2.895(2.6); 2.736(2.3); 2.679(0.4); 2.674(0.5); 2.670(0.4); 2.510(64.4); 2.505(83.9); 2.501(62.7); 2.337(0.4); 2.332(0.5); 2.328(0.4); 0.000(2.3)
Example II-18, Solvent: CDCl3, Spectrometer: 300,16 MHz 8.9339 (2.31); 8.9263 (2.36); 8.3199 (1.77); 8.3127 (1.68); 8.1805 (0.99); 8.1742 (0.97); 8.1508 (1.79); 8.1446 (1.82); 8.0918 (2.14); 8.0622 (1.06); 7.8244 (2.01); 7.8185 (1.92); 7.2672 (2.14); 3.9871 (1.97); 3.9304 (2.39); 3.8549 (16.00); 3.4536 (2.26); 3.3969 (1.87); 1.6516 (2.53); 1.5299 (0.49); 1.5198 (0.50); 1.5123 (0.35); 1.5022 (0.95); 1.4928 (0.36); 1.4844 (0.54); 1.4747 (0.56); 1.2604 (0.85); 0.8810 (0.93); 0.8578 (0.36); 0.8182 (0.37); 0.8139 (0.48); 0.8006 (0.62); 0.7952 (0.40); 0.7923 (0.39); 0.7826 (0.66); 0.7758 (0.51); 0.7679 (0.44); 0.7641 (0.42); 0.6369 (0.48); 0.6238 (0.51); 0.6180 (0.90); 0.6132 (1.36); 0.6087 (1.17); 0.5961 (0.52); 0.5902 (1.13); 0.5856 (1.21); 0.5812 (1.00); 0.5774 (0.81); 0.5636 (0.63); 0.5573 (0.42); 0.5533 (0.38); 0.5488 (0.48); 0.5436 (0.45); 0.5372 (0.49); 0.5318 (0.63); 0.5252 (0.64); 0.5195 (0.41); 0.5109 (0.44); 0.5066 (0.63); 0.4930 (0.42); 0.4881 (0.33); -0.0002 (2.72)
Example II-19, Solvent: DMSO, Spectrometer: 300,16 MHz 9.0088 (3.99); 9.0010 (4.31); 8.7672 (1.12); 8.7599 (2.86); 8.7528 (1.99); 8.2671 (2.01); 8.2607 (2.53); 8.2518 (1.25); 8.1741 (1.55); 8.1677 (131); 8.1445 (2.77); 8.1382 (2.63); 8.0799 (3.49); 8.0503 (1.88); 5.7615 (0.67);

| NMR Peak List Table 2 |
|---|
| 5.4665 (2.69); 5.4478 (2.75); 5.4027 (1.32); 5.3815 (1.36); 4.1651 (1.19); 4.1454 (1.86); 4.1243 (1.41); 4.1030 (0.33); 4.0421 (0.41); 4.0184 (0.40); 3.8780 (0.40); 3.8658 (1.27); 3.8192 (1.41); 3.8077 (2.25); 3.7907 (1.34); 3.7495 (16.00); 3.7445 (9.25); 3.6752 (2.09); 3.6170 (1.26); 3.3333 (17.80); 2.5173 (1.76); 2.5113 (3.84); 2.5052 (5.34); 2.4991 (3.91); 2.4931 (1.88); 1.9913 (1.74); 1.2429 (0.70); 1.1996 (0.53); 1.1759 (1.00); 1.1521 (0.65); 1.1414 (2.55); 1.1200 (2.55); 1.0846 (5.29); 1.0632 (5.25); 0.8568 (0.72); −0.0002 (5.16) |
| Example II-20: 1H-NMR(400.0 MHz, DMSO): |
| 8.958(3.4); 8.954(2.7); 8.951(2.4); 8.947(3.4); 8.944(2.2); 8.443(2.6); 8.422(2.7); 8.316(0.3); 8.222(5.4); 8.146(2.3); 8.141(2.0); 8.123(3.8); 8.119(3.6); 8.062(4.2); 8.040(2.5); 7.624(1.9); 7.621(2.1); 7.613(2.0); 7.611(2.1); 7.603(1.9); 7.600(2.1); 7.592(1.9); 7.590(2.0); 4.219(1.3); 4.201(4.1); 4.184(4.2); 4.166(1.4); 3.996(2.2); 3.965(2.7); 3.953(2.7); 3.922(3.2); 3.903(13.2); 3.601(2.6); 3.558(2.2); 3.538(3.1); 3.495(2.7); 3.388(0.5); 3.378(0.6); 3.370(0.9); 3.333(139.0); 3.169(1.5); 2.676(0.6); 2.672(0.8); 2.668(0.6); 2.542(0.4); 2.507(106.1); 2.503(135.6); 2.498(98.0); 2.334(0.6); 2.330(0.8); 2.325(0.6); 1.645(13.3); 1.621(16.0); 1.250(4.5); 1.233(9.3); 1.215(4.3); 0.874(0.3); 0.000(4.1) |
| Example II-21: 1H-NMR(400.0 MHz, DMSO): |
| 9.534(0.6); 9.306(1.1); 9.170(0.6); 8.320(2.1); 8.299(2.2); 8.161(2.6); 8.157(3.0); 8.084(1.4); 8.079(1.3); 8.062(1.9); 8.057(1.9); 7.955(2.8); 7.933(2.0); 7.503(2.9); 7.482(2.8); 4.215(1.6); 4.197(5.2); 4.179(5.2); 4.162(1.7); 3.978(2.6); 3.934(3.1); 3.903(7.3); 3.583(3.1); 3.540(2.5); 3.341(185.2); 3.169(0.4); 2.678(15.9); 2.512(30.6); 2.508(60.1); 2.504(78.0); 2.499(56.3); 2.335(0.3); 2.330(0.4); 1.636(16.0); 1.248(5.6); 1.230(11.4); 1.212(5.3); 0.000(1.1) |
| Example II-22, Solvent: CDCl3, Spectrometer: 250,13 MHz |
| 13.5802 (0.41); 9.0267 (2.74); 8.3822 (2.83); 8.1238 (1.68); 8.1144 (1.58); 8.0974 (1.50); 7.2747 (4.11); 7.2620 (15.76); 4.2361 (0.93); 4.1654 (1.68); 4.0007 (2.72); 3.9928 (2.66); 3.9732 (4.25); 3.9607 (16.00); 3.9280 (1.24); 3.9186 (1.00); 1.5671 (4.11); 1.5543 (15.17); 0.0121 (3.10); −0.0006 (11.00) |
| Example II-23: $^1$H-NMR(400.0 MHz, DMSO): |
| 8.949(2.6); 8.943(2.7); 8.624(1.9); 8.618(1.8); 8.221(1.8); 8.217(2.1); 8.158(0.9); 8.153(0.8); 8.136(2.0); 8.131(1.8); 8.100(2.4); 8.078(1.1); 3.992(2.0); 3.949(2.3); 3.737(16.0); 3.590(2.3); 3.546(1.9); 3.332(118.9); 2.891(0.7); 2.732(0.5); 2.525(1.0); 2.512(18.5); 2.507(37.2); 2.503(48.7); 2.498(34.6); 2.494(16.2); 1.657(11.6); 0.000(1.5) |
| Example II-24, Solvent: DMSO, Spectrometer: 250,13 MHz |
| 9.1414 (2.24); 9.1327 (2.45); 8.8890 (1.48); 8.8821 (2.08); 8.8749 (1.50); 8.3384 (1.05); 8.3299 (1.17); 8.3102 (1.05); 8.3019 (1.12); 4.1509 (1.07); 4.0769 (1.53); 3.9206 (0.44); 3.8345 (16.00); 3.7959 (1.59); 3.7480 (0.44); 3.7257 (1.05); 3.7212 (1.06); 3.4456 (0.50); 3.4280 (0.64); 3.3595 (17.60); 3.3419 (21.78); 3.3181 (2.28); 3.2733 (0.42); 3.2555 (0.52); 2.5259 (3.04); 2.5187 (6.55); 2.5115 (9.05); 2.5043 (6.49); 2.4972 (2.99) |
| Example II-25: 1H-NMR(400.0 MHz, DMSO): |
| 9.021(1.3); 9.016(1.7); 8.746(1.6); 8.308(0.3); 8.281(2.1); 8.182(1.0); 8.178(0.9); 8.160(1.7); 8.155(1.6); 8.104(1.9); 8.082(1.0); 4.085(1.2); 4.039(1.6); 3.821(16.0); 3.806(1.8); 3.760(1.3); 3.345(26.6); 3.336(138.2); 2.895(1.8); 2.736(1.5); 2.674(0.4); 2.527(1.4); 2.514(25.2); 2.510(49.5); 2.505(64.3); 2.500(45.7); 2.496(21.6); 2.332(0.4); 0.000(2.0) |
| Example II-26: 1H-NMR(300.2 MHz, CDCl3): |
| 8.935(0.7); 8.929(0.7); 8.238(0.5); 8.232(0.5); 8.149(0.5); 8.143(0.6); 8.094(0.6); 7.843(0.6); 7.837(0.5); 7.262(5.8); 4.036(0.6); 3.980(0.7); 3.837(5.2); 3.352(0.7); 3.296(0.6); 1.775(3.6); 1.565(4.0); 0.319(0.5); 0.307(16.0); 0.298(0.5); 0.296(0.6); 0.000(4.9) |
| Example II-27, Solvent: CDCl3, Spectrometer: 250,13 MHz |
| 9.0359 (1.55); 9.0275 (1.59); 8.4004 (1.19); 8.3937 (1.64); 8.3869 (1.18); 8.1168 (0.95); 8.1079 (0.99); 8.0901 (0.96); 8.0811 (0.97); 7.3038 (1.96); 5.3428 (0.70); 4.1173 (0.98); 4.1074 (1.01); 4.0467 (1.24); 4.0370 (1.22); 3.8839 (16.00); 3.4867 (1.15); 3.4760 (1.20); 3.4161 (0.98); 3.4055 (0.94); 1.8181 (12.32); 1.6045 (4.69) |
| Example II-28, Solvent: CDCl3, Spectrometer: 300,16 MHz |
| 8.9384 (4.49); 8.9308 (4.56); 8.3439 (3.34); 8.3367 (3.18); 8.1315 (2.23); 8.1021 (3.74); 8.0922 (0.39); 8.0210 (3.12); 8.0146 (3.30); 7.9916 (1.85); 7.9852 (2.13); 7.9182 (3.92); 7.9122 (3.39); 7.2899 (1.76); 4.3931 (2.14); 4.3693 (6.93); 4.3574 (0.33); 4.3455 (7.16); 4.3218 (2.40); 4.0885 (0.86); 4.0636 (3.14); 4.0388 (3.21); 4.0142 (0.94); 3.9670 (0.44); 3.9434 (1.49); 3.9360 (0.70); 3.9199 (1.62); 3.9124 (2.09); 3.8964 (0.67); 3.8889 (2.08); 3.8654 (0.66); 3.7818 (0.60); 3.7584 (2.01); 3.7508 (0.56); 3.7350 (2.12); 3.7274 (1.57); 3.7117 (0.76); 3.7040 (1.54); 3.6807 (0.49); 1.9617 (1.43); 1.4873 (0.41); 1.4292 (1.03); 1.4162 (12.64); 1.4087 (2.50); 1.4029 (8.21); 1.3914 (12.78); 1.3792 (16.00); 1.3657 (0.73); 1.3554 (7.42); 1.3391 (0.35); 1.3352 (0.41); 1.2849 (6.74); 1.2614 (14.33); 1.2380 (6.67); 1.2244 (0.58); 0.8781 (0.37); −0.0002(1.11) |
| Example II-29, Solvent: CDCl3, Spectrometer: 250,13 MHz |
| 9.0897 (0.93); 9.0839 (0.99); 9.0727 (0.97); 9.0670 (0.93); 8.2904 (0.62); 8.2847 (1.07); 8.2792 (0.63); 8.2566 (0.70); 8.2510 (1.16); 8.2453 (0.67); 8.1951 (0.98); 8.1861 (1.00); 8.1677 (0.96); 8.1588 (0.98); 7.5905 (0.99); 7.5736 (0.98); 7.5568 (0.91); 7.5399 (0.87); 4.1492 (0.98); 4.1400 (1.01); 4.0790 (1.26) 4.0695 (1.21); 3.9050 (16.00); 3.5283 (1.19); 3.5180 (1.19); 3.4578 (0.98); 3.4476 (0.97); 1.8408 (12.20); 1.3639 (0.37) |
| Example II-30: 1H-NMR(300.2 MHz, DMSO): |
| 9.087(2.6); 9.079(2.8); 8.908(1.8); 8.902(1.7); 8.149(4.5); 8.142(1.9); 8.132(0.4); 8.124(2.2); 8.118(1.4); 8.043(1.8); 8.041(1.8); 8.035(0.5); 8.011(1.0); 8.009(1.0); 5.766(3.6); 3.994(1.7); 3.937(2.1); 3.746(16.0); 3.730(0.4); 3.582(2.0); 3.525(1.6); 3.346(5.5); 2.525(0.4); 2.519(0.8); 2.512(1.0); 2.506(0.7); 2.500(0.3); 1.664(10.5); 0.000(0.7) |

NMR Peak List Table 2

Example II-31, Solvent: DMSO, Spectrometer: 300,16 MHz 9.0072 (2.77); 8.9994 (2.93); 8.7932 (2.25); 8.7861 (2.13); 8.2855 (2.28); 8.2796 (2.43); 8.1799 (1.15); 8.1736 (0.98); 8.1503 (2.04); 8.1440 (1.91); 8.0839 (2.61); 8.0543 (1.40); 4.5491 (0.97); 4.5429 (1.09); 4.5175 (1.12); 4.5119 (1.00); 3.7418 (16.00); 3.6938 (0.46); 3.3330 (33.19); 2.5162 (2.34); 2.5104 (4.86); 2.5044 (6.60); 2.4984 (4.88); 2.4927 (2.43); 2.2349 (1.12); 2.2192 (1.92); 2.2024 (2.08); 2.1883 (1.93); 2.1685 (0.54); 2.1564 (0.46); 2.1451 (0.51); 2.1355 (0.41); 2.1249 (0.36); 1.9694 (0.58); 1.9473 (0.66); 1.9251 (0.45); 1.9019 (0.55); 1.8791 (0.44); 1.8583 (0.48); 1.8439 (0.53); 1.8240 (0.51); 1.5493 (0.34); 1.5303 (0.46); 1.5183 (0.35); 1.5092 (0.41); 1.2441 (0.61); 0.8574 (0.55); −0.0002 (2.23)

Example II-32, Solvent: CDCl3, Spectrometer: 300,16 MHz 8.9535 (2.37); 8.9460 (2.39); 8.3640 (2.06); 8.3565 (1.98); 8.1253 (3.78); 8.1232 (4.16); 8.1175 (2.69); 8.0879 (0.32); 7.9501 (2.16); 7.2781 (1.86); 4.2789 (0.69); 4.2608 (1.15); 4.2439 (0.71); 4.0134 (1.72); 3.9917 (2.97); 3.9677 (1.85); 3.9010 (16.00); 3.8210 (0.98); 2.1415 (0.34); 2.1317 (0.34); 2.1242 (0.32); 2.1219 (0.32); 2.1141 (0.48); 2.0949 (0.61); 2.0774 (0.50); 2.0576 (0.34); 2.0488 (0.48); 2.0061 (0.77); 1.9903 (0.86); 1.9736 (0.43); 1.9593 (0.44); 1.9435 (0.47); 1.7832 (0.57); 1.7740 (0.67); 1.7658 (0.60); 1.7627 (0.57); 1.7409 (0.53); 1.5594 (0.32); 1.5418 (0.45); 1.5218 (0.44); 1.5047 (0.35); 1.4962 (0.36); 1.2774 (0.35); 1.2612 (0.66); 0.8799 (0.45); −0.0002 (1.07)

Example II-33: 1H-NMR(300.2 MHz, CDCl3):

8.940(2.1); 8.933(2.2); 8.325(1.6); 8.319(1.5); 8.203(0.9); 8.197(0.9); 8.173(1.6); 8.167(1.7); 8.103(1.9); 8.074(1.0); 7.831(1.8); 7.825(1.8); 7.262(20.0); 4.038(2.1); 3.982(2.4); 3.838(16.0); 3.348(2.3); 3.292(2.0); 2.730(0.6); 1.777(12.3); 1.562(1.8); 0.011(0.7); 0.000(19.0); −0.011(0.8)

Example II-34, Solvent: CDCl3, Spectrometer: 250,13 MHz 8.8550 (2.10); 8.8462 (2.38); 8.7132 (0.35); 8.5622 (0.34); 8.2562 (1.98); 8.2480 (2.12); 8.2179 (2.04); 8.1874 (2.16); 7.7289 (1.71); 7.6803 (1.79); 7.6531 (0.38); 7.1952 (4.58); 4.1518 (0.36); 4.1394 (0.33); 3.9965 (1.01); 3.9866 (1.14); 3.9258 (1.32); 3.9159 (1.41); 3.8530 (0.43); 3.7662 (1.03); 3.6825 (0.97); 3.3814 (1.28); 3.3704 (1.39); 3.3106 (1.04); 3.2997 (1.11); 3.0078 (0.38); 1.8745 (0.44); 1.8707 (0.41); 1.7829 (0.41); 1.6961 (13.16); 1.6082 (0.54); 1.3397 (0.37); 1.3236 (0.51); 1.3118 (0.40); 1.2951 (0.88); 1.2665 (1.37); 1.2360 (1.80); 1.2195 (1.52); 1.1799 (6.57); 1.0944 (0.65); 0.8763 (0.53); 0.8464 (1.05); 0.8167 (1.03); 0.8057 (1.18); 0.7781 (1.17); 0.7526 (0.83); 0.0862 (0.74); 0.0138 (1.12); −0.0006 (30.31); −0.0742 (2.52); −0.0880 (1.03)

Example II-35: 1H-NMR(400.0 MHz, DMSO):

8.958(2.5); 8.953(2.6); 8.614(1.9); 8.609(1.9); 8.229(2.0); 8.225(2.2); 8.166(1.1); 8.161(0.9); 8.144(1.8); 8.139(1.7); 8.082(2.3); 8.060(1.4); 4.593(4.4); 3.996(1.9); 3.952(3.3); 3.736(16.0); 3.592(2.3); 3.549(1.9); 3.328(130.3); 3.308(0.4); 2.891(1.1); 2.732(0.9); 2.676(2.2); 2.672(0.5); 2.667(0.4); 2.525(1.6); 2.512(28.9); 2.507(58.1); 2.503(76.4); 2.498(55.2); 2.494(26.7); 2.334(0.3); 2.329(0.5); 2.325(0.3); 1.655(11.5); 0.000(3.4)

Example II-36: 1H-NMR(300.2 MHz, DMSO):

13.874(0.9); 9.015(15.0); 9.007(16.0); 8.768(11.5); 8.761(11.0); 8.248(11.2); 8.242(12.6); 8.181(5.9); 8.174(4.7); 8.151(10.9); 8.145(10.1); 8.093(13.7); 8.063(7.0); 4.945(2.4); 4.911(6.9); 4.881(6.4); 4.847(2.5); 4.789(2.5); 4.755(6.8); 4.725(6.7); 4.692(2.5); 4.066(0.5); 4.043(1.6); 4.019(1.6); 3.995(0.6); 3.943(4.1); 3.938(4.0); 3.885(6.8); 3.879(6.9); 3.736(10.7); 3.678(6.5); 3.338(1.2); 2.518(4.4); 2.512(9.4); 2.506(13.1); 2.500(9.7); 2.494(4.8); 1.992(6.8); 1.200(1.9); 1.176(3.6); 1.153(1.9); 0.000(9.0); −0.011(0.5); −0.055(1.6)

Example II-38: 1H-NMR(400.0 MHz, DMSO):

8.698(1.6); 8.306(0.4); 8.084(1.5); 8.062(1.2); 8.057(0.9); 8.040(1.4); 8.036(1.2); 7.952(1.5); 7.826(1.4); 7.804(1.2); 4.077(16.0); 3.895(1.4); 3.852(1.5); 3.351(16.3); 2.896(11.1); 2.737(8.7); 2.679(0.4); 2.675(0.5); 2.670(0.4); 2.528(2.0); 2.515(30.3); 2.510(59.5); 2.506(77.2); 2.501(54.5); 2.497(25.3); 2.337(0.4); 2.332(0.5); 2.328(0.4); 1.557(7.1); 1.234(0.5); 0.000(2.5)

Example II-39: 1H-NMR(300.2 MHz, DMSO):

11.466(7.2); 11.328(1.4); 11.233(0.7); 9.019(3.6); 9.011(3.8); 8.772(3.1); 8.765(2.5); 8.288(2.8); 8.282(2.8); 8.187(1.4); 8.181(1.1); 8.157(2.6); 8.151(2.2); 8.093(3.4); 8.063(1.8); 4.279(0.4); 4.226(1.7); 4.167(2.6); 4.015(2.6); 3.956(1.6); 3.765(16.0); 3.717(0.5); 3.348(1.9); 2.511(4.4); 2.505(5.8); 2.499(4.3); 1.991(0.3); 1.861(16.0); 1.844(3.3); 0.000(5.2)

Example II-40: 1H-NMR(300.2 MHz, CDCl3):

8.953(2.0); 8.946(2.0); 8.336(1.7); 8.329(1.7); 8.182(0.7); 8.176(0.8); 8152(1.8); 8.146(1.9); 8.112(2.2); 8.082(0.9); 7.866(1.9); 7.860(1.8); 7.266(3.4); 4.076(0.9); 4.017(3.5); 3.980(3.4); 3.922(1.0); 3.889(15.6); 2.473(16.0); 1.624(1.8); 0.000(2.6)

Example II-41: 1H-NMR(499.9 MHz, CDCl3):

8.954(0.9); 8.949(0.9); 8.332(0.8); 8.328(0.8); 8.110(0.7); 8.093(0.7); 7.813(0.6); 7.809(0.6); 7.795(0.5); 7.792(0.5); 7.746(0.9); 7.742(0.8); 7.266(10.1); 5.011(1.6); 3.845(6.5); 1.604(16.0); 1.407(0.3); 1.398(0.4); 1.377(0.3); 1.357(0.5); 1.354(0.4); 1.341(0.5); 1.258(0.4); 1.249(0.5); 0.000(4.7)

Example II-43: 1H-NMR(400.0 MHz, DMSO):

8.973(2.6); 8.256(1.7); 8.211(0.9); 8.207(0.8); 8.189(1.1); 8.185(1.0); 8.030(1.5); 8.008(1.2); 3.936(1.3); 3.908(16.0); 3.893(1.5); 3.741(0.4); 3.514(1.4); 3.471(1.2); 3.333(37.4); 2.677(0.4); 2.547(0.4); 2.513(52.1); 2.508(65.9); 2.504(48.6); 2.335(0.4); 1.661(0.4); 1.629(8.6)

Example II-44: 1H-NMR(400.0 MHz, DMSO):

8.975(3.9); 8.254(2.1); 8.250(2.3); 8.200(1.2); 8.195(1.0); 8.177(1.5); 8.173(1.4); 8.029(2.1); 8.007(1.7); 3.980(1.9); 3.936(2.3); 3.903(11.2); 3.735(16.0); 3.576(2.2); 3.533(1.8); 3.326(66.2); 2.672(0.4); 2.511(29.1); 2.507(55.3); 2.503(70.4); 2.498(50.8); 2.494(25.0); 2.329(0.4); 1.656(12.1)

NMR Peak List Table 2

Example II-45: 1H-NMR(400.0 MHz, DMSO):

12.479(1.7); 8.542(4.3); 7.967(2.0); 7.963(2.2); 7.894(1.3); 7.889(1.2); 7.872(1.4); 7.867(1.3); 7.384(2.0); 7.362(1.8); 3.903(14.9); 3.881(1.9); 3.838(2.2); 3.738(1.1); 3.732(0.6); 3.719(16.0); 3.471(2.2); 3.428(1.8); 3.358(0.4); 3.330(119.4); 2.676(0.3); 2.672(0.5); 2.667(0.4); 2.525(1.4); 2.512(31.1); 2.507(61.9); 2.503(80.6); 2.498(58.5); 2.494(28.7); 2.334(0.4); 2.329(0.5); 2.325(0.4); 1.666(0.4); 1.660(0.7); 1.615(11.3)

Example II-46: 1H-NMR(400.0 MHz, DMSO):

9.067(3.2); 8.296(3.5); 8.274(1.6); 8.270(1.3); 8.181(1.9); 8.159(1.3); 3.947(1.5); 3.903(16.0); 3.738(0.6); 3.529(1.7); 3.486(1.5); 3.330(36.8); 2.677(0.3); 2.672(0.4); 2.668(0.3); 2.542(0.4); 2.525(1.4); 2.512(27.8); 2.508(55.1); 2.503(71.5); 2.499(51.3); 2.494(24.7); 2.330(0.4); 1.666(0.4); 1.633(9.8)

Example II-47: 1H-NMR(400.0 MHz, DMSO):

9.077(2.8); 8.297(1.9); 8.290(1.2); 8.286(0.5); 8.268(1.4); 8.264(1.1); 8.187(1.7); 8.164(1.1); 3.996(1.5); 3.953(1.7); 3.903(16.0); 3.737(12.4); 3.596(1.7); 3.553(1.4); 3.328(94.0); 2.676(0.4); 2.671(0.5); 2.667(0.4); 2.542(0.3); 2.525(1.9); 2.511(35.6); 2.507(69.8); 2.502(90.1); 2.498(64.2); 2.493(30.6); 2.334(0.4); 2.329(0.5); 2.325(0.4); 1.666(8.9)

Example II-49: 1H-NMR(400.0 MHz, DMSO):

9.026(3.5); 9.021(3.5); 8.816(3.0); 8.811(2.8); 8.279(3.2); 8.276(3.0); 8.120(1.4); 8.098(3.7); 8.075(2.9); 8.071(2.5); 8.053(1.1); 8.048(1.0); 4.332(0.6); 4.313(3.8); 4.295(7.2); 4.277(5.6); 4.260(1.6); 3.778(0.3); 3.760(1.1); 3.754(0.5); 3.742(1.2); 3.736(1.5); 3.719(1.4); 3.701(0.4); 3.620(0.4); 3.603(1.4); 3.597(0.4); 3.585(1.5); 3.579(1.2); 3.568(0.5); 3.562(1.1); 3.544(0.3); 3.329(135.2); 2.676(0.5); 2.672(0.7); 2.667(0.5); 2.507(89.3); 2.503(112.0); 2.498(80.2); 2.334(0.6); 2.330(0.7); 2.325(0.5); 1.304(5.5); 1.286(16.0); 1.268(9.1); 1.266(9.3); 1.183(4.7); 1.166(9.8); 1.148(4.5); 0.008(0.8); 0.000(23.4); -0.008(1.0)

Example II-50: 1H-NMR(400.0 MHz, DMSO):

9.011(2.0); 9.005(2.1); 8.785(1.4); 8.780(1.4); 8.253(1.4); 8.248(1.5); 8.178(0.8); 8.173(0.7); 8.156(1.2); 8.151(1.1); 8.084(1.6); 8.062(1.0); 4.026(1.1); 3.982(1.4); 3.903(16.0); 3.765(1.3); 3.722(1.0); 3.630(9.5); 3.326(20.9); 3.171(2.1); 3.163(2.1); 2.671(0.4); 2.667(0.3); 2.525(1.1); 2.511(23.0); 2.507(45.9); 2.502(59.9); 2.498(43.4); 2.493(21.2); 2.329(0.4)

Example II-51: 1H-NMR(499.9 MHz, DMSO):

9.024(2.7); 9.019(2.8); 8.783(2.2); 8.778(2.2); 8.380(2.4); 8.376(2.5); 8.175(1.2); 8.171(1.2); 8.157(1.9); 8154(1.9); 8.100(2.5); 8.082(1.5); 4.005(2.9); 3.985(3.0); 3.775(16.0); 3.290(26.9); 2.507(3.1); 2.504(6.6); 2.500(9.2); 2.497(6.8); 2.493(3.3); 2.261(1.1); 2.253(0.3); 2.248(1.1); 2.241(1.1); 2.236(0.4); 2.228(1.1); 0.825(7.7); 0.813(7.6); 0.000(4.4)

Example II-52: 1H-NMR(400.1 MHz, DMSO):

9.015(2.9); 9.009(3.0); 8.781(2.2); 8.775(2.1); 8.241(2.2); 8.237(2.4); 8.172(1.2); 8.168(1.0); 8.150(2.0); 8.146(1.8); 8.086(2.5); 8.064(1.5); 5.532(1.1); 5.517(2.6); 5.502(1.4); 4.042(0.4); 4.024(0.4); 3.878(1.6); 3.847(0.5); 3.834(2.7); 3.818(1.7); 3.803(2.7); 3.786(1.7); 3.772(0.6); 3.757(0.7); 3.743(16.0); 3.725(0.4); 3.696(2.3); 3.653(1.5); 3.338(30.3); 2.530(0.7); 2.516(13.9); 2.512(28.3); 2.508(38.0); 2.503(27.1); 2.499(12.7); 1.995(1.6); 1.197(0.4); 1.179(0.9); 1.161(0.4)

Example II-53: 1H-NMR(400.1 MHz, DMSO):

9.030(3.0); 9.025(3.1); 8.798(2.3); 8.792(2.2); 8.454(2.4); 8.450(2.3); 8.186(1.2); 8.181(1.1); 8.164(2.1); 8.159(2.0); 8.108(2.7); 8.086(1.5); 3.935(1.2); 3.923(1.5); 3.910(1.5); 3.898(1.3); 3.795(16.0); 3.308(12.3); 2.524(0.7); 2.510(15.1); 2.506(30.4); 2.502(40.9); 2.497(29.1); 2.493(13.9); 2.060(1.3); 2.046(1.4); 2.040(0.4); 2.035(1.4); 2.021(1.3); 1.989(0.7); 1.287(0.5); 1.270(1.0); 1.252(0.5); 1.175(0.4); 1.087(1.4); 1.074(2.2); 1.061(1.4); 0.000(0.7)

Example II-54: 1H-NMR(400.0 MHz, DMSO):

8.986(2.1); 8.980(2.2); 8.770(1.6); 8.765(1.5); 8.213(1.5); 8.208(1.7); 8.164(0.9); 8.159(0.7); 8.142(1.3); 8.137(1.2); 8.059(1.7); 8.037(1.1); 3.966(1.2); 3.924(1.4); 3.890(16.0); 3.386(1.4); 3.343(3.0); 3.319(30.4); 2.660(0.4); 2.513(1.3); 2.499(24.8); 2.495(48.5); 2.490(62.9); 2.486(45.8); 2.482(22.6); 2.317(0.4); 1.489(2.4); 1.482(2.3); 0.073(1.8); 0.065(39.7); 0.057(1.7); 0.000(0.5)

Example II-55: 1H-NMR(400.0 MHz, DMSO):

8.776(4.8); 8.275(2.6); 8.270(2.8); 8.204(1.6); 8.200(1.4); 8.182(2.0); 8.177(1.8); 8.020(2.7); 7.998(2.2); 4.864(6.8); 3.938(2.3); 3.903(16.0); 3.895(2.8); 3.516(2.6); 3.473(2.3); 3.332(63.0); 3.169(0.9); 2.677(0.4); 2.672(0.6); 2.668(0.4); 2.542(0.4); 2.525(2.3); 2.512(36.9); 2.508(71.9); 2.503(92.7); 2.499(66.3); 2.494(31.8); 2.334(0.4); 2.330(0.6); 2.325(0.4); 1.622(13.8)

Example II-56: 1H-NMR(400.0 MHz, DMSO):

8.783(3.7); 8.273(2.1); 8.269(2.2); 8198(1.3); 8194(1.1); 8.176(1.6); 8.171(1.5); 8.024(2.1); 8.002(1.7); 4.868(5.2); 3.986(1.9); 3.942(2.3); 3.903(11.4); 3.735(16.0); 3.583(2.2); 3.540(1.9); 3.330(106.7); 2.672(0.4); 2.525(1.6); 2.512(26.9); 2.507(51.9); 2.503(66.2); 2.498(47.4); 2.494(22.8); 2.330(0.4); 1.654(11.6)

Example II-57: 1H-NMR(400.0 MHz, DMSO):

9.026(4.8); 9.020(5.0); 8.749(3.7); 8.744(3.6); 8.316(0.4); 8.289(3.9); 8.285(4.0); 8.185(1.9); 8.181(1.7); 8.163(3.2); 8.159(3.0); 8.103(4.2); 8.081(2.5); 4.303(1.9); 4.286(6.1); 4.268(6.4); 4.250(2.1); 4.046(3.1); 4.001(4.3); 3.903(13.7); 3.795(4.2); 3.749(3.1); 3.736(0.5); 3.718(1.4); 3.713(0.7); 3.700(1.6); 3.695(2.0); 3.683(0.7); 3.677(2.0); 3.660(0.6); 3.598(0.6); 3.580(2.0); 3.575(0.7); 3.563(2.0); 3.557(1.6); 3.545(0.7); 3.539(1.5); 3.522(0.5); 3.430(0.5); 3.378(0.4); 3.372(0.4); 3.365(0.5); 3.350(2.7); 3.332(281.6); 3.310(1.5); 3.297(0.6); 3.175(0.3); 2.677(0.6); 2.672(0.8); 2.668(0.6); 2.542(0.4); 2.525(2.1); 2.512(52.6); 2.508(105.3);

| NMR Peak List Table 2 |
|---|
| 2.503(136.6); 2.499(97.9); 2.494(47.6); 2.334(0.6); 2.330(0.8); 2.325(0.6); 1.296(7.6); 1.279(16.0); 1.261(7.4); 1.165(6.3); 1.147(13.4); 1.130(6.1); 0.000(4.0)<br>Example II-58: 1H-NMR(400.0 MHz, DMSO): |
| 9.004(4.9); 8.998(5.0); 8.785(3.9); 8.780(3.6); 8.316(0.4); 8.238(3.9); 8.233(4.1); 8.174(2.1); 8.170(1.8); 8.152(3.2); 8.147(2.9); 8.077(4.1); 8.054(2.6); 4.191(2.2); 4.174(6.9); 4.156(7.0); 4.138(2.3); 4.008(3.4); 3.965(3.9); 3.903(14.6); 3.481(3.7); 3.438(3.3); 3.329(238.1); 2.676(0.8); 2.672(1.0); 2.667(0.8); 2.511(69.7); 2.507(133.2); 2.503(169.3); 2.498(120.5); 2.494(57.6); 2.334(0.7); 2.329(1.0); 2.325(0.7); 1.533(11.6); 1.256(7.7); 1.238(16.0); 1.221(7.4); 0.213(0.5); 0.066(95.3); 0.057(4.0); 0.048(0.7); 0.000(6.0); -0.085(0.5)<br>Example II-59: 1H-NMR(400.1 MHz, DMSO): |
| 9.010(3.7); 9.005(3.8); 8.777(2.6); 8.771(2.5); 8.222(2.6); 8.217(3.0); 8.177(1.7); 8.172(1.3); 8.155(2.6); 8.150(2.3); 8.087(3.0); 8.065(1.8); 5.014(0.6); 4.998(1.6); 4.982(2.2); 4.967(1.6); 4.951(0.6); 3.946(2.6); 3.903(3.2); 3.572(3.1); 3.528(2.6); 3.316(29.1); 2.530(0.7); 2.517(13.0); 2.512(26.1); 2.508(35.1); 2.503(24.3); 2.499(11.0); 1.637(16.0); 1.254(9.9); 1.243(10.6); 1.239(10.4); 1.228(9.7)<br>Example II-60: 1H-NMR(300.2 MHz, CDCl3): |
| 8.668(3.4); 8.208(1.1); 8.202(1.1); 8.179(1.5); 8.173(1.5); 8.000(2.0); 7.970(1.5); 7.808(2.1); 7.802(2.0); 7.266(4.8); 4.019(2.1); 3.963(2.4); 3.836(16.0); 3.327(2.3); 3.271(2.0); 1.774(12.6); 1.603(6.3); 1.253(0.4); 0.000(3.7)<br>Example II-61: 1H-NMR(400.1 MHz, DMSO): |
| 13.845(0.7); 9.127(0.4); 9.122(0.5); 9.103(15.6); 9.098(16.0); 8.896(12.8); 8.891(12.3); 8.596(0.4); 8.591(0.5); 8.233(12.5); 8.228(13.6); 8.170(6.9); 8.166(6.0); 8.148(10.2); 8.143(9.4); 8.123(0.4); 8.118(0.3); 8.061(13.1); 8.039(8.9); 7.890(0.7); 4.009(9.8); 3.980(0.5); 3.964(13.1); 3.735(13.0); 3.690(9.9); 3.572(7.3) 3.530(0.5); 3.452(0.5); 3.404(0.8); 3.353(88.7); 3.251(0.5); 3.171(0.6); 2.677(0.4); 2.517(26.9); 2.513(52.6); 2.508(70.0); 2.504(50.8); 2.464(0.5); 2.460(0.4); 2.340(0.3); 2.335(0.4); 2.331(0.3); 1.993(0.3); 1.287(0.5)<br>Example II-62: 1H-NMR(300.2 MHz, CDCl3): |
| 8.947(4.4); 8.940(4.5); 8.333(3.2); 8.326(3.1); 8.201(1.8); 8.194(1.7); 8.171(3.4); 8.165(3.5); 8.111(4.0); 8.082(2.0); 7.868(3.7); 7.862(3.5); 7.265(6.8); 5.301(6.5); 4.898(0.4); 4.865(4.0); 4.858(3.9); 4.825(0.5); 4.744(0.5); 4.710(3.8); 4.701(3.7); 4.668(0.6); 4.368(1.7); 4.344(3.5); 4.320(0.6); 4.296(2.1); 4.005(1.8); 3.999(1.8); 3.949(2.5); 3.942(2.5); 3.700(3.2); 3.698(3.1); 3.644(2.3); 3.641(2.2); 1.618(2.4); 1.375(7.8); 1.351(16.0); 1.328(7.7); 1.308(0.4); 1.266(1.8); 0.903(0.6); 0.881(2.1); 0.858(0.8); 0.000(5.9)<br>Example II-63: 1H-NMR(300.2 MHz, CDCl3): |
| 8.932(4.7); 8.924(4.8); 8.321(3.8); 8.314(3.7); 8.207(2.0); 8.201(2.1); 8.178(3.4); 8.171(3.5); 8.094(4.3); 8.064(2.5); 7.840(4.3); 7.834(4.2); 7.267(5.3); 5.302(5.8); 4.352(0.7); 4.339(1.0); 4.328(0.8); 4.316(3.3); 4.304(0.5); 4.295(3.9); 4.292(3.8); 4.283(0.6); 4.272(3.4); 4.259(0.9); 4.248(1.1); 4.236(0.8); 3.966(4.2); 3.910(5.0); 3.364(4.8); 3.307(4.0); 2.143(1.1); 2.140(1.1); 2.118(3.8); 2.092(4.3); 2.067(1.7); 1.647(2.1); 1.365(7.9); 1.341(16.0); 1.317(7.8); 1.060(6.1); 1.036(13.0); 1.011(5.7); 0.000(4.5)<br>Example II-64: 1H-NMR(300.2 MHz, DMSO): |
| 13.334(1.5); 9.000(7.4); 8.993(7.8); 8.748(6.7); 8.741(6.4); 8.228(6.5); 8.223(7.3); 8.179(3.3); 8.173(2.6); 8.150(5.6); 8.144(5.0); 8.077(7.3); 8.047(4.2); 3.900(4.5); 3.842(6.1); 3.560(5.8); 3.502(4.4); 3.347(1.2); 2.516(3.3); 2.510(4.4); 2.504(3.3); 2.020(1.8); 1.995(6.5); 1.971(6.5); 1.946(2.2); 1.178(0.4); 0.967(7.2); 0.942(16.0); 0.917(6.7); 0.000(3.0)<br>Example II-66: 1H-NMR(300.2 MHz, DMSO): |
| 13.608(0.4); 13.434(0.6); 13.415(0.6); 13.393(0.6); 13.372(0.6); 13.303(0.6); 13.283(0.5); 13.221(0.4); 12.627(0.5); 11.953(1.2); 9.151(0.9); 9.143(1.0); 9.121(2.9); 9.116(3.0); 9.089(1.0); 9.072(3.1); 9.065(6.5); 9.058(5.2); 9.035(4.7); 9.028(5.6); 9.000(14.3); 8.993(15.3); 8.969(1.9); 8.963(1.8); 8.947(3.3); 8.941(3.1); 8.925(1.6); 8.899(2.0); 8.893(1.9); 8.861(4.3); 8.813(4.5); 8.770(12.1); 8.763(11.6); 8.739(1.6); 8.733(1.6); 8.662(2.6); 8.656(2.9); 8.628(1.0); 8.569(2.1); 8.563(2.4); 8.543(0.9); 8.514(2.6); 8.508(2.8); 8.459(0.5); 8.426(0.4); 8.385(0.4); 8.328(3.3); 8.291(4.1); 8.269(2.7); 8.262(2.7); 8.240(15.6); 8.235(16.0); 8.213(3.8); 8.206(3.3); 8.187(7.6); 8.181(7.9); 8.158(11.4); 8.152(11.3); 8.138(3.8); 8.121(4.2); 8.110(4.1); 8.099(4.5); 8.076(13.5); 8.046(8.2); 7.995(1.2); 7.957(1.5); 7.950(1.5); 7.928(1.4); 7.920(1.5); 7.884(1.6); 7.864(1.6); 7.857(1.6); 7.834(1.4); 7.828(1.4); 7.804(1.4); 7.797(1.4); 7.774(1.2); 7.742(0.6); 7.684(0.4); 7.632(1.0); 7.582(0.4); 7.516(0.3); 7.290(2.7); 7.284(2.9); 6.997(0.5); 6.968(0.4); 5.688(0.3); 5.671(1.2); 5.654(1.2); 4.040(0.7); 3.930(7.2); 3.873(10.3); 3.772(0.4); 3.729(1.0); 3.645(9.5); 3.588(7.1); 3.544(0.8); 3.485(0.8); 3.408(1.7); 3.386(2.2); 3.325(3.1); 3.192(1.2); 3.168(1.4); 3.144(1.4); 3.125(1.2); 3.103(0.6); 3.080(0.6); 3.048(0.6); 3.025(0.5); 2.724(0.6); 2.653(0.5); 2.627(0.4); 2.511(34.0); 2.505(47.0); 2.499(36.4); 2.275(0.4); 1.960(0.4); 1.913(13.2); 1.890(14.3); 1.818(0.4); 1.464(4.4); 1.447(4.4); 1.281(0.4); 1.228(1.7); 1.192(0.9); 1.170(1.4); 1.159(0.9); 1.146(1.3); 1.124(2.0); 1.099(1.1); 1.066(2.6); 1.042(5.2); 1.018(2.8); 0.983(0.5); 0.855(0.4); 0.812(0.5); 0.750(3.5); 0.724(2.7); 0.707(1.8); 0.463(1.7); 0.442(10.6); 0.420(9.5); 0.415(9.7); 0.400(3.1); 0.266(0.4); 0.225(0.9); 0.184(10.4); 0.047(0.4); 0.010(1.7); 0.000(37.3); −0.093(0.4); -3.655(0.4); −3.703(0.3)<br>Example II-67: 1H-NMR(300.2 MHz, CDCl3): |
| 8.932(0.8); 8.925(0.8); 8.239(0.6); 8.233(0.6); 8.154(0.6); 8.148(0.6); 8.090(0.7); 8.060(0.4); 7.857(0.7); 7.851(0.6); 7.266(1.6); 4.315(0.5); 4.294(0.6); 4.291(0.6); 4.270(0.6); 3.965(0.6); 3.908(0.7); 3.366(0.7); 3.309(0.6); 2.117(0.5); 2.113(0.5); 2.092(0.5); 2.088(0.5); 1.418(0.4); 1.364(1.3); 1.340(2.7); 1.316(1.3); 1.266(0.9); 1.061(0.9); 1.036(1.9); 1.011(0.8); 0.882(1.0); 0.858(0.4); 0.320(0.6); 0.308(16.0); 0.296(0.7); 0.000(1.4) |

NMR Peak List Table 2

Example II-68: 1H-NMR(400.0 MHz, DMSO):

9.205(4.1); 8.316(0.3); 8.268(1.1); 8.264(1.8); 8.253(2.6); 8.248(3.8); 8.141(2.2); 8.117(1.6); 3.986(1.9); 3.943(2.3); 3.903(6.9); 3.736(16.0); 3.583(2.3); 3.539(1.9); 3.328(110.5); 2.676(0.5); 2.672(0.6); 2.507(78.9); 2.503(97.5); 2.499(72.5); 2.329(0.6); 1.663(12.3); 0.000(2.9)

Example II-69: 1H-NMR(300.2 MHz, DMSO):

13.368(0.4); 8.955(7.5); 8.948(7.7); 8.597(6.3); 8.591(6.0); 8.250(6.2); 8.244(6.8); 8.179(3.4); 8.172(2.8); 8.149(5.6); 8.143(5.2); 8.077(7.2); 8.047(4.1); 4.594(14.9); 3.904(4.3); 3.846(5.7); 3.816(1.2); 3.559(5.3); 3.501(4.0); 3.328(0.6); 2.518(3.1); 2.512(6.6); 2.506(9.0); 2.500(6.7); 2.494(3.3); 2.011(1.7); 1.987(5.7); 1.962(6.1); 1.938(2.1); 0.961(6.9); 0.937(16.0); 0.912(6.5); 0.000(8.0); -0.011(0.4); -0.067(0.4)

Example II-70: 1H-NMR(300.2 MHz, CDCl3):

8.930(2.0); 8.923(2.0); 8.314(2.3); 8.307(2.2); 8.176(0.9); 8.170(1.0); 8.147(1.9); 8.141(2.0); 8.095(2.5); 8.065(1.2); 7.860(2.4); 7.854(2.3); 7.284(0.6); 5.986(3.0); 5.979(3.0); 5.581(2.9); 5.573(2.8); 5.302(0.8); 4.406(2.2); 4.348(2.6); 3.902(16.0); 3.734(2.5); 3.676(2.1); 2.433(0.6); 0.000(0.4)

Example II-71: 1H-NMR(499.9 MHz, DMSO):

8.997(0.7); 8.995(0.7); 8.993(0.7); 8.977(8.7); 8.973(8.9); 8.960(0.6); 8.956(0.3); 8.661(0.4); 8.616(0.4); 8.612(0.5); 8.582(8.7); 8.578(8.2); 8.329(0.4); 8.326(0.4); 8.320(0.5); 8.289(7.8); 8.286(8.6); 8.255(0.8); 8.244(0.9); 8.232(0.8); 8.176(3.9); 8.173(4.4); 8.169(3.0); 8.159(6.3); 8.155(7.0); 8.131(1.5); 8.104(7.5); 8.087(4.6); 8.046(0.5); 8.043(0.5); 7.048(0.6); 5.760(1.7); 4.620(1.3); 4.607(1.6); 4.592(0.5); 4.438(0.4); 4.292(8.2); 4.281(6.9); 4.083(6.1); 4.046(7.8); 3.850(7.0); 3.813(5.4); 3.514(0.3); 3.372(57.3); 2.903(0.8); 2.744(0.6); 2.523(3.0); 2.519(3.6); 2.516(2.6); 2.259(1.9); 2.248(1.1); 2.210(1.8); 1.924(0.3); 1.874(0.3); 1.793(5.2); 1.784(5.2); 1.731(2.3); 1.725(2.2); 1.523(1.8); 1.509(1.9); 1.267(1.0); 1.255(1.7); 1.229(14.4); 1.217(15.4); 1.192(0.7); 1.183(0.4); 1.177(0.5); 1.168(0.3); 0.000(1.0)

Example II-72: 1H-NMR(300.2 MHz, CDCl3):

8.937(2.1); 8.930(2.2); 8.322(1.6); 8.315(1.6); 8.202(0.9); 8.196(0.9); 8.172(1.6); 8.166(1.7); 8.099(1.8); 8.069(1.0); 7.857(1.8); 7.851(1.8); 7.268(2.4); 5.327(2.5); 5.124(1.5); 5.122(1.6); 4.259(2.0); 4.202(2.3); 3.848(16.0); 3.488(2.2); 3.432(1.9); 1.892(4.7); 1.889(6.1); 1.888(6.1); 1.885(4.9); 0.000(2.0)

Example II-73: 1H-NMR(300.2 MHz, DMSO):

9.007(5.5); 8.999(5.7); 8.744(4.2); 8.737(4.0); 8.267(4.2); 8.261(4.5); 8.186(2.3); 8.179(1.9); 8.156(3.8); 8150(3.5); 8.081(4.7); 8.052(2.7); 5.207(5.1); 5.083(3.3); 5.079(4.3); 5.074(3.1); 4.106(3.2); 4.048(4.1); 3.701(3.8); 3.643(3.0); 2.545(0.5); 2.518(2.4); 2.512(4.9); 2.506(6.5); 2.500(4.7); 2.494(2.2); 1.835(16.0); 1.357(0.3); 1.183(0.4); 1.172(0.4); 0.000(6.0)

Example II-74: 1H-NMR(300.2 MHz, CDCl3):

8.965(2.4); 8.958(2.6); 8.249(2.3); 8.242(2.4); 8.051(2.0); 8.049(2.1); 7.692(2.0); 7.688(2.1); 7.306(2.4); 4.026(2.1); 3.970(2.5); 3.833(16.0); 3.755(0.5); 3.361(2.5); 3.341(4.6); 3.304(2.1); 2.792(9.7); 2.722(3.8); 2.186(6.9); 1.769(12.7); 0.000(1.7)

Example II-75: 1H-NMR(300.2 MHz, DMSO):

9.061(2.9); 9.054(3.0); 8.677(2.4); 8.670(2.3); 8.241(2.1); 8.235(3.9); 8.223(3.1); 8.218(1.7); 4.685(5.2); 4.008(1.7); 3.950(2.1); 3.751(16.0); 3.688(0.4); 3.598(2.1); 3.540(1.6); 3.339(1.3); 2.577(0.3); 2.525(0.4); 2.519(0.8); 2.513(1.1); 2.507(0.8); 2.501(0.4); 1.668(10.6); 0.000(1.2)

Example II-76: 1H-NMR(300.2 MHz, CDCl3):

9.034(2.5); 9.026(2.5); 8.349(2.4); 8.342(2.3); 8.312(2.6); 8.306(2.7); 7.742(2.3); 7.736(2.3); 7.268(3.2); 4.015(2.2); 3.959(2.5); 3.841(16.0); 3.322(2.4); 3.266(2.1); 1.779(12.5); 0.000(2.4)

Example II-77: 1H-NMR(300.2 MHz, DMSO):
9.001(11.3); 8.993(12.0); 8.932(0.8) 8.927(1.1); 8.910(1.0); 8.905(0.8); 8.759(8.6); 8.754(7.9); 8.541(0.5); 8.268(7.0); 8.262(7.6); 8.250(2.9); 8.245(2.8); 8.186(4.3); 8.180(3.8); 8.157(7.0); 8.151(6.8); 8.077(10.0); 8.048(6.5); 8.028(1.0); 8.024(0.9); 8.002(0.7); 4.208(1.2); 4.187(4.8); 4.174(2.4); 4.165(5.0); 4.153(2.3); 4.144(1.6); 3.834(4.0); 3.776(8.0); 3.706(0.4); 3.622(5.9); 3.565(3.9); 2.992(0.4); 2.905(0.4); 2.900(0.5); 2.741(0.5); 2.524(3.1); 2.518(4.2); 2.512(3.2); 1.362(0.6); 1.169(4.8); 1.148(4.9); 1.107(15.8); 1.086(16.0); 0.000(3.7)

Example II-78: 1H-NMR(300.2 MHz, DMSO):

13.344(0.7); 9.067(4.8); 9.060(51); 8.686(3.9); 8.679(3.9); 8.260(3.6); 8.254(6.2); 8.239(4.7); 8.233(3.1); 4.685(8.6); 4.067(0.4); 4.043(1.1); 4.019(1.1); 3.996(0.4); 3.958(2.6); 3.900(3.2); 3.533(3.1); 3.475(2.5); 3.338(0.7); 2.520(1.2); 2.514(2.7); 2.508(3.7); 2.502(2.7); 2.496(1.3); 1.993(5.0); 1.629(16.0); 1.201(1.4); 1.177(2.8); 1.153(1.4); 0.000(4.3)

Example II-79: 1H-NMR(300.2 MHz, DMSO):

13.357(0.8); 9.114(4.6); 9.106(4.9); 8.850(4.2); 8.842(4.1); 8.257(4.2); 8.251(5.2); 8.211(4.2); 8.206(3.5); 3.948(2.5); 3.891(3.2); 3.525(3.1); 3.467(2.5); 3.345(2.4); 2.520(1.2); 2.514(2.6); 2.508(3.5); 2.502(2.6); 2.496(1.2); 1.630(16.0); 0.000(3.7)

Example II-80: 1H-NMR(300.2 MHz, CDCl3):

8.940(2.2); 8.932(2.3); 8.285(2.0); 8.277(2.0); 8.052(1.1); 8.049(1.5); 8.046(1.5); 8.042(1.1); 7.656(1.4); 7.649(1.4); 7.262(13.5); 4.019(2.0); 3.963(2.3); 3.834(16.0); 3.336(2.2); 3.280(1.9); 2.790(7.1); 1.770(11.7); 1.556(4.4); 0.011(0.3); 0.000(10.7); -0.011(0.4)

-continued

NMR Peak List Table 2

Example II-81: 1H-NMR(300.2 MHz, DMSO):

8.969(4.6); 8.961(4.7); 8.565(4.0); 8.558(3.9); 8.047(3.7); 8.031(3.2); 8.028(3.6); 4.578(8.5); 3.941(2.6); 3.883(3.2); 3.503(3.7); 3.446(3.4); 3.387(1.1); 2.724(13.7); 2.522(1.0); 2.516(2.1); 2.510(2.9); 2.504(2.1); 2.498(1.0); 1.650(0.4); 1.622(16.0)

Example II-82: 1H-NMR(400.0 MHz, DMSO):

9.198(5.6); 8.317(0.5); 8.275(1.5); 8.271(2.0); 8.250(8.6); 8.136(2.5); 8.114(1.8); 3.936(2.4); 3.903(16.0); 3.893(3.0); 3.508(2.7); 3.465(2.3); 3.330(78.8); 3.174(0.4); 3.164(0.4); 2.676(0.7); 2.672(1.0); 2.667(0.7); 2.542(0.7); 2.525(3.0); 2.512(63.8); 2.507(126.9); 2.503(164.8); 2.498(118.3); 2.494(57.4); 2.334(0.7); 2.329(1.0); 2.325(0.7); 2.321(0.4); 1.626(14.8); 0.000(6.3)

Example II-83: 1H-NMR(400.0 MHz, DMSO):

9.107(5.7); 8.316(0.4); 8.212(3.1); 8.208(3.5); 8.184(2.0); 8.180(1.5); 8.162(2.4); 8.157(2.1); 7.983(3.1); 7.961(2.5); 3.922(2.4); 3.903(16.0); 3.879(2.8); 3.495(2.8); 3.470(0.4); 3.452(2.5); 3.333(139.2); 2.676(0.7); 2.672(0.9); 2.668(0.7); 2.542(0.5); 2.507(117.5); 2.503(150.2); 2.498(108.6); 2.334(0.7); 2.330(0.9); 2.325(0.7); 1.619(15.5); 1.234(0.5); 0.874(0.4); 0.000(4.7)

Example II-84: 1H-NMR(400.0 MHz, DMSO):

9.028(2.8); 9.022(2.8); 8.740(2.3); 8.735(2.1); 8.316(0.4); 8.296(2.3); 8.292(2.3); 8.179(1.1); 8.174(1.0); 8156(1.9); 8152(1.7); 8.101(2.5); 8.079(1.4); 4.319(2.0); 4.273(2.4); 3.903(8.2); 3.860(2.5); 3.821(15.9); 3.815(2.7); 3.330(131.1); 2.676(0.5); 2.672(0.6); 2.667(0.5); 2.565(0.4); 2.550(0.3); 2.507(79.5); 2.503(101.1); 2.498(72.8); 2.334(0.5); 2.329(0.6); 2.325(0.5); 2.216(16.0); 0.000(3.9)

Example II-85: 1H-NMR(300.2 MHz, DMSO):

9.011(4.6); 9.003(4.9); 8.727(4.3); 8.719(4.2); 8.033(7.4); 3.928(2.5); 3.871(3.2); 3.496(3.1); 3.439(2.5); 3.394(0.4); 3.371(0.6); 3.332(1.2); 2.722(13.5); 2.517(2.0); 2.511(4.4); 2.505(6.2); 2.498(4.5); 2.492(2.2); 1.618(16.0); 1.091(0.4); 0.000(2.8)

Example II-86: 1H-NMR(300.2 MHz, CDCl3):

8.972(2.3); 8.965(2.3); 8.244(2.0); 8.237(2.0); 8.058(1.2); 8.054(1.5); 8.051(1.5); 8.048(1.2); 7.721(1.5); 7.714(1.5); 7.275(1.7); 4.408(0.7); 4.406(0.7); 4.385(2.2); 4.382(2.2); 4.361(2.4); 4.359(2.2); 4.337(0.8); 4.335(0.8); 3.941(1.8); 3.882(2.4); 3.809(1.0); 3.598(2.5); 3.539(1.9); 3.515(16.0); 3.394(0.8); 3.335(0.9); 3.324(4.3); 2.800(7.5); 1.725(0.8); 1.711(1.3); 1.667(0.6); 1.411(3.8); 1.388(8.0); 1.364(3.8); 1.317(0.3); 1.307(0.5); 1.293(0.6); 0.000(1.2)

Example II-87: 1H-NMR(300.2 MHz, CDCl3):

9.048(2.5); 9.040(2.6); 8.370(2.1); 8.363(2.1); 8.326(2.6); 8.320(2.6); 7.786(2.0); 7.781(2.0); 7.274(3.6); 5.365(2.3); 5.356(2.4); 4.627(1.9); 4.618(1.9); 4.410(0.8); 4.387(2.5); 4.363(2.7); 4.340(1.0); 4.321(1.3); 4.297(3.9); 4.273(4.0); 4.249(1.4); 3.919(1.9); 3.867(0.5); 3.861(2.4); 3.809(0.6); 3.800(0.4); 3.763(0.4); 3.666(12.9); 3.567(2.5); 3.520(16.0); 3.512(1.0); 3.508(2.2); 2.046(0.7); 1.725(0.5); 1.432(0.8); 1.414(3.7); 1.390(8.0); 1.383(0.7); 1.374(0.7); 1.366(4.1); 1.360(4.6); 1.354(0.7); 1.350(0.8); 1.337(8.7); 1.331(0.9); 1.329(0.8); 1.326(0.6); 1.313(4.3); 1.307(0.6); 1.294(0.5); 1.284(0.4); 1.260(0.5); 0.000(2.5)

Example II-88: 1H-NMR(400.0 MHz DMSO):

9.023(3.0); 9.017(3.0); 8.740(2.3); 8.734(2.1); 8.291(2.3); 8.286(2.3); 8.181(1.3); 8.177(1.1); 8.159(2.0); 8154(1.8); 8.096(2.5); 8.074(1.5); 4.247(1.9); 4.2042.2); 3.903(8.2); 3.794(2.3); 3.748(1.9); 3.331(26.8); 3.169(0.4); 2.676(0.4); 2.672(0.6); 2.667(0.4); 2.512(41.0); 2.507(73.4); 2.503(90.9); 2.498(63.4); 2.494(29.4); 2.334(0.4); 2.329(0.5); 2.325(0.4); 2.214(16.0); 0.000(3.3)

Example II-89: 1H-NMR(300.2 MHz, DMSO):

9.129(3.6); 9.122(3.3); 8.843(3.6); 8.836(3.3); 8.282(10.6); 4.002(1.9); 3.941(2.7); 3.723(2.7); 3.662(1.9); 3.345(16.0); 2.543(1.7); 2.506(5.0); 1.992(0.6); 1.176(0.3); 0.000(2.8)

Example II-90: 1H-NMR(300.2 MHz, DMSO):

9.079(3.6); 9.072(3.1); 9.013(0.3); 8.711(0.7); 8.704(0.6); 8.675(3.2); 8.669(3.0); 8.622(0.6); 8.616(0.6); 8.481(0.8); 8.475(0.7); 8.317(2.9); 8.312(3.3); 8.283(3.8); 8.278(2.8); 7.567(0.5); 4.691(6.1); 4.655(0.4); 4.016(1.8); 3.955(2.6); 3.746(2.5); 3.684(1.8); 3.407(0.6); 3.374(1.1); 3.348(16.0); 3.312(0.4); 3.105(0.8); 3.081(0.7); 2.513(3.7); 2.507(4.6); 2.502(3.4); 1.285(0.4); 1.254(0.8); 1.230(1.4); 1.211(1.6); 1.187(2.0); 1.163(1.0); 0.000(3.5); -0.053(0.5)

Example II-91: 1H-NMR(300.2 MHz, CDCl3):

8.951(2.2); 8.943(2.3); 8.297(2.0); 8.289(2.0); 8.054(1.1); 8.051(1.4); 8.048(1.5); 8.045(1.1); 7.696(1.4); 7.689(1.4); 7.262(8.3); 4.407(0.7); 4.404(0.7); 4.383(2.1); 4.381(2.1); 4.359(2.3); 4.357(2.2); 4.335(0.8); 3.927(1.7); 3.868(2.4); 3.580(2.5); 3.522(2.1); 3.512(16.0); 2.799(7.0); 1.565(8.9); 1.409(3.7); 1.386(7.8); 1.362(3.6); 1.266(0.4); 0.882(0.5); 0.000(6.7)

Example II-92: 1H-NMR(300.2 MHz, DMSO):

9.027(3.1); 9.019(3.2); 8.714(3.0); 8.706(2.8); 8.103(2.6); 8.046(2.6); 3.982(1.6); 3.921(2.3); 3.686(2.2); 3.625(1.6); 3.337(16.0); 2.767(0.8); 2.730(10.5); 2.509(6.5); 2.504(8.5); 2.498(6.5); 1.179(0.4); 0.000(5.7)

Example II-93: 1H-NMR(300.2 MHz, DMSO):

8.990(2.5); 8.983(2.5); 8.560(2.3); 8.553(2.2); 8.131(2.0); 8.050(2.0); 4.589(4.4); 3.998(1.3); 3.937(2.0); 3.715(1.9); 3.654(1.4); 3.338(16.0); 2.774(0.8); 2.735(8.2); 2.509(5.7); 2.503(7.5); 2.498(5.6); 1.178(0.4); 0.000(1.9)

-continued

NMR Peak List Table 2

Example II-94: 1H-NMR(601.6 MHz, DMSO):

9.044(13.2); 9.040(13.6); 8.792(14.2); 8.789(14.1); 8.298(16.0); 8.161(5.8); 8.159(5.7); 8.146(11.0);
8.144(11.2); 8.118(14.8); 8.103(7.4); 7.172(1.3); 7.087(1.4); 7.002(1.3); 4.462(6.5); 4.432(9.4); 4.312(10.1);
4.283(7.1); 3.896(1.5); 3.420(33.7); 3.168(4.9); 2.769(0.8); 2.743(0.8); 2.668(0.6); 2.643(0.4); 2.615(2.7);
2.504(380.6); 2.388(3.1); 1.910(0.5); 1.233(0.5); 0.000(58.4); -0.100(0.4)
Example II-95: 1H-NMR(400.0 MHz, DMSO):

9.133(5.2); 8.320(2.4); 8.316(2.6); 8.258(1.1); 8.253(1.0); 8.236(1.9); 8.231(1.8); 8.176(2.9); 8.154(1.7);
4.062(1.9); 4.018(2.4); 3.904(4.4); 3.737(16.0); 3.701(2.3); 3.658(1.9); 3.331(206.2); 3.174(0.4); 3.161(0.3);
2.676(0.9); 2.671(1.1); 2.667(0.9); 2.541(0.7); 2.511(72.7); 2.507(143.8); 2.502(186.8); 2.498(135.3);
2.333(0.8); 2.329(1.1); 2.324(0.8); 1.655(12.3); 1.235(0.4); 0.008(1.8); 0.000(51.7); -0.008(2.1)
Example II-96: 1H-NMR(400.0 MHz, DMSO):

13.329(0.6); 9.128(7.2); 8.324(3.5); 8.320(3.8); 8.261(1.6); 8.256(1.5); 8.238(2.6); 8.234(2.5); 8.172(3.9);
8.150(2.4); 4.004(2.5); 3.961(3.1); 3.904(10.9); 3.631(3.0); 3.588(2.5); 3.331(267.9); 3.174(0.5); 3.161(0.5);
2.671(1.8); 2.506(236.1); 2.502(300.0); 2.498(223.1); 2.329(1.7); 1.622(16.0); 1.236(0.8); 0.000(68.6)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contain therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-D6 and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

The following Table 3 illustrates in a non limiting manner examples of compounds according to formula (V).

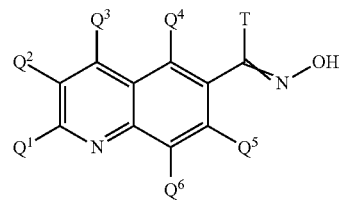

(V)

TABLE 3

| Ex-No | $Q^1$ | $Q^2$ | $Q^3$ | $Q^4$ | $Q^5$ | $Q^6$ | T | Log P |
|---|---|---|---|---|---|---|---|---|
| V-01 | H | H | H | H | F | F | H | 1.48[a] |
| V-02 | H | H | H | H | F | F | Cl | 2.04[a] |
| V-03 | H | Br | H | H | F | F | Cl | 2.92[a] |
| V-04 | H | Br | H | H | F | F | Cl | 2.92[a] |
| V-05 | H | Br | H | H | F | H | H | 2.21[a] |
| V-06 | H | Br | H | H | F | H | Cl | 2.63[a] |
| V-07 | H | I | H | H | H | H | H | 1.98[a] |
| V-08 | H | I | H | H | H | H | Cl | 2.63[a] |
| V-09 | H | Br | H | H | H | H | H | 1.88[a] |
| V-10 | H | Br | H | H | H | H | Cl | 2.52[a] |
| V-11 | H | Cl | H | H | H | H | H | 1.78[a] |
| V-12 | H | Br | H | H | H | H | Cl | |
| V-13 | H | I | H | H | H | H | H | 2.08[a] |
| V-14 | H | I | H | H | H | H | Cl | 2.77[a] |
| V-15 | H | Ethynyl | H | H | H | Me | H | 2.21[a] |
| V-16 | H | Br | H | H | H | Me | H | 2.61[a] |
| V-17 | H | Br | H | H | H | Cl | H | 2.40[a] |
| V-18 | H | Br | H | H | H | Cl | Cl | 3.10[a] |
| V-19 | H | Br | H | H | H | Me | Cl | 3.37[a] |
| V-20 | H | Br | H | H | H | H | Me | |
| V-21 | H | Br | Cl | H | H | H | H | 2.43[a] |
| V-22 | H | Br | Cl | H | H | H | Cl | 3.16[a] |
| V-23 | H | Br | H | H | H | F | H | 2.08[a] |

Measurement of logP values was performed according EEC directive 79/831 Annex V.A8 by HPLC (High Performance Liquid Chromatography) on reversed phase columns with the following methods:
[a]Measurement of LC-MS was done at pH 2.7 with 0.1% formic acid in water and with acetonitrile (contains 0.1% formic acid) as eluent with a linear gradient from 10% acetonitrile to 95% acetonitrile. Calibration was done with not branched alkan2-ones (with 3 to 16 carbon atoms) with known logP-values (measurement of logP values using retention times with linear interpolation between successive alkanones). lambda-maX-values were determined using UV-spectra from 200 nm to 400 nm and the peak values of the chromatographic signals.

NMR-Peak Lists

1H-NMR data of selected examples are written in form of 1H-NMR-peak lists. to each signal peak are listed the δ-value in ppm and the signal intensity in round brackets.

Between the δ-value—signal intensity pairs are semicolons as delimiters.

$$\delta_1 \text{ (intensity}_1\text{)}; \delta_2 \text{ (intensity}_2\text{)};......; \delta_i \text{ (intensity}_i\text{)};......; \delta_n \text{ (intensity}_a\text{)}$$

| NMR Peak List Table 3 |
|---|
| Example V-01: 1H-NMR(250.1 MHz, DMSO): |
| 12.396(1.0); 11.954(16.0); 9.045(0.4); 9.019(3.8); 9.013(4.0); 9.002(3.9); 8.996(3.9); 8.606(0.4); 8.562(4.1); 8.556(2.5); 8.534(2.6); 8.528(4.4); 8.522(2.6); 8.392(14.9); 8.229(3.3); 8.220(3.6); 8.200(3.3); 8.192(3.4); 7.799(0.9); 7.688(4.0); 7.671(3.9); 7.654(3.8); 7.638(3.6); 5.768(0.4); 3.443(0.6); 3.417(0.7); 3.352(32.9); 3.176(0.4); 2.525(5.8); 2.519(12.4); 2.511(16.9); 2.504(12.1); 2.497(5.8); 1.237(0.4) |
| Example V-02: 1H-NMR(250.1 MHz, DMSO): |
| 12.986(16.0); 9.085(4.2); 9.079(4.5); 9.068(4.5); 9.062(4.4); 8.642(4.6); 8.608(4.9); 8.342(4.0); 8.334(4.2); 8.313(4.0); 8.305(4.1); 7.749(4.3); 7.732(4.2); 7.716(4.0); 7.699(3.9); 3.554(2.3); 2.517(7.1); 2.510(9.8); 2.503(7.2) |
| Example V-03: 1H-NMR(250.1 MHz, DMSO): |
| 13.066(11.7); 9.132(5.1); 9.124(5.8); 8.995(3.9); 8.988(5.3); 8.981(3.7); 8.308(2.9); 8.299(3.0); 8.279(2.8); 8.271(2.9); 5.765(16.0); 3.535(2.3); 2.898(0.7); 2.738(0.6); 2.517(6.4); 2.510(8.6); 2.503(6.2) |
| Example V-04: 1H-NMR(250.1 MHz, DMSO): |
| 13.071(11.5); 9.137(6.1); 9.129(6.3); 9.000(4.9); 8.994(6.5); 8.313(3.4); 8.304(3.4); 8.284(3.4); 8.276(3.2); 5.766(16.0); 3.447(4.9); 2.516(11.2); 2.510(14.1); 2.503(9.9); 1.995(0.6); 1.180(0.4) |
| Example V-06: 1H-NMR(250.1 MHz, DMSO): |
| 13.001(0.4); 12.913(16.0); 12.824(0.5); 9.141(0.4); 9.075(0.4); 9.065(0.5); 9.048(6.9); 9.038(7.7); 8.950(0.4); 8.893(6.9); 8.884(6.4); 8.427(6.9); 8.395(7.0); 7.966(5.9); 7.918(5.8); 7.705(0.6); 7.693(0.5); 4.143(0.4); 4.124(0.4); 3.458(5.8); 2.574(0.7); 2.518(2.8); 2.511(3.8); 2.504(2.8); 1.992(0.6); 1.343(0.5); 1.315(0.5); 1.274(1.2); 1.230(0.4); 1.204(0.6); 1.175(0.5); 0.900(0.6); 0.870(1.3); 0.855(0.9); 0.840(0.7) |
| Example V-09: 1H-NMR(499.9 MHz, DMSO): |
| 11.548(16.0); 8.944(7.7); 8.940(8.0); 8.734(6.0); 8.730(5.7); 8.333(12.3); 8.105(2.8); 8.102(3.5); 8.093(0.4); 8.088(3.9); 8.084(6.7); 8.076(7.6); 8.036(6.1); 8.018(3.6); 3.294(25.6); 2.512(2.0); 2.508(4.2); 2.504(5.8); 2.501(4.1); 2.497(1.9); 0.000(3.2) |
| Example V-10: 1H-NMR(499.9 MHz, DMSO): |
| 12.785(16.0); 9.015(8.0); 9.010(8.4); 8.917(7.7); 8.914(7.1); 8.432(8.0); 8.429(8.2); 8.224(4.2); 8.220(4.1); 8.206(5.3); 8.202(5.2); 8.087(7.2); 8.069(5.5); 3.409(9.3); 2.901(1.6); 2.741(1.4); 2.579(0.7); 2.560(1.8); 2.549(3.5); 2.538(1.8); 2.522(3.5); 2.519(4.5); 0.000(1.8) |
| Example V-11: 1H-NMR(400.0 MHz, DMSO): |
| 11.580(9.6); 11.573(5.7); 11.570(4.3); 8.887(6.2); 8.881(9.0); 8.876(6.0); 8.593(5.6); 8.587(7.8); 8.581(4.7); 8.336(12.8); 8.311(0.9); 8.306(0.9); 8.301(0.7); 8.298(0.7); 8.096(4.8); 8.084(11.4); 8.077(16.0); 8.052(9.4); 8.029(3.3); 7.953(0.8); 3.395(0.5); 3.342(206.5); 3.338(291.3); 3.333(281.1); 3.290(0.5); 2.895(5.3); 2.736(4.4); 2.680(0.9); 2.675(1.3); 2.671(0.9); 2.528(4.3); 2.515(77.4); 2.511(153.7); 2.506(201.0); 2.502(145.2); 2.497(70.2); 2.337(0.9); 2.333(1.2); 2.328(0.9); 1.331(0.5); 1.235(0.7); 0.060(0.6); 0.000(6.5); −0.056(0.8) |
| Example V-13: 1H-NMR(300.2 MHz, DMSO): |
| 11.656(0.3); 11.629(0.4); 11.605(0.4); 11.564(0.3); 10.190(2.6); 9.292(1.4); 9.214(1.6); 9.206(1.9); 9.199(1.3); 9.144(1.4); 9.137(1.2); 9.111(0.4); 9.100(0.4); 9.093(0.5); 9.074(10.0); 9.067(10.9); 8.939(7.5); 8.933(6.8); 8.591(1.4); 8.586(1.4); 8.423(0.4); 8.327(16.0); 8.279(0.5); 8.231(0.3); 8.209(0.7); 8.203(0.5); 8.180(1.8); 8174(1.8); 8158(1.7); 8.146(0.5); 8.122(3.6); 8.116(4.0); 8.103(0.9); 8.093(5.7); 8.087(7.5); 8.052(8.6); 8.047(7.3); 8.027(8.2); 7.998(4.3); 5.762(8.9); 5.716(0.6); 5.526(2.5); 5.270(0.4); 3.941(0.7); 3.783(0.5); 3.745(0.4); 3.644(1.5); 3.454(0.5); 3.431(0.5); 3.377(1.6); 3.298(0.5); 3.170(4.0); 3.134(0.4); 3.074(0.4); 3.063(0.6); 2.724(0.3); 2.569(23.8); 2.519(6.0); 2.513(13.9); 2.507(20.0); 2.501(15.4); 2.495(7.9); 2.423(0.5); 1.081(0.5); 1.057(1.1); 1.034(0.5); 0.000(11.2); -0.011(0.6) |
| Example V-14: 1H-NMR(300.2 MHz, DMSO): |
| 12.746(1.1); 12.721(16.0); 10.188(0.7); 9.205(0.4); 9.198(0.5); 9.130(0.5); 9.124(0.5); 9.099(6.1); 9.092(8.4); 9.059(6.8); 9.053(5.1); 8.957(0.5); 8.949(0.5); 8.772(0.4); 8.763(0.4); 8.578(0.4); 8.447(0.5); 8.440(0.5); 8.386(6.1); 8.380(6.5); 8.211(3.5); 8.204(3.4); 8.191(0.9); 8.181(5.0); 8.174(5.1); 8.153(0.6); 8.110(0.6); 8.080(0.4); 8.053(6.1); 8.023(4.3); 7.957(0.4); 3.387(18.7); 2.893(2.7); 2.734(2.2); 2.569(1.6); 2.551(0.5); 2.512(9.1); 2.506(12.2); 2.500(9.1); 2.494(4.6); 1.180(0.3); 0.000(7.6) |
| Example V-15: 1H-NMR(300.2 MHz, DMSO): |
| 11.502(10.2); 8.929(4.4); 8.922(4.5); 8.547(4.1); 8.540(3.9); 8.275(7.8); 7.952(3.8); 7.929(4.0); 4.553(8.4); 3.336(6.4); 2.713(16.0); 2.519(1.4); 2.514(2.9); 2.507(4.0); 2.501(3.0); 2.496(1.5); 0.000(3.5) |
| Example V-16: 1H-NMR(300.2 MHz, DMSO): |
| 11.523(11.0); 8.965(5.1); 8.958(5.4); 8.710(4.9); 8.702(4.6); 8.274(8.1); 7.950(3.6); 7.910(3.8); 3.326(15.8); 2.709(16.0); 2.515(3.8); 2.509(8.3); 2.503(11.4); 2.497(8.4); 2.491(4.1); 0.011(0.4); 0.000(12.4); −0.011(0.6) |
| Example V-17: 1H-NMR(300.2 MHz, DMSO): |
| 11.742(16.0); 9.061(7.7); 9.053(8.3); 8.838(7.5); 8.831(7.2); 8.322(12.7); 8.202(7.4); 8.196(8.0); 8.079(7.3); 8.074(6.8); 3.346(4.2); 2.526(1.2); 2.520(2.5); 2.514(3.3); 2.508(2.5); 2.503(1.2); 0.000(3.1) |
| Example V-18: 1H-NMR(300.2 MHz, DMSO): |
| 12.886(16.0); 9.107(6.7); 9.100(7.6); 8.982(7.1); 8.974(6.6); 8.386(6.6); 8.380(7.3); 8.268(7.6); 8.262(7.1); 7.964(0.3); 2.902(2.2); 2.744(1.8); 2.581(2.8); 2.524(2.2); 2.518(3.0); 2.512(2.3); 0.000(2.6) |

-continued

NMR Peak List Table 3

Example V-19: 1H-NMR(300.2 MHz, DMSO):

12.672(12.1); 9.026(4.9); 9.018(5.4); 8.882(4.7); 8.874(4.3); 8.267(3.2); 8.260(3.4); 8.067(2.8); 8.064(3.3); 8.061(3.2); 8.057(2.5); 3.405(6.5); 2.892(0.8); 2.734(16.0); 2.706(0.5); 2.566(1.7); 2.549(0.9); 2.530(0.5); 2.515(4.8); 2.509(10.2); 2.503(14.0); 2.497(10.1); 2.491(4.8); 0.011(0.5); 0.000(15.7); −0.011(0.6)

Example V-23: 1H-NMR(300.2 MHz, DMSO):

11.668(16.0); 8.947(7.6); 8.939(8.4); 8.779(4.9); 8.773(7.2); 8.768(4.9); 8.268(8.9); 8.265(8.8); 7.868(8.1); 7.803(4.5); 7.798(4.2); 7.764(4.5); 7.759(4.3); 3.339(0.3); 2.456(3.9); 2.450(5.3); 2.444(4.0); −0.060(6.0)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1 H-NMR peak lists are similar to classical 1 H-NMR prints and contain therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

USE EXAMPLES

Example A

In Vivo Preventive Test on *Alternaria Brassicae* (Leaf Spot on Radish)

The active ingredients tested are prepared by homogenization in a mixture of acetone/tween/DMSO, and then diluted with water to obtain the desired active material concentration.

Radish plants ("Pernod Clair" variety), sown in starter cups on a 50/50 peat soil-pozzolana substrate and grown at 17° C., are treated at the 2-leaf stage by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Alternaria brassicae* spores (50 000 spores per ml). The spores are collected from a 15-day-old culture. The contaminated rice plants are incubated at 20° C. and at 100% relative humidity.

Grading (% of efficacy) is carried out 5 days after the contamination, in comparison with the control plants. Under these conditions, good (at least 70%) or total protection is observed at a dose of 500 ppm with the following compounds:

48 (97%), 52 (71%, 75%), 84 (80%), 85 (96%), 95 (70%), 98 (70%), 99 (70%), 105 (70%), 135 (100%), 161 (75%), 162 (88%), 163 (88%), 164 (88%), 170 (81%), 171 (75%), 173 (88%), 178 (75%), 180 (75%), 187 (88%), 188 (88%), 198 (98%), 208 (88%), 214 (75%), 215 (75%), 219 (75%), 220 (88%), 221 (98%), 226 (81%), 227 (75%), 234 (75%), 237 (71%), 241 (81%), 242 (94%), 244 (81%), 245 (94%), 246 (75%), 247 (75%), 273 (75%), 278 (86%), 306 (71%), 383 (83%), 384 (83%), 402 (71%), 411 (80%), 412 (70%), 415 (80%), 422 (72%), 423 (83%), 426 (78%), 427 (83%).

Example B

In Vivo Preventive Test on *Botrytis Cinerea* (Grey Mould)

The active ingredients tested are prepared by homogenization in a mixture of acetone/tween/DMSO and then diluted with water to obtain the desired active material.

Gherkin plants ("Vert petit de Paris" variety), sown in starter cups on a 50/50 peat soil-pozzolana substrate and grown at 24° C., are treated at the Z11 cotyledon stage by spraying with the active ingredient prepared as described above. Plants, used as controls, are treated with the mixture of acetone/tween/DMSO/water not containing the active material.

After 24 hours, the plants are contaminated by spraying the cotyledons with an aqueous suspension of cryopreserved *Botrytis cinerea* spores (50 000 spores per ml). The spores are suspended in a nutrient solution composed of 10 g/L of PDB, 50 g/L of D-Fructose, 2 g/L of $NH_4NO_3$ and 1 g/L of $KH_2PO_4$. The contaminated gherkin plants are incubated at 17° C. and at 80% relative humidity.

Grading (% of efficacy) is carried out 4-5 days after the contamination, in comparison with the control plants.

Under these conditions, good (at least 70%) or total protection is observed at a dose of 500 ppm with the following compounds:

14 (100%), 17 (100%), 22 (93%), 31 (93%), 32 (98%), 34 (100%), 38 (100%), 39 (100%), 40 (100%), 43 (100%), 44 (99%), 45 (98%, 100%), 47 (95%), 48 (100%), 49 (100%), 50 (100%), 51 (100%), 52 (100%), 53 (99%), 55 (99%), 64 (77%), 66 (100%), 68 (98%), 69 (99%), 70 (93%), 75 (93%), 78 (74%), 82 (95%), 83 (100%), 87 (97%), 99 (100%), 100 (97%), 103 (98%), 120 (100%), 125 (100%), 127 (80%), 128 (98%), 130 (89%), 131 (92%), 132 (98%), 147 (88%), 155 (100%), 162 (99%), 164 (71%), 167 (100%), 168 (99%), 169 (100%), 170 (100%), 178 (100%), 180 (95%), 181 (92%), 182 (99%), 185 (95%), 186 (92%), 190 (89%), 193 (74%), 195 (97%), 197 (100%), 198 (95%), 199 (99%), 202 (87%), 205 (84%), 214 (100%), 215 (87%), 216 (99%), 219 (99%), 220 (100%), 227 (92%), 234 (99%), 238 (82%), 242 (86%), 247 (100%), 259 (75%), 260 (75%), 262 (95%), 267 (85%), 268 (93%), 291 (88%), 293 (97%), 296 (97%), 298 (87%), 300 (99%), 402 (99%), 409 (100%), 414 (100%), 418 (79%), 428 (100%), 429 (100%), 442 (100%), 444 (97%), 445 (93%), 446 (98%), 447 (97%), 448 (98%), 449 (99%), 450 (100%), 455 (98%), 456 (98%), 458 (100%), 461 (99%), 462 (98%), 463 (100%), 464 (98%), 465 (88%), 470 (100%), 471 (89%), 474 (100%), 475 (100%), 476 (100%), 481 (97%), 482 (100%), 483 (100%), 493 (100%), 496 (99%), 497 (100%), 498 (92%), 500 (85%), 501 (100%), 502 (98%), 504 (99%), 505 (75%), 506 (100%), 508 (100%), 511 (100%), 512 (98%), 514 (100%), 515 (100%), 516 (100%), 517 (80%), 523 (73%), 524 (100%), 525 (100%), 527 (100%), 528 (99%), 529 (100%), 530 (100%), 531 (100%), 532 (100%), 533 (100%), 534 (100%), 535 (100%), 536 (100%), 537 (100%), 538 (100%), 539 (100%), 540 (100%), 541 (100%), 542 (100%), 543 (100%), 544 (100%), 545 (100%), 546 (100%), 547 (100%), 548 (94%), 549 (83%), 550 (98%), 551 (98%), 558 (97%), 559 (95%), 565 (100%), 567 (100%), 568 (99%), 569 (100%), 595 (100%), 596 (99%), 597 (100%), 599 (100%), 613 (100%), 614 (100%), 615 (95%), 617 (95%), 619 (73%), 621 (83%), 724 (98%), 725 (98%), 726 (99%), 727 (98%), 728 (97%), 729 (97%), 730 (85%), 734 (95%).

Example C

In Vivo Preventive Test on *Peronospora Parasitica* (Crucifer Downy Mildew)

The active ingredients tested are prepared by homogenization in a mixture of acetone/Tween/DMSO and then diluted with water to obtain the desired active material.

Cabbage plants (Eminence variety) in starter cups, sown on a 50/50 peat soil-pozzolana substrate and grown at 18-20° C., are treated at the cotyledon stage by spraying with the aqueous suspension described above. Plants, used as controls, are treated with an aqueous solution not containing the active material.

After 24 hours, the plants are contaminated by spraying them with an aqueous suspension of *Peronospora parasitica* spores (50,000 spores per ml). The spores are collected from infected plant. The contaminated cabbage plants are incubated for 5 days at 20° C., under a humid atmosphere.

Grading is carried out 5 days after the contamination, in comparison with the control plants.

Under these conditions, good (at least 70%) or total protection is observed at a dose of 500 ppm with the following compounds:

31 (90%), 34 (98%), 35 (90%), 36 (98%), 39 (100%), 41 (75%), 43 (94%), 45 (98%), 47 (100%), 48 (98%), 49 (100%).

Example D

In Vivo Preventive Test on *Phytophthora Infestans* (Tomato Late Blight)

The active ingredients tested are prepared by homogenization in a mixture of acetone/tween/DMSO and then diluted with water to obtain the desired active material.

Tomato plants ("Rentita" variety), sown in started cups on a 50/50 peat soil-pozzolana substrate and grown at 20-25° C., are treated at the Z12 leaf stage by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Phytophthora infestans* spores (20 000 spores per ml). The spores are collected from infected plants. The contaminated tomato plants are incubated at 16-18° C., under a humid atmosphere.

Grading (% of efficacy) is carried out 5 days after the contamination, in comparison with the control plants. Under these conditions, good protection (at least 70%) is observed at a dose of 500 ppm with the following compounds:

34 (99%), 39 (100%), 40 (97%), 43 (100%), 45 (76%), 48 (100%), 49 (100%), 50 (100%), 51 (75%), 70 (82%), 82 (74%), 83 (97%), 87 (100%), 88 (100%), 100 (98%), 106 (100%), 129 (85%), 146 (85%), 180 (86%), 181 (92%), 182 (83%), 183 (86%), 194 (94%), 195 (100%), 196 (94%), 197 (97%), 199 (92%), 201(92%), 206 (93%), 257 (100%), 260 (90%), 291 (87%), 298 (100%), 312 (100%), 338 (92%), 351 (100%), 365 (79%), 381 (95%), 409 (100%), 437 (70%), 438 (87%), 442 (94%), 445 (100%), 449 (100%), 455 (100%), 461 (100%), 463 (100%), 464 (100%), 465 (100%), 470 (98%), 474 (78%), 476 (85%), 477 (98%), 500 (94%), 506 (94%), 511 (100%), 514 (97%), 516 (73%), 533 (90%), 549 (96%), 550 (83%), 551 (81%), 565 (99%), 599 (85%), 724 (100%), 725 (83%), 726 (97%), 728 (100%), 730 (100%), 733 (100%).

Example E

In Vivo Preventive Test n *Pyrenophora Teres* (Net Blotch On Barley)

The active ingredients tested are prepared by homogenization in a mixture of acetone/tween/DMSO, and then diluted with water to obtain the desired active material concentration.

Barley plants ("Plaisant" variety), sown in starter cups on a 50/50 peat soil-pozzolana substrate and grown at 22° C. (12 h)/20° C. (12 h), are treated at the 1-leaf stage (10 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Pyrenophora teres* spores (12 000 spores per ml). The spores are collected from a 12-day-old culture. The contaminated barley plants are incubated for 48 hours at 20° C. and at 100% relative humidity, and then for 12 days at 80% relative humidity.

Grading (% of efficacy) is carried out 12 days after the contamination, in comparison with the control plants.

Under these conditions, good (at least 70%) or total protection is observed at a dose of 500 ppm with the following compounds:

36 (79%), 46 (75%), 47 (75%), 48 (93%), 52 (71%), 71 (83%, 88%), 105 (79%), 106 (71%, 75%), 122 (86%), 129 (88%), 169 (79%), 177 (86%), 179 (86%), 198 (86%), 200 (71%), 206 (71%), 219 (71%), 225 (79%), 256 (75%), 260 (75%), 306 (75%), 383 (86%), 384 (86%), 406 (83%), 419 (75%), 435 (83%), 436 (92%), 440 (75%), 520 (88%).

Example F

In Vivo Preventive Test on *Puccinia Recondita* (Brown Rust On Wheat)

The active ingredients tested are prepared by homogenization in a mixture of acetone/tween/DMSO, and then diluted with water to obtain the desired active material concentration.

Wheat plants ("Scipion" variety), sown in starter cups on a 50/50 peat soil-pozzolana substrate and grown at 22° C. (12 h)/20° C. (12 h), are treated at the 1-leaf stage (10 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Puccinia recondita* spores (100 000 spores per nil). The spores are collected from an infected plant and are suspended in water containing 2.5 ml/l of Tween 80 at 10%. The contaminated wheat plants are incubated for 24 hours at 20° C. and at 100% relative humidity, and then for 10 days at 20° C. and at 70% relative humidity.

Grading (% of efficacy) is carried out 10 days after the contamination, in comparison with the control plants.

Under these conditions, good (at least 70%) or total protection is observed at a dose of 500 ppm with the following compounds:

34 (75%), 36 (79%), 43 (75%), 45 (88%), 48 (89%), 50 (88%), 51 (98%), 52 (88%), 71 (94%), 74 (88%), 105 (71%), 135 (89%), 140 (81%), 146 (72%), 157 (72%), 247 (72%), 257 (81%), 262 (81%), 265 (88%), 380 (78%), 382 (79%), 383 (94%), 384 (89%), 394 (92%), 414 (89%), 420 (94%), 423 (78%), 424 (72%), 428 (89%), 429 (89%), 434 (88%), 436 (94%), 438 (88%), 441 (83%), 442 (89%), 446 (83%), 447 (89%), 450 (89%), 451 (89%), 454 (94%), 456 (83%), 457 (83%), 469 (80%), 476 (90%), 477 (90%), 480 (90%), 482 (83%), 504 (72%), 530 (79%), 536 (72%), 548 (83%), 567 (75%), 599 (88%), 617 (71%), 724 (71%).

Example G

In Vivo Preventive Test on *Septoria Tritici* (Leaf Spot On Wheat)

The active ingredients tested are prepared by homogenization in a mixture of acetone/tween/DMSO, and then diluted with water to obtain the desired active material concentration.

Wheat plants ("Scipion" variety), sown in starter cups on a 50/50 peat soil-pozzolana substrate and grown at 22° C. (12 h)/20° C. (12 h), are treated at the 1-leaf stage (10 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of cryopreserved *Septoria tritici* spores (500 000 spores per ml). The contaminated wheat plants are incubated for 72 hours at 18° C. and at 100% relative humidity, and then for 21 to 28 days at 90% relative humidity.

Grading (% of efficacy) is carried out 21 to 28 days after the contamination, in comparison with the control plants.

Under these conditions, good (at least 70%) or total protection is observed at a dose of 500 ppm with the following compounds:

5 (86%), 6 (71%), 7 (93%), 8 (100%), 17 (100%), 18 (93%), 20 (71%), 22 (83%), 23 (75%), 24 (75%), 28 (100%), 29 (100%), 30 (100%), 31 (100%), 32 (79%, 97%), 35 (97%), 36 (100%), 38 (100%), 40 (100%), 44 (93%, 97%), 45 (100%), 46 (100%), 47 (100%), 48 (100%), 49 (79%, 97%), 50 (100%), 51 (100%), 52 (93%, 97%), 53 (97%), 54 (100%), 55 (100%), 56 (70%), 59 (70%), 61 (80%), 63 (90%), 64 (70%), 66 (100%), 68 (97%), 69 (97%), 70 (100%), 71 (75%, 86%), 74 (83%), 76 (75%), 78 (97%), 82 (100%), 83 (92%), 85 (75%), 86 (75%), 91 (75%), 100 (75%), 103 (75%), 104 (92%), 105 (75%), 106 (83%, 100%), 108 (75%), 115 (75%), 120 (100%), 121 (75%), 125 (100%), 128 (83%), 129 (100%), 131 (83%), 132 (100%), 133 (100%), 134 (71%), 135 (100%), 137 (93%), 138 (93%), 140 (80%), 143 (71%), 148 (100%), 149 (93%), 150 (100%), 152 (71%), 153 (71%), 155 (100%), 160 (71%), 162 (86%), 167 (100%), 168 (71%), 169 (100%), 170 (71%), 171 (71%), 176 (93%), 178 (100%), 180 (100%), 183 (86%), 184 (71%), 185 (86%), 186 (71%), 189 (71%), 190 (71%), 191 (71%), 192 (71%), 195 (100%), 197 (86%), 198 (86%), 201 (86%), 205 (100%), 206 (100%), 213 (97%), 214 (100%), 215 (86%), 216 (100%), 222 (71%), 223 (71%), 227 (93%), 234 (86%), 238 (93%), 242 (86%), 243 (71%), 245 (71%), 247 (100%), 256 (100%), 259 (100%), 260 (98%), 261 (97%), 267 (93%), 279 (75%), 284 (100%), 285 (100%), 286 (92%), 287 (83%), 290 (96%), 291 (100%), 292 (96%), 293 (96%), 294 (70%), 295 (80%), 296 (100%), 298 (100%), 301 (80%), 304 (100%), 306 (78%), 307 (100%), 309 (86%), 310 (100%), 311 (100%), 312 (100%), 314 (100%), 322 (98%), 323 (78%), 326 (98%), 329 (100%), 330 (100%), 331 (83%), 332 (100%), 333 (98%), 334 (100%), 335 (78%), 336 (100%), 337 (78%), 338 (100%), 339 (78%), 341 (100%), 343 (100%), 345 (100%), 347 (100%), 349 (94%), 350 (100%), 351 (100%), 353 (94%), 355 (100%), 357 (78%), 361 (78%), 365 (100%), 366 (100%), 368 (100%), 371 (100%), 374 (100%), 376 (86%), 377 (100%), 378 (97%), 381 (97%), 383 (100%), 384 (100%), 388 (100%), 389 (100%), 390 (98%), 391 (100%), 392(98%), 396 (97%), 397 (75%), 402 (100%), 406 (100%), 407 (92%), 408 (100%), 409 (100%), 410 (100%), 414 (100%), 416 (100%), 417 (100%), 418 (83%), 428 (100%), 429 (100%), 434 (100%), 436 (100%), 438 (100%), 439 (93%), 441 (100%), 442 (97%), 443 (88%), 444 (100%), 445 (94%), 446 (100%), 447 (75%), 448 (98%), 449 (98%), 450 (98%), 451 (94%), 456 (100%), 457 (88%), 458 (100%), 462 (100%), 463 (100%), 464 (100%), 465 (97%), 466 (97%), 467 (97%), 468 (100%), 469 (97%), 470 (97%), 471 (97%), 472 (75%), 473 (75%), 474 (97%), 475 (83%), 476 (97%), 481 (86%), 482 (100%), 483 (100%), 489 (93%), 490 (88%), 491 (75%), 493 (97%), 496 (100%), 497 (100%), 498 (71%), 500 (86%), 501 (97%), 502 (100%), 503 (71%), 504 (100%), 506 (100%), 507 (97%), 508 (94%), 509 (97%), 511 (100%), 512 (97%), 514 (98%), 515 (97%), 520 (79%), 523 (97%), 524 (93%), 525 (93%), 527 (97%), 528 (97%), 529 (100%), 531 (100%), 532 (100%), 533 (100%), 534 (92%), 535 (100%), 536 (100%), 537 (100%), 538 (100%), 539 (83%), 540 (92%), 541 (100%), 542 (83%), 543 (100%), 544 (100%), 545 (100%), 546 (83%), 548 (100%), 549 (97%), 550

(100%), 551 (93%), 555 (71%), 556 (97%), 558 (100%), 559 (100%), 560 (97%), 561 (100%), 562 (86%), 564 (100%), 565 (100%), 566 (100%), 567 (100%), 568 (100%), 569 (100%), 595 (100%), 596 (100%), 597 (100%), 599 (100%), 613 (79%), 614 (97%), 615 (79%), 618 (93%), 619 (71%), 621 (97%), 724 (100%), 725 (100%), 726 (100%), 727 (100%), 729 (100%), 730 (100%), 731 (100%), 732 (100%), 733 (92%), 734 (100%).

Example H

In Vivo Preventive Test on *Sphaerotheca Fuliginea* (Powdery Mildew on Cucurbits)

The active ingredients tested are prepared by homogenization in a mixture of acetone/tween/DMSO and then diluted with water to obtain the desired active material.

Gherkin plants ("Vert petit de Paris" variety), sown in starter cups on a 50/50 peat soil-pozzolana substrate and grown at 24° C., are treated at the Z11 cotyledon stage by spraying with the active ingredient prepared as described above. Plants, used as controls, are treated with the mixture of acetone/tween/DMSO/water not containing the active material.

After 24 hours, the plants are contaminated by spraying the cotyledons with an aqueous suspension of *Sphaerotheca fuliginea* spores (100 000 spores per ml). The spores are collected from infected plants. The contaminated gherkin plants are incubated at about 20° C/25° C. and at 60/70% relative humidity.

Grading (% of efficacy) is carried out 12 days after the contamination, in comparison with the control plants.

Under these conditions, good (at least 70%) or total protection is observed at a dose of 500 ppm with the following compounds:

6 (89%), 17 (85%), 31 (100%), 32 (100%), 34 (94%, 98%), 38 (97%), 39 (100%), 40 (100%), 43 (100%), 44 (98%), 45 (98%), 48 (100%), 49 (98%), 50 (100%), 51 (98%), 52 (100%), 53 (88%), 55 (94%, 98%), 66 (98%), 68 (98%), 70 (100%), 71 (98%), 75 (94%, 98%), 80 (93%), 82 (97%, 98%), 83 (97%, 98%), 87 (89%), 100 (94%), 103 (78%), 105 (100%), 120 (94%), 125 (98%), 129 (80%), 132 (94%), 140 (83%), 150 (95%), 155 (89%), 162 (94%), 176 (83%), 180 (98%), 181 (98%), 182 (98%), 185 (78%), 195 (98%), 197 (98%), 199 (98%), 205 (75%), 206 (94%), 214 (78%), 216 (98%), 234 (94%), 247 (89%), 259 (94%), 261 (85%), 277 (71%), 278 (100%), 284 (100%), 291 (80%), 293 (90%), 296 (100%), 309 (100%), 312 (94%), 314 (81%), 323 (81%), 326 (88%), 332 (98%), 334 (94%), 336 (81%), 337 (88%), 338 (100%), 341 (98%), 343 (100%), 345 (94%), 351 (98%), 365 (98%), 368 (100%), 371 (98%), 374 (100%), 377 (98%), 381 (94%), 391 (95%), 392 (90%), 406 (100%), 407 (100%), 408 (100%), 409 (98%), 414 (98%), 428 (98%), 429 (83%), 436 (100%), 437 (100%), 438 (89%), 439 (78%), 440 (89%), 441 (94%), 442 (100%), 445 (94%), 446 (94%), 447 (75%), 448 (100%), 449 (100%), 450 (98%), 453 (88%), 455 (98%), 456 (98%), 458 (98%), 461 (98%), 462 (98%), 463 (97%), 464 (100%), 465 (81%), 470 (75%), 471 (98%), 474 (98%), 475 (88%), 476 (98%), 477 (75%), 482 (100%), 483 (100%), 496 (100%), 497 (98%), 500 (100%), 501 (100%), 503 (78%), 504 (100%), 505 (98%), 506 (97%), 508 (98%), 511 (88%), 512 (97%), 514 (75%), 515 (93%), 524 (93%), 527 (94%), 531 (98%), 532 (89%), 533 (100%), 534 (100%), 535 (100%), 536 (100%), 538 (100%), 540 (94%), 541 (98%), 543 (100%), 544 (98%), 545 (100%), 546 (100%), 547(100%), 548 (80%), 550 (80%), 558 (85%), 559 (85%), 565 (98%), 566 (89%), 567 (100%), 568 (94%), 569 (100%), 595 (100%), 596 (83%), 599 (100%), 613 (100%), 614 (92%), 617 (100%), 621 (97%), 724 (100%), 725 (98%), 726 (98%), 727 (98%), 728 (100%), 729 (100%), 730 (98%), 731 (75%), 733 (98%), 734 (98%).

Example I

In Vivo Preventive Test on *Uromyces Appendiculatus* (Bean Rust)

The active ingredients tested are prepared by homogenization in a mixture of acetone/tween/DMSO, and then diluted with water to obtain the desired active material concentration.

Bean plants ("Saxa" variety), sown in starter cups on a 50/50 peat soil-pozzolana substrate and grown at 24° C., are treated at the 2-leaf stage (9 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Uromyces appendiculatus* spores (150 000 spores per nil). The spores are collected from an infected plant and are suspended in water containing 2.5 ml/l of Tween 80 at 10%. The contaminated bean plants are incubated for 24 hours at 20° C. and at 100% relative humidity, and then for 10 days at 20° C. and at 70% relative humidity.

Grading (% of efficacy) is carried out 10 days after the contamination, in comparison with the control plants.

Under these conditions, good (at least 70%) or total protection is observed at a dose of 500 ppm with the following compounds:

43 (97%), 48 (96%), 105 (86%), 106 (78%), 129 (100%), 140 (96%), 205 (70%), 237 (80%), 265 (96%), 305 (80%), 306 (100%), 382 (89%), 383 (99%), 384 (79%), 414 (100%), 420 (97%), 428 (87%), 429 (71%), 434 (97%), 435 (77%), 436 (100%), 438 (97%), 441 (91%), 442 (88%), 447 (100%), 450 (91%), 476 (77%), 477 (86%), 480 (83%), 482 (98%), 515 (91%).

The invention claimed is:

1. Quinoline-isoxazoline-5-carboxylic acid and/or acid ester and/or quinoline-isoxazoline-5-thiocarboxylic acid and/or acid ester of formula (II)

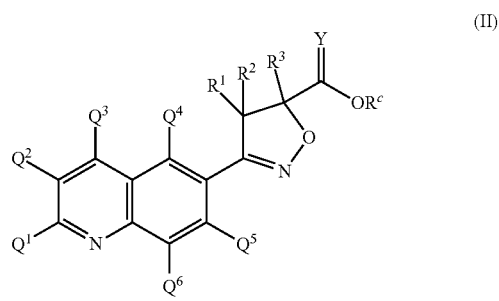

in which $R^c$ represents hydrogen, substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; substituted or non-substituted aryl; or substituted or non-substituted 5, 6 or 7 membered unsaturated heterocycle ring with 1 to 3 heteroatoms;

$R^1$ and $R^2$ independently of one another represent hydrogen; substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; cyano; isonitrile; nitro; halogen; substituted or non-substituted $C_1$-$C_8$-alkoxy; $C_1$-$C_8$-haloalkoxy; substituted or non-substituted $C_2$-$C_8$-alkenyloxy; $C_2$-$C_8$-haloalkenyloxy, substituted or non-substituted $C_2$-$C_8$-alkynyloxy; $C_1$-$C_8$-haloalkynyloxy; substituted or non-substituted $C_3$-$C_7$-cycloalkyl; substituted or non-substituted $C_1$-$C_8$-alkylsulfanyl; substituted or non-substituted $C_1$-$C_8$-alkylsulfonyl; substituted or non-substituted $C_1$-$C_8$-alkylsulfinyl; amino; substituted or non-substituted $C_1$-$C_8$-alkylamino; substituted or non-substituted di-$C_1$-$C_8$-alkylamino; substituted or non-substituted $C_1$-$C_8$-alkoxycarbonyl; substituted or non-substituted $C_1$-$C_8$-alkylcarbamoyl; substituted or non-substituted di-$C_1$-$C_8$-alkylcarbamoyl; or substituted or non-substituted N—$C_1$-$C_8$-alkyl-$C_1$-$C_8$-alkoxy-carbamoyl; or $R^1$ and $R^2$ can form together with the carbon atom to which they are attached a substituted or non-substituted $C_3$-$C_7$-cycloalkyl; or $C_3$-$C_7$-halocycloalkyl;

$R^3$ represents hydrogen; substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; cyano; isonitrile; nitro; halogen; substituted or non-substituted $C_1$-$C_8$-alkoxy; $C_1$-$C_8$-haloalkoxy; substituted or non-substituted $C_2$-$C_8$-alkenyloxy; $C_2$-$C_8$-haloalkenyloxy, substituted or non-substituted $C_2$-$C_8$-alkynyloxy; $C_1$-$C_8$-haloalkynyloxy; substituted or non-substituted $C_3$-$C_7$-cycloalkyl; substituted or non-substituted $C_1$-$C_8$-alkylsulfanyl; substituted or non-substituted $C_1$-$C_8$-alkylsulfonyl; substituted or non-substituted $C_1$-$C_8$-alkylsulfinyl; amino; substituted or non-substituted $C_1$-$C_8$-alkylamino; substituted or non-substituted di-$C_1$-$C_8$-alkylamino; substituted or non-substituted tri($C_1$-$C_8$)alkylsilyl-$C_1$-$C_8$-alkyl; substituted or non-substituted tri($C_1$-$C_8$)alkylsilyl-$C_2$-$C_8$-alkenyl; substituted or non-substituted tri($C_1$-$C_8$)alkylsilyl-$C_2$-$C_8$-alkynyl; substituted or non-substituted $C_1$-$C_8$-alkoxycarbonyl; substituted or non-substituted $C_1$-$C_8$-alkylcarbamoyl; substituted or non-substituted di-$C_1$-$C_8$-alkylcarbamoyl; or substituted or non-substituted N—$C_1$-$C_8$-alkyl-$C_1$-$C_8$-alkoxy-carbamoyl; substituted or non-substituted aryl; or substituted or non-substituted 5, 6 or 7 membered heterocycle ring with 1 to 3 heteroatoms; or $R^3$ together with $R^1$ or $R^2$ together with the carbon atoms to which they are attached can form a substituted or non-substituted $C_3$-$C_7$ cycloalkyl; $C_3$-$C_7$-halocycloalkyl; or a substituted or non-substituted saturated 5, 6 or 7 membered heterocycle;

Y represents an oxygen or sulfur atom;

$Q^1$, $Q^2$, $Q^3$, $Q^4$, $Q^5$ and $Q^6$ independently of one another represent hydrogen; halogen; nitro; cyano; isonitrile; hydroxyl; amino; sulfanyl; pentafluoro-$\lambda^6$-sulfanyl; formyl; formyloxy; formylamino; substituted or non-substituted (hydroxyimino)-$C_1$-$C_8$-alkyl; substituted or non-substituted ($C_1$-$C_8$-alkoxyimino)-$C_1$-$C_8$-alkyl; substituted or non-substituted ($C_2$-$C_8$-alkenyloxyimino)-$C_1$-$C_8$-alkyl; substituted or non-substituted ($C_2$-$C_8$-alkynyloxyimino)-$C_1$-$C_8$-alkyl; substituted or non-substituted (benzyloxyimino)-$C_1$-$C_8$-alkyl; carboxy; carbamoyl; N-hydroxycarbamoyl; carbamate; substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; substituted or non-substituted $C_1$-$C_8$-alkoxy; $C_1$-$C_8$-haloalkoxy; substituted or non-substituted $C_1$-$C_8$-alkylsulfanyl; $C_1$-$C_8$-haloalkylsulfanyl; substituted or non-substituted $C_1$-$C_8$-alkylsulfinyl; $C_1$-$C_8$-haloalkylsulfinyl; substituted or non-substituted $C_1$-$C_8$-alkylsulfonyl; $C_1$-$C_8$-haloalkylsulfonyl; substituted or non-substituted $C_1$-$C_8$-alkylamino; substituted or non-substituted di-$C_1$-$C_8$-alkylamino; substituted or non-substituted $C_2$-$C_8$-alkenyloxy; $C_2$-$C_8$-haloalkenyloxy; substituted or non-substituted $C_3$-$C_8$-alkynyloxy; $C_2$-$C_8$-haloalkynyloxy; substituted or non-substituted $C_3$-$C_7$-cycloalkyl; $C_3$-$C_7$-halocycloalkyl; substituted or non-substituted ($C_3$-$C_7$-cycloalkyl)-$C_1$-$C_8$-alkyl; substituted or non-substituted $C_4$-$C_7$-cycloalkenyl; $C_4$-$C_7$-halocycloalkenyl; substituted or non-substituted ($C_3$-$C_7$-cycloalkyl)-$C_2$-$C_8$-alkenyl; substituted or non-substituted ($C_3$-$C_7$-cycloalkyl)-$C_2$-$C_8$-alkynyl; substituted or non-substituted tri($C_1$-$C_8$)alkylsilyl; substituted or non-substituted tri($C_1$-$C_8$)alkylsilyl-$C_1$-$C_8$-alkyl; substituted or non-substituted tri($C_1$-$C_8$)alkylsilyl-$C_2$-$C_8$-alkenyl; substituted or non-substituted tri($C_1$-$C_8$)alkylsilyl-$C_2$-$C_8$-alkynyl; substituted or non-substituted $C_1$-$C_8$-alkylcarbonyl; $C_1$-$C_8$-haloalkylcarbonyl; substituted or non-substituted $C_1$-$C_8$-alkylcarbonyloxy; $C_1$-$C_8$-haloalkylcarbonyloxy; substituted or non-substituted $C_1$-$C_8$-alkylcarbonylamino; $C_1$-$C_8$-haloalkylcarbonylamino; substituted or non-substituted $C_1$-$C_8$-alkoxycarbonyl; $C_1$-$C_8$-haloalkoxycarbonyl; substituted or non-substituted $C_1$-$C_8$-alkyloxycarbonyloxy; $C_1$-$C_8$-haloalkoxycarbonyloxy; substituted or non-substituted $C_1$-$C_8$-alkylcarbamoyl; substituted or non-substituted di-$C_1$-$C_8$-alkylcarbamoyl; substituted or non-substituted $C_1$-$C_8$-alkylaminocarbonyloxy; substituted or non-substituted di-$C_1$-$C_8$-alkylaminocarbonyloxy; substituted or non-substituted N—($C_1$-$C_8$-alkyl)hydroxy carbamoyl; substituted or non-substituted $C_1$-$C_8$-alkoxycarbamoyl; substituted or non-substituted N—($C_1$-$C_8$-alkyl)-$C_1$-$C_8$-alkoxycarbamoyl; aryl which is optionally substituted by up to 6 identical or different groups $R^a$; $C_1$-$C_8$-arylalkyl which is optionally substituted by up to 6 identical or different groups $R^a$; $C_2$-$C_8$-arylalkenyl which is optionally substituted by up to 6 identical or different groups $R^a$; $C_2$-$C_8$-arylalkynyl which is optionally substituted by up to 6 identical or different groups $R^a$; aryloxy which is optionally substituted by up to 6 identical or different groups $R^a$; arylsulfanyl which is optionally substituted by up to 6 identical or different groups $R^a$; arylamino which is optionally substituted by up to 6 identical or different groups $R^a$; $C_1$-$C_8$-arylalkyloxy which is optionally substituted by up to 6 identical or different groups $R^a$; $C_1$-$C_8$-arylalkylsulfanyl which is optionally substituted by up to 6 identical or different groups $R^a$; $C_1$-$C_8$-arylalkylamino which is optionally substituted by up to 6 identical or different groups $R^a$; 5, 6 or 7 membered heterocycle with 1 to 3 heteroatoms which is optionally substituted by up to 4 identical or different groups $R^a$;

$R^a$ independently of one another represent halogen; cyano; nitro; substituted or non-substituted $C_1$-$C_8$-alkyl; $C_1$-$C_8$-haloalkyl; substituted or non-substituted $C_1$-$C_8$-alkoxy; $C_1$-$C_8$-haloalkoxy; substituted or non-substituted $C_1$-$C_8$-alkylsulfanyl; $C_1$-$C_8$-haloalkylsulfanyl; substituted or non-substituted tri($C_1$-$C_8$)alkylsilyl; substituted or non-substituted tri($C_1$-$C_8$)alkylsilyl-$C_1$-$C_8$-alkyl; substituted or non-substituted ($C_1$-$C_8$-alkoxyimino)-$C_1$-$C_8$-alkyl; or substituted or non-substituted (benzyloxyimino)-$C_1$-$C_8$-alkyl,
and/or a salt thereof.

2. A compound of formula (III)

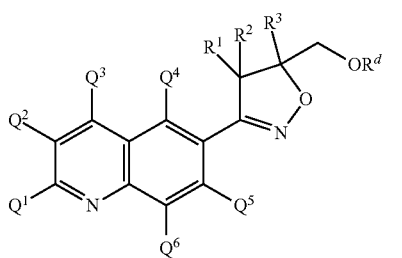

in which
$R^d$ represents hydrogen; substituted or non-substituted $C_1$-$C_8$-alkyl; $C_1$-$C_8$-haloalkyl; $C_3$-$C_7$-cycloalkyl; substituted or non-substituted $C_1$-$C_8$-alkylcarbonyl, substituted or non-substituted $C_1$-$C_8$-alkylaminocarbonyl; substituted or non-substituted aryl; or substituted or non-substituted 5, 6 or 7 membered unsaturated heterocycle ring with 1 to 3 heteroatoms, $R^1$ and $R^2$ independently of one another represent hydrogen; substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; cyano; isonitrile; nitro; halogen; substituted or non-substituted $C_1$-$C_8$-alkoxy; $C_1$-$C_8$-haloalkoxy; substituted or non-substituted $C_2$-$C_8$-alkenyloxy; $C_2$-$C_8$-haloalkenyloxy, substituted or non-substituted $C_2$-$C_8$-alkynyloxy; $C_1$-$C_8$-haloalkynyloxy; substituted or non-substituted $C_3$-$C_7$-cycloalkyl; substituted or non-substituted $C_1$-$C_8$-alkylsulfanyl; substituted or non-substituted $C_1$-$C_8$-alkylsulfonyl; substituted or non-substituted $C_1$-$C_8$-alkylsulfinyl; amino; substituted or non-substituted $C_1$-$C_8$-alkylamino; substituted or non-substituted di-$C_1$-$C_8$-alkylamino; substituted or non-substituted $C_1$-$C_8$-alkoxycarbonyl; substituted or non-substituted $C_1$-$C_8$-alkylcarbamoyl; substituted or non-substituted di-$C_1$-$C_8$-alkylcarbamoyl; or substituted or non-substituted N—$C_1$-$C_8$-alkyl-$C_1$-$C_8$-alkoxy-carbamoyl; or $R^1$ and $R^2$ can form together with the carbon atom to which they are attached a substituted or non-substituted $C_3$-$C_7$-cycloalkyl; or $C_3$-$C_7$-halocycloalkyl;

$R^3$ represents hydrogen; substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; cyano; isonitrile; nitro; halogen; substituted or non-substituted $C_1$-$C_8$-alkoxy; $C_1$-$C_8$-haloalkoxy; substituted or non-substituted $C_2$-$C_8$-alkenyloxy; $C_2$-$C_8$-haloalkenyloxy, substituted or non-substituted $C_2$-$C_8$-alkynyloxy; $C_1$-$C_8$-haloalkynyloxy; substituted or non-substituted $C_3$-$C_7$-cycloalkyl; substituted or non-substituted $C_1$-$C_8$-alkylsulfanyl; substituted or non-substituted $C_1$-$C_8$-alkylsulfonyl; substituted or non-substituted $C_1$-$C_8$-alkylsulfinyl; amino; substituted or non-substituted $C_1$-$C_8$-alkylamino; substituted or non-substituted di-$C_1$-$C_8$-alkylamino; substituted or non-substituted tri($C_1$-$C_8$)alkylsilyl-$C_1$-$C_8$-alkyl; substituted or non-substituted tri($C_1$-$C_8$)alkylsilyl-$C_2$-$C_8$-alkenyl; substituted or non-substituted tri($C_1$-$C_8$)alkylsilyl-$C_2$-$C_8$-alkynyl; substituted or non-substituted $C_1$-$C_8$-alkoxycarbonyl; substituted or non-substituted $C_1$-$C_8$-alkylcarbamoyl; substituted or non-substituted di-$C_1$-$C_8$-alkylcarbamoyl; or substituted or non-substituted N—$C_1$-$C_8$-alkyl-$C_1$-$C_8$-alkoxy-carbamoyl; substituted or non-substituted aryl; or substituted or non-substituted 5, 6 or 7 membered heterocycle ring with 1 to 3 heteroatoms; or $R^3$ together with $R^1$ or $R^2$ together with the carbon atoms to which they are attached can form a substituted or non-substituted $C_3$-$C_7$ cycloalkyl; $C_3$-$C_7$-halocycloalkyl; or a substituted or non-substituted saturated 5, 6 or 7 membered heterocycle;

$Q^1$, $Q^2$, $Q^3$, $Q^4$, $Q^5$ and $Q^6$ independently of one another represent hydrogen; halogen; nitro; cyano; isonitrile; hydroxyl; amino; sulfanyl; pentafluoro-$\lambda^6$-sulfanyl; formyl; formyloxy; formylamino; substituted or non-substituted (hydroxyimino)-$C_1$-$C_8$-alkyl; substituted or non-substituted ($C_1$-$C_8$-alkoxyimino)-$C_1$-$C_8$-alkyl; substituted or non-substituted ($C_2$-$C_8$-alkenyloxyimino)-$C_1$-$C_8$-alkyl; substituted or non-substituted ($C_2$-$C_8$-alkynyloxyimino)-$C_1$-$C_8$-alkyl; substituted or non-substituted (benzyloxyimino)-$C_1$-$C_8$-alkyl; carboxy; carbamoyl; N-hydroxycarbamoyl; carbamate; substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; substituted or non-substituted $C_1$-$C_8$-alkoxy; $C_1$-$C_8$-haloalkoxy; substituted or non-substituted $C_1$-$C_8$-alkylsulfanyl; $C_1$-$C_8$-haloalkylsulfanyl; substituted or non-substituted $C_1$-$C_8$-alkylsulfinyl; $C_1$-$C_8$-haloalkylsulfinyl; substituted or non-substituted $C_1$-$C_8$-alkylsulfonyl; $C_1$-$C_8$-haloalkylsulfonyl; substituted or non-substituted $C_1$-$C_8$-alkylamino; substituted or non-substituted di-$C_1$-$C_8$-alkylamino; substituted or non-substituted $C_2$-$C_8$-alkenyloxy; $C_2$-$C_8$-haloalkenyloxy; substituted or non-substituted $C_3$-$C_8$-alkynyloxy; $C_2$-$C_8$-haloalkynyloxy; substituted or non-substituted $C_3$-$C_7$-cycloalkyl; $C_3$-$C_7$-halocycloalkyl; substituted or non-substituted ($C_3$-$C_7$-cycloalkyl)-$C_1$-$C_8$-alkyl; substituted or non-substituted $C_4$-$C_7$-cycloalkenyl; $C_4$-$C_7$-halocycloalkenyl; substituted or non-substituted ($C_3$-$C_7$-cycloalkyl)-$C_2$-$C_8$-alkenyl; substituted or non-substituted ($C_3$-$C_7$-cycloalkyl)-$C_2$-$C_8$-alkynyl; substituted or non-substituted tri($C_1$-$C_8$)alkylsilyl; substituted or non-substituted tri($C_1$-$C_8$)alkylsilyl-$C_1$-$C_8$-alkyl; substituted or non-substituted tri($C_1$-$C_8$)alkylsilyl-$C_2$-$C_8$-alkenyl; substituted or non-substituted tri ($C_1$-$C_8$)alkylsilyl-$C_2$-$C_8$-alkynyl; substituted or non-substituted $C_1$-$C_8$-alkylcarbonyl; $C_1$-$C_8$-haloalkylcarbonyl; substituted or non-substituted $C_1$-$C_8$-alkylcarbonyloxy; $C_1$-$C_8$-haloalkylcarbonyloxy; substituted or non-substituted $C_1$-$C_8$-alkylcarbonylamino; $C_1$-$C_8$-haloalkylcarbonylamino; substituted or non-substituted $C_1$-$C_8$-alkoxycarbonyl; $C_1$-$C_8$-haloalkoxycarbonyl; substituted or non-substituted $C_1$-$C_8$-alkyloxycarbonyloxy; $C_1$-$C_8$-haloalkoxycarbonyloxy; substituted or non-substituted $C_1$-$C_8$-alkylcarbamoyl; substituted or non-substituted di-$C_1$-$C_8$-alkylcarbamoyl; substituted or non-substituted $C_1$-$C_8$-alkylaminocarbonyloxy; substituted or non-substituted di-$C_1$-$C_8$-alkylaminocarbonyloxy; substituted or non-substituted N—($C_1$-$C_8$-alkyl)hydroxy carbamoyl; substituted or non-substituted $C_1$-$C_8$-alkoxycarbamoyl;

substituted or non-substituted N—($C_1$-$C_8$-alkyl)-$C_1$-$C_8$-alkoxycarbamoyl; aryl which is optionally substituted by up to 6 identical or different groups $R^a$; $C_1$-$C_8$-arylalkyl which is optionally substituted by up to 6 identical or different groups $R^a$; $C_2$-$C_8$-arylalkenyl which is optionally substituted by up to 6 identical or different groups $R^a$; $C_2$-$C_8$-arylalkynyl which is optionally substituted by up to 6 identical or different groups $R^a$; aryloxy which is optionally substituted by up to 6 identical or different groups $R^a$; arylsulfanyl which is optionally substituted by up to 6 identical or different groups $R^a$; arylamino which is optionally substituted by up to 6 identical or different groups $R^a$; $C_1$-$C_8$-arylalkyloxy which is optionally substituted by up to 6 identical or different groups $R^a$; $C_1$-$C_8$-arylalkylsulfanyl which is optionally substituted by up to 6 identical or different groups $R^a$; $C_1$-$C_8$-arylalkylamino which is optionally substituted by up to 6 identical or different groups $R^a$; 5, 6 or 7 membered heterocycle with 1 to 3 heteroatoms which is optionally substituted by up to 4 identical or different groups $R^a$;

$R^a$ independently of one another represent halogen; cyano; nitro; substituted or non-substituted $C_1$-$C_8$-alkyl; $C_1$-$C_8$-haloalkyl; substituted or non-substituted $C_1$-$C_8$-alkoxy; $C_1$-$C_8$-haloalkoxy; substituted or non-substituted $C_1$-$C_8$-alkylsulfanyl; $C_1$-$C_8$-haloalkylsulfanyl; substituted or non-substituted tri($C_1$-$C_8$)alkylsilyl; substituted or non-substituted tri($C_1$-$C_8$)alkylsilyl-$C_1$-$C_8$-alkyl; substituted or non-substituted ($C_1$-$C_8$-alkoxyimino)-$C_1$-$C_8$-alkyl; or substituted or non-substituted (benzyloxyimino)-$C_1$-$C_8$-alkyl, and/or a salt thereof.

3. Aldehyde compound of formula (IV)

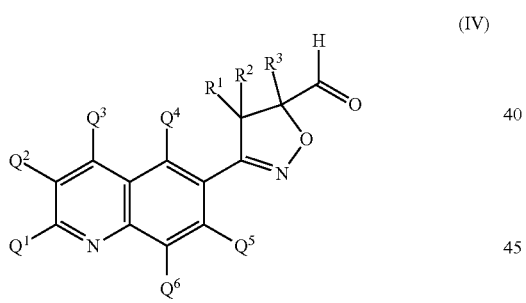

(IV)

in which $R^1$ and $R^2$ independently of one another represent hydrogen; substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; cyano; isonitrile; nitro; halogen; substituted or non-substituted $C_1$-$C_8$-alkoxy; $C_1$-$C_8$-haloalkoxy; substituted or non-substituted $C_2$-$C_8$-alkenyloxy; $C_2$-$C_8$-haloalkenyloxy, substituted or non-substituted $C_2$-$C_8$-alkynyloxy; $C_1$-$C_8$-haloalkynyloxy; substituted or non-substituted $C_3$-$C_7$-cycloalkyl; substituted or non-substituted $C_1$-$C_8$-alkylsulfanyl; substituted or non-substituted $C_1$-$C_8$-alkylsulfonyl; substituted or non-substituted $C_1$-$C_8$-alkylsulfinyl; amino; substituted or non-substituted $C_1$-$C_8$-alkylamino; substituted or non-substituted di-$C_1$-$C_8$-alkylamino; substituted or non-substituted $C_1$-$C_8$-alkoxycarbonyl; substituted or non-substituted $C_1$-$C_8$-alkylcarbamoyl; substituted or non-substituted di-$C_1$-$C_8$-alkylcarbamoyl; or substituted or non-substituted N—$C_1$-$C_8$-alkyl-$C_1$-$C_8$-alkoxy-carbamoyl; or $R^1$ and $R^2$ can form together with the carbon atom to which they are attached a substituted or non-substituted $C_3$-$C_7$-cycloalkyl; or $C_3$-$C_7$-halocycloalkyl;

$R^3$ represents hydrogen; substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; cyano; isonitrile; nitro; halogen; substituted or non-substituted $C_1$-$C_8$-alkoxy; $C_1$-$C_8$-haloalkoxy; substituted or non-substituted $C_2$-$C_8$-alkenyloxy; $C_2$-$C_8$-haloalkenyloxy, substituted or non-substituted $C_2$-$C_8$-alkynyloxy; $C_1$-$C_8$-haloalkynyloxy; substituted or non-substituted $C_3$-$C_7$-cycloalkyl; substituted or non-substituted $C_1$-$C_8$-alkylsulfanyl; substituted or non-substituted $C_1$-$C_8$-alkylsulfonyl; substituted or non-substituted $C_1$-$C_8$-alkylsulfinyl; amino; substituted or non-substituted $C_1$-$C_8$-alkylamino; substituted or non-substituted di-$C_1$-$C_8$-alkylamino; substituted or non-substituted tri($C_1$-$C_8$)alkylsilyl-$C_1$-$C_8$-alkyl; substituted or non-substituted tri($C_1$-$C_8$)alkylsilyl-$C_2$-$C_8$-alkenyl; substituted or non-substituted tri($C_1$-$C_8$)alkylsilyl-$C_2$-$C_8$-alkynyl; substituted or non-substituted $C_1$-$C_8$-alkoxycarbonyl; substituted or non-substituted $C_1$-$C_8$-alkylcarbamoyl; substituted or non-substituted di-$C_1$-$C_8$-alkylcarbamoyl; or substituted or non-substituted N—$C_1$-$C_8$-alkyl-$C_1$-$C_8$-alkoxy-carbamoyl; substituted or non-substituted aryl; or substituted or non-substituted 5, 6 or 7 membered heterocycle ring with 1 to 3 heteroatoms; or $R^3$ together with $R^1$ or $R^2$ together with the carbon atoms to which they are attached can form a substituted or non-substituted $C_3$-$C_7$ cycloalkyl; $C_3$-$C_7$-halocycloalkyl; or a substituted or non-substituted saturated 5, 6 or 7 membered heterocycle;

$Q^1$, $Q^2$, $Q^3$, $Q^4$, $Q^5$ and $Q^6$ independently of one another represent hydrogen; halogen; nitro; cyano; isonitrile; hydroxyl; amino; sulfanyl; pentafluoro-$\lambda^6$-sulfanyl; formyl; formyloxy; formylamino; substituted or non-substituted (hydroxyimino)-$C_1$-$C_8$-alkyl; substituted or non-substituted ($C_1$-$C_8$-alkoxyimino)-$C_1$-$C_8$-alkyl; substituted or non-substituted ($C_2$-$C_8$-alkenyloxyimino)-$C_1$-$C_8$-alkyl; substituted or non-substituted ($C_2$-$C_8$-alkynyloxyimino)-$C_1$-$C_8$-alkyl; substituted or non-substituted (benzyloxyimino)-$C_1$-$C_8$-alkyl; carboxy; carbamoyl; N-hydroxycarbamoyl; carbamate; substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; substituted or non-substituted $C_1$-$C_8$-alkoxy; $C_1$-$C_8$-haloalkoxy; substituted or non-substituted $C_1$-$C_8$-alkylsulfanyl; $C_1$-$C_8$-haloalkylsulfanyl; substituted or non-substituted $C_1$-$C_8$-alkylsulfinyl; $C_1$-$C_8$-haloalkylsulfinyl; substituted or non-substituted $C_1$-$C_8$-alkylsulfonyl; $C_1$-$C_8$-haloalkylsulfonyl; substituted or non-substituted $C_1$-$C_8$-alkylamino; substituted or non-substituted di-$C_1$-$C_8$-alkylamino; substituted or non-substituted $C_2$-$C_8$-alkenyloxy; $C_2$-$C_8$-haloalkenyloxy; substituted or non-substituted $C_3$-$C_8$-alkynyloxy; $C_2$-$C_8$-haloalkynyloxy; substituted or non-substituted $C_3$-$C_7$-cycloalkyl; $C_3$-$C_7$-halocycloalkyl; substituted or non-substituted ($C_3$-$C_7$-cycloalkyl)-$C_1$-$C_8$-alkyl; substituted or non-substituted $C_4$-$C_7$-cycloalkenyl; $C_4$-$C_7$-halocycloalkenyl; substituted or non-substituted ($C_3$-$C_7$-cycloalkyl)-$C_2$-$C_8$-alkenyl; substituted or non-substituted ($C_3$-$C_7$-cycloalkyl)-$C_2$-$C_8$-alkynyl; substituted or non-substituted tri($C_1$-$C_8$)alkylsilyl; substituted or non-substituted tri($C_1$-$C_8$)alkylsilyl-$C_1$-$C_8$-alkyl; substituted or non-substituted tri($C_1$-$C_8$)alkylsilyl-$C_2$-$C_8$-alkenyl; substituted or non-substituted tri($C_1$-$C_8$)alkylsilyl-$C_2$-$C_8$-alkynyl; substituted or non-substituted $C_1$-$C_8$-alkylcarbonyl; $C_1$-$C_8$-haloalkylcarbonyl; substituted or non-substituted $C_1$-$C_8$-alkylcarbonyloxy; $C_1$-$C_8$-haloalkylcarbonyloxy; substituted or non-substituted $C_1$-$C_8$-alkylcarbonylamino; $C_1$-$C_8$-haloalkylcarbonylamino; substituted or non-substituted $C_1$-$C_8$-alkoxycarbonyl; $C_1$-$C_8$-haloalkoxycarbonyl; substituted or non-substituted $C_1$-$C_8$-alkyloxycarbonyloxy; $C_1$-$C_8$-haloalkoxycarbonyloxy; substituted or non-substituted $C_1$-$C_8$-alkylcarbamoyl; substituted or non-substituted di-$C_1$-$C_8$-alkylcarbamoyl; substituted or non-substituted $C_1$-$C_8$-alkylaminocarbonyloxy; substituted or non-substituted di-$C_1$-$C_8$-alkylaminocarbonyloxy; substituted or non-substituted N—($C_1$-$C_8$-alkyl)hydroxy carbamoyl; substituted or non-substituted $C_1$-$C_8$-alkoxycarbamoyl; substituted or non-substituted N—($C_1$-$C_8$-alkyl)-$C_1$-$C_8$-alkoxycarbamoyl; aryl which is optionally substituted by up to 6 identical or different groups $R^a$; $C_1$-$C_8$-arylalkyl which is optionally substituted by up to 6 identical or different groups $R^a$; $C_2$-$C_8$-arylalkenyl which is optionally substituted by up to 6 identical or different groups $R^a$; $C_2$-$C_8$-arylalkynyl which is optionally substituted by up to 6 identical or different groups $R^a$; aryloxy which is optionally substituted by up to 6 identical or different groups $R^a$; arylsulfanyl which is optionally substituted by up to 6 identical or different groups $R^a$; arylamino which is optionally substituted by up to 6 identical or different groups $R^a$; $C_1$-$C_8$-arylalkyloxy which is optionally substituted by up to 6 identical or different groups $R^a$; $C_1$-$C_8$-arylalkylsulfanyl which is optionally substituted by up to 6 identical or different groups $R^a$; $C_1$-$C_8$-arylalkylamino which is optionally substituted by up to 6 identical or different groups $R^a$; 5, 6 or 7 membered heterocycle with 1 to 3 heteroatoms which is optionally substituted by up to 4 identical or different groups $R^a$;

$R^a$ independently of one another represent halogen; cyano; nitro; substituted or non-substituted $C_1$-$C_8$-alkyl; $C_1$-$C_8$-haloalkyl; substituted or non-substituted $C_1$-$C_8$-alkoxy; $C_1$-$C_8$-haloalkoxy; substituted or non-substituted $C_1$-$C_8$-alkylsulfanyl; $C_1$-$C_8$-haloalkylsulfanyl; substituted or non-substituted tri($C_1$-$C_8$)alkylsilyl; substituted or non-substituted tri($C_1$-$C_8$)alkylsilyl-$C_1$-$C_8$-alkyl; substituted or non-substituted ($C_1$-$C_8$-alkoxyimino)-$C_1$-$C_8$-alkyl; or substituted or non-substituted (benzyloxyimino)-$C_1$-$C_8$-alkyl;

and/or a salt thereof.

4. A compound of formula (V)

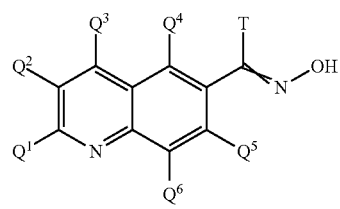

T represents H or Cl, $Q^1$, $Q^2$, $Q^3$, $Q^4$, $Q^5$ and $Q^6$ independently of one another represent hydrogen; halogen; nitro; cyano; isonitrile; hydroxyl; amino; sulfanyl; pentafluoro-$\lambda^6$-sulfanyl; formyl; formyloxy; formylamino; substituted or non-substituted (hydroxyimino)-$C_1$-$C_8$-alkyl; substituted or non-substituted ($C_1$-$C_8$-alkoxyimino)-$C_1$-$C_8$-alkyl; substituted or non-substituted ($C_2$-$C_8$-alkenyloxyimino)-$C_1$-$C_8$-alkyl; substituted or non-substituted ($C_2$-$C_8$-alkynyloxyimino)-$C_1$-$C_8$-alkyl; substituted or non-substituted (benzyloxyimino)-$C_1$-$C_8$-alkyl; carboxy; carbamoyl; N-hydroxycarbamoyl; carbamate; substituted or non-substituted $C_1$-$C_8$-alkyl; $C_1$-$C_8$-haloalkyl; substituted or non-substituted $C_2$-$C_8$-alkenyl; $C_2$-$C_8$-haloalkenyl; substituted or non-substituted $C_2$-$C_8$-alkynyl; $C_2$-$C_8$-haloalkynyl; substituted or non-substituted $C_1$-$C_8$-alkoxy; $C_1$-$C_8$-haloalkoxy; substituted or non-substituted $C_1$-$C_8$-alkylsulfanyl; $C_1$-$C_8$-haloalkylsulfanyl; substituted or non-substituted $C_1$-$C_8$-alkylsulfinyl; $C_1$-$C_8$-haloalkylsulfinyl; substituted or non-substituted $C_1$-$C_8$-alkylsulfonyl; $C_1$-$C_8$-haloalkylsulfonyl; substituted or non-substituted $C_1$-$C_8$-alkylamino; substituted or non-substituted di-$C_1$-$C_8$-alkylamino; substituted or non-substituted $C_2$-$C_8$-alkenyloxy; $C_2$-$C_8$-haloalkenyloxy; substituted or non-substituted $C_3$-$C_8$-alkynyloxy; $C_2$-$C_8$-haloalkynyloxy; substituted or non-substituted $C_3$-$C_7$-cycloalkyl; $C_3$-$C_7$-halocycloalkyl; substituted or non-substituted ($C_3$-$C_7$-cycloalkyl)-$C_1$-$C_8$-alkyl; substituted or non-substituted $C_4$-$C_7$-cycloalkenyl; $C_4$-$C_7$-halocycloalkenyl; substituted or non-substituted ($C_3$-$C_7$-cycloalkyl)-$C_2$-$C_8$-alkenyl; substituted or non-substituted ($C_3$-$C_7$-cycloalkyl)-$C_2$-$C_8$-alkynyl; substituted or non-substituted tri($C_1$-$C_8$)alkylsilyl; substituted or non-substituted tri($C_1$-$C_8$)alkylsilyl-$C_1$-$C_8$-alkyl; substituted or non-substituted tri($C_1$-$C_8$)alkylsilyl-$C_2$-$C_8$-alkenyl; substituted or non-substituted tri($C_1$-$C_8$)alkylsilyl-$C_2$-$C_8$-alkynyl; substituted or non-substituted $C_1$-$C_8$-alkylcarbonyl; $C_1$-$C_8$-haloalkylcarbonyl; substituted or non-substituted $C_1$-$C_8$-alkylcarbonyloxy; $C_1$-$C_8$-haloalkylcarbonyloxy; substituted or non-substituted $C_1$-$C_8$-alkylcarbonylamino; $C_1$-$C_8$-haloalkylcarbonylamino; substituted or non-substituted $C_1$-$C_8$-alkoxycarbonyl; $C_1$-$C_8$-haloalkoxycarbonyl; substituted or non-substituted $C_1$-$C_8$-alkyloxycarbonyloxy; $C_1$-$C_8$-haloalkoxycarbonyloxy; substituted or non-substituted $C_1$-$C_8$-alkylcarbamoyl; substituted or non-substituted di-$C_1$-$C_8$-alkylcarbamoyl; substituted or non-substituted $C_1$-$C_8$-alkylaminocarbonyloxy; substituted or non-substituted di-$C_1$-$C_8$-alkylaminocarbonyloxy; substituted or non-substituted N—($C_1$-$C_8$-alkyl)hydroxy carbamoyl; substituted or non-substituted $C_1$-$C_8$-alkoxycarbamoyl; substituted or non-substituted N—($C_1$-$C_8$-alkyl)-$C_1$-$C_8$-alkoxycarbamoyl; aryl which is optionally substituted by up to 6 identical or different groups $R^a$; $C_1$-$C_8$-arylalkyl which is optionally substituted by up to 6 identical or different groups $R^a$; $C_2$-$C_8$-arylalkenyl which is optionally substituted by up to 6 identical or different groups $R^a$; $C_2$-$C_8$-arylalkynyl which is optionally substituted by up to 6 identical or different groups $R^a$; aryloxy which is optionally substituted by up to 6 identical or different groups $R^a$; arylsulfanyl which is optionally substituted by up to 6 identical or different groups $R^a$; arylamino which is optionally substituted by up to 6 identical or different groups $R^a$; $C_1$-$C_8$-arylalkyloxy which is optionally substituted by up to 6 identical or different groups $R^a$; $C_1$-$C_8$-arylalkylsulfanyl which is optionally substituted by up to 6 identical or different groups $R^a$; $C_1$-$C_8$-arylalkylamino which is optionally substituted by up to 6 identical or different groups $R^a$; 5, 6 or 7 membered heterocycle with 1 to 3 heteroatoms which is optionally substituted by up to 4 identical or different groups $R^a$;

$R^a$ independently of one another represent halogen; cyano; nitro; substituted or non-substituted $C_1$-$C_8$-alkyl; $C_1$-$C_8$-haloalkyl; substituted or non-substituted $C_1$-$C_8$-alkoxy; $C_1$-$C_8$-haloalkoxy; substituted or non-substituted $C_1$-$C_8$-alkylsulfanyl; $C_1$-$C_8$-haloalkylsulfanyl; substituted or non-substituted tri($C_1$-$C_8$)alkylsilyl; substituted or non-substituted tri($C_1$-$C_8$)alkylsilyl-$C_1$-$C_8$-alkyl; substituted or non-substituted ($C_1$-$C_8$-alkoxyimino)-$C_1$-$C_8$-alkyl; or substituted or non-substituted (benzyloxyimino)-$C_1$-$C_8$-alkyl, and/or a salt thereof, except for the compounds N-hydroxyquinoline-6-carboximidoyl chloride, N-hydroxyquinoline-6-carboximidoyl chloride hydrochloride (1:1), (E)-N-hydroxy-1-(quinolin-6-yl)methanimine, 6-[(E)-(hydroxyimino)methyl]quinolin-5-amine, (E)-N-hydroxy-1-(5-nitroquinolin-6-yl)methanimine, (Z)-N-hydroxy-1-(5-nitroquinolin-6-yl)methanimine, (1R,2R)-6-(dimethylamino)-1-{6-[(E)-(hydroxyimino)methyl]-2-methoxyquinolin-3-yl}-1,2-diphenylhexan-2-ol, (1R,2S)-4-(dimethylamino)-1-{6-[(E)-(hydroxyimino)methyl]-2-methoxyquinolin-3-yl}-2-(1-naphthyl)-1-phenylbutan-2-ol, (1R,2R)-4-(dimethylamino)-1-{6-[(E)-(hydroxyimino)methyl]-2-methoxyquinolin-3-yl}-2-(1-naphthyl)-1-phenylbutan-2-ol, (1R,2S)-6-(dimethylamino)-1-{6-[(E)-(hydroxyimino)methyl]-2-methoxyquinolin-3-yl}-2-(2-naphthyl)-1-phenylhexan-2-ol, (1R,2R)-6-(dimethylamino)-1-{6-[(E)-(hydroxyimino)methyl]-2-methoxyquinolin-3-yl}-2-(2-naphthyl)-1-phenylhexan-2-ol, (5R,6S)-6-[(1R)-1-hydroxyethyl]-3-{2-[(E)-(hydroxyimino)methyl]phenanthridin-8-yl}-7-oxo-1-azabicyclo[3.2.0]hept-2-ene-2-carboxylic acid, (5R,6S)-6-[(1R)-1-hydroxyethyl]-3-{ 2-[(E)-(hydroxyimino)methyl]phenanthridin-8-yl }-7-oxo-1-azabicyclo [3.2.0]hept-2-ene-2-carboxylic acid-sodium (1:1), (3aS,4R,9R,10R,11R,13R,15R,15aR)-4-ethyl-7-fluoro-11-{[(2Z)-3-{6-[(E)-(hydroxyimino)methyl]quinolin-3-yl}prop -2-en-1-yl]oxy}3a,7,9,11,13,15-hexamethyl-2,6,8,14-tetraoxotetradecahydro-2H-oxacyclotetradecino[4,3-d][1,3]oxazol-10-yl-3,4,6-trideoxy-3-(dimethylamino)-beta-D-xylohexopyrano side.

* * * * *